(12) United States Patent
Van Eenennaam et al.

(10) Patent No.: US 10,851,164 B2
(45) Date of Patent: Dec. 1, 2020

(54) ANTI-SIRPα ANTIBODIES

(71) Applicant: ADURO BIOTECH HOLDINGS, EUROPE B.V., Oss (NL)

(72) Inventors: Hans Van Eenennaam, Oss (NL); Andrea Van Elsas, Oss (NL); Erik Voets, Oss (NL); Paul Vink, Oss (NL); David Lutje Hulsik, Oss (NL)

(73) Assignee: ADURO BIOTECH HOLDINGS, EUROPE B.V., Oss (NL)

( * ) Notice: Subject to any disclaimer, the term of this patent is extended or adjusted under 35 U.S.C. 154(b) by 48 days.

(21) Appl. No.: 15/953,201

(22) Filed: Apr. 13, 2018

(65) Prior Publication Data
US 2018/0312587 A1    Nov. 1, 2018

(30) Foreign Application Priority Data

Apr. 13, 2017  (NL) ................................ 2018708
Jul. 3, 2017   (NL) ................................ 2019166

(51) Int. Cl.
*A61K 35/17*    (2015.01)
*C07K 16/28*    (2006.01)
*G01N 33/68*    (2006.01)
*G01N 33/574*   (2006.01)

(52) U.S. Cl.
CPC ... *C07K 16/2803* (2013.01); *G01N 33/57484* (2013.01); *G01N 33/6854* (2013.01); *C07K 2317/24* (2013.01); *C07K 2317/33* (2013.01); *C07K 2317/34* (2013.01); *C07K 2317/70* (2013.01); *C07K 2317/76* (2013.01); *C07K 2317/92* (2013.01); *G01N 2333/70503* (2013.01)

(58) Field of Classification Search
CPC ............... A61K 39/0011; A61K 35/17; C07K 16/2863; C07K 2317/565
USPC .......................................... 424/133.1, 178.1
See application file for complete search history.

(56) References Cited

U.S. PATENT DOCUMENTS

| | | |
|---|---|---|
| 4,399,216 A | 8/1983 | Axel et al. |
| 4,740,461 A | 4/1988 | Kaufman et al. |
| 4,816,567 A | 3/1989 | Cabilly et al. |
| 4,912,040 A | 3/1990 | Kaufman et al. |
| 4,959,455 A | 9/1990 | Clark et al. |
| 5,225,539 A | 7/1993 | Winter |
| 5,260,203 A | 11/1993 | Ladner et al. |
| 5,530,101 A | 6/1996 | Queen et al. |
| 5,585,089 A | 12/1996 | Queen et al. |
| 5,624,821 A | 4/1997 | Winter et al. |
| 5,648,260 A | 7/1997 | Winter et al. |
| 5,677,425 A | 10/1997 | Bodmer et al. |
| 5,693,762 A | 12/1997 | Queen et al. |
| 5,714,350 A | 2/1998 | Co et al. |
| 5,869,046 A | 2/1999 | Presta et al. |
| 6,121,022 A | 9/2000 | Presta et al. |
| 6,165,745 A | 12/2000 | Ward et al. |
| 6,194,551 B1 | 2/2001 | Idusogie et al. |
| 6,277,375 B1 | 8/2001 | Ward |
| 6,331,415 B1 | 12/2001 | Cabilly et al. |
| 6,350,861 B1 | 2/2002 | Co et al. |
| 6,946,292 B2 | 9/2005 | Kanda et al. |
| 7,029,872 B2 | 4/2006 | Gerngross et al. |
| 7,125,689 B2 | 10/2006 | Carr et al. |
| 7,214,775 B2 | 5/2007 | Hanai et al. |
| 7,449,308 B2 | 11/2008 | Gerngross et al. |
| 8,562,997 B2 | 10/2013 | Jaiswal et al. |
| 9,352,037 B2 | 5/2016 | Van Den Berg |
| 9,399,682 B2 | 7/2016 | Jaiswal et al. |
| 9,493,575 B2 | 11/2016 | Jaiswal et al. |
| 9,605,076 B2 | 3/2017 | Jaiswal et al. |
| 9,611,329 B2 | 4/2017 | Jaiswal et al. |
| 9,624,305 B2 | 4/2017 | Jaiswal et al. |
| 9,765,143 B2 | 9/2017 | Jaiswal et al. |
| 9,790,275 B2 | 10/2017 | Van Den Berg |
| 9,920,122 B2 | 3/2018 | Van Den Berg |
| 10,081,680 B2 | 9/2018 | Weiskopf et al. |
| 2006/0057702 A1 | 3/2006 | Rosenthal et al. |
| 2017/0073414 A1 | 3/2017 | Weiskopf et al. |
| 2018/0037652 A1 | 2/2018 | Liu et al. |
| 2019/0153095 A1 | 5/2019 | Matozaki et al. |

FOREIGN PATENT DOCUMENTS

| | | |
|---|---|---|
| CA | 2939293 A1 | 9/2015 |
| EP | 0216846 A1 | 4/1987 |
| EP | 0256055 A1 | 2/1988 |
| EP | 0323997 A1 | 7/1989 |
| EP | 0338841 A1 | 10/1989 |
| EP | 0404097 A2 | 12/1990 |
| WO | 8801649 A1 | 3/1988 |
| WO | 8901036 A1 | 2/1989 |
| WO | 9311161 A1 | 6/1993 |
| WO | 9429351 A2 | 12/1994 |

(Continued)

OTHER PUBLICATIONS

Voets et al. Journal for ImmunoTherapy of Cancer Dec. 4, 2019; 7(1):340.*
Zhao et al. PNAS 108(45):18342-18347 (Nov. 8, 2011).*
Alexander and Hughes, Monitoring of IgG antibody thermal stability by micellar electrokinetic capillary chromatography and matrix-assisted laser desorption/ionization mass spectrometry. Anal Chem. Oct. 15, 1995;67(20):3626-3632.
Altschul et al., A protein alignment scoring system sensitive at all evolutionary distances. J Mol Evol. Mar. 1993;36(3):290-300.
Altschul et al., Basic local alignment search tool. J Mol Biol. Oct. 5, 1990;215(3):403-410.
Altschul et al., Gapped BLAST and PSI-BLAST: a new generation of protein database search programs. Nucleic Acids Res. Sep. 1, 1997;25(17):3389-3402.

(Continued)

Primary Examiner — Lynn A Bristol
(74) Attorney, Agent, or Firm — Acuity Law Group, PC; Michael A. Whittaker

(57) ABSTRACT

The present invention relates to anti-SIRPα antibodies, as well as use of these antibodies in the treatment of diseases such as cancer and infectious disease.

19 Claims, 34 Drawing Sheets

Specification includes a Sequence Listing.

(56) References Cited

FOREIGN PATENT DOCUMENTS

| | | |
|---|---|---|
| WO | 0066159 A1 | 11/2000 |
| WO | 03086310 A2 | 10/2003 |
| WO | 2005120571 A2 | 12/2005 |
| WO | 2013056352 A1 | 4/2013 |
| WO | 2015138600 A2 | 9/2015 |
| WO | 2017178653 A2 | 10/2017 |
| WO | 2018057669 A1 | 3/2018 |
| WO | 2018107058 A1 | 6/2018 |
| WO | 2018190719 A2 | 10/2018 |
| WO | 2018210793 A2 | 11/2018 |
| WO | 2019023347 A1 | 1/2019 |

OTHER PUBLICATIONS

Altschul et al., Protein database searches using compositionally adjusted substitution matrices. FEBS J. Oct. 2005;272(20):5101-5109.

Altschul, Amino acid substitution matrices from an information theoretic perspective. J Mol Biol. Jun. 5, 1991;219(3):555-565.

Altschul, Evaluating the statistical significance of multiple distinct local alignments. In Theoretical and Computational Methods in Genome Research (S. Suhai, ed.), 1997:1-14.

Angal et al., A single amino acid substitution abolishes the heterogeneity of chimeric mouse/human (IgG4) antibody. Mol Immunol. Jan. 1993;30(1):105-108.

Barclay and Brown, The SIRP family of receptors and immune regulation. Nat Rev Immunol. Jun. 2006;6(6):457-464.

Bischoff and Kolbe, Deamidation of asparagine and glutamine residues in proteins and peptides: structural determinants and analytical methodology. J Chromatogr B Biomed Appl. Dec. 9, 1994;662(2):261-278.

Camacho et al., BLAST+: architecture and applications. BMC Bioinformatics. Dec. 15, 2009;10:421.

Chen et al., Influence of Histidine on the Stability and Physical Properties of a Fully Human Antibody in Aqueous and Solid Forms. Pharm Res Dec. 2003;20(12):1952-1960.

Choi et al, Use of combinatorial genetic libraries to humanize N-linked glycosylation in the yeast Pichia pastoris. Proc Natl Acad Sci U S A. Apr. 29, 2003;100(9):5022-5027.

Chothia and Lesk, Canonical Structures for the Hypervariable Regions of Immunoglobulins. J Mol Biol. Aug. 20, 1987;196(4):901-917.

Clark, Antibody humanization: a case of the 'Emperor's new clothes'? Immunol Today. Aug. 2000;21(8):397-402.

David and Reisfeld, Protein Iodination with Solid State Lactoperoxidase. Biochemistry. Feb. 26, 1974;13(5): 1014-1021.

Dayhoff et al., A Model of Evolutionary Change in Proteins. Atlas of Protein Sequence and Structure, M.O. Dayhoff (ed.), 1978; 5(suppl. 3): 345-352.

Dembo et al., Limit distribution of Maximal Non-Aligned Two-Sequence Segmental Score. Ann Prob. 1994;22:2022-2039 (pp. 1-16).

Gala and Morrison, V Region Carbohydrate and Antibody Expression. J Immunol. May 1, 2004;172(9):5489-5494.

Gao et al., Monoclonal antibody humanness score and its applications. BMC Biotechnol. Jul. 5, 2013;13:55.

Gardai et al., By Binding SIRPα or Calreticulin/CD91, Lung Collectins Act as Dual Function Surveillance Molecules to Suppress or Enhance Inflammation. Cell. Oct. 3, 2003;115(1):13-23.

Ghirlando et al., Glycosylation of human IgG-Fc: influences on structure revealed by differential scanning micro-calorimetry. Immunol Lett. May 3, 1999;68(1):47-52.

Gish and States, Identification of protein coding regions by database similarity search. Nat Genet. Mar. 1993;3(3): 266-272.

Giudicelli et al., IMGT/GENE-DB: a comprehensive database for human and mouse immunoglobulin and T cell receptor genes. Nucleic Acids Res. Jan. 1, 2005;33(Database issue):D256-D261.

Götze et al., Stavrox—A Software for Analyzing Crosslinked Products in Protein Interaction Studies. J Am Soc Mass Spectrom. Jan. 2012;23(1):76-87.

Hamilton and Gerngross, Glycosylation engineering in yeast: the advent of fully humanized yeast. Curr Opin Biotechnol. Oct. 2007;18(5):387-392.

Hamilton et al., Humanization of Yeast to Produce Complex Terminally Sialylated Glycoproteins. Science. Sep. 8, 2006;313(5792):1441-1443.

Hamilton et al., Production of Complex Human Glycoproteins in Yeast. Science. Aug. 29, 2003;301(5637):1244-1246.

Hancock and Armstrong, SIMPLE34: an improved and enhanced implementation for VAX and Sun computers of the SIMPLE algorithm for analysis of clustered repetitive motifs in nucleotide sequences. Comput Appl Biosci. Feb. 1994:10(1):67-70.

Hatherley et al., Paired Receptor Specificity Explained by Structures of Signal Regulatory Proteins Alone and Complexed with CD47. Mol Cell. Jul. 25, 2008;31(2):266-277.

Henikoff and Henikoff, Amino acid substitution matrices from protein blocks. Proc Natl Acad Sci U S A. Nov. 15, 1992;89(22):10915-10919.

Herold et al., Anti-CD3 Monoclonal Antibody in New-Onset Type 1 Diabetes Mellitus. N Engl J Med. May 30, 2002;346(22):1692-1698.

Holliger and Hudson, Engineered antibody fragments and the rise of single domains. Nat Biotechnol. Sep. 2005;23(9):1126-1136.

Holliger et al., "Diabodies": Small bivalent and bispecific antibody fragments. Proc Natl Acad Sci U S A. Jul. 15, 1993;90(14):6444-6448.

Hunter and Greenwood, Preparation of iodine-131 labelled human growth hormone of high specific activity. Nature. May 5, 1962;194:495-496.

Jones et al., Replacing the complementarity-determining regions in a human antibody with those from a mouse. Nature. May 29-Jun. 4, 1986;321(6069):522-525.

Kabat et al., Unusual Distributions of Amino Acids in Complementarity-determining (Hypervariable) Segments of Heavy and Light Chains of Immunoglobulins and Their Possible Roles in Specificity of Antibody-combining Sites. J Biol Chem. Oct. 10, 1977;252(19):6609-6616.

Kabat, The Structural Basis of Antibody Complementarity. Adv Protein Chem. 1978;32:1-75.

Karlin and Altschul, Applications and statistics for multiple high-scoring segments in molecular sequences. Proc Natl Acad Sci U S A. Jun. 15, 1993;90(12):5873-5877.

Karlin and Altschul, Methods for assessing the statistical significance of molecular sequence features by using general scoring schemes. Proc Natl Acad Sci U S A. Mar. 1990;87(6):2264-2268.

Kostelny et al., Formation of a bispecific antibody by the use of leucine zippers. J Immunol. Mar. 1, 1992;148(5):1547-1553.

Krishnamurthy and Manning, The Stability Factor: Importance in Formulation Development. Curr Pharm Biotechnol. Dec. 2002;3(4):361-371.

Labrijn et al., Efficient generation of stable bispecific IgG1 by controlled Fab-arm exchange. Proc Natl Acad Sci U S A. Mar. 26, 2013;110(13):5145-5150.

Lee et al., Prolonged Circulating Lives of Single-Chain Fv Proteins Conjugated with Polyethylene Glycol: A Comparison of Conjugation Chemistries and Compounds. Bioconjug Chem. Nov.-Dec. 1999;10(6):973-981.

Lee, Mass spectrometric analysis of cross-linking sites for the structure of proteins and protein complexes. Mol Biosyst. Aug. 2008;4(8):816-823.

Lefranc et al., IMGT, the international ImMunoGeneTics database. Nucleic Acids Res. Jan. 1, 1999;27(1):209-212.

Li et al., Optimization of humanized IgGs in glycoengineered Pichia pastoris. Nat Biotechnol. Feb. 2006;24(2):210-215.

Liu and Blumhardt, Randomised, double blind, placebo controlled study of interferon beta-1a in relapsing-remitting multiple sclerosis analysed by area under disability/time curves. J Neurol Neurosurg Psychiatry. Oct. 1999;67(4):451-456.

Madden et al., Applications of Network BLAST Server. Methods Enzymol. 1996;266:131-141.

(56) References Cited

OTHER PUBLICATIONS

Marshall, Glycoproteins. Annu Rev Biochem. 1972;41:673-702.
The International Search Report and Written Opinion issued in PCT/NL2018/050234 dated Sep. 23, 2019.
Jackson, In Vitro Antibody Maturation Improvement of a High Affinity, Neutralizing Antibody Against IL-1 beta. J Immunol. Apr. 1, 1995;154(7):3310-3319.
Matlung et al., The CD47-SIRPα signaling axis as an innate immune checkpoint in cancer. Immunol Rev. Mar. 2017;276(1):145-164.
Rudikoff et al., Single amino acid substitution altering antigen-binding specificity. Proc Natl Acad Sci U S A. Mar. 1982;79(6):1979-1983.
Theocharides et al., Disruption of SIRPα signaling in macrophages eliminates human acute myeloid leukemia stem cells in xenografts. J Exp Med. Sep. 24, 2012;209(10):1883-1899.
Weiskopf et al., Engineered SIRPα Variants as Immunotherapeutic Adjuvants to Anticancer Antibodies. Science. Jul. 5, 2013;341(6141):88-91.
Wong et al., Structural Requirements for a Specificity Switch and for Maintenance of Affinity Using Mutational Analysis of a Phage-Displayed Anti-Arsonate Antibody of Fab Heavy Chain First Complementarity-Determining Region. J Immunol. Jun. 15, 1998;160(12):5990-5997.
Yanagita et al., Anti-SIRPα antibodies as a potential new tool for cancer immunotherapy. JCI Insight. Jan. 12, 2017;2(1);e89140 (15 pages).
Mimura et al., The influence of glycosylation on the thermal stability and effector function expression of human IgG1-Fc: properties of a series of truncated glycoforms. Mol Immunol. Aug.-Sep. 2000;37(12-13):697-706.
Morrison et al., Chimeric human antibody molecules: Mouse antigen-binding domains with human constant region domains. Proc Natl Acad Sci U S A Nov. 1984;81(21):6851-6855.
Murray et al., Epitope Affinity Chromatography and Biophysical Studies of Monoclonal Antibodies and Recombinant Antibody Fragments. J Chromatogr Sci. Jul. 2002;40(6):343-349.
Nett et al., A combinatorial genetic library approach to target heterologous glycosylation enzymes to the endoplasmic reticulum or the Golgi apparatus of Pichia pastoris. Yeast Mar. 2011;28(3):237-252.
Nygren, Conjugation of Horseradish Peroxidase to Fab Fragments with Different Homobifunctional and Heterobifunctional Cross-Linking Reagents. A Comparative Study. J Histochem Cytochem. May 1982;30(5):407-412.
Oldenborg et al., Role of CD47 as a marker of self on red blood cells. Science. Jun. 16, 2000;288(5473):2051-2054.
Pain and Surolia, Preparation of Protein A-Peroxidase Monoconjugate Using a Heterobifunctional Reagent, and its Use in Enzyme Immunoassays. J Immunol Methods. 1981;40(2):219-30.
Parekh et al., Association of rheumatoid arthritis and primary osteoarthritis with changes in the glycosylation pattern of total serum IgG. Nature. Aug. 1-7, 1985;316(6027):452-457.
Parry et al., Dinaciclib (SCH 727965), a Novel and Potent Cyclin-Dependent Kinase Inhibitor. Mol Cancer Ther. Aug. 2010;9(8):2344-2353.
Portielji et al., IL-12: a promising adjuvant for cancer vaccination. Cancer Immunol Immunother. Mar. 2003;52(3):133-144.
Presta, Antibody engineering. Curr Opin Struct Biol., Aug. 1992;2(4):593-596.
Presta, Selection, design, and engineering of therapeutic antibodies. J Allergy Clin Immunol. Oct. 2005;116(4):731-736.
Raghunathan et al, Antigen-binding site anatomy and somatic mutations in antibodies that recognize different types of antigens. J Mol Recognit. Mar. 2012;25(3):103-113.
Reissner and Aswad, Deamidation and isoaspartate formation in proteins: unwanted alterations or surreptitious signals? Cell Mol Life Sci. Jul. 2003;60(7):1281-1295.
Retter et al., VBASE2, an integrative V gene database. Nucleic Acids Res. Jan. 1, 2005;33(Database issue):D671-D674.
Riechmann et al., Reshaping human antibodies for therapy. Nature. Mar. 24, 1988;332(6162):323-327.
Ring et al., Anti-SIRPα antibody immunotherapy enhances neutrophil and macrophage antitumor activity. Proc Natl Acad Sci U S A. Dec. 5, 2017;114(49):E10578-E10585.
Rowley et al., Phage display for epitope determination: a paradigm for identifying receptor-ligand interactions. Biotechnol Annu Rev. 2004;10:151-188.
Schuurman et. al., The inter-heavy chain disulfide bonds of IgG4 are in equilibrium with intra-chain disulfide bonds. Mol Immunol. Jan. 2001;38(1):1-8.
Shinkawa et al., The Absence of Fucose but Not The Presence of Galactose or Bisecting N-Acetylglucosamine of Human IgG1 Complex-type Oligosaccharides Shows the Critical Role of Enhancing Antibody-dependent Cellular Cytotoxicity. J Biol Chem. Jan. 31, 2003;278(5)3466-3473.
Songsivilai and Lachmann, Bispecific antibody: a tool for diagnosis and treatment of disease. Clin Exp Immunol. Mar. 1990;79(3):315-321.
Spiro, Protein glycosylation: nature, distribution, enzymatic formation, and disease implications of glycopeptide bonds. Glycobiology. Apr. 2002;12(4):43R-56R.
States et al., Improved Sensitivity of Nucleic Acid Database Searches Using Application-Specific Scoring Matrices. Meth Enzymol. 1991; 3(1):66-70.
Steenbakkers et al., A new approach to the generation of human or murine antibody producing hybridomas. J Immunol Methods. Jul. 31, 1992;152(1):69-77.
Steenbakkers et al., Efficient generation of monoclonal antibodies from preselected antigen-specific B cells. Efficient immortalization of preselected B cells. Mol Biol Rep. Mar. 1994;19(2):125-134.
Takenaka et al., Polymorphism in Sirpa modulates engraftment of human hematopoietic stem cells. Nat Immunol. Dec. 2007;8(12):1313-1323.
Traunecker et al., Janusin: New Molecular Design for Bispecific Reagents. Int J Cancer Suppl. 1992;7:51-52.
Wallick et al., Glycosylation of a VH Residue of a Monoclonal Antibody Against alpha (1->6) Dextran Increases its Affinity for Antigen. J Exp Med. Sep. 1, 1988;168(3):1099-1109.
Ward et al., Binding activities of a repertoire of single immunoglobulin variable domains secreted from *Escherichia coli*. Nature. Oct. 12, 1989;341(6242):544-546.
Wen et al., Poly(ethylene glycol)-Conjugated Anti-EGF Receptor Antibody C225 with Radiometal Chelator Attached to be Termini of Polymer Chains. Bioconjug Chem. Jul.-Aug. 2001;12(4):545-553.
Wootton et al., Statistics of Local Complexity in Amino Acid Sequences and Sequence Databases. Comput Chem. 1993;17(2):149-163.
Yang et al., A Randomized Trial of Bevacizumab, an Anti-Vascular Endothelial Growth Factor Antibody, for Metastatic Renal Cancer. N Engl J Med. Jul. 31, 2003;349(5):427-434.
Ye et al., IgBLAST: an immunoglobulin variable domain sequence analysis tool. Nucleic Acids Res. Jul. 2013;41(Web Server issue):W34-40.
Zhang and Madden, PowerBLAST: A New Network BLAST Application for Interactive or Automated Sequence Analysis and Annotation. Genome Res. Jun. 1997;7(6):649-656.
Oflazoglu and Audoly, "Evolution of anti-CD20 monoclonal antibody therapeutics in oncology", mAbs, 2009, 2(1):14-19.
Schlothauer et al., "Novel human IgG1 and IgG4 Fc-engineered antibodies with completely abolished immune affector functions", Protein Enginerring, Design & Selection, 2016, 29(10):457-466.

* cited by examiner

FIG. 10A

```
hSIRPαV1  EEELQVIQPDKSVLVAAGETATLRCTATSLIPVGPIQWFRGAGPGRELIYNQKEGHFPRV
hSIRPαV2  EEELQVIQPDKSVSVAAGESAILHCTVTSLIPVGPIQWFRGAGPARELIYNQKEGHFPRV
hSIRPβ1   EDELQVIQPEKSVSVAAGESATLRCAMTSLIPVGPIMWFRGAGAGRELIYNQKEGHFPRV
          * ****:*.****:::.*******:**.*************** hSIRPαV1  TTVSDLTKRNNMDFSIRIGNITPADAGTYYCVKFRKGSPDDVEFKSG
hSIRPαV2  TTVSESTKRENMDFSISISNITPADAGTYYCVKFRKGSPD-TEFKSG
hSIRPβ1   TTVSELTKRNNLDFSISISNITPADAGTYYCVKFRKGSPDDVEFKSG
          ****: ***:*:****.*.************************ ..****
```

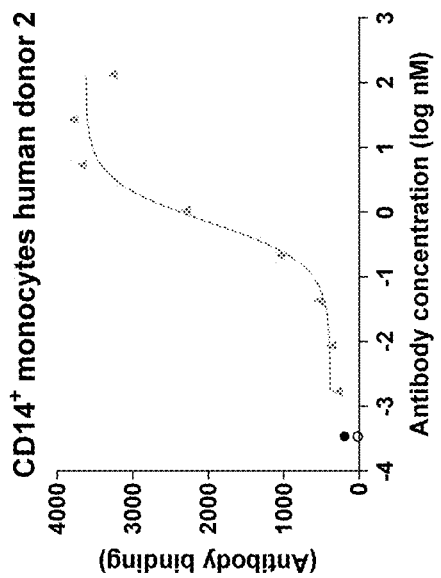
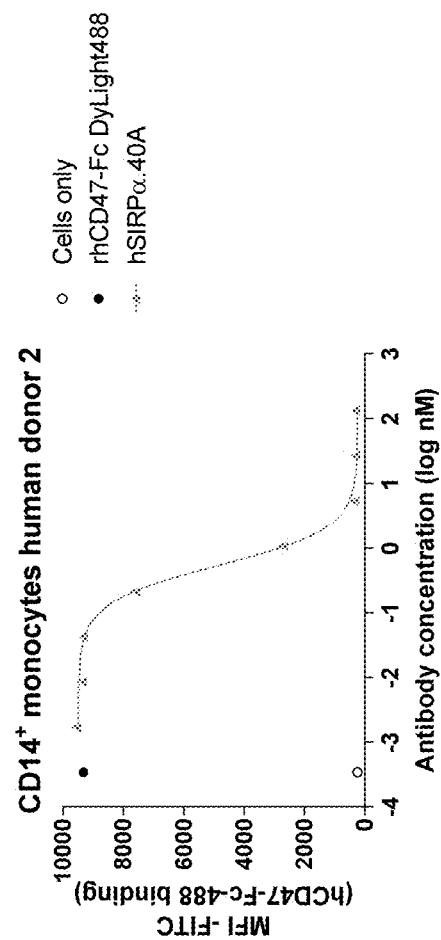
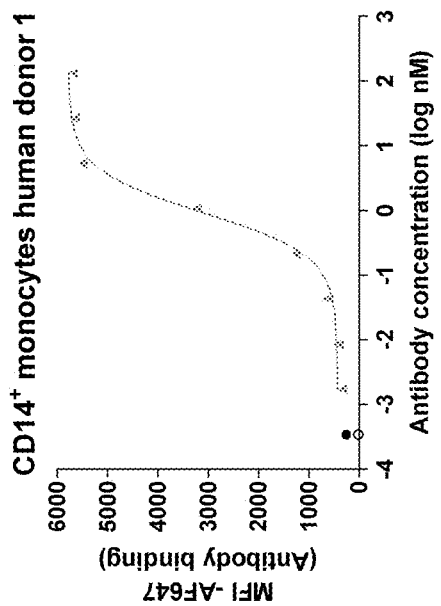
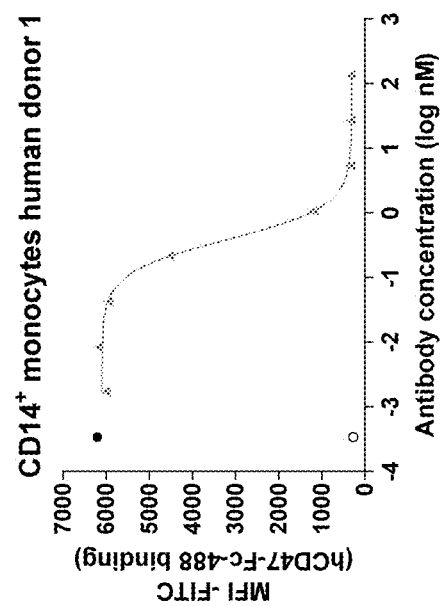

ANTI-SIRPα ANTIBODIES

The present application claims the benefit of Netherlands Patent Application 2018708, filed Apr. 13, 2017, and of Netherlands Patent Application 2019166, filed Jul. 3, 2017, each of which is hereby incorporated by reference in its entirety including all tables, figures, and claims.

REFERENCE TO SEQUENCE LISTING SUBMITTED VIA EFS-WEB

This application includes an electronically submitted sequence listing in .txt format. The .txt file contains a sequence listing entitled "ABE-0007-UT_SeqListing.txt" created on Jul. 17, 2018 and is 237,308 bytes in size. The sequence listing contained in this .txt file is part of the specification and is hereby incorporated by reference herein in its entirety.

FIELD OF THE INVENTION

The present invention relates to anti-SIRPα antibodies, as well as use of these antibodies in the treatment of diseases.

BACKGROUND OF THE INVENTION

Signal regulatory protein alpha (SIRPα) is membrane glycoprotein from the SIRP family. Members of the SIRP family share certain common structural motifs. These include a transmembrane segment and an N-terminal extracellular domain that contains three Ig-like loops connected by three pairs of disulfide bonds. The C-terminal intracellular domain, however, differs between SIRP family members. SIRPα has an extended intracellular domain containing four tyrosine residues that form two immunoreceptor tyrosine-based inhibitory motifs (ITIMs), while SIRPβ1 contains a lysine residue in the transmembrane domain followed by a short intracellular tail lacking ITIMs serving as a receptor for DAP12. Eight SIRPα single nucleotide polymorphisms have been identified, with the most prevalent being SIRPαV1 and SIRPαV2 (Takenaka et al., $Nat.$ $Immunol.$ 2007, 8:1313-23).

"Eat-me" signals (i.e. "altered self") are extracellular players specifically produced by and displayed on the surface of apoptotic cells, but not healthy cells, and are key to the initiation of phagocytosis by activating phagocytic receptors and subsequent signaling cascades. Eat-me signals require extracellular trafficking in order to be displayed on apoptotic cells. A particular category of eat-me signals is provided by membrane-anchored proteins such as phosphatidylserine (PtdSer) and calreticulin (CRT). Externalized PtdSer binds to its receptors on phagocytes to facilitate clearance of apoptotic cells (a process known as efferocytosis). Likewise, CRT is upregulated on the surface of apoptotic cells and binds to LDL-receptor-related protein 1 (LRP1) on the phagocyte thereby mediating engulfment.

SIRPα is broadly expressed on phagocytes (e.g., macrophages, granulocytes, and dendritic cells) and acts as an inhibitory receptor through its interaction with a transmembrane protein CD47. This interaction mediates a response referred to as the "don't eat me" signal. This interaction negatively regulates effector function of innate immune cells such as host cell phagocytosis. As CD47 is often present on tumor cells, this "don't eat me" signal is thought to contribute to the resistance of tumors to phagocyte-dependent clearance. Despite the similarities in the extracellular domains of SIRPα and SIRPβ1 functional differences exist among the SIRP family members. For example, SIRPβ1 does not bind CD47 at detectable levels and so does not mediate the "don't eat me" signal. Instead, SIRPβ1 is involved in the activation of myeloid cells.

Disruption of CD47-SIRPα signalling (e.g., by antagonistic monoclonal antibodies that bind to either CD47 or SIRPα) reportedly results in enhanced phagocytosis of both solid and hematopoietic tumor cells, including increased phagocytosis of glioblastoma cells in vitro and significant anti-tumor activity in vivo.

SUMMARY OF THE INVENTION

In a first aspect, the invention provides anti-SIRPα antibodies and antigen binding fragments thereof comprising the structural and functional features specified below.

In various embodiments, the invention provides an antibody or antigen binding fragment thereof that binds to human SIRPα comprising one, two, or all three of (i), (ii) and (iii): (i) a heavy chain variable region CDR1 comprising the amino acid sequence of SEQ ID NO: 1 or an amino acid sequence differing from SEQ ID NO: 1 by 1, 2, 3, or more conservative substitutions; (ii) a heavy chain variable region CDR2 comprising the amino acid sequence of SEQ ID NO: 2 or an amino acid sequence differing from SEQ ID NO: 2 by 1, 2, 3, or more conservative substitutions; and/or (iii) a heavy chain variable region CDR3 comprising the amino acid sequence of SEQ ID NO: 3 or an amino acid sequence differing from SEQ ID NO: 3 by 1, 2, 3, or more conservative substitutions.

In various other embodiments, the invention provides an antibody or antigen binding fragment thereof that binds to human SIRPα comprising one, two, or all three of (i), (ii) and (iii): (i) a heavy chain variable region CDR1 comprising the amino acid sequence of SEQ ID NO: 69 or an amino acid sequence differing from SEQ ID NO: 1 by 1, 2, 3, or more conservative substitutions; (ii) a heavy chain variable region CDR2 comprising the amino acid sequence of SEQ ID NO: 70 or an amino acid sequence differing from SEQ ID NO: 2 by 1, 2, 3, or more conservative substitutions; and/or (iii) a heavy chain variable region CDR3 comprising the amino acid sequence of SEQ ID NO: 71 or an amino acid sequence differing from SEQ ID NO: 3 by 1, 2, 3, or more conservative substitutions.

In certain embodiments, the antibody or antigen binding fragment thereof comprises a heavy chain variable region comprising an amino acid sequence selected from the group consisting of:

SEQ ID NO: 75 or an amino acid sequence at least 90%, 95%, 97%, 98%, or 99% similar or identical thereto,
SEQ ID NO: 78 or an amino acid sequence at least 90%, 95%, 97%, 98%, or 99% similar or identical thereto,
SEQ ID NO: 80 or an amino acid sequence at least 90%, 95%, 97%, 98%, or 99% similar or identical thereto,
SEQ ID NO: 82 or an amino acid sequence at least 90%, 95%, 97%, 98%, or 99% similar or identical thereto,
SEQ ID NO: 84 or an amino acid sequence at least 90%, 95%, 97%, 98%, or 99% similar or identical thereto,
SEQ ID NO: 86 or an amino acid sequence at least 90%, 95%, 97%, 98%, or 99% similar or identical thereto,
SEQ ID NO: 88 or an amino acid sequence at least 90%, 95%, 97%, 98%, or 99% identical thereto,
SEQ ID NO: 102 or an amino acid sequence at least 90%, 95%, 97%, 98%, or 99% identical thereto,
SEQ ID NO: 7 or an amino acid sequence at least 90%, 95%, 97%, 98%, or 99% similar or identical thereto, SEQ ID NO: 10 or an amino acid sequence at least 90%, 95%, 97%, 98%, or 99% similar or identical thereto, SEQ ID NO: 12 or an amino acid sequence at least 90%, 95%, 97%, 98%, or 99% similar or identical thereto, SEQ ID NO: 14 or an amino acid sequence at least 90%, 95%, 97%, 98%, or 99% similar or identical thereto, SEQ ID NO: 16 or an amino acid sequence at least 90%, 95%, 97%, 98%, or 99% similar or identical thereto, SEQ ID NO: 18 or an amino acid sequence at least 90%, 95%, 97%, 98%, or 99% similar or identical thereto, and SEQ ID NO: 30 or an amino acid sequence at least 90%, 95%, 97%, 98%, or 99% similar or identical thereto.

In various embodiments, the invention also provides an antibody or antigen binding fragment thereof that binds to human SIRPα comprising one, two, or all three of (i), (ii) and (iii): (i) a light chain variable region CDR1 comprising the amino acid sequence of SEQ ID NO: 4 or an amino acid sequence differing from SEQ ID NO: 4 by 1, 2, 3, or more conservative substitutions; (ii) a light chain variable region CDR2 comprising the amino acid sequence of SEQ ID NO: 5 or an amino acid sequence differing from SEQ ID NO: 5 by 1, 2, 3, or more conservative substitutions; and/or (iii) a light chain variable region CDR3 comprising the amino acid sequence of SEQ ID NO: 6 or an amino acid sequence differing from SEQ ID NO: 6 by 1, 2, 3, or more conservative substitutions.

In various other embodiments, the invention also provides an antibody or antigen binding fragment thereof that binds to human SIRPα comprising one, two, or all three of (i), (ii) and (iii): (i) a light chain variable region CDR1 comprising the amino acid sequence of SEQ ID NO: 72 or an amino acid sequence differing from SEQ ID NO: 4 by 1, 2, 3, or more conservative substitutions; (ii) a light chain variable region CDR2 comprising the amino acid sequence of SEQ ID NO: 73 or an amino acid sequence differing from SEQ ID NO: 5 by 1, 2, 3, or more conservative substitutions; and/or (iii) a light chain variable region CDR3 comprising the amino acid sequence of SEQ ID NO: 74 or an amino acid sequence differing from SEQ ID NO: 6 by 1, 2, 3, or more conservative substitutions.

In certain embodiments, the antibody or antigen binding fragment thereof comprises a light chain variable region comprising an amino acid sequence selected from the group consisting of:

SEQ ID NO: 76 or an amino acid sequence at least 90%, 95%, 97%, 98%, or 99% similar or identical thereto, SEQ ID NO: 90 or an amino acid sequence at least 90%, 95%, 97%, 98%, or 99% similar or identical thereto, SEQ ID NO: 92 or an amino acid sequence at least 90%, 95%, 97%, 98%, or 99% similar or identical thereto, SEQ ID NO: 94 or an amino acid sequence at least 90%, 95%, 97%, 98%, or 99% similar or identical thereto, SEQ ID NO: 96 or an amino acid sequence at least 90%, 95%, 97%, 98%, or 99% similar or identical thereto, SEQ ID NO: 98 or an amino acid sequence at least 90%, 95%, 97%, 98%, or 99% similar or identical thereto, SEQ ID NO: 100 or an amino acid sequence at least 90%, 95%, 97%, 98%, or 99% similar or identical thereto, SEQ ID NO: 104 or an amino acid sequence at least 90%, 95%, 97%, 98%, or 99% identical thereto, SEQ ID NO: 8 or an amino acid sequence at least 90%, 95%, 97%, 98%, or 99% similar or identical thereto, SEQ ID NO: 20 or an amino acid sequence at least 90%, 95%, 97%, 98%, or 99% similar or identical thereto, SEQ ID NO: 22 or an amino acid sequence at least 90%, 95%, 97%, 98%, or 99% similar or identical thereto, SEQ ID NO: 24 or an amino acid sequence at least 90%, 95%, 97%, 98%, or 99% similar or identical thereto, SEQ ID NO: 26 or an amino acid sequence at least 90%, 95%, 97%, 98%, or 99% similar or identical thereto, SEQ ID NO: 28 or an amino acid sequence at least 90%, 95%, 97%, 98%, or 99% similar or identical thereto, and SEQ ID NO: 32 or an amino acid sequence at least 90%, 95%, 97%, 98%, or 99% similar or identical thereto.

In various embodiments, the invention provides an antibody or antigen binding fragment thereof that binds to human SIRPα comprising:

(i) a heavy chain variable region CDR1 comprising the amino acid sequence of SEQ ID NO: 1 or an amino acid sequence differing from SEQ ID NO: 1 by 1, 2, 3, or more conservative substitutions; (ii) a heavy chain variable region CDR2 comprising the amino acid sequence of SEQ ID NO: 2 or an amino acid sequence differing from SEQ ID NO: 2 by 1, 2, 3, or more conservative substitutions; and/or (iii) a heavy chain variable region CDR3 comprising the amino acid sequence of SEQ ID NO: 3 or an amino acid sequence differing from SEQ ID NO: 3 by 1, 2, 3, or more conservative substitutions; and (iv) a light chain variable region CDR1 comprising the amino acid sequence of SEQ ID NO: 4 or an amino acid sequence differing from SEQ ID NO: 4 by 1, 2, 3, or more conservative substitutions; (v) a light chain variable region CDR2 comprising the amino acid sequence of SEQ ID NO: 5 or an amino acid sequence differing from SEQ ID NO: 5 by 1, 2, 3, or more conservative substitutions; and/or (vi) a light chain variable region CDR3 comprising the amino acid sequence of SEQ ID NO: 6 or an amino acid sequence differing from SEQ ID NO: 6 by 1, 2, 3, or more conservative substitutions.

In various other embodiments, the invention provides an antibody or antigen binding fragment thereof that binds to human SIRPα comprising:

(i) a heavy chain variable region CDR1 comprising the amino acid sequence of SEQ ID NO: 69 or an amino acid sequence differing from SEQ ID NO: 1 by 1, 2, 3, or more conservative substitutions; (ii) a heavy chain variable region CDR2 comprising the amino acid sequence of SEQ ID NO: 70 or an amino acid sequence differing from SEQ ID NO: 2 by 1, 2, 3, or more conservative substitutions; and/or (iii) a heavy chain variable region CDR3 comprising the amino acid sequence of SEQ ID NO: 71 or an amino acid sequence differing from SEQ ID NO: 3 by 1, 2, 3, or more conservative substitutions; and (iv) a light chain variable region CDR1 comprising the amino acid sequence of SEQ ID NO: 72 or an amino acid sequence differing from SEQ ID NO: 4 by 1, 2, 3, or more conservative substitutions; (v) a light chain variable region CDR2 comprising the amino acid sequence of SEQ ID NO: 73 or an amino acid sequence differing from SEQ ID NO: 5 by 1, 2, 3, or more conservative substitutions; and/or (vi) a light chain variable region CDR3 comprising the amino acid sequence of SEQ ID NO: 6 or an amino acid sequence differing from SEQ ID NO: 74 by 1, 2, 3, or more conservative substitutions.

In still other embodiments, the invention provides an antibody or antigen binding fragment thereof that binds to human SIRPα comprising: a heavy chain variable region comprising an amino acid sequence selected from the group consisting of:

SEQ ID NO: 7 or an amino acid sequence at least 90%, 95%, 97%, 98%, or 99% similar or identical thereto, SEQ ID NO: 10 or an amino acid sequence at least 90%, 95%, 97%, 98%, or 99% similar or identical thereto, SEQ ID NO: 12 or an amino acid sequence at least 90%, 95%, 97%, 98%, or 99% similar or identical thereto, SEQ ID NO: 14 or an amino acid sequence at least 90%, 95%, 97%, 98%, or 99% similar or identical thereto, SEQ ID NO: 16 or an amino acid sequence at least 90%, 95%, 97%, 98%, or 99% similar or identical thereto, SEQ ID NO: 18 or an amino acid sequence at least 90%, 95%, 97%, 98%, or 99% similar or identical thereto, and SEQ ID NO: 30 or an amino acid sequence at least 90%, 95%, 97%, 98%, or 99% similar or identical thereto;

and a light chain variable region comprising an amino acid sequence selected from the group consisting of:

SEQ ID NO: 8 or an amino acid sequence at least 90%, 95%, 97%, 98%, or 99% similar or identical thereto, SEQ ID NO: 20 or an amino acid sequence at least 90%, 95%, 97%, 98%, or 99% similar or identical thereto, SEQ ID NO: 22 or an amino acid sequence at least 90%, 95%, 97%, 98%, or 99% similar or identical thereto, SEQ ID NO: 24 or an amino acid sequence at least 90%, 95%, 97%, 98%, or 99% similar or identical thereto, SEQ ID NO: 26 or an amino acid sequence at least 90%, 95%, 97%, 98%, or 99% similar or identical thereto, and SEQ ID NO: 28 or an amino acid sequence at least 90%, 95%, 97%, 98%, or 99% similar or identical thereto, and SEQ ID NO: 32 or an amino acid sequence at least 90%, 95%, 97%, 98%, or 99% similar or identical thereto.

In still other embodiments, the invention provides an antibody or antigen binding fragment thereof that binds to human SIRPα comprising:

a heavy chain variable region comprising an amino acid sequence selected from the group consisting of:

SEQ ID NO: 75 or an amino acid sequence at least 90%, 95%, 97%, 98%, or 99% similar or identical thereto, SEQ ID NO: 78 or an amino acid sequence at least 90%, 95%, 97%, 98%, or 99% similar or identical thereto, SEQ ID NO: 80 or an amino acid sequence at least 90%, 95%, 97%, 98%, or 99% similar or identical thereto, SEQ ID NO: 82 or an amino acid sequence at least 90%, 95%, 97%, 98%, or 99% similar or identical thereto, SEQ ID NO: 84 or an amino acid sequence at least 90%, 95%, 97%, 98%, or 99% similar or identical thereto, SEQ ID NO: 86 or an amino acid sequence at least 90%, 95%, 97%, 98%, or 99% similar or identical thereto, SEQ ID NO: 88 or an amino acid sequence at least 90%, 95%, 97%, 98%, or 99% similar or identical thereto; and SEQ ID NO: 102 or an amino acid sequence at least 90%, 95%, 97%, 98%, or 99% identical thereto, and a light chain variable region comprising an amino acid sequence selected from the group consisting of:

SEQ ID NO: 76 or an amino acid sequence at least 90%, 95%, 97%, 98%, or 99% similar or identical thereto, SEQ ID NO: 90 or an amino acid sequence at least 90%, 95%, 97%, 98%, or 99% similar or identical thereto, SEQ ID NO: 92 or an amino acid sequence at least 90%, 95%, 97%, 98%, or 99% similar or identical thereto, SEQ ID NO: 94 or an amino acid sequence at least 90%, 95%, 97%, 98%, or 99% similar or identical thereto, SEQ ID NO: 96 or an amino acid sequence at least 90%, 95%, 97%, 98%, or 99% similar or identical thereto, SEQ ID NO: 98 or an amino acid sequence at least 90%, 95%, 97%, 98%, or 99% similar or identical thereto, SEQ ID NO: 100 or an amino acid sequence at least 90%, 95%, 97%, 98%, or 99% similar or identical thereto, and SEQ ID NO: 104 or an amino acid sequence at least 90%, 95%, 97%, 98%, or 99% identical thereto.

In this context, "sequence similarity" is based on the extent of identity combined with the extent of conservative changes. The percentage of "sequence similarity" is the percentage of amino acids or nucleotides which is either identical or conservatively changed viz. "sequence similarity"=percent sequence identity)+percent conservative changes). Thus, for the purpose of this invention "conservative changes" and "identity" are considered to be species of the broader term "similarity". Thus, whenever the term sequence "similarity" is used it embraces sequence "identity" and "conservative changes". According to certain embodiments the conservative changes are disregarded and the percent sequence similarity refers to percent sequence identity. In certain embodiments, the changes in a sequence permitted by the referenced percent sequence identity are all or nearly all conservative changes; that is, when a sequence is 90% identical, the remaining 10% are all or nearly all conservative changes. The term "nearly all" in this context refers to at least 75% of the permitted sequence changes are conservative changes, more preferably at least 85%, still more preferably at least 90%, and most preferably at least 95%. In certain embodiments of antibody heavy and/or light chains, the permitted sequence changes are within the framework regions and not in the CDRs.

Preferably said antibody has a heavy chain according to SEQ ID NO: 7. Further preferably said antibody has a light chain according to SEQ ID NO: 8. More preferably, the heavy chain is chosen from any of SEQ ID NO: 10, 12, 14, 16, 18, or 30. More preferably, the light chain is chosen from any of SEQ ID NO: 20, 22, 24, 26, 28, or 32.

Alternatively, said antibody has a heavy chain according to SEQ ID NO: 75. Further preferably said antibody has a light chain according to SEQ ID NO: 76. More preferably, the heavy chain is chosen from any of SEQ ID NO: 78, 80, 82, 84, 86, 88 or 102. More preferably, the light chain is chosen from any of SEQ ID NO: 90, 92, 94, 96, 98, 100 or 104.

In any of the above embodiments, the antibody or antigen binding fragment thereof may be isolated, as that term is defined herein.

In any of the above embodiments, the antibody or antigen binding fragment thereof is a recombinant antibody, as that term is defined herein.

In any of the above embodiments, the antibody or antigen binding fragment thereof is a full-length antibody, as that term is defined herein.

Antibodies or antigen binding fragments of the present invention may be obtained from a variety of species. For example, the antibodies of the present invention may comprise immunoglobulin sequences which are rabbit, mouse, rat, guinea pig, chicken, goat, sheep, donkey, human, llama or camelid sequences, or combinations of such sequences (so-called chimeric antibodies). Most preferably, the antibodies or antigen binding fragments are human or humanized antibodies or antigen binding fragments.

The term antibody includes antigen-binding portions, i.e., "antigen binding sites," (e.g., fragments, subsequences, complementarity determining regions (CDRs)) that retain capacity to bind antigen, including (i) a Fab fragment, a monovalent fragment consisting of the $V_L$, $V_H$, $C_L$ and $C_H1$ domains; (ii) a F(ab')2 fragment, a bivalent fragment comprising two Fab fragments linked by a disulfide bridge at the hinge region; (iii) a Fd fragment consisting of the $V_H$ and $C_H1$ domains; (iv) a Fv fragment consisting of the $V_L$ and $V_H$ domains of a single arm of an antibody, (v) a dAb fragment (Ward et al., (1989) Nature 341:544-546), which consists of a VH domain; and (vi) an isolated complementarity determining region (CDR). Single chain antibodies are also included by reference in the term "antibody." Preferred therapeutic antibodies are intact IgG antibodies. The term "intact IgG" as used herein is meant as a polypeptide belonging to the class of antibodies that are substantially encoded by a recognized immunoglobulin gamma gene. In humans this class comprises IgG1, IgG2, IgG3, and IgG4. In mice this class comprises IgG1, IgG2a, IgG2b, and IgG3. The known Ig domains in the IgG class of antibodies are $V_H$, Cγ1, Cγ2, Cγ3, $V_L$, and $C_L$.

In any of the above embodiments, the antibody or antigen binding fragment thereof is a human or humanized antibody comprising two heavy chains and two light chains. In one embodiment, the antibody is an IgG. In preferred embodiments, antibody is an IgG1, IgG2, or IgG4, and preferably a human IgG1, IgG2, or IgG4.

In any of the above-mentioned embodiments, the antibody or antigen binding fragment thereof of the invention can comprise any of the light chain variable regions described above and a human kappa or lambda light chain constant domain and an IgG1, IgG2, or IgG4 heavy chain constant domain. Exemplary light (kappa) and heavy (IgG2 and IgG4) constant region sequences which may be used in accordance with the invention are recited in SEQ ID NOs: 63, 65, 67 (each a nucleotide sequence), 64, 66, and 68 (each a polypeptide sequence).

By way of example only, in various embodiments such antibody or antigen binding fragment thereof comprises one of the following combinations of heavy chain sequence/light chain variable region sequences:

SEQ ID NO: 10/SEQ ID NO: 20 (referred to herein as hSIRPα.50A.H1L1)
SEQ ID NO: 10/SEQ ID NO: 22 (referred to herein as hSIRPα.50A.H1L2)
SEQ ID NO: 10/SEQ ID NO: 24 (referred to herein as hSIRPα.50A.H1L3)
SEQ ID NO: 10/SEQ ID NO: 26 (referred to herein as hSIRPα.50A.H1L4)
SEQ ID NO: 10/SEQ ID NO: 28 (referred to herein as hSIRPα.50A.H1L5)
SEQ ID NO: 12/SEQ ID NO: 20 (referred to herein as hSIRPα.50A.H2L1)
SEQ ID NO: 12/SEQ ID NO: 22 (referred to herein as hSIRPα.50A.H2L2)
SEQ ID NO: 12/SEQ ID NO: 24 (referred to herein as hSIRPα.50A.H2L3)
SEQ ID NO: 12/SEQ ID NO: 26 (referred to herein as hSIRPα.50A.H2L4)
SEQ ID NO: 12/SEQ ID NO: 28 (referred to herein as hSIRPα.50A.H2L5)
SEQ ID NO: 14/SEQ ID NO: 20 (referred to herein as hSIRPα.50A.H3L1)
SEQ ID NO: 14/SEQ ID NO: 22 (referred to herein as hSIRPα.50A.H3L2)
SEQ ID NO: 14/SEQ ID NO: 24 (referred to herein as hSIRPα.50A.H3L3)
SEQ ID NO: 14/SEQ ID NO: 26 (referred to herein as hSIRPα.50A.H3L4)
SEQ ID NO: 14/SEQ ID NO: 28 (referred to herein as hSIRPα.50A.H3L5)
SEQ ID NO: 16/SEQ ID NO: 20 (referred to herein as hSIRPα.50A.H4L1)
SEQ ID NO: 16/SEQ ID NO: 22 (referred to herein as hSIRPα.50A.H4L2)
SEQ ID NO: 16/SEQ ID NO: 24 (referred to herein as hSIRPα.50A.H4L3)
SEQ ID NO: 16/SEQ ID NO: 26 (referred to herein as hSIRPα.50A.H4L4)
SEQ ID NO: 16/SEQ ID NO: 28 (referred to herein as hSIRPα.50A.H4L5)
SEQ ID NO: 18/SEQ ID NO: 20 (referred to herein as hSIRPα.50A.H5L1)
SEQ ID NO: 18/SEQ ID NO: 22 (referred to herein as hSIRPα.50A.H5L2)
SEQ ID NO: 18/SEQ ID NO: 24 (referred to herein as hSIRPα.50A.H5L3)
SEQ ID NO: 18/SEQ ID NO: 26 (referred to herein as hSIRPα.50A.H5L4)
SEQ ID NO: 18/SEQ ID NO: 28 (referred to herein as hSIRPα.50A.H5L5)
SEQ ID NO: 78/SEQ ID NO: 90 (referred to herein as hSIRPα.40A.H1L1)
SEQ ID NO: 78/SEQ ID NO: 92 (referred to herein as hSIRPα.40A.H1L2)
SEQ ID NO: 78/SEQ ID NO: 94 (referred to herein as hSIRPα.40A.H1L3)
SEQ ID NO: 78/SEQ ID NO: 96 (referred to herein as hSIRPα.40A.H1L4)
SEQ ID NO: 78/SEQ ID NO: 98 (referred to herein as hSIRPα.40A.H1L5)
SEQ ID NO: 78/SEQ ID NO: 100 (referred to herein as hSIRPα.40A.H1L6)
SEQ ID NO: 80/SEQ ID NO: 90 (referred to herein as hSIRPα.40A.H2L1)
SEQ ID NO: 80/SEQ ID NO: 92 (referred to herein as hSIRPα.40A.H2L2)
SEQ ID NO: 80/SEQ ID NO: 94 (referred to herein as hSIRPα.40A.H2L3)
SEQ ID NO: 80/SEQ ID NO: 96 (referred to herein as hSIRPα.40A.H2L4)
SEQ ID NO: 80/SEQ ID NO: 98 (referred to herein as hSIRPα.40A.H2L5)
SEQ ID NO: 80/SEQ ID NO: 100 (referred to herein as hSIRPα.40A.H2L6)
SEQ ID NO: 82/SEQ ID NO: 90 (referred to herein as hSIRPα.40A.H3L1)

SEQ ID NO: 82/SEQ ID NO: 92 (referred to herein as hSIRPα.40A.H3L2)
SEQ ID NO: 82/SEQ ID NO: 94 (referred to herein as hSIRPα.40A.H3L3)
SEQ ID NO: 82/SEQ ID NO: 96 (referred to herein as hSIRPα.40A.H3L4)
SEQ ID NO: 82/SEQ ID NO: 98 (referred to herein as hSIRPα.40A.H3L5)
SEQ ID NO: 82/SEQ ID NO: 100 (referred to herein as hSIRPα.40A.H3L6)
SEQ ID NO: 84/SEQ ID NO: 90 (referred to herein as hSIRPα.40A.H4L1)
SEQ ID NO: 84/SEQ ID NO: 92 (referred to herein as hSIRPα.40A.H4L2)
SEQ ID NO: 84/SEQ ID NO: 94 (referred to herein as hSIRPα.40A.H4L3)
SEQ ID NO: 84/SEQ ID NO: 96 (referred to herein as hSIRPα.40A.H4L4)
SEQ ID NO: 84/SEQ ID NO: 98 (referred to herein as hSIRPα.40A.H4L5)
SEQ ID NO: 84/SEQ ID NO: 100 (referred to herein as hSIRPα.40A.H4L6)
SEQ ID NO: 86/SEQ ID NO: 90 (referred to herein as hSIRPα.40A.H5L1)
SEQ ID NO: 86/SEQ ID NO: 92 (referred to herein as hSIRPα.40A.H5L2)
SEQ ID NO: 86/SEQ ID NO: 94 (referred to herein as hSIRPα.40A.H5L3)
SEQ ID NO: 86/SEQ ID NO: 96 (referred to herein as hSIRPα.40A.H5L4)
SEQ ID NO: 86/SEQ ID NO: 98 (referred to herein as hSIRPα.40A.H5L5)
SEQ ID NO: 86/SEQ ID NO: 100 (referred to herein as hSIRPα.40A.H5L6)
SEQ ID NO: 88/SEQ ID NO: 90 (referred to herein as hSIRPα.40A.H6L1)
SEQ ID NO: 88/SEQ ID NO: 92 (referred to herein as hSIRPα.40A.H6L2)
SEQ ID NO: 88/SEQ ID NO: 94 (referred to herein as hSIRPα.40A.H6L3)
SEQ ID NO: 88/SEQ ID NO: 96 (referred to herein as hSIRPα.40A.H6L4)
SEQ ID NO: 88/SEQ ID NO: 98 (referred to herein as hSIRPα.40A.H6L5)
SEQ ID NO: 88/SEQ ID NO: 100 (referred to herein as hSIRPα.40A.H6L6)
or, in each case, at least 90%, 95%, 97%, 98%, or 99% similar or identical to a respective SEQ ID NO.

In some preferred embodiments, the antibody or antigen binding fragment is a humanized antibody that comprises two heavy chains and two light chains, wherein each heavy chain comprises SEQ ID NO: 10 and each light chain comprises SEQ ID NO: 20, or, in each case, at least 90%, 95%, 97%, 98%, or 99% similar or identical to a respective SEQ ID NO, and most preferably each light chain comprises a human kappa light chain or a human lambda light chain constant domain; and each heavy chain comprises a human IgG1, IgG2, or IgG4 constant region.

In other preferred embodiments, the antibody or antigen binding fragment is a humanized antibody that comprises two heavy chains and two light chains, wherein each heavy chain comprises SEQ ID NO: 16 and each light chain comprises SEQ ID NO: 28, or, in each case, at least 90%, 95%, 97%, 98%, or 99% similar or identical to a respective SEQ ID NO, and most preferably each light chain comprises a human kappa light chain or a human lambda light chain constant domain; and each heavy chain comprises a human IgG1, IgG2, or IgG4 constant region.

In still other preferred embodiments, the antibody or antigen binding fragment is a humanized antibody that comprises two heavy chains and two light chains, wherein each heavy chain comprises SEQ ID NO: 18 and each light chain comprises SEQ ID NO: 20, or, in each case, at least 90%, 95%, 97%, 98%, or 99% similar or identical to a respective SEQ ID NO, and most preferably each light chain comprises a human kappa light chain or a human lambda light chain constant domain; and each heavy chain comprises a human IgG1, IgG2, or IgG4 constant region.

In some preferred embodiments, the antibody or antigen binding fragment is a humanized antibody that comprises two heavy chains and two light chains, wherein each heavy chain comprises SEQ ID NO: 80 and each light chain comprises SEQ ID NO: 90, or, in each case, at least 90%, 95%, 97%, 98%, or 99% similar or identical to a respective SEQ ID NO, and most preferably each light chain comprises a human kappa light chain or a human lambda light chain constant domain; and each heavy chain comprises a human IgG1, IgG2, or IgG4 constant region.

In some preferred embodiments, the antibody or antigen binding fragment is a humanized antibody that comprises two heavy chains and two light chains, wherein each heavy chain comprises SEQ ID NO: 80 and each light chain comprises SEQ ID NO: 92, or, in each case, at least 90%, 95%, 97%, 98%, or 99% similar or identical to a respective SEQ ID NO, and most preferably each light chain comprises a human kappa light chain or a human lambda light chain constant domain; and each heavy chain comprises a human IgG1, IgG2, or IgG4 constant region.

In some preferred embodiments, the antibody or antigen binding fragment is a humanized antibody that comprises two heavy chains and two light chains, wherein each heavy chain comprises SEQ ID NO: 80 and each light chain comprises SEQ ID NO: 96, or, in each case, at least 90%, 95%, 97%, 98%, or 99% similar or identical to a respective SEQ ID NO, and most preferably each light chain comprises a human kappa light chain or a human lambda light chain constant domain; and each heavy chain comprises a human IgG1, IgG2, or IgG4 constant region.

In one embodiment, the anti-SIRPα antibody of the invention comprises a full length antibody structure having two light chains and two heavy chains as recited above, wherein each light chain comprises a human kappa light chain or a human lambda light chain constant domain; and each heavy chain comprises a human IgG1 constant region.

In one embodiment, the anti-SIRPα antibody of the invention comprises a full length antibody structure having two light chains and two heavy chains as recited above, wherein each light chain comprises a human kappa light chain or a human lambda light chain constant domain; and each heavy chain comprises a human IgG2 constant region.

In one embodiment, the anti-SIRPα antibody of the invention comprises a full-length antibody structure having two light chains and two heavy chains as recited above, wherein each light chain comprises a human kappa light chain or a human lambda light chain constant domain; and each heavy chain comprises a human IgG4 constant region.

In certain embodiments, the antibodies or antigen binding fragments of the present invention have one, two, three, four, or more, and preferably each of, the following functional characteristics:
  binds human SIRPαV1 protein having the sequence of SEQ ID NO: 34 with an $EC_{50}<1$ nM; and exhibits at least a 100-fold higher $EC_{50}$ for SIRPαV1(P74A) having the sequence of SEQ ID NO: 62; and optionally also at least a 100-fold higher $EC_{50}$ for human SIRPβ1 protein having the sequence of SEQ ID NO: 38 (in each case wherein the reduced $EC_{50}$ is relative to the $EC_{50}$ for human SIRPαV1 protein having the sequence of SEQ ID NO: 34, and in each case preferably when measured by cellular ELISA (CELISA) as described hereinafter;

binds to a cell expressing human SIRPαV1 protein with an $EC_{50}$<10 nM, preferably <5 nM, more preferably <1.5 nM, still more preferably <1.0 nM, even more preferably <0.5 nM, and most preferably about 0.3 nM or less;

binds to a cell expressing human SIRPαV2 protein with an $EC_{50}$<10 nM, preferably <5 nM, more preferably <1.5 nM, still more preferably <1.0 nM, even more preferably <0.5 nM, and most preferably about 0.3 nM or less;

does not appreciably bind to SIRPβ1 protein at an antibody concentration of 50 nM, preferably 67 nM, and more preferably 100 nM; or alternatively at a concentration that is 10-fold greater, preferably 50-fold greater, more preferably 100-fold greater, and still more preferably 200-fold greater than the antibody's $EC_{50}$ for SIRPαV1 or SIRPαV2;

inhibits binding between human SIRPα and CD47 with an $IC_{50}$<10.0 nM, more preferably <5.0 nM, still more preferably <2.5 nM, and most preferably about 1.0 nM or less; and exhibits a T20 "humanness" score of at least 79, and more preferably 85.

Preferably, the anti-SIRPα antibodies or antigen binding fragments of the invention do not appreciably bind to one or both of SIRPαV1(P74A) and SIRPβ1 protein at an antibody concentration of 100 nM or alternatively at an antibody concentration that is 200-fold greater than the antibody's $EC_{50}$ for SIRPαV1 or SIRPαV2, while binding to a cell expressing human SIRPαV1 protein with an EC50<10 nM. Most preferably, each light chain comprises a human kappa light chain or a human lambda light chain constant domain; and each heavy chain comprises a human IgG1, IgG2, or IgG4 constant region.

In certain embodiments, the anti-SIRPα antibody or antigen binding fragment thereof of the invention can be conjugated to at least one therapeutic agent. In one embodiment, the therapeutic agent is a second antibody or fragment thereof, an immunomodulator, a hormone, a cytotoxic agent, an enzyme, a radionuclide, or a second antibody conjugated to at least one immunomodulator, enzyme, radioactive label, hormone, antisense oligonucleotide, or cytotoxic agent, or a combination thereof.

The invention also provides isolated polypeptides comprising the amino acid sequence of any one of SEQ ID NOs: 75, 78, 80, 82, 84, 86, 88, 76, 90, 92, 94, 96, 98, 100, 102, 104, 7, 10, 12, 14, 16, 18, 30, 8, 20, 22, 24, 26, 28, and 32 or a fragment of any said sequences, or an amino acid sequence at least 90%, 95%, 97%, 98%, or 99% identical thereto.

The invention also provides isolated nucleic acids encoding anyone of the anti-SIRPα antibodies or antigen binding fragments of the invention.

In one embodiment, the invention provides an isolated nucleic acid which encodes an amino acid sequence selected from the group consisting of:

SEQ ID NO: 75 or an amino acid sequence at least 90%, 95%, 97%, 98%, or 99% similar or identical thereto, SEQ ID NO: 78 or an amino acid sequence at least 90%, 95%, 97%, 98%, or 99% similar or identical thereto, SEQ ID NO: 80 or an amino acid sequence at least 90%, 95%, 97%, 98%, or 99% similar or identical thereto, SEQ ID NO: 82 or an amino acid sequence at least 90%, 95%, 97%, 98%, or 99% similar or identical thereto, SEQ ID NO: 84 or an amino acid sequence at least 90%, 95%, 97%, 98%, or 99% similar or identical thereto, SEQ ID NO: 86 or an amino acid sequence at least 90%, 95%, 97%, 98%, or 99% similar or identical thereto, SEQ ID NO: 88 or an amino acid sequence at least 90%, 95%, 97%, 98%, or 99% similar or identical thereto, SEQ ID NO: 102 or an amino acid sequence at least 90%, 95%, 97%, 98%, or 99% similar or identical thereto, SEQ ID NO: 10 or an amino acid sequence at least 90%, 95%, 97%, 98%, or 99% similar or identical thereto, SEQ ID NO: 12 or an amino acid sequence at least 90%, 95%, 97%, 98%, or 99% similar or identical thereto, SEQ ID NO: 14 or an amino acid sequence at least 90%, 95%, 97%, 98%, or 99% similar or identical thereto, SEQ ID NO: 16 or an amino acid sequence at least 90%, 95%, 97%, 98%, or 99% similar or identical thereto, SEQ ID NO: 18 or an amino acid sequence at least 90%, 95%, 97%, 98%, or 99% similar or identical thereto, and SEQ ID NO: 30 or an amino acid sequence at least 90%, 95%, 97%, 98%, or 99% similar or identical thereto.

In certain embodiments, the amino acid sequence of SEQ ID NO: 10 or an amino acid sequence at least 90%, 95%, 97%, 98%, or 99% similar or identical thereto is encoded by a nucleic acid sequence of SEQ ID NO: 9 or a nucleic acid sequence at least 90%, 95%, 97%, 98%, or 99% identical thereto.

In certain embodiments, the amino acid sequence of SEQ ID NO: 12 or an amino acid sequence at least 90%, 95%, 97%, 98%, or 99% similar or identical thereto is encoded by a nucleic acid sequence of SEQ ID NO: 11 or a nucleic acid sequence at least 90%, 95%, 97%, 98%, or 99% identical thereto.

In certain embodiments, the amino acid sequence of SEQ ID NO: 14 or an amino acid sequence at least 90%, 95%, 97%, 98%, or 99% similar or identical thereto is encoded by a nucleic acid sequence of SEQ ID NO: 13 or a nucleic acid sequence at least 90%, 95%, 97%, 98%, or 99% identical thereto.

In certain embodiments, the amino acid sequence of SEQ ID NO: 16 or an amino acid sequence at least 90%, 95%, 97%, 98%, or 99% similar or identical thereto is encoded by a nucleic acid sequence of SEQ ID NO: 15 or a nucleic acid sequence at least 90%, 95%, 97%, 98%, or 99% identical thereto.

In certain embodiments, the amino acid sequence of SEQ ID NO: 18 or an amino acid sequence at least 90%, 95%, 97%, 98%, or 99% similar or identical thereto is encoded by a nucleic acid sequence of SEQ ID NO: 17 or a nucleic acid sequence at least 90%, 95%, 97%, 98%, or 99% identical thereto.

In certain embodiments, the amino acid sequence of SEQ ID NO: 30 or an amino acid sequence at least 90%, 95%, 97%, 98%, or 99% similar or identical thereto is encoded by a nucleic acid sequence of SEQ ID NO: 29 or a nucleic acid sequence at least 90%, 95%, 97%, 98%, or 99% identical thereto.

In certain embodiments, the amino acid sequence of SEQ ID NO: 78 or an amino acid sequence at least 90%, 95%, 97%, 98%, or 99% similar or identical thereto is encoded by a nucleic acid sequence of SEQ ID NO: 77 or a nucleic acid sequence at least 90%, 95%, 97%, 98%, or 99% identical thereto.

In certain embodiments, the amino acid sequence of SEQ ID NO: 80 or an amino acid sequence at least 90%, 95%, 97%, 98%, or 99% similar or identical thereto is encoded by a nucleic acid sequence of SEQ ID NO: 79 or a nucleic acid sequence at least 90%, 95%, 97%, 98%, or 99% identical thereto.

In certain embodiments, the amino acid sequence of SEQ ID NO: 82 or an amino acid sequence at least 90%, 95%, 97%, 98%, or 99% similar or identical thereto is encoded by a nucleic acid sequence of SEQ ID NO: 81 or a nucleic acid sequence at least 90%, 95%, 97%, 98%, or 99% identical thereto.

In certain embodiments, the amino acid sequence of SEQ ID NO: 84 or an amino acid sequence at least 90%, 95%, 97%, 98%, or 99% similar or identical thereto is encoded by a nucleic acid sequence of SEQ ID NO: 83 or a nucleic acid sequence at least 90%, 95%, 97%, 98%, or 99% identical thereto.

In certain embodiments, the amino acid sequence of SEQ ID NO: 86 or an amino acid sequence at least 90%, 95%, 97%, 98%, or 99% similar or identical thereto is encoded by a nucleic acid sequence of SEQ ID NO: 85 or a nucleic acid sequence at least 90%, 95%, 97%, 98%, or 99% identical thereto.

In certain embodiments, the amino acid sequence of SEQ ID NO: 88 or an amino acid sequence at least 90%, 95%, 97%, 98%, or 99% similar or identical thereto is encoded by a nucleic acid sequence of SEQ ID NO: 87 or a nucleic acid sequence at least 90%, 95%, 97%, 98%, or 99% identical thereto.

In certain embodiments, the amino acid sequence of SEQ ID NO: 102 or an amino acid sequence at least 90%, 95%, 97%, 98%, or 99% similar or identical thereto is encoded by a nucleic acid sequence of SEQ ID NO: 101 or a nucleic acid sequence at least 90%, 95%, 97%, 98%, or 99% identical thereto.

In one embodiment, the invention provides an isolated nucleic acid which encodes an amino acid sequence selected from the group consisting of:
SEQ ID NO: 76 or an amino acid sequence at least 90%, 95%, 97%, 98%, or 99% similar or identical thereto,
SEQ ID NO: 90 or an amino acid sequence at least 90%, 95%, 97%, 98%, or 99% similar or identical thereto,
SEQ ID NO: 92 or an amino acid sequence at least 90%, 95%, 97%, 98%, or 99% similar or identical thereto,
SEQ ID NO: 94 or an amino acid sequence at least 90%, 95%, 97%, 98%, or 99% similar or identical thereto,
SEQ ID NO: 96 or an amino acid sequence at least 90%, 95%, 97%, 98%, or 99% similar or identical thereto,
SEQ ID NO: 98 or an amino acid sequence at least 90%, 95%, 97%, 98%, or 99% similar or identical thereto,
SEQ ID NO: 100 or an amino acid sequence at least 90%, 95%, 97%, 98%, or 99% similar or identical thereto,
SEQ ID NO: 104 or an amino acid sequence at least 90%, 95%, 97%, 98%, or 99% similar or identical thereto,
SEQ ID NO: 8 or an amino acid sequence at least 90%, 95%, 97%, 98%, or 99% similar or identical thereto,
SEQ ID NO: 20 or an amino acid sequence at least 90%, 95%, 97%, 98%, or 99% similar or identical thereto,
SEQ ID NO: 22 or an amino acid sequence at least 90%, 95%, 97%, 98%, or 99% similar or identical thereto,
SEQ ID NO: 24 or an amino acid sequence at least 90%, 95%, 97%, 98%, or 99% similar or identical thereto,
SEQ ID NO: 26 or an amino acid sequence at least 90%, 95%, 97%, 98%, or 99% similar or identical thereto,
SEQ ID NO: 28 or an amino acid sequence at least 90%, 95%, 97%, 98%, or 99% similar or identical thereto, and
SEQ ID NO: 32 or an amino acid sequence at least 90%, 95%, 97%, 98%, or 99% similar or identical thereto.

In certain embodiments, the amino acid sequence of SEQ ID NO: 20 or an amino acid sequence at least 90%, 95%, 97%, 98%, or 99% similar or identical thereto is encoded by a nucleic acid sequence of SEQ ID NO: 19 or a nucleic acid sequence at least 90%, 95%, 97%, 98%, or 99% identical thereto.

In certain embodiments, the amino acid sequence of SEQ ID NO: 22 or an amino acid sequence at least 90%, 95%, 97%, 98%, or 99% similar or identical thereto is encoded by a nucleic acid sequence of SEQ ID NO: 21 or a nucleic acid sequence at least 90%, 95%, 97%, 98%, or 99% identical thereto.

In certain embodiments, the amino acid sequence of SEQ ID NO: 24 or an amino acid sequence at least 90%, 95%, 97%, 98%, or 99% similar or identical thereto is encoded by a nucleic acid sequence of SEQ ID NO: 23 or a nucleic acid sequence at least 90%, 95%, 97%, 98%, or 99% identical thereto.

In certain embodiments, the amino acid sequence of SEQ ID NO: 26 or an amino acid sequence at least 90%, 95%, 97%, 98%, or 99% similar or identical thereto is encoded by a nucleic acid sequence of SEQ ID NO: 25 or a nucleic acid sequence at least 90%, 95%, 97%, 98%, or 99% identical thereto.

In certain embodiments, the amino acid sequence of SEQ ID NO: 28 or an amino acid sequence at least 90%, 95%, 97%, 98%, or 99% similar or identical thereto is encoded by a nucleic acid sequence of SEQ ID NO: 27 or a nucleic acid sequence at least 90%, 95%, 97%, 98%, or 99% identical thereto.

In certain embodiments, the amino acid sequence of SEQ ID NO: 32 or an amino acid sequence at least 90%, 95%, 97%, 98%, or 99% similar or identical thereto is encoded by a nucleic acid sequence of SEQ ID NO: 31 or a nucleic acid sequence at least 90%, 95%, 97%, 98%, or 99% identical thereto.

In certain embodiments, the amino acid sequence of SEQ ID NO: 90 or an amino acid sequence at least 90%, 95%, 97%, 98%, or 99% similar or identical thereto is encoded by a nucleic acid sequence of SEQ ID NO: 89 or a nucleic acid sequence at least 90%, 95%, 97%, 98%, or 99% identical thereto.

In certain embodiments, the amino acid sequence of SEQ ID NO: 92 or an amino acid sequence at least 90%, 95%, 97%, 98%, or 99% similar or identical thereto is encoded by a nucleic acid sequence of SEQ ID NO: 91 or a nucleic acid sequence at least 90%, 95%, 97%, 98%, or 99% identical thereto.

In certain embodiments, the amino acid sequence of SEQ ID NO: 94 or an amino acid sequence at least 90%, 95%, 97%, 98%, or 99% similar or identical thereto is encoded by a nucleic acid sequence of SEQ ID NO: 93 or a nucleic acid sequence at least 90%, 95%, 97%, 98%, or 99% identical thereto.

In certain embodiments, the amino acid sequence of SEQ ID NO: 96 or an amino acid sequence at least 90%, 95%, 97%, 98%, or 99% similar or identical thereto is encoded by a nucleic acid sequence of SEQ ID NO: 95 or a nucleic acid sequence at least 90%, 95%, 97%, 98%, or 99% identical thereto.

In certain embodiments, the amino acid sequence of SEQ ID NO: 98 or an amino acid sequence at least 90%, 95%, 97%, 98%, or 99% similar or identical thereto is encoded by a nucleic acid sequence of SEQ ID NO: 97 or a nucleic acid sequence at least 90%, 95%, 97%, 98%, or 99% identical thereto.

In certain embodiments, the amino acid sequence of SEQ ID NO: 100 or an amino acid sequence at least 90%, 95%, 97%, 98%, or 99% similar or identical thereto is encoded by a nucleic acid sequence of SEQ ID NO: 99 or a nucleic acid sequence at least 90%, 95%, 97%, 98%, or 99% identical thereto.

In certain embodiments, the amino acid sequence of SEQ ID NO: 104 or an amino acid sequence at least 90%, 95%, 97%, 98%, or 99% similar or identical thereto is encoded by a nucleic acid sequence of SEQ ID NO: 103 or a nucleic acid sequence at least 90%, 95%, 97%, 98%, or 99% identical thereto.

In certain embodiments, the isolated nucleic acids of the present invention can optionally comprise a leader sequence.

Such nucleic acids can comprise one or more of the following nucleic acid sequences:

- a nucleic acid sequence of SEQ ID NO: 77 or a nucleic acid sequence at least 90%, 95%, 97%, 98%, or 99% identical thereto,
- a nucleic acid sequence of SEQ ID NO: 79 or a nucleic acid sequence at least 90%, 95%, 97%, 98%, or 99% identical thereto,
- a nucleic acid sequence of SEQ ID NO: 81 or a nucleic acid sequence at least 90%, 95%, 97%, 98%, or 99% identical thereto,
- a nucleic acid sequence of SEQ ID NO: 83 or a nucleic acid sequence at least 90%, 95%, 97%, 98%, or 99% identical thereto,
- a nucleic acid sequence of SEQ ID NO: 85 or a nucleic acid sequence at least 90%, 95%, 97%, 98%, or 99% identical thereto,
- a nucleic acid sequence of SEQ ID NO: 87 or a nucleic acid sequence at least 90%, 95%, 97%, 98%, or 99% identical thereto,
- a nucleic acid sequence of SEQ ID NO: 101 or a nucleic acid sequence at least 90%, 95%, 97%, 98%, or 99% identical thereto,
- a nucleic acid sequence of SEQ ID NO: 89 or a nucleic acid sequence at least 90%, 95%, 97%, 98%, or 99% identical thereto,
- a nucleic acid sequence of SEQ ID NO: 91 or a nucleic acid sequence at least 90%, 95%, 97%, 98%, or 99% identical thereto,
- a nucleic acid sequence of SEQ ID NO: 93 or a nucleic acid sequence at least 90%, 95%, 97%, 98%, or 99% identical thereto,
- a nucleic acid sequence of SEQ ID NO: 95 or a nucleic acid sequence at least 90%, 95%, 97%, 98%, or 99% identical thereto,
- a nucleic acid sequence of SEQ ID NO: 97 or a nucleic acid sequence at least 90%, 95%, 97%, 98%, or 99% identical thereto,
- a nucleic acid sequence of SEQ ID NO: 99 or a nucleic acid sequence at least 90%, 95%, 97%, 98%, or 99% identical thereto,
- a nucleic acid sequence of SEQ ID NO: 101 or a nucleic acid sequence at least 90%, 95%, 97%, 98%, or 99% identical thereto,
- a nucleic acid sequence of SEQ ID NO: 103 or a nucleic acid sequence at least 90%, 95%, 97%, 98%, or 99% identical thereto,
- a nucleic acid sequence of SEQ ID NO: 9 or a nucleic acid sequence at least 90%, 95%, 97%, 98%, or 99% identical thereto,
- a nucleic acid sequence of SEQ ID NO: 11 or a nucleic acid sequence at least 90%, 95%, 97%, 98%, or 99% identical thereto,
- a nucleic acid sequence of SEQ ID NO: 13 or a nucleic acid sequence at least 90%, 95%, 97%, 98%, or 99% identical thereto,
- a nucleic acid sequence of SEQ ID NO: 15 or a nucleic acid sequence at least 90%, 95%, 97%, 98%, or 99% identical thereto,
- a nucleic acid sequence of SEQ ID NO: 17 or a nucleic acid sequence at least 90%, 95%, 97%, 98%, or 99% identical thereto,
- a nucleic acid sequence of SEQ ID NO: 29 or a nucleic acid sequence at least 90%, 95%, 97%, 98%, or 99% identical thereto,
- a nucleic acid sequence of SEQ ID NO: 19 or a nucleic acid sequence at least 90%, 95%, 97%, 98%, or 99% identical thereto,
- a nucleic acid sequence of SEQ ID NO: 21 or a nucleic acid sequence at least 90%, 95%, 97%, 98%, or 99% identical thereto,
- a nucleic acid sequence of SEQ ID NO: 23 or a nucleic acid sequence at least 90%, 95%, 97%, 98%, or 99% identical thereto,
- a nucleic acid sequence of SEQ ID NO: 25 or a nucleic acid sequence at least 90%, 95%, 97%, 98%, or 99% identical thereto,
- a nucleic acid sequence of SEQ ID NO: 27 or a nucleic acid sequence at least 90%, 95%, 97%, 98%, or 99% identical thereto, and/or
- a nucleic acid sequence of SEQ ID NO: 31 or a nucleic acid sequence at least 90%, 95%, 97%, 98%, or 99% identical thereto.

In certain embodiments, the nucleic acid can encode a human or humanized antibody, and includes nucleic acid sequences for both heavy and light chains. In one embodiment, the antibody is an IgG. In preferred embodiments, antibody is an IgG1, IgG2, or IgG4, and preferably a human IgG1, IgG2, or IgG4. In certain embodiments, the light chain sequence comprises a human kappa light chain or a human lambda light chain constant domain sequence; and each heavy chain sequence comprises a human IgG1, IgG2, or IgG4 constant region sequence.

Preferably, such nucleic acids comprise the following combination heavy chain and light chain variable region nucleic acid sequences:

SEQ ID NO: 9/SEQ ID NO: 19 (referred to herein as hSIRPα.50A.H1L1)

SEQ ID NO: 9/SEQ ID NO: 21 (referred to herein as hSIRPα.50A.H1L2)

SEQ ID NO: 9/SEQ ID NO: 23 (referred to herein as hSIRPα.50A.H1L3)

SEQ ID NO: 9/SEQ ID NO: 25 (referred to herein as hSIRPα.50A.H1L4)

SEQ ID NO: 9/SEQ ID NO: 27 (referred to herein as hSIRPα.50A.H1L5)

SEQ ID NO: 11/SEQ ID NO: 19 (referred to herein as hSIRPα.50A.H2L1)

SEQ ID NO: 11/SEQ ID NO: 21 (referred to herein as hSIRPα.50A.H2L2)

SEQ ID NO: 11/SEQ ID NO: 23 (referred to herein as hSIRPα.50A.H2L3)

SEQ ID NO: 11/SEQ ID NO: 25 (referred to herein as hSIRPα.50A.H2L4)

SEQ ID NO: 11/SEQ ID NO: 27 (referred to herein as hSIRPα.50A.H2L5)
SEQ ID NO: 13/SEQ ID NO: 19 (referred to herein as hSIRPα.50A.H3L1)
SEQ ID NO: 13/SEQ ID NO: 21 (referred to herein as hSIRPα.50A.H3L2)
SEQ ID NO: 13/SEQ ID NO: 23 (referred to herein as hSIRPα.50A.H3L3)
SEQ ID NO: 13/SEQ ID NO: 25 (referred to herein as hSIRPα.50A.H3L4)
SEQ ID NO: 13/SEQ ID NO: 27 (referred to herein as hSIRPα.50A.H3L5)
SEQ ID NO: 15/SEQ ID NO: 19 (referred to herein as hSIRPα.50A.H4L1)
SEQ ID NO: 15/SEQ ID NO: 21 (referred to herein as hSIRPα.50A.H4L2)
SEQ ID NO: 15/SEQ ID NO: 23 (referred to herein as hSIRPα.50A.H4L3)
SEQ ID NO: 15/SEQ ID NO: 25 (referred to herein as hSIRPα.50A.H4L4)
SEQ ID NO: 15/SEQ ID NO: 27 (referred to herein as hSIRPα.50A.H4L5)
SEQ ID NO: 17/SEQ ID NO: 19 (referred to herein as hSIRPα.50A.H5L1)
SEQ ID NO: 17/SEQ ID NO: 21 (referred to herein as hSIRPα.50A.H5L2)
SEQ ID NO: 17/SEQ ID NO: 23 (referred to herein as hSIRPα.50A.H5L3)
SEQ ID NO: 17/SEQ ID NO: 25 (referred to herein as hSIRPα.50A.H5L4)
SEQ ID NO: 17/SEQ ID NO: 27 (referred to herein as hSIRPα.50A.H5L5)
SEQ ID NO: 77/SEQ ID NO: 89 (referred to herein as hSIRPα.40A.H1L1)
SEQ ID NO: 77/SEQ ID NO: 91 (referred to herein as hSIRPα.40A.H1L2)
SEQ ID NO: 77/SEQ ID NO: 93 (referred to herein as hSIRPα.40A.H1L3)
SEQ ID NO: 77/SEQ ID NO: 95 (referred to herein as hSIRPα.40A.H1L4)
SEQ ID NO: 77/SEQ ID NO: 97 (referred to herein as hSIRPα.40A.H1L5)
SEQ ID NO: 77/SEQ ID NO: 99 (referred to herein as hSIRPα.40A.H1L6)
SEQ ID NO: 79/SEQ ID NO: 89 (referred to herein as hSIRPα.40A.H2L1)
SEQ ID NO: 79/SEQ ID NO: 91 (referred to herein as hSIRPα.40A.H2L2)
SEQ ID NO: 79/SEQ ID NO: 93 (referred to herein as hSIRPα.40A.H2L3)
SEQ ID NO: 79/SEQ ID NO: 95 (referred to herein as hSIRPα.40A.H2L4)
SEQ ID NO: 79/SEQ ID NO: 97 (referred to herein as hSIRPα.40A.H2L5)
SEQ ID NO: 79/SEQ ID NO: 99 (referred to herein as hSIRPα.40A.H2L6)
SEQ ID NO: 81/SEQ ID NO: 89 (referred to herein as hSIRPα.40A.H3L1)
SEQ ID NO: 81/SEQ ID NO: 91 (referred to herein as hSIRPα.40A.H3L2)
SEQ ID NO: 81/SEQ ID NO: 93 (referred to herein as hSIRPα.40A.H3L3)
SEQ ID NO: 81/SEQ ID NO: 95 (referred to herein as hSIRPα.40A.H3L4)
SEQ ID NO: 81/SEQ ID NO: 97 (referred to herein as hSIRPα.40A.H3L5)
SEQ ID NO: 81/SEQ ID NO: 99 (referred to herein as hSIRPα.40A.H3L6)
SEQ ID NO: 83/SEQ ID NO: 89 (referred to herein as hSIRPα.40A.H4L1)
SEQ ID NO: 83/SEQ ID NO: 91 (referred to herein as hSIRPα.40A.H4L2)
SEQ ID NO: 83/SEQ ID NO: 93 (referred to herein as hSIRPα.40A.H4L3)
SEQ ID NO: 83/SEQ ID NO: 95 (referred to herein as hSIRPα.40A.H4L4)
SEQ ID NO: 83/SEQ ID NO: 97 (referred to herein as hSIRPα.40A.H4L5)
SEQ ID NO: 83/SEQ ID NO: 99 (referred to herein as hSIRPα.40A.H4L6)
SEQ ID NO: 85/SEQ ID NO: 89 (referred to herein as hSIRPα.40A.H5L1)
SEQ ID NO: 85/SEQ ID NO: 91 (referred to herein as hSIRPα.40A.H5L2)
SEQ ID NO: 85/SEQ ID NO: 93 (referred to herein as hSIRPα.40A.H5L3)
SEQ ID NO: 85/SEQ ID NO: 95 (referred to herein as hSIRPα.40A.H5L4)
SEQ ID NO: 85/SEQ ID NO: 97 (referred to herein as hSIRPα.40A.H5L5)
SEQ ID NO: 85/SEQ ID NO: 99 (referred to herein as hSIRPα.40A.H5L6)
SEQ ID NO: 87/SEQ ID NO: 89 (referred to herein as hSIRPα.40A.H6L1)
SEQ ID NO: 87/SEQ ID NO: 91 (referred to herein as hSIRPα.40A.H6L2)
SEQ ID NO: 87/SEQ ID NO: 93 (referred to herein as hSIRPα.40A.H6L3)
SEQ ID NO: 87/SEQ ID NO: 95 (referred to herein as hSIRPα.40A.H6L4)
SEQ ID NO: 87/SEQ ID NO: 97 (referred to herein as hSIRPα.40A.H6L5)
SEQ ID NO: 87/SEQ ID NO: 99 (referred to herein as hSIRPα.40A.H6L6)
or, in each case, at least 90%, 95%, 97%, 98%, or 99% identical to a respective SEQ ID NO.

In some preferred embodiments, the nucleic acid comprises SEQ ID NO: 9 and SEQ ID NO: 19 or, in each case, at least 90%, 95%, 97%, 98%, or 99% identical to a respective SEQ ID NO.

In some preferred embodiments, the nucleic acid comprises SEQ ID NO: 15 and SEQ ID NO: 27 or, in each case, at least 90%, 95%, 97%, 98%, or 99% identical to a respective SEQ ID NO.

In some preferred embodiments, the nucleic acid comprises SEQ ID NO: 17 and SEQ ID NO: 19 or, in each case, at least 90%, 95%, 97%, 98%, or 99% identical to a respective SEQ ID NO.

In some preferred embodiments, the nucleic acid comprises SEQ ID NO: 79 and SEQ ID NO: 89 or, in each case, at least 90%, 95%, 97%, 98%, or 99% identical to a respective SEQ ID NO.

In some preferred embodiments, the nucleic acid comprises SEQ ID NO: 79 and SEQ ID NO: 91 or, in each case, at least 90%, 95%, 97%, 98%, or 99% identical to a respective SEQ ID NO.

In some preferred embodiments, the nucleic acid comprises SEQ ID NO: 79 and SEQ ID NO: 95 or, in each case, at least 90%, 95%, 97%, 98%, or 99% identical to a respective SEQ ID NO.

The invention also provides expression vectors comprising one or more nucleic acids of the present invention. An expression vector is a DNA molecule comprising the regulatory elements necessary for transcription of a target nucleic acid in a host cell. Typically, the target nucleic acid is placed under the control of certain regulatory elements including constitutive or inducible promoters, tissue-specific regulatory elements, and enhancer elements. Such a target nucleic acid is said to be "operably linked to" the regulatory elements when the regulating element controls the expression of the gene.

These isolated nucleic acids and the expression vectors comprising them may be used to express the antibodies of the invention or antigen binding fragments thereof in recombinant host cells. Thus, the invention also provides host cells comprising an expression vector of the present invention.

Such expression vectors can comprise one or more of the following nucleic acid sequences operably linked to regulatory elements:

- a nucleic acid sequence of SEQ ID NO: 77 or a nucleic acid sequence at least 90%, 95%, 97%, 98%, or 99% identical thereto,
- a nucleic acid sequence of SEQ ID NO: 79 or a nucleic acid sequence at least 90%, 95%, 97%, 98%, or 99% identical thereto,
- a nucleic acid sequence of SEQ ID NO: 81 or a nucleic acid sequence at least 90%, 95%, 97%, 98%, or 99% identical thereto,
- a nucleic acid sequence of SEQ ID NO: 83 or a nucleic acid sequence at least 90%, 95%, 97%, 98%, or 99% identical thereto,
- a nucleic acid sequence of SEQ ID NO: 85 or a nucleic acid sequence at least 90%, 95%, 97%, 98%, or 99% identical thereto,
- a nucleic acid sequence of SEQ ID NO: 87 or a nucleic acid sequence at least 90%, 95%, 97%, 98%, or 99% identical thereto,
- a nucleic acid sequence of SEQ ID NO: 101 or a nucleic acid sequence at least 90%, 95%, 97%, 98%, or 99% identical thereto,
- a nucleic acid sequence of SEQ ID NO: 89 or a nucleic acid sequence at least 90%, 95%, 97%, 98%, or 99% identical thereto,
- a nucleic acid sequence of SEQ ID NO: 91 or a nucleic acid sequence at least 90%, 95%, 97%, 98%, or 99% identical thereto,
- a nucleic acid sequence of SEQ ID NO: 93 or a nucleic acid sequence at least 90%, 95%, 97%, 98%, or 99% identical thereto,
- a nucleic acid sequence of SEQ ID NO: 95 or a nucleic acid sequence at least 90%, 95%, 97%, 98%, or 99% identical thereto,
- a nucleic acid sequence of SEQ ID NO: 97 or a nucleic acid sequence at least 90%, 95%, 97%, 98%, or 99% identical thereto,
- a nucleic acid sequence of SEQ ID NO: 99 or a nucleic acid sequence at least 90%, 95%, 97%, 98%, or 99% identical thereto,
- a nucleic acid sequence of SEQ ID NO: 103 or a nucleic acid sequence at least 90%, 95%, 97%, 98%, or 99% identical thereto,
- a nucleic acid sequence of SEQ ID NO: 11 or a nucleic acid sequence at least 90%, 95%, 97%, 98%, or 99% identical thereto,
- a nucleic acid sequence of SEQ ID NO: 13 or a nucleic acid sequence at least 90%, 95%, 97%, 98%, or 99% identical thereto,
- a nucleic acid sequence of SEQ ID NO: 15 or a nucleic acid sequence at least 90%, 95%, 97%, 98%, or 99% identical thereto,
- a nucleic acid sequence of SEQ ID NO: 17 or a nucleic acid sequence at least 90%, 95%, 97%, 98%, or 99% identical thereto,
- a nucleic acid sequence of SEQ ID NO: 29 or a nucleic acid sequence at least 90%, 95%, 97%, 98%, or 99% identical thereto,
- a nucleic acid sequence of SEQ ID NO: 19 or a nucleic acid sequence at least 90%, 95%, 97%, 98%, or 99% identical thereto,
- a nucleic acid sequence of SEQ ID NO: 21 or a nucleic acid sequence at least 90%, 95%, 97%, 98%, or 99% identical thereto,
- a nucleic acid sequence of SEQ ID NO: 23 or a nucleic acid sequence at least 90%, 95%, 97%, 98%, or 99% identical thereto,
- a nucleic acid sequence of SEQ ID NO: 25 or a nucleic acid sequence at least 90%, 95%, 97%, 98%, or 99% identical thereto,
- a nucleic acid sequence of SEQ ID NO: 27 or a nucleic acid sequence at least 90%, 95%, 97%, 98%, or 99% identical thereto, and/or
- a nucleic acid sequence of SEQ ID NO: 31 or a nucleic acid sequence at least 90%, 95%, 97%, 98%, or 99% identical thereto.

In certain embodiments, the expression vector comprises nucleic acid sequences encoding both a heavy chain sequence and a light chain sequence of an anti-SIRPα antibody of the present invention. Preferably, such expression vectors comprise the following combination heavy chain and light chain variable region nucleic acid sequences:

SEQ ID NO: 9/SEQ ID NO: 19 (referred to herein as hSIRPα.50A.H1L1)
SEQ ID NO: 9/SEQ ID NO: 21 (referred to herein as hSIRPα.50A.H1L2)
SEQ ID NO: 9/SEQ ID NO: 23 (referred to herein as hSIRPα.50A.H1L3)
SEQ ID NO: 9/SEQ ID NO: 25 (referred to herein as hSIRPα.50A.H1L4)
SEQ ID NO: 9/SEQ ID NO: 27 (referred to herein as hSIRPα.50A.H1L5)
SEQ ID NO: 11/SEQ ID NO: 19 (referred to herein as hSIRPα.50A.H2L1)
SEQ ID NO: 11/SEQ ID NO: 21 (referred to herein as hSIRPα.50A.H2L2)
SEQ ID NO: 11/SEQ ID NO: 23 (referred to herein as hSIRPα.50A.H2L3)
SEQ ID NO: 11/SEQ ID NO: 25 (referred to herein as hSIRPα.50A.H2L4)
SEQ ID NO: 11/SEQ ID NO: 27 (referred to herein as hSIRPα.50A.H2L5)
SEQ ID NO: 13/SEQ ID NO: 19 (referred to herein as hSIRPα.50A.H3L1)
SEQ ID NO: 13/SEQ ID NO: 21 (referred to herein as hSIRPα.50A.H3L2)
SEQ ID NO: 13/SEQ ID NO: 23 (referred to herein as hSIRPα.50A.H3L3)
SEQ ID NO: 13/SEQ ID NO: 25 (referred to herein as hSIRPα.50A.H3L4)
SEQ ID NO: 13/SEQ ID NO: 27 (referred to herein as hSIRPα.50A.H3L5)
SEQ ID NO: 15/SEQ ID NO: 19 (referred to herein as hSIRPα.50A.H4L1)
SEQ ID NO: 15/SEQ ID NO: 21 (referred to herein as hSIRPα.50A.H4L2)
SEQ ID NO: 15/SEQ ID NO: 23 (referred to herein as hSIRPα.50A.H4L3)

SEQ ID NO: 15/SEQ ID NO: 25 (referred to herein as hSIRPα.50A.H4L4)
SEQ ID NO: 15/SEQ ID NO: 27 (referred to herein as hSIRPα.50A.H4L5)
SEQ ID NO: 17/SEQ ID NO: 19 (referred to herein as hSIRPα.50A.H5L1)
SEQ ID NO: 17/SEQ ID NO: 21 (referred to herein as hSIRPα.50A.H5L2)
SEQ ID NO: 17/SEQ ID NO: 23 (referred to herein as hSIRPα.50A.H5L3)
SEQ ID NO: 17/SEQ ID NO: 25 (referred to herein as hSIRPα.50A.H5L4)
SEQ ID NO: 17/SEQ ID NO: 27 (referred to herein as hSIRPα.50A.H5L5)
SEQ ID NO: 77/SEQ ID NO: 89 (referred to herein as hSIRPα.40A.H1L1)
SEQ ID NO: 77/SEQ ID NO: 91 (referred to herein as hSIRPα.40A.H1L2)
SEQ ID NO: 77/SEQ ID NO: 93 (referred to herein as hSIRPα.40A.H1L3)
SEQ ID NO: 77/SEQ ID NO: 95 (referred to herein as hSIRPα.40A.H1L4)
SEQ ID NO: 77/SEQ ID NO: 97 (referred to herein as hSIRPα.40A.H1L5)
SEQ ID NO: 77/SEQ ID NO: 99 (referred to herein as hSIRPα.40A.H1L6)
SEQ ID NO: 79/SEQ ID NO: 89 (referred to herein as hSIRPα.40A.H2L1)
SEQ ID NO: 79/SEQ ID NO: 91 (referred to herein as hSIRPα.40A.H2L2)
SEQ ID NO: 79/SEQ ID NO: 93 (referred to herein as hSIRPα.40A.H2L3)
SEQ ID NO: 79/SEQ ID NO: 95 (referred to herein as hSIRPα.40A.H2L4)
SEQ ID NO: 79/SEQ ID NO: 97 (referred to herein as hSIRPα.40A.H2L5)
SEQ ID NO: 79/SEQ ID NO: 99 (referred to herein as hSIRPα.40A.H2L6)
SEQ ID NO: 81/SEQ ID NO: 89 (referred to herein as hSIRPα.40A.H3L1)
SEQ ID NO: 81/SEQ ID NO: 91 (referred to herein as hSIRPα.40A.H3L2)
SEQ ID NO: 81/SEQ ID NO: 93 (referred to herein as hSIRPα.40A.H3L3)
SEQ ID NO: 81/SEQ ID NO: 95 (referred to herein as hSIRPα.40A.H3L4)
SEQ ID NO: 81/SEQ ID NO: 97 (referred to herein as hSIRPα.40A.H3L5)
SEQ ID NO: 81/SEQ ID NO: 99 (referred to herein as hSIRPα.40A.H3L6)
SEQ ID NO: 83/SEQ ID NO: 89 (referred to herein as hSIRPα.40A.H4L1)
SEQ ID NO: 83/SEQ ID NO: 91 (referred to herein as hSIRPα.40A.H4L2)
SEQ ID NO: 83/SEQ ID NO: 93 (referred to herein as hSIRPα.40A.H4L3)
SEQ ID NO: 83/SEQ ID NO: 95 (referred to herein as hSIRPα.40A.H4L4)
SEQ ID NO: 83/SEQ ID NO: 97 (referred to herein as hSIRPα.40A.H4L5)
SEQ ID NO: 83/SEQ ID NO: 99 (referred to herein as hSIRPα.40A.H4L6)
SEQ ID NO: 85/SEQ ID NO: 89 (referred to herein as hSIRPα.40A.H5L1)
SEQ ID NO: 85/SEQ ID NO: 91 (referred to herein as hSIRPα.40A.H5L2)
SEQ ID NO: 85/SEQ ID NO: 93 (referred to herein as hSIRPα.40A.H5L3)
SEQ ID NO: 85/SEQ ID NO: 95 (referred to herein as hSIRPα.40A.H5L4)
SEQ ID NO: 85/SEQ ID NO: 97 (referred to herein as hSIRPα.40A.H5L5)
SEQ ID NO: 85/SEQ ID NO: 99 (referred to herein as hSIRPα.40A.H5L6)
SEQ ID NO: 87/SEQ ID NO: 89 (referred to herein as hSIRPα.40A.H6L1)
SEQ ID NO: 87/SEQ ID NO: 91 (referred to herein as hSIRPα.40A.H6L2)
SEQ ID NO: 87/SEQ ID NO: 93 (referred to herein as hSIRPα.40A.H6L3)
SEQ ID NO: 87/SEQ ID NO: 95 (referred to herein as hSIRPα.40A.H6L4)
SEQ ID NO: 87/SEQ ID NO: 97 (referred to herein as hSIRPα.40A.H6L5)
SEQ ID NO: 87/SEQ ID NO: 99 (referred to herein as hSIRPα.40A.H6L6)
or, in each case, at least 90%, 95%, 97%, 98%, or 99% identical to a respective SEQ ID NO.

In any of the above embodiments, the expression vector can encode for expression a human or humanized antibody, and includes nucleic acid sequences for both heavy and light chains. In one embodiment, the antibody is an IgG. In preferred embodiments, antibody is an IgG1, IgG2, or IgG4, and preferably a human IgG1, IgG2, or IgG4. In certain embodiments, the light chain sequence comprises a human kappa light chain or a human lambda light chain constant domain sequence; and each heavy chain sequence comprises a human IgG4 constant region sequence.

In some preferred embodiments, the expression vector encodes for expression a human or humanized antibody, wherein the heavy chain nucleic acid sequence comprises SEQ ID NO: 9 and the light chain nucleic acid sequence comprises SEQ ID NO: 19, or, in each case, at least 90%, 95%, 97%, 98%, or 99% identical to a respective SEQ ID NO, and is most preferably an IgG1, IgG2, or IgG4 isotype.

In some preferred embodiments, the expression vector encodes for expression a human or humanized antibody, wherein the heavy chain nucleic acid sequence comprises SEQ ID NO: 15 and the light chain nucleic acid sequence comprises SEQ ID NO: 27, or, in each case, at least 90%, 95%, 97%, 98%, or 99% identical to a respective SEQ ID NO, and is most preferably an IgG1, IgG2, or IgG4 isotype.

In some preferred embodiments, the expression vector encodes for expression a human or humanized antibody, wherein the heavy chain nucleic acid sequence comprises SEQ ID NO: 17 and the light chain nucleic acid sequence comprises SEQ ID NO: 19, or, in each case, at least 90%, 95%, 97%, 98%, or 99% identical to a respective SEQ ID NO or, in each case, at least 90%, 95%, 97%, 98%, or 99% identical to a respective SEQ ID NO, and is most preferably an IgG1, IgG2, or IgG4 isotype.

In some preferred embodiments, the expression vector encodes for expression a human or humanized antibody, wherein the heavy chain nucleic acid sequence comprises SEQ ID NO: 79 and the light chain nucleic acid sequence comprises SEQ ID NO: 89, or, in each case, at least 90%, 95%, 97%, 98%, or 99% identical to a respective SEQ ID NO, and is most preferably an IgG1, IgG2, or IgG4 isotype.

In some preferred embodiments, the expression vector encodes for expression a human or humanized antibody, wherein the heavy chain nucleic acid sequence comprises SEQ ID NO: 79 and the light chain nucleic acid sequence comprises SEQ ID NO: 91, or, in each case, at least 90%, 95%, 97%, 98%, or 99% identical to a respective SEQ ID NO, and is most preferably an IgG1, IgG2, or IgG4 isotype.

In some preferred embodiments, the expression vector encodes for expression a human or humanized antibody, wherein the heavy chain nucleic acid sequence comprises SEQ ID NO: 79 and the light chain nucleic acid sequence comprises SEQ ID NO: 95, or, in each case, at least 90%, 95%, 97%, 98%, or 99% identical to a respective SEQ ID NO, and is most preferably an IgG1, IgG2, or IgG4 isotype.

In one embodiment, the host cell is Chinese hamster ovary (CHO) cell. In one embodiment, the host cell is a mammalian cell (e.g., a human cell such as an HEK293 cell, a hamster cell such as a CHO cell, etc.), a bacterial cell (e.g., an *E. coli* cell) a yeast cell (e.g., a *Pichia pastoris* cell, etc.), a plant cell (e.g., a *Nicotiana benthamiana* cell), etc. Mammalian cells are preferred due to glycosylation patterns that are most favorable.

The invention also provides pharmaceutical compositions comprising an antibody or antigen binding fragment of the invention and a pharmaceutically acceptable carrier or diluent.

In one embodiment, the composition comprises one or more further therapeutic agents. In one embodiment, the further therapeutic agent is selected from the group consisting of: an anti-CD27 antibody or an antigen binding fragment thereof; an anti-LAG3 antibody or an antigen binding fragment thereof; an anti-APRIL antibody or an antigen binding fragment thereof; an anti-TIGIT antibody or antigen biding fragment thereof; an anti-VISTA antibody or an antigen binding fragment thereof; an anti-BTLA antibody or an antigen binding fragment thereof; an anti-TIM3 antibody or an antigen binding fragment thereof; an anti-CTLA4 antibody or an antigen binding fragment thereof; an anti-HVEM antibody or an antigen binding fragment thereof; an anti-CD70 antibody or an antigen binding fragment thereof; an anti-CD137 antibody or an antigen binding fragment thereof; an anti-OX40 antibody or an antigen binding fragment thereof; an anti-CD28 antibody or an antigen binding fragment thereof; thereof; an anti-PD1 antibody or an antigen binding fragment thereof; an anti-PDL1 antibody or an antigen binding fragment thereof; an anti-PDL2 antibody or an antigen binding fragment thereof; an anti-GITR antibody or an antigen binding fragment thereof; an anti-ICOS antibody or an antigen binding fragment thereof; an anti-ILT2 antibody or antigen binding fragment thereof; an anti-ILT3 antibody or antigen binding fragment thereof; an anti-ILT4 antibody or antigen binding fragment thereof; and an anti-ILT5 antibody or an antigen binding fragment thereof; an anti 4-1BB antibody or an antigen binding fragment thereof; an anti-NKG2A antibody or an antigen binding fragment thereof; an anti-NKG2C antibody or an antigen binding fragment thereof; an anti-NKG2E antibody or an antigen binding fragment thereof; an anti-TSLP antibody or an antigen binding fragment thereof; an anti-IL-10 antibody or an antigen binding fragment thereof; IL-10 or PEGylated IL-10; an agonist (e.g., an agonistic antibody or antigen-binding fragment thereof, or a soluble fusion) of a TNF receptor protein; an Immunoglobulin-like protein; a cytokine receptor; an integrin; a signaling lymphocytic activation molecules (SLAM proteins); an activating NK cell receptor; a Toll like receptor; OX40; CD2; CD7; CD27; CD28; CD30; CD40; ICAM-1; LFA-1 (CD11a/CD18); 4-1BB (CD137); B7-H3; ICOS (CD278); GITR; BAFFR; LIGHT; HVEM (LIGHTR); KIRDS2; SLAMF7; NKp80 (KLRF1); NKp44; NKp30; NKp46; CD19; CD4; CD8alpha; CD8beta; IL2R beta; IL2R gamma; IL7R alpha; ITGA4; VLA1; CD49a; ITGA4; IA4; CD49D; ITGA6; VLA-6; CD49f; ITGAD; CD11d; ITGAE; CD103; ITGAL; ITGAM; CD11b; ITGAX; CD11c; ITGB1; CD29; ITGB2; CD18; ITGB7; NKG2D; NKG2C; TNFR2; TRANCE/ RANKL; DNAM1 (CD226); SLAMF4 (CD244; 2B4); CD84; CD96 (Tactile); CEACAM1; CRTAM; Ly9 (CD229); CD160 (BY55); PSGL1; CD100 (SEMA4D); CD69; SLAMF6 (NTB-A; Lyl08); SLAM (SLAMF1, CD150, IPO-3); SLAM7; BLAME (SLAMF8); SELPLG (CD162); LTBR; LAT; GADS; PAG/Cbp; CD19a; a ligand that specifically binds with CD83; an inhibitor of CD47, PD-1, PD-L1; PD-L2; CTLA4; TIM3; LAG3; CEACAM (e.g.; CEACAM-1, -3 and/or -5); VISTA; BTLA; TIGIT; LAIR1; IDO; TDO; CD160; TGFR beta; and a cyclic dinculeotide or other STING pathway agonist.

The invention also comprises a combination comprising an antibody or antigen binding fragment of the invention and a second antibody that induces ADCC, wherein said antibody or antigen binding fragment of the invention enhances the antibody-mediated destruction of cells by the second antibody. Antibody-dependent cell-mediated cytotoxicity (ADCC) is a mechanism of cell-mediated immune defense whereby an effector cell of the immune system actively lyses a target cell, whose membrane-surface antigens have been bound by specific antibodies. ADCC is often thought of as being mediated by natural killer (NK) cells, but dendritic cells, macrophages, monocytes, and granulocytes can also mediate ADCC.

The invention also comprises a combination comprising an antibody or antigen binding fragment of the invention and a second antibody that induces ADCP, wherein said antibody or antigen binding fragment of the invention enhances the antibody-mediated phagocytosis of cells by the second antibody. Antibody-dependent cell-mediated phagocytosis (ADCP) is a mechanism of cell-mediated immune defense whereby target cells are killed via granulocyte, monocyte, dendritic cell, or macrophage-mediated phagocytosis.

Natural killer (NK) cells play a major role in cancer immunotherapies that involve tumor-antigen targeting by monoclonal antibodies (mAbs). In the context of targeting cells, NK cells can be "specifically activated" through certain Fc receptors that are expressed on their cell surface. NK cells can express FcγRIIIA and/or FcγRIIC, which can bind to the Fc portion of immunoglobulins, transmitting activating signals within NK cells. Once activated through Fc receptors by antibodies bound to target cells, NK cells are able to lyse target cells without priming, and secrete cytokines like interferon gamma to recruit adaptive immune cells. Likewise, tumor-associated macrophages (TAMs) express surface receptors that bind the Fc fragment of antibodies and enable them to engage in Ab-dependent cellular cytotoxicity/phagocytosis (ADCC/ADCP). Because SIRPα/CD47 signalling induces a "don't eat me" response that reduces ADCC/ADCP, blocking of this signaling by the anti-SIRPα antibodies or antigen binding fragments of the invention can enhance ADCC of tumor cells bearing the antigenic determinant to which the therapeutic antibody is directed.

This ADCC/ADCP as a mode of action may be utilized in the treatment of various cancers and infectious diseases. An exemplary list of ADCC/ADCP-inducing antibodies and antibody conjugates that can be combined with the antibodies or antigen binding fragments of the present invention includes, but is not limited to, Rituximab, ublituximab, margetuximab, IMGN-529, SCT400, veltuzumab, Obinutuzumab, ADCT-502, Hu14.18K322A, Hu3F8, Dinituximab, Trastuzumab, Cetuximab, Rituximab-RLI, c.60C3-RLI, Hu14.18-IL2, KM2812, AFM13, and (CD20)$_2$xCD16, erlotinib (Tarceva), daratumumab, alemtuzumab, pertuzumab, brentuximab, elotuzumab, ibritumomab, ifabotuzumab, farletuzumab, otlertuzumab, carotuximab, epratuzumab, inebilizumab, lumretuzumab, 4G7SDIE, AFM21, AFM22, LY-3022855, SNDX-6352, AFM-13, BI-836826, BMS-986012, BVX-20, mogamulizumab, ChiLob-7/4, leukotuximab, isatuximab, DS-8895, FPA144, GM102, GSK-2857916, IGN523, IT1208, ADC-1013, CAN-04, XOMA-213, PankoMab-GEX, chKM-4927, IGN003, IGN004, IGN005, MDX-1097, MOR202, MOR-208, oportuzumab, ensituximab, vedotin (Adcetris), ibritumomab tiuxetan, ABBV-838, HuMax-AXL-ADC, and ado-trastuzumab emtansine (Kadcyla). An exemplary list of target antigens for such ADCC/ADCP-inducing antibodies includes, but is not limited to, AMHR2, AXL, BCMA, CA IX, CD4, CD16, CD19, CD20, CD22, CD30, CD37, CD38, CD40, CD52, CD98, CSF1R, GD2, CCR4, CS1, EpCam, EGFR, EGFRvIII, Endoglin, EPHA2, EphA3, FGFR2b, folate receptor alpha, fucosyl-GM1, HER2, HER3, IL1RAP, kappa myeloma antigen, MS4A1, prolactin receptor, TA-MUC1, and PSMA.

In certain embodiments, the second antibody or antigen binding fragment thereof induces ADCP. By way of example only, such antibodies may be selected from the group consisting of Rituximab, ublituximab, margetuximab, IMGN-529, SCT400, veltuzumab, Obinutuzumab, Trastuzumab, Cetuximab, alemtuzumab, ibritumomab, farletuzumab, inebilizumab, lumretuzumab, 4G7SDIE, BMS-986012, BVX-20, mogamulizumab, ChiLob-7/4, GM102, GSK-2857916, PankoMab-GEX, chKM-4927, MDX-1097, MOR202, and MOR-208.

In embodiments where the antibodies or antigen binding fragments of the present invention are combined with one or more ADCC/ADCP-inducing antibodies and antibody conjugates, such combinations may also be used optionally in association with a further therapeutic agent or therapeutic procedure. In one embodiment, the further therapeutic agent is selected from the group consisting of: an anti-LAG3 antibody or an antigen binding fragment thereof; an anti-APRIL antibody or an antigen binding fragment thereof; an anti-TIGIT antibody or an antigen binding fragment thereof; an anti-VISTA antibody or an antigen binding fragment thereof; an anti-BTLA antibody or an antigen binding fragment thereof; an anti-TIM3 antibody or an antigen binding fragment thereof; an anti-CTLA4 antibody or an antigen binding fragment thereof; an anti-HVEM antibody or an antigen binding fragment thereof; an anti-CD70 antibody or an antigen binding fragment thereof; an anti-CD137 antibody or an antigen binding fragment thereof; an anti-OX40 antibody or an antigen binding fragment thereof; an anti-CD28 antibody or an antigen binding fragment thereof; thereof; an anti-PD1 antibody or an antigen binding fragment thereof; an anti-PDL1 antibody or an antigen binding fragment thereof; an anti-PDL2 antibody or an antigen binding fragment thereof; an anti-GITR antibody or an antigen binding fragment thereof; an anti-ICOS antibody or an antigen binding fragment thereof; an anti-ILT2 antibody or antigen binding fragment thereof; an anti-ILT3 antibody or antigen binding fragment thereof; an anti-ILT4 antibody or antigen binding fragment thereof; an anti-ILT5 antibody or an antigen binding fragment thereof; and an anti-4-1BB antibody or an antigen binding fragment thereof; an anti-NKG2A antibody or an antigen binding fragment thereof; an anti-NKG2C antibody or an antigen binding fragment thereof; an anti-NKG2E antibody or an antigen binding fragment thereof; an anti-TSLP antibody or an antigen binding fragment thereof; an anti-IL-10 antibody or an antigen binding fragment thereof; and IL-10 or PEGylated IL-10.

The invention also provides a vessel or injection device comprising anyone of the anti-SIRPα antibodies or antigen binding fragments of the invention.

The invention also provides a method of producing an anti-SIRPα antibody or antigen binding fragment of the invention comprising: culturing a host cell comprising a polynucleotide encoding a heavy chain and/or light chain of an antibody of the invention (or an antigen binding fragment thereof) under conditions favorable to expression of the polynucleotide; and optionally, recovering the antibody or antigen binding fragment from the host cell and/or culture medium. In one embodiment, the polynucleotide encoding the heavy chain and the polynucleotide encoding the light chain are in a single vector. In another embodiment, the polynucleotide encoding the heavy chain and the polynucleotide encoding the light chain are in different vectors.

The invention also provides a method of treating cancer in a subject in need thereof, comprising administering to the subject an effective amount of an anti-SIRPα antibody or antigen binding fragment of the invention, optionally in association with a further therapeutic agent or therapeutic procedure.

In one embodiment, the subject to be treated is a human subject. In one embodiment, the further therapeutic agent is selected from the group consisting of: an anti-LAG3 antibody or an antigen binding fragment thereof; an anti-APRIL antibody or an antigen binding fragment thereof; an anti-TIGIT antibody or an antigen binding fragment thereof; an anti-VISTA antibody or an antigen binding fragment thereof; an anti-BTLA antibody or an antigen binding fragment thereof; an anti-TIM3 antibody or an antigen binding fragment thereof; an anti-CTLA4 antibody or an antigen binding fragment thereof; an anti-HVEM antibody or an antigen binding fragment thereof; an anti-CD70 antibody or an antigen binding fragment thereof; an anti-CD137 antibody or an antigen binding fragment thereof; an anti-OX40 antibody or an antigen binding fragment thereof; an anti-CD28 antibody or an antigen binding fragment thereof; thereof; an anti-PD1 antibody or an antigen binding fragment thereof; an anti-PDL1 antibody or an antigen binding fragment thereof; an anti-PDL2 antibody or an antigen binding fragment thereof; an anti-GITR antibody or an antigen binding fragment thereof; an anti-ICOS antibody or an antigen binding fragment thereof; an anti-ILT2 antibody or antigen binding fragment thereof; an anti-ILT3 antibody or antigen binding fragment thereof; an anti-ILT4 antibody or antigen binding fragment thereof; an anti-ILT5 antibody or an antigen binding fragment thereof; and an anti-4-1BB antibody or an antigen binding fragment thereof; an anti-NKG2A antibody or an antigen binding fragment thereof; an anti-NKG2C antibody or an antigen binding fragment thereof; an anti-NKG2E antibody or an antigen binding fragment thereof; an anti-TSLP antibody or an antigen binding fragment thereof; an anti-IL-10 antibody or an antigen binding fragment thereof; and IL-10 or PEGylated IL-10.

The invention also provides a method of treating an infection or infectious disease in a subject, comprising administering to the subject an effective amount of an antibody or antigen binding fragment of the invention, optionally in association with a further therapeutic agent or therapeutic procedure. In one embodiment, the subject to be treated is a human subject.

In one embodiment, the further therapeutic agent is selected from the group consisting of: an anti-LAG3 antibody or an antigen binding fragment thereof; an anti-APRIL antibody or an antigen binding fragment thereof; an anti-TIGIT antibody or an antigen binding fragment thereof; an anti-VISTA antibody or an antigen binding fragment thereof; an anti-BTLA antibody or an antigen binding fragment thereof; an anti-TIM3 antibody or an antigen binding fragment thereof; an anti-CTLA4 antibody or an antigen binding fragment thereof; an anti-HVEM antibody or an antigen binding fragment thereof; an anti-CD70 antibody or an antigen binding fragment thereof; an anti-CD137 antibody or an antigen binding fragment thereof; an anti-OX40 antibody or an antigen binding fragment thereof; an anti-CD28 antibody or an antigen binding fragment thereof; thereof; an anti-PD1 antibody or an antigen binding fragment thereof; an anti-PDL1 antibody or an antigen binding fragment thereof; an anti-PDL2 antibody or an antigen binding fragment thereof; an anti-GITR antibody or an antigen binding fragment thereof; an anti-ICOS antibody or an antigen binding fragment thereof; an anti-ILT2 antibody or an antigen binding fragment thereof; an anti-ILT3 antibody or an antigen binding fragment thereof; an anti-ILT4 antibody or an antigen binding fragment thereof; an anti-ILT5 antibody or an antigen binding fragment thereof; and an anti-4-1BB antibody or an antigen binding fragment thereof; an anti-NKG2A antibody or an antigen binding fragment thereof; an anti-NKG2C antibody or an antigen binding fragment thereof; an anti-NKG2E antibody or an antigen binding fragment thereof; an anti-TSLP antibody or an antigen binding fragment thereof; an anti-IL-10 antibody or an antigen binding fragment thereof; and IL-10 or PEGylated IL-10.

The invention also provides a method for detecting the presence of a SIRPα peptide or a fragment thereof in a sample comprising contacting the sample with an antibody or antigen binding fragment thereof of the invention and detecting the presence of a complex between the antibody or fragment and the peptide; wherein detection of the complex indicates the presence of the SIRPα peptide.

BRIEF DESCRIPTION OF THE FIGURES

FIG. 10A depicts an alignment of the hSIRPαV1 (SEQ ID NO: 133), hSIRPαV2 (SEQ ID NO: 134) and hSIRPβ1 (SEQ ID NO: 135) IgV domain amino acid sequences.

FIG. 14A depicts binding of hSIRP?.40A antibody to primary CD14+ enriched monocytes from a human donor.

FIG. 14B depicts binding of hSIRP?.40A antibody to primary CD14+ enriched monocytes from a second human donor.

FIG. 14C depicts the ability of hSIRP?.40A antibody to block hCD47 binding to primary CD14+ enriched monocytes from a human donor.

FIG. 14D depicts the ability of hSIRP?.40A antibody to block hCD47 binding to primary CD14+ enriched monocytes from a second human donor.

DETAILED DESCRIPTION

Abbreviations

Figure 1:
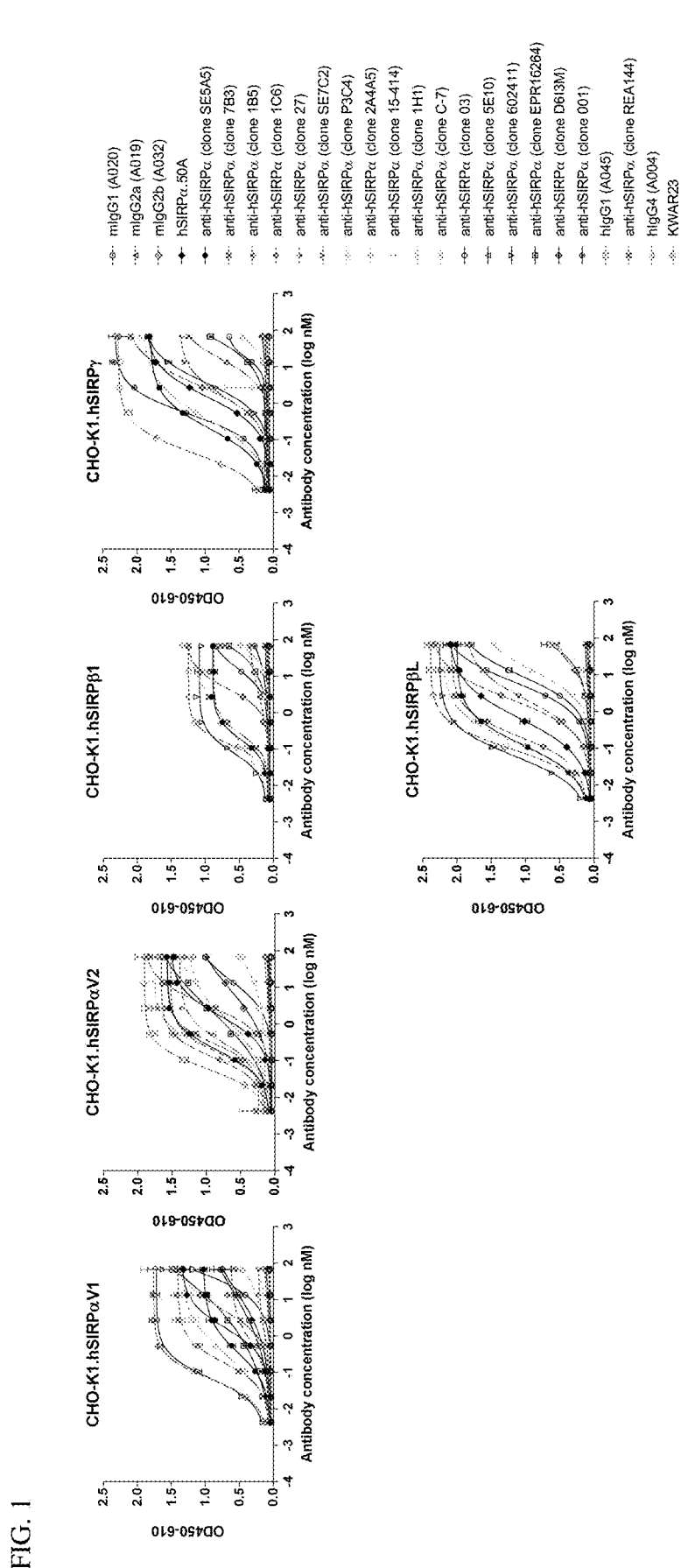
FIG. 1 depicts cross-reactivity of commercially available anti-hSIRPα antibodies with hSIRPβ1 and allele-specific binding to hSIRPαV1 and hSIRPαV2.

Throughout the detailed description and examples of the invention the following abbreviations will be used:
ADCC Antibody-dependent cellular cytotoxicity
ADCP Antibody-dependent cellular phagocytosis
CDC Complement-dependent cytotoxicity
CDR Complementarity determining region in the immunoglobulin variable regions, defined using the Kabat numbering system
CHO Chinese hamster ovary
EC50 Concentration at which 50% of the total binding signal is observed
ELISA Enzyme-linked immunosorbant assay
FR Antibody framework region: the immunoglobulin variable regions excluding the CDR regions.
HRP Horseradish peroxidase
IFN interferon
IC50 concentration resulting in 50% inhibition
IgG Immunoglobulin G
Kabat An immunoglobulin alignment and numbering system pioneered by Elvin A. Kabat ((1991) Sequences of Proteins of Immunological Interest, 5th Ed. Public Health Service, National Institutes of Health, Bethesda, Md.)
mAb or Mab or MAb Monoclonal antibody
SEB *Staphylococcus* Enterotoxin B
TT Tetanus toxoid
V region The segment of Ig chains which is variable in sequence between different antibodies. It extends to Kabat residue 109 in the light chain and 113 in the heavy chain.
VH Immunoglobulin heavy chain variable region
VK Immunoglobulin kappa light chain variable region
VL Immunoglobulin light chain variable region

Definitions

So that the invention may be more readily understood, certain technical and scientific terms are specifically defined below. Unless specifically defined elsewhere in this document, all other technical and scientific terms used herein have the meaning commonly understood by one of ordinary skill in the art to which this invention belongs.

As used herein, including the appended claims, the singular forms of words such as "a," "an," and "the," include their corresponding plural references unless the context clearly dictates otherwise.

"Administration" and "treatment," as it applies to an animal, human, experimental subject, cell, tissue, organ, or biological fluid, refers to contact of an exogenous pharmaceutical, therapeutic, diagnostic agent, or composition to the animal, human, subject, cell, tissue, organ, or biological fluid. Treatment of a cell encompasses contact of a reagent to the cell, as well as contact of a reagent to a fluid, where the fluid is in contact with the cell. "Administration" and "treatment" also means in vitro and ex vivo treatments, e.g., of a cell, by a reagent, diagnostic, binding compound, or by another cell.

"Treat" or "treating" means to administer a therapeutic agent, such as a composition containing any of the antibodies or antigen-binding fragments of the present invention, internally or externally to a subject or patient having one or more disease symptoms, or being suspected of having a disease, for which the agent has therapeutic activity. Typically, the agent is administered in an amount effective to alleviate one or more disease symptoms in the treated subject or population, whether by inducing the regression of or inhibiting the progression of such symptom(s) by any clinically measurable degree. The amount of a therapeutic agent that is effective to alleviate any particular disease symptom may vary according to factors such as the disease state, age, and weight of the patient, and the ability of the drug to elicit a desired response in the subject. Whether a disease symptom has been alleviated can be assessed by any clinical measurement typically used by physicians or other skilled healthcare providers to assess the severity or progression status of that symptom.

"Recombinant expression" of a protein means the transcription and translation of an exogenous gene in a host organism to generate the protein, which is referred to herein as a "recombinant protein."

SIRPα and Associated Proteins

SIRPα belongs to a class of membrane proteins known as "paired receptors" that contain several genes coding for proteins (e.g., SIRPα, SIRPβ1, and SIRPγ) with similar extracellular regions but different transmembrane and/or cytoplasmic regions having opposite (activating or inhibitory) signaling abilities. Like SIRPα, there are several examples of paired receptors on NK cells and some on myeloid cells, including the SIRP and CD200 receptor families (Hatherley et al., *Mol Cell.* 2008; 31: 266-277).

SIRPα contains an extracellular region that can be subdivided into three separate domains: the Ig-like (immunoglobulin-like) V-type (IgV), Ig-like C1-type (IgC1), and Ig-like C2-type (IgC2) domain. The IgV domain is also known as the ligand-binding N-terminal domain of SIRPα.

Like SIRPα, also the related proteins SIRPβ1 and SIRPγ comprise an extracellular region that can be subdivided into an IgV, IgC1, and IgC2 domain. However, SIRPα, SIRPβ1 and SIRPγ have different cytoplasmic regions. SIRPβ1 has a very short cytoplasmic region of only 6 amino acids and lacks signalling motifs for association with phosphatases. Instead, this protein associates with DNAX activation protein 12 (DAP12), a dimeric adaptor protein that binds an amino acid with a basic side chain in the transmembrane region of SIRPβ1 and is able to transmit activating signals through its immunoreceptor tyrosine-based activation motif (ITAM). SIRPγ also has a short cytoplasmic region of 4 amino acids, but it lacks a charged amino-acid side chain in the transmembrane region and therefore does not associate with DAP12. Hence, SIRPγ is annotated as a non-signalling protein (Barclay, A. N. and Brown, M. H., *Nat Rev Immunol.* 2006; 6: 457-464).

The major ligand of SIRPα is CD47, which consists of one extracellular IgV domain, a five times transmembrane-spanning domain, and a short cytoplasmic tail. CD47 functions as a cellular ligand with binding mediated through the NH2-terminal IgV domain of SIRPα. Evidence that CD47 contributes to recognition of self comes from the observation that splenic macrophages derived from CD47-expressing mice clear infused blood cells from CD47$^{-/-}$ mice (Oldenborg et al., *Science.* 2000; 288: 2051-2054).

In addition to CD47, two other SIRPα ligands have been reported, known as surfactant proteins A and D (Sp-A and Sp-D), both of which belong to the collectin family. Sp-D has been reported to bind to the membrane-proximal IgC2 domain of SIRPα in a calcium- and saccharide-dependent manner. It is thought that Sp-A and Sp-D help maintain an anti-inflammatory environment in the lung by stimulating SIRPα on alveolar macrophages (Gardai et al., *Cell.* 2003; 115: 13-23).

The amino acid sequence of eight human SIRPα variants are listed in SEQ ID NOs: 34, 36, 44, 46, 48, 50, 52, and 54; exemplary nucleic acid sequences encoding these variants are listed in SEQ ID NOs: 33, 35, 43, 45, 47, 49, 51, and 53, respectively.

For comparison, the amino acid sequence of human SIRPβ1 and SIRPγ are listed in SEQ ID NOs: 38 and 40, respectively, and exemplary nucleic acid sequences in SEQ ID NOs: 37 and 39, respectively.

The amino acid sequence of human CD47 is listed in SEQ ID NO: 42, and an exemplary nucleic acid sequence in SEQ ID NO: 41.

Modified SIRPα polypeptides hSIRPα-VβC1αC2α, hSIRPα-VαC1βC2α, hSIRPα-VαC1αC2β, and hSIRPαV1 (P74A) discussed hereinafter are listed in SEQ ID NOs: 56, 58, 60, and 62; exemplary nucleic acid sequences encoding these variants are listed in SEQ ID NOs: 55, 57, 59, and 61, respectively.

Anti-SIRPα Antibodies and Antigen-Binding Fragments Thereof

The present invention provides antibodies or antigen-binding fragments thereof that bind human SIRPα and uses of such antibodies or fragments. In some embodiments, the anti-SIRPα antibodies are isolated.

Whether an antibody specifically binds to a polypeptide sequence (e.g., human SIRPα, hSIRPβ1, etc.) can be determined using any assay known in the art. Examples of assays known in the art to determining binding affinity include surface plasmon resonance (e.g., BIACORE™ SPR system, (General Electric Company)) or a similar technique (e.g. KinExa® (Sapidyne Instruments) or OCTET® (ForteBio, Inc.) systems).

As used herein, the term "antibody" refers to any form of antibody that exhibits the desired biological activity. The term antibody includes antigen-binding portions, i.e., "antigen binding sites," (e.g., fragments, subsequences, complementarity determining regions (CDRs)) that retain capacity to bind antigen, including (i) a Fab fragment, a monovalent fragment consisting of the $V_L$, $V_H$, $C_L$ and $C_H1$ domains; (ii) a F(ab')2 fragment, a bivalent fragment comprising two Fab fragments linked by a disulfide bridge at the hinge region; (iii) a Fd fragment consisting of the $V_H$ and $C_H1$ domains; (iv) a Fv fragment consisting of the $V_L$ and $V_H$ domains of a single arm of an antibody, (v) a dAb fragment (Ward et al., (1989) Nature 341:544-546), which consists of a VH domain; and (vi) an isolated complementarity determining region (CDR). Single chain antibodies are also included by reference in the term "antibody." Preferred therapeutic antibodies are intact IgG antibodies. The term "intact IgG" as used herein is meant as a polypeptide belonging to the class of antibodies that are substantially encoded by a recognized immunoglobulin gamma gene. In humans this class comprises IgG1, IgG2, IgG3, and IgG4. In mice this class comprises IgG1, IgG2a, IgG2b, IgG3. The known Ig domains in the IgG class of antibodies are $V_H$, Cγ1, Cγ2, Cγ3, $V_L$, and $C_L$.

The present invention includes anti-SIRPα antigen-binding fragments and methods of use thereof.

As used herein, a "full length antibody" is, in the case of an IgG1, a bivalent molecule comprising two heavy chains and two light chains. Each heavy chain comprises a $V_H$ domain followed by a constant domain ($C_{H1}$), a hinge region, and two more constant ($C_{H2}$ and $C_{H3}$) domains; while each light chain comprises one $V_L$ domain and one constant ($C_L$) domain. A full length antibody in the case of an IgM is a decavalent or dodecavalent molecule comprising 5 or 6 linked immunoglobulins in which immunoglobulin each monomer has two antigen binding sites formed of a heavy and light chain.

As used herein, unless otherwise indicated, "antibody fragment" or "antigen-binding fragment" refers to antigen-binding fragments of antibodies, i.e. antibody fragments that retain the ability to bind specifically to the antigen bound by the full-length antibody, e.g. fragments that retain one or more CDR regions. Examples of antigen-binding fragments include, but are not limited to, Fab, Fab', F(ab')$_2$, and Fv fragments; diabodies; linear antibodies; single-chain antibody molecules, e.g., sc-Fv; nanobodies and multispecific antibodies formed from antibody fragments.

The present invention includes anti-SIRPα Fab fragments and methods of use thereof. A "Fab fragment" is comprised of one light chain and the $C_H1$ and variable regions of one heavy chain. The heavy chain of a Fab molecule cannot form a disulfide bond with another heavy chain molecule. A "Fab fragment" can be the product of papain cleavage of an antibody.

The present invention includes anti-SIRPα antibodies and antigen-binding fragments thereof which comprise an Fc region and methods of use thereof. An "Fc" region contains two heavy chain fragments comprising the $C_H3$ and $C_H2$ domains of an antibody. The two heavy chain fragments are held together by two or more disulfide bonds and by hydrophobic interactions of the $C_H3$ domains.

The present invention includes anti-SIRPα Fab' fragments and methods of use thereof. A "Fab' fragment" contains one light chain and a portion or fragment of one heavy chain that contains the $V_H$ domain and the C H1 domain and also the region between the $C_H1$ and $C_H2$ domains, such that an interchain disulfide bond can be formed between the two heavy chains of two Fab' fragments to form a F(ab')$_2$ molecule.

The present invention includes anti-SIRPα F(ab')$_2$ fragments and methods of use thereof. A "F(ab')$_2$ fragment" contains two light chains and two heavy chains containing a portion of the constant region between the $C_{H1}$ and $C_{H2}$ domains, such that an interchain disulfide bond is formed between the two heavy chains. A F(ab') 2 fragment thus is composed of two Fab' fragments that are held together by a disulfide bond between the two heavy chains. An "F(ab')$_2$ fragment" can be the product of pepsin cleavage of an antibody.

The present invention includes anti-SIRPα Fv fragments and methods of use thereof. The "Fv region" comprises the variable regions from both the heavy and light chains, but lacks the constant regions.

The present invention includes anti-SIRPα scFv fragments and methods of use thereof. The term "single-chain Fv" or "scFv" antibody refers to antibody fragments comprising the $V_H$ and $V_L$ domains of an antibody, wherein these domains are present in a single polypeptide chain. Generally, the Fv polypeptide further comprises a polypeptide linker between the $V_H$ and $V_L$ domains which enables the scFv to form the desired structure for antigen-binding. For a review of scFv, see Pluckthun (1994) THE PHARMACOLOGY OF MONO-CLONAL ANTIBODIES, vol. 113, Rosenburg and Moore eds. Springer-Verlag, New York, pp. 269-315. See also, International Patent Application Publication No. WO 88/01649 and U.S. Pat. Nos. 4,946,778 and 5,260,203.

The present invention includes anti-SIRPα domain antibodies and methods of use thereof. A "domain antibody" is an immunologically functional immunoglobulin fragment containing only the variable region of a heavy chain or the variable region of a light chain. In some instances, two or more $V_H$ regions are covalently joined with a peptide linker to create a bivalent domain antibody. The two $V_H$ regions of a bivalent domain antibody may target the same or different antigens.

The present invention includes anti-SIRPα bivalent antibodies and methods of use thereof. A "bivalent antibody" comprises two antigen-binding sites. In some instances, the two binding sites have the same antigen specificities. However, bivalent antibodies may be bispecific (see below).

The present invention includes anti-SIRPα diabodies and methods of use thereof. As used herein, the term "diabodies" refers to small antibody fragments with two antigen-binding sites, which fragments comprise a heavy chain variable domain ($V_H$) connected to a light chain variable domain ($V_L$) in the same polypeptide chain ($V_H$-$V_L$ or $V_L$-$V_H$). By using a linker that is too short to allow pairing between the two domains on the same chain, the domains are forced to pair with the complementary domains of another chain and create two antigen-binding sites. Diabodies are described more fully in, e.g., EP 404,097; WO 93/11161; and Holliger et al. (1993) *Proc. Natl. Acad. Sci. USA* 90: 6444-6448. Duobodies are described in Labrijn et al., 2013, *Proc. Natl. Acad. Sci. USA* 110 (13): 5145-5150. For a review of engineered antibody variants generally see Holliger and Hudson (2005) *Nat. Biotechnol.* 23:1126-1136.

Typically, an antibody or antigen-binding fragment of the invention which is modified in some way retains at least 10% of its binding activity (when compared to the parental antibody) when that activity is expressed on a molar basis. Preferably, an antibody or antigen-binding fragment of the invention retains at least 20%, 50%, 70%, 80%, 90%, 95% or 100% or more of the SIRPα binding affinity as the parental antibody. It is also intended that an antibody or antigen-binding fragment of the invention can include conservative or non-conservative amino acid substitutions (referred to as "conservative variants" or "function conserved variants" of the antibody) that do not substantially alter its biologic activity.

The present invention includes isolated anti-SIRPα antibodies and antigen-binding fragments thereof and methods of use thereof. Herein, the term "isolated" is not intended to refer to a complete absence of such biological molecules or to an absence of water, buffers, or salts or to components of a pharmaceutical formulation that includes the antibodies or fragments. An "isolated" antibody, antigen-binding fragment, nucleic acid, etc., is one which has been identified and separated and/or recovered from one or more components of its natural environment. In preferred embodiments, the antibody, antigen-binding fragment, nucleic acid, etc., is purified to 75% by weight or more, more preferably to 90% by weight or more, still more preferably to 95% by weight or more, an still more preferably to 98% by weight or more. Thus, "isolated" biological molecules are at least partially free of other biological molecules from the cells or cell cultures in which they are produced. Such biological molecules include nucleic acids, proteins, lipids, carbohydrates, or other material such as cellular debris and growth medium. An isolated antibody or antigen-binding fragment may further be at least partially free of expression system components such as biological molecules from a host cell or of the growth medium thereof.

The present invention includes anti-SIRPα chimeric antibodies (e.g., human constant domain/mouse variable domain) and methods of use thereof. As used herein, a "chimeric antibody" is an antibody having the variable domain from a first antibody and the constant domain from a second antibody, where the first and second antibodies are from different species. (U.S. Pat. No. 4,816,567; and Morrison et al., (1984) *Proc. Natl. Acad. Sci. USA* 81: 6851-6855). Typically, the variable domains are obtained from an antibody from an experimental animal (the "parental antibody"), such as a rodent, and the constant domain sequences are obtained from human antibodies, so that the resulting chimeric antibody will be less likely to elicit an adverse immune response in a human subject than the parental (e.g., mouse) antibody.

The present invention includes anti-SIRPα humanized antibodies and antigen-binding fragments thereof (e.g., rat or mouse antibodies that have been humanized) and methods of use thereof. As used herein, the term "humanized antibody" refers to forms of antibodies that contain sequences from both human and non-human (e.g., mouse or rat) antibodies. In general, the humanized antibody will comprise substantially of at least one, and typically two, variable domains, in which all or substantially all of the hypervariable loops correspond to those of a non-human immunoglobulin, and all or substantially all of the framework (FR) regions are those of a human immunoglobulin sequence. The humanized antibody may optionally comprise at least a portion of a human immunoglobulin constant region (Fc). For more details about humanized antibodies, see, e.g., Jones et al., *Nature,* 321:522-525 (1986); Reichmann et al., *Nature,* 332:323-329 (1988); Presta, *Curr. Op. Struct. Biol.,* 2:593-596 (1992); and Clark, *Immunol. Today* 21: 397-402 (2000).

In general, the basic antibody structural unit comprises a tetramer. Each tetramer includes two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of the heavy chain may define a constant region primarily responsible for effector function. Typically, human light chains are classified as kappa and lambda light chains. Furthermore, human heavy chains are typically classified as mu, delta, gamma, alpha, or epsilon, and define the antibody's isotype as IgM, IgD, IgG, IgA, and IgE, respectively. Within light and heavy chains, the variable and constant regions are joined by a "J" region of about 12 or more amino acids, with the heavy chain also including a "D" region of about 10 more amino acids. See generally, *Fundamental Immunology* Ch. 7 (Paul, W., ed., 2nd ed. Raven Press, N.Y. (1989)).

The variable regions of each light/heavy chain pair form the antibody binding site. Thus, in general, an intact antibody has two binding sites. Except in bifunctional or bispecific antibodies, the two binding sites are, in general, the same.

Typically, the variable domains of both the heavy and light chains comprise three hypervariable regions, also called complementarity determining regions (CDRs), located within relatively conserved framework regions (FR). The CDRs are usually aligned by the framework regions, enabling binding to a specific epitope. In general, from N-terminal to C-terminal, both light and heavy chains variable domains comprise FR1, CDR1, FR2, CDR2, FR3, CDR3 and FR4. The assignment of amino acids to each domain is, generally, in accordance with the definitions of *Sequences of Proteins of Immunological Interest*, Kabat, et al.; National Institutes of Health, Bethesda, Md.; 5$^{th}$ ed.; NIH Publ. No. 91-3242 (1991); Kabat (1978) *Adv. Prot. Chem.* 32:1-75; Kabat, et al., (1977) *J. Biol. Chem.* 252: 6609-6616; Chothia, et al., (1987) *J Mol. Biol.* 196:901-917 or Chothia, et al., (1989) *Nature* 342:878-883.

As used herein, the term "hypervariable region" refers to the amino acid residues of an antibody or antigen-binding fragment thereof that are responsible for antigen-binding. The hypervariable region comprises amino acid residues from a "complementarity determining region" or "CDR" (i.e. CDRL1, CDRL2 and CDRL3 in the light chain variable domain and CDRH1, CDRH2 and CDRH3 in the heavy chain variable domain). See Kabat et al. (1991) Sequences of Proteins of Immunological Interest, 5th Ed. Public Health Service, National Institutes of Health, Bethesda, Md. (defining the CDR regions of an antibody by sequence); see also Chothia and Lesk (1987) *J. Mol. Biol.* 196: 901-917 (defining the CDR regions of an antibody by structure). As used herein, the term "framework" or "FR" residues refers to those variable domain residues other than the hypervariable region residues defined herein as CDR residues.

"Isolated nucleic acid molecule" or "isolated polynucleotide" means a DNA or RNA of genomic, mRNA, cDNA, or synthetic origin or some combination thereof which is not associated with all or a portion of a polynucleotide in which the isolated polynucleotide is found in nature, or is linked to a polynucleotide to which it is not linked in nature. For purposes of this disclosure, it should be understood that "a nucleic acid molecule comprising" a particular nucleotide sequence does not encompass intact chromosomes. Isolated nucleic acid molecules "comprising" specified nucleic acid sequences may include, in addition to the specified sequences, coding sequences for up to ten or even up to twenty or more other proteins or portions or fragments thereof, or may include operably linked regulatory sequences that control expression of the coding region of the recited nucleic acid sequences, and/or may include vector sequences.

The phrase "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to use promoters, polyadenylation signals, and enhancers.

A nucleic acid or polynucleotide is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, but not always, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

As used herein, the expressions "cell," "cell line," and "cell culture" are used interchangeably and all such designations include progeny. Thus, the words "transformants" and "transformed cells" include the primary subject cell and cultures derived therefrom without regard for the number of transfers. It is also understood that not all progeny will have precisely identical DNA content, due to deliberate or inadvertent mutations. Mutant progeny that have the same function or biological activity as screened for in the originally transformed cell are included. Where distinct designations are intended, it will be clear from the context.

As used herein, "germline sequence" refers to a sequence of unrearranged immunoglobulin DNA sequences. Any suitable source of unrearranged immunoglobulin sequences may be used. Human germline sequences may be obtained, for example, from JOINSOLVER germline databases on the website for the National Institute of Arthritis and Musculoskeletal and Skin Diseases of the United States National Institutes of Health. Mouse germline sequences may be obtained, for example, as described in Giudicelli et al. (2005) *Nucleic Acids Res.* 33: D256-D261.

Physical and Functional Properties of the Exemplary Anti-SIRPα Antibodies

The present invention provides anti-SIRPα antibodies and antigen-binding fragments thereof having specified structural and functional features, and methods of use of the antibodies or antigen-binding fragments thereof in the treatment or prevention of disease (e.g., cancer or infectious disease).

As stated above, antibodies and fragments that bind to the same epitope as any of the anti-SIRPα antibodies or antigen-binding fragments thereof of the present invention also form part of the present invention. In one embodiment, the invention provides an antibody or antigen binding fragment thereof that binds to the same epitope of human SIRPα as an antibody comprising one of the following combinations of heavy chain sequence/light chain sequence (or in each case an amino acid sequence at least 90%, 95%, 97%, 98%, or 99% identical thereto):

SEQ ID NO: 10/SEQ ID NO: 20 (referred to herein as hSIRPα.50A.H1L1)
SEQ ID NO: 10/SEQ ID NO: 22 (referred to herein as hSIRPα.50A.H1L2)
SEQ ID NO: 10/SEQ ID NO: 24 (referred to herein as hSIRPα.50A.H1L3)
SEQ ID NO: 10/SEQ ID NO: 26 (referred to herein as hSIRPα.50A.H1L4)
SEQ ID NO: 10/SEQ ID NO: 28 (referred to herein as hSIRPα.50A.H1L5)
SEQ ID NO: 12/SEQ ID NO: 20 (referred to herein as hSIRPα.50A.H2L1)
SEQ ID NO: 12/SEQ ID NO: 22 (referred to herein as hSIRPα.50A.H2L2)
SEQ ID NO: 12/SEQ ID NO: 24 (referred to herein as hSIRPα.50A.H2L3)
SEQ ID NO: 12/SEQ ID NO: 26 (referred to herein as hSIRPα.50A.H2L4)
SEQ ID NO: 12/SEQ ID NO: 28 (referred to herein as hSIRPα.50A.H2L5)
SEQ ID NO: 14/SEQ ID NO: 20 (referred to herein as hSIRPα.50A.H3L1)
SEQ ID NO: 14/SEQ ID NO: 22 (referred to herein as hSIRPα.50A.H3L2)
SEQ ID NO: 14/SEQ ID NO: 24 (referred to herein as hSIRPα.50A.H3L3)
SEQ ID NO: 14/SEQ ID NO: 26 (referred to herein as hSIRPα.50A.H3L4)
SEQ ID NO: 14/SEQ ID NO: 28 (referred to herein as hSIRPα.50A.H3L5)
SEQ ID NO: 16/SEQ ID NO: 20 (referred to herein as hSIRPα.50A.H4L1)
SEQ ID NO: 16/SEQ ID NO: 22 (referred to herein as hSIRPα.50A.H4L2)
SEQ ID NO: 16/SEQ ID NO: 24 (referred to herein as hSIRPα.50A.H4L3)
SEQ ID NO: 16/SEQ ID NO: 26 (referred to herein as hSIRPα.50A.H4L4)
SEQ ID NO: 16/SEQ ID NO: 28 (referred to herein as hSIRPα.50A.H4L5)
SEQ ID NO: 18/SEQ ID NO: 20 (referred to herein as hSIRPα.50A.H5L1)
SEQ ID NO: 18/SEQ ID NO: 22 (referred to herein as hSIRPα.50A.H5L2)
SEQ ID NO: 18/SEQ ID NO: 24 (referred to herein as hSIRPα.50A.H5L3)
SEQ ID NO: 18/SEQ ID NO: 26 (referred to herein as hSIRPα.50A.H5L4)
SEQ ID NO: 18/SEQ ID NO: 28 (referred to herein as hSIRPα.50A.H5L5)
SEQ ID NO: 78/SEQ ID NO: 90 (referred to herein as hSIRPα.40A.H1L1)
SEQ ID NO: 78/SEQ ID NO: 92 (referred to herein as hSIRPα.40A.H1L2)
SEQ ID NO: 78/SEQ ID NO: 94 (referred to herein as hSIRPα.40A.H1L3)
SEQ ID NO: 78/SEQ ID NO: 96 (referred to herein as hSIRPα.40A.H1L4)
SEQ ID NO: 78/SEQ ID NO: 98 (referred to herein as hSIRPα.40A.H1L5)
SEQ ID NO: 78/SEQ ID NO: 100 (referred to herein as hSIRPα.40A.H1L6)
SEQ ID NO: 80/SEQ ID NO: 90 (referred to herein as hSIRPα.40A.H2L1)
SEQ ID NO: 80/SEQ ID NO: 92 (referred to herein as hSIRPα.40A.H2L2)
SEQ ID NO: 80/SEQ ID NO: 94 (referred to herein as hSIRPα.40A.H2L3)
SEQ ID NO: 80/SEQ ID NO: 96 (referred to herein as hSIRPα.40A.H2L4)
SEQ ID NO: 80/SEQ ID NO: 98 (referred to herein as hSIRPα.40A.H2L5)
SEQ ID NO: 80/SEQ ID NO: 100 (referred to herein as hSIRPα.40A.H2L6)
SEQ ID NO: 82/SEQ ID NO: 90 (referred to herein as hSIRPα.40A.H3L1)
SEQ ID NO: 82/SEQ ID NO: 92 (referred to herein as hSIRPα.40A.H3L2)
SEQ ID NO: 82/SEQ ID NO: 94 (referred to herein as hSIRPα.40A.H3L3)
SEQ ID NO: 82/SEQ ID NO: 96 (referred to herein as hSIRPα.40A.H3L4)
SEQ ID NO: 82/SEQ ID NO: 98 (referred to herein as hSIRPα.40A.H3L5)
SEQ ID NO: 82/SEQ ID NO: 100 (referred to herein as hSIRPα.40A.H3L6)
SEQ ID NO: 84/SEQ ID NO: 90 (referred to herein as hSIRPα.40A.H4L1)
SEQ ID NO: 84/SEQ ID NO: 92 (referred to herein as hSIRPα.40A.H4L2)
SEQ ID NO: 84/SEQ ID NO: 94 (referred to herein as hSIRPα.40A.H4L3)
SEQ ID NO: 84/SEQ ID NO: 96 (referred to herein as hSIRPα.40A.H4L4)
SEQ ID NO: 84/SEQ ID NO: 98 (referred to herein as hSIRPα.40A.H4L5)
SEQ ID NO: 84/SEQ ID NO: 100 (referred to herein as hSIRPα.40A.H4L6)
SEQ ID NO: 86/SEQ ID NO: 90 (referred to herein as hSIRPα.40A.H5L1)
SEQ ID NO: 86/SEQ ID NO: 92 (referred to herein as hSIRPα.40A.H5L2)
SEQ ID NO: 86/SEQ ID NO: 94 (referred to herein as hSIRPα.40A.H5L3)
SEQ ID NO: 86/SEQ ID NO: 96 (referred to herein as hSIRPα.40A.H5L4)
SEQ ID NO: 86/SEQ ID NO: 98 (referred to herein as hSIRPα.40A.H5L5)
SEQ ID NO: 86/SEQ ID NO: 100 (referred to herein as hSIRPα.40A.H5L6)
SEQ ID NO: 88/SEQ ID NO: 90 (referred to herein as hSIRPα.40A.H6L1)
SEQ ID NO: 88/SEQ ID NO: 92 (referred to herein as hSIRPα.40A.H6L2)
SEQ ID NO: 88/SEQ ID NO: 94 (referred to herein as hSIRPα.40A.H6L3)
SEQ ID NO: 88/SEQ ID NO: 96 (referred to herein as hSIRPα.40A.H6L4)
SEQ ID NO: 88/SEQ ID NO: 98 (referred to herein as hSIRPα.40A.H6L5)
SEQ ID NO: 88/SEQ ID NO: 100 (referred to herein as hSIRPα.40A.H6L6).

There are several methods available for mapping antibody epitopes on target antigens, including: H/D-Ex mass spectrometry, crosslinking coupled mass spectrometry, X-ray crystallography, pepscan analysis and site directed mutagenesis. For example, HDX (Hydrogen Deuterium Exchange) coupled with proteolysis and mass spectrometry can be used to determine the epitope of an antibody on a specific antigen Y. HDX-MS relies on the accurate measurement and comparison of the degree of deuterium incorporation by an antigen when incubated in $D_2O$ on its own and in presence of its antibody at various time intervals. Deuterium is exchanged with hydrogen on the amide backbone of the proteins in exposed areas whereas regions of the antigen bound to the antibody will be protected and will show less or no exchange after analysis by LC-MS/MS of proteolytic fragments. Crosslinking coupled mass spectrometry begins by binding the antibody and the antigen with a mass labeled chemical crosslinker. Next the presence of the complex is confirmed using high mass MALDI detection. Because after crosslinking chemistry the Ab/Ag complex is extremely stable, many various enzymes and digestion conditions can be applied to the complex to provide many different overlapping peptides. Identification of these peptides is performed using high resolution mass spectrometry and MS/MS techniques. Identification of the crosslinked peptides is determined using mass tag linked to the cross-linking reagents. After MS/MS fragmentation and data analysis, both epitope and paratope are determined in the same experiment.

The scope of the present invention also includes isolated anti-SIRPα antibodies and antigen-binding fragments thereof (e.g., humanized antibodies), comprising a variant of an immunoglobulin chain set forth herein, wherein the variant exhibits one or more of the following properties:

- binds human SIRPαV1 protein having the sequence of SEQ ID NO: 34 with an $EC_{50}$<1 nM; and exhibits at least a 100-fold higher $EC_{50}$ for SIRPαV1(P74A) having the sequence of SEQ ID NO: 62; and optionally also at least a 100-fold higher $EC_{50}$ for human SIRPβ1 protein having the sequence of SEQ ID NO: 38 (in each case wherein the reduced $EC_{50}$ is relative to the $EC_{50}$ for human SIRPαV1 protein having the sequence of SEQ ID NO: 34, and in each case preferably when measured by cellular ELISA (CELISA) as described hereinafter;
- binds to a cell expressing human SIRPαV1 protein with an $EC_{50}$<10 nM, preferably <5 nM, more preferably <1.5 nM, still more preferably <1.0 nM, even more preferably <0.5 nM, and most preferably about 0.3 nM or less;
- binds to a cell expressing human SIRPαV2 protein with an $EC_{50}$<10 nM, preferably <5 nM, more preferably <1.5 nM, still more preferably <1.0 nM, even more preferably <0.5 nM, and most preferably about 0.3 nM or less;
- does not appreciably bind to SIRPβ1 protein at an antibody concentration of 50 nM, preferably 67 nM, and more preferably 100 nM; or alternatively at a concentration that is 10-fold greater, preferably 50-fold greater, more preferably 100-fold greater, and still more preferably 200-fold greater than the antibody's $EC_{50}$ for SIRPαV1 or SIRPαV2;
- inhibits binding between human SIRPα and CD47 with an $IC_{50}$<10.0 nM, more preferably <5.0 nM, still more preferably <2.5 nM, and most preferably about 1.0 nM or less; and
- exhibits a T20 "humanness" of at least 79, and more preferably 85%.

In other embodiments, the invention provides antibodies or antigen-binding fragment thereof that bind human SIRPα (e.g., humanized antibodies) and have $V_H$ domains and $V_L$ domains with at least 90% sequence identity with SEQ ID NOs: 75, 78, 80, 82, 84, 86, 88, 102, 7, 10, 12, 14, 16, 18, and 30; and 76, 90, 92, 94, 96, 98, 100, 104, 8, 20, 22, 24, 26, 28, and 32. In other embodiments, the invention provides antibodies or antigen-binding fragment thereof that bind human SIRPα (e.g., humanized antibodies) and have $V_H$ domains and $V_L$ domains with at least 95% sequence identity with SEQ ID NOs: 75, 78, 80, 82, 84, 86, 88, 102, 7, 10, 12, 14, 16, 18, and 30; and 76, 90, 92, 94, 96, 98, 100, 104, 8, 20, 22, 24, 26, 28, and 32. In other embodiments, the invention provides antibodies or antigen-binding fragment thereof that bind human SIRPα (e.g., humanized antibodies) and have $V_H$ domains and $V_L$ domains with at least 97% sequence identity with SEQ ID NOs: 75, 78, 80, 82, 84, 86, 88, 102, 7, 10, 12, 14, 16, 18, and 30; and 76, 90, 92, 94, 96, 98, 100, 104, 8, 20, 22, 24, 26, 28, and 32. In other embodiments, the invention provides antibodies or antigen-binding fragment thereof that bind human SIRPα (e.g., humanized antibodies) and have $V_H$ domains and $V_L$ domains with at least 98% sequence identity with SEQ ID NOs: 75, 78, 80, 82, 84, 86, 88, 102, 7, 10, 12, 14, 16, 18, and 30; and 76, 90, 92, 94, 96, 98, 100, 104, 8, 20, 22, 24, 26, 28, and 32. In other embodiments, the invention provides antibodies or antigen-binding fragment thereof that bind human SIRPα (e.g., humanized antibodies) and have $V_H$ domains and $V_L$ domains with at least 99% sequence identity with SEQ ID NOs: 75, 78, 80, 82, 84, 86, 88, 102, 7, 10, 12, 14, 16, 18, and 30; and 76, 90, 92, 94, 96, 98, 100, 104, 8, 20, 22, 24, 26, 28, and 32. Preferably, in each case, the sequence differences between SEQ ID NOs: 75, 78, 80, 82, 84, 86, 88, 102, 7, 10, 12, 14, 16, 18, and 30; and 76, 90, 92, 94, 96, 98, 100, 104, 8, 20, 22, 24, 26, 28, and 32 and the variants consist of conservative substitutions and are most preferably limited to substitutions within the framework residues.

The following references relate to BLAST algorithms often used for sequence analysis: BLAST ALGORITHMS: Camacho, C. et al. (2009): *BMC Bioinformatics* 10:421; Altschul et al. (2005) *FEBS J.* 272(20): 5101-5109; Altschul, S. F., et al., (1990) *J. Mol. Biol.* 215:403-410; Gish, W., et al., (1993) *Nature Genet.* 3:266-272; Madden, T. L., et al., (1996) *Meth. Enzymol.* 266:131-141; Altschul, S. F., et al., (1997) *Nucleic Acids Res.* 25:3389-3402; Zhang, J., et al., (1997) *Genome Res.* 7:649-656; Wootton, J. C., et al., (1993) *Comput. Chem.* 17:149-163; Hancock, J. M. et al., (1994) *Comput. Appl. Biosci.* 10:67-70; ALIGNMENT SCORING SYSTEMS: Dayhoff, M. O., et al., "A model of evolutionary change in proteins." in *Atlas of Protein Sequence and Structure*, (1978) vol. 5, suppl. 3. M. O. Dayhoff (ed.), pp. 345-352, Natl. Biomed. Res. Found., Washington, D.C.; Schwartz, R. M., et al., "Matrices for detecting distant relationships." in *Atlas of Protein Sequence and Structure*, (1978) vol. 5, suppl. 3." M. O. Dayhoff (ed.), pp. 353-358, Natl. Biomed. Res. Found., Washington, D.C.; Altschul, S. F., (1991) *J. Mol. Biol.* 219:555-565; States, D. J., et al., (1991) *Methods* 3:66-70; Henikoff, S., et al., (1992) *Proc. Natl. Acad. Sci. USA* 89:10915-10919; Altschul, S. F., et al., (1993) *J. Mol. Evol.* 36:290-300; ALIGNMENT STATISTICS: Karlin, S., et al., (1990) *Proc. Natl. Acad. Sci. USA* 87:2264-2268; Karlin, S., et al., (1993) *Proc. Natl. Acad. Sci. USA* 90:5873-5877; Dembo, A., et al., (1994) *Ann. Prob.* 22:2022-2039; and Altschul, S. F. "Evaluating the statistical significance of multiple distinct local alignments." in *Theoretical and Computational Methods in Genome Research* (S. Suhai, ed.), (1997) pp. 1-14, Plenum, New York. In the present application, percent identity comparisons are preferably performed by a BLAST algorithm wherein the parameters of the algorithm are selected to give the largest match between the respective sequences over the entire length of the respective reference sequences (e.g. expect threshold: 10; word size: 6; max matches in a query range: 0; BLOSUM 62 matrix; gap costs: existence 11, extension 1; conditional compositional score matrix adjustment).

"Conservatively modified variants" or "conservative substitution" refers to substitutions of amino acids in a protein with other amino acids having similar characteristics (e.g. charge, side-chain size, hydrophobicity/hydrophilicity, backbone conformation and rigidity, etc.), such that the changes can frequently be made without altering the biological activity of the protein. Those of skill in this art recognize that, in general, single amino acid substitutions in non-essential regions of a polypeptide do not substantially alter biological activity (see, e.g., Watson et al. (1987) *Molecular Biology of the Gene*, The Benjamin/Cummings Pub. Co., p. 224 (4th Ed.)). In addition, substitutions of structurally or functionally similar amino acids are less likely to disrupt biological activity. Exemplary conservative substitutions are set forth the following Table 1.

TABLE 1

Exemplary Conservative Amino Acid Substitutions

| Original residue | Conservative substitution |
| --- | --- |
| Ala (A) | Gly; Ser |
| Arg (R) | Lys; His |
| Asn (N) | Gln; His |
| Asp (D) | Glu; Asn |
| Cys (C) | Ser; Ala |
| Gln (Q) | Asn |
| Glu (E) | Asp; Gln |
| Gly (G) | Ala |
| His (H) | Asn; Gln |
| Ile (I) | Leu; Val |
| Leu (L) | Ile; Val |
| Lys (K) | Arg; His |
| Met (M) | Leu; Ile; Tyr |
| Phe (F) | Tyr; Met; Leu |
| Pro (P) | Ala |
| Ser (S) | Thr |
| Thr (T) | Ser |
| Trp (W) | Tyr; Phe |
| Tyr (Y) | Trp; Phe |
| Val (V) | Ile; Leu |

Function-conservative variants of the antibodies of the invention are also contemplated by the present invention. "Function-conservative variants," as used herein, refers to antibodies or fragments in which one or more amino acid residues have been changed without altering a desired property, such an antigen affinity and/or specificity. Such variants include, but are not limited to, replacement of an amino acid with one having similar properties, such as the conservative amino acid substitutions of Table 1. Also provided are isolated polypeptides comprising the $V_L$ domains of the anti-SIRPα antibodies of the invention (e.g., SEQ ID NOs: 76, 90, 92, 94, 96, 98, 100, 8, 20, 22, 24, 26, 28, and 32), and isolated polypeptides comprising the $V_H$ domains of the anti-SIRPα antibodies of the invention (e.g., SEQ ID NOs: 75, 78, 80, 82, 84, 86, 88, 7, 10, 12, 14, 16, 18, and 30) having up to 0, 1, 2, 3, 4, 5, 6, 7, 8, 9, 10 or more amino acid substitutions, and preferably conservative substitutions.

The present invention further comprises the polynucleotides encoding any of the polypeptides or immunoglobulin chains of anti-SIRPα antibodies and antigen-binding fragments thereof of the invention. For example, the present invention includes the polynucleotides encoding the amino acids described in any one of SEQ ID NOs: 75, 78, 80, 82, 84, 86, 88, 102, 7, 10, 12, 14, 16, 18, and 30; and SEQ ID NOs: 76, 90, 92, 94, 96, 98, 100, 104, 8, 20, 22, 24, 26, 28, and 32.

In one embodiment, an isolated polynucleotide, for example DNA, encoding the polypeptide chains of the isolated antibodies or antigen-binding fragments set forth herein is provided. In one embodiment, the isolated polynucleotide encodes an antibody or antigen-binding fragment thereof comprising at least one mature immunoglobulin light chain variable (VL) domain according to the invention and/or at least one mature immunoglobulin heavy chain variable (VH) domain according to the invention. In some embodiments, the isolated polynucleotide encodes both a light chain and a heavy chain on a single polynucleotide molecule, and in other embodiments the light and heavy chains are encoded on separate polynucleotide molecules. In another embodiment, the polynucleotides further encodes a signal sequence.

This present invention also provides vectors, e.g., expression vectors, such as plasmids, comprising the isolated polynucleotides of the invention, wherein the polynucleotide is operably linked to control sequences that are recognized by a host cell when the host cell is transfected with the vector. Also provided are host cells comprising a vector of the present invention and methods for producing the antibody or antigen-binding fragment thereof or polypeptide disclosed herein comprising culturing a host cell harboring an expression vector or a nucleic acid encoding the immunoglobulin chains of the antibody or antigen-binding fragment thereof in culture medium, and isolating the antigen or antigen-binding fragment thereof from the host cell or culture medium.

Binding Affinity

By way of example, and not limitation, the antibodies and antigen-binding fragments disclosed herein may hind human SIRPα bivalently with a KD value of 10×10-9 M or lower) as determined by surface plasmon resonance (e.g., BIACORE™) or a similar technique (e.g. KinExa® or bio-layer interferometry (OCTET®)). In one embodiment, the antibodies and antigen-binding fragments disclosed herein may bind human SIRPα or bivalently with a KD value of about 5-10×10-9 M as determined by surface plasmon resonance (e.g., BIACORE™) or a similar technique (e.g. KinExa® or OCTET®). Affinity is calculated as KD=koff/kon (koff is the dissociation rate constant, Kon is the association rate constant and KD is the equilibrium constant). Affinity can be determined at equilibrium by measuring the fraction bound (r) of labeled ligand at various concentrations (c). The data are graphed using the Scatchard equation: r/c=K(n−r): where r=moles of hound ligand/mole of receptor at equilibrium; c=free ligand concentration at equilibrium; K=equilibrium association constant; and n=number of ligand binding sites per receptor molecule. By graphical analysis, r/c is plotted on the Y-axis versus r on the X-axis, thus producing a Scatchard plot. Antibody affinity measurement by Scatchard analysis is well known in the art. See, e.g., van Erp et al., J. Immunoassay 12: 425-43, 1991; Nelson and Griswold, Comput. Methods Programs Biomed. 27: 65-8, 1988.

Humanness

For purposes of this document, "humanness" is measured using the T20 score analyzer to quantify the humanness of the variable region of monoclonal antibodies as described in Gao S H, Huang K, Tu H, Adler A S. Monoclonal antibody humanness score and its applications. *BMC Biotechnology.* 2013: 13:55. doi: 10.1186/1472-6750-13-55).

A web-based tool is provided to calculate the T20 score of antibody sequences using the T20 Cutoff Human Databases: http://abAnalyzer.lakepharma.com. In computing a T20 score, an input VH, VK, or VL variable region protein sequence is first assigned Kabat numbering, and CDR residues are identified. The full-length sequence or the framework only sequence (with CDR residues removed) is compared to every sequence in a respective antibody database using the blastp protein-protein BLAST algorithm. The sequence identity between each pairwise comparison is isolated, and after every sequence in the database has been analyzed, the sequences are sorted from high to low based on the sequence identity to the input sequence. The percent identity of the Top 20 matched sequences is averaged to obtain the T20 score.

For each chain type (VH, VK, VL) and sequence length (full-length or framework only) in the "All Human Databases," each antibody sequence was scored with its respective database using the T20 score analyzer. The T20 score was obtained for the top 20 matched sequences after the input sequence itself was excluded (the percent identity of sequences 2 through 21 were averaged since sequence 1 was always the input antibody itself). The T20 scores for each group were sorted from high to low. The decrease in score was roughly linear for most of the sequences; however the T20 scores for the bottom ~15% of antibodies started decreasing sharply. Therefore, the bottom 15 percent of sequences were removed and the remaining sequences formed the T20 Cutoff Human Databases, where the T20 score cutoff indicates the lowest T20 score of a sequence in the new database.

As used herein, a "Human" antibody is one that has a T20 humanness score of at least 79%, and more preferably at least 85%.

Ability of Anti-hSIRPα Antibodies to Block Binding to CD47

In some embodiments, the anti-SIRPα antibodies or antigen binding fragments of the invention are able to block binding of human SIRPα to human CD47. The ability to block binding of human SIRPα to human CD47 can be determined using any method known in the art. In one embodiment, the ability of the antibodies to block binding of human SIRPα to human CD47 is determined using an ELISA assay.

Methods of Making Antibodies and Antigen-Binding Fragments Thereof

Thus, the present invention includes methods for making an anti-SIRPα antibody or antigen-binding fragment thereof of the present invention comprising culturing a hybridoma cell that expresses the antibody or fragment under condition favorable to such expression and, optionally, isolating the antibody or fragment from the hybridoma and/or the growth medium (e.g. cell culture medium).

The anti-SIRPα antibodies disclosed herein may also be produced recombinantly (e.g., in an *E. coli*/T7 expression system, a mammalian cell expression system or a lower eukaryote expression system). In this embodiment, nucleic acids encoding the antibody immunoglobulin molecules of the invention (e.g., $V_H$ or $V_L$) may be inserted into a pET-based plasmid and expressed in the *E. coli*/T7 system. For example, the present invention includes methods for expressing an antibody or antigen-binding fragment thereof or immunoglobulin chain thereof in a host cell (e.g., bacterial host cell such as *E. coli* such as BL21 or BL21DE3) comprising expressing T7 RNA polymerase in the cell which also includes a polynucleotide encoding an immunoglobulin chain that is operably linked to a T7 promoter. For example, in an embodiment of the invention, a bacterial host cell, such as a *E. coli*, includes a polynucleotide encoding the T7 RNA polymerase gene operably linked to a lac promoter and expression of the polymerase and the chain is induced by incubation of the host cell with IPTG (isopropyl-beta-D-thiogalactopyranoside).

There are several methods by which to produce recombinant antibodies which are known in the art. One example of a method for recombinant production of antibodies is disclosed in U.S. Pat. No. 4,816,567.

Transformation can be by any known method for introducing polynucleotides into a host cell. Methods for introduction of heterologous polynucleotides into mammalian cells are well known in the art and include dextran-mediated transfection, calcium phosphate precipitation, polybrene-mediated transfection, protoplast fusion, electroporation, encapsulation of the polynucleotide(s) in liposomes, biolistic injection and direct microinjection of the DNA into nuclei. In addition, nucleic acid molecules may be introduced into mammalian cells by viral vectors. Methods of transforming cells are well known in the art. See, for example, U.S. Pat. Nos. 4,399,216; 4,912,040; 4,740,461 and 4,959,455.

Thus, the present invention includes recombinant methods for making an anti-SIRPα antibody or antigen-binding fragment thereof of the present invention, or an immunoglobulin chain thereof, comprising introducing a polynucleotide encoding one or more immunoglobulin chains of the antibody or fragment (e.g., heavy and/or light immunoglobulin chain); culturing the host cell (e.g., CHO or *Pichia* or *Pichia pastoris*) under condition favorable to such expression and, optionally, isolating the antibody or fragment or chain from the host cell and/or medium in which the host cell is grown.

Anti-SIRPα antibodies can also be synthesized by any of the methods set forth in U.S. Pat. No. 6,331,415.

Eukaryotic and prokaryotic host cells, including mammalian cells as hosts for expression of the antibodies or fragments or immunoglobulin chains disclosed herein are well known in the art and include many immortalized cell lines available from the American Type Culture Collection (ATCC). These include, inter alia, Chinese hamster ovary (CHO) cells, NSO, SP2 cells, HeLa cells, baby hamster kidney (BHK) cells, monkey kidney cells (COS), human hepatocellular carcinoma cells (e.g., Hep G2), A549 cells, 3T3 cells, HEK-293 cells and a number of other cell lines. Mammalian host cells include human, mouse, rat, dog, monkey, pig, goat, bovine, horse and hamster cells. Cell lines of particular preference are selected through determining which cell lines have high expression levels. Other cell lines that may be used are insect cell lines, such as Sf9 cells, amphibian cells, bacterial cells, plant cells and fungal cells. Fungal cells include yeast and filamentous fungus cells including, for example, *Pichia pastoris, Pichia finlandica, Pichia trehalophila, Pichia koclamae, Pichia membranaefaciens, Pichia minuta* (*Ogataea minuta, Pichia lindneri*), *Pichia opuntiae, Pichia thermotolerans, Pichia salictaria, Pichia guercuum, Pichia pijperi, Pichia stiptis, Pichia methanolica, Pichia* sp., *Saccharomyces cerevisiae, Saccharomyces* sp., *Hansenula polymorpha, Kluyveromyces* sp., *Kluyveromyces lactis, Candida albicans, Aspergillus nidu-*

*lans, Aspergillus niger, Aspergillus oryzae, Trichoderma reesei, Chrysosporium lucknowense, Fusarium* sp., *Fusarium gramineum, Fusarium venenatum, Physcomitrella patens* and *Neurospora crassa. Pichia* sp., any *Saccharomyces* sp., *Hansenula polymorpha*, any *Kluyveromyces* sp., *Candida albicans*, any *Aspergillus* sp., *Trichoderma reesei, Chrysosporium lucknowense*, any *Fusarium* sp., *Yarrowia lipolytica*, and *Neurospora crassa*. When recombinant expression vectors encoding the heavy chain or antigen-binding portion or fragment thereof, and/or the light chain or antigen-binding fragment thereof are introduced into mammalian host cells, the antibodies are produced by culturing the host cells for a period of time sufficient to allow for expression of the antibody or fragment or chain in the host cells or secretion into the culture medium in which the host cells are grown.

Antibodies and antigen-binding fragments thereof and immunoglobulin chains can be recovered from the culture medium using standard protein purification methods. Further, expression of antibodies and antigen-binding fragments thereof and immunoglobulin chains of the invention (or other moieties therefrom) from production cell lines can be enhanced using a number of known techniques. For example, the glutamine synthetase gene expression system (the GS system) is a common approach for enhancing expression under certain conditions. The GS system is discussed in whole or part in connection with European Patent Nos. 0216846, 0256055, and 0323997 and 0338841. Thus, in an embodiment of the invention, the mammalian host cells (e.g., CHO) lack a glutamine synthetase gene and are grown in the absence of glutamine in the medium wherein, however, the polynucleotide encoding the immunoglobulin chain comprises a glutamine synthetase gene which complements the lack of the gene in the host cell.

The present invention includes methods for purifying an anti-SIRPα antibody or antigen-binding fragment thereof of the present invention comprising introducing a sample comprising the antibody or fragment to a purification medium (e.g., cation exchange medium, anion exchange medium, hydrophobic exchange medium, affinity purification medium (e.g., protein-A, protein-G, protein-A/G, protein-L)) and either collecting purified antibody or fragment from the flow-through fraction of said sample that does not bind to the medium; or, discarding the flow-through fraction and eluting bound antibody or fragment from the medium and collecting the eluate. In an embodiment of the invention, the medium is in a column to which the sample is applied. In an embodiment of the invention, the purification method is conducted following recombinant expression of the antibody or fragment in a host cell, e.g., wherein the host cell is first lysed and, optionally, the lysate is purified of insoluble materials prior to purification on a medium.

In general, glycoproteins produced in a particular cell line or transgenic animal will have a glycosylation pattern that is characteristic for glycoproteins produced in the cell line or transgenic animal. Therefore, the particular glycosylation pattern of an antibody will depend on the particular cell line or transgenic animal used to produce the antibody. However, all antibodies encoded by the nucleic acid molecules provided herein, or comprising the amino acid sequences provided herein, comprise the instant invention, independent of the glycosylation pattern the antibodies may have. Similarly, in particular embodiments, antibodies with a glycosylation pattern comprising only non-fucosylated N-glycans may be advantageous, because these antibodies have been shown to typically exhibit more potent efficacy than their fucosylated counterparts both in vitro and in vivo (See for example, Shinkawa et al., *J. Biol. Chem.* 278: 3466-3473 (2003); U.S. Pat. Nos. 6,946,292 and 7,214,775). These antibodies with non-fucosylated N-glycans are not likely to be immunogenic because their carbohydrate structures are a normal component of the population that exists in human serum IgG.

The present invention includes bispecific and bifunctional antibodies and antigen-binding fragments having a binding specificity for SIRPα and another antigen such as, for example, CD19, CD20, CD22, CD24, CD25, CD30, CD33, CD38, CD44, CD52, CD56, CD70, CD96, CD97, CD99, CD117, CD123, c-Met, CEA, EGFR, EpCAM, HER2, HER3, PSMA, PTHR2, mesothelin, PD-1, PD-L1, TIM3, and methods of use thereof. A bispecific or bifunctional antibody is an artificial hybrid antibody having two different heavy/light chain pairs and two different binding sites. Bispecific antibodies can be produced by a variety of methods including fusion of hybridomas or linking of Fab' fragments. See, e.g., Songsivilai, et al., (1990) *Clin. Exp. Immunol.* 79: 315-321, Kostelny, et al., (1992) *J Immunol.* 148:1547-1553. In addition, bispecific antibodies may be formed as "diabodies" (Holliger, et al., (1993) *PNAS USA* 90:6444-6448) or as "Janusins" (Traunecker, et al., (1991) *EMBO J.* 10:3655-3659 and Traunecker, et al., (1992) *Int. J. Cancer* Suppl. 7:51-52). Included are "Duobodies," which are bispecific antibodies with normal IgG structures (Labrijn et al., 2013, *Proc. Natl. Acad. Sci. USA* 110 (13): 5145-5150).

The present invention further includes anti-SIRPα antigen-binding fragments of the anti-SIRPα antibodies disclosed herein. The antibody fragments include $F(ab)_2$ fragments, which may be produced by enzymatic cleavage of an IgG by, for example, pepsin. Fab fragments may be produced by, for example, reduction of $F(ab)_2$ with dithiothreitol or mercaptoethylamine.

Immunoglobulins may be assigned to different classes depending on the amino acid sequences of the constant domain of their heavy chains. In some embodiments, different constant domains may be appended to humanized $V_L$ and $V_H$ regions derived from the CDRs provided herein. There are at least five major classes of immunoglobulins: IgA, IgD, IgE, IgG and IgM, and several of these may be further divided into subclasses (isotypes), e.g. IgG1, IgG2, IgG3 and IgG4; IgA1 and IgA2. The invention comprises antibodies and antigen-binding fragments of any of these classes or subclasses of antibodies.

In one embodiment, the antibody or antigen-binding fragment comprises a heavy chain constant region, e.g. a human constant region, such as γ1, γ2, γ3, or γ4 human heavy chain constant region or a variant thereof. In another embodiment, the antibody or antigen-binding fragment comprises a light chain constant region, e.g. a human light chain constant region, such as lambda or kappa human light chain region or variant thereof. By way of example, and not limitation the human heavy chain constant region can be γ4 and the human light chain constant region can be kappa. In an alternative embodiment, the Fc region of the antibody is γ4 with a Ser228Pro mutation (Schuurman, J et. al., *Mol. Immunol.* 38: 1-8, 2001).

In one embodiment, the antibody or antigen-binding fragment comprises a heavy chain constant region of the IgG1 subtype. In one embodiment, the antibody or antigen-binding fragment comprises a heavy chain constant region of the IgG2 subtype. In one embodiment, the antibody or antigen-binding fragment comprises a heavy chain constant region of the IgG4 subtype.

Antibody Engineering

Further included are embodiments in which the anti-SIRPα antibodies and antigen-binding fragments thereof are engineered antibodies to include modifications to framework residues within the variable domains the antibody, e.g. to improve the properties of the antibody or fragment. Typically, such framework modifications are made to decrease the immunogenicity of the antibody or fragment. This is usually accomplished by replacing non-CDR residues in the variable domains (i.e. framework residues) in a parental (e.g. rodent) antibody or fragment with analogous residues from the immune repertoire of the species in which the antibody is to be used, e.g. human residues in the case of human therapeutics. Such an antibody or fragment is referred to as a "humanized" antibody or fragment. In some cases, it is desirable to increase the affinity, or alter the specificity of an engineered (e.g. humanized) antibody. One approach is to mutate one or more framework residues to the corresponding germline sequence. More specifically, an antibody or fragment that has undergone somatic mutation can contain framework residues that differ from the germline sequence from which the antibody is derived. Such residues can be identified by comparing the antibody or fragment framework sequences to the germline sequences from which the antibody or fragment is derived. Another approach is to revert to the original parental (e.g., rodent) residue at one or more positions of the engineered (e.g. humanized) antibody, e.g. to restore binding affinity that may have been lost in the process of replacing the framework residues. (See, e.g., U.S. Pat. Nos. 5,693,762, 5,585,089 and 5,530,101).

In certain embodiments, the anti-SIRPα antibodies and antigen-binding fragments thereof are engineered (e.g. humanized) to include modifications in the framework and/or CDRs to improve their properties. Such engineered changes can be based on molecular modelling. A molecular model for the variable region for the parental (non-human) antibody sequence can be constructed to understand the structural features of the antibody and used to identify potential regions on the antibody that can interact with the antigen. Conventional CDRs are based on alignment of immunoglobulin sequences and identifying variable regions. Kabat et al., (1991) Sequences of Proteins of Immunological Interest, Kabat, et al.; National Institutes of Health, Bethesda, Md.; 5$^{th}$ ed.; NIH Publ. No. 91-3242; Kabat (1978) Adv. Prot. Chem. 32:1-75; Kabat, et al., (1977) J. Biol. Chem. 252:6609-6616. Chothia and coworkers carefully examined conformations of the loops in crystal structures of antibodies and proposed hypervariable loops. Chothia, et al., (1987) J Mol. Biol. 196:901-917 or Chothia, et al., (1989) Nature 342:878-883. There are variations between regions classified as "CDRs" and "hypervariable loops". Later studies (Raghunathan et al, (2012) J. Mol Recog. 25, 3, 103-113) analyzed several antibody-antigen crystal complexes and observed that the antigen binding regions in antibodies do not necessarily conform strictly to the "CDR" residues or "hypervariable" loops. The molecular model for the variable region of the non-human antibody can be used to guide the selection of regions that can potentially bind to the antigen. In practice the potential antigen binding regions based on the model differ from the conventional "CDR"s or "hypervariable" loops. Commercial scientific software such as Discovery Studio (BIOVIA, Dassault Systems)) can be used for molecular modeling. Human frameworks can be selected based on best matches with the non-human sequence both in the frameworks and in the CDRs. For FR4 (framework 4) in VH, VJ regions for the human germlines are compared with the corresponding non-human region. In the case of FR4 (framework 4) in VL, J-kappa and J-Lambda regions of human germline sequences are compared with the corresponding non-human region. Once suitable human frameworks are identified, the CDRs are grafted into the selected human frameworks. In some cases, certain residues in the VL-VH interface can be retained as in the non-human (parental) sequence. Molecular models can also be used for identifying residues that can potentially alter the CDR conformations and hence binding to antigen. In some cases, these residues are retained as in the non-human (parental) sequence. Molecular models can also be used to identify solvent exposed amino acids that can result in unwanted effects such as glycosylation, deamidation and oxidation. Developability filters can be introduced early on in the design stage to eliminate/minimize these potential problems.

Another type of framework modification involves mutating one or more residues within the framework region, or even within one or more CDR regions, to remove T cell epitopes to thereby reduce the potential immunogenicity of the antibody. This approach is also referred to as "deimmunization" and is described in further detail in U.S. Pat. No. 7,125,689.

In particular embodiments, it will be desirable to change certain amino acids containing exposed side-chains to another amino acid residue in order to provide for greater chemical stability of the final antibody, so as to avoid deamidation or isomerization. The deamidation of asparagine may occur on NG, DG, NG, NS, NA, NT, QG or QS sequences and result in the creation of an isoaspartic acid residue that introduces a kink into the polypeptide chain and decreases its stability (isoaspartic acid effect). Isomerization can occur at DG, DS, DA or DT sequences. In certain embodiments, the antibodies of the present disclosure do not contain deamidation or asparagine isomerism sites.

For example, an asparagine (Asn) residue may be changed to Gln or Ala to reduce the potential for formation of isoaspartate at any Asn-Gly sequences, particularly within a CDR. A similar problem may occur at a Asp-Gly sequence. Reissner and Aswad (2003) Cell. Mol. Life Sci. 60:1281. Isoaspartate formation may debilitate or completely abrogate binding of an antibody to its target antigen. See, Presta (2005) J. Allergy Clin. Immunol. 116:731 at 734. In one embodiment, the asparagine is changed to glutamine (Gln). It may also be desirable to alter an amino acid adjacent to an asparagine (Asn) or glutamine (Gln) residue to reduce the likelihood of deamidation, which occurs at greater rates when small amino acids occur adjacent to asparagine or glutamine. See, Bischoff & Kolbe (1994) J. Chromatog. 662:261. In addition, any methionine residues (typically solvent exposed Met) in CDRs may be changed to Lys, Leu, Ala, or Phe or other amino acids in order to reduce the possibility that the methionine sulfur would oxidize, which could reduce antigen-binding affinity and also contribute to molecular heterogeneity in the final antibody preparation. Id. Additionally, in order to prevent or minimize potential scissile Asn-Pro peptide bonds, it may be desirable to alter any Asn-Pro combinations found in a CDR to Gln-Pro, Ala-Pro, or Asn-Ala. Antibodies with such substitutions are subsequently screened to ensure that the substitutions do not decrease the affinity or specificity of the antibody for SIRPα, or other desired biological activity to unacceptable levels.

TABLE 2

Exemplary stabilizing CDR variants

| CDR Residue | Stabilizing Variant Sequence |
|---|---|
| Asn-Gly (N-G) | Gln-Gly, Ala-Gly, or Asn-Ala (Q-G), (A-G), or (N-A) |

TABLE 2-continued

Exemplary stabilizing CDR variants

| CDR Residue | Stabilizing Variant Sequence |
|---|---|
| Asp-Gly (D-G) | Glu-Gly, Ala-Gly or Asp-Ala (E-G), (A-G), or (D-A) |
| Met (M) | Lys, Leu, Ala, or Phe (K), (L), (A), or (F) |
| Asn (N) | Gln or Ala (Q) or (A) |
| Asn-Pro (N-P) | Gln-Pro, Ala-Pro, or Asn-Ala (Q-P), (A-P), or (N-A) |

Another type of framework modification involves mutating one or more residues within the framework regions to prevent aggregation. The risk of an antibody to aggregate can be assessed using the spatial aggregation propensity— See, Chennamsetty, N et al (2010) *J. Phys. Chem.* 114, 6614-6624. The method requires the calculation of the Solvent Accessible Area (SAA) for each atom. The molecular aggregation score is then calculated as the sum of all atomic scores. For a given radius and size of molecule, this is an approximate indication of its overall tendency to aggregate. Residues with a high aggregation score are replaced by residues with a lower score (e.g. more hydrophilic amino acids).

Antibody Engineering of the Fc Region

The antibodies (e.g., humanized antibodies) and antigen-binding fragments thereof disclosed herein can also be engineered to include modifications within the Fc region, typically to alter one or more properties of the antibody, such as serum half-life, complement fixation, Fc receptor binding, and/or effector function (e.g., antigen-dependent cellular cytotoxicity). Furthermore, the antibodies and antigen-binding fragments thereof disclosed herein can be chemically modified (e.g., one or more chemical moieties can be attached to the antibody) or be modified to alter its glycosylation, again to alter one or more properties of the antibody or fragment. Each of these embodiments is described in further detail below. The numbering of residues in the Fc region is that of the EU index of Kabat.

The antibodies and antigen-binding fragments thereof disclosed herein also include antibodies and fragments with modified (or blocked) Fc regions to provide altered effector functions. See, e.g., U.S. Pat. No. 5,624,821; WO2003/086310; WO2005/120571; WO2006/0057702. Such modifications can be used to enhance or suppress various reactions of the immune system, with possible beneficial effects in diagnosis and therapy. Alterations of the Fc region include amino acid changes (substitutions, deletions and insertions), glycosylation or deglycosylation, and adding multiple Fc regions. Changes to the Fc can also alter the half-life of antibodies in therapeutic antibodies, enabling less frequent dosing and thus increased convenience and decreased use of material. See Presta (2005) *J. Allergy Clin. Immunol.* 116: 731 at 734-35.

In one embodiment, the antibody or antigen-binding fragment of the invention is an IgG4 isotype antibody or fragment comprising a Serine to Proline mutation at a position corresponding to position 228 (S228P; EU index; SEQ ID NO: 66) in the hinge region of the heavy chain constant region. This mutation has been reported to abolish the heterogeneity of inter-heavy chain disulfide bridges in the hinge region (Angal et al (1993). *Mol. Immunol.* 30:105-108; position 241 is based on the Kabat numbering system).

In one embodiment of the invention, the hinge region of CH1 is modified such that the number of cysteine residues in the hinge region is increased or decreased. This approach is described further in U.S. Pat. No. 5,677,425. The number of cysteine residues in the hinge region of CH1 is altered, for example, to facilitate assembly of the light and heavy chains or to increase or decrease the stability of the antibody.

In another embodiment, the Fc hinge region of an antibody or antigen-binding fragment of the invention is mutated to decrease the biological half-life of the antibody or fragment. More specifically, one or more amino acid mutations are introduced into the CH2-CH3 domain interface region of the Fc-hinge fragment such that the antibody or fragment has impaired Staphylococcyl protein A (SpA) binding relative to native Fc-hinge domain SpA binding. This approach is described in further detail in U.S. Pat. No. 6,165,745.

In another embodiment, the antibody or antigen-binding fragment of the invention is modified to increase its biological half-life. Various approaches are possible. For example, one or more of the following mutations can be introduced: T252L, T254S, T256F, as described in U.S. Pat. No. 6,277,375. Alternatively, to increase the biological half-life, the antibody can be altered within the CH1 or CL region to contain a salvage receptor binding epitope taken from two loops of a CH2 domain of an Fc region of an IgG, as described in U.S. Pat. Nos. 5,869,046 and 6,121,022.

In yet other embodiments, the Fc region is altered by replacing at least one amino acid residue with a different amino acid residue to alter the effector function(s) of the antibody or antigen-binding fragment. For example, one or more amino acids selected from amino acid residues 234, 235, 236, 237, 297, 318, 320 and 322 can be replaced with a different amino acid residue such that the antibody has an altered affinity for an effector ligand and retains the antigen-binding ability of the parent antibody. The effector ligand to which affinity is altered can be, for example, an Fc receptor or the C1 component of complement. This approach is described in further detail in U.S. Pat. Nos. 5,624,821 and 5,648,260.

In another example, one or more amino acids selected from amino acid residues 329, 331 and 322 can be replaced with a different amino acid residue such that the antibody has altered C1q binding and/or reduced or abolished complement dependent cytotoxicity (CDC). This approach is described in further detail in U.S. Pat. No. 6,194,551.

In another example, one or more amino acid residues within amino acid positions 231 and 239 are altered to thereby alter the ability of the antibody to fix complement. This approach is described further in PCT Publication WO 94/29351.

The proteins of the invention, which are preferably antibodies and most preferably IgG antibodies or fragments thereof, may have altered (e.g., relative to an unmodified antibody) FcγR binding properties (examples of binding properties include but are not limited to, binding specificity, equilibrium dissociation constant ($K_D$), dissociation and association rates ($k_{off}$ and $k_{on}$ respectively), binding affinity and/or avidity) and that certain alterations are more or less desirable. It is known in the art that the equilibrium dissociation constant ($K_D$) is defined as $k_{off}/k_{on}$, and $K_a$ is the reciprocal of $K_D$.

The affinities and binding properties of an Fc region for its ligand, may be determined by a variety of in vitro assay methods (biochemical or immunological based assays) known in the art for determining Fc-FcγR interactions, i.e., specific binding of an Fc region to an FcγR including but not limited to, equilibrium methods (e.g., enzyme-linked immuno absorbent assay (ELISA) or radioimmunoassay (RIA)), or kinetics (e.g. BIACORE™, Octet®, or KinExa® analysis), and other methods such as indirect binding assays, competitive inhibition assays, fluorescence resonance energy transfer (FRET), gel electrophoresis and chromatography (e.g., gel filtration). These and other methods may utilize a label on one or more of the components being examined and/or employ a variety of detection methods including but not limited to chromogenic, fluorescent, luminescent, or isotopic labels.

In certain embodiments, the proteins of the present invention bind to one or more human FcγRs selected from the group consisting of FcγRI, FcγRIIB, FcγRIIC, FcγRIIIA-F158, and FcγRIIIA-V158 with an affinity at least 10-fold, preferably at least 30-fold, and more preferably at least 100-fold, less than equivalent protein having a wild-type human IgG1 heavy chain constant domain (SEQ ID NO: 119) Fc region or a wild-type human IgG4 heavy chain constant domain (SEQ ID NO: 66) Fc region.

In various embodiments, the proteins of the invention comprise an immunoglobulin Fc region comprising an immunoglobulin C2 region and an immunoglobulin C3 region and an immunoglobulin hinge region. By way of example, the immunoglobulin Fc region may be an IgG Fc region, an IgE Fc region, or an IgA Fc region. In certain preferred embodiments, the protein comprises two immunoglobulin Fc regions, each immunoglobulin Fc region comprising an immunoglobulin C2 region and an immunoglobulin C3 region and an immunoglobulin hinge region, wherein the hinge region of one of the immunoglobulin Fc regions is bound to the hinge region of the other immunoglobulin Fc region to form a dimeric Fc structure. Most preferably, such a protein is a human or humanized IgG protein.

In certain embodiments, the proteins of the invention comprise a mutated IgG4 Fc region, and preferably the protein is an IgG comprising two mutated IgG4 Fc regions to form a dimeric Fc structure. By way of example, a mutated IgG4 Fc region may comprise one of the mutations, or mutational combinations, recited in Table 3. The numbering system of the constant region referred to in this table is that of the EU index as set forth in Kabat et al. (1991, NIH Publication 91-3242, National Technical Information Service, Springfield, Va.). In the table, the first letter and number represent the unmodified amino acid and its position and the second letter represents the substituted amino acid at said position. For those entries that include combinations of more than one mutation, each mutation in the combination is separated by a "/".

TABLE 3

| | | |
|---|---|---|
| N297Q | L235E | N297Q/L235E |
| F234A | Q268A | F234A/L235A/ G237A/P238A |
| F234A/L235A/ ΔG236/G237A/ P238A | F234A/L235A/ G237A/P238A/ Q268A | F234A/L235A/ ΔG236/G237A/ P238A/Q268A |
| F234A/L235A | L235E/P329G | L235A/G237A/ E318A |
| F234A/L235A/ G237A/P238S | F234A/L235A/ ΔG236/G237A/ P238S | F234A/L235A/ G237A/P238S/ Q268A |
| F234A/L235A/ ΔG236/G237A/ P238S/Q268A | | |

In certain embodiments, the proteins of the invention comprise a mutated IgG1 Fc region, and preferably the protein is an IgG comprising two mutated IgG1 Fc regions to form a dimeric Fc structure. By way of example, a mutated IgG1 Fc region may comprise one of the mutations recited in Table 4. The numbering system of the constant region referred to in this table is that of the EU index as set forth in Kabat et al. (1991, NIH Publication 91-3242, National Technical Information Service, Springfield, Va.). In the table, the first letter and number represent the unmodified amino acid and its position and the second letter represents the substituted amino acid at said position.

TABLE 4

| | | |
|---|---|---|
| K222Y | P232K | A231K |
| E233N | E233Q | E233R |
| E233S | E233T | E233H |
| E233A | E233V | E233L |
| E233F | E233M | E233Y |
| E233W | E233G | L234D |
| L234E | L234N | L234Q |
| L234T | L234H | L234F |
| L234K | L234R | L234S |
| L234A | L234M | L234V |
| L235E | L235T | L235F |
| L235K | L235R | L235A |
| L235M | L235W | L235N |
| L235Q | L235H | L235V |
| G236A | G236N | G236R |
| G236H | G236L | G236F |
| G236P | G237A | G237E |
| G237N | G237Q | G237K |
| G237R | G237S | G237T |
| G237H | G237L | G237I |
| G237F | G237M | G237Y |
| G237P | P238K | P238N |
| P238R | P238S | P238T |
| P238Y | P238G | P238A |
| S239A | S239N | S239F |
| S239K | S239R | S239V |
| S239W | S239P | S239H |
| S239Y | D249H | V240A |
| F241W | F241L | F243W |
| F243L | F243E | P244H |
| P245A | P247V | P247G |
| V253I | V263I | V263T |
| V263M | V264D | V264E |
| V264K | V264F | V264M |
| V264H | V264W | V264G |
| V264Q | V264A | V264L |
| D265A | D265E | D265Q |
| D265S | D265H | D265V |
| D265L | D265F | D265M |
| D265Y | D265N | D265G |
| V266T | V266M | V266A |
| S267G | S267H | S267N |
| S267P | S267R | S267T |
| S267F | S267W | E269A |
| E269K | E269S | E269V |
| E269F | E269I | E269M |
| E269W | E269H | E269T |
| E269L | E269N | E269Y |
| E269R | E269P | E269G |
| D270A | D270N | D270E |
| D270Q | D270T | D270H |
| D270R | D270S | D270L |
| D270I | D270F | D270W |
| D270P | D270G | P271H |
| P271Q | P271K | P271R |
| P271S | P271V | P271F |
| P271W | D280L | D280W |
| D280P | E293F | E294A |
| E293Y | E294K | E294R |
| E294S | E294V | E294L |
| E294F | Q295A | Q295W |
| Q295P | Q295G | Y296E |
| Y296Q | Y296D | Y296N |
| Y296S | Y296T | Y296L |

TABLE 4-continued

| | | |
|---|---|---|
| Y296I | Y296A | Y296V |
| Y296M | N297S | N297D |
| N297Q | N297A | S298T |
| S298N | S298H | S298R |
| T299A | T299H | T299D |
| T299E | T299N | T299Q |
| T299K | T299R | T299I |
| T299F | T299M | T299Y |
| T299W | T299S | T299V |
| T299P | T299G | Y300E |
| Y300K | Y300R | Y300S |
| Y300P | Y300W | V303A |
| V303D | W313F | E318A |
| E318V | E318Q | E318H |
| E318L | E318Y | K320A |
| K322A | K322E | N325A |
| N325V | N325H | N325K |
| N325Y | N325W | N325P |
| N325G | N325Q | N325D |
| N325E | N325L | N325I |
| A327Q | A327E | A327N |
| A327L | A327I | A327F |
| A327W | L328N | L328F |
| L328H | L328R | L328T |
| L328V | L328I | L328P |
| L328M | L328E | L328A |
| P329A | P329F | P329D |
| P329N | P329Q | P329K |
| P329S | P329T | P329H |
| P329V | P329L | P329M |
| P329Y | P329W | P329G |
| P329R | A330L | A330R |
| A330P | A330T | A330V |
| A330F | A330H | P331A |
| P331S | P331N | P331E |
| I332K | I332N | I332Q |
| I332T | I332H | I332Y |
| I332A | I332R | E333N |
| E333R | I336E | I336Y |
| S337H | | |

In certain embodiments, a mutated IgG1 Fc region may comprise one of the mutational combinations recited in Table 5. The numbering system of the constant region referred to in this table is that of the EU index as set forth in Kabat et al. (1991, *NIH Publication* 91-3242, National Technical Information Service, Springfield, Va.). In the table, the first letter and number represent the unmodified amino acid and its position and the second letter represents the substituted amino acid at said position. For each of the combinations of more than one mutation, each mutation in the combination is separated by a "/" and deletions are indicated by a

TABLE 5

| | | |
|---|---|---|
| C220S/C226S/C229S/P238S | C226S/C229S/E233P/L234V/L235A | E233P/L234V/L235A |
| E233P/L234V/L235A/ΔG236 | E233P/L234V/L235A/ΔG236/A327G/A330S/P331S | L234A/L235A |
| L235A/G237A | L235A/G237A/E318S/K320S/K322S | L235A/G237A/P331A |
| L234F/L235E | L234F/L235E/D265A | L234F/L235E/D265A/N297Q/P331S |
| L234F/L235E/N297Q | L234F/L235E/P329G | L234F/L235A/K322Q/M252Y/S254T/T256E |
| L234F/L235Q/K322Q/M252Y/S254T/T256E | L234F/L235Q/P331G/M252Y/S254T/T256E | G236R/L328R |
| S239D/D265I/N297D/I332E | S239D/D265L/N297D/I332E | S239D/D265F/N297D/I332E |
| S239D/D265Y/N297D/I332E | S239D/D265T/N297D/I332E | S239D/N297D/A330Y/I332E |
| S239D/F241S/F243H/V262T/V264T/N297D/K326E/I332E | V264E/N297D/I332E | D265A/P331S |

TABLE 5-continued

| | | |
|---|---|---|
| D265A/N297Q | N297D/D265Y/T299L/I332E | N297D/D265Y/I332E |
| N297D/I332E/Y296D | N297D/I332E | N297D/I332E/Y296E |
| N297D/I332E/Y296N | N297D/I332E/Y296Q | N297D/I332E/Y296H |
| N297D/I332E/Y296T | N297D/I332E/T299V | N297D/I332E/T299I |
| N297D/I332E/T299L | N297D/I332E/T299F | N297D/I332E/T299H |
| N297D/I332E/T299E | N297D/I332E/A330Y | N297D/I332E/S298A/A330Y |
| N297E/D265F/I332E | N297E/I332E | F241E/F243R/V262E/V264R |
| F241E/F243Q/V262T/V264E | F241L/F243L/V262I/V264I | F241W/F243W |
| F241W/F243W/V262A/V264A | F241L/V262I | F243L/V262I/V264W |
| F241Y/F243Y/V262T/V264T | F241E/F243R/V262E/V264R | F241E/F243Q/V262T/V264E |
| F241R/F243Q/V262T/V264R | F241E/F243Y/V262T/V264R | P244H/P245A/P247V |
| F241E/F243R/V262E/V264R/I332E | F241E/F243Y/V262T/V264R | F241E/F243Y/V262T/V264R/I332E |
| S239E/D265G | S239E/D265N | S239E/D265Q |
| M252Y/S254T/T256E | S267Q/A327S | S267L/A327S |
| N297S/I332E | S239N/I332N | S239N/I332Q |
| S239Q/I332N | S239Q/I332Q | S298N/Y300S |
| S298N/T299A/Y300S | N297Q/S298N/Y300S | E318S/K320S/K322S |
| E318S/K320S/K322S/P311A | L328E/I332E | L328N/I332E |
| L234A/L235A/G237A/P238A/H268A/A330S/P331S | L234A/L235A/G237A/P238S/H268A/A330S/P331S | L234A/L235A/G237A/P238A/H268A/A330S/P331S |
| L328Q/I332E | L328H/I332E | |

In certain embodiments, the proteins of the invention comprise a wild type or mutated IgG2 Fc region, and preferably the protein is an IgG comprising two wild type or mutated IgG2 Fc regions to form a dimeric Fc structure. A mutated IgG2 Fc region may comprise one of the mutations, or mutational combinations, recited in Table 6. The numbering system of the constant region referred to in this table is that of the EU index as set forth in Kabat et al. (1991, *NIH Publication* 91-3242, National Technical Information Service, Springfield, Va.). In the table, the first letter and number represent the unmodified amino acid and its position and the second letter represents the substituted amino acid at said position. For those entries that include combinations of more than one mutation, each mutation in the combination is separated by a "/".

TABLE 6

| | | |
|---|---|---|
| V234A | G237A | A235E/G237A |
| V234A/A235E/G237A | V234A/G237A | V234A/G237A/P238S |
| H268Q/V309L/A330S/P331S | V234A/G237A/H268A/V309L/A330S/P331S | V234A/G237A/H268Q/V309L/A330S/P331S |
| V234A/G237A/P238S/H268A/V309L/A330S/P331S | P233S/V234A/G237A/P238S | P233S/V234A/G237A/H268A/V309L/A330S/P331S |
| P233S/V234A/G237A/H268Q/V309L/A330S/P331S | P233S/V234A/G237A/P238S/H268A/V309L/A330S/P331S | |

Production of Antibodies with Modified Glycosylation

In still another embodiment, the antibodies or antigen-binding fragments of the invention comprise a particular glycosylation pattern. For example, an afucosylated or an aglycosylated antibody or fragment can be made (i.e., the antibody lacks fucose or glycosylation, respectively). The glycosylation pattern of an antibody or fragment may be altered to, for example, increase the affinity or avidity of the antibody or fragment for a SIRPα antigen. Such modifications can be accomplished by, for example, altering one or more of the glycosylation sites within the antibody or fragment sequence. For example, one or more amino acid substitutions can be made that result in removal of one or more of the variable region framework glycosylation sites to thereby eliminate glycosylation at that site. Such deglycosylation may increase the affinity or avidity of the antibody or fragment for antigen. See, e.g., U.S. Pat. Nos. 5,714,350 and 6,350,861.

Antibodies and antigen-binding fragments disclosed herein may further include those produced in lower eukaryote host cells, in particular fungal host cells such as yeast and filamentous fungi have been genetically engineered to produce glycoproteins that have mammalian- or human-like glycosylation patterns (See for example, Choi et al, (2003) *Proc. Natl. Acad. Sci.* 100: 5022-5027; Hamilton et al., (2003) *Science* 301: 1244-1246; Hamilton et al., (2006) *Science* 313: 1441-1443; Nett et al., *Yeast* 28(3):237-52 (2011); Hamilton et al., *Curr Opin Biotechnol.* 18(5): 387-92 (2007)). A particular advantage of these genetically modified host cells over currently used mammalian cell lines is the ability to control the glycosylation profile of glycoproteins that are produced in the cells such that compositions of glycoproteins can be produced wherein a particular N-glycan structure predominates (see, e.g., U.S. Pat. Nos. 7,029,872 and 7,449,308). These genetically modified host cells have been used to produce antibodies that have predominantly particular N-glycan structures (See for example, Li et al., (2006) *Nat. Biotechnol.* 24: 210-215).

In particular embodiments, the antibodies and antigen-binding fragments thereof disclosed herein further include those produced in lower eukaryotic host cells and which comprise fucosylated and non-fucosylated hybrid and complex N-glycans, including bisected and multiantennary species, including but not limited to N-glycans such as $GlcNAc_{(1-4)}Man_3GlcNAc_2$; $Gal_{(1-4)}GlcNAc_{(1-4)}Man_3GlcNAc_2$; $NANA_{(1-4)}Gal_{(1-4)}GlcNAc_{(1-4)}Man_3GlcNAc_2$.

In particular embodiments, the antibodies and antigen-binding fragments thereof provided herein may comprise antibodies or fragments having at least one hybrid N-glycan selected from the group consisting of $GlcNAcMan_5GlcNAc_2$; $GalGlcNAcMan_5GlcNAc_2$; and $NANAGalGlcNAcMan_5GlcNAc_2$. In particular aspects, the hybrid N-glycan is the predominant N-glycan species in the composition.

In particular embodiments, the antibodies and antigen-binding fragments thereof provided herein comprise antibodies and fragments having at least one complex N-glycan selected from the group consisting of $GlcNAcMan_3GlcNAc_2$; $GalGlcNAcMan_3GlcNAc_2$; $NANAGalGlcNAcMan_3GlcNAc_2$; $GlcNAc_2Man_3GlcNAc_2$; $GalGlcNAc_2Man_3GlcNAc_2$; $Gal_2GlcNAc_2Man_3GlcNAc_2$; $NANAGal_2GlcNAc_2Man_3GlcNAc_2$; and $NANA_2Gal_2GlcNAc_2Man_3GlcNAc_2$. In particular aspects, the complex N-glycan are the predominant N-glycan species in the composition. In further aspects, the complex N-glycan is a particular N-glycan species that comprises about 30%, 40%, 50%, 60%, 70%, 80%, 90%, 95%, 97%, 98%, 99%, or 100% of the complex N-glycans in the composition. In one embodiment, the antibody and antigen binding fragments thereof provided herein comprise complex N-glycans, wherein at least 50%, 60%, 70%, 80%, 90%, 95%, 97%, 98%, 99%, or 100% of the complex N-glycans comprise the structure $NANA_2Gal_2GlcNAc_2Man_3GlcNAc_2$, wherein such structure is afucosylated. Such structures can be produced, e.g., in engineered *Pichia pastoris* host cells.

In particular embodiments, the N-glycan is fucosylated. In general, the fucose is in an α1,3-linkage with the GlcNAc at the reducing end of the N-glycan, an α1,6-linkage with the GlcNAc at the reducing end of the N-glycan, an α1,2-linkage with the Gal at the non-reducing end of the N-glycan, an α1,3-linkage with the GlcNac at the non-reducing end of the N-glycan, or an α1,4-linkage with a GlcNAc at the non-reducing end of the N-glycan.

Therefore, in particular aspects of the above the glycoprotein compositions, the glycoform is in an α1,3-linkage or α1,6-linkage fucose to produce a glycoform selected from the group consisting of $Man_5GlcNAc_2(Fuc)$, $GlcNAcMan_5GlcNAc_2(Fuc)$, $Man_3GlcNAc_2(Fuc)$, $GlcNAcMan_3GlcNAc_2(Fuc)$, $GlcNAc_2Man_3GlcNAc_2(Fuc)$, $GalGlcNAc_2Man_3GlcNAc_2(Fuc)$, $Gal_2GlcNAc_2Man_3GlcNAc_2(Fuc)$, $NANAGal_2GlcNAc_2Man_3GlcNAc_2(Fuc)$, and $NANA_2Gal_2GlcNAc_2Man_3GlcNAc_2(Fuc)$; in an α1,3-linkage or α1,4-linkage fucose to produce a glycoform selected from the group consisting of $GlcNAc(Fuc)Man_5GlcNAc_2$, $GlcNAc(Fuc)Man_3GlcNAc_2$, $GlcNAc_2(Fuc_{1-2})Man_3GlcNAc_2$, $GalGlcNAc_2(Fuc_{1-2})Man_3GlcNAc_2$, $Gal_2GlcNAc_2(Fuc_{1-2})Man_3GlcNAc_2$, $NANAGal_2GlcNAc_2(Fuc_{1-2})Man_3GlcNAc_2$, and $NANA_2Gal_2GlcNAc_2(Fuc_{1-2})Man_3GlcNAc_2$; or in an $α_{1,2}$-linkage fucose to produce a glycoform selected from the group consisting of $Gal(Fuc)GlcNAc_2Man_3GlcNAc_2$, $Gal_2(Fuc_{1-2})GlcNAc_2Man_3GlcNAc_2$, $NANAGal_2(Fuc_{1-2})GlcNAc_2Man_3GlcNAc_2$, and $NANA_2Gal_2(Fuc_{1-2})GlcNAc_2Man_3GlcNAc_2$.

In further aspects, the antibodies (e.g., humanized antibodies) or antigen-binding fragments thereof comprise high mannose N-glycans, including but not limited to, $Man_5GlcNAc_2$, $Man_7GlcNAc_2$, $Man_6GlcNAc_2$, $Man_5GlcNAc_2$, $Man_4GlcNAc_2$, or N-glycans that consist of the $Man_3GlcNAc_2$ N-glycan structure.

In further aspects of the above, the complex N-glycans further include fucosylated and non-fucosylated bisected and multiantennary species.

As used herein, the terms "N-glycan" and "glycoform" are used interchangeably and refer to an N-linked oligosaccharide, for example, one that is attached by an asparagine-N-acetylglucosamine linkage to an asparagine residue of a polypeptide. N-linked glycoproteins contain an N-acetylglucosamine residue linked to the amide nitrogen of an asparagine residue in the protein. The predominant sugars found on glycoproteins are glucose, galactose, mannose, fucose, N-acetylgalactosamine (GalNAc), N-acetylglucosamine (GlcNAc) and sialic acid (e.g., N-acetylneuraminic acid (NANA)). The processing of the sugar groups occurs co-translationally in the lumen of the ER and continues post-translationally in the Golgi apparatus for N-linked glycoproteins.

N-glycans have a common pentasaccharide core of $Man_3GlcNAc_2$ ("Man" refers to mannose; "Glc" refers to glucose; and "NAc" refers to N-acetyl; GlcNAc refers to N-acetylglucosamine). Usually, N-glycan structures are presented with the non-reducing end to the left and the reducing end to the right. The reducing end of the N-glycan is the end that is attached to the Asn residue comprising the glycosylation site on the protein. N-glycans differ with respect to the number of branches (antennae) comprising peripheral sugars (e.g., GlcNAc, galactose, fucose and sialic acid) that are added to the $Man_3GlcNAc_2$ ("Man3") core structure which is also referred to as the "trimannose core", the "pentasaccharide core" or the "paucimannose core". N-glycans are classified according to their branched constituents (e.g., high mannose, complex or hybrid). A "high mannose" type N-glycan has five or more mannose residues. A "complex" type N-glycan typically has at least one GlcNAc attached to the 1,3 mannose arm and at least one GlcNAc attached to the 1,6 mannose arm of a "trimannose" core. Complex N-glycans may also have galactose ("Gal") or N-acetylgalactosamine ("GalNAc") residues that are optionally modified with sialic acid or derivatives (e.g., "NANA" or "NeuAc", where "Neu" refers to neuraminic acid and "Ac" refers to acetyl). Complex N-glycans may also have intrachain substitutions comprising "bisecting" GlcNAc and core fucose ("Fuc"). Complex N-glycans may also have multiple antennae on the "trimannose core," often referred to as "multiple antennary glycans." A "hybrid" N-glycan has at least one GlcNAc on the terminal of the 1,3 mannose arm of the trimannose core and zero or more mannoses on the 1,6 mannose arm of the trimannose core. The various N-glycans are also referred to as "glycoforms."

With respect to complex N-glycans, the terms "G-2", "G-1", "G0", "G1", "G2", "A1", and "A2" mean the following. "G-2" refers to an N-glycan structure that can be characterized as $Man_3GlcNAc_2$; the term "G-1" refers to an N-glycan structure that can be characterized as $GlcNAcMan_3GlcNAc_2$; the term "G0" refers to an N-glycan structure that can be characterized as $GlcNAc_2Man_3GlcNAc_2$; the term "G1" refers to an N-glycan structure that can be characterized as $GalGlcNAc_2Man_3GlcNAc_2$; the term "G2" refers to an N-glycan structure that can be characterized as $Gal_2GlcNAc_2Man_3GlcNAc_2$; the term "A1" refers to an N-glycan structure that can be characterized as $NANAGal_2GlcNAc_2Man_3GlcNAc_2$; and, the term "A2" refers to an N-glycan structure that can be characterized as $NANA_2Gal_2GlcNAc_2Man_3GlcNAc_2$. Unless otherwise indicated, the terms G-2", "G-1", "G0", "G1", "G2", "A1", and "A2" refer to N-glycan species that lack fucose attached to the GlcNAc residue at the reducing end of the N-glycan. When the term includes an "F", the "F" indicates that the N-glycan species contains a fucose residue on the GlcNAc residue at the reducing end of the N-glycan. For example, G0F, G1F, G2F, A1F, and A2F all indicate that the N-glycan further includes a fucose residue attached to the GlcNAc residue at the reducing end of the N-glycan. Lower eukaryotes such as yeast and filamentous fungi do not normally produce N-glycans that produce fucose.

With respect to multiantennary N-glycans, the term "multiantennary N-glycan" refers to N-glycans that further comprise a GlcNAc residue on the mannose residue comprising the non-reducing end of the 1,6 arm or the 1,3 arm of the N-glycan or a GlcNAc residue on each of the mannose residues comprising the non-reducing end of the 1,6 arm and the 1,3 arm of the N-glycan. Thus, multiantennary N-glycans can be characterized by the formulas $GlcNAc_{(2-4)}Man_3GlcNAc_2$, $Gal_{(1-4)}GlcNAc_{(2-4)}Man_3GlcNAc_2$, or $NANA_{(1-4)}Gal_{(1-4)}GlcNAc_{(2-4)}Man_3GlcNAc_2$. The term "1-4" refers to 1, 2, 3, or 4 residues.

With respect to bisected N-glycans, the term "bisected N-glycan" refers to N-glycans in which a GlcNAc residue is linked to the mannose residue at the reducing end of the N-glycan. A bisected N-glycan can be characterized by the formula $GlcNAc_3Man_3GlcNAc_2$ wherein each mannose residue is linked at its non-reducing end to a GlcNAc residue. In contrast, when a multiantennary N-glycan is characterized as $GlcNAc_3Man_3GlcNAc_2$, the formula indicates that two GlcNAc residues are linked to the mannose residue at the non-reducing end of one of the two arms of the N-glycans and one GlcNAc residue is linked to the mannose residue at the non-reducing end of the other arm of the N-glycan.

In certain embodiments, the proteins of the invention comprise an aglycosylated Fc region. By way of example, an IgG1 Fc region may be aglycosylayed by deleting or substituting residue N297.

Antibody Physical Properties

The antibodies and antigen-binding fragments thereof disclosed herein may further contain one or more glycosylation sites in either the light or heavy chain immunoglobulin variable region. Such glycosylation sites may result in increased immunogenicity of the antibody or fragment or an alteration of the pK of the antibody due to altered antigen-binding (Marshall et al. (1972) *Annu Rev Biochem* 41:673-702; Gala and Morrison (2004) *J Immunol* 172:5489-94; Wallick et al (1988) *J Exp Med* 168:1099-109; Spiro (2002) *Glycobiology* 12:43R-56R; Parekh et al (1985) *Nature* 316: 452-7; Mimura et al. (2000) *Mol Immunol* 37:697-706). Glycosylation has been known to occur at motifs containing an N-X-S/T sequence.

Each antibody or antigen-binding fragment will have a unique isoelectric point (pI), which generally falls in the pH range between 6 and 9.5. The pI for an IgG1 antibody typically falls within the pH range of 7-9.5 and the pI for an IgG4 antibody typically falls within the pH range of 6-8.

Each antibody or antigen-binding fragment will have a characteristic melting temperature, with a higher melting temperature indicating greater overall stability in vivo (Krishnamurthy R and Manning M C (2002) *Curr Pharm Biotechnol* 3:361-71). In general, the $T_{M1}$ (the temperature of initial unfolding) may be greater than 60° C., greater than 65° C., or greater than 70° C. The melting point of an antibody or fragment can be measured using differential scanning calorimetry (Chen et al (2003) *Pharm Res* 20:1952-60; Ghirlando et al (1999) *Immunol Lett* 68:47-52) or circular dichroism (Murray et al. (2002) *J. Chromatogr Sci* 40:343-9).

In a further embodiment, antibodies and antigen-binding fragments thereof are selected that do not degrade rapidly. Degradation of an antibody or fragment can be measured using capillary electrophoresis (CE) and MALDI-MS (Alexander A J and Hughes D E (1995) *Anal Chem* 67:3626-32).

In a further embodiment, antibodies and antigen-binding fragments thereof are selected that have minimal aggregation effects, which can lead to the triggering of an unwanted immune response and/or altered or unfavorable pharmacokinetic properties. Generally, antibodies and fragments are acceptable with aggregation of 25% or less, 20% or less, 15% or less, 10% or less, or 5% or less. Aggregation can be measured by several techniques, including size-exclusion column (SEC), high performance liquid chromatography (HPLC), and light scattering.

Antibody Conjugates

The anti-SIRPα antibodies and antigen-binding fragments thereof disclosed herein may also be conjugated to a chemical moiety. The chemical moiety may be, inter alia, a polymer, a radionucleotide or a cytotoxic factor. In particular embodiments, the chemical moiety is a polymer which increases the half-life of the antibody or fragment in the body of a subject. Suitable polymers include, but are not limited to, hydrophilic polymers which include but are not limited to polyethylene glycol (PEG) (e.g., PEG with a molecular weight of 2 kDa, 5 kDa, 10 kDa, 12 kDa, 20 kDa, 30 kDa or 40 kDa), dextran and monomethoxypolyethylene glycol (mPEG). Lee, et al., (1999) (Bioconj. Chem. 10:973-981) discloses PEG conjugated single-chain antibodies. Wen, et al., (2001) (Bioconj. Chem. 12:545-553) disclose conjugating antibodies with PEG which is attached to a radiometal chelator (diethylenetriaminpentaacetic acid (DTPA)).

The antibodies and antigen-binding fragments thereof disclosed herein may also be conjugated with labels such as $^{99}Tc$, $^{90}Y$, $^{111}In$, $^{32}P$, $^{14}C$, $^{125}I$, $^{3}H$, $^{131}I$, $^{11}C$, $^{15}O$, $^{13}N$, $^{18}F$, $^{35}S$, $^{51}Cr$, $^{57}To$, $^{226}Ra$, $^{60}Co$, $^{59}Fe$, $^{57}Se$, $^{152}Eu$, $^{67}CU$, $^{217}Ci$, $^{211}At$, $^{212}Pb$, $^{47}Sc$, $^{109}Pd$, $^{234}Th$, and $^{40}K$, $^{157}Gd$, $^{55}Mn$, $^{52}Tr$, and $^{56}Fe$.

The antibodies and antigen-binding fragments disclosed herein may also be PEGylated, for example to increase its biological (e.g., serum) half-life. To PEGylate an antibody or fragment, the antibody or fragment, typically is reacted with a reactive form of polyethylene glycol (PEG), such as a reactive ester or aldehyde derivative of PEG, under conditions in which one or more PEG groups become attached to the antibody or antibody fragment. In particular embodiments, the PEGylation is carried out via an acylation reaction or an alkylation reaction with a reactive PEG molecule (or an analogous reactive water-soluble polymer). As used herein, the term "polyethylene glycol" is intended to encompass any of the forms of PEG that have been used to derivatize other proteins, such as mono (C1-C10) alkoxy- or aryloxy-polyethylene glycol or polyethylene glycol-maleimide. In certain embodiments, the antibody or fragment to be PEGylated is an aglycosylated antibody or fragment. Methods for PEGylating proteins are known in the art and can be applied to the antibodies of the invention. See, e.g., EP 0 154 316 and EP 0 401 384.

The antibodies and antigen-binding fragments disclosed herein may also be conjugated with fluorescent or chemiluminescent labels, including fluorophores such as rare earth chelates, fluorescein and its derivatives, rhodamine and its derivatives, isothiocyanate, phycoerythrin, phycocyanin, allophycocyanin, o-phthaladehyde, fluorescamine, $^{152}Eu$, dansyl, umbelliferone, luciferin, luminal label, isoluminal label, an aromatic acridinium ester label, an imidazole label, an acridimium salt label, an oxalate ester label, an aequorin label, 2,3-dihydrophthalazinediones, biotin/avidin, spin labels and stable free radicals.

The antibodies and antigen-binding fragments thereof of the invention may also be conjugated to a cytotoxic factor such as diptheria toxin, *Pseudomonas aeruginosa* exotoxin A chain, ricin A chain, abrin A chain, modeccin A chain, alpha-sarcin, *Aleurites fordii* proteins and compounds (e.g., fatty acids), dianthin proteins, *Phytoiacca americana* proteins PAPI, PAPII, and PAP-S, *Momordica charantia* inhibitor, curcin, crotin, *Saponaria officinalis* inhibitor, mitogellin, restrictocin, phenomycin, and enomycin.

Any method known in the art for conjugating the antibodies and antigen-binding fragments thereof of the invention to the various moieties may be employed, including those methods described by Hunter, et al., (1962) *Nature* 144:945; David, et al., (1974) *Biochemistry* 13:1014; Pain, et al., (1981) *J. Immunol. Meth.* 40:219; and Nygren, J., (1982) *Histochem. and Cytochem.* 30:407. Methods for conjugating antibodies and fragments are conventional and very well known in the art.

Therapeutic Uses of Anti-SIRPα Antibodies

Further provided are methods for treating subjects, including human subjects, in need of treatment with the isolated antibodies or antigen-binding fragments thereof disclosed herein. In one embodiment of the invention, such subject suffers from an infection or an infectious disease.

In another embodiment of the invention, such subject suffers from cancer. In one embodiment the cancer is, e.g., osteosarcoma, rhabdomyosarcoma, neuroblastoma, kidney cancer, leukemia, renal transitional cell cancer, bladder cancer, Wilm's cancer, ovarian cancer, pancreatic cancer, breast cancer, prostate cancer, bone cancer, lung cancer (e.g., non-small cell lung cancer), gastric cancer, colorectal cancer, cervical cancer, synovial sarcoma, head and neck cancer, squamous cell carcinoma, multiple myeloma, renal cell cancer, retinoblastoma, hepatoblastoma, hepatocellular carcinoma, melanoma, rhabdoid tumor of the kidney, Ewing's sarcoma, chondrosarcoma, brain cancer, glioblastoma, meningioma, pituitary adenoma, vestibular schwannoma, a primitive neuroectodermal tumor, medulloblastoma, astrocytoma, anaplastic astrocytoma, oligodendroglioma, ependymoma, choroid plexus papilloma, polycythemia vera, thrombocythemia, idiopathic myelfibrosis, soft tissue sarcoma, thyroid cancer, endometrial cancer, carcinoid cancer or liver cancer, breast cancer or gastric cancer. In an embodiment of the invention, the cancer is metastatic cancer, e.g., of the varieties described above.

Cancers that may be treated by the antibodies or antigen-binding fragments, compositions and methods of the invention include, but are not limited to: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma) colorectal; Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre tumor cervical dysplasia), ovaries (ovarian carcinoma [serous cystadenocarcinoma, mucinous cystadenocarcinoma, unclassified carcinoma], granulosa thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma), breast; Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non Hodgkin's lymphoma [malignant lymphoma]; Skin: malignant melanoma, basal cell carcinoma, squamous cell carcinoma, Karposi's sarcoma, moles dysplastic nevi, lipoma, angioma, dermatofibroma, keloids, psoriasis; and Adrenal glands: neuroblastoma. Thus, the term "cancerous cell" as provided herein, includes a cell afflicted by any one of the above-identified conditions.

In one embodiment, cancers that may be treated by the antibodies or antigen-binding fragments thereof disclosed herein, compositions and methods of the invention include, but are not limited to: breast cancer, gastric cancer, esophageal cancer, gastroesophageal junction carcinoma, colorectal cancer, head and neck cancer, non-small cell lung cancer, osteosarcoma, neuroblastoma, bladder cancer, cervical cancer, endometrial cancer, ovarian cancer, lung cancer, squamous cell carcinoma, melanoma, pancreatic cancer, prostate cancer, small cell lung cancer, kidney cancer, renal cell carcinoma, thyroid cancer, glioblastoma multiforme, fallopian tube cancer, peritoneal cancer, angiosarcoma, hepatocellular carcinoma, choriocarcinoma, soft tissue sarcoma, chronic lymphocytic leukemia, chronic myelocytic leukemia, non-Hodgkin's lymphoma, B-cell non-hodgkin's lymphoma, diffuse large B-cell lymphoma, follicular lymphoma, mantle cell lymphoma, myelodysplastic syndrome, acute myelocytic leukemia, T-cell lymphoma, natural killer cell lymphoma, extranodal marginal zone B-cell lymphoma, acute lymphocytic leukemia, multiple myeloma.

In one embodiment, the antibodies or antigen-binding fragments thereof disclosed herein may be used for the treatment of infections and infectious diseases. As used herein, the term "infection" refers to any state in at least one cell of an organism (i.e., a subject) is infected by an infectious agent (e.g., a subject has an intracellular pathogen infection, e.g., a chronic intracellular pathogen infection). As used herein, the term "infectious agent" refers to a foreign biological entity (i.e. a pathogen) that induces CD47 expression (e.g., increased CD47 expression) in at least one cell of the infected organism. For example, infectious agents include, but are not limited to bacteria, viruses, protozoans, and fungi.

Intracellular pathogens are of particular interest. Infectious diseases are disorders caused by infectious agents. Some infectious agents cause no recognizable symptoms or disease under certain conditions, but have the potential to cause symptoms or disease under changed conditions. The subject methods can be used in the treatment of chronic pathogen infections, for example including but not limited to viral infections, e.g. retrovirus, lentivirus, hepadna virus, herpes viruses, pox viruses, human papilloma viruses, etc.; intracellular bacterial infections, e.g. *Mycobacterium, Chlamydophila, Ehrlichia, Rickettsia, Brucella, Legionella, Francisella, Listeria, Coxiella, Neisseria, Salmonella, Yersinia* sp, *Helicobacter pylori* etc.; and intracellular protozoan pathogens, e.g. *Plasmodium* sp, *Trypanosoma* sp., *Giardia* sp., *Toxoplasma* sp., *Leishmania* sp., etc.

In an embodiment, the invention provides methods for treating subjects using an anti-SIRPα antibody or antigen-binding fragment thereof of the invention, wherein the subject suffers from a viral infection. In one embodiment, the viral infection is an infection with a virus selected from the group consisting of human immunodeficiency virus (HIV), hepatitis virus (A, B, or C), herpes virus (e.g., VZV, HSV-I, HAV-6, HSV-II, and CMV, Epstein Barr virus), adenovirus, influenza virus, flaviviruses, echovirus, rhinovirus, coxsackie virus, coronavirus, respiratory syncytial virus, mumps virus, rotavirus, measles virus, rubella virus, parvovirus, vaccinia virus, HTLV virus, dengue virus, papillomavirus, molluscum virus, poliovirus, rabies virus, JC virus or arboviral encephalitis virus.

In an embodiment, the invention provides methods for treating subjects using an anti-SIRPα antibody or antigen-binding fragment thereof of the invention, wherein the subject suffers from a bacterial infection. In one embodiment, the bacterial infection is infection with a bacteria selected from the group consisting of *Chlamydia*, rickettsial bacteria, mycobacteria, staphylococci, streptococci, pneumonococci, meningococci and gonococci, *klebsiella, proteus, serratia, pseudomonas, Legionella, Corynebacterium diphtheriae, Salmonella*, bacilli, *Vibrio cholerae, Clostridium tetan, Clostridium botulinum, Bacillus anthricis, Yersinia pestis, Mycobacterium leprae, Mycobacterium lepromatosis*, and *Borriella*.

In an embodiment, the invention provides methods for treating subjects using an anti-SIRPα antibody or antigen-binding fragment thereof of the invention, wherein the subject suffers from a fungal infection. In one embodiment, the fungal infection is an infection with a fungus selected from the group consisting of *Candida* (*albicans, krusei, glabrata, tropicalis*, etc.), *Cryptococcus neoformans, Aspergillus* (*fumigatus, niger*, etc.), Genus *Mucorales* (*mucor, absidia, rhizopus*), *Sporothrix schenkii, Blastomyces dermatitidis, Paracoccidioides brasiliensis, Coccidioides immitis* and *Histoplasma capsulatum*.

In an embodiment, the invention provides methods for treating subjects using an anti-SIRPα antibody or antigen-binding fragment thereof of the invention, wherein the subject suffers from a parasitic infection. In one embodiment, the parasitic infection is infection with a parasite selected from the group consisting of *Entamoeba histolytica, Balantidium coli, Naegleria fowleri, Acanthamoeba, Giardia lambia, Cryptosporidium, Pneumocystis carinii, Plasmodium vivax, Babesia microti, Trypanosoma brucei, Trypanosoma cruzi, Leishmania donovani, Toxoplasma gondii* and *Nippostrongylus brasiliensis*.

A "subject" may be a mammal such as a human, dog, cat, horse, cow, mouse, rat, monkey (e.g., cynomolgous monkey, e.g., *Macaca fascicularis*) or rabbit. In preferred embodiments of the invention, the subject is a human subject.

The term "in association with" indicates that the components administered in a method of the present invention (e.g., an anti-SIRPα antibody (e.g., humanized antibody) or antigen-binding fragment thereof along with an anti-cancer agent can be formulated into a single composition for simultaneous delivery or formulated separately into two or more compositions (e.g., a kit). Each component can be administered to a subject at a different time than when the other component is administered; for example, each administration may be given non-simultaneously (e.g., separately or sequentially) at several intervals over a given period of time. Moreover, the separate components may be administered to a subject by the same or by a different route.

In particular embodiments, the antibodies or antigen-binding fragments thereof disclosed herein may be used alone, or in association with other, further therapeutic agents and/or therapeutic procedures, for treating or preventing any disease such as cancer, e.g., as discussed herein, in a subject in need of such treatment or prevention. Compositions, e.g., pharmaceutical compositions comprising a pharmaceutically acceptable carrier, comprising such antibodies and fragments in association with further therapeutic agents are also part of the present invention.

Therefore, the present invention provides a method of treating cancer in a human subject, comprising administering to the subject an effective amount of the antibody or antigen binding fragment disclosed herein, optionally in association with a further therapeutic agent or therapeutic procedure. The present invention also provides a method of treating an infection or infectious disease in a human subject, comprising administering to the subject an effective amount of the antibody or antigen binding fragment disclosed herein, optionally in association with a further therapeutic agent or therapeutic procedure. The present invention also provides a method of increasing the activity of an immune cell, comprising administering to a subject in need thereof an effective amount of an antibody or antigen binding fragment disclosed herein. In one embodiment, the method is used for: the treatment of cancer; the treatment of an infection or infectious disease; or as a vaccine adjuvant.

In particular embodiments, the antibodies or antigen-binding fragments thereof disclosed herein may be used alone, or in association with tumor vaccines. Examples of tumor vaccines include but are not limited to vaccines for Human Papillomavirus (HPV) infection caused cancer such as Gardasil®, Gardisil9® and Cervarix®; vaccines that prevent hepatitis B virus caused liver cancer such as Engerix-B® and Recombivax HB®; oncolytic virus therapy that triggers immune response such as Imlygic®; DNA vaccines such as Synchotrope MA2M plasmid DNA vaccine and ZYC101; mammaglobin-a DNA vaccine (see Clinical Cancer Res. 2014 20(23):5964-75); vector based vaccines such as PSA-TRICOM (prostvac), PANVAC-VF, *Listeria monocytogenes*-based vaccines (see, e.g., Therapeutic Advances in Vaccines, 2014, 2(5) 137-148), *Listeria*-based vaccines (*Listeria* expressing one or more cancer vaccines such as *Listeria*-mesothelin (e.g., CRS-207), ADXS-HPV, Axalimogene Filolisbac, *Listeria*-HER2/Neu, *Listeria*-EGFRvIII), Adeno-CEA; allogeneic vaccines such as GVAX, BLP-25 (anti-Ankara-mucin 1), Belagenpumatucel-L, TG4010, CIMAvax epidermal growth factor vaccine, NY-ESO, GM.CD40L-CCL21; autologous vaccines such as: Adeno-CD40L, BCG, INGN-225, Dendritic cell vaccines such as Provenge® (Sipuleucel-T), rF-CEA-MUC1-TRI-COM (panvac-DC); antigen vaccines such as MUC-1 (stimuvax), NY-ESO-1, GP-100, MAGE-A3 (melanoma antigen encoding gene A3), INGN-225 (see Pharmacology & Therapeutics 153 (2015) 1-9).

Eat-me signals could be elevated by cytotoxic therapies like radiotherapy or chemotherapeutic agents including, but not limited to anthracyclines (doxorubicin, epirubicin, daunorubicin, idarubicin, mitoxantrone), oxaliplatin, bortezomib, cyclophosphamide, bleomycin, vorinostat, paclitaxel, 5-fluorouracil, cytarabine, prednisolone, docetaxel, mitomycin C, topotecan/camptothecin, etoposide, zoledronic acid, methotrexate, ibrutinib, aflibercept, bevacizumab, toremifene, vinblastine, vincristine, idelalisib, mercaptopurine, thalidomide, sorafenib. Thus, in certain embodiments, the antibodies or antigen-binding fragments thereof disclosed herein may be used in association with chemotherapeutic agents, in association with radiation therapy, etc. In particular embodiments, the antibodies or antigen-binding fragments thereof disclosed herein may be used alone, or in association with targeted therapies. Examples of targeted therapies include: hormone therapies, signal transduction inhibitors (e.g., EGFR inhibitors, such as cetuximab (Erbitux) and erlotinib (Tarceva)); CD20 inhibitors (e.g., rituximab (Rituxan) and ofatumumab (Arzerra)); CD38 inhibitors (e.g., daratumumab (DARZALEX)); CD52 inhibitors (e.g., alemtuzumab (Campath)); HER2 inhibitors (e.g., trastuzumab (Herceptin) and pertuzumab (Perjeta)); BCR-ABL inhibitors (such as imatinib (Gleevec) and dasatinib (Sprycel)); ALK inhibitors (such as crizotinib (Xalkori) and ceritinib (Zykadia)); BRAF inhibitors (such as vemurafenib (Zelboraf) and dabrafenib (Tafinlar)), gene expression modulators (e.g., decitabine (Dacogen) and Vorinostat (Zolinza)), apoptosis inducers (e.g., bortezomib (Velcade) and carfilzomib (Kyprolis)), angiogenesis inhibitors (e.g., bevacizumab (Avastin) and ramucirumab (Cyramza)), immunomodulatory imide drugs (e.g., thalidomide, lenalidomide, pomalidomide, and apremilast), monoclonal antibodies attached to toxins (e.g., brentuximab vedotin (Adcetris) and ado-trastuzumab emtansine (Kadcyla)).

The antibodies or antigen-binding fragments thereof disclosed herein may preferably find use in association with targeted therapies in which antibodies are employed to mediate ADCC/ADCP. Functional bioassays are available to analyze the mode of action of an antibody drug and to distinguish ADCP as a mode of action from ADCC. By way of example, an antibody-dependent cell-mediated cytotoxicity (ADCC) assay typically utilizes normal human peripheral blood mononuclear cells (PBMCs) or effector cells isolated thereof. Assay variation can be reduced by using selective donor pools with defined Fcγ receptor IIa (FcγRIIa/CD32a), IIIa (FcγRIIIa/CD16a) or IIIb (FcγRIIIb/CD16b) gene copy number variation (CNV) or genotypes such as FcγRIIIa-158 V/V versus V/F or F/F, FcγRIIIa-131 H/H versus H/R or R/R, and the FcγRIIIb-NA1 and -NA2 polymorphic variants. Alternatively, effector cells such as PBMCs, PBMC-derived natural killer (NK) cells, granulocytes, monocytes, monocyte-derived macrophages, or dendritic cells (DCs) can be replaced with a FcγRIIIa-expressing cell line (for example, engineered NK92). Killing of the target cells can be assessed by measuring the release of specific probes from pre-labelled target cells, using $^{51}$chromium ($Cr^{51}$) or fluorescent dyes such as calcein-acetoxymethyl (calcein-AM), carboxyfluorescein succinimidyl ester (CFSE), 2',7'-bis-(2-carboxyethyl)-5-(and-6)-carboxyfluorescein (BCECF), europium (Eu) or propidium iodide (PI), or by measuring the release of cytosolic enzymes such as lactate dehydrogenase (LDH) or the release of nucleoside triphosphate (ATP).

In contrast, antibody-dependent cellular phagocytosis (ADCP) may be assessed by measuring the destruction of target cells via granulocyte, monocyte, dendritic cell, or macrophage-mediated phagocytosis. ADCP assays use PBMC-derived cells or myeloid cell lines such as HL-60, THP-1, and U937 cells differentiated into macrophages or granulocytes. Stimuli that are commonly used to induce macrophage differentiation in monocytic cell lines include phorbol-12-myristate-13-acetate (PMA), 1,25-dihydroxyvitamin D3 (VD3), and retinoic acid (RA). RA is also known to induce terminal granulocytic differentiation of for example HL-60 cells. Phagocytosis of the target cells can be assessed by monitoring effector cells for the internalization of specific probes from target cells pre-labelled with fluorescent dyes such as cell proliferation dye eFluor450, CFSE, and pH-sensitive dyes including pHrodo and CypHer5E. Phagocytosis is measured by an increase in fluorescently labelled effector cells using flow cytometry or fluorescence microscopy. "Reporter gene" assays are also available to assess ADCP. In order to measure ADCP function in a reporter gene assay, target cells are first incubated with a titration of an antibody of interest. Once the antibody is bound to its cognate target on the target cell surface, engineered Jurkat effector cells are added. If ADCP pathway activation ensues, the Jurkat cells produce a luciferase product by expression of the reporter gene NFAT-RE-luc2. Luciferase activity is then measured following a 4-24 hour induction period, after addition of the luciferase assay reagent. The dose-dependent response in the microtiter plate-based assay can be used to quantify the relative biological activity of the therapeutic antibody compared to the dose-response curve of a suitable reference item.

In particular embodiments, the anti-SIRPα antibodies or antigen-binding fragments thereof of the invention may be used in combination with an anti-cancer therapeutic agent or immunomodulatory drug such as an immunomodulatory receptor inhibitor, e.g., an antibody or antigen-binding fragment thereof that specifically binds to the receptor.

In an embodiment of the invention, an anti-SIRPα antibody or antigen-binding fragment thereof of the invention is in association with one or more of:
  an agonist (e.g., an agonistic antibody or antigen-binding fragment thereof, or a soluble fusion) of a TNF receptor protein, an Immunoglobulin-like protein, a cytokine receptor, an integrin, a signaling lymphocytic activation molecules (SLAM proteins), an activating NK cell receptor, a Toll like receptor, OX40, CD2, CD7, CD27, CD28, CD30, CD40, ICAM-1, LFA-1 (CD11a/CD18), 4-1BB (CD137), B7-H3, ICOS (CD278), GITR, BAFFR, LIGHT, HVEM (LIGHTR), KIRDS2, SLAMF7, NKp80 (KLRF1), NKp44, NKp30, NKp46, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD1id, ITGAE, CD103, ITGAL, ITGAM, CD11b, ITGAX, CD11c, ITGB1, CD29, ITGB2, CD18, ITGB7, NKG2D, NKG2C, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Lyl08), SLAM (SLAMF1, CD150, IPO-3), SLAM7, BLAME (SLAMF8), SELPLG (CD162), LTBR, LAT, GADS, PAG/Cbp, CD19a, and a ligand that specifically binds with CD83; or
  an inhibitor of CD47, PD-1, PD-L1, PD-L2, CTLA4, TIM3, LAG3, CEACAM (e.g., CEACAM-1, -3 and/or -5), VISTA, BTLA, TIGIT, LAIR1, IDO, TDO, CD160 and/or TGFR beta.

In an embodiment of the invention, an anti-SIRPα antibody or antigen-binding fragment thereof of the invention is in association with one or more cyclic dinucleotides or other STING pathway agonists. STING (stimulator of interferon genes, also known as TMEM 173, MITA, ERIS, and MPYS) is a transmembrane protein localized to the ER that undergoes a conformational change in response to direct binding of cyclic dinucleotides (CDNs), resulting in a downstream signaling cascade involving TBK1 activation, IRF-3 phosphorylation, and production of IFN-β and other cytokines. The STING pathway in tumor-resident host antigen presenting c3ellss is involved in the induction of a spontaneous CD8+ T cell response against tumor-derived antigens. Activation of this pathway and the subsequent production of IFN-β also reportedly contributes to the anti-tumor effect of radiation. STING agonists and their uses are described in, for example, US20060040887, US20080286296, US20120041057, US20140205653, WO2014179335, WO 2014179760, US20150056224, WO 2015185565, WO 2016096174, WO 2016145102, WO 2017011444, WO 2017027645, WO 2017027646, WO 2017123657, WO 2017123669, WO 2017175147, WO 2017175156, WO 2018045204, WO 2018009648, WO 2018006652, WO 2018013887, WO 2018013908, US20180002369, US20180092937, and US20180093964.

In an embodiment of the invention, an anti-SIRPα antibody or antigen-binding fragment thereof of the invention is in association with one or more of: anti-CD47 antibody, anti-PD-1 antibody (e.g., nivolumab, pembrolizumab, anti-PDL1 antibody, anti-TIGIT antibody, anti-APRIL antibody, anti-CTLA4 antibody, anti-CS1 antibody (e.g., elotuzumab), anti-KIR2DL1/2/3 antibody (e.g., lirilumab), anti-CD137 antibody (e.g., urelumab), anti-GITR antibody (e.g., TRX518), anti-PD-L1 antibody (e.g., BMS-936559, MSB0010718C or MPDL3280A), anti-PD-L2 antibody, anti-ILT1 antibody, anti-ILT2 antibody, anti-ILT3 antibody, anti-ILT4 antibody, anti-ILT5 antibody, anti-ILT6 antibody, anti-ILT7 antibody, anti-ILT8 antibody, anti-CD40 antibody, anti-OX40 antibody, anti-ICOS, anti-KIR2DL1 antibody, anti-KIR2DL2/3 antibody, anti-KIR2DL4 antibody, anti-KIR2DL5A antibody, anti-KIR2DL5B antibody, anti-KIR3DL1 antibody, anti-KIR3DL2 antibody, anti-KIR3DL3 antibody, anti-NKG2A antibody, anti-NKG2C antibody, anti-NKG2E antibody, anti-4-1BB antibody (e.g., PF-05082566), anti-TSLP antibody, anti-IL-10 antibody, IL-10 or PEGylated IL-10, or any small organic molecule inhibitor of such targets.

In an embodiment of the invention, an anti-SIRPα antibody or antigen-binding fragment thereof of the invention is in association with an anti-CD20 antibody (e.g., rituximab, ofatumumab, ocrelizumab, obinutuzumab, ocaratuzumab, ublituximab, veltuzumab, ibritumomab tiuxetan, tositumomab, BVX-20, SCT-400 or PRO131921).

In an embodiment of the invention, an anti-SIRPα antibody or antigen-binding fragment thereof of the invention is in association with an anti-CD38 antibody (e.g., daratumumab, isatuximab or MOR202).

In an embodiment of the invention, an anti-SIRPα antibody or antigen-binding fragment thereof of the invention is in association with an anti-EGFR antibody (e.g., cetuximab, CetuGEX, panitumumab, nimotuzumab, depatuxizumab or AFM-21).

In an embodiment of the invention, an anti-SIRPα antibody or antigen-binding fragment thereof of the invention is in association with an anti-HER2 antibody (e.g., trastuzumab, TrasGEX, pertuzumab, margetuximab or ADCT-502).

In an embodiment of the invention, an anti-SIRPα antibody or antigen-binding fragment thereof of the invention is in association with an anti-HER3 antibody (e.g., lumretuzumab, patritumab or LJM716).

In an embodiment of the invention, an anti-SIRPα antibody or antigen-binding fragment thereof of the invention is in association with an anti-CD19 antibody (e.g., inebilizumab, blinatumomab, DI-B4, MDX-1342, MEDI-551, MOR208 or 4-G7SDIE).

In an embodiment of the invention, an anti-SIRPα antibody or antigen-binding fragment thereof of the invention is in association with an anti-CD52 antibody (e.g., alemtuzumab).

In an embodiment of the invention, an anti-SIRPα antibody or antigen-binding fragment thereof of the invention is in association with an anti-EpCAM antibody (e.g., adecatumumab, catumaxomab, edrecolomab or ING-1).

In an embodiment of the invention, an anti-SIRPα antibody or antigen-binding fragment thereof of the invention is in association with an anti-SLAMF7 antibody (e.g., elotuzumab or ABBV-838).

In an embodiment of the invention, an anti-SIRPα antibody or antigen-binding fragment thereof of the invention is in association with an anti-PD-1 antibody (e.g., nivolumab or pembrolizumab).

In an embodiment of the invention, an anti-SIRPα antibody or antigen-binding fragment thereof of the invention is in association with an anti-PD-L1 antibody (e.g., BMS-936559, MSB0010718C or MPDL3280A).

In an embodiment of the invention, an anti-SIRPα antibody or antigen-binding fragment thereof of the invention is in association with an anti-CTLA4 antibody (e.g., ipilimumab or tremelimumab).

In an embodiment of the invention, an anti-SIRPα antibody or antigen-binding fragment thereof of the invention is in association with an anti-CD137 antibody (e.g., urelumab).

In an embodiment of the invention, an anti-SIRPα antibody or antigen-binding fragment thereof of the invention is in association with an anti-GITR antibody (e.g., TRX518 or FPA154).

In an embodiment of the invention, an anti-SIRPα antibody or antigen-binding fragment thereof of the invention is in association with an anti-OX40 antibody (e.g., MEDI6469, MOXR0916 or INCAGN1949).

In an embodiment of the invention, an anti-SIRPα antibody or antigen-binding fragment thereof of the invention is in association with an anti-CD40 antibody (e.g., lucatumumab, dacetuzmumab, APX005M, ChiLob7/4, CP-870,893 or JNJ-64457107) In an embodiment of the invention, an anti-SIRPα antibody or antigen-binding fragment thereof of the invention is in association with an anti-CS1 antibody.

In an embodiment of the invention, an anti-SIRPα antibody or antigen-binding fragment thereof of the invention is in association with an anti-KIR2DL1/2/3 antibody.

In an embodiment of the invention, an anti-SIRPα antibody or antigen-binding fragment thereof of the invention is in association with an anti-CD137 (e.g., urelumab) antibody.

In an embodiment of the invention, an anti-SIRPα antibody or antigen-binding fragment thereof of the invention is in association with an anti-GITR (e.g., TRX518) antibody.

In an embodiment of the invention, an anti-SIRPα antibody or antigen-binding fragment thereof of the invention is in association with an anti-PD-L2 antibody.

In an embodiment of the invention, an anti-SIRPα antibody or antigen-binding fragment thereof of the invention is in association with an anti-ITL1 antibody.

In an embodiment of the invention, an anti-SIRPα antibody or antigen-binding fragment thereof of the invention is in association with an anti-ITL2 antibody.

In an embodiment of the invention, an anti-SIRPα antibody or antigen-binding fragment thereof of the invention is in association with an anti-ITL3 antibody.

In an embodiment of the invention, an anti-SIRPα antibody or antigen-binding fragment thereof of the invention is in association with an anti-ITL4 antibody.

In an embodiment of the invention, an anti-SIRPα antibody or antigen-binding fragment thereof of the invention is in association with an anti-ITL5 antibody.

In an embodiment of the invention, an anti-SIRPα antibody or antigen-binding fragment thereof of the invention is in association with an anti-ITL6 antibody.

In an embodiment of the invention, an anti-SIRPα antibody or antigen-binding fragment thereof of the invention is in association with an anti-ITL7 antibody.

In an embodiment of the invention, an anti-SIRPα antibody or antigen-binding fragment thereof of the invention is in association with an anti-ITL8 antibody.

In an embodiment of the invention, an anti-SIRPα antibody or antigen-binding fragment thereof of the invention is in association with an anti-CD40 antibody.

In an embodiment of the invention, an anti-SIRPα antibody or antigen-binding fragment thereof of the invention is in association with an anti-OX40 antibody.

In an embodiment of the invention, an anti-SIRPα antibody or antigen-binding fragment thereof of the invention is in association with an anti-KIR2DL1 antibody.

In an embodiment of the invention, an anti-SIRPα antibody or antigen-binding fragment thereof of the invention is in association with an anti-KIR2DL2/3 antibody.

In an embodiment of the invention, an anti-SIRPα antibody or antigen-binding fragment thereof of the invention is in association with an anti-KIR2DL4 antibody.

In an embodiment of the invention, an anti-SIRPα antibody or antigen-binding fragment thereof of the invention is in association with an anti-KIR2DL5A antibody.

In an embodiment of the invention, an anti-SIRPα antibody or antigen-binding fragment thereof of the invention is in association with an anti-KIR2DL5B antibody.

In an embodiment of the invention, an anti-SIRPα antibody or antigen-binding fragment thereof of the invention is in association with an anti-KIR3DL1 antibody.

In an embodiment of the invention, an anti-SIRPα antibody or antigen-binding fragment thereof of the invention is in association with an anti-KIR3DL2 antibody.

In an embodiment of the invention, an anti-SIRPα antibody or antigen-binding fragment thereof of the invention is in association with an anti-KIR3DL3 antibody.

In an embodiment of the invention, an anti-SIRPα antibody or antigen-binding fragment thereof of the invention is in association with an anti-NKG2A antibody.

In an embodiment of the invention, an anti-SIRPα antibody or antigen-binding fragment thereof of the invention is in association with an anti-NKG2C antibody.

In an embodiment of the invention, an anti-SIRPα antibody or antigen-binding fragment thereof of the invention is in association with an anti-ICOS antibody.

In an embodiment of the invention, an anti-SIRPα antibody or antigen-binding fragment thereof of the invention is in association with an anti-4-1BB antibody.

In an embodiment of the invention, an anti-SIRPα antibody or antigen-binding fragment thereof of the invention is in association with an anti-IL-10 antibody.

In an embodiment of the invention, an anti-SIRPα antibody or antigen-binding fragment thereof of the invention is in association with an anti-TSLP antibody.

In an embodiment of the invention, an anti-SIRPα antibody or antigen-binding fragment thereof of the invention is in association with IL-10 or PEGylated IL-10.

In an embodiment of the invention, an anti-SIRPα antibody or antigen-binding fragment thereof of the invention is in association with one or more of an inhibitor (e.g., a small organic molecule or an antibody or antigen-binding fragment thereof) such as: an MTOR (mammalian target of rapamycin) inhibitor, a cytotoxic agent, a platinum agent, an EGFR inhibitor, a VEGF inhibitor, a microtubule stabilizer, a taxane, a CD20 inhibitor, a CD52 inhibitor, a CD30 inhibitor, a RANK (Receptor activator of nuclear factor kappa-B) inhibitor, a RANKL (Receptor activator of nuclear factor kappa-B ligand) inhibitor, an ERK inhibitor, a MAP Kinase inhibitor, an AKT inhibitor, a MEK inhibitor, a PI3K inhibitor, a HER1 inhibitor, a HER2 inhibitor, a HER3 inhibitor, a HER4 inhibitor, a Bcl2 inhibitor, a CD22 inhibitor, a CD79b inhibitor, an ErbB2 inhibitor, or a farnesyl protein transferase inhibitor.

In an embodiment of the invention, an anti-SIRPα antibody or antigen-binding fragment thereof of the invention is in association with any one or more of: 13-cis-retinoic acid, 3-[5-(methylsulfonylpiperadinemethyl)-indolyl]-quinolone, 4-hydroxytamoxifen, 5-deoxyuridine, 5'-deoxy-5-fluorouridine, 5-fluorouracil, 6-mecaptopurine, 7-hydroxystaurosporine, A-443654, abirateroneacetate, abraxane, ABT-578, acolbifene, ADS-100380, ALT-110, altretamine, amifostine, aminoglutethimide, amrubicin, Amsacrine, anagrelide, anastrozole, angiostatin, AP-23573, ARQ-197, arzoxifene, AS-252424, AS-605240, asparaginase, AT-9263, atrasentan, axitinib, AZD1152, *Bacillus* Calmette-Guerin (BCG) vaccine, batabulin, BC-210, besodutox, bevacizumab, bicalutamide, Biol 11, BIO140, bleomycin, BMS-214662, BMS-247550, BMS-275291, BMS-310705, bortezomib, buserelin, busulfan, calcitriol, camptothecin, canertinib, capecitabine, carboplatin, carmustine, CC8490, Cediranib, CG-1521, CG-781, chlamydocin, chlorambucil, chlorotoxin, cilengitide, cimitidine, cisplatin, cladribine, clodronate, COL-3, CP-724714, cyclophosphamide, cyproterone, cyproteroneacetate, cytarabine, cytosinearabinoside, dacarbazine, dacinostat, dactinomycin, dalotuzumab, danusertib, dasatanib, daunorubicin, decatanib, deguelin, denileukin, deoxycoformycin, depsipeptide, diarylpropionitrile, diethylstilbestrol, diftitox, docetaxel, dovitinib, doxorubicin, droloxifene, edotecarin, yttrium-90 labeled-edotreotide, edotreotide, EKB-569, EMD121974, endostatin, enzalutamide, enzastaurin, epirubicin, epithilone B, ERA-923, Erbitux, erlotinib, estradiol, estramustine, etoposide, everolimus, exemestane, ficlatuzumab, finasteride, flavopiridol, floxuridine, fludarabine, fludrocortisone, fluoxymesterone, flutamide, FOLFOX regimen, Fulvestrant, galeterone, gefitinib, gemcitabine, gimatecan, goserelin, goserelin acetate, gossypol, GSK461364, GSK690693, HMR-3339, hydroxyprogesteronecaproate, hydroxyurea, IC87114, idarubicin, idoxyfene, ifosfamide, IM862, imatinib, IMC-1C11, INCB24360, INO1001, interferon, interleukin-12, ipilimumab, irinotecan, JNJ-16241199, ketoconazole, KRX-0402, thalidomide, lenalidomide, pomalidomide, apremilast, lapatinib, lasofoxifene, letrozole, leucovorin, leuprolide, leuprolide acetate, levamisole, liposome entrapped paclitaxel, lomustine, lonafarnib, lucanthone, LY292223, LY292696, LY293646, LY293684, LY294002, LY317615, marimastat, mechlorethamine, medroxyprogesteroneacetate, megestrolacetate, melphalan, mercaptopurine, mesna, methotrexate, mithramycin, mitomycin, mitotane, mitoxantrone, tozasertib, MLN8054, neovastat, Neratinib, neuradiab, nilotinib, nilutimide, nolatrexed, NVP-BEZ235, oblimersen, octreotide, ofatumumab, oregovomab, orteronel, oxaliplatin, paclitaxel, palbociclib, pamidronate, panitumumab, pazopanib, PD0325901, PD184352, PEG-interferon, pemetrexed, pentostatin, perifosine, phenylalaninemustard, PI-103, pictilisib, PIK-75, pipendoxifene, PKI-166, plicamycin, porfimer, prednisone, procarbazine, progestins, PX-866, R-763, raloxifene, raltitrexed, razoxin, ridaforolimus, rituximab, romidepsin, RTA744, rubitecan, scriptaid, Sdx102, seliciclib, selumetinib, semaxanib, SF1126, sirolimus, SN36093, sorafenib, spironolactone, squalamine, SR13668, streptozocin, SU6668, suberoylanalide hydroxamic acid, sunitinib, synthetic estrogen, talampanel, talimogene laherparepvec, tamoxifen, temozolomide, temsirolimus, teniposide, tesmilifene, testosterone, tetrandrine, TGX-221, thalidomide, thioguanine, thiotepa, tremelimumab, tipifarnib, tivozanib, TKI-258, TLK286, topotecan, toremifene citrate, trabectedin, trastuzumab, tretinoin, trichostatin A, triciribinephosphate monohydrate, triptorelin pamoate, TSE-424, uracil mustard, valproic acid, valrubicin, vandetanib, vatalanib, VEGF trap, vinblastine, vincristine, vindesine, vinorelbine, vitaxin, vitespan, vorinostat, VX-745, wortmannin, Xr311, zanolimumab, ZK186619, ZK-304709, ZM336372, ZSTK474.

Non-limiting examples of suitable anti-cancer agents to be used in combination with an anti-SIRPα antibody or antigen-binding fragment thereof of the invention include cytostatic agents, immune modulating imide drugs, cytotoxic agents, targeted therapeutic agents (small molecules, biologics, siRNA and microRNA) against cancer and neoplastic diseases, 1) anti-metabolites (such as methotrexate, 5-fluorouracil, gemcitabine, fludarabine, capecitabine);
2) alkylating agents, such as temozolomide, cyclophosphamide,
3) DNA interactive and DNA damaging agents, such as cisplatin, oxaliplatin, doxorubicin,
4) Ionizing irradiation, such as radiation therapy,
5) topoisomerase II inhibitors, such as etoposide, doxorubicin,
6) topoisomerase I inhibitors, such as irinotecan, topotecan,
7) tubulin interacting agents, such as paclitaxel, docetaxel, Abraxane, epothilones,
8) kinesin spindle protein inhibitors,
9) spindle checkpoint inhibitors,
10) Poly(ADP-ribose) polymerase (PARP) inhibitors, such as olaparib, MK-4827 and veliparib
11) Matrix metalloprotease (MMP) inhibitors
12) Protease inhibitors, such as cathepsin D and cathepsin K inhibitors
13) Proteosome or ubiquitination inhibitors, such as bortezomib,
14) Activator of mutant p53 to restore its wild-type p53 activity
15) Adenoviral-p53
16) Bcl-2 inhibitors, such as ABT-263
17) Heat shock protein (HSP) modulators, such as geldanamycin and 17-AAG
18) Histone deacetylase (HDAC) inhibitors, such as vorinostat (SAHA),
19) sex hormone modulating agents,
    a. anti-estrogens, such as tamoxifen, fulvestrant,
    b. selective estrogen receptor modulators (SERM), such as raloxifene,
    c. anti-androgens, such as bicalutamide, flutamide
    d. LHRH agonists, such as leuprolide,
    e. 5α-reductase inhibitors, such as finasteride,
    f. Cytochrome P450 C17 lyase (CYP450c17, also called 17αC);
    g. aromatase inhibitors, such as letrozole, anastrozole, exemestane,
20) EGFR kinase inhibitors, such as geftinib, erlotinib, laptinib
21) dual erbB1 and erbB2 inhibitors, such as Lapatinib
22) multi-targeted kinases (serine/threonine and/or tyrosine kinase) inhibitors, a. ABL kinase inhibitors, imatinib and nilotinib, dasatinib
b. VEGFR-1, VEGFR-2, PDGFR, KDR, FLT, c-Kit, Tie2, Raf, MEK and ERK inhibitors, such as sunitinib, sorafenib, Vandetanib, pazopanib, PLX-4032, Axitinib, PTK787, GSK-1120212
c. Polo-like kinase inhibitors
d. Aurora kinase inhibitors
e. JAK inhibitor
f. c-MET kinase inhibitors
g. Cyclin-dependent kinase inhibitors, such as CDK1 and CDK2 inhibitor Dinaciclib SCH 727965 (see Parry et al, *Molecular Cancer Therapeutics* 9 (8): 2344-53 (2010)) and CDK4/6 inhibitors, such as Ribociclib, Palbociclib, Abemaciclib, and Trilaciclib.
h. PI3K and mTOR inhibitors, such as GDC-0941, BEZ-235, BKM-120 and AZD-8055
i. Rapamycin and its analogs, such as Temsirolimus, everolimus, and deforolimus 23) and other anti-cancer (also know as anti-neoplastic) agents include but are not limited to ara-C, adriamycin, cytoxan, Carboplatin, Uracil mustard, Clormethine, Ifosfsmide, Melphalan, Chlorambucil, Pipobroman, Triethylenemelamine, Triethylenethiophosphoramine, Busulfan, Carmustine, Lomustine, Streptozocin, Dacarbazine, Floxuridine, Cytarabine, 6-Mercaptopurine, 6-Thioguanine, Fludarabine phosphate, Pentostatine, Vinblastine, Vincristine, Vindesine, Vinorelbine, Navelbine, Bleomycin, Dactinomycin, Daunorubicin, Doxorubicin, Epirubicin, teniposide, cytarabine, pemetrexed, Idarubicin, Mithramycin, Deoxycoformycin, Mitomycin-C, L-Asparaginase, Teniposide, Ethinylestradiol, Diethylstilbestrol, Testosterone, Prednisone, Fluoxymesterone, Dromostanolone propionate, Testolactone, Megestrolacetate, Methylprednisolone, Methyltestosterone, Prednisolone, Triamcinolone, Chlorotrianisene, Hydroxyprogesterone, Aminoglutethimide, Estramustine, Flutamide Medroxyprogesteroneacetate, Toremifene, goserelin, Carboplatin, Hydroxyurea, Amsacrine, Procarbazine, Mitotane, Mitoxantrone, Levamisole, Drolloxafine, Hexamethylmelamine, Bexxar, Zevalin, Trisenox, Profimer, Thiotepa, Altretamine, Doxil, Ontak, Depocyt, Aranesp, Neupogen, Neulasta, Kepivance.
24) Farnesyl protein transferase inhibitors, such as, SARASAR™ (4-[2-[4-[(11R)-3,10-dibromo-8-chloro-6, 11-dihydro-5H-benzo[5,6]cyclohepta[1,2-b]pyridin-11-yl-]-1-piperidinyl]-2-oxoethyl]-piperidinecarboxamide, tipifarnib
25) interferons, such as Intron A, Peg-Intron,
26) anti-erbB1 antibodies, such as cetuximab, panitumumab,
27) anti-erbB2 antibodies, such as trastuzumab,
28) anti-CD52 antibodies, such as Alemtuzumab,
29) anti-CD20 antibodies, such as Rituximab
30) anti-CD33 antibodies, such as Gemtuzumab ozogamicin
31) anti-VEGF antibodies, such as Avastin,
32) TRIAL ligands, such as Lexatumumab, mapatumumab, and AMG-655
33) anti-CTLA-4 antibodies, such as ipilimumab
34) antibodies against CTA1, CEA, CD5, CD19, CD22, CD30, CD44, CD44V6, CD55, CD56, EpCAM, FAP, MHCII, HGF, IL-6, MUC1, PSMA, TAL6, TAG-72, TRAILR, VEGFR, IGF-2, FGF,
35) anti-IGF-1R antibodies, such as dalotuzumab (MK-0646) and robatumumab (SCH 717454).

"Estrogen receptor modulators" refers to compounds that interfere with or inhibit the binding of estrogen to the receptor, regardless of mechanism. Examples of estrogen receptor modulators include, but are not limited to, tamoxifen, raloxifene, idoxifene, LY353381, LY117081, toremifene, fulvestrant, 4-[7-(2,2-dimethyl-1-oxopropoxy-4-methyl-2-[4-[2-(1-piperidinyl)ethoxy]phenyl]-2H-1-benzopyran-3-yl]-phenyl-2,2-dimethylpropanoate, 4,4'-dihydroxybenzophenone-2,4-dinitrophenyl-hydrazone, and SH646.

"Androgen receptor modulators" refers to compounds which interfere or inhibit the binding of androgens to the receptor, regardless of mechanism. Examples of androgen receptor modulators include finasteride and other 5α-reductase inhibitors, nilutamide, flutamide, bicalutamide, liarozole, and abiraterone acetate.

"Retinoid receptor modulators" refers to compounds which interfere or inhibit the binding of retinoids to the receptor, regardless of mechanism. Examples of such retinoid receptor modulators include bexarotene, tretinoin, 13-cis-retinoic acid, 9-cis-retinoic acid, α-difluoromethylornithine, ILX23-7553, trans-N-(4'-hydroxyphenyl) retinamide, and N-4-carboxyphenyl retinamide.

"Cytotoxic/cytostatic agents" refer to compounds which cause cell death or inhibit cell proliferation primarily by interfering directly with the cell's functioning or inhibit or interfere with cell myosis, including alkylating agents, tumor necrosis factors, intercalators, hypoxia activatable compounds, microtubule inhibitors/microtubule-stabilizing agents, inhibitors of mitotic kinesins, histone deacetylase inhibitors, inhibitors of kinases involved in mitotic progression, inhibitors of kinases involved in growth factor and cytokine signal transduction pathways, antimetabolites, biological response modifiers, hormonal/anti-hormonal therapeutic agents, haematopoietic growth factors, monoclonal antibody targeted therapeutic agents, topoisomerase inhibitors, proteosome inhibitors, ubiquitin ligase inhibitors, and aurora kinase inhibitors.

Examples of cytotoxic/cytostatic agents include, but are not limited to, platinum coordinator compounds, sertenef, cachectin, ifosfamide, tasonermin, lonidamine, carboplatin, altretamine, prednimustine, dibromodulcitol, ranimustine, fotemustine, nedaplatin, oxaliplatin, temozolomide, heptaplatin, estramustine, improsulfan tosilate, trofosfamide, nimustine, dibrospidium chloride, pumitepa, lobaplatin, satraplatin, profiromycin, cisplatin, irofulven, dexifosfamide, cis-aminedichloro(2-methyl-pyridine)platinum, benzylguanine, glufosfamide, GPX100, (trans, trans, trans)-bis-mu-(hexane-1,6-diamine)-mu-[diamine-platinum(II)]bis [diamine(chloro)platinum (II)]tetrachloride, diarizidinylspermine, arsenic trioxide, 1-(11-dodecylamino-10-hydroxyundecyl)-3,7-dimethylxanthine, zorubicin, idarubicin, daunorubicin, bisantrene, mitoxantrone, pirarubicin, pinafide, valrubicin, amrubicin, antineoplaston, 3'-deamino-3'-morpholino-13-deoxo-10-hydroxycarminomycin, annamycin, galarubicin, elinafide, MEN10755, 4-demethoxy-3-deamino-3-aziridinyl-4-methylsulphonyl-daunorubicin (see WO 00/50032).

An example of a hypoxia activatable compound is tirapazamine.

Examples of proteosome inhibitors include but are not limited to lactacystin and MLN-341 (Velcade).

Examples of microtubule inhibitors/microtubule-stabilising agents include taxanes in general. Specific compounds include paclitaxel (Taxol®), vindesine sulfate, 3',4'-didehydro-4'-deoxy-8'-norvincaleukoblastine, docetaxol (Taxotere®), rhizoxin, dolastatin, mivobulin isethionate, auristatin, cemadotin, RPR109881, BMS184476, vinflunine, cryptophycin, 2,3,4,5,6-pentafluoro-N-(3-fluoro-4-methoxyphenyl) benzene sulfonamide, anhydrovinblastine, N,N-dimethyl-L-valyl-1-valyl-N-methyl-L-valyl-L-prolyl-L-proline-t-butylamide, TDX258, the epothilones (see for example U.S. Pat. Nos. 6,284,781 and 6,288,237) and BMS188797.

Some examples of topoisomerase inhibitors are topotecan, hycaptamine, irinotecan, rubitecan, 6-ethoxypropionyl-3',4'-O-exo-benzylidene-chartreusin, 9-methoxy-N,N-dimethyl-5-nitropyrazolo[3,4,5-kl]acridine-2-(6H) propanamine, 1-amino-9-ethyl-5-fluoro-2,3-dihydro-9-hydroxy-4-methyl-1H, 12H-benzo[de]pyrano[3',4':b,7]-indolizino[1,2b]quinoline-10,13(9H,15H)dione, lurtotecan, 7-[2-(N-isopropylamino)ethyl]-(20S)camptothecin, BNP1350, BNPI1100, BN80915, BN80942, etoposide phosphate, teniposide, sobuzoxane, 2'-dimethylamino-2'-deoxy-etoposide, GL331, N-[2-(dimethylamino)ethyl]-9-hydroxy-5,6-dimethyl-6H-pyrido[4,3-b]carbazole-1-carboxamide, asulacrine, (5a, 5aB, 8aa,9b)-9-[2-[N-[2-(dimethylamino)ethyl]-N-methylamino]ethyl]-5-[4-hydroOxy-3,5-dimethoxyphenyl]-5,5a,6,8,8a,9-hexohydrofuro(3',4':6,7) naphtho(2,3-d)-1,3-dioxol-6-one, 2,3-(methylenedioxy)-5-methyl-7-hydroxy-8-methoxybenzo[c]-phenanthridinium, 6,9-bis[(2-aminoethyl)amino]benzo[g]isoguinoline-5,10-dione, 5-(3-aminopropylamino)-7,10-dihydroxy-2-(2-hydroxyethylaminomethyl)-6H-pyrazolo[4,5,1-de]acridin-6-one, N-[1-[2(diethylamino)ethylamino]-7-methoxy-9-oxo-9H-thioxanthen-4-ylmethyl]formamide, N-(2-(dimethylamino)ethyl)acridine-4-carboxamide, 6-[[2-(dimethylamino)ethyl]amino]-3-hydroxy-7H-indeno[2,1-c]quinolin-7-one, and dimesna.

Examples of inhibitors of mitotic kinesins, and in particular the human mitotic kinesin KSP, are described in Publications WO03/039460, WO03/050064, WO03/050122, WO03/049527, WO03/049679, WO03/049678, WO04/039774, WO03/079973, WO03/099211, WO03/105855, WO03/106417, WO04/037171, WO04/058148, WO04/058700, WO04/126699, WO05/018638, WO05/019206, WO05/019205, WO05/018547, WO05/017190, US2005/0176776. In an embodiment inhibitors of mitotic kinesins include, but are not limited to inhibitors of KSP, inhibitors of MKLP1, inhibitors of CENP-E, inhibitors of MCAK and inhibitors of Rab6-KIFL.

Examples of "histone deacetylase inhibitors" include, but are not limited to, SAHA, TSA, oxamflatin, PXD101, MG98 and scriptaid. Further reference to other histone deacetylase inhibitors may be found in the following manuscript; Miller, T. A. et al. *J. Med. Chem.* 46(24):5097-5116 (2003).

"Inhibitors of kinases involved in mitotic progression" include, but are not limited to, inhibitors of aurora kinase, inhibitors of Polo-like kinases (PLK; in particular inhibitors of PLK-1), inhibitors of bub-1 and inhibitors of bub-R1. An example of an "aurora kinase inhibitor" is VX-680.

"Antiproliferative agents" includes antisense RNA and DNA oligonucleotides such as G3139, ODN698, RVASKRAS, GEM231, and INX3001, and antimetabolites such as enocitabine, carmofur, tegafur, pentostatin, doxifluridine, trimetrexate, fludarabine, capecitabine, galocitabine, cytarabine ocfosfate, fosteabine sodium hydrate, raltitrexed, paltitrexid, emitefur, tiazofurin, decitabine, nolatrexed, pemetrexed, nelzarabine, 2'-deoxy-2'-methylidenecytidine, 2'-fluoromethylene-2'-deoxycytidine, N-[5-(2,3-dihydrobenzofuryl)sulfonyl]-N'-(3,4-dichlorophenyl)urea, N6-[4-deoxy-4-[N2-[2(E),4(E)-tetradecadienoyl]glycylamino]-L-glycero-B-L-manno-heptopyranosyl]adenine, aplidine, ecteinascidin, troxacitabine, 4-[2-amino-4-oxo-4,6,7,8-tetrahydro-3H-pyrimidino[5,4-b][1,4]thiazin-6-yl-(S)-ethyl]-2,5-thienoyl-L-glutamic acid, aminopterin, 5-flurouracil, alanosine, 11-acetyl-8-(carbamoyloxymethyl)-4-formyl-6-methoxy-14-oxa-1,11-diazatetracyclo(7.4.1.0.0)-tetradeca-2,4,6-trien-9-yl acetic acid ester, swainsonine, lometrexol, dexrazoxane, methioninase, 2'-cyano-2'-deoxy-N4-palmitoyl-1-B-D-arabino furanosyl cytosine, 3-aminopyridine-2-carboxaldehyde thiosemicarbazone and trastuzumab.

Examples of monoclonal antibody targeted therapeutic agents include those therapeutic agents which have cytotoxic agents or radioisotopes attached to a cancer cell specific or target cell specific monoclonal antibody. Examples include Bexxar.

"Prenyl-protein transferase inhibitor" refers to a compound which inhibits any one or any combination of the prenyl-protein transferase enzymes, including farnesyl-protein transferase (FPTase), geranylgeranyl-protein transferase type I (GGPTase-I), and geranylgeranyl-protein transferase type-II (GGPTase-II, also called Rab GGPTase).

Examples of prenyl-protein transferase inhibitors can be found in the following publications and patents: WO 96/30343, WO 97/18813, WO 97/21701, WO 97/23478, WO 97/38665, WO 98/28980, WO 98/29119, WO 95/32987, U.S. Pat. Nos. 5,420,245, 5,523,430, 5,532,359, 5,510,510, 5,589,485, 5,602,098, European Patent Publ. 0 618 221, European Patent Publ. 0 675 112, European Patent Publ. 0 604 181, European Patent Publ. 0 696 593, WO 94/19357, WO 95/08542, WO 95/11917, WO 95/12612, WO 95/12572, WO 95/10514, U.S. Pat. No. 5,661,152, WO 95/10515, WO 95/10516, WO 95/24612, WO 95/34535, WO 95/25086, WO 96/05529, WO 96/06138, WO 96/06193, WO 96/16443, WO 96/21701, WO 96/21456, WO 96/22278, WO 96/24611, WO 96/24612, WO 96/05168, WO 96/05169, WO 96/00736, U.S. Pat. No. 5,571,792, WO 96/17861, WO 96/33159, WO 96/34850, WO 96/34851, WO 96/30017, WO 96/30018, WO 96/30362, WO 96/30363, WO 96/31111, WO 96/31477, WO 96/31478, WO 96/31501, WO 97/00252, WO 97/03047, WO 97/03050, WO 97/04785, WO 97/02920, WO 97/17070, WO 97/23478, WO 97/26246, WO 97/30053, WO 97/44350, WO 98/02436, and U.S. Pat. No. 5,532,359. For an example of the role of a prenyl-protein transferase inhibitor on angiogenesis see *European J. of Cancer*, Vol. 35, No. 9, pp. 1394-1401 (1999).

"Angiogenesis inhibitors" refers to compounds that inhibit the formation of new blood vessels, regardless of mechanism. Examples of angiogenesis inhibitors include, but are not limited to, tyrosine kinase inhibitors, such as inhibitors of the tyrosine kinase receptors Flt-1 (VEGFR1) and Flk-1/KDR (VEGFR2), inhibitors of epidermal-derived, fibroblast-derived, or platelet derived growth factors, MMP (matrix metalloprotease) inhibitors, integrin blockers, interferon-α, interleukin-12, pentosan polysulfate, cyclooxygenase inhibitors, including nonsteroidal anti-inflammatories (NSAIDs) like aspirin and ibuprofen as well as selective cyclooxy-genase-2 inhibitors like celecoxib and rofecoxib (*PNAS*, Vol. 89, p. 7384 (1992); JNCI, Vol. 69, p. 475 (1982); *Arch. Opthalmol.*, Vol. 108, p. 573 (1990); *Anat. Rec.*, Vol. 238, p. 68 (1994); *FEBS Letters*, Vol. 372, p. 83 (1995); *Clin, Orthop.* Vol. 313, p. 76 (1995); *J. Mol. Endocrinol.*, Vol. 16, p. 107 (1996); *Jpn. J. Pharmacol.*, Vol. 75, p. 105 (1997); *Cancer Res.*, Vol. 57, p. 1625 (1997); Cell, Vol. 93, p. 705 (1998); *Intl. J. Mol. Med.*, Vol. 2, p. 715 (1998); *J. Biol. Chem.*, Vol. 274, p. 9116 (1999)), steroidal anti-inflammatories (such as corticosteroids, mineralocorticoids, dexamethasone, prednisone, prednisolone, methylpred, betamethasone), carboxyamidotriazole, combretastatin A-4, squalamine, 6-O-chloroacetyl-carbonyl)-fumagillol, thalidomide, angiostatin, troponin-1, angiotensin II antagonists (see Fernandez et al., *J. Lab. Clin. Med.* 105: 141-145 (1985)), and antibodies to VEGF (see, Nature Biotechnology, Vol. 17, pp. 963-968 (October 1999); Kim et al., *Nature*, 362, 841-844 (1993); WO 00/44777; and WO 00/61186).

Other examples of angiogenesis inhibitors include, but are not limited to, endostatin, ukrain, ranpirnase, IM862, 5-methoxy-4-[2-methyl-3-(3-methyl-2-butenyl)oxiranyl]-1-oxaspiro[2,5]oct-6-yl(chloroacetyl)carbamate, acetyldinanaline, 5-amino-1-[[3,5-dichloro-4-(4-chlorobenzoyl)phenyl]methyl]-1H-1,2,3-triazole-4-carboxamide, CM101, squalamine, combretastatin, RPI4610, NX31838, sulfated mannopentaose phosphate, 7,7-(carbonyl-bis[imino-N-methyl-4,2-pyrrolocarbonylimino[N-methyl-4,2-pyrrole]-carbonylimino]-bis-(1,3-naphthalene disulfonate), and 3-[(2,4-dimethylpyrrol-5-yl)methylene]-2-indolinone (SU5416).

Other therapeutic agents that modulate or inhibit angiogenesis and may also be used in combination with the compounds of the instant invention include agents that modulate or inhibit the coagulation and fibrinolysis systems (see review in *Clin. Chem. La. Med.* 38:679-692 (2000)). Examples of such agents that modulate or inhibit the coagulation and fibrinolysis pathways include, but are not limited to, heparin (see *Thromb. Haemost.* 80:10-23 (1998)), low molecular weight heparins and carboxypeptidase U inhibitors (also known as inhibitors of active thrombin activatable fibrinolysis inhibitor [TAFIa]) (see *Thrombosis Res.* 101: 329-354 (2001)). TAFIa inhibitors have been described in U.S. Ser. Nos. 60/310,927 (filed Aug. 8, 2001) and 60/349,925 (filed Jan. 18, 2002).

"Agents that interfere with cell cycle checkpoints" refer to compounds that inhibit protein kinases that transduce cell cycle checkpoint signals, thereby sensitizing the cancer cell to DNA damaging agents. Such agents include inhibitors of ATR, ATM, the CHK11 and CHK12 kinases and cdk and cdc kinase inhibitors and are specifically exemplified by 7-hydroxystaurosporin, flavopiridol, CYC202 (Cyclacel) and BMS-387032.

"Agents that interfere with receptor tyrosine kinases (RTKs)" refer to compounds that inhibit RTKs and therefore mechanisms involved in oncogenesis and tumor progression. Such agents include inhibitors of c-Kit, Eph, PDGF, Flt3 and c-Met. Further agents include inhibitors of RTKs as described by Bume-Jensen and Hunter, *Nature*, 411:355-365, 2001.

"Inhibitors of cell proliferation and survival signalling pathway" refer to compounds that inhibit signal transduction cascades downstream of cell surface receptors. Such agents include inhibitors of serine/threonine kinases (including but not limited to inhibitors of Akt such as described in WO 02/083064, WO 02/083139, WO 02/083140, US 2004-0116432, WO 02/083138, US 2004-0102360, WO 03/086404, WO 03/086279, WO 03/086394, WO 03/084473, WO 03/086403, WO 2004/041162, WO 2004/096131, WO 2004/096129, WO 2004/096135, WO 2004/096130, WO 2005/100356, WO 2005/100344, US 2005/029941, US 2005/44294, US 2005/43361, 60/734,188, 60/652,737, 60/670,469), inhibitors of Raf kinase (for example PLX-4032), inhibitors of MEK (for example Arry-162, RO-4987655 and GSK-1120212), inhibitors of mTOR (for example AZD-8055, BEZ-235 and everolimus), and inhibitors of PI3K (for example GDC-0941, BKM-120).

As used above, "integrin blockers" refers to compounds which selectively antagonize, inhibit or counteract binding of a physiological ligand to the $\alpha_v\beta_3$ integrin, to compounds which selectively antagonize, inhibit or counteract binding of a physiological ligand to the $\alpha v\beta 5$ integrin, to compounds which antagonize, inhibit or counteract binding of a physiological ligand to both the $\alpha v\beta_3$ integrin and the $\alpha_v\beta_5$ integrin, and to compounds which antagonize, inhibit or counteract the activity of the particular integrin(s) expressed on capillary endothelial cells. The term also refers to antagonists of the $\alpha_v\beta_6$, $\alpha_v\beta_8$, $\alpha_1\beta_1$, $\alpha_2\beta_1$, $\alpha_5\beta_1$, $\alpha_6\beta_1$, and $\alpha_6\beta_4$ integrins. The term also refers to antagonists of any combination of $\alpha_v\beta_3$, $\alpha_v\beta_5$, $\alpha_v\beta_8$, $\alpha_2\beta_1$, $\alpha_2\beta_1$, $\alpha_5\beta_1$, $\alpha_6\beta_1$, and $\alpha_6\beta_4$ integrins.

Some specific examples of tyrosine kinase inhibitors include N-(trifluoromethylphenyl)-5-methylisoxazol-4-carboxamide, 3-[(2,4-dimethylpyrrol-5-yl)methylidenyl)indolin-2-one, 17-(allylamino)-17-demethoxygeldanamycin, 4-(3-chloro-4-fluorophenylamino)-7-methoxy-6-[3-(4-morpholinyl)propoxyl]quinazoline, N-(3-ethynylphenyl)-6,7-bis(2-methoxyethoxy)-4-quinazolinamine, BIBX1382, 2,3,9,10,11,12-hexahydro-10-(hydroxymethyl)-10-hydroxy-9-methyl-9,12-epoxy-1H-diindolo[1,2,3-fg:3',2',1'-kl]pyrrolo[3,4-i][1,6]benzodiazocin-1-one, SH268, genistein, STI571, CEP2563, 4-(3-chlorophenylamino)-5,6-dimethyl-7H-pyrrolo[2,3-d]pyrimidinemethane sulfonate, 4-(3-bromo-4-hydroxyphenyl)amino-6,7-dimethoxyquinazoline, 4-(4'-hydroxyphenyl)amino-6,7-dimethoxyquinazoline, SU6668, STI571A, N-4-chlorophenyl-4-(4-pyridylmethyl)-1-phthalazinamine, and EMD121974.

Combinations of the instantly claimed antibodies or antigen binding fragments with PPAR-γ (i.e., PPAR-gamma) agonists and PPAR-δ (i.e., PPAR-delta) agonists may be useful in the treatment of certain malignancies. PPAR-γ and PPAR-δ are the nuclear peroxisome proliferator-activated receptors γ and δ. The expression of PPAR-γ on endothelial cells and its involvement in angiogenesis has been reported in the literature (see *J. Cardiovasc. Pharmacol.* 1998; 31: 909-913; *J. Biol. Chem.* 1999; 274: 9116-9121; *Invest. Ophthalmol Vis. Sci.* 2000; 41: 2309-2317). More recently, PPAR-γ agonists have been shown to inhibit the angiogenic response to VEGF in vitro; both troglitazone and rosiglitazone maleate inhibit the development of retinal neovascularization in mice. (Arch. Ophthalmol. 2001; 119: 709-717). Examples of PPAR-γ agonists and PPAR-γ/α agonists include, but are not limited to, Lynparza®, Rucaparib®, Talazoparib®, niraparib, Veliparib®, thiazolidinediones (such as DRF2725, CS-011, troglitazone, rosiglitazone, and pioglitazone), fenofibrate, gemfibrozil, clofibrate, GW2570, SB219994, AR-H039242, JTT-501, MCC-555, GW2331, GW409544, NN2344, KRP297, NP0110, DRF4158, NN622, GI262570, PNU182716, DRF552926, 2-[(5,7-dipropyl-3-trifluoromethyl-1,2-benzisoxazol-6-yl)oxy]-2-methylpropionic acid, and 2(R)-7-(3-(2-chloro-4-(4-fluorophenoxy) phenoxy)propoxy)-2-ethylchromane-2-carboxylic acid.

The antibody or antigen binding fragment of the instant invention may also be useful for treating or preventing breast cancer in combination with aromatase inhibitors. Examples of aromatase inhibitors include but are not limited to: anastrozole, letrozole and exemestane.

The antibody or antigen binding fragment of the instant invention may also be useful for treating cancer in combination with the following chemotherapeutic agents: abarelix (Plenaxis Depot®); aldesleukin (Prokine®); Aldesleukin (Proleukin®); Alemtuzumab (Campath®); alitretinoin (Panretin®); allopurinol (Zyloprim®); altretamine (Hexalen®);

amifostine (Ethyol®); anastrozole (Arimidex®); arsenic trioxide (Trisenox®); asparaginase (Elspar®); azacitidine (Vidaza®); bendamustine hydrochloride (Treanda®); bevacuzimab (Avastin®); bexarotene capsules (Targretin®); bexarotene gel (Targretin®); bleomycin (Blenoxane®); bortezomib (Velcade®); brefeldin A; busulfan intravenous (Busulfex®); busulfan oral (Myleran®); calusterone (Methosarb®); capecitabine (Xeloda®); carboplatin (Paraplatin®); carmustine (BCNU®, BiCNU®); carmustine (Gliadel®); carmustine with Polifeprosan 20 Implant (Gliadel Wafer®); celecoxib (Celebrex®); cetuximab (Erbitux®); chlorambucil (Leukeran®); cisplatin (Platinol®); cladribine (Leustatin®, 2-CdA®); clofarabine (Clolar®); cyclophosphamide (Cytoxan®, Neosar®); cyclophosphamide (Cytoxan Injection®); cyclophosphamide (Cytoxan Tablet®); cytarabine (Cytosar-U®); cytarabine liposomal (DepoCyt®); dacarbazine (DTIC-Dome®); dactinomycin, actinomycin D (Cosmegen®); dalteparin sodium injection (Fragmin®); daratumumab (DARZALEX®); Darbepoetin alfa (Aranesp®); dasatinib (Sprycel®); daunorubicin liposomal (DanuoXome®); daunorubicin, daunomycin (Daunorubicin®); daunorubicin, daunomycin (Cerubidine®); degarelix (Firmagon®); Denileukin diftitox (Ontak®); dexrazoxane (Zinecard®); dexrazoxane hydrochloride (Totect®); didemnin B; 17-DMAG; docetaxel (Taxotere®); doxorubicin (Adriamycin PFS®); doxorubicin (Adriamycin®, Rubex®); doxorubicin (Adriamycin PFS Injection®); doxorubicin liposomal (Doxil®); dromostanolone propionate (Dromostanolone®); dromostanolone propionate (Masterone Injection®); eculizumab injection (Soliris®); Elliott's B Solution (Elliott's B Solution®); eltrombopag (Promacta®); epirubicin (Ellence®); Epoetin alfa (Epogen®); erlotinib (Tarceva®); estramustine (Emcyt®); ethinyl estradiol; etoposide phosphate (Etopophos®); etoposide, VP-16 (Vepesid®); everolimus tablets (Afinitor®); exemestane (Aromasin®); ferumoxytol (Feraheme Injection®); Filgrastim (Neupogen®); floxuridine (intraarterial) (FUDR®); fludarabine (Fludara®); fluorouracil, 5-FU (Adrucil®); fulvestrant (Faslodex®); gefitinib (Iressa®); geldanamycin; gemcitabine (Gemzar®); gemtuzumab ozogamicin (Mylotarg®); goserelin acetate (Zoladex Implant®); goserelin acetate (Zoladex®); histrelin acetate (Histrelin Implant®); hydroxyurea (Hydrea®); Ibritumomab Tiuxetan (Zevalin®); idarubicin (Idamycin®); ifosfamide (IFEX®); imatinib mesylate (Gleevec®); interferon alfa 2a (Roferon A®); Interferon alfa-2b (Intron A®); iobenguane I 123 injection (AdreView®); irinotecan (Camptosar®); ixabepilone (Ixempra®); lapatinib tablets (Tykerb®); lenalidomide (Revlimid®); letrozole (Femara®); leucovorin (Wellcovorin®, Leucovorin®); Leuprolide Acetate (Eligard®); levamisole (Ergamisol®); lomustine, CCNU (CeeBU®); meclorethamine, nitrogen mustard (Mustargen®); megestrol acetate (Megace®); melphalan, L-PAM (Alkeran®); mercaptopurine, 6-MP (Purinethol®); mesna (Mesnex®); mesna (Mesnex Tabs®); methotrexate (Methotrexate®); methoxsalen (Uvadex®); 8-methoxypsoralen; mitomycin C (Mutamycin®); mitotane (Lysodren®); mitoxantrone (Novantrone®); mitramycin; nandrolone phenpropionate (Durabolin-50®); nelarabine (Arranon®); nilotinib (Tasigna®); Nofetumomab (Verluma®); ofatumumab (Arzerra®); Oprelvekin (Neumega®); oxaliplatin (Eloxatin®); paclitaxel (Paxene®); paclitaxel (Taxol®); paclitaxel protein-bound particles (Abraxane®); palifermin (Kepivance®); pamidronate (Aredia®); panitumumab (Vectibix®); pazopanib tablets (Votrienttm®); pegademase (Adagen (Pegademase Bovine)®); pegaspargase (Oncaspar®); Pegfilgrastim (Neulasta®); pemetrexed disodium (Alimta®); pentostatin (Nipent®); pipobroman (Vercyte®); plerixafor (Mozobil®); plicamycin, mithramycin (Mithracin®); porfimer sodium (Photofrin®); pralatrexate injection (Folotyn®); procarbazine (Matulane®); quinacrine (Atabrine®); rapamycin; Rasburicase (Elitek®); raloxifene hydrochloride (Evista®); Rituximab (Rituxan®); romidepsin (Istodax®); romiplostim (Nplate®); sargramostim (Leukine®); Sargramostim (Prokine®); sorafenib (Nexavar®); streptozocin (Zanosar®); sunitinib maleate (Sutent®); talc (Sclerosol®); tamoxifen (Nolvadex®); temozolomide (Temodar®); temsirolimus (Torisel®); teniposide, VM-26 (Vumon®); testolactone (Teslac®); thioguanine, 6-TG (Thioguanine®); thiopurine; thiotepa (Thioplex®); topotecan (Hycamtin®); toremifene (Fareston®); Tositumomab (Bexxar®); Tositumomab/I-131 tositumomab (Bexxar®); trans-retinoic acid; Trastuzumab (Herceptin®); tretinoin, ATRA (Vesanoid®); triethylenemelamine; Uracil Mustard (Uracil Mustard Capsules®); valrubicin (Valstar®); vinblastine (Velban®); vincristine (Oncovin®); vinorelbine (Navelbine®); vorinostat (Zolinza®); wortmannin; and zoledronate (Zometa®).

In an embodiment of the invention, an anti-SIRPα antibody or antigen-binding fragment thereof of the invention is in association with one or more antiemetics including, but not limited to: casopitant (GlaxoSmithKline), Netupitant (MGI-Helsinn) and other NK-1 receptor antagonists, palonosetron (sold as Aloxi by MGI Pharma), aprepitant (sold as Emend by Merck and Co.; Rahway, N.J.), diphenhydramine (sold as Benadryl® by Pfizer; New York, N.Y.), hydroxyzine (sold as Atarax® by Pfizer; New York, N.Y.), metoclopramide (sold as Reglan® by AH Robins Co; Richmond, Va.), lorazepam (sold as Ativan® by Wyeth; Madison, N.J.), alprazolam (sold as Xanax® by Pfizer; New York, N.Y.), haloperidol (sold as Haldol® by Ortho-McNeil; Raritan, N.J.), droperidol (Inapsine®), dronabinol (sold as Marinol® by Solvay Pharmaceuticals, Inc.; Marietta, Ga.), dexamethasone (sold as Decadron® by Merck and Co.; Rahway, N.J.), methylprednisolone (sold as Medrol® by Pfizer; New York, N.Y.), prochlorperazine (sold as Compazine® by Glaxosmithkline; Research Triangle Park, N.C.), granisetron (sold as Kytril® by Hoffmann-La Roche Inc.; Nutley, N.J.), ondansetron (sold as Zofran® by Glaxosmithkline; Research Triangle Park, N.C.), dolasetron (sold as Anzemet® by Sanofi-Aventis; New York, N.Y.), tropisetron (sold as Navoban® by Novartis; East Hanover, N.J.).

Other side effects of cancer treatment include red and white blood cell deficiency. Accordingly, in an embodiment of the invention, an anti-SIRPα antibody or antigen-binding fragment thereof is in association with an agent which treats or prevents such a deficiency, such as, e.g., filgrastim, PEG-filgrastim, erythropoietin, epoetin alfa or darbepoetin alfa.

In an embodiment of the invention, an anti-SIRPα antibody or antigen-binding fragment thereof of the invention is administered in association with anti-cancer radiation therapy. For example, in an embodiment of the invention, the radiation therapy is external beam therapy (EBT): a method for delivering a beam of high-energy X-rays to the location of the tumor. The beam is generated outside the patient (e.g., by a linear accelerator) and is targeted at the tumor site. These X-rays can destroy the cancer cells and careful treatment planning allows the surrounding normal tissues to be spared. No radioactive sources are placed inside the patient's body. In an embodiment of the invention, the radiation therapy is proton beam therapy: a type of conformal therapy that bombards the diseased tissue with protons instead of X-rays. In an embodiment of the invention, the radiation therapy is conformal external beam radiation therapy: a procedure that uses advanced technology to tailor the radiation therapy to an individual's body structures. In an embodiment of the invention, the radiation therapy is brachytherapy: the temporary placement of radioactive materials within the body, usually employed to give an extra dose—or boost—of radiation to an area.

In an embodiment of the invention, a surgical procedure is administered in association with an anti-SIRPα antibody or antigen-binding fragment thereof is surgical tumorectomy.

Experimental and Diagnostic Uses

The anti-SIRPα antibodies and antigen-binding fragments thereof disclosed herein may be used as affinity purification agents. In this process, the anti-SIRPα antibodies and antigen-binding fragments thereof are immobilized on a solid phase such a Sephadex, glass or agarose resin or filter paper, using methods well known in the art. The immobilized antibody or fragment is contacted with a sample containing the SIRPα protein (or a fragment thereof) to be purified, and thereafter the support is washed with a suitable solvent that will remove substantially all the material in the sample except the SIRPα protein, which is bound to the immobilized antibody or fragment. Finally, the support is washed with a solvent which elutes the bound SIRPα (e.g., protein A). Such immobilized antibodies and fragments form part of the present invention.

Further provided are antigens for generating secondary antibodies which are useful for example for performing Western blots and other immunoassays discussed herein.

Anti-SIRPα antibodies (e.g., humanized antibodies) and antigen-binding fragments thereof may also be useful in diagnostic assays for SIRPα protein, e.g., detecting its expression in specific cells, tissues, or serum, e.g., myeloid cells such as monocytes, macrophages, neutrophils, basophils, eosinophils, and dendritic cells. Such diagnostic methods may be useful in various disease diagnoses.

The present invention includes ELISA assays (enzyme-linked immunosorbent assay) incorporating the use of an anti-SIRPα antibody or antigen-binding fragment thereof disclosed herein.

For example, such a method comprises the following steps:
(a) coat a substrate (e.g., surface of a microtiter plate well, e.g., a plastic plate) with anti-SIRPα antibody or antigen-binding fragment thereof;
(b) apply a sample to be tested for the presence of SIRPα to the substrate;
(c) wash the plate, so that unbound material in the sample is removed;
(d) apply detectably labeled antibodies (e.g., enzyme-linked antibodies) which are also specific to the SIRPα antigen;
(e) wash the substrate, so that the unbound, labeled antibodies are removed;
(f) if the labeled antibodies are enzyme linked, apply a chemical which is converted by the enzyme into a fluorescent signal; and
(g) detect the presence of the labeled antibody.

Detection of the label associated with the substrate indicates the presence of the SIRPα protein.

In a further embodiment, the labeled antibody or antigen-binding fragment thereof is labeled with peroxidase which react with ABTS (e.g., 2,2'-azino-bis(3-ethylbenzthiazoline-6-sulphonic acid)) or 3,3',5,5'-Tetramethylbenzidine to produce a color change which is detectable. Alternatively, the labeled antibody or fragment is labeled with a detectable radioisotope (e.g., $^3H$) which can be detected by scintillation counter in the presence of a scintillant.

An anti-SIRPα antibody or antigen-binding fragment thereof of the invention may be used in a Western blot or immune-protein blot procedure. Such a procedure forms part of the present invention and includes e.g.:
(1) optionally transferring proteins from a sample to be tested for the presence of SIRPα (e.g., from a PAGE or SDS-PAGE electrophoretic separation of the proteins in the sample) onto a membrane or other solid substrate using a method known in the art (e.g., semi-dry blotting or tank blotting); contacting the membrane or other solid substrate to be tested for the presence of bound SIRPα or a fragment thereof with an anti-SIRPα antibody or antigen-binding fragment thereof of the invention.
(2) washing the membrane one or more times to remove unbound anti-SIRPα antibody or fragment and other unbound substances; and
(3) detecting the bound anti-SIRPα antibody or fragment.

Such a membrane may take the form of a nitrocellulose or vinyl-based (e.g., polyvinylidene fluoride (PVDF)) membrane to which the proteins to be tested for the presence of SIRPα in a non-denaturing PAGE (polyacrylamide gel electrophoresis) gel or SDS-PAGE (sodium dodecyl sulfate polyacrylamide gel electrophoresis) gel have been transferred (e.g., following electrophoretic separation in the gel). Before contacting the membrane with the anti-SIRPα antibody or fragment, the membrane is optionally blocked, e.g., with non-fat dry milk or the like so as to bind non-specific protein binding sites on the membrane.

Detection of the bound antibody or fragment indicates that the SIRPα protein is present on the membrane or substrate and in the sample. Detection of the bound antibody or fragment may be by binding the antibody or fragment with a secondary antibody (an anti-immunoglobulin antibody) which is detectably labeled and, then, detecting the presence of the secondary antibody.

The anti-SIRPα antibodies and antigen-binding fragments thereof disclosed herein may also be used for immunohistochemistry. Such a method forms part of the present invention and comprises, e.g.,
(1) contacting a cell (e.g., a sample containing myeloid cells such as monocytes, macrophages, neutrophils, basophils, eosinophils, and dendritic cells) to be tested for the presence of SIRPα protein with an anti-SIRPα antibody or antigen-binding fragment thereof of the invention; and
(2) detecting the antibody or fragment on or in the cell.

If the antibody or fragment itself is detectably labeled, it can be detected directly. Alternatively, the antibody or fragment may be bound by a detectably labeled secondary antibody which is detected.

Certain anti-SIRPα antibodies and antigen-binding fragments thereof disclosed herein may also be used for in vivo tumor imaging. Such a method may include injection of a radiolabeled anti-SIRPα antibody or antigen-binding fragment thereof into the body of a patient to be tested for the presence of a tumor associated with SIRPα expression (e.g., which expresses SIRPα, for example, on the tumor cell surface) followed by nuclear imaging of the body of the patient to detect the presence of the labeled antibody or fragment e.g., at loci comprising a high concentration of the antibody or fragment which are bound to the tumor. The detection of the loci indicates the presence of the SIRPα+ tumor and tumor cells.

Imaging techniques include SPECT imaging (single photon emission computed tomography) or PET imaging (positron emission tomography). Labels include e.g., iodine-123 ($^{123}$I) and technetium-99m ($^{99m}$Tc), e.g., in conjunction with SPECT imaging or $^{11}$C, $^{13}$N, $^{15}$O or $^{18}$F, e.g., in conjunction with PET imaging or Indium-111 (See e.g., Gordon et al., (2005) International Rev. Neurobiol. 67:385-440).

Pharmaceutical Compositions and Administration

To prepare pharmaceutical or sterile compositions of the anti-SIRPα antibodies and antigen-binding fragments of the invention, the antibody or antigen-binding fragment thereof is admixed with a pharmaceutically acceptable carrier or excipient. See, e.g., *Remington's Pharmaceutical Sciences* and *U.S. Pharmacopeia: National Formulary*, Mack Publishing Company, Easton, Pa. (1984).

Formulations of therapeutic and diagnostic agents may be prepared by mixing with acceptable carriers, excipients, or stabilizers in the form of, e.g., lyophilized powders, slurries, aqueous solutions or suspensions (see, e.g., Hardman, et al. (2001) *Goodman and Gilman's The Pharmacological Basis of Therapeutics*, McGraw-Hill, New York, N.Y.; Gennaro (2000) *Remington: The Science and Practice of Pharmacy*, Lippincott, Williams, and Wilkins, New York, N.Y.; Avis, et al. (eds.) (1993) *Pharmaceutical Dosage Forms: Parenteral Medications*, Marcel Dekker, NY; Lieberman, et al. (eds.) (1990) *Pharmaceutical Dosage Forms: Tablets*, Marcel Dekker, NY; Lieberman, et al. (eds.) (1990) *Pharmaceutical Dosage Forms: Disperse Systems*, Marcel Dekker, NY; Weiner and Kotkoskie (2000) *Excipient Toxicity and Safety*, Marcel Dekker, Inc., New York, N.Y.).

Toxicity and therapeutic efficacy of the antibodies of the invention, administered alone or in combination with another therapeutic agent, can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index ($LD_{50}/ED_{50}$). The data obtained from these cell culture assays and animal studies can be used in formulating a range of dosage for use in human. The dosage of such compounds lies preferably within a range of circulating concentrations that include the $ED_{50}$ with little or no toxicity. The dosage may vary within this range depending upon the dosage form employed and the route of administration.

In a further embodiment, a further therapeutic agent that is administered to a subject in association with an anti-SIRPα antibody or antigen-binding fragment thereof of the invention in accordance with the Physicians' Desk Reference 2003 (Thomson Healthcare; 57th edition (Nov. 1, 2002)).

The mode of administration can vary. Routes of administration include oral, rectal, transmucosal, intestinal, parenteral; intramuscular, subcutaneous, intradermal, intramedullary, intrathecal, direct intraventricular, intravenous, intraperitoneal, intranasal, intraocular, inhalation, insufflation, topical, cutaneous, transdermal, or intra-arterial.

In particular embodiments, the anti-SIRPα antibodies or antigen-binding fragments thereof of the invention can be administered by an invasive route such as by injection. In further embodiments of the invention, an anti-SIRPα antibody or antigen-binding fragment thereof, or pharmaceutical composition thereof, is administered intravenously, subcutaneously, intramuscularly, intraarterially, intratumorally, or by inhalation, aerosol delivery. Administration by non-invasive routes (e.g., orally; for example, in a pill, capsule or tablet) is also within the scope of the present invention.

The present invention provides a vessel (e.g., a plastic or glass vial, e.g., with a cap or a chromatography column, hollow bore needle or a syringe cylinder) comprising any of the antibodies or antigen-binding fragments of the invention or a pharmaceutical composition thereof. The present invention also provides an injection device comprising any of the antibodies or antigen-binding fragments of the invention or a pharmaceutical composition thereof. An injection device is a device that introduces a substance into the body of a patient via a parenteral route, e.g., intramuscular, subcutaneous or intravenous. For example, an injection device may be a syringe (e.g., pre-filled with the pharmaceutical composition, such as an autoinjector) which, for example, includes a cylinder or barrel for holding fluid to be injected (e.g., antibody or fragment or a pharmaceutical composition thereof), a needle for piecing skin and/or blood vessels for injection of the fluid; and a plunger for pushing the fluid out of the cylinder and through the needle bore. In an embodiment of the invention, an injection device that comprises an antibody or antigen-binding fragment thereof of the present invention or a pharmaceutical composition thereof is an intravenous (IV) injection device. Such a device includes the antibody or fragment or a pharmaceutical composition thereof in a cannula or trocar/needle which may be attached to a tube which may be attached to a bag or reservoir for holding fluid (e.g., saline; or lactated ringer solution comprising NaCl, sodium lactate, KCl, $CaCl_2$ and optionally including glucose) introduced into the body of the patient through the cannula or trocar/needle. The antibody or fragment or a pharmaceutical composition thereof may, in an embodiment of the invention, be introduced into the device once the trocar and cannula are inserted into the vein of a subject and the trocar is removed from the inserted cannula. The IV device may, for example, be inserted into a peripheral vein (e.g., in the hand or arm); the superior vena cava or inferior vena cava, or within the right atrium of the heart (e.g., a central IV); or into a subclavian, internal jugular, or a femoral vein and, for example, advanced toward the heart until it reaches the superior vena cava or right atrium (e.g., a central venous line). In an embodiment of the invention, an injection device is an autoinjector; a jet injector or an external infusion pump. A jet injector uses a high-pressure narrow jet of liquid which penetrate the epidermis to introduce the antibody or fragment or a pharmaceutical composition thereof to a patient's body. External infusion pumps are medical devices that deliver the antibody or fragment or a pharmaceutical composition thereof into a patient's body in controlled amounts. External infusion pumps may be powered electrically or mechanically. Different pumps operate in different ways, for example, a syringe pump holds fluid in the reservoir of a syringe, and a moveable piston controls fluid delivery, an elastomeric pump holds fluid in a stretchable balloon reservoir, and pressure from the elastic walls of the balloon drives fluid delivery. In a peristaltic pump, a set of rollers pinches down on a length of flexible tubing, pushing fluid forward. In a multi-channel pump, fluids can be delivered from multiple reservoirs at multiple rates.

The pharmaceutical compositions disclosed herein may also be administered with a needleless hypodermic injection device; such as the devices disclosed in U.S. Pat. Nos. 6,620,135; 6,096,002; 5,399,163; 5,383,851; 5,312,335; 5,064,413; 4,941,880; 4,790,824 or 4,596,556. Such needleless devices comprising the pharmaceutical composition are also part of the present invention. The pharmaceutical compositions disclosed herein may also be administered by infusion. Examples of well-known implants and modules for administering the pharmaceutical compositions include those disclosed in: U.S. Pat. No. 4,487,603, which discloses an implantable micro-infusion pump for dispensing medication at a controlled rate; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments. Many other such implants, delivery systems, and modules are well known to those skilled in the art and those comprising the pharmaceutical compositions of the present invention are within the scope of the present invention.

Alternately, one may administer the anti-SIRPα antibody or antigen-binding fragment of the invention in a local rather than systemic manner, for example, via injection of the antibody or fragment directly into a tumor. Furthermore, one may administer the antibody or fragment in a targeted drug delivery system, for example, in a liposome coated with a tissue-specific antibody, targeting, for example, a tumor. The liposomes will be targeted to and taken up selectively by the afflicted tissue. Such methods and liposomes are part of the present invention.

The administration regimen depends on several factors, including the serum or tissue turnover rate of the therapeutic antibody or antigen-binding fragment, the level of symptoms, the immunogenicity of the therapeutic antibody, and the accessibility of the target cells in the biological matrix. Preferably, the administration regimen delivers sufficient therapeutic antibody or fragment to effect improvement in the target disease state, while simultaneously minimizing undesired side effects. Accordingly, the amount of biologic delivered depends in part on the particular therapeutic antibody and the severity of the condition being treated. Guidance in selecting appropriate doses of therapeutic antibodies or fragments is available (see, e.g., Wawrzynczak (1996) *Antibody Therapy*, Bios Scientific Pub. Ltd, Oxfordshire, UK; Kresina (ed.) (1991) *Monoclonal Antibodies, Cytokines and Arthritis*, Marcel Dekker, New York, N.Y.; Bach (ed.) (1993) *Monoclonal Antibodies and Peptide Therapy in Autoimmune Diseases*, Marcel Dekker, New York, N.Y.; Baert, et al. (2003) *New Engl. J. Med.* 348:601-608; Milgrom et al. (1999) *New Engl. J. Med.* 341:1966-1973; Slamon et al. (2001) *New Engl. J. Med.* 344:783-792; Beniaminovitz et al. (2000) *New Engl. J. Med.* 342:613-619; Ghosh et al. (2003) *New Engl. J. Med.* 348:24-32; Lipsky et al. (2000) *New Engl. J. Med.* 343:1594-1602).

Determination of the appropriate dose is made by the clinician, e.g., using parameters or factors known or suspected in the art to affect treatment. Generally, the dose begins with an amount somewhat less than the optimum dose and it is increased by small increments thereafter until the desired or optimum effect is achieved relative to any negative side effects. Important diagnostic measures include those of symptoms of, e.g., the inflammation or level of inflammatory cytokines produced. In general, it is desirable that a biologic that will be used is derived from the same species as the animal targeted for treatment, thereby minimizing any immune response to the reagent. In the case of human subjects, for example, humanized and fully human antibodies may be desirable.

Antibodies or antigen-binding fragments thereof disclosed herein may be provided by continuous infusion, or by doses administered, e.g., daily, 1-7 times per week, weekly, biweekly, monthly, bimonthly, quarterly, semiannually, annually etc. Doses may be provided, e.g., intravenously, subcutaneously, topically, orally, nasally, rectally, intramuscular, intracerebrally, intraspinally, or by inhalation. A total weekly dose is generally at least 0.05 µg/kg body weight, more generally at least 0.2 µg/kg, 0.5 µg/kg, 1 µg/kg, 10 µg/kg, 100 µg/kg, 0.25 mg/kg, 1.0 mg/kg, 2.0 mg/kg, 5.0 mg/mL, 10 mg/kg, 25 mg/kg, 50 mg/kg or more (see, e.g., Yang, et al. (2003) *New Engl. J. Med.* 349:427-434; Herold, et al. (2002) *New Engl. J. Med.* 346:1692-1698; Liu, et al. (1999) *J. Neurol. Neurosurg. Psych.* 67: 451-456; Portielji, et al. (20003) Cancer *Immunol. Immunother.* 52: 151-144). Doses may also be provided to achieve a pre-determined target concentration of anti-SIRPα antibody in the subject's serum, such as 0.1, 0.3, 1, 3, 10, 30, 100, 300 µg/mL or more. In other embodiments, An anti-SIRPα antibody of the present invention is administered, e.g., subcutaneously or intravenously, on a weekly, biweekly, "every 4 weeks," monthly, bimonthly, or quarterly basis at 10, 20, 50, 80, 100, 200, 500, 1000 or 2500 mg/subject.

As used herein, the term "effective amount" refer to an amount of an anti-SIRPα or antigen-binding fragment thereof of the invention that, when administered alone or in combination with an additional therapeutic agent to a cell, tissue, or subject, is effective to cause a measurable improvement in one or more symptoms of disease, for example cancer or the progression of cancer. An effective dose further refers to that amount of the antibody or fragment sufficient to result in at least partial amelioration of symptoms, e.g., tumor shrinkage or elimination, lack of tumor growth, increased survival time. When applied to an individual active ingredient administered alone, an effective dose refers to that ingredient alone. When applied to a combination, an effective dose refers to combined amounts of the active ingredients that result in the therapeutic effect, whether administered in combination, serially or simultaneously. An effective amount of a therapeutic will result in an improvement of a diagnostic measure or parameter by at least 10%; usually by at least 20%; preferably at least about 30%; more preferably at least 40%, and most preferably by at least 50%. An effective amount can also result in an improvement in a subjective measure in cases where subjective measures are used to assess disease severity.

Kits

Further provided are kits comprising one or more components that include, but are not limited to, an anti-SIRPα antibody or antigen-binding fragment, as discussed herein in association with one or more additional components including, but not limited to a pharmaceutically acceptable carrier and/or a therapeutic agent, as discussed herein. The antibody or fragment and/or the therapeutic agent can be formulated as a pure composition or in combination with a pharmaceutically acceptable carrier, in a pharmaceutical composition.

In one embodiment, the kit includes an anti-SIRPα antibody or antigen-binding fragment thereof of the invention or a pharmaceutical composition thereof in one container (e.g., in a sterile glass or plastic vial) and/or a therapeutic agent and a pharmaceutical composition thereof in another container (e.g., in a sterile glass or plastic vial).

In another embodiment, the kit comprises a combination of the invention, including an anti-SIRPα antibody or antigen-binding fragment thereof of the invention along with a pharmaceutically acceptable carrier, optionally in combination with one or more therapeutic agents formulated together, optionally, in a pharmaceutical composition, in a single, common container.

If the kit includes a pharmaceutical composition for parenteral administration to a subject, the kit can include a device for performing such administration. For example, the kit can include one or more hypodermic needles or other injection devices as discussed above.

The kit can include a package insert including information concerning the pharmaceutical compositions and dosage forms in the kit. Generally, such information aids patients and physicians in using the enclosed pharmaceutical compositions and dosage forms effectively and safely. For example, the following information regarding a combination of the invention may be supplied in the insert: pharmacokinetics, pharmacodynamics, clinical studies, efficacy parameters, indications and usage, contraindications, warnings, precautions, adverse reactions, overdosage, proper dosage and administration, how supplied, proper storage conditions, references, manufacturer/distributor information and patent information.

The kit can also comprise a second therapeutic, for example one or more of: anti-CD47 antibody, anti-APRIL antibody, anti-PD-1 antibody (e.g., nivolumab, pembrolizumab, anti-PDL1 antibody, anti-TIGIT antibody, anti-CTLA4 antibody, anti-CS1 antibody (e.g., elotuzumab), anti-KIR2DL1/2/3 antibody (e.g., lirilumab), anti-CD137 antibody (e.g., urelumab), anti-GITR antibody (e.g., TRX518), anti-PD-L antibody (e.g., BMS-936559, MSB0010718C or MPDL3280A), anti-PD-L2 antibody, anti-ILT1 antibody, anti-ILT2 antibody, anti-ILT3 antibody, anti-ILT4 antibody, anti-ILT5 antibody, anti-ILT6 antibody, anti-ILT7 antibody, anti-ILT8 antibody, anti-CD40 antibody, anti-OX40 antibody, anti-ICOS, anti-KIR2DL1 antibody, anti-KIR2DL2/3 antibody, anti-KIR2DL4 antibody, anti-KIR2DL5A antibody, anti-KIR2DL5B antibody, anti-KIR3DL1 antibody, anti-KIR3DL2 antibody, anti-KIR3DL3 antibody, anti-NKG2A antibody, anti-NKG2C antibody, anti-NKG2E antibody, anti-4-1BB antibody (e.g., PF-05082566), anti-TSLP antibody, anti-IL-10 antibody, IL-10 or PEGylated IL-10, or any small organic molecule inhibitor of such targets; an antibody or antigen binding fragment thereof binds to an antigen selected from the group consisting of AMHR2, AXL, BCMA, CA IX, CD4, CD16, CD19, CD20, CD22, CD30, CD37, CD38, CD40, CD52, CD98, CSF1R, GD2, CCR4, CS1, EpCam, EGFR, EGFRvIII, Endoglin, EPHA2, EphA3, FGFR2b, folate receptor alpha, fucosyl-GM1, HER2, HER3, IL1RAP, kappa myeloma antigen, MS4A1, prolactin receptor, TA-MUC1, and PSMA; Rituximab, ublituximab, margetuximab, IMGN-529, SCT400, veltuzumab, Obinutuzumab, ADCT-502, Hu14.18K322A, Hu3F8, Dinituximab, Trastuzumab, Cetuximab, Rituximab-RLI, c.60C3-RLI, Hu14.18-IL2, KM2812, AFM13, and (CD20)$_2$xCD16, erlotinib (Tarceva), daratumumab, alemtuzumab, pertuzumab, brentuximab, elotuzumab, ibritumomab, ifabotuzumab, farletuzumab, otlertuzumab, carotuximab, epratuzumab, inebilizumab, lumretuzumab, 4G7SDIE, AFM21, AFM22, LY-3022855, SNDX-6352, AFM-13, BI-836826, BMS-986012, BVX-20, mogamulizumab, ChiLob-7/4, leukotuximab, isatuximab, DS-8895, FPA144, GM102, GSK-2857916, IGN523, IT1208, ADC-1013, CAN-04, XOMA-213, PankoMab-GEX, chKM-4927, IGN003, IGN004, IGN005, MDX-1097, MOR202, MOR-208, oportuzumab, ensituximab, vedotin (Adcetris), ibritumomab tiuxetan, ABBV-838, HuMax-AXL-ADC, and ado-trastuzumab emtansine (Kadcyla); radiotherapy or chemotherapeutic agents including, but not limited to Anthracyclines (Doxorubicin, Epirubicin, Daunorubicin, Idarubicin, Mitoxantrone), Oxaliplatin, Bortezomib, Cyclophosphamide, Bleomycin, Vorinostat, Paclitaxel, 5-Fluorouracil, Cytarabine, Prednisolone, Docetaxel, Mitomycin C, Topotecan/Camptothecin, Etoposide, Zoledronic acid, Methotrexate, Ibrutinib, Aflibercept, Bevacizumab, Toremifene, Vinblastine, Vincristine, Idelalisib, Mercaptopurine, Thalidomide, Sorafenib; a cyclic dinucleotide or other STING pathway agonist; etc.

Detection Kits and Therapeutic Kits

As a matter of convenience, an anti-SIRP antibody or antigen-binding fragment thereof of the invention can be provided in a kit, i.e., a packaged combination of reagents in predetermined amounts with instructions for performing the diagnostic or detection assay. Where the antibody or fragment is labeled with an enzyme, the kit will include substrates and cofactors required by the enzyme (e.g., a substrate precursor which provides the detectable chromophore or fluorophore). In addition, other additives may be included such as stabilizers, buffers (e.g., a block buffer or lysis buffer) and the like. The relative amounts of the various reagents may be varied widely to provide for concentrations in solution of the reagents which substantially optimize the sensitivity of the assay. Particularly, the reagents may be provided as dry powders, usually lyophilized, including excipients which on dissolution will provide a reagent solution having the appropriate concentration.

Also provided are diagnostic or detection reagents and kits comprising one or more such reagents for use in a variety of detection assays, including for example, immunoassays such as ELISA (sandwich-type or competitive format). The kit's components may be pre-attached to a solid support, or may be applied to the surface of a solid support when the kit is used. In some embodiments of the invention, the signal generating means may come pre-associated with an antibody or fragment of the invention or may require combination with one or more components, e.g., buffers, antibody-enzyme conjugates, enzyme substrates, or the like, prior to use. Kits may also include additional reagents, e.g., blocking reagents for reducing nonspecific binding to the solid phase surface, washing reagents, enzyme substrates, and the like. The solid phase surface may be in the form of a tube, a bead, a microtiter plate, a microsphere, or other materials suitable for immobilizing proteins, peptides, or polypeptides. In particular aspects, an enzyme that catalyzes the formation of a chemilluminescent or chromogenic product or the reduction of a chemilluminescent or chromogenic substrate is a component of the signal generating means. Such enzymes are well known in the art. Kits may comprise any of the capture agents and detection reagents described herein. Optionally the kit may also comprise instructions for carrying out the methods of the invention.

Also provided is a kit comprising an anti-SIRPα antibody (e.g., humanized antibody) or antigen-binding fragment thereof packaged in a container, such as a vial or bottle, and further comprising a label attached to or packaged with the container, the label describing the contents of the container and providing indications and/or instructions regarding use of the contents of the container to treat one or more disease states as described herein.

In one aspect, the kit is for treating cancer and comprises an anti-SIRPα antibody (e.g., humanized antibody) or antigen-binding fragment thereof and a further therapeutic agent or a vaccine. The kit may optionally further include a syringe for parenteral, e.g., intravenous, administration. In another aspect, the kit comprises an anti-SIRPα antibody (e.g., humanized antibody) or antigen-binding fragment thereof and a label attached to or packaged with the container describing use of the antibody or fragment with the vaccine or further therapeutic agent. In yet another aspect, the kit comprises the vaccine or further therapeutic agent and a label attached to or packaged with the container describing use of the vaccine or further therapeutic agent with the anti-SIRPα antibody or fragment. In certain embodiments, an anti-SIRPα antibody and vaccine or further therapeutic agent are in separate vials or are combined together in the same pharmaceutical composition.

As discussed above in the combination therapy section, concurrent administration of two therapeutic agents does not require that the agents be administered at the same time or by the same route, as long as there is an overlap in the time period during which the agents are exerting their therapeutic effect. Simultaneous or sequential administration is contemplated, as is administration on different days or weeks.

The therapeutic and detection kits disclosed herein may also be prepared that comprise at least one of the antibody, peptide, antigen-binding fragment, or polynucleotide disclosed herein and instructions for using the composition as a detection reagent or therapeutic agent. Containers for use in such kits may typically comprise at least one vial, test tube, flask, bottle, syringe or other suitable container, into which one or more of the detection and/or therapeutic composition(s) may be placed, and preferably suitably aliquoted. Where a second therapeutic agent is also provided, the kit may also contain a second distinct container into which this second detection and/or therapeutic composition may be placed. Alternatively, a plurality of compounds may be prepared in a single pharmaceutical composition, and may be packaged in a single container means, such as a vial, flask, syringe, bottle, or other suitable single container. The kits disclosed herein will also typically include a means for containing the vial(s) in close confinement for commercial sale, such as, e.g., injection or blow-molded plastic containers into which the desired vial(s) are retained. Where a radiolabel, chromogenic, fluorigenic, or other type of detectable label or detecting means is included within the kit, the labeling agent may be provided either in the same container as the detection or therapeutic composition itself, or may alternatively be placed in a second distinct container means into which this second composition may be placed and suitably aliquoted. Alternatively, the detection reagent and the label may be prepared in a single container means, and in most cases, the kit will also typically include a means for containing the vial(s) in close confinement for commercial sale and/or convenient packaging and delivery.

A device or apparatus for carrying out the detection or monitoring methods described herein is also provided. Such an apparatus may include a chamber or tube into which sample can be input, a fluid handling system optionally including valves or pumps to direct flow of the sample through the device, optionally filters to separate plasma or serum from blood, mixing chambers for the addition of capture agents or detection reagents, and optionally a detection device for detecting the amount of detectable label bound to the capture agent immunocomplex. The flow of sample may be passive (e.g., by capillary, hydrostatic, or other forces that do not require further manipulation of the device once sample is applied) or active (e.g., by application of force generated via mechanical pumps, electroosmotic pumps, centrifugal force, or increased air pressure), or by a combination of active and passive forces.

In further embodiments, also provided is a processor, a computer readable memory, and a routine stored on the computer readable memory and adapted to be executed on the processor to perform any of the methods described herein. Examples of suitable computing systems, environments, and/or configurations include personal computers, server computers, hand-held or laptop devices, multiprocessor systems, microprocessor-based systems, set top boxes, programmable consumer electronics, network PCs, mini-computers, mainframe computers, distributed computing environments that include any of the above systems or devices, or any other systems known in the art.

PREFERRED EMBODIMENTS

Embodiment 1

An antibody or antigen binding fragment thereof that binds to human SIRPα, wherein the antibody or antigen binding fragment comprises one or more, and optionally each, of:
  a. a heavy chain variable region CDR1 comprising the amino acid sequence of SEQ ID NO:69 or an amino acid sequence differing from SEQ ID NO: 1 by 1, 2, or 3 conservative substitutions,
  b. a heavy chain variable region CDR2 comprising the amino acid sequence of SEQ ID NO:70 or an amino acid sequence differing from SEQ ID NO: 2 by 1, 2, or 3 conservative substitutions,
  c. a heavy chain variable region CDR3 comprising the amino acid sequence of SEQ ID NO:71 or an amino acid sequence differing from SEQ ID NO: 3 by 1, 2, or 3 conservative substitutions,
  d. a light chain variable region CDR1 comprising the amino acid sequence of SEQ ID NO:72 or an amino acid sequence differing from SEQ ID NO: 4 by 1, 2, or 3 conservative substitutions,
  e. a light chain variable region CDR2 comprising the amino acid sequence of SEQ ID NO:73 or an amino acid sequence differing from SEQ ID NO: 5 by 1, 2, or 3 conservative substitutions, and
  f. a light chain variable region CDR3 comprising the amino acid sequence of SEQ ID NO:74 or an amino acid sequence differing from SEQ ID NO: 6 by 1, 2, or 3 conservative substitutions.
or wherein the antibody or antigen binding fragment comprises one or more, and optionally each, of:
  g. a heavy chain variable region CDR1 comprising the amino acid sequence of SEQ ID NO: 1 or an amino acid sequence differing from SEQ ID NO: 1 by 1, 2, or 3 conservative substitutions,
  h. a heavy chain variable region CDR2 comprising the amino acid sequence of SEQ ID NO:2 or an amino acid sequence differing from SEQ ID NO: 2 by 1, 2, or 3 conservative substitutions,
  i. a heavy chain variable region CDR3 comprising the amino acid sequence of SEQ ID NO:3 or an amino acid sequence differing from SEQ ID NO: 3 by 1, 2, or 3 conservative substitutions,
  j. a light chain variable region CDR1 comprising the amino acid sequence of SEQ ID NO:4 or an amino acid sequence differing from SEQ ID NO: 4 by 1, 2, or 3 conservative substitutions,
  k. a light chain variable region CDR2 comprising the amino acid sequence of SEQ ID NO:5 or an amino acid sequence differing from SEQ ID NO: 5 by 1, 2, or 3 conservative substitutions, and l. a light chain variable region CDR3 comprising the amino acid sequence of SEQ ID NO:6 or an amino acid sequence differing from SEQ ID NO: 6 by 1, 2, or 3 conservative substitutions.

Embodiment 2

The antibody or antigen binding fragment of embodiment 1,
wherein the antibody or antigen binding fragment comprises
each of a heavy chain sequence comprising the amino acid sequence of SEQ ID NO:69 or an amino acid sequence differing from SEQ ID NO: 69 by 1, 2, or 3 conservative substitutions; the amino acid sequence of SEQ ID NO:70 or an amino acid sequence differing from SEQ ID NO: 70 by 1, 2, or 3 conservative substitutions; and the amino acid sequence of SEQ ID NO: 71 or an amino acid sequence differing from SEQ ID NO: 71 by 1, 2, or 3 conservative substitutions;
and/or
each of a light chain sequence comprising the amino acid sequence of SEQ ID NO: 72 or an amino acid sequence differing from SEQ ID NO: 72 by 1, 2, or 3 conservative substitutions; the amino acid sequence of SEQ ID NO: 73 or an amino acid sequence differing from SEQ ID NO: 73 by 1, 2, or 3 conservative substitutions; and the amino acid sequence of SEQ ID NO: 74 or an amino acid sequence differing from SEQ ID NO: 74 by 1, 2, or 3 conservative substitutions;
or wherein the antibody or antigen binding fragment comprises
each of a heavy chain sequence comprising the amino acid sequence of SEQ ID NO: 1 or an amino acid sequence differing from SEQ ID NO: 1 by 1, 2, or 3 conservative substitutions; the amino acid sequence of SEQ ID NO:2 or an amino acid sequence differing from SEQ ID NO: 2 by 1, 2, or 3 conservative substitutions; and the amino acid sequence of SEQ ID NO:3 or an amino acid sequence differing from SEQ ID NO: 3 by 1, 2, or 3 conservative substitutions;
and/or
each of a light chain sequence comprising the amino acid sequence of SEQ ID NO:4 or an amino acid sequence differing from SEQ ID NO: 4 by 1, 2, or 3 conservative substitutions; the amino acid sequence of SEQ ID NO:5 or an amino acid sequence differing from SEQ ID NO: 5 by 1, 2, or 3 conservative substitutions; and the amino acid sequence of SEQ ID NO:6 or an amino acid sequence differing from SEQ ID NO: 6 by 1, 2, or 3 conservative substitutions.

Embodiment 3

The antibody or antigen binding fragment of embodiment 2,
wherein the antibody or antigen binding fragment comprises one or both of:
a heavy chain variable region comprising an amino acid sequence selected from the group consisting of:
SEQ ID NO: 75 or an amino acid sequence at least 90%, 95%, 97%, 98%, or 99% identical thereto,
SEQ ID NO: 78 or an amino acid sequence at least 90%, 95%, 97%, 98%, or 99% identical thereto,
SEQ ID NO: 80 or an amino acid sequence at least 90%, 95%, 97%, 98%, or 99% identical thereto,
SEQ ID NO: 82 or an amino acid sequence at least 90%, 95%, 97%, 98%, or 99% identical thereto,
SEQ ID NO: 84 or an amino acid sequence at least 90%, 95%, 97%, 98%, or 99% identical thereto,
SEQ ID NO: 86 or an amino acid sequence at least 90%, 95%, 97%, 98%, or 99% identical thereto,
SEQ ID NO: 88 or an amino acid sequence at least 90%, 95%, 97%, 98%, or 99% identical thereto, and
SEQ ID NO: 102 or an amino acid sequence at least 90%, 95%, 97%, 98%, or 99% identical thereto;
and
a light chain variable region comprising an amino acid sequence selected from the group consisting of:
SEQ ID NO: 76 or an amino acid sequence at least 90%, 95%, 97%, 98%, or 99% identical thereto,
SEQ ID NO: 90 or an amino acid sequence at least 90%, 95%, 97%, 98%, or 99% identical thereto,
SEQ ID NO: 92 or an amino acid sequence at least 90%, 95%, 97%, 98%, or 99% identical thereto,
SEQ ID NO: 94 or an amino acid sequence at least 90%, 95%, 97%, 98%, or 99% identical thereto,
SEQ ID NO: 96 or an amino acid sequence at least 90%, 95%, 97%, 98%, or 99% identical thereto,
SEQ ID NO: 98 or an amino acid sequence at least 90%, 95%, 97%, 98%, or 99% identical thereto,
SEQ ID NO: 100 or an amino acid sequence at least 90%, 95%, 97%, 98%, or 99% identical thereto, and
SEQ ID NO: 104 or an amino acid sequence at least 90%, 95%, 97%, 98%, or 99% identical thereto;
or wherein the antibody or antigen binding fragment comprises one or both of:
a heavy chain variable region comprising an amino acid sequence selected from the group consisting of:
SEQ ID NO: 7 or an amino acid sequence at least 90%, 95%, 97%, 98%, or 99% identical thereto,
SEQ ID NO: 10 or an amino acid sequence at least 90%, 95%, 97%, 98%, or 99% identical thereto,
SEQ ID NO: 12 or an amino acid sequence at least 90%, 95%, 97%, 98%, or 99% identical thereto,
SEQ ID NO: 14 or an amino acid sequence at least 90%, 95%, 97%, 98%, or 99% identical thereto,
SEQ ID NO: 16 or an amino acid sequence at least 90%, 95%, 97%, 98%, or 99% identical thereto,
SEQ ID NO: 18 or an amino acid sequence at least 90%, 95%, 97%, 98%, or 99% identical thereto, and
SEQ ID NO: 30 or an amino acid sequence at least 90%, 95%, 97%, 98%, or 99% identical thereto;
and
a light chain variable region comprising an amino acid sequence selected from the group consisting of:
SEQ ID NO: 8 or an amino acid sequence at least 90%, 95%, 97%, 98%, or 99% identical thereto,
SEQ ID NO: 20 or an amino acid sequence at least 90%, 95%, 97%, 98%, or 99% identical thereto,
SEQ ID NO: 22 or an amino acid sequence at least 90%, 95%, 97%, 98%, or 99% identical thereto,
SEQ ID NO: 24 or an amino acid sequence at least 90%, 95%, 97%, 98%, or 99% identical thereto,
SEQ ID NO: 26 or an amino acid sequence at least 90%, 95%, 97%, 98%, or 99% identical thereto, and
SEQ ID NO: 28 or an amino acid sequence at least 90%, 95%, 97%, 98%, or 99% identical thereto, and
SEQ ID NO: 32 or an amino acid sequence at least 90%, 95%, 97%, 98%, or 99% identical thereto.

Embodiment 4

The antibody or antigen binding fragment of embodiment 3, wherein the antibody or fragment thereof has the following characteristics:

binds to a cell expressing human SIRPαV1 protein with an $EC_{50}$<10 nM, preferably <5 nM, more preferably <1.5 nM, still more preferably <1.0 nM, even more preferably <0.5 nM, and most preferably about 0.3 nM or less;

binds to a cell expressing human SIRPαV2 protein with an $EC_{50}$<10 nM, preferably <5 nM, more preferably <1.5 nM, still more preferably <1.0 nM, even more preferably <0.5 nM, and most preferably about 0.3 nM or less;

does not appreciably bind to SIRPβ1 protein at an antibody concentration of 50 nM, preferably 67 nM, and more preferably 100 nM; or alternatively at a concentration that is 10-fold greater, preferably 50-fold greater, more preferably 100-fold greater, and still more preferably 200-fold greater than the antibody's $EC_{50}$ for SIRPαV1 or SIRPαV2;

inhibits binding between human SIRPα and CD47 with an $IC_{50}$<10.0 nM, more preferably <5.0 nM, still more preferably <2.5 nM, and most preferably about 1.0 nM or less; and exhibits a T20 "humanness" score of at least 79, and more preferably 85.

Embodiment 5

The antibody or antigen binding fragment of embodiment 1, wherein the antibody or antigen binding fragment thereof comprises one of the following combinations of heavy chain sequence/light chain sequence:
SEQ ID NO: 78/SEQ ID NO: 90,
SEQ ID NO: 78/SEQ ID NO: 92,
SEQ ID NO: 78/SEQ ID NO: 94,
SEQ ID NO: 78/SEQ ID NO: 96,
SEQ ID NO: 78/SEQ ID NO: 98,
SEQ ID NO: 78/SEQ ID NO: 100,
SEQ ID NO: 80/SEQ ID NO: 90,
SEQ ID NO: 80/SEQ ID NO: 92,
SEQ ID NO: 80/SEQ ID NO: 94,
SEQ ID NO: 80/SEQ ID NO: 96,
SEQ ID NO: 80/SEQ ID NO: 98,
SEQ ID NO: 80/SEQ ID NO: 100,
SEQ ID NO: 82/SEQ ID NO: 90,
SEQ ID NO: 82/SEQ ID NO: 92,
SEQ ID NO: 82/SEQ ID NO: 94,
SEQ ID NO: 82/SEQ ID NO: 96,
SEQ ID NO: 82/SEQ ID NO: 98,
SEQ ID NO: 82/SEQ ID NO: 100,
SEQ ID NO: 84/SEQ ID NO: 90,
SEQ ID NO: 84/SEQ ID NO: 92,
SEQ ID NO: 84/SEQ ID NO: 94,
SEQ ID NO: 84/SEQ ID NO: 96,
SEQ ID NO: 84/SEQ ID NO: 98,
SEQ ID NO: 84/SEQ ID NO: 100,
SEQ ID NO: 86/SEQ ID NO: 90,
SEQ ID NO: 86/SEQ ID NO: 92,
SEQ ID NO: 86/SEQ ID NO: 94,
SEQ ID NO: 86/SEQ ID NO: 96,
SEQ ID NO: 86/SEQ ID NO: 98,
SEQ ID NO: 86/SEQ ID NO: 100,
SEQ ID NO: 88/SEQ ID NO: 90,
SEQ ID NO: 88/SEQ ID NO: 92,
SEQ ID NO: 88/SEQ ID NO: 94,
SEQ ID NO: 88/SEQ ID NO: 96,
SEQ ID NO: 88/SEQ ID NO: 98,
SEQ ID NO: 88/SEQ ID NO: 100,
SEQ ID NO: 10/SEQ ID NO: 20,
SEQ ID NO: 10/SEQ ID NO: 22,
SEQ ID NO: 10/SEQ ID NO: 24,
SEQ ID NO: 10/SEQ ID NO: 26,
SEQ ID NO: 10/SEQ ID NO: 28,
SEQ ID NO: 12/SEQ ID NO: 20,
SEQ ID NO: 12/SEQ ID NO: 22,
SEQ ID NO: 12/SEQ ID NO: 24,
SEQ ID NO: 12/SEQ ID NO: 26,
SEQ ID NO: 12/SEQ ID NO: 28,
SEQ ID NO: 14/SEQ ID NO: 20,
SEQ ID NO: 14/SEQ ID NO: 22,
SEQ ID NO: 14/SEQ ID NO: 24,
SEQ ID NO: 14/SEQ ID NO: 26,
SEQ ID NO: 14/SEQ ID NO: 28,
SEQ ID NO: 16/SEQ ID NO: 20,
SEQ ID NO: 16/SEQ ID NO: 22,
SEQ ID NO: 16/SEQ ID NO: 24,
SEQ ID NO: 16/SEQ ID NO: 26,
SEQ ID NO: 16/SEQ ID NO: 28,
SEQ ID NO: 18/SEQ ID NO: 20,
SEQ ID NO: 18/SEQ ID NO: 22,
SEQ ID NO: 18/SEQ ID NO: 24,
SEQ ID NO: 18/SEQ ID NO: 26,
SEQ ID NO: 18/SEQ ID NO: 28,
or, in each case, at least 90%, 95%, 97%, 98%, or 99% identical to a respective SEQ ID.

Embodiment 6

The antibody or antigen binding fragment of one of embodiments 1-5, wherein the antibody is an intact IgG.

Embodiment 7

The antibody or antigen binding fragment of one of embodiments 1-6, wherein the antibody comprises a wild-type or mutated IgG2 Fc region.

Embodiment 8

The antibody or antigen binding fragment of one of embodiments 1-6, wherein the antibody comprises a mutated IgG1 Fc region.

Embodiment 9

The antibody or antigen binding fragment of one of embodiments 1-6, wherein the antibody comprises a mutated IgG4 Fc region.

Embodiment 10

An antibody or antigen binding fragment thereof that binds to the same epitope of human SIRPα as an antibody as an antibody according to embodiment 5.

Embodiment 11

The antibody or antigen binding fragment of any of embodiments 1-10, wherein the antibody or antigen binding fragment is humanized.

Embodiment 12

The antibody or antigen binding fragment of any of embodiments 1-11 that is a humanized antibody that comprises two heavy chains and two light chains, wherein each heavy chain comprises SEQ ID NO: 10 and each light chain comprises SEQ ID NO: 20.

Embodiment 13

The antibody or antigen binding fragment of any of embodiments 1-11 that is a humanized antibody that comprises two heavy chains and two light chains, wherein each heavy chain comprises SEQ ID NO: 16 and each light chain comprises SEQ ID NO: 28.

Embodiment 14

The antibody or antigen binding fragment of any of embodiments 1-11 that is a humanized antibody that comprises two heavy chains and two light chains, wherein each heavy chain comprises SEQ ID NO: 18 and each light chain comprises SEQ ID NO: 20.

Embodiment 15

The antibody or antigen binding fragment of any of embodiments 1-11 that is a humanized antibody that comprises two heavy chains and two light chains, wherein each heavy chain comprises SEQ ID NO: 80 and each light chain comprises SEQ ID NO: 90.

Embodiment 16

The antibody or antigen binding fragment of any of embodiments 1-11 that is a humanized antibody that comprises two heavy chains and two light chains, wherein each heavy chain comprises SEQ ID NO: 80 and each light chain comprises SEQ ID NO: 92.

Embodiment 17

The antibody or antigen binding fragment of any of embodiments 1-11 that is a humanized antibody that comprises two heavy chains and two light chains, wherein each heavy chain comprises SEQ ID NO: 80 and each light chain comprises SEQ ID NO: 95.

Embodiment 18

The antibody or antigen binding fragment of any one of embodiments 1-17 that comprises a glycosylation pattern characteristic of expression by a mammalian cell, and optionally is glycosylated by expression from a CHO cell.

Embodiment 19

An isolated polypeptide comprising the amino acid sequence of any one of SEQ ID NOs: 75, 78, 80, 82, 84, 86, 88, 76, 90, 92, 94, 96, 98, 100, 102, 104, 7, 10, 12, 14, 16, 18, 30, 8, 20, 22, 24, 26, 28, and 32, or an amino acid sequence at least 90%, 95%, 97%, 98%, or 99% identical thereto.

Embodiment 20

An isolated nucleic acid encoding any one of the antibodies or antigen binding fragments of embodiments 1-18, or any one of the polypeptides of embodiment 19.

Embodiment 21

An isolated nucleic acid of embodiment 20 comprising:
a nucleic acid sequence of SEQ ID NO: 77 or a nucleic acid sequence at least 90%, 95%, 97%, 98%, or 99% identical thereto,
a nucleic acid sequence of SEQ ID NO: 79 or a nucleic acid sequence at least 90%, 95%, 97%, 98%, or 99% identical thereto,
a nucleic acid sequence of SEQ ID NO: 81 or a nucleic acid sequence at least 90%, 95%, 97%, 98%, or 99% identical thereto,
a nucleic acid sequence of SEQ ID NO: 83 or a nucleic acid sequence at least 90%, 95%, 97%, 98%, or 99% identical thereto,
a nucleic acid sequence of SEQ ID NO: 85 or a nucleic acid sequence at least 90%, 95%, 97%, 98%, or 99% identical thereto,
a nucleic acid sequence of SEQ ID NO: 87 or a nucleic acid sequence at least 90%, 95%, 97%, 98%, or 99% identical thereto,
a nucleic acid sequence of SEQ ID NO: 101 or a nucleic acid sequence at least 90%, 95%, 97%, 98%, or 99% identical thereto,
a nucleic acid sequence of SEQ ID NO: 89 or a nucleic acid sequence at least 90%, 95%, 97%, 98%, or 99% identical thereto,
a nucleic acid sequence of SEQ ID NO: 91 or a nucleic acid sequence at least 90%, 95%, 97%, 98%, or 99% identical thereto,
a nucleic acid sequence of SEQ ID NO: 93 or a nucleic acid sequence at least 90%, 95%, 97%, 98%, or 99% identical thereto,
a nucleic acid sequence of SEQ ID NO: 95 or a nucleic acid sequence at least 90%, 95%, 97%, 98%, or 99% identical thereto,
a nucleic acid sequence of SEQ ID NO: 97 or a nucleic acid sequence at least 90%, 95%, 97%, 98%, or 99% identical thereto,
a nucleic acid sequence of SEQ ID NO: 99 or a nucleic acid sequence at least 90%, 95%, 97%, 98%, or 99% identical thereto,
a nucleic acid sequence of SEQ ID NO: 103 or a nucleic acid sequence at least 90%, 95%, 97%, 98%, or 99% identical thereto,
a nucleic acid sequence of SEQ ID NO: 9 or a nucleic acid sequence at least 90%, 95%, 97%, 98%, or 99% identical thereto,
a nucleic acid sequence of SEQ ID NO: 11 or a nucleic acid sequence at least 90%, 95%, 97%, 98%, or 99% identical thereto,
a nucleic acid sequence of SEQ ID NO: 13 or a nucleic acid sequence at least 90%, 95%, 97%, 98%, or 99% identical thereto,
a nucleic acid sequence of SEQ ID NO: 15 or a nucleic acid sequence at least 90%, 95%, 97%, 98%, or 99% identical thereto,
a nucleic acid sequence of SEQ ID NO: 17 or a nucleic acid sequence at least 90%, 95%, 97%, 98%, or 99% identical thereto,
a nucleic acid sequence of SEQ ID NO: 29 or a nucleic acid sequence at least 90%, 95%, 97%, 98%, or 99% identical thereto,
a nucleic acid sequence of SEQ ID NO: 19 or a nucleic acid sequence at least 90%, 95%, 97%, 98%, or 99% identical thereto, a nucleic acid sequence of SEQ ID NO: 21 or a nucleic acid sequence at least 90%, 95%, 97%, 98%, or 99% identical thereto,
a nucleic acid sequence of SEQ ID NO: 23 or a nucleic acid sequence at least 90%, 95%, 97%, 98%, or 99% identical thereto,
a nucleic acid sequence of SEQ ID NO: 25 or a nucleic acid sequence at least 90%, 95%, 97%, 98%, or 99% identical thereto,
a nucleic acid sequence of SEQ ID NO: 27 or a nucleic acid sequence at least 90%, 95%, 97%, 98%, or 99% identical thereto, and/or
a nucleic acid sequence of SEQ ID NO: 31 or a nucleic acid sequence at least 90%, 95%, 97%, 98%, or 99% identical thereto.

Embodiment 22

An expression vector comprising the isolated nucleic acid of embodiment 20 or 21.

Embodiment 23

An expression vector of embodiment 22, encoding both a heavy chain sequence and a light chain sequence of an anti-SIRPα antibody, the expression vectors comprising the following a first nucleic acid sequence/second nucleic acid sequence selected from the group consisting of:
SEQ ID NO: 77/SEQ ID NO: 89,
SEQ ID NO: 77/SEQ ID NO: 91,
SEQ ID NO: 77/SEQ ID NO: 93,
SEQ ID NO: 77/SEQ ID NO: 95,
SEQ ID NO: 77/SEQ ID NO: 97,
SEQ ID NO: 77/SEQ ID NO: 99,
SEQ ID NO: 79/SEQ ID NO: 89,
SEQ ID NO: 79/SEQ ID NO: 91,
SEQ ID NO: 79/SEQ ID NO: 93,
SEQ ID NO: 79/SEQ ID NO: 95,
SEQ ID NO: 79/SEQ ID NO: 97,
SEQ ID NO: 79/SEQ ID NO: 99,
SEQ ID NO: 81/SEQ ID NO: 89,
SEQ ID NO: 81/SEQ ID NO: 91,
SEQ ID NO: 81/SEQ ID NO: 93,
SEQ ID NO: 81/SEQ ID NO: 95,
SEQ ID NO: 81/SEQ ID NO: 97,
SEQ ID NO: 81/SEQ ID NO: 99,
SEQ ID NO: 83/SEQ ID NO: 89,
SEQ ID NO: 83/SEQ ID NO: 91,
SEQ ID NO: 83/SEQ ID NO: 93,
SEQ ID NO: 83/SEQ ID NO: 95,
SEQ ID NO: 83/SEQ ID NO: 97,
SEQ ID NO: 83/SEQ ID NO: 99,
SEQ ID NO: 85/SEQ ID NO: 89,
SEQ ID NO: 85/SEQ ID NO: 91,
SEQ ID NO: 85/SEQ ID NO: 93,
SEQ ID NO: 85/SEQ ID NO: 95,
SEQ ID NO: 85/SEQ ID NO: 97,
SEQ ID NO: 85/SEQ ID NO: 99,
SEQ ID NO: 87/SEQ ID NO: 89,
SEQ ID NO: 87/SEQ ID NO: 91,
SEQ ID NO: 87/SEQ ID NO: 93,
SEQ ID NO: 87/SEQ ID NO: 95,
SEQ ID NO: 87/SEQ ID NO: 97,
SEQ ID NO: 87/SEQ ID NO: 99,
SEQ ID NO: 9/SEQ ID NO: 19,
SEQ ID NO: 9/SEQ ID NO: 21,
SEQ ID NO: 9/SEQ ID NO: 23,
SEQ ID NO: 9/SEQ ID NO: 25,
SEQ ID NO: 9/SEQ ID NO: 27,
SEQ ID NO: 11/SEQ ID NO: 19,
SEQ ID NO: 11/SEQ ID NO: 21,
SEQ ID NO: 11/SEQ ID NO: 23,
SEQ ID NO: 11/SEQ ID NO: 25,
SEQ ID NO: 11/SEQ ID NO: 27,
SEQ ID NO: 13/SEQ ID NO: 19,
SEQ ID NO: 13/SEQ ID NO: 21,
SEQ ID NO: 13/SEQ ID NO: 23,
SEQ ID NO: 13/SEQ ID NO: 25,
SEQ ID NO: 13/SEQ ID NO: 27,
SEQ ID NO: 15/SEQ ID NO: 19,
SEQ ID NO: 15/SEQ ID NO: 21,
SEQ ID NO: 15/SEQ ID NO: 23,
SEQ ID NO: 15/SEQ ID NO: 25,
SEQ ID NO: 15/SEQ ID NO: 27,
SEQ ID NO: 17/SEQ ID NO: 19,
SEQ ID NO: 17/SEQ ID NO: 21,
SEQ ID NO: 17/SEQ ID NO: 23,
SEQ ID NO: 17/SEQ ID NO: 25, and
SEQ ID NO: 17/SEQ ID NO: 27,
or, in each case, at least 90%, 95%, 97%, 98%, or 99% identical to a respective SEQ ID NO.

Embodiment 24

A host cell comprising expression vector of embodiment 22 or 23.

Embodiment 25

A host cell of embodiment 24 which produces a full length anti-SIRPα antibody.

Embodiment 26

The host cell of one of embodiments 24 or 25, which is a bacterial cell, a human cell, a mammalian cell, a *Pichia* cell, a plant cell, an HEK293 cell, or a Chinese hamster ovary cell.

Embodiment 27

A composition comprising the antibody or antigen binding fragment of any one of embodiments 1-18 and a pharmaceutically acceptable carrier or diluent.

Embodiment 28

The composition of embodiment 27, further comprising a second antibody or antigen binding fragment thereof that induces ADCC and/or ADCP, wherein said antibody or antigen binding fragment of the invention enhances the antibody-mediated destruction of cells by the second antibody.

Embodiment 29

The composition according to embodiment 28, wherein the second antibody or antigen binding fragment thereof binds to an antigen selected from the group consisting of AMHR2, AXL, BCMA, CA IX, CD4, CD16, CD19, CD20, CD22, CD30, CD37, CD38, CD40, CD52, CD98, CSF1R, GD2, CCR4, CS1, EpCam, EGFR, EGFRvIII, Endoglin, EPHA2, EphA3, FGFR2b, folate receptor alpha, fucosyl-

Embodiment 30

The composition according to embodiment 29, wherein the second antibody or antigen binding fragment thereof is selected from the group consisting of Rituximab, ublituximab, margetuximab, IMGN-529, SCT400, veltuzumab, Obinutuzumab, ADCT-502, Hu14.18K322A, Hu3F8, Dinituximab, Trastuzumab, Cetuximab, Rituximab-RLI, c.60C3-RLI, Hul4.18-IL2, KM2812, AFM13, (CD20)$_2$xCD16, erlotinib (Tarceva), daratumumab, alemtuzumab, pertuzumab, brentuximab, elotuzumab, ibritumomab, ifabotuzumab, farletuzumab, otlertuzumab, carotuximab, epratuzumab, inebilizumab, lumretuzumab, 4G7SDIE, AFM21, AFM22, LY-3022855, SNDX-6352, AFM-13, BI-836826, BMS-986012, BVX-20, mogamulizumab, ChiLob-7/4, leukotuximab, isatuximab, DS-8895, FPA144, GM102, GSK-2857916, IGN523, IT1208, ADC-1013, CAN-04, XOMA-213, PankoMab-GEX, chKM-4927, IGN003, IGN004, IGN005, MDX-1097, MOR202, MOR-208, oportuzumab, ensituximab, vedotin (Adcetris), ibritumomab tiuxetan, ABBV-838, HuMax-AXL-ADC, and ado-trastuzumab emtansine (Kadcyla).

Embodiment 31

The composition according to embodiment 28, wherein the second antibody or antigen binding fragment thereof induces ADCP.

Embodiment 32

The composition according to embodiment 31, wherein the second antibody or antigen binding fragment thereof is selected from the group consisting of Rituximab, ublituximab, margetuximab, IMGN-529, SCT400, veltuzumab, Obinutuzumab, Trastuzumab, Cetuximab, alemtuzumab, ibritumomab, farletuzumab, inebilizumab, lumretuzumab, 4G7SDIE, BMS-986012, BVX-20, mogamulizumab, ChiLob-7/4, GM102, GSK-2857916, PankoMab-GEX, chKM-4927, MDX-1097, MOR202, and MOR-208.

Embodiment 33

The composition of embodiment 27, further comprising one or more agents selected from the group consisting of anti-CD27 antibody, anti-CD47 antibody, anti-APRIL antibody, anti-PD-1 antibody, anti-PD-L1 antibody, anti-TIGIT antibody, anti-CTLA4 antibody, anti-CS1 antibody, anti-KIR2DL1/2/3 antibody, anti-CD137 antibody, anti-GITR antibody, anti-PD-L2 antibody, anti-ILT1 antibody, anti-ILT2 antibody, anti-ILT3 antibody, anti-ILT4 antibody, anti-ILT5 antibody, anti-ILT6 antibody, anti-ILT7 antibody, anti-ILT8 antibody, anti-CD40 antibody, anti-OX40 antibody, anti-ICOS, anti-KIR2DL1 antibody, anti-KIR2DL2/3 antibody, anti-KIR2DL4 antibody, anti-KIR2DL5A antibody, anti-KIR2DL5B antibody, anti-KIR3DL1 antibody, anti-KIR3DL2 antibody, anti-KIR3DL3 antibody, anti-NKG2A antibody, anti-NKG2C antibody, anti-NKG2E antibody, anti-4-1BB antibody, anti-TSLP antibody, anti-IL-10 antibody, IL-10 PEGylated IL-10, an agonist (e.g., an agonistic antibody or antigen-binding fragment thereof, or a soluble fusion) of a TNF receptor protein, an Immunoglobulin-like protein, a cytokine receptor, an integrin, a signaling lymphocytic activation molecules (SLAM proteins), an activating NK cell receptor, a Toll like receptor, OX40, CD2, CD7, CD27, CD28, CD30, CD40, ICAM-1, LFA-1 (CD11a/CD18), 4-1BB (CD137), B7-H3, ICOS (CD278), GITR, BAFFR, LIGHT, HVEM (LIGHTR), KIRDS2, SLAMF7, NKp80 (KLRF1), NKp44, NKp30, NKp46, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, ITGAM, CD11b, ITGAX, CD11c, ITGB1, CD29, ITGB2, CD18, ITGB7, NKG2D, NKG2C, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Lyl08), SLAM (SLAMF1, CD150, IPO-3), SLAM7, BLAME (SLAMF8), SELPLG (CD162), LTBR, LAT, GADS, PAG/Cbp, CD19a, a ligand that specifically binds with CD83, inhibitor of CD47, an inhibitor of PD-1, an inhibitor of PD-L1, an inhibitor of PD-L2, an inhibitor of CTLA4, an inhibitor of TIM3, an inhibitor of LAG3, an inhibitor of CEACAM (e.g., CEACAM-1, -3 and/or -5), an inhibitor of VISTA, an inhibitor of BTLA, an inhibitor of TIGIT, an inhibitor of LAIR1, an inhibitor of IDO, an inhibitor of TDO, an inhibitor of CD160 an inhibitor of TGFR beta, and a cyclic dinculeotide or other STING pathway agonist.

Embodiment 34

A method of producing an antibody or antigen binding fragment comprising:
culturing a host cell comprising a polynucleotide encoding the heavy chain and/or the light chain of any one of the antibodies or antigen binding fragments of embodiments 1-18 under conditions favorable to expression of the polynucleotide; and optionally, recovering the antibody or antigen binding fragment from the host cell and/or culture medium.

Embodiment 35

A method for detecting the presence of a SIRPα peptide or a fragment thereof in a sample comprising contacting the sample with an antibody or fragment of any of embodiments 1-18 and detecting the presence of a complex between the antibody or fragment and the peptide; wherein detection of the complex indicates the presence of the SIRPα peptide.

Embodiment 36

An antibody or antigen binding fragment according to any one of embodiments 1-18 or a composition according to any one of embodiments 21-25, for the treatment of cancer or an infectious disease.

Embodiment 37

An antibody or antigen binding fragment of embodiments 1-18 or a composition according to any one of embodiments 27-33 for decreasing SIRPα/CD47 signalling in a human subject.

Embodiment 38

A method of treating cancer in a human subject, comprising administering to the subject an effective amount of an antibody or antigen binding fragment of any one of embodiments 1-18, or an expression vector according to one of embodiments 22 or 23, or a host cell according to one of embodiments 24-26, or a composition according one of embodiments 27-33, optionally in association with a further therapeutic agent or therapeutic procedure.

Embodiment 39

A method of treating cancer in a human subject, comprising: administering to the subject an effective amount of
(i) an antibody or antigen binding fragment thereof that induces ADCC and/or ADCP; and
(ii) an antibody or antigen binding fragment of any one of embodiments 1-18, or an expression vector according to one of embodiments 22 or 23, or a host cell according to one of embodiments 24-26, or a composition according one of embodiments 27-33, optionally in association with a further therapeutic agent or therapeutic procedure,
wherein the administration of (ii) enhances the antibody-mediated destruction of cells by the antibody or antigen binding fragment thereof that induces ADCC and/or ADCP.

Embodiment 40

The method according to embodiment 39, wherein the antibody or antigen binding fragment thereof that induces ADCC and/or ADCP binds to an antigen selected from the group consisting of AMHR2, AXL, BCMA, CA IX, CD4, CD16, CD19, CD20, CD22, CD30, CD37, CD38, CD40, CD52, CD98, CSF1R, GD2, CCR4, CS1, EpCam, EGFR, EGFRvIII, Endoglin, EPHA2, EphA3, FGFR2b, folate receptor alpha, fucosyl-GM1, HER2, HER3, IL1RAP, kappa myeloma antigen, MS4A1, prolactin receptor, TA-MUC1, and PSMA.

Embodiment 41

The method according to embodiment 40, wherein the antibody or antigen binding fragment thereof that induces ADCC and/or ADCP is selected from the group consisting of Rituximab, ublituximab, margetuximab, IMGN-529, SCT400, veltuzumab, Obinutuzumab, ADCT-502, Hu14.18K322A, Hu3F8, Dinituximab, Trastuzumab, Cetuximab, Rituximab-RLI, c.60C3-RLI, Hu14.18-IL2, KM2812, AFM13, (CD20)$_2$xCD16, erlotinib (Tarceva), daratumumab, alemtuzumab, pertuzumab, brentuximab, elotuzumab, ibritumomab, ifabotuzumab, farletuzumab, otlertuzumab, carotuximab, epratuzumab, inebilizumab, lumretuzumab, 4G7SDIE, AFM21, AFM22, LY-3022855, SNDX-6352, AFM-13, BI-836826, BMS-986012, BVX-20, mogamulizumab, ChiLob-7/4, leukotuximab, isatuximab, DS-8895, FPA144, GM102, GSK-2857916, IGN523, IT1208, ADC-1013, CAN-04, XOMA-213, PankoMab-GEX, chKM-4927, IGN003, IGN004, IGN005, MDX-1097, MOR202, MOR-208, oportuzumab, ensituximab, vedotin (Adcetris), ibritumomab tiuxetan, ABBV-838, HuMax-AXL-ADC, and ado-trastuzumab emtansine (Kadcyla).

Embodiment 42

The method according to embodiment 39 or 40, wherein the second antibody or antigen binding fragment thereof induces ADCP.

Embodiment 43

The method according to embodiment 42, wherein the second antibody or antigen binding fragment thereof is selected from the group consisting of Rituximab, ublituximab, margetuximab, IMGN-529, SCT400, veltuzumab, Obinutuzumab, Trastuzumab, Cetuximab, alemtuzumab, ibritumomab, farletuzumab, inebilizumab, lumretuzumab, 4G7SDIE, BMS-986012, BVX-20, mogamulizumab, ChiLob-7/4, GM102, GSK-2857916, PankoMab-GEX, chKM-4927, MDX-1097, MOR202, and MOR-208.

Embodiment 44

A method of treating an infection or infectious disease in a human subject, comprising administering to the subject an effective amount of an antibody or antigen binding fragment of any one of embodiments 1-18, or an expression vector according to one of embodiments 22 or 23, or a host cell according to one of embodiments 24-26, or a composition according one of embodiments 27-33, optionally in association with a further therapeutic agent or therapeutic procedure.

Embodiment 45

An antibody having one or more of the following characteristics:
 binds human SIRPαV1 protein having the sequence of SEQ ID NO: 34 with an $EC_{50}$<1 nM; exhibits at least a 100-fold higher $EC_{50}$ for SIRPαV1(P74A) having the sequence of SEQ ID NO: 62; and exhibits at least a 100-fold higher $EC_{50}$ for human SIRPβ1 protein having the sequence of SEQ ID NO: 38, preferably when measured by cellular ELISA;
 binds to a cell expressing human SIRPαV1 protein with an $EC_{50}$<10 nM, preferably <5 nM, more preferably <1.5 nM, still more preferably <1.0 nM, even more preferably <0.5 nM, and most preferably about 0.3 nM or less;
 binds to a cell expressing human SIRPαV2 protein with an $EC_{50}$<10 nM, preferably <5 nM, more preferably <1.5 nM, still more preferably <1.0 nM, even more preferably <0.5 nM, and most preferably about 0.3 nM or less;
 does not appreciably bind to SIRPβ1 protein at an antibody concentration of 50 nM, preferably 67 nM, and more preferably 100 nM; or alternatively at a concentration that is 10-fold greater, preferably 50-fold greater, more preferably 100-fold greater, and still more preferably 200-fold greater than the antibody's $EC_{50}$ for SIRPαV1 or SIRPαV2;
 inhibits binding between human SIRPα and CD47 with an $IC_{50}$<10.0 nM, more preferably <5.0 nM, still more preferably <2.5 nM, and most preferably about 1.0 nM or less; and
 exhibits a T20 "humanness" score of at least 79, and more preferably 85.

Embodiment 46

The antibody or antigen binding fragment of embodiment 45 that binds human SIRPαV1 protein having the sequence of SEQ ID NO: 34 with an $EC_{50}$<1 nM; exhibits at least a 100-fold higher $EC_{50}$ for SIRPαV1(P74A) having the sequence of SEQ ID NO: 62; and exhibits at least a 100-fold higher $EC_{50}$ for human SIRPβ1 protein having the sequence of SEQ ID NO: 38.

Embodiment 47

The antibody or antigen binding fragment of embodiment 45 or 46 that comprises one or two light chains comprising SEQ ID NO: 20 or a sequence at least 90%, 95%, 97%, 98%, or 99% identical thereto and one or two heavy chains comprising SEQ ID NO: 10 or a sequence at least 90%, 95%, 97%, 98%, or 99% identical thereto.

Embodiment 48

The antibody or antigen binding fragment of embodiment 45 or 46 that comprises one or two light chains comprising SEQ ID NO: 28 or a sequence at least 90%, 95%, 97%, 98%, or 99% identical thereto and one or two heavy chains comprising SEQ ID NO: 16 or a sequence at least 90%, 95%, 97%, 98%, or 99% identical thereto.

Embodiment 49

The antibody or antigen binding fragment of embodiment 45 or 46 that comprises one or two light chains comprising SEQ ID NO: 20 or a sequence at least 90%, 95%, 97%, 98%, or 99% identical thereto and one or two heavy chains comprising SEQ ID NO: 18 or a sequence at least 90%, 95%, 97%, 98%, or 99% identical thereto.

Embodiment 50

The antibody or antigen binding fragment of embodiment 45 or 46 that comprises one or two light chains comprising SEQ ID NO: 90 or a sequence at least 90%, 95%, 97%, 98%, or 99% identical thereto and one or two heavy chains comprising SEQ ID NO: 80 or a sequence at least 90%, 95%, 97%, 98%, or 99% identical thereto.

Embodiment 51

The antibody or antigen binding fragment of embodiment 45 or 46 that comprises one or two light chains comprising SEQ ID NO: 92 or a sequence at least 90%, 95%, 97%, 98%, or 99% identical thereto and one or two heavy chains comprising SEQ ID NO: 80 or a sequence at least 90%, 95%, 97%, 98%, or 99% identical thereto.

Embodiment 52

The antibody or antigen binding fragment of embodiment 45 or 46 that comprises one or two light chains comprising SEQ ID NO: 96 or a sequence at least 90%, 95%, 97%, 98%, or 99% identical thereto and one or two heavy chains comprising SEQ ID NO: 80 or a sequence at least 90%, 95%, 97%, 98%, or 99% identical thereto.

Embodiment 53

The antibody or antigen binding fragment of one of embodiments 45-52, wherein the antibody is an intact IgG.

Embodiment 54

The antibody or antigen binding fragment of one of embodiments 45-52, wherein the antibody comprises a wild-type or mutated IgG2 Fc region.

Embodiment 55

The antibody or antigen binding fragment of one of embodiments 45-52, wherein the antibody comprises a mutated IgG1 Fc region.

Embodiment 56

The antibody or antigen binding fragment of one of embodiments 45-52, wherein the antibody comprises a mutated IgG4 Fc region.

Embodiment 57

An antibody or antigen binding fragment thereof that binds to the same epitope of human SIRPα as an antibody as an antibody according to one of embodiments 45-52.

Embodiment 58

The antibody or antigen binding fragment of any of embodiments 45-52, wherein the antibody or antigen binding fragment is humanized.

Embodiment 59

A composition comprising the antibody or antigen binding fragment of any one of embodiments 45-52 and a pharmaceutically acceptable carrier or diluent.

Embodiment 60

An antibody or antigen binding fragment according to any one of embodiments 45-52 or a composition according to embodiment 59, for the treatment of cancer or an infectious disease.

Embodiment 61

An antibody or antigen binding fragment according to any one of embodiments 45-52 or a composition according to embodiment 59 for decreasing SIRPα/CD47 signalling in a human subject.

Embodiment 62

A method of treating cancer in a human subject, comprising administering to the subject an effective amount of an antibody or antigen binding fragment according to any one of embodiments 45-52 or a composition according to embodiment 59, optionally in association with a further therapeutic agent or therapeutic procedure.

Embodiment 63

A method of treating an infection or infectious disease in a human subject, comprising administering to the subject an effective amount of an antibody or antigen binding fragment according to any one of embodiments 45-52 or a composition according to embodiment 59, optionally in association with a further therapeutic agent or therapeutic procedure.

GENERAL METHODS

Standard methods in molecular biology are described Sambrook, Fritsch and Maniatis (1982 & 1989 $2^{nd}$ Edition, 2001 $3^{rd}$ Edition) *Molecular Cloning, A Laboratory Manual*, Cold Spring Harbor Laboratory Press, Cold Spring Harbor, N.Y.; Sambrook and Russell (2001) *Molecular Cloning, $3^{rd}$ ed.*, Cold Spring Harbor Laboratory Press, Cold Spring Harbor, N.Y.; Wu (1993) *Recombinant DNA*, Vol. 217, Academic Press, San Diego, Calif.). Standard methods also appear in Ausbel, et al. (2001) *Current Protocols in Molecu-* lar Biology, Vols. 1-4, John Wiley and Sons, Inc. New York, N.Y., which describes cloning in bacterial cells and DNA mutagenesis (Vol. 1), cloning in mammalian cells and yeast (Vol. 2), glycoconjugates and protein expression (Vol. 3), and bioinformatics (Vol. 4).

Methods for protein purification including immunoprecipitation, chromatography, electrophoresis, centrifugation, and crystallization are described (Coligan, et al. (2000) *Current Protocols in Protein Science*, Vol. 1, John Wiley and Sons, Inc., New York). Chemical analysis, chemical modification, post-translational modification, production of fusion proteins, glycosylation of proteins are described (see, e.g., Coligan, et al. (2000) *Current Protocols in Protein Science*, Vol. 2, John Wiley and Sons, Inc., New York; Ausubel, et al. (2001) *Current Protocols in Molecular Biology*, Vol. 3, John Wiley and Sons, Inc., NY, NY, pp. 16.0.5-16.22.17; Sigma-Aldrich, Co. (2001) *Products for Life Science Research*, St. Louis, Mo.; pp. 45-89; Amersham Pharmacia Biotech (2001) *BioDirectory*, Piscataway, N.J., pp. 384-391). Production, purification, and fragmentation of polyclonal and monoclonal antibodies are described (Coligan, et al. (2001) *Current Protcols in Immunology, Vol. 1*, John Wiley and Sons, Inc., New York; Harlow and Lane (1999) *Using Antibodies*, Cold Spring Harbor Laboratory Press, Cold Spring Harbor, N.Y.; Harlow and Lane, supra). Standard techniques for characterizing ligand/receptor interactions are available (see, e.g., Coligan, et al. (2001) *Current Protocols in Immunology, Vol. 4*, John Wiley, Inc., New York).

Monoclonal, polyclonal, and humanized antibodies can be prepared (see, e.g., Sheperd and Dean (eds.) (2000) *Monoclonal Antibodies*, Oxford Univ. Press, New York, N.Y.; Kontermann and Dubel (eds.) (2001) *Antibody Engineering*, Springer-Verlag, New York; Harlow and Lane (1988) *Antibodies A Laboratory Manual*, Cold Spring Harbor Laboratory Press, Cold Spring Harbor, N.Y., pp. 139-243; Carpenter, et al. (2000) *J. Immunol.* 165:6205; He, et al. (1998) *J. Immunol.* 160:1029; Tang et al. (1999) *J. Biol. Chem.* 274:27371-27378; Baca et al. (1997) *J. Biol. Chem.* 272:10678-10684; Chothia et al. (1989) *Nature* 342:877-883; Foote and Winter (1992) *J. Mol. Biol.* 224:487-499; U.S. Pat. No. 6,329,511).

An alternative to humanization is to use human antibody libraries displayed on phage or human antibody libraries in transgenic mice (Vaughan et al. (1996) *Nature Biotechnol.* 14:309-314; Barbas (1995) *Nature Medicine* 1:837-839; Mendez et al. (1997) *Nature Genetics* 15:146-156; Hoogenboom and Chames (2000) *Immunol. Today* 21:371-377; Barbas et al. (2001) *Phage Display: A Laboratory Manual*, Cold Spring Harbor Laboratory Press, Cold Spring Harbor, N.Y.; Kay et al. (1996) *Phage Display of Peptides and Proteins: A Laboratory Manual*, Academic Press, San Diego, Calif.; de Bruin et al. (1999) *Nature Biotechnol.* 17:397-399).

Single chain antibodies and diabodies are described (see, e.g., Malecki et al. (2002) *Proc. Natl. Acad. Sci. USA* 99:213-218; Conrath et al. (2001) *J. Biol. Chem.* 276:7346-7350; Desmyter et al. (2001) *J. Biol. Chem.* 276:26285-26290; Hudson and Kortt (1999) *J. Immunol. Methods* 231:177-189; and U.S. Pat. No. 4,946,778). Bifunctional antibodies are provided (see, e.g., Mack, et al. (1995) *Proc. Natl. Acad. Sci. USA* 92:7021-7025; Carter (2001) *J. Immunol. Methods* 248:7-15; Volkel, et al. (2001) *Protein Engineering* 14:815-823; Segal, et al. (2001) *J. Immunol. Methods* 248:1-6; Brennan, et al. (1985) *Science* 229:81-83; Raso, et al. (1997) *J. Biol. Chem.* 272:27623; Morrison (1985) *Science* 229:1202-1207; Traunecker, et al. (1991) *EMBO J.* 10:3655-3659; and U.S. Pat. Nos. 5,932,448, 5,532,210, and 6,129,914).

Bispecific antibodies are also provided (see, e.g., Azzoni et al. (1998) *J. Immunol.* 161:3493; Kita et al. (1999) *J. Immunol.* 162:6901; Merchant et al. (2000) *J. Biol. Chem.* 74:9115; Pandey et al. (2000) *J. Biol. Chem.* 275:38633; Zheng et al. (2001) *J. Biol Chem.* 276:12999; Propst et al. (2000) *J. Immunol.* 165:2214; Long (1999) *Ann. Rev. Immunol.* 17:875). Purification of antigen is not necessary for the generation of antibodies. Animals can be immunized with cells bearing the antigen of interest. Splenocytes can then be isolated from the immunized animals, and the splenocytes can fused with a myeloma cell line to produce a hybridoma (see, e.g., Meyaard et al. (1997) *Immunity* 7:283-290; Wright et al. (2000) *Immunity* 13:233-242; Preston et al., supra; Kaithamana et al. (1999) *J. Immunol.* 163:5157-5164).

Antibodies can be conjugated, e.g., to small drug molecules, enzymes, liposomes, polyethylene glycol (PEG). Antibodies are useful for therapeutic, diagnostic, kit or other purposes, and include antibodies coupled, e.g., to dyes, radioisotopes, enzymes, or metals, e.g., colloidal gold (see, e.g., Le Doussal et al. (1991) *J. Immunol.* 146:169-175; Gibellini et al. (1998) *J. Immunol.* 160:3891-3898; Hsing and Bishop (1999) *J. Immunol.* 162:2804-2811; Everts et al. (2002) *J. Immunol.* 168:883-889).

Methods for flow cytometry, including fluorescence activated cell sorting (FACS), are available (see, e.g., Owens, et al. (1994) *Flow Cytometry Principles for Clinical Laboratory Practice*, John Wiley and Sons, Hoboken, N.J.; Givan (2001) *Flow Cytometry*, $2^{nd}$ ed.; Wiley-Liss, Hoboken, N.J.; Shapiro (2003) *Practical Flow Cytometry*, John Wiley and Sons, Hoboken, N.J.). Fluorescent reagents suitable for modifying nucleic acids, including nucleic acid primers and probes, polypeptides, and antibodies, for use, e.g., as diagnostic reagents, are available (Molecular Probes (2003) Catalogue, Molecular Probes, Inc., Eugene, Oreg.; Sigma-Aldrich (2003) Catalogue, St. Louis, Mo.).

Standard methods of histology of the immune system are described (see, e.g., Muller-Harmelink (ed.) (1986) *Human Thymus: Histopathology and Pathology*, Springer Verlag, New York, N.Y.; Hiatt, et al. (2000) *Color Atlas of Histology*, Lippincott, Williams, and Wilkins, Phila, Pa.; Louis, et al. (2002) *Basic Histology: Text and Atlas*, McGraw-Hill, New York, N.Y.).

Software packages and databases for determining, e.g., antigenic fragments, leader sequences, protein folding, functional domains, glycosylation sites, and sequence alignments, are available (see, e.g., GenBank, Vector NTI® Suite (Informax, Inc, Bethesda, Md.); GCG Wisconsin Package (Accelrys, Inc., San Diego, Calif.); DeCypher® (TimeLogic Corp., Crystal Bay, Nev.); Menne, et al. (2000) *Bioinformatics* 16: 741-742; Menne, et al. (2000) *Bioinformatics Applications Note* 16:741-742; Wren, et al. (2002) *Comput. Methods Programs Biomed.* 68:177-181; von Heijne (1983) *Eur. J. Biochem.* 133:17-21; von Heijne (1986) *Nucleic Acids Res.* 14:4683-4690).

EXAMPLES

The following examples serve to illustrate the present invention. These examples are in no way intended to limit the scope of the invention.

Example 1: Specificity of Commercial hSIRPα Antibodies

The specificity of various commercially available monoclonal anti-hSIRPα antibodies (Table 7) for binding to hSIRPα variant 1 (hSIRPαV1; GenBank accession: NM_001040022.1) (SEQ ID NO: 34), hSIRPα variant 2 (hSIRPαV2; GenBank accession: D86043.1) (SEQ ID NO: 36), hSIRPβ1 (GenBank accession: NM_006065.4) (SEQ ID NO: 38), hSIRPβ1 transcript variant 3/hSIRPβL (NCBI accession: NM_001135844.3) (SEQ ID NO: 117), and hSIRPγ (NCBI accession: NM_018556.3) (SEQ ID NO: 40) was evaluated by cellular ELISA (CELISA). Reactivity was confirmed using CHO-K1 cells (ATCC CCL-61) that had been transiently transfected, using Lipofectamine 2000, with cDNA encoding the full length open reading frame of hSIRPαV1, hSIRPαV2, hSIRPβ1, hSIRPβL, and hSIRPγ subcloned into the pCI-neo vector (Promega, Madison, Wis.). CHO-K1.hSIRPαV1, CHO-K1.hSIRPαV2, CHO-K1.hSIRPβ1, CHO-K1.hSIRPβL, and CHO-K1.hSIRPγ cells were seeded in culture medium (DMEM-F12 (Gibco) supplemented with 5% New Born Calf Serum (BioWest) and Pen/Strep (Gibco)) in 96-well flat-bottom tissue culture plates and incubated at 37° C., 5% $CO_2$ and 95% humidity for 24 hours. Subsequently, culture medium was removed and cells were incubated for 1 hour at 37° C., 5% $CO_2$ and 95% humidity with purified hSIRPα antibodies (used at 10 μg/mL and dilutions thereof). Next, cells were washed with PBS-T and incubated for 1 hour at 37° C., 5% $CO_2$ and 95% humidity with goat-anti-mouse IgG-HRP (Southern Biotech). Subsequently, cells were washed three times with PBS-T and immunoreactivity against hSIRPαV1, hSIRPαV2, hSIRPβ1, hSIRPβL, and hSIRPγ was visualized with TMB Stabilized Chromogen (Invitrogen). Reactions were stopped with 0.5 M $H_2SO_4$ and absorbances were read at 450 and 610 nm. EC50 values, the concentration at which 50% of the total binding signal is observed, were calculated using GraphPad Prism 6 (GraphPad Software, Inc.).

TABLE 7

Commercially available hSIRPα antibodies used for comparison with antibodies generated herein.

| Target | Clone | Cat.# | Company | Species | Reactivity | Isotype |
|---|---|---|---|---|---|---|
| hSIRPα | SE5A5 | 323802 | Biolegend | mouse | human | IgG1 |
| hSIRPα | 7B3 | LS-C340387 | LifeSpan Biosciences | mouse | human | IgG1 |
| hSIRPα | 1B5 | LS-C338479 | LifeSpan Biosciences | mouse | human | IgG1 |
| hSIRPα | 1C6 | LS-C338477 | LifeSpan Biosciences | mouse | human | IgG1 |
| hSIRPα | 27 | sc-136067 | Santa Cruz Biotechnology | mouse | human, mouse, rat | IgG1 |
| hSIRPα | SE7C2 | sc-23863 | Santa Cruz Biotechnology | mouse | human | IgG1 |
| hSIRPα | P3C4 | LS-C179629-100 | CliniSciences | mouse | human | IgG2a |
| hSIRPα | 2A4A5 | W172-3 | MBL International | mouse | human | IgG2a |
| hSIRPα | 15-414 | LS-C58098 | LifeSpan Biosciences | mouse | human | IgG2a |
| hSIRPα | 1H1 | LS-C338476 | LifeSpan Biosciences | mouse | human | IgG2a |
| hSIRPα | C-7 | sc-376884 | Santa Cruz Biotechnology | mouse | human | IgG2a |
| hSIRPα | 03 | 11612-MM03-100 | Sino Biological Inc. | mouse | human | IgG2b |
| hSIRPα | 5E10 | LS C83566 | LifeSpan Biosciences | mouse | human | IgG2b |
| hSIRPα | 602411 | MAB4546 | R&D | mouse | human | IgG2b |
| hSIRPα | EPR16264 | ab191419 | Abcam | rabbit | human, mouse, rat | IgG |
| hSIRPα | D6I3M | 13379S | Cell Signaling Technology | rabbit | human, mouse, rat, monkey | IgG |
| hSIRPα | 001 | 50956-R001_100ug | Sino Biological Inc. | rabbit | mouse, human | IgG |
| hSIRPα | REA144 | 130-099-768 | Miltenyi Biotec | human | human | IgG1 |
| hSIRPα | KWAR23 | TAB-453CT | Creative Biolabs | human | human | IgG4 |

As depicted in FIG. 1 and the following Table 8, commercially available hSIRPα antibodies cross-react with at least hSIRPβ1, hSIRPβL, or hSIRPγ or demonstrate allele-specific binding to hSIRPαV2. The KWAR23 antibody cross-reacts with all members of the SIRP receptor family tested: it binds to hSIRPαV1, hSIRPαV2, hSIRPβ1, hSIRPβL, and hSIRPγ.

TABLE 8

| Antibody | hSIRPαV1 binding EC50 (nM) | hSIRPαV2 binding EC50 (nM) | hSIRPβ1 binding EC50 (nM) | hSIRPγ binding EC50 (nM) | hSIRPβL binding EC50 (nM) |
|---|---|---|---|---|---|
| hSIRPα.50A | 1.626 | 1.627 | nd | 1.475 | 0.639 |
| anti-hSIRPα (clone SE5A5) | 0.372 | 0.186 | 0.185 | 0.200 | 0.122 |
| anti-hSIRPα (clone 7B3) | 0.187 | 0.300 | 0.255 | nd | 0.206 |
| anti-hSIRPα (clone 1B5) | nd | 0.122 | nd | nd | nd |
| anti-hSIRPα (clone 1C6) | 0.739 | 0.167 | 2.965 | 15.589 | 2.008 |
| anti-hSIRPα (clone 27) | nd | nd | nd | nd | nd |
| anti-hSIRPα (clone SE7C2) | 1.269* | 0.300 | nd | 1.525 | 26.818* |
| anti-hSIRPα (clone P3C4) | 0.288 | 2.154 | 0.383 | 0.365 | 0.136 |
| anti-hSIRPα (clone 2A4A5) | nd | 1.005 | 8.633 | nd | 12.156* |
| anti-hSIRPα (clone 15-414) | nd | nd | nd | nd | nd |

TABLE 8-continued

| Antibody | hSIRPαV1 binding EC50 (nM) | hSIRPαV2 binding EC50 (nM) | hSIRPβ1 binding EC50 (nM) | hSIRPγ binding EC50 (nM) | hSIRPβL binding EC50 (nM) |
|---|---|---|---|---|---|
| anti-hSIRPα (clone 1H1) | nd | 0.204 | nd | nd | nd |
| anti-hSIRPα (clone C-7) | nd | nd | nd | nd | nd |
| anti-hSIRPα (clone 03) | 96.016* | 15.059* | 16.043* | 17.303* | 9.109* |
| anti-hSIRPα (clone 5E10) | nd | nd | nd | nd | nd |
| anti-hSIRPα (clone 602411) | 0.068 | nd | 0.081 | 3.622 | 0.060 |
| anti-hSIRPα (clone EPR16264) | nd | 2.450* | nd | nd | nd |
| anti-hSIRPα (clone D6I3M) | 18.690* | 8.762* | nd | nd | nd |
| anti-hSIRPα (clone 001) | 18.081* | nd | nd | 0.494 | 6.253* |
| anti-hSIRPα (clone REA144) | 5.243* | 3.274* | 4.534* | 3.212* | 2.147* |
| KWAR23 | 0.067 | 0.062 | 0.140 | 0.043 | 0.097 |

Values indicated with * were extrapolated;
nd, not detected

Example 2: Immunization and Selection of Anti-hSIRPα Antibodies

To generate SIRPα antibodies that bind to all known SIRPα alleles and are not binding SIRPβ1 mice were immunized with a pCI-neo expression construct encoding hSIRPαV1 and hSIRPαV2. Mice were immunized by gene gun immunization using a Helios Gene gun (BioRad, Hercules, Calif.) and DNA coated gold bullets (BioRad) following manufacturer's instructions. Briefly, 1 m gold particles were coated with pCI-neo-hSIRPαV1 or pCI-neo-hSIRPαV2 cDNA and commercial expression vectors for mouse Flt3L and mouse GM-CSF in a 2:1:1 ratio (both from Aldevron, Fargo, N. Dak.). A total of 1 µg of plasmid DNA was used to coat 500 µg of gold particles. Specifically, 7-8 weeks old female BALB/C mice (Harlan) were immunized in the ears with a gene gun, receiving 3 administration cycles in both ears.

For positive and negative B-cell selection and CELISA purposes, CHO-K1.hSIRPαV1, CHO-K1.hSIRPαV2, CHO-K1.hSIRPβ1, and CHO-K1.hCD47 stable cell lines were generated by transfecting CHO-K1 cells with pCI-neo vector encoding the full length open reading frame of hSIRPαV1, hSIRPαV2, hSIRPβ1, and hCD47 (NCBI accession: NM_001777.3) (SEQ ID NO: 42), respectively. Stable clones were obtained by limiting dilution.

Antibody titer was assessed by CELISA, using the CHO-K1.hSIRPαV1 and CHO-K1.hSIRPαV2 stable cell lines. These hSIRPα-expressing CHO-K1 cell lines were maintained in DMEM-F12 (Gibco) supplemented with 10% Fetal Bovine Serum (Hyclone) and 80 U Pen/Strep (Gibco). Cells were seeded into 96-well flat-bottom tissue culture plates at $8 \times 10^4$ cells/well and cultured at 37° C., 5% $CO_2$ and 95% humidity until cell layers were confluent. Cells were incubated with each sample of the diluted mouse sera for 1 hour at 37° C., 5% $CO_2$ and 95% humidity. Next, cells were washed with Phosphate buffered Saline (PBS)/0.05% Tween-20 (PBS-T) and incubated with goat-anti-mouse IgG-HRP conjugate (Southern Biotech) for 1 hour at 37° C., 5% $CO_2$ and 95% humidity. Subsequently, cells were washed three times with PBS-T and anti-hSIRPα immunoreactivity was visualized with TMB Stabilized Chromogen (Invitrogen). Reactions were stopped with 0.5 M $H_2SO_4$ and absorbances were read at 450 and 610 nm. The anti-hSIRPα titer was higher than 1:2,500 in each individual mouse serum sample as detected after two DNA immunizations. All mice that demonstrated reactivity against hSIRPαV1 and hSIRPαV2 were immunized for a final, third time and sacrificed 14 days later. Erythrocyte-depleted spleen and lymph-node cell populations were prepared as described previously (Steenbakkers et al., 1992, J. Immunol. Meth. 152: 69-77; Steenbakkers et al., 1994, Mol. Biol. Rep. 19: 125-134) and frozen at −180° C.

To select anti-hSIRPα antibody producing B-cells, a selection strategy was designed and developed that preferentially bound B-cells expressing antibodies that bind to hSIRPαV1 and hSIRPαV2. Splenocytes and lymph nodes were harvested from the hSIRPαV1/V2 immunized mice and isolated cells were incubated with CHO-K1.hSIRPβ1 that were seeded into T25 culture flasks and irradiated at 30 Gray. After 1 hour unbound cells were gently removed by moving the flask back and forth. Medium containing unbound cells was then transferred to a new T25 flask containing irradiated CHO-K1.hSIRPβ1 cells. This procedure was followed for in total three times on ice in order to negatively select hSIRPβ1-reactive B-cells. Next, medium containing unbound B-cells was incubated with CHO-K1.hSIRPαV1 and CHO-K1.hSIRPαV2 cells that were irradiated at 3,000 Gray. After 1.5 hours incubation on ice unbound cells were removed with multiple wash steps using culture medium. Subsequently, T25 flasks containing CHO-K1.hSIRPαV1 and CHO-K1.hSIRPαV2 cells with bound lymphocytes were harvested with Trypsin-EDTA (Sigma). Bound B-cells were cultured, as described by Steenbakkers et al., 1994, Mol. Biol. Rep. 19: 125-134. Briefly, selected B-cells were mixed with 10% (v/v) T-cell supernatant and 50,000 irradiated (25 Gray) EL-4 B5 feeder cells in a final volume of 200 µl medium in 96-well flat-bottom tissue culture plates. On day eight, supernatants were screened for hSIRPαV1 and hSIRPαV2 reactivity by CELISA as described below.

CHO-K1.hSIRPαV1, CHO-K1.hSIRPαV2, and CHO-K1.hSIRPβ1 were seeded in culture medium (DMEM-F12 (Gibco) supplemented with 10% Fetal Bovine Serum (Hyclone) and 80 U Pen/Strep (Gibco)) in 96-well flat-bottom tissue culture plates and cultured at 37° C., 5% $CO_2$ and 95% humidity until they were confluent. Subsequently, culture medium was removed and cells were incubated for 1 hour at 37° C., 5% $CO_2$ and 95% humidity with supernatants from the B-cell cultures. Next, cells were washed with PBS-T and incubated for 1 hour at 37° C., 5% $CO_2$ and 95% humidity with goat-anti-mouse IgG-HRP conjugate (Southern Biotech). Subsequently, cells were washed three times with PBS-T and anti-hSIRPαV1, anti-hSIRPαV2, and anti-hSIRPβ1 immunoreactivity was visualized with TMB Stabilized Chromogen (Invitrogen). Reactions were stopped with 0.5 M $H_2SO_4$ and absorbances were read at 450 and 610 nm.

Immunoreactivity to human SIRPγ was assessed by ELISA using recombinant hSIRPγ/Fc-protein (R&D Systems, Cat.#4486-SB-050; SEQ ID NO: 108) coated 96-well MaxiSorp flat-bottom plates. Protein coated 96-well plates were blocked in PBS/1% bovine serum albumin (BSA) for 1 hour at room temperature (RT). PBS/1% BSA was removed and plates were incubated for 1 hour at RT with supernatants from the B-cell cultures. Next, plates were washed with PBS-T and incubated for 1 hour at RT with goat-anti-mouse IgG-HRP conjugate (Southern Biotech). Subsequently, wells were washed three times with PBS-T and anti-hSIRPγ immunoreactivity was visualized with TMB Stabilized Chromogen (Invitrogen). Reactions were stopped with 0.5 M $H_2SO_4$ and absorbances were read at 450 and 610 nm.

B-cell clones from the hSIRPα reactive supernatants, which were not or which were minimally reactive to hSIRPβ1 were immortalized by mini-electrofusion following published procedures (Steenbakkers et al., 1992, *J. Immunol. Meth.* 152: 69-77; Steenbakkers et al., 1994, *Mol. Biol. Rep.* 19:125-34) with some minor deviations (e.g. pronase reaction was omitted). Briefly, B-cells were mixed with $10^6$ Sp2/0-Ag14 murine myeloma cells (ATCC CRL-1581) in Electrofusion Isomolar Buffer (Eppendorf). Electrofusions were performed in a 50 μL fusion chamber by an alternating electric field of 15 s, 1 MHz, 23 Vrms AC followed by a square, high field DC pulse of 10 as, 180 Volt DC and again by an alternating electric field of 15 s, 1 MHz, 23 Vrms AC. Content of the chamber was transferred to hybridoma selective medium and plated in a 96-well plate under limiting dilution conditions. On day 10 following the electrofusion, hybridoma supernatants were screened for hSIRPαV1, hSIRPαV2, hSIRPβ1, and hSIRPγ binding activity by CELISA and ELISA, as described above. Hybridomas that secreted antibodies in the supernatant that specifically bound hSIRPαV1 and hSIRPαV2 were both frozen at −180° C. (−1 batch) and subcloned by limited dilution to safeguard their integrity and stability. Stable hybridomas were frozen at −180° C. (−LD1 batch) until cell layers were confluent.

Further selection of the hybridomas was performed by assessing the blocking abilities of the hSIRPαV1/hCD47 interaction in CELISA format. For the assessment of hCD47 blockade CHO-K1.hCD47 cells were seeded in 384-well flat-bottom tissue culture plates and incubated at 37° C., 5% $CO_2$ and 95% humidity in culture medium. Recombinant hSIRPα/Fc-protein (R&D Systems, Cat.#4546-SA-050; SEQ ID NO: 107) was pre-incubated with a dilution series of the hybridoma supernatants containing hSIRPα reactive antibodies and control antibodies (at 10 g/mL and dilutions thereof) for 30 minutes at 37° C., 5% $CO_2$ and 95% humidity. Confluent CHO-K1.hCD47 cells were washed with PBS-T and incubated for 1 hour with the mixtures containing hSIRPα reactive antibodies and recombinant hSIRPα/Fc-protein at 37° C., 5% $CO_2$ and 95% humidity. Next, cells were washed with PBS-T followed by addition of goat-anti-human IgG-HRP conjugate (Jackson Immuno Research) to the cells, which was incubated for 1 hour at 37° C., 5% $CO_2$ and 95% humidity. Subsequently cells were washed three times with PBS-T and binding of hSIRPα/Fc-protein was visualized with TMB Stabilized Chromogen (Invitrogen). Reactions were stopped with 0.5 M $H_2SO_4$ and absorbances were read at 450 and 610 nm.

Selected stable hybridomas were cultured in serum-free media for 7 days; supernatants were harvested and antibodies were purified using MabSelect Sure Protein A resin according to the manufacturer's instructions (GE Healthcare). Antibody concentrations were quantified using spectrophotometry. Supernatants of the hybridoma cultures were used to isotype the hybridomas. In short, isotyping was done using a mouse monoclonal antibody isotyping kit (Biorad) based on a dipstick with immobilized goat-anti-mouse antibody bands to each of the common mouse isotypes and light chains. Recovered antibodies were all identified as mouse IgG1. Antibody sequences were elucidated by sequencing of variable regions of the mouse IgG1 hybridoma material performed at LakePharma, using the following method: the total RNA of the hybridoma cells was extracted, which allowed cDNA synthesis. Rapid Amplification of cDNA Ends (RACE) was performed that allowed cloning of positive fragments in a TOPO (Thermo Fisher Scientific) vector. TOPO clones were sequenced and sequences were annotated using VBASE2 (Retter et al., VBASE2, an integrative V gene database. *Nucleic Acids Res.* 2005 Jan. 1; 33(Database issue):D671-4).

Example 3: Characterization of hSIRPα Antibodies

Figure 2:
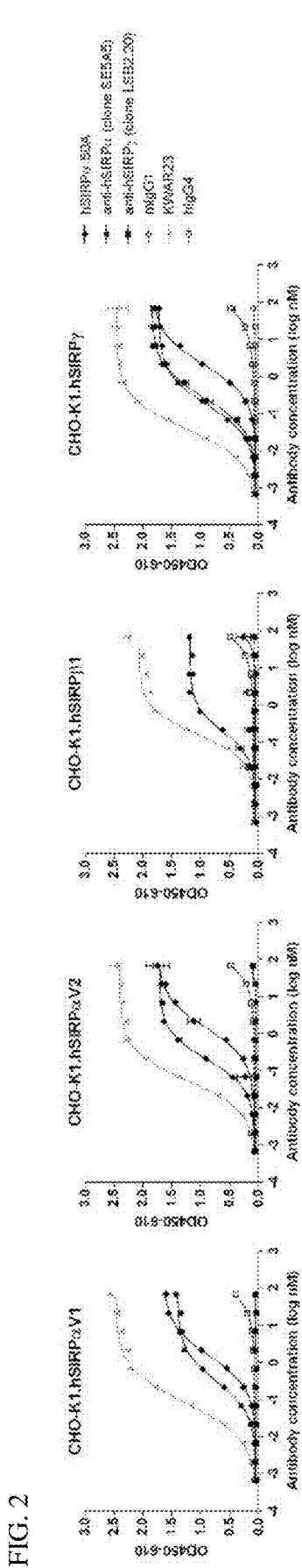
FIG. 2 depicts reactivity of KWAR23 antibody with hSIRPαV1, hSIRPαV2, hSIRPβ1, and hSIRPγ.

The binding specificity of antibody hSIRPα.50A to hSIRPα was compared antibody KWAR23 (Canadian Patent 2939293 A1), in a CELISA format. CHO-K1 cells were transiently transfected with hSIRPαV1, hSIRPαV2, hSIRPβ1, and hSIRPγ (GenBank accession: NM_018556.3) (SEQ ID NO: 39) cDNAs. Subsequently, hSIRPα binding was assessed by CELISA using CHO-K1.hSIRPαV1, CHO-K1.hSIRPαV2, CHO-K1.hSIRPβ1, and CHO-K1.hSIRPγ cells. Detection of bound antibody was performed with goat-anti-mouse IgG-HRP (Southern Biotech) for mouse antibodies including hSIRPα.50A and control antibodies or, alternatively, with goat-anti-human IgG-HRP conjugate (Jackson Immuno Research) for the KWAR23 antibody. KWAR23 (SEQ ID NO: 130; SEQ ID NO: 131) was expressed as a chimeric human IgG4 kappa antibody in CHO cells. As shown in FIG. 2 and the following Table 9, KWAR23 antibody cross-reacts with all members of the SIRP receptor family tested: it binds to hSIRPαV1, hSIRPαV2, hSIRPβ1, and hSIRPγ. EC50 values represent the concentration at which 50% of the total binding signal is observed (average and SD were calculated from values of two independent experiments).

TABLE 9

| Antibody | hSIRPαV1 binding EC50 (nM) | | hSIRPαV2 binding EC50 (nM) | |
|---|---|---|---|---|
| | Average | SD | Average | SD |
| KWAR23 | 0.081 | 0.001 | 0.051 | 0.004 |
| hSIRPα.50A | 1.365 | 0.164 | 1.296 | 0.186 |
| anti-hSIRPα (clone SE5A5) | 0.304 | | 0.200 | |
| anti-hSIRPγ (clone LSB2.20) | nd | | nd | |

| Antibody | hSIRPβ1 binding EC50 (nM) | | hSIRPγ binding EC50 (nM) | |
|---|---|---|---|---|
| | Average | SD | Average | SD |
| KWAR23 | 0.161 | 0.007 | 0.040 | 0.002 |
| hSIRPα.50A | nd | nd | 1.249 | 0.179 |
| anti-hSIRPα (clone SE5A5) | 0.192 | | 0.168 | |
| anti-hSIRPγ (clone LSB2.20) | nd | | 0.265 | |

Empty squares indicate n = 1 measurements.
nd, not detected

Figure 3:
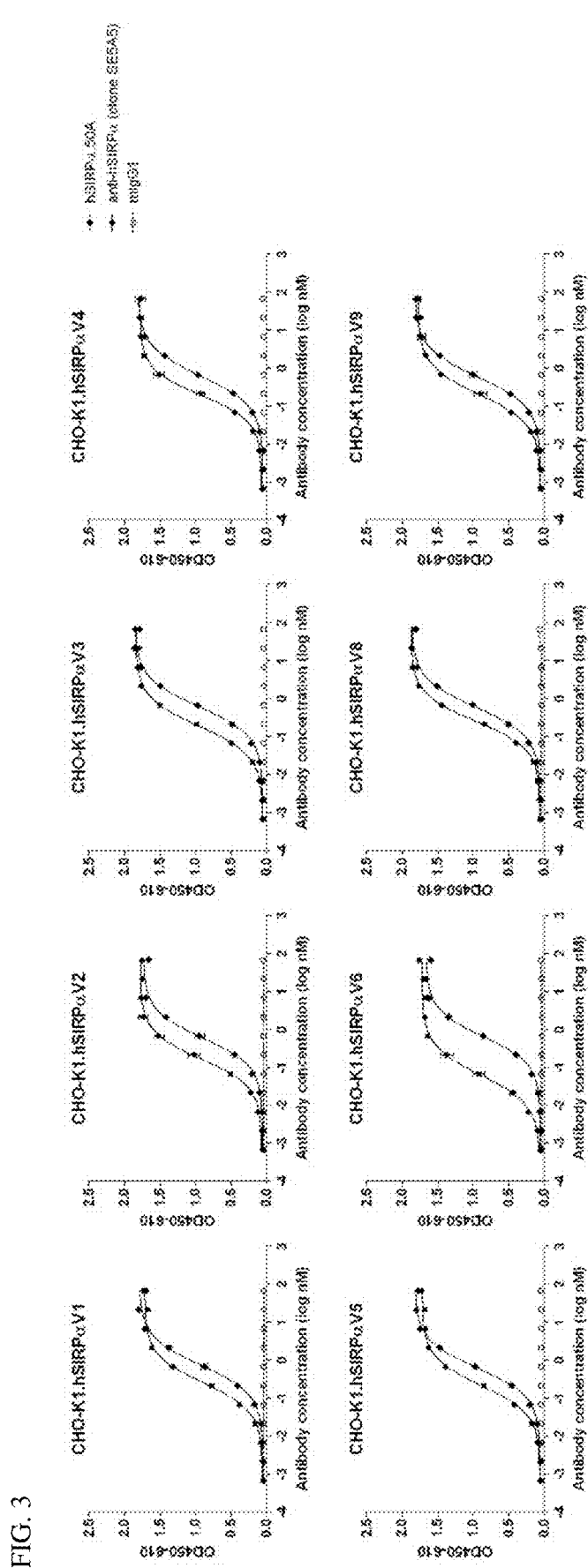
FIG. 3 depicts reactivity of antibody clone hSIRPα.50A for various hSIRPα alleles.

In addition, the specificity of hSIRPα.50A for all known of hSIRPα alleles (allelic variants as described by Takenaka et al., 2007, *Nat Immunol.* 8:1313-1323) was further investigated by CELISA using the same strategy as above. To this end, hSIRPα.50A binding was assessed using CHO-K1 cells that were transiently transfected with cDNAs encoding full length hSIRPαV1, hSIRPαV2, hSIRPαV3 (NA07056_V3) (SEQ ID NO: 43), hSIRPαV4 (NA11832_V4) (SEQ ID NO: 45), hSIRPαV5 (NA18502_V5) (SEQ ID NO: 47), hSIRPαV6 (NA18507_V6) (SEQ ID NO: 49), hSIRPαV8 (NA18570_V8) (SEQ ID NO: 51), and hSIRPαV9 (NA18943_V9) (SEQ ID NO: 53). FIG. 3 and the following Table 10 demonstrate the reactivity of antibody clone hSIRPα.50A for each of these hSIRPα alleles. EC50 values represent the concentration at which 50% of the total binding signal is observed (average and SD were calculated from values of two independent experiments).

TABLE 10

| | | Antibody | |
| --- | --- | --- | --- |
| | | hSIRPα.50A | anti-hSIRPα (clone SE5A5) |
| hSIRPαV1 | EC50 (nM) | 0.936 | 0.327 |
| | SD | 0.285 | 0.107 |
| hSIRPαV2 | EC50 (nM) | 0.665 | 0.200 |
| | SD | 0.106 | 0.046 |
| hSIRPαV3 | EC50 (nM) | 0.688 | 0.226 |
| | SD | 0.097 | 0.052 |
| hSIRPαV4 | EC50 (nM) | 0.824 | 0.256 |
| | SD | 0.280 | 0.085 |
| hSIRPαV5 | EC50 (nM) | 0.765 | 0.276 |
| | SD | 0.210 | 0.086 |
| hSIRPαV6 | EC50 (nM) | 0.954 | 0.098 |
| | SD | 0.437 | 0.050 |
| hSIRPαV8 | EC50 (nM) | 0.644 | 0.300 |
| | SD | 0.066 | 0.061 |
| hSIRPαV9 | EC50 (nM) | 0.733 | 0.260 |
| | SD | 0.205 | 0.079 |

Example 4: hCD47 Blocking Ability of hSIRPα.50A

The hSIRPα.50A antibody was analyzed by flow cytometry for its ability to block recombinant hCD47/Fc-protein (R&D Systems, Cat.#4670-CD-050; SEQ ID NO: 109) binding to cell surface expressed hSIRPα. For this purpose, THP-1 (ATCC TIB-202) and U-937 (ATCC CRL-1593.2) monocyte cell lines were used as the source of hSIRPα in the assay. THP-1 and U-937 cells were seeded in 96-well round bottomed tissue culture plates and incubated for 45 minutes with FcR Blocking Reagent (Miltenyi Biotec) and hSIRPα.50A antibody (200 μg/mL and dilutions thereof) in PBS/1% BSA at 4° C. Next, cells were washed three times with PBS/1% BSA and incubated with DyLight 488-labeled recombinant hCD47/Fc-protein for 30 minutes at 4° C. After this labeling procedure, cells were washed two times, resuspended in PBS/1% BSA containing 0.1 μg/mL DAPI (BioLegend), and analysed by flow cytometry on the FACSCanto II (BD Biosciences). Data were processed and analysed with FlowJo V10 software (FlowJo, LLC).

Figure 4:
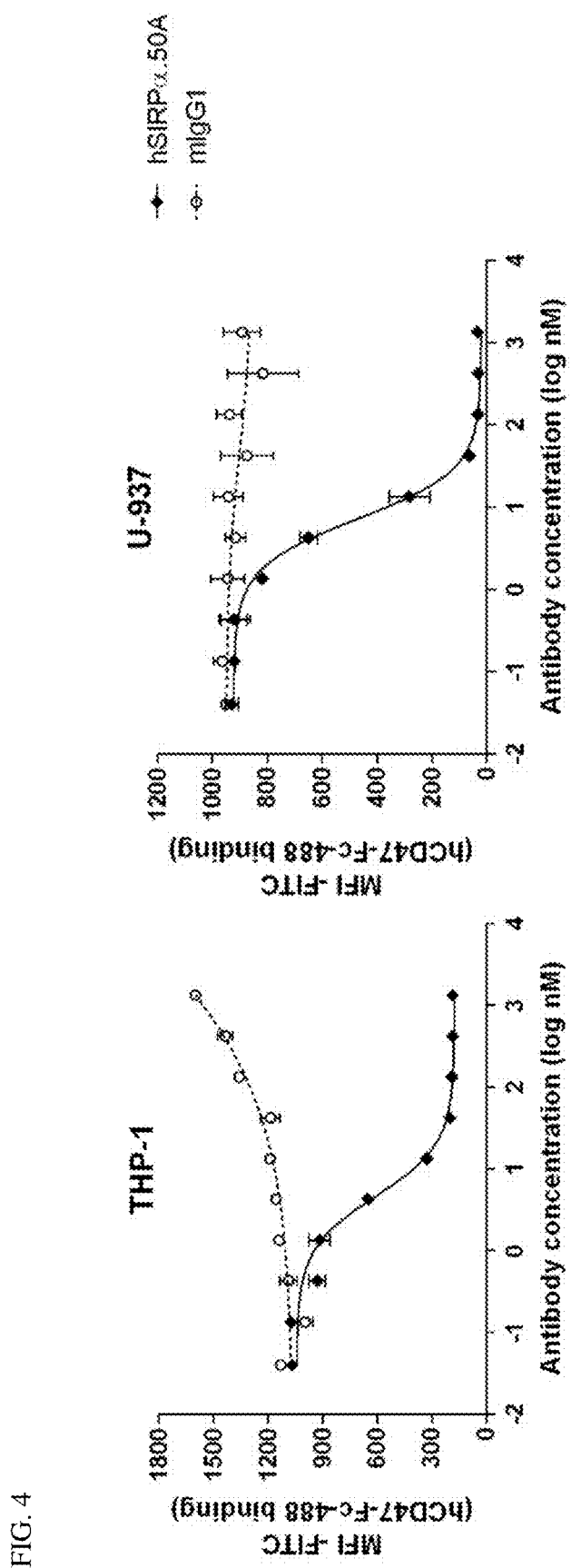
FIG. 4 depicts the ability of hSIRPα.50A antibody to block recombinant hCD47/Fc-protein binding to cell surface expressed hSIRPα.

As depicted in FIG. 4 and the following Table 11, binding of recombinant hCD47 fused to an Fc domain of human IgG1 was monitored in the presence of increasing amounts of the hSIRPα.50A antibody. Antibody hSIRPα.50A blocked the hSIRPα/hCD47 interaction, using the flow cytometry-based method described above. IC50 values for the blockade of hCD47 were calculated from this data. IC50 values represent the concentration at which half of the inhibition is observed.

TABLE 11

| Antibody | THP-1 IC50 (nM) | U-937 IC50 (nM) |
| --- | --- | --- |
| hSIRPα.50A | 4.605 | 7.164 |

Next, the binding of hSIRPα.50A to hSIRPα expressed on primary human CD14+ monocytes was investigated. In addition, the ability of hSIRPα.50A to block the interaction between hSIRPα and recombinant hCD47/Fc-protein was assessed. For this purpose, CD14+ monocytes were isolated from Ficoll-purified human peripheral blood mononuclear cells (PBMCs) using RosetteSep human monocyte enrichment cocktail (Stemcell). The percentage of monocytes present after the enrichment was determined by flow cytometry on the FACSVerse (BD Biosciences) based on CD14 staining using an APC-Cy7-conjugated mouse-anti-human CD14 detection antibody (BD Biosciences). Subsequently, CD14+ enriched PBMCs were seeded in 96-well round bottomed tissue culture plates and incubated for 40 minutes with FcR Blocking Reagent (Miltenyi Biotec) containing hSIRPα.50A antibody (25 μg/mL and dilutions thereof) in PBS/1% BSA at 4° C. Next, cells were washed three times with PBS/1% BSA and incubated with a FITC-labeled goat-anti-mouse Ig (BD Biosciences) detection antibody in PBS/1% BSA for 40 minutes at 4° C. After this labeling procedure, cells were washed two times, resuspended in PBS/1% BSA containing 0.1 μg/mL DAPI (BioLegend), and analysed by flow cytometry on the FACSVerse (BD Biosciences). Data were processed and analysed with FlowJo V10 software (FlowJo, LLC).

Figures 5A, 5B:
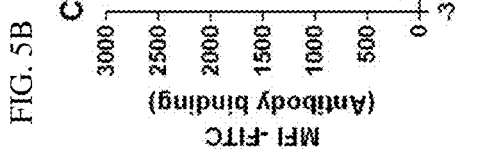
FIG. 5A depicts binding of hSIRP?.50A antibody to primary CD14+ enriched monocytes from a human donor.
FIG. 5B depicts binding of hSIRP?.50A antibody to primary CD14+ enriched monocytes from a second human donor.
Figure 5C:
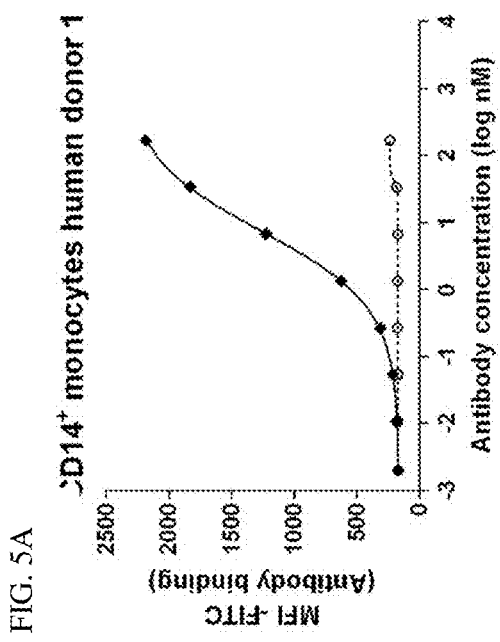
FIG. 5C depicts the ability of hSIRP?.50A antibody to block hCD47 binding to primary CD14+ enriched monocytes from a human donor.
Figure 5D:
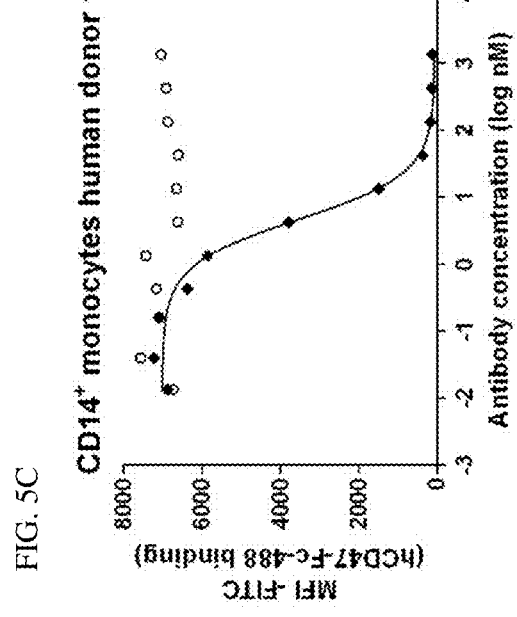
FIG. 5D depicts the ability of hSIRP?.50A antibody to block hCD47 binding to primary CD14+ enriched monocytes from a second human donor.

FIGS. 5A and B and the following Table 12 indicates that hSIRPα.50A binds to primary human CD14+ enriched monocytes. EC50 values represent the concentration at which 50% of the total binding signal is observed. To assess the blocking ability of hSIRPα.50A, CD14+ enriched monocytes cells were seeded in 96-well round bottomed tissue culture plates and incubated for 45 minutes with FcR Blocking Reagent (Miltenyi Biotec) and hSIRPα.50A antibody (200 μg/mL and dilutions thereof) in PBS/1% BSA at 4° C. Thereafter, cells were washed three times with PBS/1% BSA and incubated with 10 μg/mL DyLight 488-labeled recombinant hCD47/Fc-protein for 45 minutes at 4° C. After this labeling procedure, cells were washed two times, resuspended in PBS/1% BSA containing 0.1 μg/mL DAPI (BioLegend), and analysed by flow cytometry on the FACSVerse (BD Biosciences). Data were processed and analysed with FlowJo V10 software (FlowJo, LLC). FIGS. 5 C and D and the following Table 12 demonstrates the ability of antibody hSIRPα.50A to block the hSIRPα/hCD47 interaction. IC50 values for the blockade of hCD47 were calculated from this data. IC50 values represent the concentration at which half of the inhibition is observed.

TABLE 12

| | Donor 1 | | Donor 2 | |
| --- | --- | --- | --- | --- |
| Antibody | EC50 (nM) | IC50 (nM) | EC50 (nM) | IC50 (nM) |
| hSIRPα.50A | 7.381 | 4.618 | 3.081 | 1.035 |

Figure 6A:
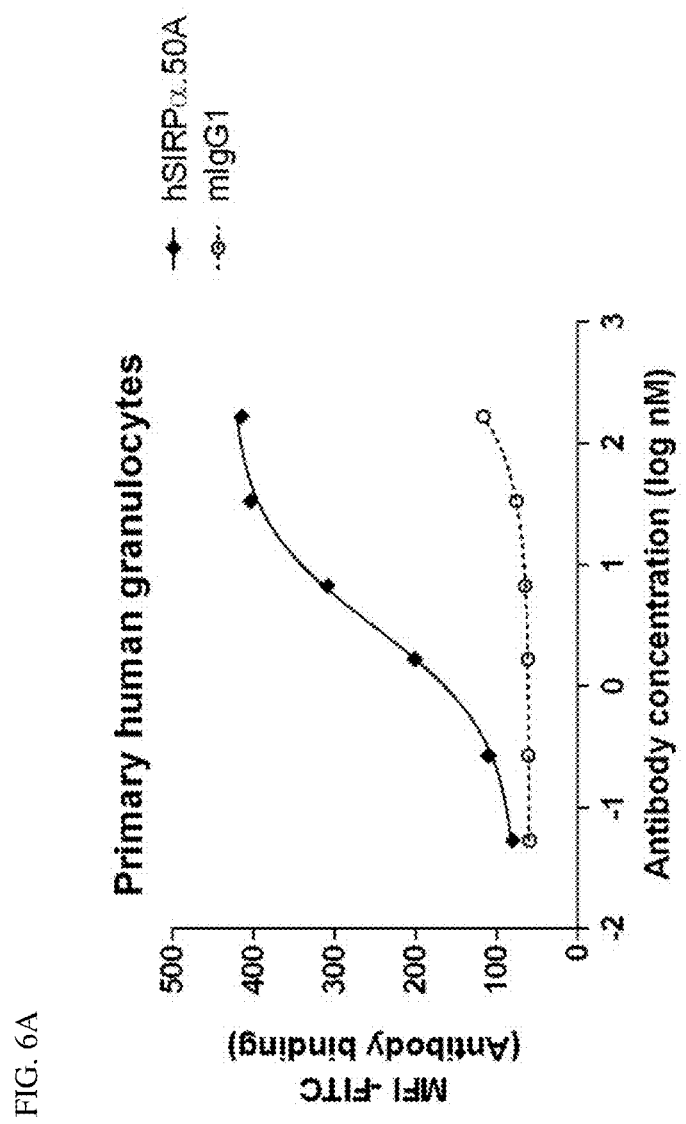
FIG. 6A depicts binding of hSIRPα.50A antibody to primary human granulocytes.

Example 5: Functionality of hSIRPα.50A mAb in the Human Granulocyte Phagocytosis Assay To confirm the functionality of hSIRPα.50A in primary immune cells, granulocytes (e.g. effector cells) were isolated from healthy human donor EDTA blood. First, the EDTA blood of each donor was pooled and centrifuged at 300 g for 6 minutes at 20° C. Next, plasma was removed by aspiration, and the remaining blood cells were gently resuspended. Cells were recovered in red blood cell (RBC) lysis buffer (155 mM NH4Cl; 10 mM KHCO3) and incubated for 10 minutes on ice. Next, cells were centrifuged at 300 g for 7 minutes. Supernatants containing lysed RBCs were removed by aspiration, and the remaining blood cells were gently resuspended in RBC lysis buffer and kept on ice for 1 minute. RBC lysis was neutralized by adding assay medium (IMDM (Gibco) supplemented with 10% Fetal Bovine Serum (Gibco) and Pen/Strep (Gibco)). Blood cells were centrifuged at 300 g for 6 minutes and supernatants were removed by aspiration to remove remaining RBCs as much as possible. Subsequently, erythrocyte-lysed blood cells were resuspended in assay medium containing 10 ng/mL IFNγ and cells were incubated for 1 hour at 37° C., 5% $CO_2$ and 95% humidity. Non-adherent blood cells containing human granulocytes were collected by mild washing of the tissue culture plate with assay medium (monocytes are depleted due to adherence to the plastic surface). The percentage of granulocytes present in the cell suspension was determined by flow cytometry on the FACSCanto II (BD Biosciences) based on high forward scatter (FSC) and side scatter (SSC). Binding of hSIRPα.50A to human granulocytes was assessed by incubating the cells for 30 minutes at 4° C. with hSIRPα.50A antibody (25 µg/mL and dilutions thereof) in PBS/1% BSA containing 10% autologous serum (PBS/1% BSA/10% serum). Next, cells were washed three times with PBS/1% BSA/10% serum and incubated for 30 minutes at 4° C. with a FITC-labeled goat-anti-mouse Ig (BD Biosciences) detection antibody. After this labeling procedure, cells were washed two times, resuspended in PBS/1% BSA/10% serum and analysed by flow cytometry on the FACSCanto II (BD Biosciences). Data were processed and analysed with FlowJo V10 software (FlowJo, LLC). FIG. 6A shows that hSIRPα.50A binds to primary human granulocytes. EC50 values represent the concentration at which 50% of the total binding signal is observed.

Next, target cells were fluorescently labeled with either cell proliferation dye eFluor450 (eBioscience) in the case of Raji (ECACC 85011429), Daudi (ECACC 85011437), Ramos (ECACC 85030802), and BJAB (DSMZ ACC-757) lymphoma cells or, alternatively, with Vybrant DiD cell-labeling solution (Thermo Fisher Scientific) for FaDu cells. Labeling was performed according to manufacturer's instructions. Labeled target cells were co-cultured for 2-3 hours at 37° C., 5% $CO_2$ and 95% humidity with isolated primary human granulocytes in a 1:1 ratio ($7.5*10^4$ cells of each target and effector per well of a 96-well round bottomed tissue culture plate) in the presence of 0.1 µg/mL rituximab (anti-hCD20). In addition, cells were co-cultured with 0.1 µg/mL rituximab in presence of 10 µg/mL hSIRPα.50A. Phagocytosis was assayed by determining the percentage of granulocytes positive for eFluor450 (or DID) using flow cytometry on the FACSCanto II (BD Biosciences). Data were processed and analysed with FlowJo V10 software (FlowJo, LLC).

Figure 6B:
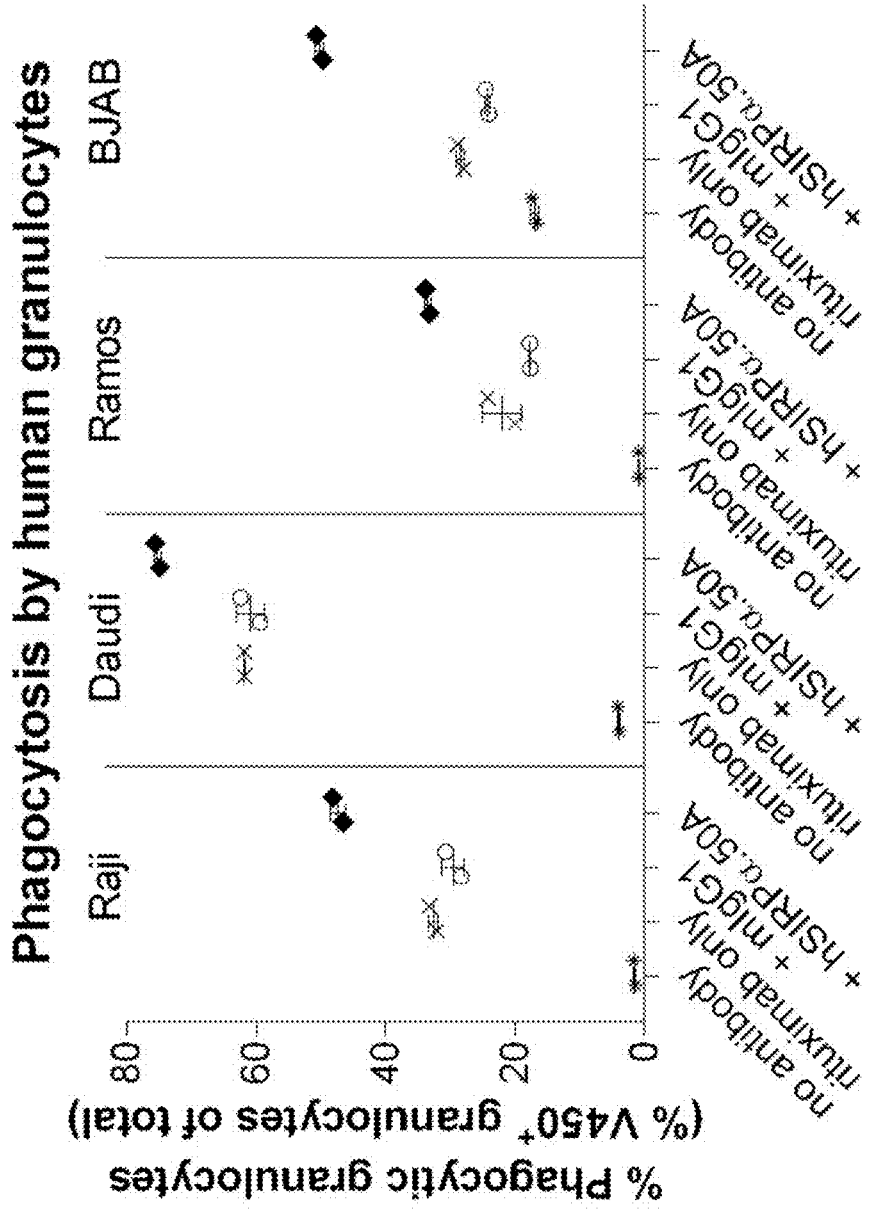
FIG. 6B depicts phagocytosis of tumor cells by primary human granulocytes in the presence of rituximab plus or minus the hSIRPα.50A antibody.
Figure 6C:
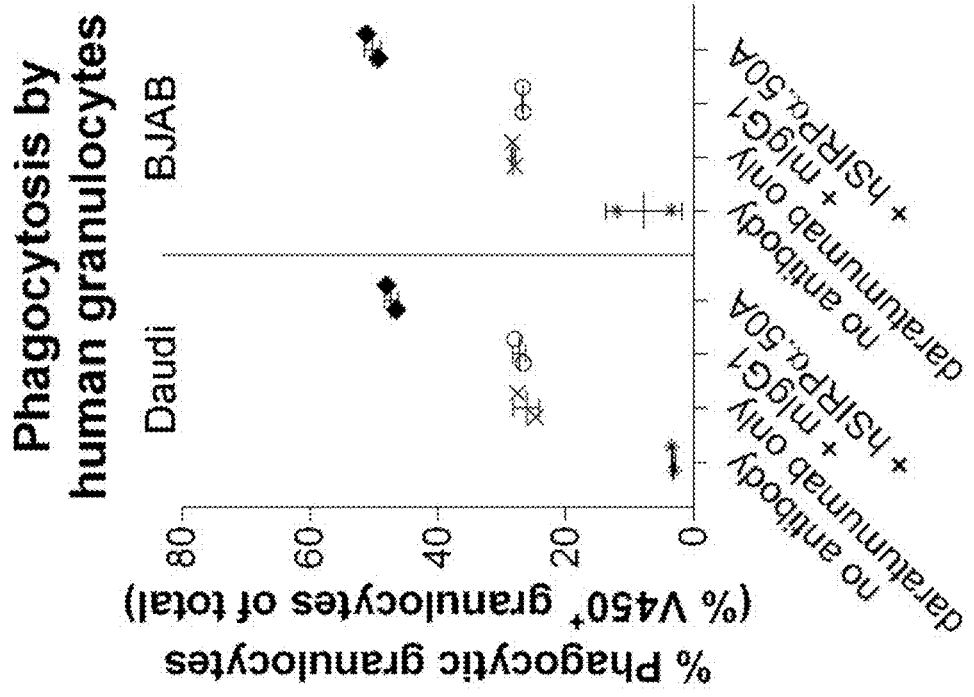
FIG. 6C depicts phagocytosis of tumor cells by primary human granulocytes in the presence of daratumumab plus or minus the hSIRPα.50A antibody.
Figure 6D:
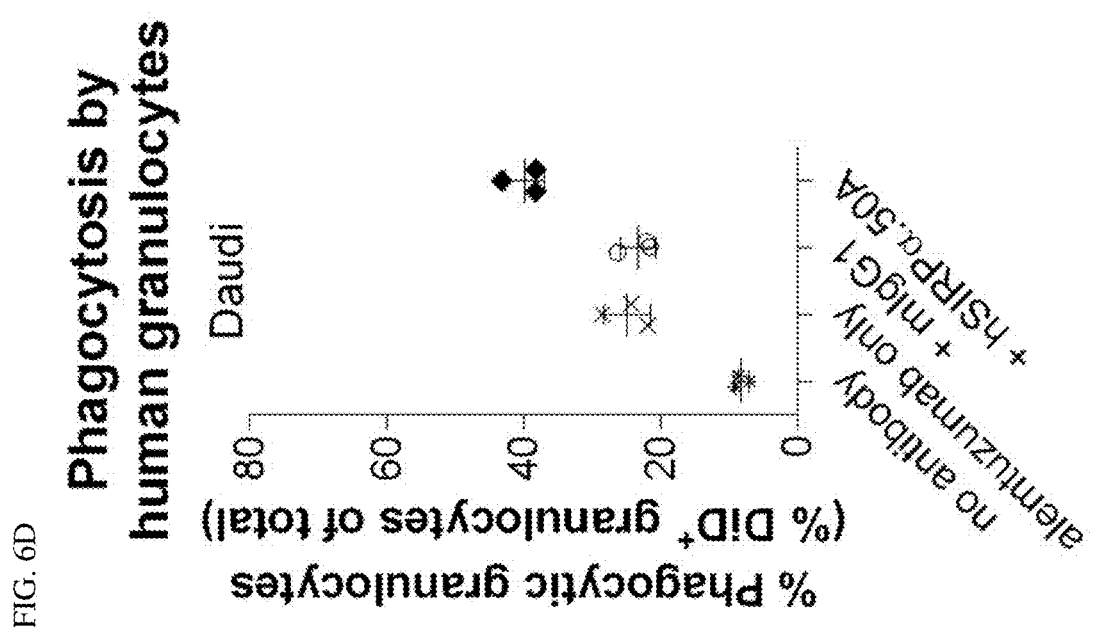
FIG. 6D depicts phagocytosis of tumor cells by primary human granulocytes in the presence of alemtuzumab plus or minus the hSIRPα.50A antibody.
Figure 6E:
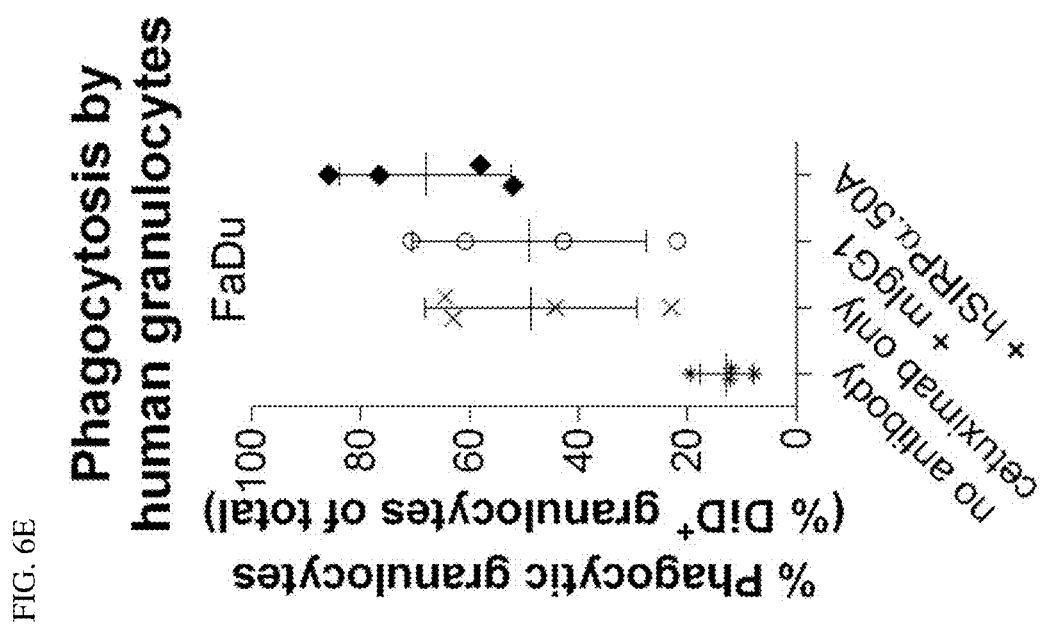
FIG. 6E depicts phagocytosis of tumor cells by primary human granulocytes in the presence of cetuximab plus or minus the hSIRPα.50A antibody.

Compared to the mouse IgG1 isotype control, hSIRPα.50A potently enhances tumor cell phagocytosis induced by rituximab (FIG. 6B). The same procedure was followed with other existing therapeutic antibodies such as 0.05 µg/mL daratumumab (anti-hCD38), 0.1 µg/mL alemtuzumab (anti-hCD52), and 0.1 µg/mL cetuximab (anti-hEGFR) (FIG. 6C-E). These data demonstrate that hSIRPα.50A enhances antibody-mediated tumor cell phagocytosis by human granulocytes.

Example 6: Functionality of hSIRPα.50A mAb in the Human Macrophage Phagocytosis Assay Blockade of CD47 by hSIRPα.50A enhances the phagocytosis of human lymphoma cells tumor cells by human macrophages. Human macrophages were generated by first enriching CD14+ monocytes from Ficoll-purified human peripheral blood mononuclear cells (PBMCs) using RosetteSep human monocyte enrichment cocktail (Stemcell). Monocytes were seeded into CellCarrier 96-well flat-bottom microplates (Perkin Elmer) and cultured in macrophage medium (IMDM (Gibco) supplemented with 8.5% Fetal Bovine Serum (Gibco) and Pen/Strep (Gibco)) containing 50 ng/mL human monocyte colony stimulating factor (M-CSF) for 7 days at 37° C., 5% $CO_2$ and 95% humidity to promote differentiation into macrophages. These monocyte-derived macrophages (MDMs) become adherent allowing other cells to be washed away. Human Raji, Daudi, Ramos, and BJAB lymphoma cells were counted and labeled with cell proliferation dye eFluor450 (eBioscience) following manufacturer's instructions. After labeling, the lymphoma cells were mixed with assay medium (RPMI (Gibco) supplemented with 10% Fetal Bovine Serum (Gibco) and Pen/Strep (Gibco)) containing 10 µg/mL anti-hSIRPα antibodies, respective isotype controls and either 0.1 µg/mL rituximab (anti-hCD20) or 0.05 µg/mL daratumumab (anti-hCD38). The lymphoma cells were then added to the individual wells containing MDMs at a ratio of 2.5:1 tumor cells per phagocyte, mixed and incubated at 37° C., 5% $CO_2$ and 95% humidity for 2 hours. After the incubation, the wells were washed with PBS to remove most of the non-phagocytosed tumor cells, and cells were fixed with 2% formaldehyde for 10 min at RT. The wells were then washed and maintained in PBS/3% BSA in dark at 4° C. overnight. Lymphoma cells present in the wells were stained with biotin-conjugated anti-human CD19 clone HIB 19 (eBioscience) for 1 hour at RT, and subsequently were counterstained with Alexa Fluor 488-conjugated streptavidin (Thermo Fisher Scientific) for 1 hour at RT. Next, nuclei were stained with DRAQ5 (Thermo Fisher Scientific) for 10 minutes at RT, mixture was removed, and PBS was added to each well. Cells were analysed with the Operetta automated fluorescence microscope (Perkin Elmer). Data were processed and analysed with Columbus V2.6 software.

Figure 7:
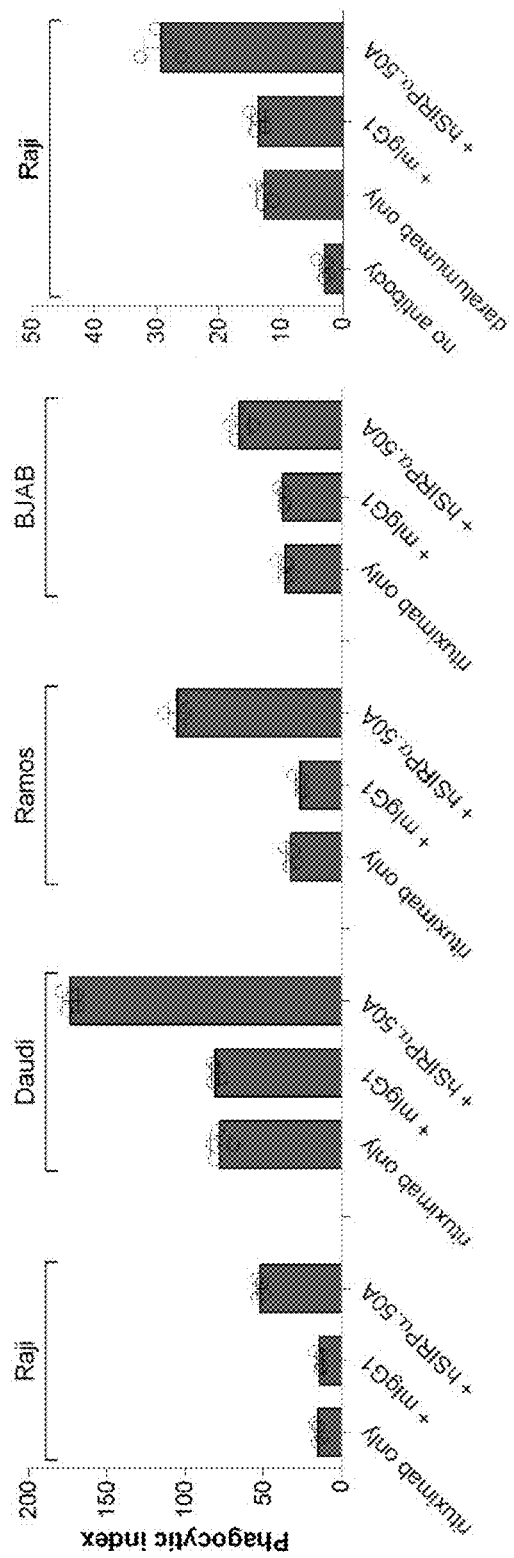
FIG. 7 depicts phagocytosis of tumor cells by human macrophages in the presence of the indicated antibody (rituximab or daratumumab) plus or minus the hSIRPα.50A antibody.

As shown in FIG. 7, hSIRPα.50A enhances rituximab and daratumumab-mediated phagocytosis activity. The phagocytosis of human lymphoma cells was quantified using a phagocytosis index, as follows: (number of tumor cells inside macrophages/number of macrophages)*100; counting at least 200 macrophages per sample.

Example 7: Humanized Antibody Design and CDR Grafting

The mouse hSIRPα.50A antibody was humanized using CDR-grafting technology (see e.g. U.S. Pat. No. 5,225,539 and Williams, D. G. et al., 2010, *Antibody Engineering*, volume 1, Chapter 21).

First, human germline sequences were identified using IgBLAST (Ye J. et al., 2013, Nucleic Acids Res. 41:W34-40). For the hSIRPα.50A VH human germline sequence, V-gene IGHV1/OR15-2*02 was identified (75.2% identity) and for the VL human germline sequence IGKV1-27*01 was identified (74.0% identity). These two germline sequences were used to directly graft the mouse CDRs, resulting in the following two cDNA constructs: SEQ ID NO: 17 (VH) and SEQ ID NO: 25 (VL).

Next, a database was constructed containing all human sequences available in the IMGT database (Lefranc, M.-P. et al., 1999, *Nucleic Acid Res.* 27:209-212) identifying 85,848 individual sequences. These sequences were queried using TBLASTN (2.2.31+) to identify template sequences that demonstrated the highest identify to the framework of hSIRPα.50A VH and VL sequences. Three VH and three VL sequences were identified that demonstrated a similarity score of 75% or higher and that displayed similar CDR lengths, preferably identical to those in hSIRPα.50A VH CDR1, CDR2, CDR3 and VL CDR1, CDR2 and CDR3, respectively.

For the heavy chain, the frameworks encoded by GenBank (Benson, D. A. et al., 2013, Nucleic Acids Res. 41(D1): D36-42) accession #AB066948, AB067235, and U84168 were selected as templates for straight grafting of the hSIRPα.50A VH CDRs, resulting in the following cDNA constructs: SEQ ID NO: 9, 11 and 13, respectively. For the light chain, the frameworks encoded by GenBank accession #JF894288, AB363321, and L12101 were selected as templates for straight grafting of the hSIRPα.50A VL CDRs, resulting in the following cDNA constructs: SEQ ID NO: 19, 21 and 23. Framework and CDR definition were those as described by Kabat et al. ("Sequences of Proteins of Immunological Interest", Kabat, E., et al., US Department of Health and Human Services, (1983)).

To understand the effect of humanized framework residues on the structure of the Fv, a homology model of the mouse hSIRPα.50A Fv was made using the 'Antibody Modeling Cascade' (default parameters) within Discovery Studio 4.5. The homology model was built on basis of PDB ID 1CIC, for the light chain and Fv, and PDB ID 4QOX for the heavy chain. The CDRs were grafted in silico to study residues that are close to any of the CDRs and which might affect the loop conformation, referred as Vernier residues. Residues that might affect the loop conformation, and which are within <5 Å to the CDR surface were identified and substituted with the mouse amino acid at this position. The resulting templates were checked for the presence of post translational modification (PTM) motifs using Discovery Studio 4.5 and where possible (i.e. non-CDR, non-Vernier residues) changed to prevent a PTM. For the heavy chain, removal of the predicted sequence PTM motifs and structural considerations (i.e. rigidity of the backbone) in the hSIRPα.50A VH resulted in the design of one additional construct: SEQ ID NO: 15. For the light chain the PTM removal resulted in the following construct: SEQ ID NO: 27.

CDRs were grafted on each of the identified templates, expressed as a human IgG4 (SEQ ID NO: 65), kappa (SEQ ID NO: 63) antibody cloned in the pcDNA3.1(+) vector (Thermo Fisher Scientific) and for transient transfection in FreeStyle 293-F human embryonic kidney cells (HEK293T/17, ATCC CRL-11268). In each case, an IgG4 version carrying the stabilizing Adair mutation (Angal S. et al., 1993, Mol Immunol. 30: 105-108), where Serine 228 is converted to Proline, was used.

Example 8: Synthesis, Expression and Purification of Humanized Constructs

Plasmids encoding the heavy chain and light chain constructs were mixed in a 1:1 ratio (30 µg in total) and transiently expressed by transfection into FreeStyle 293-F cells using 293fectin transfection reagent (Invitrogen) following the manufacturer's instructions. Supernatants (30 ml) were harvested after 7 days and antibodies were purified using MabSelect Sure Protein A resin according to the manufacturer's instructions (GE Healthcare). Buffer was exchanged for 10 mM Histidine, 100 mM NaCl pH 5.5 buffer using Zeba desalting columns (Thermo Fisher Scientific). The concentration of purified antibodies was determined based on OD280 (Nanodrop ND-1000). Endotoxin level was determined by LAL-test according to the manufacturer's instructions (Lonza).

Example 9: Binding of Humanized SIRPα Antibodies

Binding of the humanized antibodies to hSIRPα was studied in CELISA format. Binding of the hSIRPα antibodies to human SIRPαV1, SIRPαV2, hSIRPβ1, and hSIRPγ was confirmed using CHO-K1 cells that had been transiently transfected with cDNA encoding the full length open reading frame of each of these respective targets subcloned into the pCI-neo vector. CHO-K1.hSIRPαV1, CHO-K1.hSIRPαV2, CHO-K1.hSIRPβ1, and CHO-K1.hSIRPγ cells were seeded in culture medium (DMEM-F12 (Gibco) supplemented with 5% New Born Calf Serum (BioWest) and Pen/Strep (Gibco)) in 96-well flat-bottom tissue culture plates and incubated at 37° C., 5% $CO_2$ and 95% humidity until cell layers were confluent. Subsequently, culture medium was removed and cells were incubated for 1 hour at 37° C., 5% $CO_2$ and 95% humidity with purified hSIRPα antibodies (10 µg/mL and dilutions thereof). Next, cells were washed with PBS-T and incubated for 1 hour at 37° C., 5% $CO_2$ and 95% humidity with goat-anti-human IgG-HRP conjugate (Jackson Immuno Research) or goat-anti-mouse IgG-HRP (Southern Biotech). Subsequently, cells were washed three times with PBS-T and anti-hSIRPα immunoreactivity was visualized with TMB Stabilized Chromogen (Invitrogen). Reactions were stopped with 0.5 M $H_2SO_4$ and absorbances were read at 450 and 610 nm. EC50 values, the concentration at which 50% of the total binding signal is observed, were calculated using GraphPad Prism 6 (GraphPad Software, Inc.). In Table 13 the EC50 values of the humanized hSIRPα antibodies are depicted.

Table 13: Binding of humanized and parental hSIRPα.50A antibodies to CHO-K1.hSIRPαV1, CHO-K1.hSIRPαV2, CHO-K1.hSIRPβ1, and CHO-K1.hSIRPγ cells. EC50 values represent the concentration at which 50% of the total binding signal is observed (average and SD were calculated from values of two independent experiments).

TABLE 13

| Antibody | hSIRPαV1 binding EC50 (nM) | | hSIRPαV2 binding EC50 (nM) | | hSIRPβ1 binding EC50 (nM) | | hSIRPγ binding EC50 (nM) | |
|---|---|---|---|---|---|---|---|---|
| | Average | SD | Average | SD | Average | SD | Average | SD |
| hSIRPα.50H 1L1 | 0.883 | 0.212 | 0.864 | 0.109 | nd | nd | 1.485* | 0.120 |
| hSIRPα.50H 1L2 | 0.781 | 0.104 | 0.816 | 0.161 | nd | nd | 1.259* | 0.155 |
| hSIRPα.50H 1L3 | 1.094 | 0.112 | 1.107 | 0.238 | nd | nd | 2.579* | 0.672 |
| hSIRPα.50H 1L4 | 1.488 | 0.259 | 1.621 | 0.320 | nd | nd | 7.435* | 0.208 |

TABLE 13-continued

| Antibody | hSIRPαV1 binding EC50 (nM) Average | SD | hSIRPαV2 binding EC50 (nM) Average | SD | hSIRPβ1 binding EC50 (nM) Average | SD | hSIRPγ binding EC50 (nM) Average | SD |
|---|---|---|---|---|---|---|---|---|
| hSIRPα.50H 1L5 | 0.962 | 0.235 | 0.848 | 0.239 | nd | nd | 1.013* | 0.115 |
| hSIRPα.50H 3L1 | 1.097 | 0.286 | 1.056 | 0.303 | nd | nd | 1.424* | 0.080 |
| hSIRPα.50H 3L2 | 1.055 | 0.347 | 0.999 | 0.450 | nd | nd | 1.502* | 0.305 |
| hSIRPα.50H 3L3 | 1.159 | 0.417 | 1.160 | 0.429 | nd | nd | 2.471* | 0.530 |
| hSIRPα.50H 3L4 | 1.261 | 0.317 | 1.520 | 0.333 | nd | nd | 5.175* | 0.210 |
| hSIRPα.50H 3L5 | 0.878 | 0.097 | 0.868 | 0.190 | nd | nd | 1.199* | 0.120 |
| hSIRPα.50H 4L1 | 0.683 | 0.027 | 0.681 | 0.156 | nd | nd | 0.950* | 0.171 |
| hSIRPα.50H 4L2 | 0.737 | 0.110 | 0.651 | 0.147 | nd | nd | 0.871* | 0.062 |
| hSIRPα.50H 4L3 | 0.933 | 0.078 | 0.898 | 0.133 | nd | nd | 1.596* | 0.144 |
| hSIRPα.50H 4L4 | 1.197 | 0.175 | 1.240 | 0.238 | nd | nd | 1.980* | 0.681 |
| hSIRPα.50H 4L5 | 0.701 | 0.136 | 0.661 | 0.161 | nd | nd | 0.808* | 0.038 |
| hSIRPα.50H 5L1 | 0.731 | 0.039 | 0.709 | 0.063 | nd | nd | 1.028* | 0.087 |
| hSIRPα.50H 5L2 | 0.675 | 0.086 | 0.572 | 0.023 | nd | nd | 0.822* | 0.046 |
| hSIRPα.50H 5L3 | 1.029 | 0.084 | 0.796 | 0.004 | nd | nd | 1.612* | 0.247 |
| hSIRPα.50H 5L4 | 1.169 | 0.197 | 1.115 | 0.060 | nd | nd | 4.028* | 0.342 |
| hSIRPα.50H 5L5 | 0.681 | 0.066 | 0.611 | 0.030 | nd | nd | 0.868* | 0.028 |
| hSIRPα.50A | 1.365 | 0.164 | 1.296 | 0.186 | nd | nd | 1.249* | 0.179 |

Note that variants with the H2 heavy chain could not be expressed in FreeStyle 293-F cells; values indicated with * were extrapolated; nd, not detected Binding of the parental and humanized hSIRPα antibodies to hSIRPγ was further assessed using NK-92MI cells (ATCC CRL-2408), an interleukin-2 (IL-2) independent natural killer cell line derived from the NK-92 cell line. NK-92MI cells were seeded in 96-well round bottomed tissue culture plates and incubated for 30 minutes with the humanized hSIRPα.50A antibody variants (100 µg/mL and dilutions thereof) in PBS/1% BSA at 4° C. Next, cells were washed three times with PBS/1% BSA and incubated for 30 minutes at 4° C. with a FITC-labeled mouse-anti-human IgG4 (Abcam) or donkey-anti-mouse IgG (Jackson Immuno Research) detection antibody in PBS/1% BSA. After this labeling procedure, cells were washed two times, resuspended in PBS/1% BSA and analysed by flow cytometry on the FACSCanto II (BD Biosciences). Data were processed and analysed with FlowJo V10 software (FlowJo, LLC).

Example 10: Blockade of hCD47 Binding to hSIRPα by Humanized hSIRPα.50A Antibodies hCD47 blockade was assessed by flow cytometry for the full panel of humanized hSIRPα.50A antibodies. To this end, HEK293 cells (ATCC CRL-1573) were transiently transfected using Lipofectamine 2000 (Invitrogen) with the pCI-neo vector encoding the full length open reading frame of human SIRPαV1. The transfected cells were cultured at 37° C., 5% $CO_2$ and 95% humidity in medium (DMEM-F12 (Gibco) with 10% Fetal Bovine Serum (Gibco) and Pen/Strep (Gibco)) until confluent. Subsequently, cells were dissociated and seeded in 96-well round bottomed tissue culture plates and incubated for 30 minutes with the humanized hSIRPα.50A antibody variants (100 µg/mL and dilutions thereof) in PBS/1% BSA at 4° C. Next, cells were washed three times with PBS/1% BSA and incubated with recombinant hCD47/Fc-protein (ModiQuest; SEQ ID NO: 42) for 30 minutes at 4° C. Afterwards, cells were washed three times with PBS/1% BSA and incubated for 30 minutes at 4° C. with a mouse-anti-human IgG1 Hinge-FITC (Southern Biotech) detection antibody. After this labeling procedure, cells were washed two times, resuspended in PBS/1% BSA and analysed by flow cytometry on the FACSCanto II (BD Biosciences). Data were processed and analysed with FlowJo V10 software (FlowJo, LLC) and plotted using GraphPad Prism 6 (GraphPad Software, Inc.) (FIG. 8).

Figure 8:
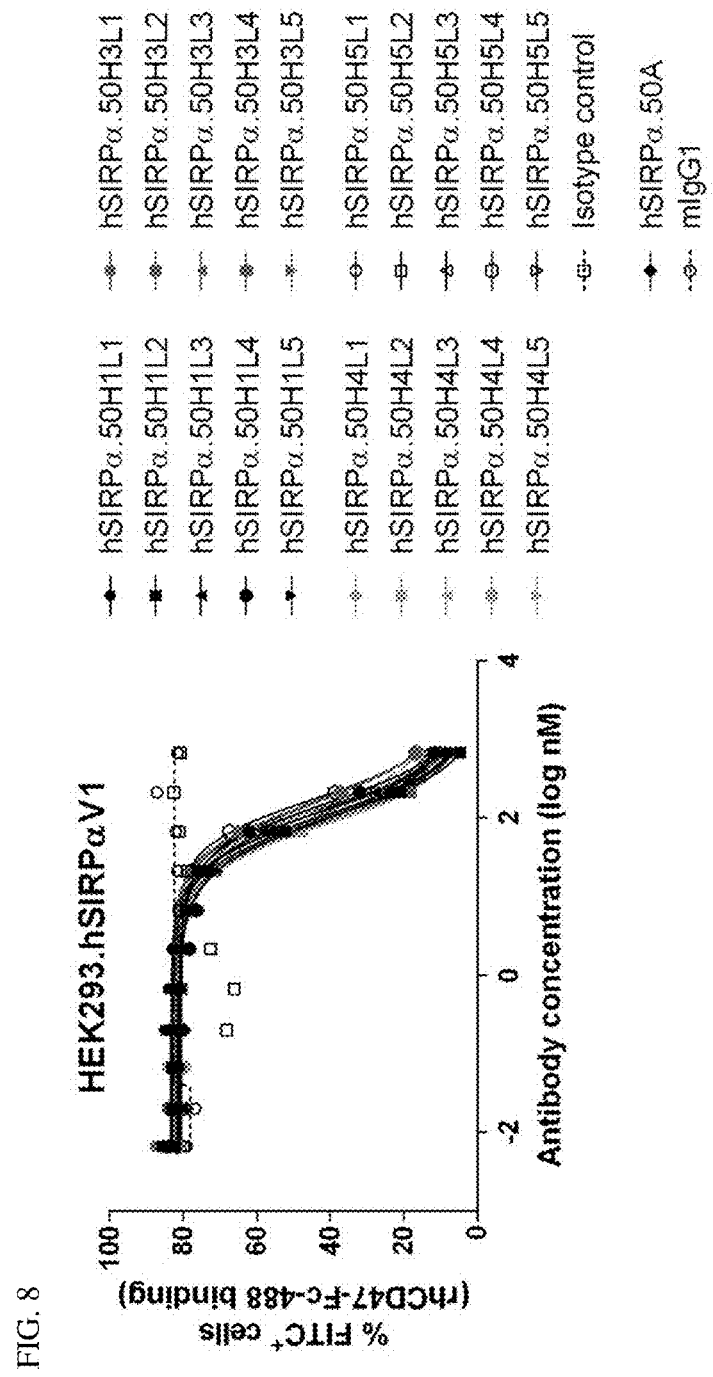
FIG. 8 depicts blocking of the hSIRPα/hCD47 interaction by mouse hSIRPα.50A and humanized hSIRPα.50A antibodies to hSIRPα.
Figure 9:
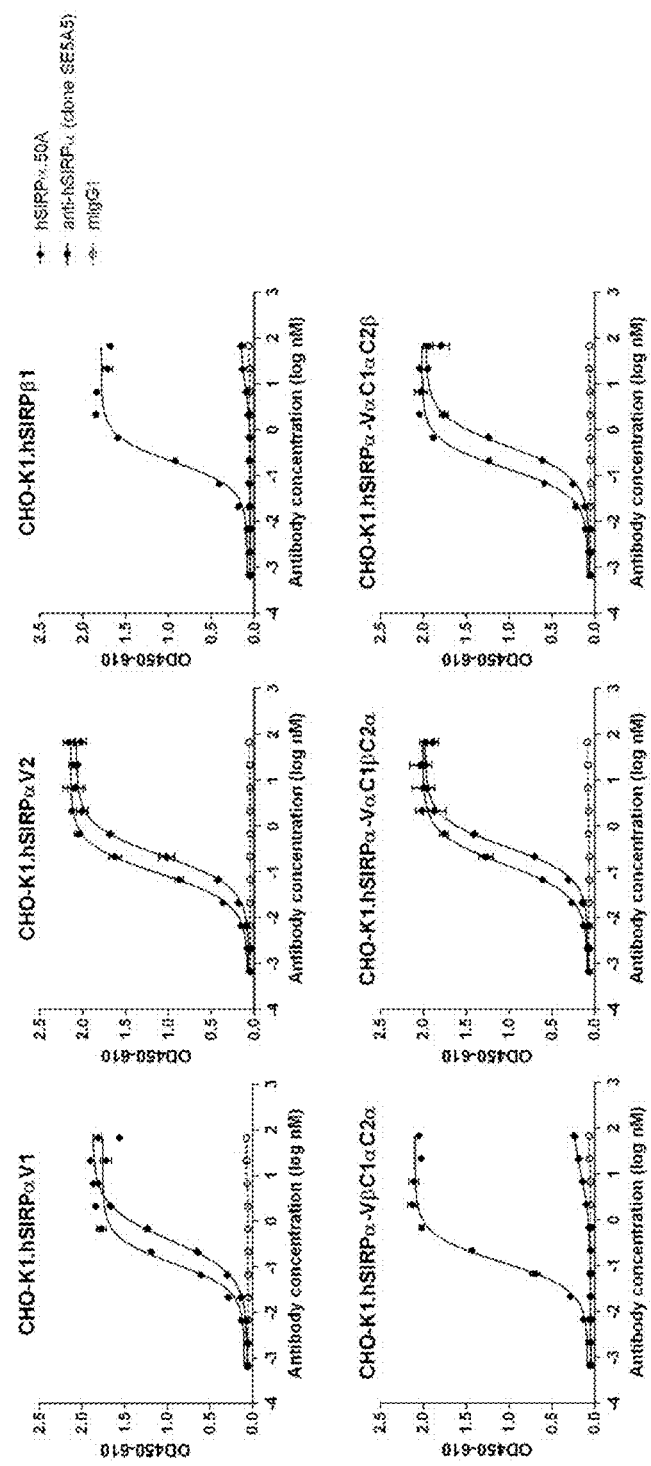
FIG. 9 depicts hSIRPα.50A antibody binding to hSIRPαV1, hSIRPαV2, hSIRPβ1, hSIRPα-VβC1αC2α, hSIRPα-VαC1βC2α, and hSIRPα-VαC1αC2β.

As depicted in FIG. 8, binding of recombinant hCD47 fused to an Fc domain of human IgG1 was monitored in the presence of increasing amounts of the humanized hSIRPα.50A antibody variants. All antibody variants blocked the hSIRPα/hCD47 interaction.

Example 11: Binding Domain of hSIRPα.50A

To identify the binding region of hSIRPα.50A, several SIRPα exchange-mutants were designed based on the human SIRPαV1 and hSIRPβ1 amino acid sequence. Based on the fold of SIRPα, the extracellular region can be subdivided into three separate domains: the Ig-like (immunoglobulin-like) V-type (IgV), Ig-like C1-type (IgC1), and Ig-like C2-type (IgC2) domain. The IgV domain is also known as the ligand-binding N-terminal domain of SIRPα (which binds to CD47). The human SIRPαV1/β1 mutants were designed on the basis of the full length hSIRPαV1 sequence (SEQ ID NO: 33) and each individual Ig-like domain was substituted for the equivalent domain of human SIRPβ1 (SEQ ID NO: 37). The cDNAs encoding the constructs, hSIRPα-VβC1αC2α (SEQ ID NO: 55), hSIRPα-VαC1βC2α (SEQ ID NO: 57), and hSIRPα-VαC1αC2β (SEQ ID NO: 59) were synthesized (GeneArt) and subcloned into the pCI-neo vector. Binding of hSIRPα.50A to the exchange mutants was tested using CELISA. To this end, CHO-K1 cells were transiently transfected, using Lipofectamine 2000, with the pCI-neo vectors encoding hSIRPαV1, hSIRPαV2, hSIRPβ1, hSIRPα-VβC1αC2α, hSIRPα-VαC1βC2α, and hSIRPα-VαC1αC2β, respectively. The transfected cells were cultured at 37° C., 5% $CO_2$ and 95% humidity in medium (DMEM-F12 (Gibco) with 5% New Born Calf serum (Biowest) and Pen/Strep (Gibco)) until confluent. Subsequently, cells were trypsinized and seeded in 96-well flat-bottom tissue culture plates and cultured at 37° C., 5% $CO_2$ and 95% humidity in culture medium until confluent. Then, culture medium was removed and cells were incubated for 1 hour at 37° C., 5% $CO_2$ and 95% humidity with hSIRPα.50A and anti-hSIRPα clone SE5A5 antibodies. Next, cells were washed with PBS-T and incubated for 1 hour at 37° C., 5% $CO_2$ and 95% humidity with goat-anti-mouse IgG-HRP conjugate (Southern Biotech). After that, cells were washed three times with PBS-T and anti-hSIRPα immunoreactivity was visualized with TMB Stabilized Chromogen (Invitrogen). Reactions were stopped with 0.5 M $H_2SO_4$ and absorbances were read at 450 and 610 nm.

The antibody of the present invention demonstrated loss of binding to the hSIRPα-VβC1αC2α mutant, indicating that hSIRPα.50A binds to the IgV domain of hSIRPα (FIG.

9; Table 14). EC50 values represent the concentration at which 50% of the total binding signal is observed (average and SD were calculated from values of two independent experiments).

TABLE 14

|  |  | Antibody | |
|---|---|---|---|
|  |  | hSIRPα.50A | anti-hSIRPα (clone SE5A5) |
| hSIRPαV1 | EC50 (nM) | 0.321 | 0.117 |
|  | SD | 0.018 | 0.001 |
| hSIRPαV2 | EC50 (nM) | 0.215 | 0.084 |
|  | SD | 0.012 | 0.012 |
| hSIRPβ1 | EC50 (nM) | nd | 0.180 |
|  | SD | nd | 0.025 |
| hSIRPα-VβC1αC2α | EC50 (nM) | nd | 0.121 |
|  | SD | nd | 0.003 |
| hSIRPα-VαC1βC2α | EC50 (nM) | 0.345 | 0.135 |
|  | SD | 0.008 | 0.013 |
| hSIRPα-VαC1αC2β | EC50 (nM) | 0.408 | 0.127 |
|  | SD | 0.039 | 0.028 |

Figure 10B:
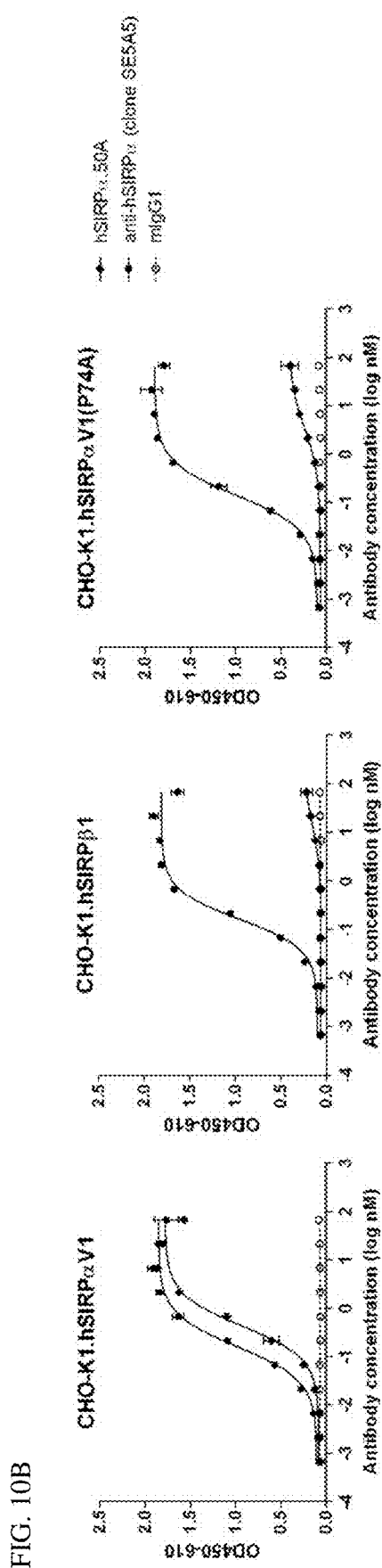
FIG. 10B depicts loss of hSIRPα.50A antibody binding to hSIRPαV1(P74A).

To pinpoint the amino acids for interaction of hSIRPα.50A with the IgV domain, several point mutants of hSIRPαV1 were generated based on single amino acid differences between hSIRPαV1/V2 and hSIRPβ1. FIG. 10A shows an alignment of the hSIRPα and hSIRPβ1 IgV domain. Amino acids in the hSIRPα IgV domain that are altered in hSIRPβ1 were mutated by using the QuikChange II Site-Directed Mutagenesis Kit (Stratagene) and the full length hSIRPαV1 sequence (SEQ ID NO: 33) as donor cDNA. Binding of hSIRPα.50A to hSIRPαV1 point mutants was tested using CELISA. To this end, CHO-K1 cells were transiently transfected, using Lipofectamine 2000, with cDNA encoding the full length open reading frame of hSIRPαV1 and mutants thereof, and hSIRPβ1 subcloned into the pCI-neo vector. Transfected cells were seeded in culture medium (DMEM-F12 (Gibco) supplemented with 5% New Born Calf Serum (BioWest) and Pen/Strep (Gibco)) in 96-well flat-bottom tissue culture plates and incubated at 37° C., 5% CO$_2$ and 95% humidity for 24 hours. Subsequently, culture medium was removed and cells were incubated for 1 hour at 37° C., 5% CO$_2$ and 95% humidity with purified hSIRPα antibodies (used at 10 µg/mL and dilutions thereof). Next, cells were washed with PBS-T and incubated for 1 hour at 37° C., 5% CO$_2$ and 95% humidity with goat-anti-mouse IgG-HRP (Southern Biotech). Subsequently, cells were washed three times with PBS-T and immunoreactivity against hSIRPαV1, hSIRPαV1 mutants, and hSIRPβ1 was visualized with TMB Stabilized Chromogen (Invitrogen). Reactions were stopped with 0.5 M H$_2$SO$_4$ and absorbances were read at 450 and 610 nm. EC50 values, the concentration at which 50% of the total binding signal is observed, were calculated using GraphPad Prism 6 (Graph-Pad Software, Inc.) (average and SD were calculated from values of two independent experiments). As shown in FIG. 10B and the following Table 15, the Proline at position 74 (P74) constitutes a crucial amino acid for the specific binding of hSIRPα.50A to hSIRPαV1. Expression of hSIRPαV1(P74A) (SEQ ID NO: 61), where P74 is converted to Alanine, on CHO-K1 cells results in loss of hSIRPα.50A antibody binding. This proline is absent in the IgV domain sequence of hSIRPβ1.

TABLE 15

| | hSIRPαV1 binding EC50 (nM) | | hSIRPβ1 binding EC50 (nM) | | hSIRPαV1(P74A) binding EC50 (nM) | |
|---|---|---|---|---|---|---|
| Antibody | Average | SD | Average | SD | Average | SD |
| hSIRPα.50A | 0.535 | 0.152 | nd | nd | nd | nd |
| anti-hSIRPα (clone SE5A5) | 0.164 | 0.008 | 0.156 | 0.009 | 0.150 | 0.013 |

Example 12: Characterization of hSIRPα.40A and hSIRPα.50A Antibodies

Figure 11:
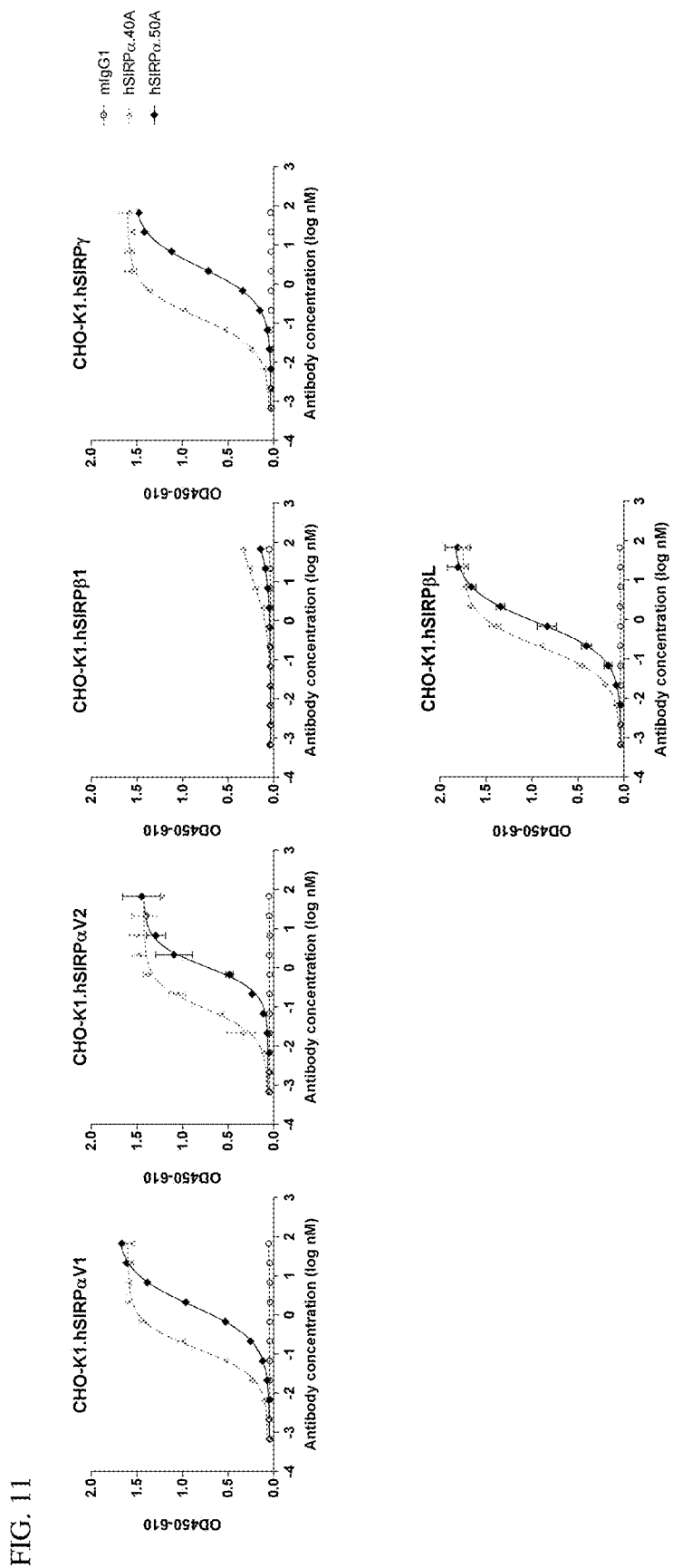
FIG. 11 depicts binding of hSIRPα.40A and hSIRPα.50A antibodies to hSIRPαV1, hSIRPαV2, hSIRPβ1, hSIRPβL, and hSIRPγ.

The binding specificity of antibodies hSIRPα.40A and hSIRPα.50A to hSIRPα were compared in a CELISA format. In short, CHO-K1 cells were transiently transfected with hSIRPαV1, hSIRPαV2, hSIRPβ1, hSIRPβL, and hSIRPγ cDNAs. Subsequently, hSIRPα binding was assessed by CELISA using CHO-K1.hSIRPαV1, CHO-K1.hSIRPαV2, CHO-K1.hSIRPβ1, CHO-K1.hSIRPβL, and CHO-K1.hSIRPγ cells. Detection of bound antibody was done with goat-anti-mouse IgG-HRP (Southern Biotech). As shown in FIG. 11 and the following Table 16, hSIRPα.40A and hSIRPα.50A antibodies bind to hSIRPαV1, hSIRPαV2, hSIRPβL, and hSIRPγ, but do not display detectable hSIRPβ1 binding. EC50 values represent the concentration at which 50% of the total binding signal is observed (average and SD were calculated from values of two independent experiments).

TABLE 16

| | hSIRPαV1 binding EC50 (nM) | | hSIRPαV2 binding EC50 (nM) | | hSIRPβ1 binding EC50 (nM) | | hSIRPγ binding EC50 (nM) | | hSIRPβL binding EC50 (nM) | |
|---|---|---|---|---|---|---|---|---|---|---|
| Antibody | Average | SD | Average | SD | Average | SD | Average | SD | Average | SD |
| hSIRPα.40A | 0.109 | 0.036 | 0.088 | 0.002 | nd | nd | 0.099 | 0.055 | 0.141 | 0.078 |
| hSIRPα.50A | 1.428 | 0.371 | 1.156 | 0.127 | nd | nd | 1.990 | 0.827 | 0.632 | 0.277 | nd, not detected

Figure 12:
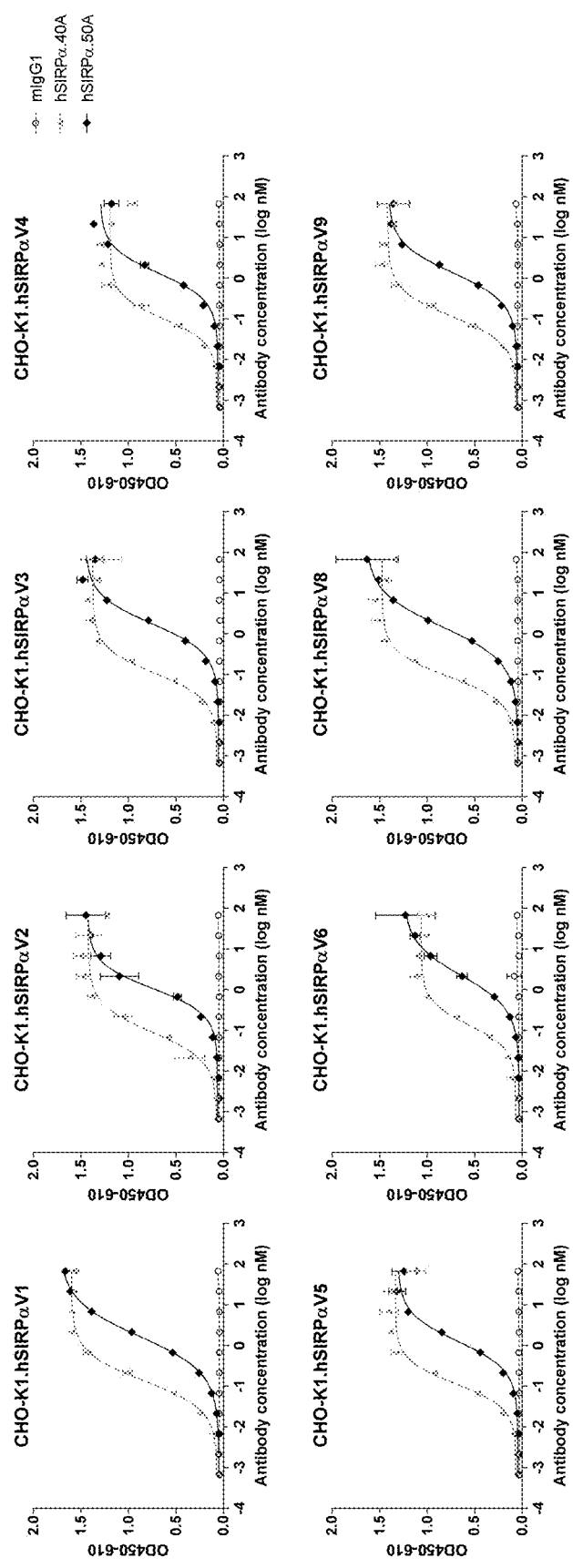
FIG. 12 depicts binding of hSIRPα.40A and hSIRPα.50A antibodies to hSIRPαV1, hSIRPαV2, hSIRPαV3, hSIRPαV4, hSIRPαV5, hSIRPαV6, hSIRPαV8, and hSIRPαV9.

In addition, the specificity of hSIRPα.40A for all known of hSIRPα alleles (allelic variants as described by Takenaka et al., Nat Immunol. 8:1313-1323 (2007) was further investigated by CELISA using the same strategy as above. To this end, hSIRPα.40A binding was assessed using CHO-K1 cells that were transiently transfected with cDNAs encoding full length hSIRPαV1, hSIRPαV2, hSIRPαV3 (NA07056_V3) (SEQ ID NO: 44), hSIRPαV4 (NA11832_V4) (SEQ ID NO: 46), hSIRPαV5 (NA18502_V5) (SEQ ID NO: 48), hSIRPαV6 (NA18507_V6) (SEQ ID NO: 50), hSIRPαV8 (NA18570_V8) (SEQ ID NO: 52), and hSIRPαV9 (NA18943_V9) (SEQ ID NO: 54). FIG. 12 and the following Table 17 demonstrates the reactivity of antibody clone hSIRPα.40A for each of these hSIRPα alleles. EC50 values represent the concentration at which 50% of the total binding signal is observed (average and SD were calculated from values of two independent experiments).

TABLE 17

|  | Antibody | |
| --- | --- | --- |
|  | hSIRPα.40A | hSIRPα.50A |
| hSIRPαV1 EC50 (nM) | 0.134 | 1.690 |
| hSIRPαV2 EC50 (nM) | 0.089 | 1.066 |
| hSIRPαV3 EC50 (nM) | 0.107 | 1.767 |
| hSIRPαV4 EC50 (nM) | 0.100 | 1.297 |
| hSIRPαV5 EC50 (nM) | 0.115 | 1.260 |
| hSIRPαV6 EC50 (nM) | 0.136 | 2.219 |
| hSIRPαV8 EC50 (nM) | 0.089 | 1.508 |
| hSIRPαV9 EC50 (nM) | 0.115 | 1.367 |

Example 13: hCD47 Blocking Ability of hSIRPα.40A

The hSIRPα.40A antibody was analyzed by flow cytometry for its ability to block recombinant hCD47/Fc-protein (R&D Systems, Cat.#4670-CD-050; SEQ ID NO: 109) binding to cell surface expressed hSIRPα. For this purpose, THP-1 (ATCC TIB-202) and U-937 (ATCC CRL-1593.2) monocyte cell lines were used as the source of hSIRPα in the assay. THP-1 and U-937 cells were seeded in 96-well round bottomed tissue culture plates and incubated for 45 minutes with FcR Blocking Reagent (Miltenyi Biotec) and hSIRPα.40A antibody (100 μg/mL and dilutions thereof) in PBS/1% BSA at 4° C. Next, cells were washed three times with PBS/1% BSA and incubated with DyLight 488-labeled recombinant hCD47/Fc-protein for 30 minutes at 4° C. After this labeling procedure, cells were washed two times, resuspended in PBS/1% BSA containing 0.1 μg/mL DAPI (BioLegend), and analysed by flow cytometry on the FACSCanto II (BD Biosciences). Data were processed and analysed with FlowJo V10 software (FlowJo, LLC).

Figure 13:
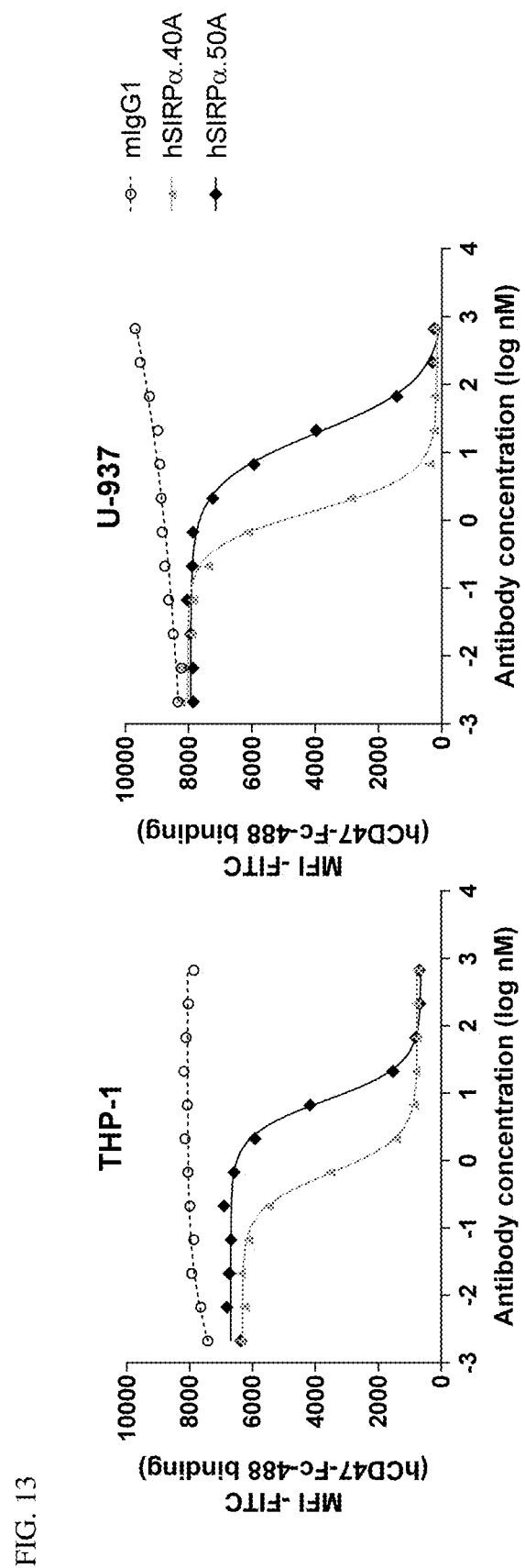
FIG. 13 depicts the ability of hSIRPα.40A and hSIRPα.50A antibodies to block recombinant hCD47/Fc-protein binding to cell surface expressed hSIRPα.

As depicted in FIG. 13 and the following Table 18, binding of recombinant hCD47 fused to an Fc domain of human IgG1 was monitored in the presence of increasing amounts of the hSIRPα.40A antibody. Antibody hSIRPα.40A blocked the hSIRPα/hCD47 interaction, using the flow cytometry-based method described above. IC50 values for the blockade of hCD47 were calculated from this data. IC50 values represent the concentration at which half of the inhibition is observed.

TABLE 18

| Antibody | THP-1 IC50 (nM) | U-937 IC50 (nM) |
| --- | --- | --- |
| hSIRPα.40A | 0.646 | 1.344 |
| hSIRPα.50A | 7.833 | 19.501 |

Next, the binding of hSIRPα.40A to hSIRPα expressed on primary human CD14+ monocytes was investigated. In addition, the ability of hSIRPα.40A to block the interaction between hSIRPα and recombinant hCD47/Fc-protein was assessed. For this purpose, CD14+ monocytes were isolated from Ficoll-purified human peripheral blood mononuclear cells (PBMCs) using RosetteSep human monocyte enrichment cocktail (Stemcell). The percentage of monocytes present after the enrichment was determined by flow cytometry on the FACSVerse (BD Biosciences) based on CD14 staining using an APC-Cy7-conjugated mouse-anti-human CD14 detection antibody (BD Biosciences). Subsequently, CD14+ enriched PBMCs were seeded in 96-well round bottomed tissue culture plates and incubated for 40 minutes with FcR Blocking Reagent (Miltenyi Biotec) containing hSIRPα.40A antibody (20 μg/mL and dilutions thereof) in PBS/1% BSA at 4° C. Next, cells were washed three times with PBS/1% BSA and incubated with an Alexa Fluor 647-labeled goat-anti-mouse IgG (Invitrogen) detection antibody in PBS/1% BSA for 40 minutes at 4° C. After this labeling procedure, cells were washed two times, resuspended in PBS/1% BSA containing 0.1 μg/mL DAPI (BioLegend), and analysed by flow cytometry on the FACSVerse (BD Biosciences). Data were processed and analysed with FlowJo V10 software (FlowJo, LLC).

FIGS. 14A and B shows that hSIRPα.40A binds to primary human CD14+ enriched monocytes. EC50 values represent the concentration at which 50% of the total binding signal is observed. To assess the blocking ability of hSIRPα.40A, CD14+ enriched monocytes cells were seeded in 96-well round bottomed tissue culture plates and incubated for 45 minutes with FcR Blocking Reagent (Miltenyi Biotec) and hSIRPα.40A antibody (20 μg/mL and dilutions thereof) in PBS/1% BSA at 4° C. Thereafter, cells were washed three times with PBS/1% BSA and incubated with 10 μg/mL DyLight 488-labeled recombinant hCD47/Fc-protein for 45 minutes at 4° C. After this labeling procedure, cells were washed two times, resuspended in PBS/1% BSA containing 0.1 μg/mL DAPI (BioLegend), and analysed by flow cytometry on the FACSVerse (BD Biosciences). Data were processed and analysed with FlowJo V10 software (FlowJo, LLC). FIGS. 14 C and D demonstrates the ability of antibody hSIRPα.40A to block the hSIRPα/hCD47 interaction. IC50 values for the blockade of hCD47 were calculated from this data. IC50 values represent the concentration at which half of the inhibition is observed.

Example 14: Functionality of hSIRPα.40A mAb in the Human Granulocyte Phagocytosis Assay To confirm the functionality of hSIRPα.40A in primary immune cells, granulocytes (e.g. effector cells) were isolated from healthy human donor EDTA blood. First, the EDTA blood of each donor was pooled and centrifuged at 300 g for 6 minutes at 20° C. Next, plasma was removed by aspiration, and the remaining blood cells were gently resuspended. Cells were recovered in red blood cell (RBC) lysis buffer (155 mM NH4Cl; 10 mM KHCO3) and incubated for 10 minutes on ice. Next, cells were centrifuged at 300 g for 7 minutes. Supernatants containing lysed RBCs were removed by aspiration, and the remaining blood cells were gently resuspended in RBC lysis buffer and kept on ice for 1 minute. RBC lysis was neutralized by adding assay medium (IMDM (Gibco) supplemented with 10% Fetal Bovine Serum (Gibco) and Pen/Strep (Gibco)). Blood cells were centrifuged at 300 g for 6 minutes and supernatants were removed by aspiration to remove remaining RBCs as much as possible. Subsequently, erythrocyte-lysed blood cells were resuspended in assay medium containing 10 ng/mL IFNγ and cells were incubated for 1 hour at 37° C., 5% $CO_2$ and 95% humidity. Non-adherent blood cells containing human granulocytes were collected by mild washing of the tissue culture plate with assay medium (monocytes are depleted due to adherence to the plastic surface). The percentage of granulocytes present in the cell suspension was determined by flow cytometry on the FACSCanto II (BD Biosciences) based on high forward scatter (FSC) and side scatter (SSC). Binding of hSIRPα.40A to human granulocytes was assessed by incubating the cells for 30 minutes at 4° C. with hSIRPα.40A antibody (25 μg/mL and dilutions thereof) in PBS/1% BSA containing 10% autologous serum (PBS/1% BSA/10% serum). Next, cells were washed three times with PBS/1% BSA/10% serum and incubated for 30 minutes at 4° C. with a FITC-labeled goat-anti-mouse Ig (BD Biosciences) detection antibody. After this labeling procedure, cells were washed two times, resuspended in PBS/1% BSA/10% serum and analysed by flow cytometry on the FACSCanto II (BD Biosciences). Data were processed and analysed with FlowJo V10 software (FlowJo, LLC). FIG. 15A and the following Table 19 shows that hSIRPα.40A binds to primary human granulocytes. EC50 values represent the concentration at which 50% of the total binding signal is observed.

TABLE 19

| Antibody | Donor 1 EC50 (nM) |
|---|---|
| hSIRPα.40A | 1.227 |
| hSIRPα.50A | 4.298 |

Next, Ramos (ECACC 85030802) target cells were fluorescently labeled with cell proliferation dye eFluor450 (eBioscience). Labeling was performed according to manufacturer's instructions. Labeled target cells were co-cultured for 2-3 hours at 37° C., 5% $CO_2$ and 95% humidity with isolated primary human granulocytes in a 1:1 ratio ($7.5*10^4$ cells of each target and effector per well of a 96-well round bottomed tissue culture plate) in the presence of 0.1 μg/mL rituximab (anti-hCD20). In addition, cells were co-cultured with 0.1 μg/mL rituximab in presence of 10 μg/mL hSIRPα.40A. Phagocytosis was assayed by determining the percentage of granulocytes positive for eFluor450 using flow cytometry on the FACSCanto II (BD Biosciences). Data were processed and analysed with FlowJo V10 software (FlowJo, LLC).

Figure 15B:
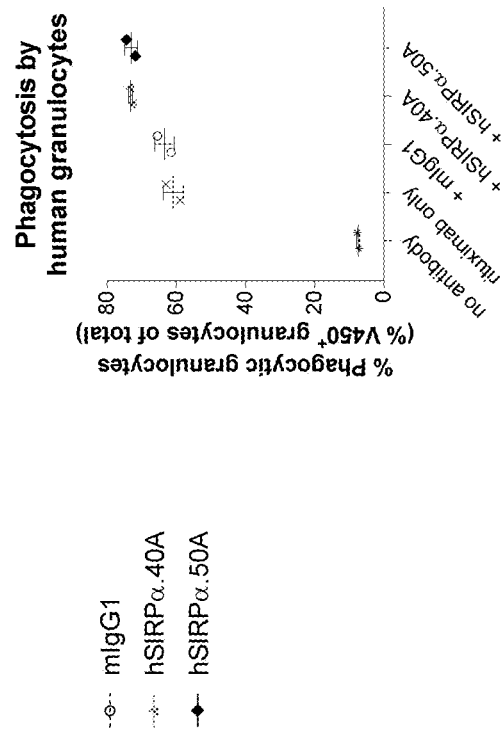
FIG. 15B depicts phagocytosis of Ramos cells by primary human granulocytes in the presence of rituximab plus or minus the hSIRPα.40A and hSIRPα.50A antibodies.
Figure 15A:
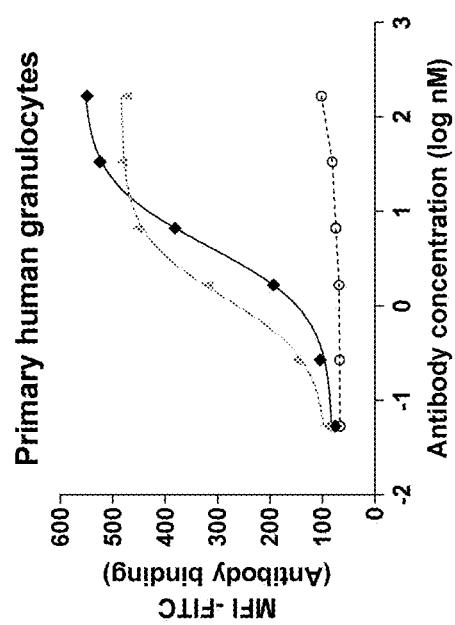
FIG. 15A depicts binding of hSIRPα.40A and hSIRPα.50A antibodies to primary human granulocytes.

Compared to the mouse IgG1 isotype control, hSIRPα.40A potently enhances tumor cell phagocytosis induced by rituximab (FIG. 15B).

Example 15: Functionality of hSIRPα.40A mAb in the Human Macrophage Phagocytosis Assay Blockade of CD47 by hSIRPα.40A enhances the phagocytosis of human lymphoma cells tumor cells by human macrophages. Human macrophages were generated by first enriching CD14+ monocytes from Ficoll-purified human peripheral blood mononuclear cells (PBMCs) using RosetteSep human monocyte enrichment cocktail (Stemcell). Monocytes were seeded into CellCarrier 96-well flat-bottom microplates (Perkin Elmer) and cultured in macrophage medium (IMDM (Gibco) supplemented with 8.5% Fetal Bovine Serum (Gibco) and Pen/Strep (Gibco)) containing 50 ng/mL human monocyte colony stimulating factor (M-CSF) for 7 days at 37° C., 5% $CO_2$ and 95% humidity to promote differentiation into macrophages. These monocyte-derived macrophages (MDMs) become adherent allowing other cells to be washed away. Human Raji lymphoma cells were counted and labeled with cell proliferation dye eFluor450 (eBioscience) following manufacturer's instructions. After labeling, the lymphoma cells were mixed with assay medium (RPMI (Gibco) supplemented with 10% Fetal Bovine Serum (Gibco) and Pen/Strep (Gibco)) containing 100 μg/mL anti-hSIRPα antibodies and dilutions thereof, the respective isotype control antibody, and 1 μg/mL rituximab (anti-hCD20). The lymphoma cells were then added to the individual wells containing MDMs at a ratio of 2.5:1 tumor cells per phagocyte, mixed and incubated at 37° C., 5% $CO_2$ and 95% humidity for 2 hours. After the incubation, the wells were washed with PBS to remove most of the non-phagocytosed tumor cells, and cells were fixed with 2% formaldehyde for 10 min at RT. The wells were then washed and maintained in PBS/3% BSA in dark at 4° C. overnight. Lymphoma cells present in the wells were stained with biotin-conjugated anti-human CD19 clone HIB 19 (eBioscience) for 1 hour at RT, and subsequently were counterstained with Alexa Fluor 488-conjugated streptavidin (Thermo Fisher Scientific) for 1 hour at RT. Next, nuclei were stained with DRAQ5 (Thermo Fisher Scientific) for 10 minutes at RT, mixture was removed, and PBS was added to each well. Cells were analysed with the Operetta automated fluorescence microscope (Perkin Elmer). Data were processed and analysed with Columbus V2.6 software.

Figure 16:
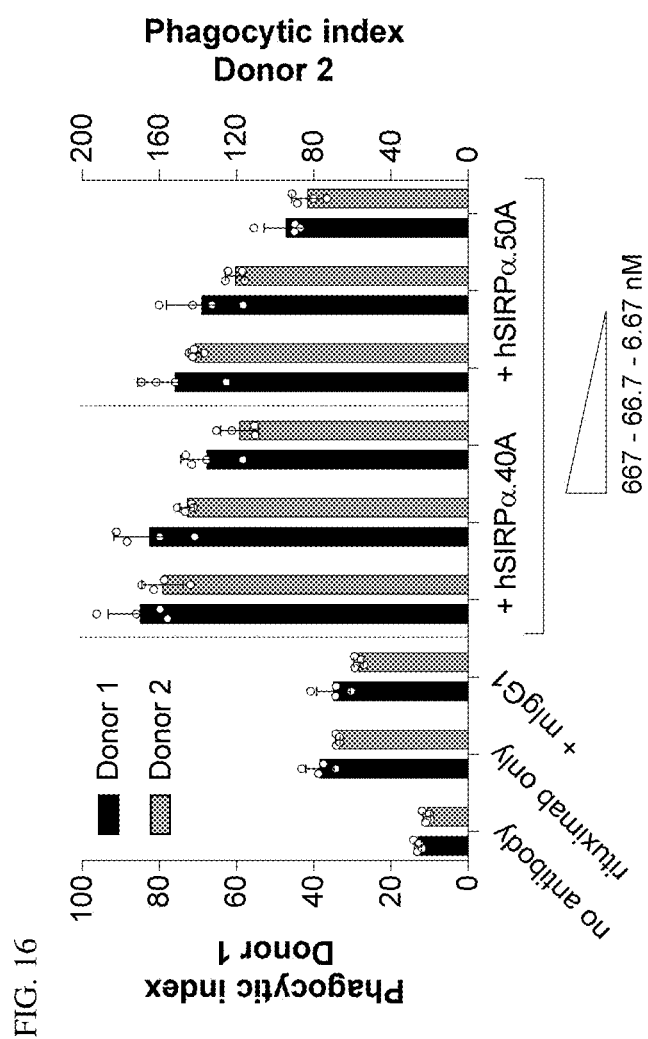
FIG. 16 depicts enhancement of rituximab-induced Raji cell phagocytosis by hSIRPα.40A and hSIRPα.50A antibodies.

As shown in FIG. 16, hSIRPα.40A enhances rituximab-mediated phagocytosis activity. The phagocytosis of human lymphoma cells was quantified using a phagocytosis index, as follows: (number of tumor cells inside macrophages/number of macrophages)*100; counting at least 200 macrophages per sample.

Example 16: Humanized Antibody Design and CDR Grafting

The mouse hSIRPα.40A antibody was humanized using CDR-grafting technology (see e.g. U.S. Pat. No. 5,225,539 and Williams, D. G. et al., 2010, Antibody Engineering, volume 1, Chapter 21). First, human germline sequences were identified using IgBLAST (Ye J. et al., Nucleic Acids Res. 41:W34-40 (2013). For the hSIRPα.40A VH human germline sequence, V-gene IGHV1-46*01 was identified (62.2% identity) and for the VL human germline sequence IGKV1-39*01 was identified (68.4% identity). These two germline sequences were used as template to graft the mouse CDRs, resulting in the following two cDNA constructs: SEQ ID NO: 87 (VH) and SEQ ID NO: 99 (VL).

Next, a database was constructed containing all human sequences available in the IMGT database (Lefranc, M.-P. et al., Nucleic Acid Res. 27:209-212 (1999)) identifying 85,848 individual sequences. These sequences were queried using TBLASTN (2.2.31+) to identify template sequences that demonstrated the highest identify to the framework of hSIRPα.40A VH and VL sequences. Four VH and four VL sequences were identified that demonstrated a similarity score of 80% or higher and that displayed similar CDR lengths, preferably identical to those in hSIRPα.40A VH CDR1, CDR2, CDR3 and VL CDR1, CDR2 and CDR3, respectively.

For the heavy chain, the frameworks encoded by GenBank (Benson, D. A. et al., Nucleic Acids Res. 41(D1):D36-42 (2013)) accession #L39130, DJ031925, DJ326840, and EF177968 were selected as templates for grafting of the hSIRPα.40A VH CDRs, resulting in the following cDNA constructs: SEQ ID NO: 77, 79, 81 and 83, respectively. For the light chain, the frameworks encoded by GenBank accession #AY731031, DQ840993, AY942002 and DQ535171 were selected as templates for straight grafting of the hSIRPα.40A VL CDRs, resulting in the following cDNA constructs: SEQ ID NO: 89, 91, 93 and 95. Additionally, a database was constructed containing all humanized antibody sequences available in the public domain, identifying 300 sequences. These sequences were queried using BLASTP (2.2.31+) to identify template sequences that demonstrated the highest identify to the framework of hSIRPα.40A VH and VL sequences. For the heavy chain, the framework of Gemtuzumab was selected as template, for grafting of the hSIRPα.40A VH CDRs, resulting in the following cDNA construct: SEQ ID NO: 85. For the light chain, the framework of Alacizumab was selected as template, for grafting of the hSIRPα.40A VL CDRs, resulting in the following cDNA construct: SEQ ID NO: 97

Framework and CDR definition were those as described by Kabat et al. ("Sequences of Proteins of Immunological Interest", Kabat, E., et al., US Department of Health and Human Services, (1983)).

To study the effect of humanized framework residues on the structure of the Fv, a homology model of the mouse hSIRPα.40A Fv was made using the 'Antibody Modeling Cascade' (default parameters) within Discovery Studio 4.5. The homology model was built on basis of PDB ID 3UMT, for the light chain, PDB ID 1EHL for the heavy chain, and PDB ID 3BGF for the Fv. The CDRs were grafted in silico to study residues that are close to any of the CDRs and which might affect the loop conformation, referred to as Vernier residues. Residues that might affect the loop conformation, and which are within <5A to the CDR surface were identified and substituted with the mouse amino acid at this position. The resulting templates were checked for the presence of post translational modification (PTM) motifs using Discovery Studio 4.5 and where possible (i.e. non-CDR, non-Vernier residues) changed to prevent a PTM. The VH CDR2 contained a glycosylation site that was removed by an aspargine to serine mutation.

CDRs were grafted on each of the identified templates, expressed as a human IgG2 (SEQ ID NO: 68), kappa (SEQ ID NO: 64) antibody cloned in the pcDNA3.1(+) vector (Thermo Fisher Scientific) and for transient transfection in FreeStyle 293-F human embryonic kidney cells (HEK293T/17, ATCC CRL-11268).

Example 17: Synthesis, Expression and Purification of Chimeric and Humanized Constructs Plasmids encoding the heavy chain and light chain humanized constructs were mixed in a 1:1 ratio (30 μg in total) and transiently expressed by transfection into Free-Style 293-F cells using 293fectin transfection reagent (Invitrogen) following the manufacturer's instructions. Supernatants (30 ml) were harvested after 7 days, filtered over a 0.22 m filter, and antibodies were purified using MabSelect Sure Protein A resin according to the manufacturer's instructions (GE Healthcare). Buffer was exchanged for 10 mM Histidine, 100 mM NaCl pH 5.5 buffer using Zeba desalting columns (Thermo Fisher Scientific). The concentration of purified antibodies was determined based on OD280 (Nanodrop ND-1000). Endotoxin level was determined by LAL-test according to the manufacturer's instructions (Lonza).

Example 18: Binding of Humanized SIRPα Antibodies

Figure 17:
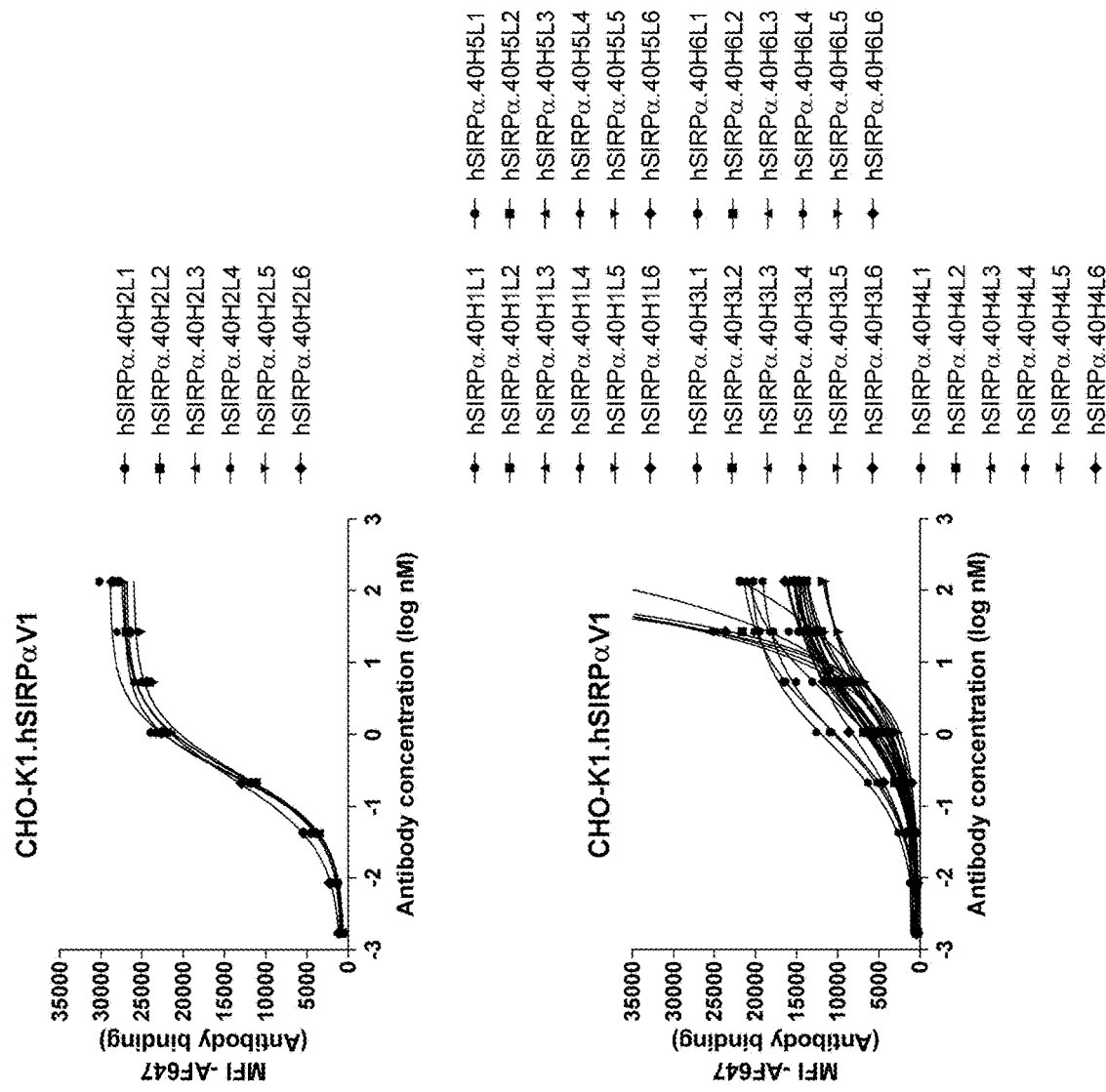
FIG. 17 depicts binding of mouse hSIRPα.40A and humanized hSIRPα.40A antibodies to hSIRPα.

Binding of the parental and humanized antibodies to hSIRPα was assessed by flow cytometry using the CHO-K1.hSIRPαV1 stable cell line. CHO-K1.hSIRPαV1 cells were seeded in 96-well round bottomed tissue culture plates and incubated for 40 minutes with the humanized hSIRPα.40A antibody variants (20 μg/mL and dilutions thereof) in PBS/1% BSA at 4° C. Next, cells were washed three times with PBS/1% BSA and incubated for 40 minutes at 4° C. with either an Alexa Fluor 647-labeled goat-anti-mouse IgG (Invitrogen), or an Alexa Fluor 647-labeled donkey-anti-human IgG (Jackson Immuno Research) detection antibody in PBS/1% BSA. After this labeling procedure, cells were washed two times, resuspended in PBS/1% BSA, containing 0.1 μg/mL DAPI (BioLegend), and analysed by flow cytometry on the FACSVerse (BD Biosciences). Data were processed and analysed with FlowJo V10 software (FlowJo, LLC). EC50 values, the concentration at which 50% of the total binding signal is observed, were calculated using GraphPad Prism 6 (GraphPad Software, Inc.) (FIG. 17 and Table 20).

TABLE 20

| Antibody | hSIRPαV1 EC50 (nM) |
| --- | --- |
| hSIRPα.40A | 0.022 |
| hSIRPα.40H1L1 | nd |
| hSIRPα.40H1L2 | nd |
| hSIRPα.40H1L3 | nd |
| hSIRPα.40H1L4 | nd |
| hSIRPα.40H1L5 | nd |
| hSIRPα.40H1L6 | nd |
| hSIRPα.40H2L1 | 0.264 |
| hSIRPα.40H2L2 | 0.298 |
| hSIRPα.40H2L3 | 0.300 |
| hSIRPα.40H2L4 | 0.315 |
| hSIRPα.40H2L5 | 0.284 |
| hSIRPα.40H2L6 | 0.251 |
| hSIRPα.40H3L1 | 1.644 |
| hSIRPα.40H3L2 | 1.404 |
| hSIRPα.40H3L3 | 1.501 |
| hSIRPα.40H3L4 | 0.693 |
| hSIRPα.40H3L5 | 2.302 |
| hSIRPα.40H3L6 | 0.833 |
| hSIRPα.40H4L1 | 3.308 |
| hSIRPα.40H4L2 | 3.360 |
| hSIRPα.40H4L3 | 3.072 |
| hSIRPα.40H4L4 | 3.471 |
| hSIRPα.40H4L5 | 4.828 |
| hSIRPα.40H4L6 | 3.028 |
| hSIRPα.40H5L1 | 2.011 |
| hSIRPα.40H5L2 | 1.919 |
| hSIRPα.40H5L3 | 2.268 |
| hSIRPα.40H5L4 | 0.869 |
| hSIRPα.40H5L5 | 2.954 |
| hSIRPα.40H5L6 | 2.197 |
| hSIRPα.40H6L1 | 2.349 |
| hSIRPα.40H6L2 | 3.002 |
| hSIRPα.40H6L3 | 3.014 |
| hSIRPα.40H6L4 | 1.279 |
| hSIRPα.40H6L5 | 3.785 |
| hSIRPα.40H6L6 | 2.677 | nd, not detected

Example 19: Blockade of hCD47 Binding to hSIRPα by Humanized hSIRPα.40A Antibodies hCD47 blockade was assessed by flow cytometry for the full panel of humanized hSIRPα.40A antibodies. To this end, the U-937 (ATCC CRL-1593.2) monocyte cell line was used as the source of hSIRPα in the assay. U-937 cells were seeded in 96-well round bottomed tissue culture plates and incubated for 45 minutes with FcR Blocking Reagent (Miltenyi Biotec) and the parental or humanized hSIRPα.40A antibody variants (20 μg/mL and dilutions thereof) in PBS/1% BSA at 4° C. Next, cells were washed three times with PBS/1% BSA and incubated with 10 μg/mL DyLight 488-labeled recombinant hCD47/Fc-protein for 30 minutes at 4° C. After this labeling procedure, cells were washed two times, resuspended in PBS/1% BSA containing 0.1 µg/mL DAPI (BioLegend), and analysed by flow cytometry on the FACSVerse (BD Biosciences). Data were processed and analysed with FlowJo V10 software (FlowJo, LLC) and plotted using GraphPad Prism 6 (GraphPad Software, Inc.).

Figure 18:
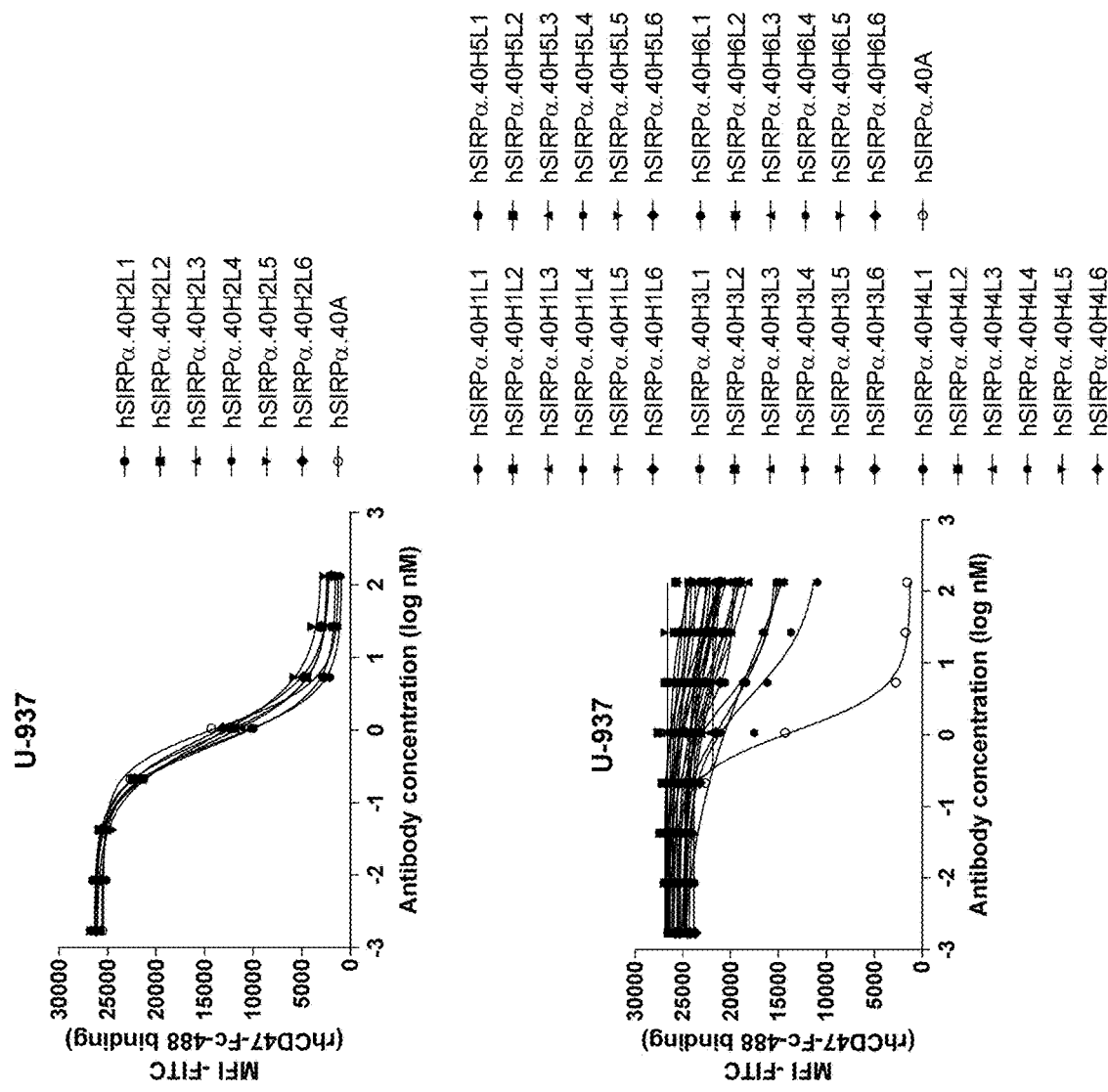
FIG. 18 depicts the blockade of hCD47 binding to hSIRPα in the presence of humanized hSIRPα.40A antibody variants.

As depicted in FIG. 18 and the following Table 21, binding of recombinant hCD47 fused to an Fc domain of human IgG1 was monitored in the presence of increasing amounts of the humanized hSIRPα.40A antibody variants. Humanized hSIRPα.40A blocked the hSIRPα/hCD47 interaction, using the flow cytometry-based method described above. IC50 values for the blockade of hCD47 were calculated from this data. IC50 values represent the concentration at which half of the inhibition is observed.

TABLE 21

| Antibody | U-937 IC50 (nM) |
|---|---|
| hSIRPα.40A | 1.122 |
| hSIRPα.40H1L1 | nd |
| hSIRPα.40H1L2 | nd |
| hSIRPα.40H1L3 | nd |
| hSIRPα.40H1L4 | nd |
| hSIRPα.40H1L5 | nd |
| hSIRPα.40H1L6 | nd |
| hSIRPα.40H2L1 | 0.638 |
| hSIRPα.40H2L2 | 0.773 |
| hSIRPα.40H2L3 | 0.685 |
| hSIRPα.40H2L4 | 0.718 |
| hSIRPα.40H2L5 | 0.745 |
| hSIRPα.40H2L6 | 0.901 |
| hSIRPα.40H3L1 | 0.980* |
| hSIRPα.40H3L2 | nd |
| hSIRPα.40H3L3 | 2.625* |
| hSIRPα.40H3L4 | 1.784* |
| hSIRPα.40H3L5 | 2.435* |
| hSIRPα.40H3L6 | 97.762* |
| hSIRPα.40H4L1 | 10.002* |
| hSIRPα.40H4L2 | 7.579* |
| hSIRPα.40H4L3 | 75.422* |
| hSIRPα.40H4L4 | 3.153* |
| hSIRPα.40H4L5 | 5.171* |
| hSIRPα.40H4L6 | 3.512* |
| hSIRPα.40H5L1 | 34.977* |
| hSIRPα.40H5L2 | nd |
| hSIRPα.40H5L3 | nd |
| hSIRPα.40H5L4 | 10.772* |
| hSIRPα.40H5L5 | nd |
| hSIRPα.40H5L6 | 0.247* |
| hSIRPα.40H6L1 | 2.391* |
| hSIRPα.40H6L2 | 20.427* |
| hSIRPα.40H6L3 | 9.208* |
| hSIRPα.40H6L4 | 3.797* |
| hSIRPα.40H6L5 | 20.421* |
| hSIRPα.40H6L6 | 9.750* |

Values indicated with * were extrapolated;
nd, not detected

Example 20: Binding Domain of hSIRPα.40A

To identify the binding region of hSIRPα.40A, several SIRPβ1 exchange-mutants were designed based on the human SIRPβ1 and SIRPγ amino acid sequences. Based on the fold of SIRPα/β1/γ, the extracellular region can be subdivided into three separate domains: the Ig-like (immunoglobulin-like) V-type (IgV), Ig-like C1-type (IgC1), and Ig-like C2-type (IgC2) domain. The IgV domain is also known as the ligand-binding N-terminal domain of SIRPα and SIRPγ (which binds to CD47). The human SIRPβ1/γ mutants were designed based on the full length hSIRPβ1 sequence (SEQ ID NO: 38) and each individual Ig-like domain was substituted for the equivalent domain of human SIRPγ (SEQ ID NO: 40). The cDNAs encoding the constructs, hSIRP-VγC1βC2β(SEQ ID NO: 110), hSIRP-VβC1γC2β(SEQ ID NO: 112), and hSIRP-VβC1βC2γ (SEQ ID NO: 114) were synthesized (GeneArt) and subcloned into the pCI-neo vector. Binding of hSIRPα.40A to the exchange mutants was tested using CELISA. To this end, CHO-K1 cells were transiently transfected, using Lipofectamine 2000, with the pCI-neo vectors encoding hSIRPαV1, hSIRPαV2, hSIRPβ1, hSIRP-VγC1βC2β, hSIRP-VβC1γC2β, and hSIRP-VβC1βC2γ, respectively. The transfected cells were cultured at 37° C., 5% $CO_2$ and 95% humidity in medium (DMEM-F12 (Gibco) with 5% New Born Calf serum (Biowest) and Pen/Strep (Gibco)) until confluent. Subsequently, cells were trypsinized and seeded in 96-well flat-bottom tissue culture plates and cultured at 37° C., 5% $CO_2$ and 95% humidity in culture medium until confluent. Then, culture medium was removed and cells were incubated for 1 hour at 37° C., 5% $CO_2$ and 95% humidity with hSIRPα.40A, hSIRPα.50A, and anti-hSIRPα clone SE5A5 antibodies. Next, cells were washed with PBS-T and incubated for 1 hour at 37° C., 5% $CO_2$ and 95% humidity with goat-anti-mouse IgG-HRP conjugate (Southern Biotech). After that, cells were washed three times with PBS-T and anti-hSIRPα immunoreactivity was visualized with TMB Stabilized Chromogen (Invitrogen). Reactions were stopped with 0.5 M $H_2SO_4$ and absorbances were read at 450 and 610 nm.

Figure 19:
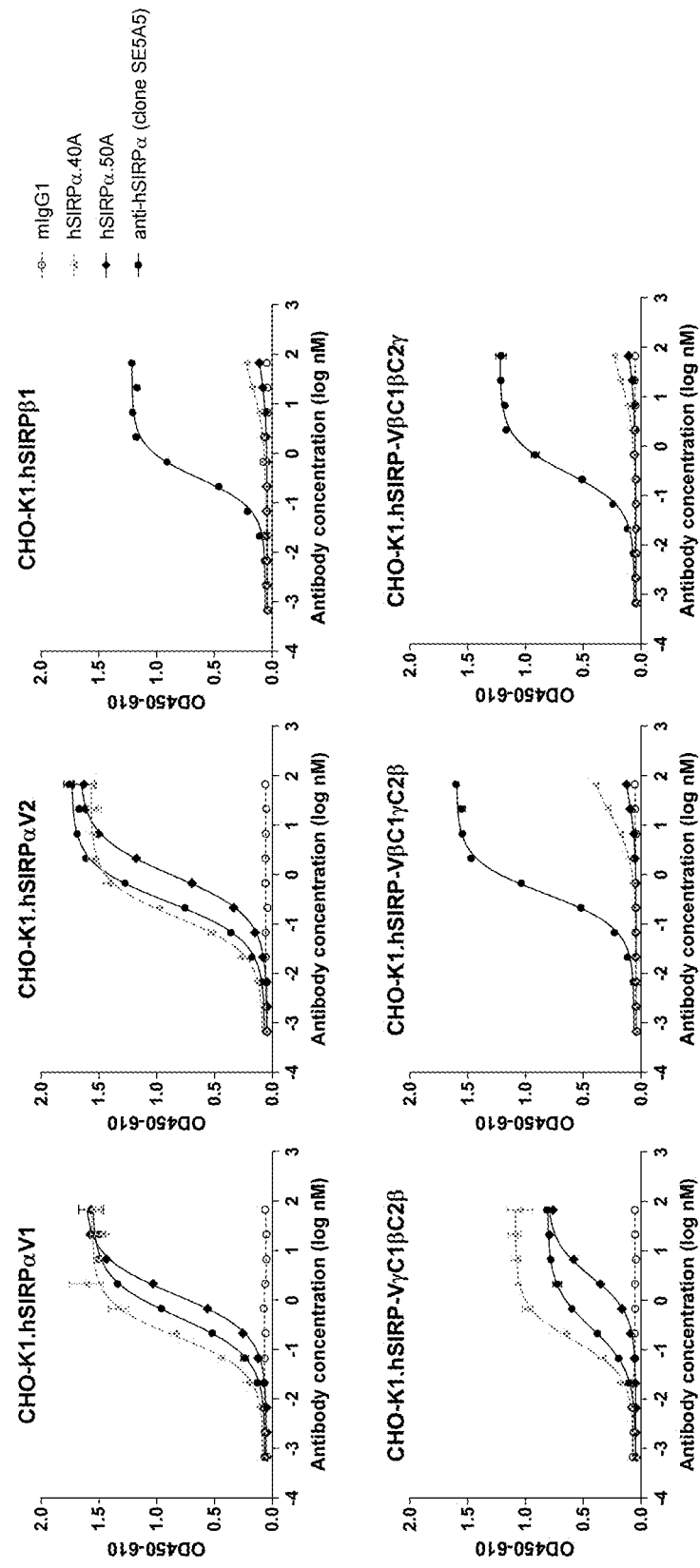
FIG. 19 depicts binding of hSIRPα.40A and hSIRPα.50A antibodies to hSIRPαV1, hSIRPαV2, hSIRPβ1, hSIRP-VγC1βC2β, hSIRP-VβC1γC2β, and hSIRP-VβC1βC2γ.

The antibody of the present invention demonstrated gain of binding to the hSIRP-VγC1βC2β mutant, indicating that hSIRPα.40A binds to the IgV domain of hSIRPα and hSIRPγ (FIG. 19 and Table 22). EC50 values represent the concentration at which 50% of the total binding signal is observed (average and SD were calculated from values of two independent experiments).

TABLE 22

| | | Antibody | | |
|---|---|---|---|---|
| | | hSIRPα.40A | hSIRPα.50A | anti-hSIRPα (clone SE5A5) |
| hSIRPαV1 | EC50 (nM) | 0.133 | 0.968 | 0.350 |
| | SD | 0.065 | 0.432 | 0.136 |
| hSIRPαV2 | EC50 (nM) | 0.101 | 0.821 | 0.224 |
| | SD | 0.051 | 0.183 | 0.076 |
| hSIRPβ1 | EC50 (nM) | nd | nd | 0.249 |
| | SD | nd | nd | 0.091 |
| hSIRP-VγC1βC2β | EC50 (nM) | 0.123 | 2.524 | 0.287 |
| | SD | 0.040 | 0.609 | 0.026 |
| hSIRP-VβC1γC2β | EC50 (nM) | nd | nd | 0.309 |
| | SD | nd | nd | 0.140 |
| hSIRP-VβC1βC2γ | EC50 (nM) | nd | nd | 0.231 |
| | SD | nd | nd | 0.079 | nd, not detected

To pinpoint the amino acids for interaction of hSIRPα.40A with the IgV domain, several point mutants of hSIRPαV1 were generated based on single amino acid differences between hSIRPαV1/V2 and hSIRPβ1. The following sequence alignment shows an alignment of the hSIRPα and hSIRPβ1 IgV domain.

Sequence Alignment of the IgV Domain:

```
                                                      P74
hSIRPαV1    EEELQVIQPDKSVLVAAGETATLRCTATSLIPVGPIQWFRGAGPGRELIYNQKEGHFPRV
hSIRPαV2    EEELQVIQPDKSVSVAAGESAILHCTVTSLIPVGPIQWFRGAGPARELIYNQKEGHFPRV
hSIRPβ1     EDELQVIQPEKSVSVAAGESATLRCAMTSLIPVGPIMWFRGAGAGRELIYNQKEGHFPRV
            *:*****:* *****:* *:*: ******* **.************* hSIRPαV1    TTVSDLTKRNNMDFSIRIGNITPADAGTYYCVKFRKGSPDDVEFKSG  (SEQ ID NO: 133)
hSIRPαV2    TTVSESTKRENMDFSISISNITPADAGTYYCVKFRKGSPD-TEFKSG  (SEQ ID NO: 134)
hSIRPβ1     TTVSELTKRNNLDFSISISNITPADAGTYYCVKFRKGSPDDVEFKSG  (SEQ ID NO: 135)
            ****: ***.*:**** *.********************** .*****
```

Amino acids in the hSIRPα IgV domain that are altered in hSIRPβ1 were mutated by using the QuikChange II Site-Directed Mutagenesis Kit (Stratagene) and the full length hSIRPαV1 sequence (SEQ ID NO: 33) as donor cDNA. Binding of hSIRPα.40A to hSIRPαV1 point mutants was tested using CELISA. To this end, CHO-K1 cells were transiently transfected, using Lipofectamine 2000, with cDNA encoding the full length open reading frame of hSIRPαV1 and mutants thereof, and hSIRPβ1 subcloned into the pCI-neo vector. Transfected cells were seeded in culture medium (DMEM-F12 (Gibco) supplemented with 5% New Born Calf Serum (BioWest) and Pen/Strep (Gibco)) in 96-well flat-bottom tissue culture plates and incubated at 37° C., 5% $CO_2$ and 95% humidity for 24 hours. Subsequently, culture medium was removed and cells were incubated for 1 hour at 37° C., 5% $CO_2$ and 95% humidity with purified hSIRPα antibodies (used at 10 µg/mL and dilutions thereof). Next, cells were washed with PBS-T and incubated for 1 hour at 37° C., 5% $CO_2$ and 95% humidity with goat-anti-mouse IgG-HRP (Southern Biotech). Subsequently, cells were washed three times with PBS-T and immunoreactivity against hSIRPαV1, hSIRPαV1 mutants, and hSIRPβ1 was visualized with TMB Stabilized Chromogen (Invitrogen). Reactions were stopped with 0.5 M $H_2SO_4$ and absorbances were read at 450 and 610 nm. EC50 values, the concentration at which 50% of the total binding signal is observed, were calculated using GraphPad Prism 6 (GraphPad Software, Inc.) (average and SD were calculated from values of two independent experiments).

Figure 20:
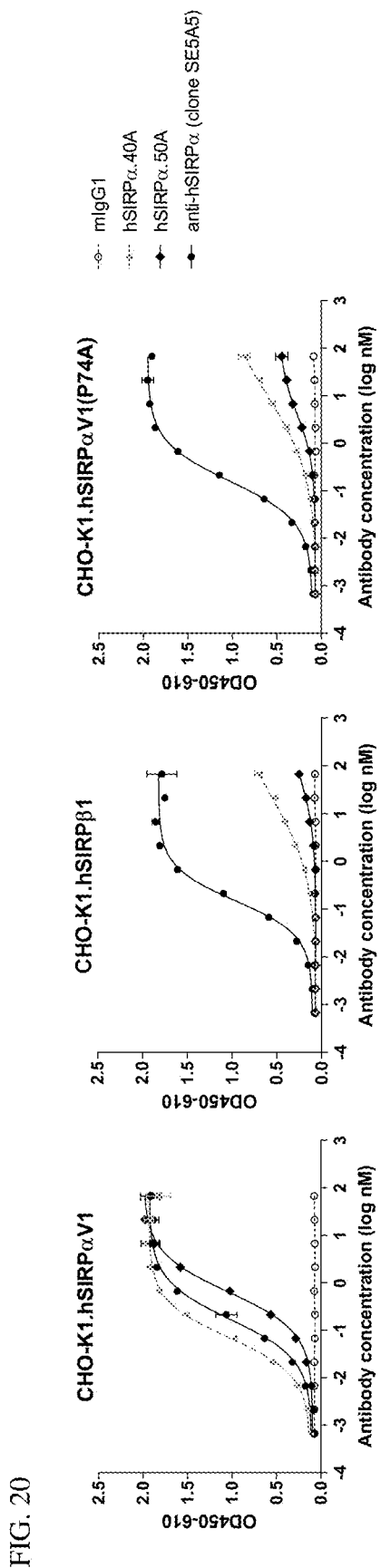
FIG. 20 depicts loss of hSIRPα.40A and hSIRPα.50A antibody binding to hSIRPαV1(P74A).

As shown in FIG. 20 and the following Table 23, the Proline at position 74 (P74) constitutes a crucial amino acid for the specific binding of hSIRPα.40A to hSIRPαV1. Expression of hSIRPαV1(P74A) (SEQ ID NO: 61), where P74 is converted to Alanine, on CHO-K1 cells results in loss of hSIRPα.40A antibody binding. This proline is not present in the IgV domain sequence of hSIRPβ1, and could play a role in the correct conformation of the IgV domain.

TABLE 23

| Antibody | hSIRPαV1 binding EC50 (nM) | | hSIRPβ1 binding EC50 (nM) | | hSIRPαV1(P74A) binding EC50 (nM) | |
|---|---|---|---|---|---|---|
| | Average | SD | Average | SD | Average | SD |
| hSIRPα.40A | 0.065 | 0.006 | nd | nd | nd | nd |
| hSIRPα.50A | 0.534 | 0.152 | nd | nd | nd | nd |
| anti-hSIRPα (clone SE5A5) | 0.163 | 0.008 | 0.156 | 0.009 | 0.149 | 0.013 | nd, not detected

Example 21: Functionality of Chimeric hSIRPα.40A mAb Variants in the Human Macrophage Phagocytosis Assay The functionality of hSIRPα.40A variable domains, grafted on different Fc constant domains, was assessed by an in vitro phagocytosis assay using human macrophages. Experimental conditions for the human macrophage phagocytosis assay were similar as explained in Example 15 above. Labelled Raji lymphoma cells were mixed with assay medium containing either 10 µg/mL or 1 µg/mL chimeric hSIRPα.40A antibody variants and 1 µg/mL rituximab and then added to MDMs at a ratio of 2.5:1 tumor cells per phagocyte. Cells were incubated at 37° C., 5% $CO_2$ and 95% humidity for 2 hours.

Analysis was performed with the Operetta automated fluorescence microscope (Perkin Elmer) and data were processed and analysed with Columbus V2.6 software. The phagocytosis of human lymphoma cells was quantified using a phagocytosis index, as follows: (number of tumor cells inside macrophages/number of macrophages)*100; counting at least 200 macrophages per sample.

Figure 21:
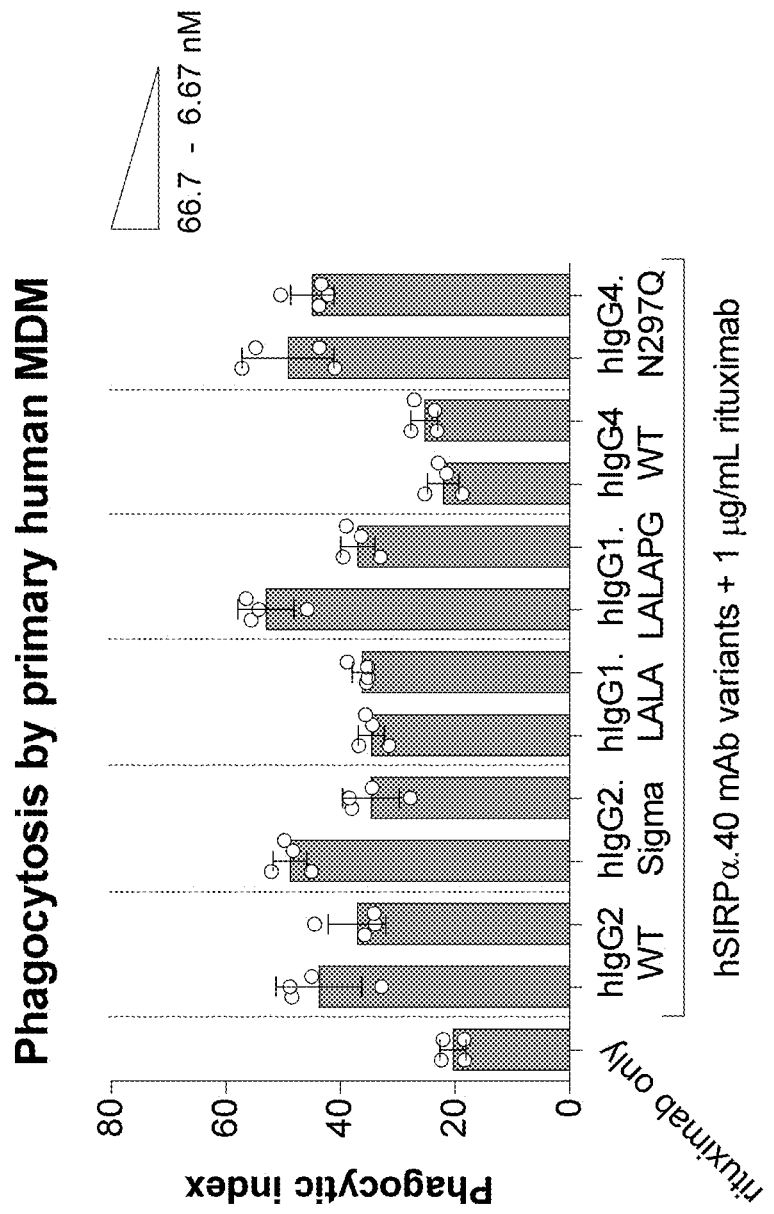
FIG. 21 depicts the ability of chimeric hSIRPα.40A antibody variants to affect rituximab-mediated phagocytosis.

As shown in FIG. 21, the wild-type (WT) chimeric hSIRPα.40A.hIgG4 antibody does not enhance rituximab-mediated phagocytosis, whereas inert chimeric hSIRPα.40A.hIgG1 (SEQ ID NO: 119) antibody variants containing N297Q (SEQ ID NO: 126), L234A.L235A (LALA) (SEQ ID NO: 123), or L234A.L235A.P329G (LA-LAPG) (SEQ ID NO: 125) mutations enhance rituximab-mediated phagocytosis activity in a concentration-dependent manner. Likewise, hSIRPα.40A.hIgG2 and the inert chimeric hSIRPα.40A.hIgG2 antibody variant containing V234A.G237A.P238S.H268A.V309L.A330S.P331S (Sigma) (SEQ ID NO: 122) mutations enhance rituximab-mediated phagocytosis activity in a concentration-dependent manner.

Example 22: Functionality of Humanized hSIRPα.40A mAb Variants in the Human Macrophage Phagocytosis Assay The functionality of a selected set of the humanized hSIRPα.40A antibody variants was assessed by an in vitro phagocytosis assay using human macrophages. Experimental conditions for the human macrophage phagocytosis assay were similar as explained in Example 6.

Figure 22:
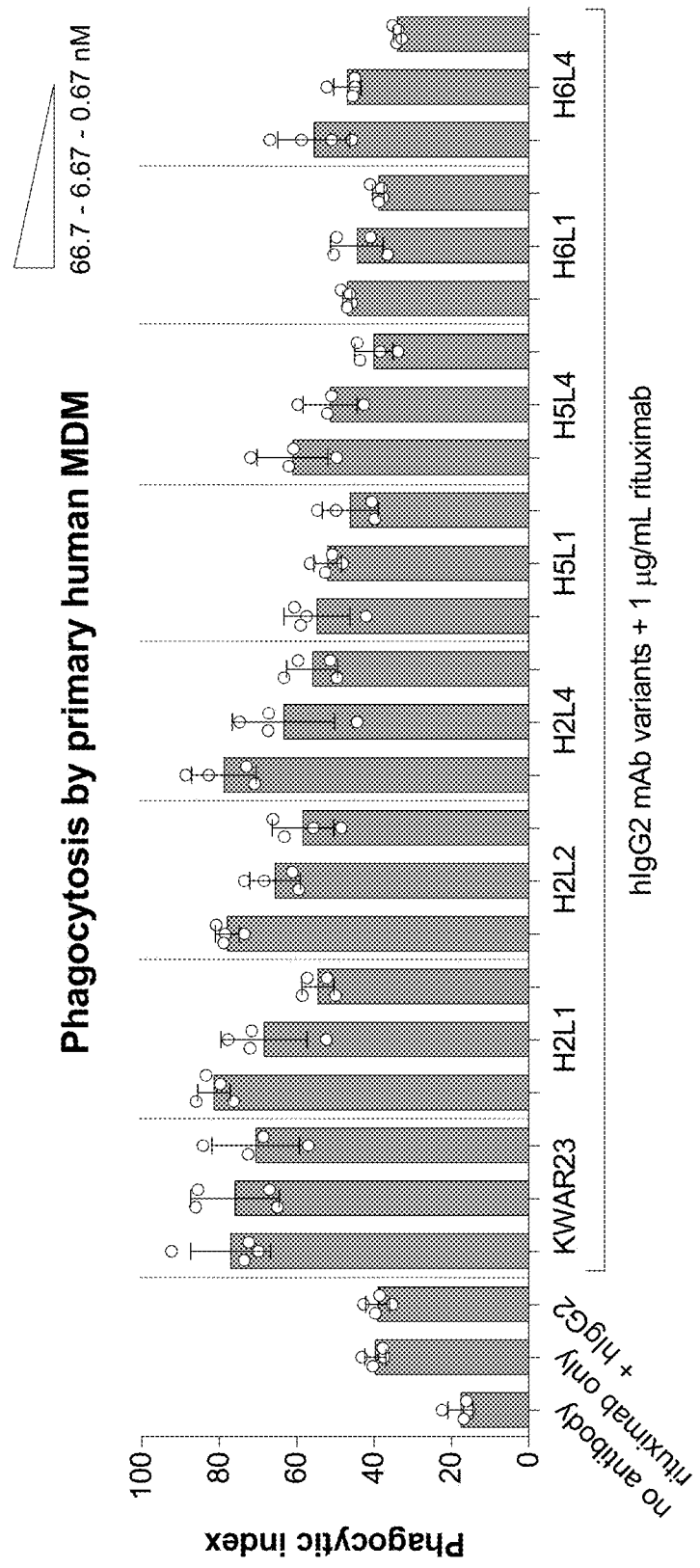
FIG. 22 depicts the ability of humanized hSIRPα.40A antibody variants to affect rituximab-mediated phagocytosis.

As shown in FIG. 22, the humanized hSIRPα.40A antibody variants enhance rituximab-mediated phagocytosis activity in a concentration-dependent manner similar to antibody KWAR23 grafted on a hIgG2 Fc.

Figure 23A:
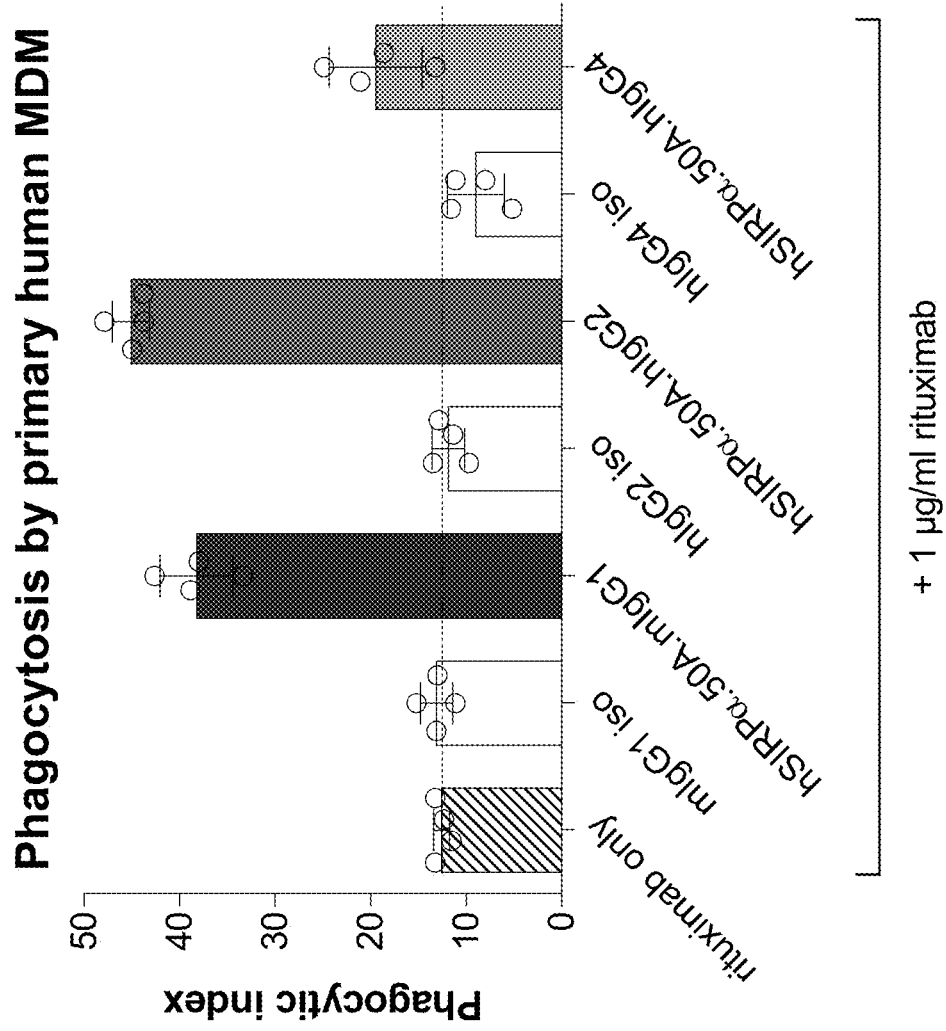
FIG. 23A depicts the ability of mouse hSIRPα.50A and chimeric hSIRPα.50A hIgG2 and hIgG4 antibody variants to affect rituximab-mediated phagocytosis.
Figure 23B:
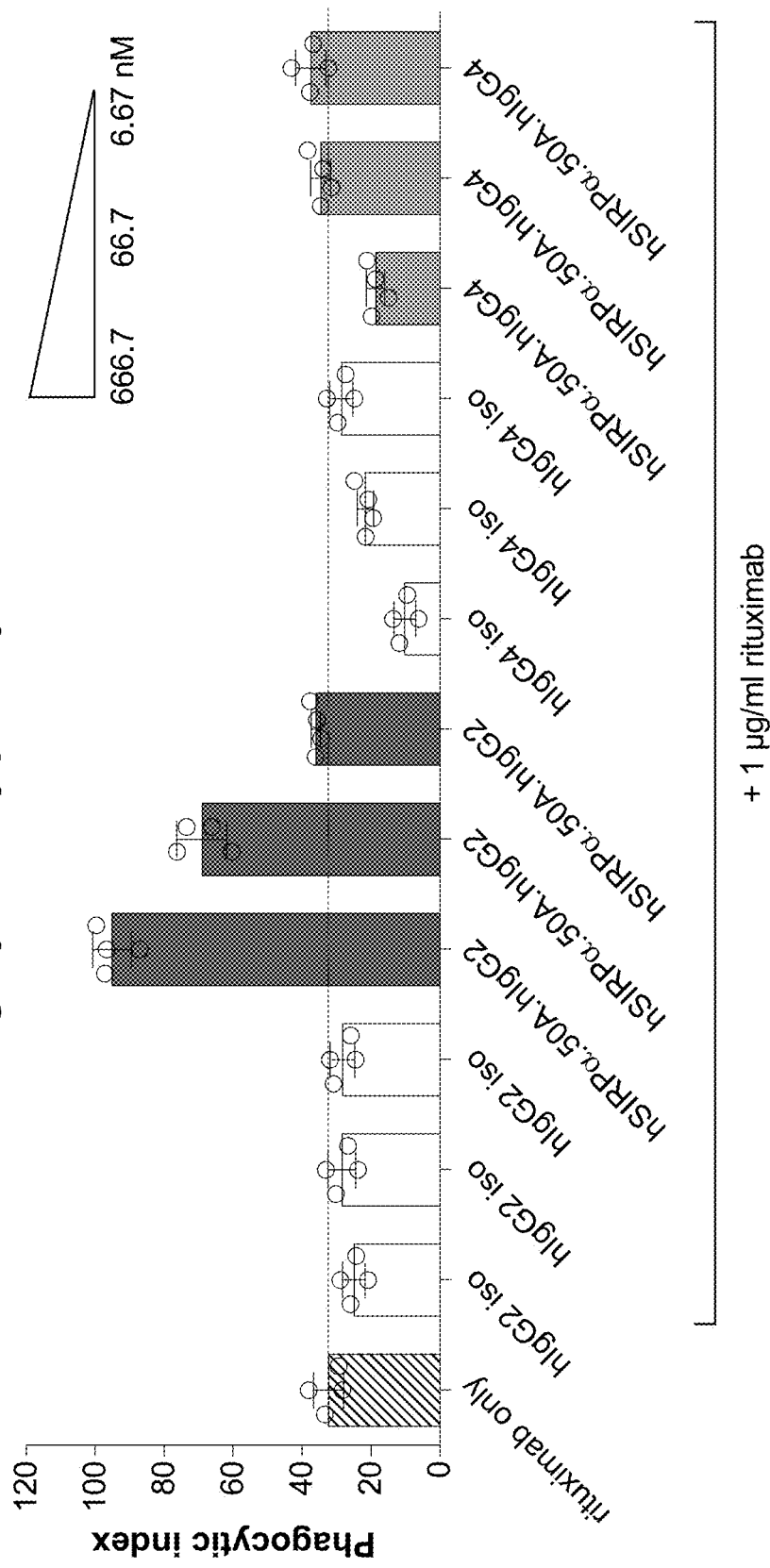
FIG. 23B depicts the ability of chimeric hSIRPα.50A hIgG2 and hIgG4 antibody variants to affect rituximab-mediated phagocytosis.
Figure 23C:
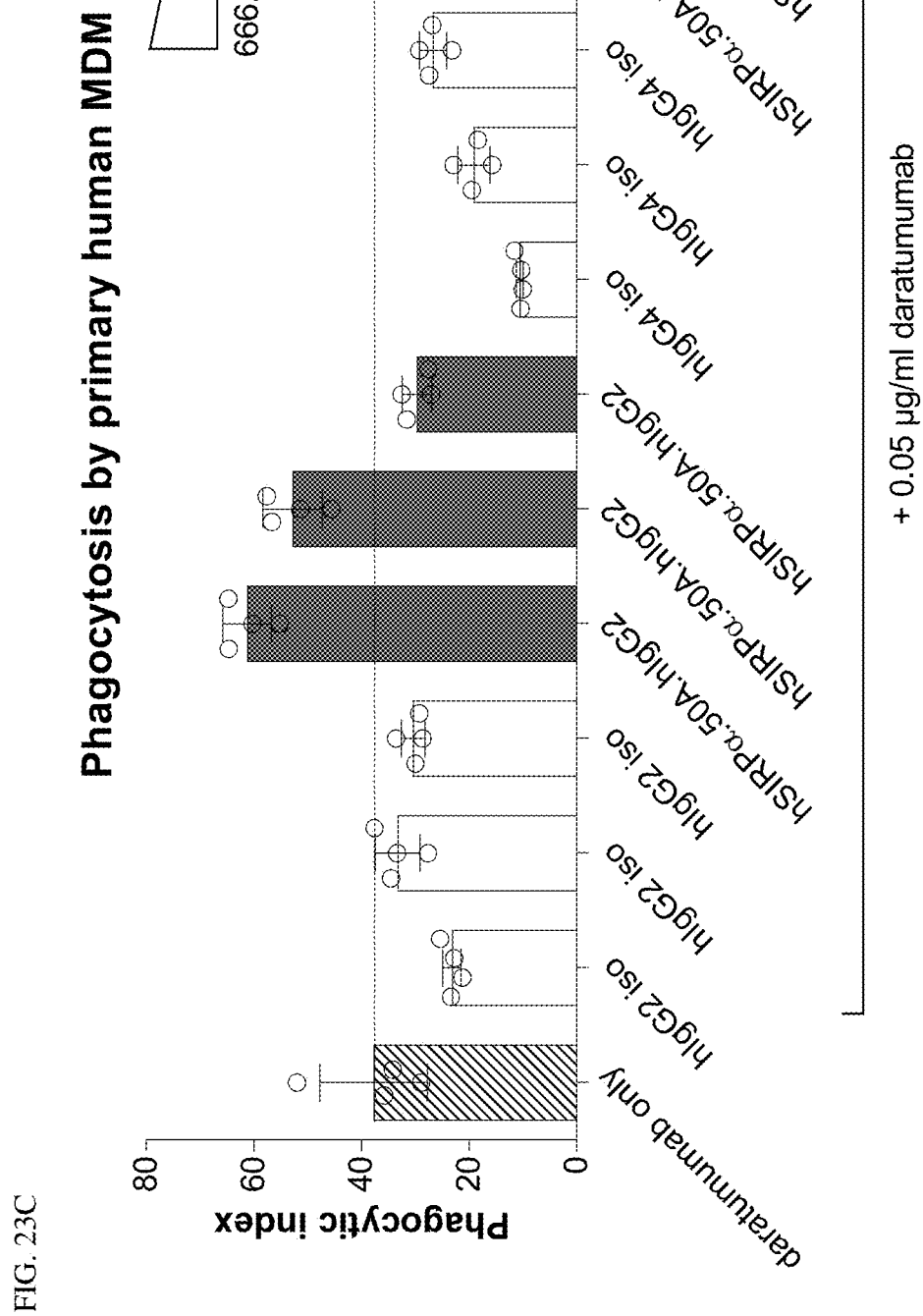
FIG. 23C depicts the ability of chimeric hSIRPα.50A hIgG2 and hIgG4 antibody variants to affect daratumumab-mediated phagocytosis.

Example 23: Functionality of Chimeric hSIRPα.50A mAb Variants in the Human Macrophage Phagocytosis Assay The functionality of hSIRPα.50A variable domains, grafted on different Fc constant domains, was assessed by in vitro phagocytosis assays using human macrophages. As shown in FIG. 23A, the chimeric hSIRPα.50A.hIgG4 antibody marginally enhances rituximab-mediated phagocytosis, whereas the chimeric hSIRPα.50A.hIgG2 antibody enhances rituximab-mediated phagocytosis activity similar to the murine hSIRPα.50A.mIgG1 (SEQ ID NO: 120) antibody. FIG. 23B demonstrates that the chimeric hSIRPα.50A.hIgG2 antibody potently enhances tumor cell phagocytosis induced by rituximab in a concentration-dependent manner as compared to the human IgG2 isotype control. Similarly, hSIRPα.50A.hIgG2 enhanced daratumumab-mediated phagocytosis (anti-hCD38, used at 0.05 µg/mL) (FIG. 23C).

Figure 23D:
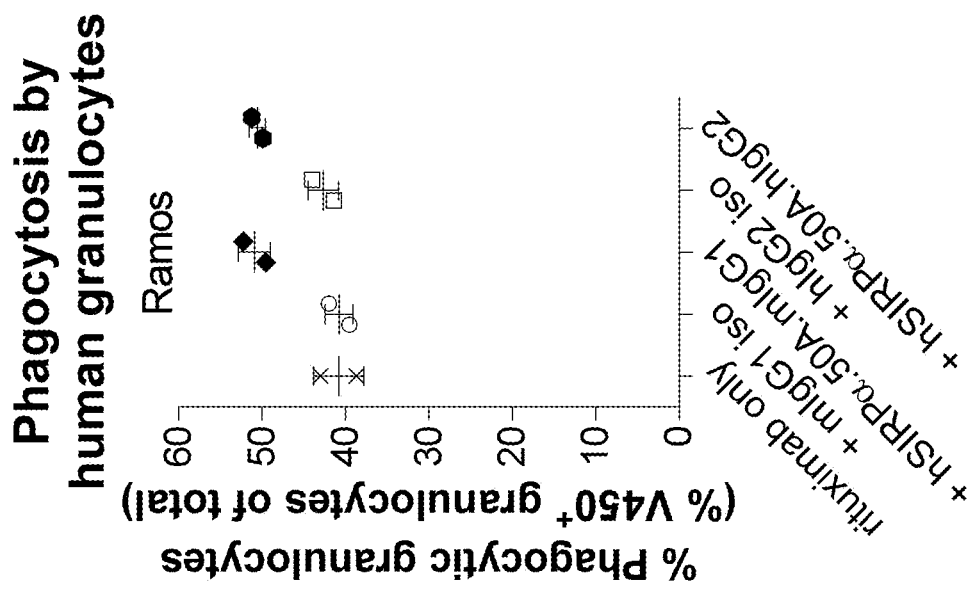
FIG. 23D depicts the ability of mouse hSIRPα.50A and chimeric hSIRPα.50A hIgG2 antibody variants to affect rituximab-mediated phagocytosis in granulocytes.
Figure 24A:
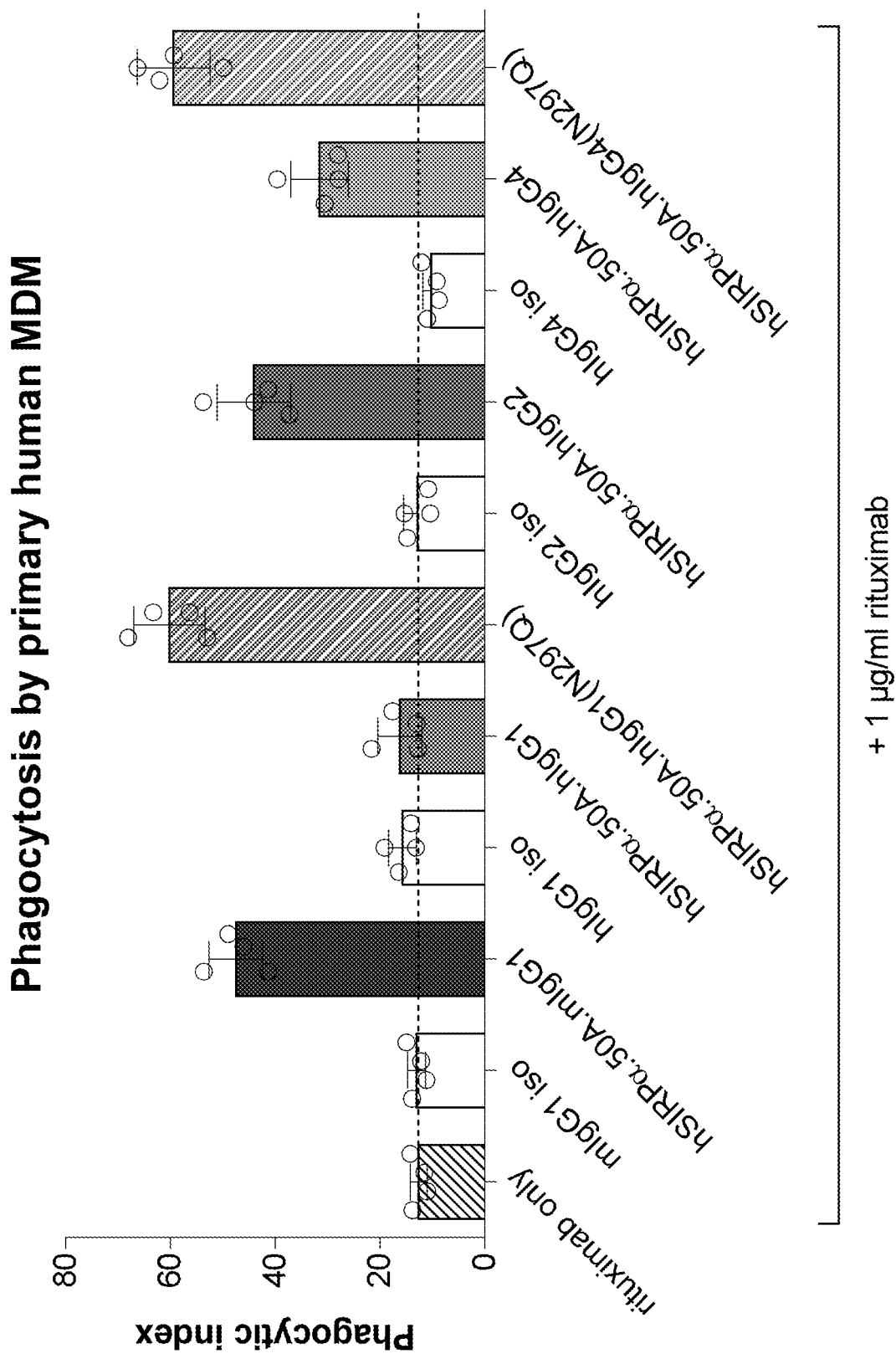
FIG. 24A depicts the ability of mouse hSIRPα.50A and chimeric hSIRPα.50A.hIgG1.N297Q, hSIRPα.50A.hIgG4.N297Q or hSIRPα.50A.hIgG2 antibody variants to affect rituximab-mediated phagocytosis.
Figure 24B:
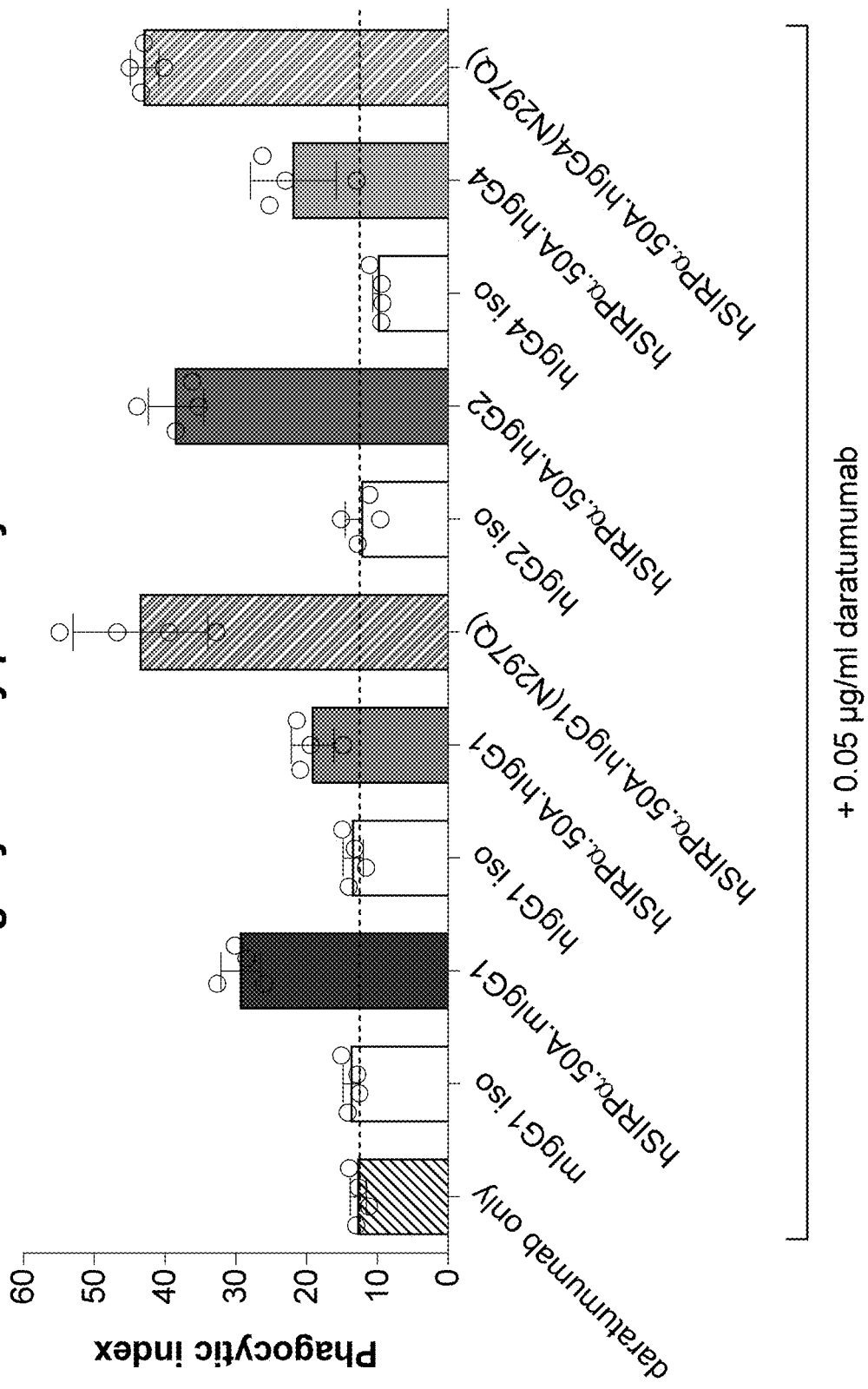
FIG. 24B depicts the ability of mouse hSIRPα.50A and chimeric hSIRPα.50A.hIgG1.N297Q, hSIRPα.50A.hIgG4.N297Q or hSIRPα.50A.hIgG2 antibody variants to affect daratumumab-mediated phagocytosis.
Figure 25:
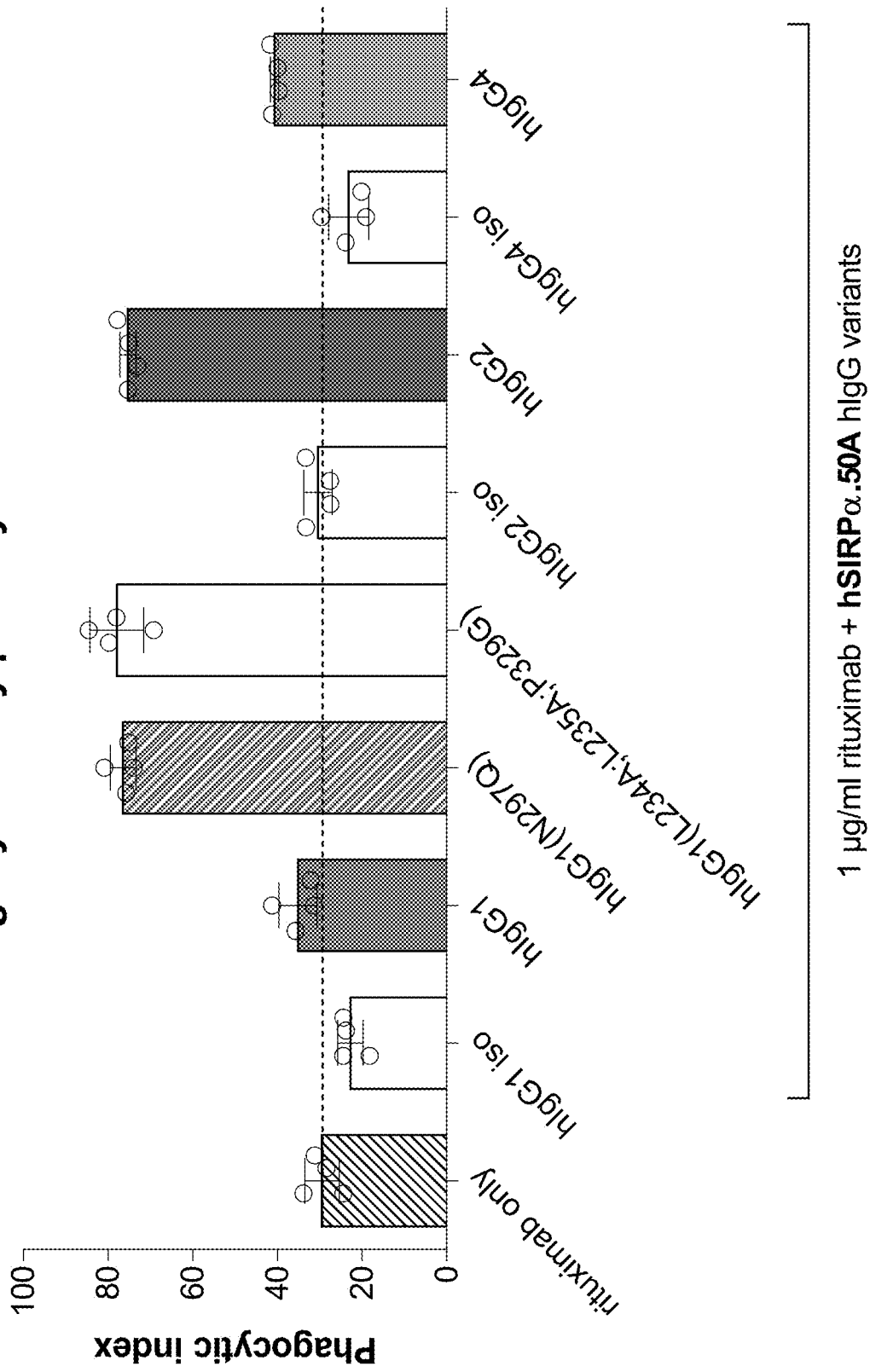
FIG. 25 depicts the ability of chimeric hSIRPα.50A.hIgG1.N297Q, hSIRPα.50A hIgG1.L234A.L235A.P329G, and hSIRPα.50A hIgG2 or hIgG4 antibody variants to affect rituximab-mediated phagocytosis.

In addition, hSIRPα.50A.hIgG2 also enhanced rituximab-mediated phagocytosis in human granulocytes. As shown in FIG. 23D, the chimeric hSIRPα.50A.hIgG2 antibody enhances phagocytosis activity induced by rituximab to a similar extend as the murine hSIRPα.50A.mIgG1 antibody. Likewise, as shown in FIG. 24A, the chimeric hSIRPα.50A.hIgG1.N297Q, hSIRPα.50A.hIgG4.N297Q (SEQ ID NO: 127) or hSIRPα.50A.hIgG2 antibodies enhance rituximab-mediated phagocytosis activity by human MDMs to a similar extent as the murine hSIRPα.50A.mIgG1 antibody (rituximab used at 1 µg/mL). Similar observations were made in FIG. 24B when phagocytosis was induced by daratumumab (0.05 µg/mL). As shown in FIG. 25, the chimeric hSIRPα.50A.hIgG1.N297Q and hSIRPα.50A hIgG1.L234A.L235A.P329G antibodies also enhance rituximab-mediated phagocytosis activity by human MDMs to a similar extent as the or hSIRPα.50A.hIgG2 antibody (rituximab used at 1 µg/mL). Chimeric variants of hSIRPα.50A mAb containing a wild-type hIgG1 or hIgG4 Fc region did not enhance tumor cell phagocytosis.

Example 24: Comparison of KWAR23, Clone 18D5, hSIRPα.50A, and hSIRPα.40A Antibodies A direct comparison of the specificity of monoclonal anti-hSIRPα antibodies KWAR23, clone 18D5 (SEQ ID NO: 128; SEQ ID NO: 129) from WO2017/178653, hSIRPα.50A, and hSIRPα.40A for binding to hSIRPαV1, hSIRPαV1(P74A), hSIRPαV2, and hSIRPβ1 was evaluated by CELISA. Reactivity was confirmed using CHO-K1 cells (ATCC CCL-61) expressing a cDNA encoding the full length open reading frame of hSIRPαV1, hSIRPαV1 (P74A), hSIRPαV2, and hSIRPβ1 subcloned into the pCI-neo vector (Promega, Madison, Wis.). CHO-K1.hSIRPαV1, CHO-K1.hSIRPαV1(P74A), CHO-K1.hSIRPαV2, and CHO-K1.hSIRPβ1 cells were seeded in culture medium (DMEM-F12 (Gibco) supplemented with 5% New Born Calf Serum (BioWest) and Pen/Strep (Gibco)) in 96-well flat-bottom tissue culture plates and incubated at 37° C., 5% $CO_2$ and 95% humidity for 24 hours. Subsequently, culture medium was removed and cells were incubated for 1 hour at 37° C., 5% $CO_2$ and 95% humidity with purified hSIRPα antibodies (used at 10 µg/mL and dilutions thereof). Next, cells were washed with PBS-T and incubated for 1 hour at 37° C., 5% $CO_2$ and 95% humidity with goat-anti-mouse IgG-HRP (Southern Biotech). Subsequently, cells were washed three times with PBS-T and immunoreactivity against hSIRPαV1, hSIRPαV1(P74A), hSIRPαV2, and hSIRPβ1 was visualized with TMB Stabilized Chromogen (Invitrogen). Reactions were stopped with 0.5 M $H_2SO_4$ and absorbances were read at 450 and 610 nm. EC50 values, the concentration at which 50% of the total binding signal is observed, were calculated using GraphPad Prism 6 (GraphPad Software, Inc.).

Binding to hSIRPγ was assessed by flow cytometry using the Jurkat E6.1 T cell leukemia cell line (ECACC 88042803). Jurkat cells were seeded in 96-well round bottomed tissue culture plates and incubated for 40 minutes with the anti-hSIRPα antibodies (20 µg/mL and dilutions thereof) in PBS/1% BSA at 4° C. Next, cells were washed three times with PBS/1% BSA and incubated for 40 minutes at 4° C. with an Alexa Fluor 647-labeled goat-anti-mouse IgG (Invitrogen) detection antibody in PBS/1% BSA. After this labeling procedure, cells were washed two times, resuspended in PBS/1% BSA, containing 0.1 µg/mL DAPI (BioLegend), and analysed by flow cytometry on the FACSVerse (BD Biosciences). Data were processed and analysed with FlowJo V10 software (FlowJo, LLC). EC50 values, the concentration at which 50% of the total binding signal is observed, were calculated using GraphPad Prism 6 (GraphPad Software, Inc.).

As depicted in Table 24, KWAR23 and clone 18D5 antibodies cross-react with at least hSIRPβ1 and the P74A variant of hSIRPαV1. The hSIRPα.50A, and hSIRPα.40A antibodies of the present invention do not bind to either hSIRPβ1 or the P74A variant of hSIRPαV1 under the tested conditions. In this regard, the hSIRPα.50A, and hSIRPα.40A antibodies of the present invention similarly distinguish from antibody clone SIRP29 from WO2013/056352. FIGS. 7A and B of WO2017/178653 compares clone SIRP29 and KWAR23 binding to SIRPβ1 (referred to as "sirp-b", Product No. ABIN3077231 from antibodies-online.com), demonstrating that each of clone SIRP29 and KWAR23 has nanomolar affinity for SIRPβ1.

TABLE 24

| Antibody | hSIRPαV1 binding EC50 (nM) | hSIRPαV1 (P74A) binding EC50 (nM) | hSIRPαV2 binding EC50 (nM) | hSIRPβ1 binding EC50 (nM) | hSIRPγ binding EC50 (nM) |
|---|---|---|---|---|---|
| hSIRPα.40A | 0.114 | nd | 0.093 | nd | 0.369 |
| hSIRPα.50A | 0.773 | nd | 0.645 | nd | — |
| KWAR23 | 0.070 | 0.049 | 0.049 | 0.033 | 0.003 |
| 18D5 | 0.134 | 0.055 | nd | 0.055 | nd | nd, not detected;
—, not tested hCD47 blockade for the KWAR23, clone 18D5, and hSIRPα.40A antibodies was assessed by flow cytometry. For this purpose, THP-1 (ATCC TIB-202) and U-937 (ATCC CRL-1593.2) monocyte cell lines were used as the source of hSIRPα in the assay. THP-1 and U-937 cells were seeded in 96-well round bottomed tissue culture plates and incubated for 45 minutes with FcR Blocking Reagent (Miltenyi Biotec) and indicated anti-hSIRPα antibodies (20 µg/mL and dilutions thereof) in PBS/1% BSA at 4° C. Next, cells were washed three times with PBS/1% BSA and incubated with 10 µg/mL DyLight 488-labeled recombinant hCD47/Fc-protein for 30 minutes at 4° C. After this labeling procedure, cells were washed two times, resuspended in PBS/1% BSA containing 0.1 µg/mL DAPI (BioLegend), and analysed by flow cytometry on the FACSVerse (BD Biosciences). Data were processed and analysed with FlowJo V10 software (FlowJo, LLC) and plotted using GraphPad Prism 6 (GraphPad Software, Inc.). Binding of recombinant hCD47 fused to an Fc domain of human IgG1 was monitored in the presence of increasing amounts of the anti-hSIRPα antibodies. IC50 values for the blockade of hCD47 were calculated from this data. IC50 values represent the concentration at which half of the inhibition is observed.

As depicted in Table 18 and Table 25, hSIRPα.40A, hSIRPα.50A, and KWAR23 antibodies block rhCD47/Fc binding to both the THP-1 and U-937 monocyte cell lines which express the hSIRPαV2 and hSIRPαV1 allele, respectively. Antibody clone 18D5 blocks rhCD47/Fc binding to the U-937 monocyte cell line but does not block rhCD47/Fc binding to the THP-1 monocyte cell line, in line with the observation that 18D5 does not bind to hSIRPαV2 (Table 24). In this regard, the hSIRPα.50A, and hSIRPα.40A antibodies of the present invention similarly distinguish from antibody clone 18D5.

TABLE 25

| Antibody | THP-1 IC50 (nM) | U-937 IC50 (nM) |
|---|---|---|
| hSIRPα.40A | 0.548 | 1.417 |
| KWAR23 | 0.132 | 0.284 |
| 18D5 | nd | 1.522 | nd, not detected

Example 25: Mapping the Interaction Interface Between hSIRPα-hSIRPα.40A and hSIRPα-hSIRPα.50A The amino acids on hSIRPα that are bound by hSIRPα.40A or hSIRPα.50A were elucidated by a procedure that involves deuterated chemical cross-linking followed by enzymatic digestion and detection using mass spectrometry. First, antibody hSIRPα.40A and antigen rhSIRPα-HIS (SinoBiological 11612-H08H-100, SEQ ID NO: 132), or antibody hSIRPα.50A and antigen rhSIRPα-HIS were incubated to promote binding and integrity and aggregation level were verified by Ultraflex III MALDI TOF mass spectrometer (Bruker) equipped with a HM4 interaction module (CovalX). For these control experiments a dilution series of 10 µL samples of antibody or antigen (1- to 128-fold dilution, starting at 1 mg/mL) were prepared. Of each sample 9 µL was submitted to cross-linking using K200 MALDI MS analysis kit, according to the manufacturer's instructions (CovalX) and incubated for 180 minutes, while 1 µL was directly used for mass spectrometry analysis (High-Mass MALDI). The mass spectrometry analysis showed the antibody and antigen had the expected molecular weight: hSIRPα.40A=151.68 kDa (152.78 kDa with cross-linker), hSIRPα.50A=151.80 kD (153.17 kDa with cross-linker), and rhSIRPα-HIS=46.05 kDa (48.67 kDa with cross-linker). For characterization of the antigen-antibody complex, a mixture was made with an excess of antigen (antigen:antibody ratio for rhSIRPα-HIS:hSIRPα.40A 10.8 µM:8.5 µM, and antigen:antibody ratio for rhSIRPα-HIS: hSIRPα.50A 5.4 µM:2.13 µM). A 9 µL sample of the antigen-antibody mixture was submitted to cross-linking using K200 MALDI MS analysis kit, according to the manufacturer's instructions, while 1 µL was directly used for mass spectrometry analysis. The detected mass of the antibody and antigen (hSIRPα.40A: 151.18 kDa, rhSIRPα-HIS 45.93 kDa, hSIRPα.50A: 151.69 kDa, rhSIRPα-HIS 46.18 kDa) corresponds to the molecular weight as detected previously. The antigen-antibody complexes, after cross-linking, were detected as two non-covalent complexes with a 1:1 (195.24 kDa) and 2:1 (240.48 kDa) stoichiometry for rhSIRPα-HIS:hSIRPα.40A, and as one non-covalent complex with a 1:1 (198.24 kDa) stoichiometry for rhSIRPα-HIS:hSIRPα.50A. Antibody and antigen bound non-covalent; non-covalent aggregates or non-specific multimers were not detected.

Next, peptide mass fingerprinting of rhSIRPα-HIS was performed. Samples were submitted to ASP-N, trypsin, chymotrypsin, elastase and thermolysin (Roche Diagnostic) proteolysis, following manufacturer's instructions followed by analysis by nLC-LTQ Orbitrap MS/MS using an Ultimate 3000 (Dionex) system in line with a LTQ Orbitrap XL mass spectrometer (Thermo Scientific). This proteolysis array resulted in 98% of the sequence being covered by the identified peptides.

To determine the interacting amino acids of antibody hSIRPα.40A and hSIRPα.50A on rhSIRPα-HIS antigen with high resolution, the antigen-antibody complex (rhSIRPα-HIS:hSIRPα.40A ratio 10.8 µM:8.5 µM, rhSIRPα-HIS:hSIRPα.50A ratio 5.4 µM:2.13 PM) was incubated with deuterated cross-linkers d0/d12 (K200 MALDI Kit) for 180 minutes and subjected to multi-enzymatic cleavage with the enzymes ASP-N, trypsin, chymotrypsin, elastase and thermolysin. After enrichment of the cross-linked peptides, the samples were analyzed by high-resolution mass spectrometry (nLC-Orbitrap MS) and the data generated were analyzed using XQuest (Jin Lee, Mol. Biosyst. 4:816-823 (2008)) and Stavrox (Gitze et al., J. Am. Soc. Mass Spectrom. 23:76-87 (2012)). The interacting amino acids of hSIRPα.40A and hSIRPα.50A to rhSIRPα-HIS were mapped onto human SIRPαV1 (SEQ ID NO: 34). Cross-linked residues of hSIRPα.40A are depicted as bold, boxed, and hSIRPα.50A as bold, underlined:

```
MEPAGPAPGRLGPLLCLLLAASCAWSGVAGEEELQVIQPDKSVLVAAGETATLRCTATSLIPVG

PIQWFRGAGPGRELIYNQKEGHFPRVTTVSDLTKRNNMDFSIRIGNITPADAGTYYCVKFRKGS

PDDVEFKSGAGTELSVRAKPSAPVVSGPAARATPQHTVSFTCESHGFSPRDITLKWFKNGNELS

DFQTNVDPVGESVSYSIHSTAKVVLTREDVHSQVICEVAHVTLQGDPLRGTANLSETIRVPPTL

EVTQQPVRAENQVNVTCQVRKFYPQRLQLTWLENGNVSRTETASTVTENKDGTYNWMSWLLVNV

SAHRDDVKLTCQVEHDGQPAVSKSHDLKVSAHPKEQGSNTAAENTGSNERNIYIVVGVVCTLLV

ALLMAALYLVRIRQKKAQGSTSSTRLHEPEKNAREITQDTNDITYADLNLPKGKKPAPQAAEPN

NHTEYASIQTSPQPASEDTLTYADLDMVHLNRTPKQPAPKPEPSFSEYASVQVPRK
```

The C-alpha distance between residue P74 and the identified cross-linked residues was measured in Discovery Studio using the crystal structure of SIRPα (PDB ID 4CMM). The cross-linked residues identified for hSIRPα.50A are within 14.0 to 21.4 angstrom C-alpha atom distance from residue P74; the cross-linked residues identified for hSIRPα.40A are within 16.2 to 33.5 angstrom C-alpha atom distance from residue P74. The C-alpha distances fit within the expected range for an epitope-paratope surface area of 700 Å$^2$ (Rowley et al., Biotech. Ann. Rev. 10:151-188 (2004)). The identified residues and surface area are distinctly different from the binding epitope of antihSIRPα antibody KWAR23 (Ring et al., Proc. Natl Acad. Sci. USA 114:E10578-E10585 (2017)).

Example 26: Comparison of hSIRPα Antibodies for Binding to hSIRPαV1, hSIRPαV1(P74A), and hSIRPβ1

The specificity of monoclonal anti-hSIRPα antibodies (e.g., including the hSIRPα antibodies known in the art, KWAR23 (U.S. Patent CA2939293 A1), 18D5 (Patent WO2017/178653 A2), and various commercially available hSIRPα antibodies) for binding to hSIRPαV1, hSIRPαV1 (P74A), and hSIRPβ1 was evaluated by CELISA. Reactivity was confirmed using CHO-K1 cells (ATCC CCL-61) expressing a cDNA encoding the full length open reading frame of hSIRPαV1, hSIRPαV1(P74A), and hSIRPβ1 subcloned into the pCI-neo vector (Promega, Madison, Wis.). CHO-K1.hSIRPαV1, CHO-K1.hSIRPαV1(P74A), and CHO-K1.hSIRPβ1 cells were seeded in culture medium (DMEM-F12 (Gibco) supplemented with 5% New Born Calf Serum (BioWest) and Pen/Strep (Gibco)) in 96-well flat-bottom tissue culture plates and incubated at 37° C., 5% $CO_2$ and 95% humidity for 24 hours. Subsequently, culture medium was removed and cells were incubated for 1 hour at 37° C., 5% $CO_2$ and 95% humidity with purified hSIRPα antibodies (used at 10 µg/ml and dilutions thereof). Next, cells were washed with PBS-T and incubated for 1 hour at 37° C., 5% $CO_2$ and 95% humidity with either goat-anti-mouse IgG-HRP (Southern Biotech), goat-anti-human IgG-HRP (Jackson Immuno Research), or goat-anti-rabbit IgG-HRP (Southern Biotech). Subsequently, cells were washed three times with PBS-T and immunoreactivity against hSIRPαV1, hSIRPαV1(P74A), and hSIRPβ1 was visualized with TMB Stabilized Chromogen (Invitrogen). Reactions were stopped with 0.5 M $H_2SO_4$ and absorbances were read at 450 and 610 nm. EC50 values, the concentration at which 50% of the total binding signal is observed, were calculated using GraphPad Prism 6 (GraphPad Software, Inc.)

As depicted in Table 26, KWAR23, clone 18D5, and all commercially available monoclonal anti-hSIRPα antibodies are able to bind to the P74A variant of hSIRPαV1 whereas the hSIRPα.40A and hSIRPα.50A antibodies of the present invention do not bind to the P74A variant of hSIRPαV1 under the tested conditions.

TABLE 26

| Antibody | hSIRPαV1 binding EC50 (nM) | hSIRPαV1 (P74A) binding EC50 (nM) | hSIRPβ1 binding EC50 (nM) |
| --- | --- | --- | --- |
| hSIRPα.40A | 0.053 | nd | nd |
| hSIRPα.50A | 0.307 | nd | nd |
| KWAR23 | 0.135 | 0.077 | 0.065 |
| 18D5 | 0.128 | 0.073 | 0.064 |
| anti-hSIRPα (clone SE5A5) | 0.156 | 0.207 | 0.105 |
| anti-hSIRPα (clone 7B3) | 0.122 | 0.141 | 0.115 |
| anti-hSIRPα (clone 1C6) | 0.329 | 0.440 | >2.817 |
| anti-hSIRPα (clone 27) | nd | nd | nd |
| anti-hSIRPα (clone SE7C2) | >7.010 | >6.139 | nd |
| anti-hSIRPα (clone P3C4) | 0.179 | 0.197 | 0.160 |
| anti-hSIRPα (clone 2A4A5) | nd | nd | >6.456 |
| anti-hSIRPα (clone 15-414) | nd | nd | nd |
| anti-hSIRPα (clone 1H1) | nd | nd | nd |
| anti-hSIRPα (clone C-7) | nd | nd | nd |
| anti-hSIRPα (clone 03) | >8.247 | >8.992 | >6.092 |
| anti-hSIRPα (clone 5E10) | nd | nd | nd |
| anti-hSIRPα (clone 602411) | 0.047 | 0.076 | 0.051 |
| anti-hSIRPα (clone EPR16264) | >1.166 | >1.999 | nd |
| anti-hSIRPα (clone D6I3M) | >6.413 | >121.509 | nd |
| anti-hSIRPα (clone 001) | >0.868 | >1.192 | nd |
| anti-hSIRPα (clone REA144) | >3.661 | >4.793 | >3.075 | nd, not detected

Example 27: Sequences Referred to in the Specification

| Description | SEQ ID NO: | SEQUENCE |
| --- | --- | --- |
| 50A heavy chain CDR1 (amino acid sequence) | 1 | NYYIH |
| 50A heavy chain CDR2 (amino acid sequence) | 2 | WIYPGNVNTKYNEKFKA |
| 50A heavy chain CDR3 (amino acid sequence) | 3 | PTIIATDFDV |
| 50A light chain CDR1 (amino acid sequence) | 4 | KASQGVGTAVG |
| 50A light chain CDR2 (amino acid sequence) | 5 | WASTRHT |
| 50A light chain CDR3 (amino acid sequence) | 6 | QQYSTYPFT |
| humanized 50 heavy chain variable region (consensus sequence) | 7 | EVQLX$_1$X$_2$SGX$_3$EX$_4$VKPGASVX$_5$X$_6$SCKASGFTFTNYYTHWVRQX$_7$PX$_8$QGLEWX$_9$GWIYPGNVNTKYNEKFKAX$_{10}$X$_{11}$X$_{12}$X$_{13}$TADKSTSTX$_{14}$YMX$_{15}$LSSLX$_{16}$SX$_{17}$DX$_{18}$AVYYCARPTIIATDFDVWGQGTX$_{19}$VTVSS |

| Description | SEQ ID NO: | SEQUENCE |
|---|---|---|
| | | wherein:<br>$X_1$ = Q, V<br>$X_2$ = Q, E<br>$X_3$ = A, S<br>$X_4$ = V, L<br>$X_5$ = K, M<br>$X_6$ = V, I<br>$X_7$ = A, R<br>$X_8$ = G, E<br>$X_9$ = I, M<br>$X_{10}$ = R, K<br>$X_{11}$ = V, A<br>$X_{12}$ = T, I<br>$X_{13}$ = I, M<br>$X_{14}$ = A, V<br>$X_{15}$ = D, E, Q<br>$X_{16}$ = R, T<br>$X_{17}$ = E, D<br>$X_{18}$ = T, M<br>$X_{19}$ = T, L |
| humanized 50 light chain variable region (consensus sequence) | 8 | $X_1X_2X_3X_4$TQSPSX$_5$LSASVGDRVTITCKASQGVGTAVGWYQX$_6$KPGK X$_7$PKLLIYWASTRHTGVPDRFSGSGSGTX$_8$FTLX$_9$IX$_{10}$X$_{11}$LQPED X$_{12}$AX$_{13}$YYCQQYSTYPFTFGGGTKX$_{14}$EIK<br>wherein:<br>$X_1$ = D, E<br>$X_2$ = I, L<br>$X_3$ = V, Q<br>$X_4$ = L, M<br>$X_5$ = F, S<br>$X_6$ = Q, K<br>$X_7$ = A, S, V<br>$X_8$ = E, D<br>$X_9$ = T, A<br>$X_{10}$ = S, N<br>$X_{11}$ = S, N, G<br>$X_{12}$ = F, I, V<br>$X_{13}$ = A, D, T<br>$X_{14}$ = L, V |
| hSIRPα.50AVH1 (nucleotide sequence) | 9 | GAAGTGCAGCTGCAGCAGTCTGGCGCCGAGGTCGTGAAACCTGGCG CCTCTGTGAAGGTGTCCTGCAAGGCCTCCGGCTTCACCTTCACCAA CTACTACATCCACTGGGTGCGACAGGCCCCAGGCCAGGGACTGGAA TGGATCGGCTGGATCTACCCCGGCAACGTGAACACCAAGTACAACG AGAAGTTCAAGGCCCGCGTGACCATCACCGCCGACAAGTCTACCTC CACCGCCTACATGGACCTGTCCTCCCTGAGATCCGAGGACACCGCC GTGTACTACTGCGCCAGACCCACCATCATTGCCACCGACTTCGACG TGTGGGGCCAGGGCACAACCGTGACCGTGTCCTCT |
| hSIRPα.50AVH1 (amino acid sequence) | 10 | EVQLQQSGAEVVKPGASVKVSCKASGFTFTNYYIHWVRQAPGQGLE WIGWIYPGNVNTKYNEKFKARVTITADKSTSTAYMDLSSLRSEDTA VYYCARPTIIATDFDVWGQGTTVTVSS |
| hSIRPα.50AVH2 (nucleotide sequence) | 11 | GAAGTGCAGCTGGTGGAATCCGGCTCCGAGCTCGTGAAGCCTGGCG CCTCCGTGAAGGTGTCCTGCAAGGCCTCTGGCTTCACCTTCACCAA CTACTACATCCACTGGGTGCGACAGGCCCCAGGCCAGGGACTGGAA TGGATGGGCTGGATCTACCCCGGCAACGTGAACACCAAGTACAACG AGAAGTTCAAGGCCAAGGCCACCATCACCGCCGACAAGTCCACCTC CACCGCCTACATGGAACTGTCCTCCCTGCGGAGCGAGGACACCGCC GTGTACTACTGTGCCCGGCCTACCATCATTGCCACCGACTTCGATG TGTGGGGCCAGGGCACACTCGTGACCGTGTCCTCT |
| hSIRPα.50AVH2 (amino acid sequence) | 12 | EVQLVESGSELVKPGASVKVSCKASGFTFTNYYIHWVRQAPGQGLE WMGWIYPGNVNTKYNEKFKAKATITADKSTSTAYMELSSLRSEDTA VYYCARPTIIATDFDVWGQGTLVTVSS |
| hSIRPα.50AVH3 (nucleotide sequence) | 13 | GAAGTGCAGCTGGTGCAGTCTGGCGCCGAGGTCGTGAAACCTGGCG CCTCCGTGATGATCTCCTGCAAGGCCTCCGGCTTCACCTTCACCAA CTACTACATCCACTGGGTGCGACAGCGGCCAGGCCAGGGACTGGAA TGGATCGGCTGGATCTACCCCGGCAACGTGAACACCAAGTACAACG AGAAGTTCAAGGCCCGCGTGATCATGACCGCCGACAAGTCCACCTC CACCGTGTACATGCAGCTGTCCTCCCTGACCTCCGAGGACACCGCC GTGTACTACTGCGCCAGACCCACCATCATTGCCACCGACTTCGACG TGTGGGGCCAGGGCACACTCGTGACCGTGTCCTCT |

-continued

| Description | SEQ ID NO: | SEQUENCE |
|---|---|---|
| hSIRPα.50AVH3 (amino acid sequence) | 14 | EVQLVQSGAEVVKPGASVMISCKASGFTFTNYYIHWVRQRPGQLE<br>WIGWIYPGNVNTKYNEKFKARVIMTADKSTSTVYMQLSSLTSEDTA<br>VYYCARPTIIATDFDVWGQGTLVTVSS |
| hSIRPα.50AVH4 (nucleotide sequence) | 15 | GAAGTGCAGCTGCAGCAGTCTGGCGCCGAGCTCGTGAAACCTGGCG<br>CCTCTGTGAAGGTGTCCTGCAAGGCCTCCGGCTTCACCTTCACCAA<br>CTACTACATCCACTGGGTGCGACAGCGCCAGGCCAGGGACTGGAA<br>TGGATGGGCTGGATCTACCCCGGCAACGTGAACACCAAGTACAACG<br>AGAAGTTCAAGGCCAAGGCCACCATCACCGCCGACAAGTCCACCTC<br>CACCGCCTACATGGAACTGTCCTCCCTGACCTCCGAGGACACCGCC<br>GTGTACTACTGCGCCAGACCCACCATCATTGCCACCGACTTCGACG<br>TGTGGGGCCAGGGCACAACCGTGACCGTGTCCTCT |
| hSIRPα.50AVH4 (amino acid sequence) | 16 | EVQLQQSGAELVKPGASVKVSCKASGFTFTNYYIHWVRQRPGQLE<br>WMGWIYPGNVNTKYNEKFKAKATITADKSTSTAYMELSSLTSEDTA<br>VYYCARPTIIATDFDVWGQGTTVTVSS |
| hSIRPα.50AVH5 (nucleotide sequence) | 17 | GAAGTGCAGCTGGTGCAGTCTGGCGCCGAGGTCGTGAAACCTGGCG<br>CCTCTGTGAAGGTGTCCTGCAAGGCCTCCGGCTTCACCTTCACCAA<br>CTACTACATCCACTGGGTGCGACAGGCCCCCGAGCAGGGACTGGAA<br>TGGATCGGCTGGATCTACCCCGGCAACGTGAACACCAAGTACAACG<br>AGAAGTTCAAGGCCCGCGTGACCATGACCGCCGACAAGTCTACCTC<br>CACCGCCTACATGGAACTGTCCTCCCTGCGGAGCGACGACATGGCC<br>GTGTACTACTGCGCCAGACCCACCATCATTGCCACCGACTTCGACG<br>TGTGGGGCCAGGGCACAACCGTGACCGTGTCCTCT |
| hSIRPα.50AVH5 (amino acid sequence) | 18 | EVQLVQSGAEVVKPGASVKVSCKASGFTFTNYYIHWVRQAPEQGLE<br>WIGWIYPGNVNTKYNEKFKARVTMTADKSTSTAYMELSSLRSDDMA<br>VYYCARPTIIATDFDVWGQGTTVTVSS |
| hSIRPα.50AVL1 (nucleotide sequence) | 19 | GACATCGTGCTGACCCAGTCCCCCAGCTTCCTGTCTGCCTCTGTGG<br>GCGACAGAGTGACCATCACATGCAAGGCCTCTCAGGGCGTGGGCAC<br>CGCTGTGGGATGGTATCAGCAGAAGCCTGGCAAGGCCCCCAAGCTG<br>CTGATCTACTGGGCCTCTACCAGACACACCGGCGTGCCCGACAGAT<br>TCTCCGGCTCTGGCTCTGGCACCGAGTTTACCCTGACCATCTCCAG<br>CCTGCAGCCCGAGGATTTCGCCGCCTACTACTGCCAGCAGTACTCC<br>ACCTACCCCTTCACCTTCGGCGGAGGCACCAAGCTGGAAATCAAG |
| hSIRPα.50AVL1 (amino acid sequence) | 20 | DIVLTQSPSFLSASVGDRVTITCKASQGVGTAVGWYQQKPGKAPKL<br>LIYWASTRHTGVPDRFSGSGSGTEFTLTISSLQPEDFAAYYCQQYS<br>TYPFTFGGGTKLEIK |
| hSIRPα.50AVL2 (nucleotide sequence) | 21 | GACATCGTGATGACCCAGTCCCCCTCCAGCCTGTCTGCCTCTGTGG<br>GCGACAGAGTGACCATCACATGCAAGGCCTCTCAGGGCGTGGGCAC<br>CGCTGTGGGATGGTATCAGCAGAAGCCTGGCAAGGCCCCCAAGCTG<br>CTGATCTACTGGGCCTCTACCAGACACACCGGCGTGCCCGACAGAT<br>TCTCCGGCTCTGGCTCTGGCACCGACTTCACCCTGACCATCTCCAA<br>CCTGCAGCCCGAGGACTTCGCCGACTACTACTGCCAGCAGTACTCC<br>ACCTACCCCTTCACCTTCGGCGGAGGCACCAAGGTGGAAATCAAG |
| hSIRPα.50AVL2 (amino acid sequence) | 22 | DIVMTQSPSSLSASVGDRVTITCKASQGVGTAVGWYQQKPGKAPKL<br>LIYWASTRHTGVPDRFSGSGSGTDFTLTISNLQPEDFADYYCQQYS<br>TYPFTFGGGTKVEIK |
| hSIRPα.50AVL3 (nucleotide sequence) | 23 | GAGCTCGTGATGACCCAGTCCCCTTCCAGCCTGTCTGCCTCCGTGG<br>GCGACAGAGTGACCATCACATGCAAGGCCTCTCAGGGCGTGGGCAC<br>CGCTGTGGGATGGTATCAGCAGAAGCCTGGCAAGGCCCCCAAGCTG<br>CTGATCTACTGGGCCTCTACCAGACACACCGGCGTGCCCGACAGAT<br>TCTCCGGCTCTGGCTCTGGCACCGACTTTACCCTGGCCATCTCCAG<br>CCTGCAGCCCGAGGATATCGCCGACTACTACTGCCAGCAGTACTCC<br>ACCTACCCCTTCACCTTCGGCGGAGGCACCAAGGTGGAAATCAAG |
| hSIRPα.50AVL3 (amino acid sequence) | 24 | ELVMTQSPSSLSASVGDRVTITCKASQGVGTAVGWYQQKPGKAPKL<br>LIYWASTRHTGVPDRFSGSGSGTDFTLAISSLQPEDIADYYCQQYS<br>TYPFTFGGGTKVEIK |
| hSIRPα.50AVL4 (nucleotide sequence) | 25 | GACATCCAGATGACCCAGTCCCCCTCCAGCCTGTCTGCCTCTGTGG<br>GCGACAGAGTGACCATCACATGCAAGGCCTCTCAGGGCGTGGGCAC<br>CGCTGTGGGCTGGTATCAGAAAAAGCCCGGCAAGGTGCCCAAGCTG<br>CTGATCTACTGGGCCTCCACCAGACACACCGGCGTGCCCGATAGAT<br>TCTCCGGCTCTGGCTCTGGCACCGACTTCACCCTGACCATCAACGG<br>CCTGCAGCCTGAGGACGTGGCCACCTACTACTGCCAGCAGTACTCC<br>ACCTACCCCTTCACCTTCGGCGGAGGCACCAAGCTGGAAATCAAG |

-continued

| Description | SEQ ID NO: | SEQUENCE |
|---|---|---|
| hSIRPα.50AVL4 (amino acid sequence) | 26 | DIQMTQSPSSLSASVGDRVTITCKASQGVGTAVGWYQKKPGKVPKL LIYWASTRHTGVPDRFSGSGSGTDFTLTINGLQPEDVATYYCQQYS TYPFTFGGGTKLEIK |
| hSIRPα.50AVL5 (nucleotide sequence) | 27 | GACATCGTGCTGACCCAGTCCCCCAGCTTCCTGTCTGCCTCTGTGG GCGACAGAGTGACCATCACATGCAAGGCCTCTCAGGGCGTGGGCAC CGCTGTGGGATGGTATCAGCAGAAGCCCGGCAAGTCCCCCAAGCTG CTGATCTACTGGGCCTCCACCAGACACACCGGCGTGCCCGATAGAT TCTCCGGCTCTGGCTCTGGCACCGAGTTCACCCTGACCATCTCCAA CCTGCAGCCCGAGGACTTCGCCGCCTACTACTGCCAGCAGTACTCC ACCTACCCCTTCACCTTCGGCGGAGGCACCAAGCTGGAAATCAAG |
| hSIRPα.50AVL5 (amino acid sequence) | 28 | DIVLTQSPSFLSASVGDRVTITCKASQGVGTAVGWYQQKPGKSPKL LIYWASTRHTGVPDRFSGSGSGTEFTLTISNLQPEDFAAYYCQQYS TYPFTFGGGTKLEIK |
| hSIRPα.50A mouse VH (nucleotide sequence) | 29 | CAGGTCCAGCTGCAGCAGTCTGGACCTGAACTGGTGAAGCCTGGGG CTTCAGTTAGGATATCCTGCAAGGCTTCTGGCTTCACCTTCACAA CTACTATATACACTGGGTGAAGCAGAGGCCTGGACAGGGACTTGAG TGGATTGGATGGATTTATCCTGGAAATGTTAATACTAAGTACAATG AGAAGTTCAAGGCCAAGGCCACACTGACTGCAGACAAATCCTCCAC CACAGCCTACATGCAGCTCAGCAGCCTGGCCTCTGAGGACTCTGCG GTCTATTTCTGTGCAAGACCTACGATAATAGCTACGGACTTCGATG TCTGGGGCGCAGGGACCACGGTCACCGTCTCCTCA |
| hSIRPα.50A mouse VH (amino acid sequence) | 30 | QVQLQQSGPELVKPGASVRISCKASGFTFTNYYIHWVKQRPGQGLE WIGWIYPGNVNTKYNEKFKAKATLTADKSSTTAYMQLSSLASEDSA VYFCARPTIIATDFDVWGAGTTVTVSS |
| hSIRPα.50A mouse VL (nucleotide sequence) | 31 | GACATTGTCATGACCCAGTCTCACAAATTCATGTCCACATCAGTAG GAGACAGGGTCAACATCACCTGCAAGGCCAGTCAGGGTGTGGGTAC TGCTGTAGGCTGGTATCAACAGAAACCAGGGCAATCTCCTAGACTA CTGATTTACTGGGCATCCACCCGGCACACTGGAGTCCCTGATCGCT TCACAGGCAGTGGATCTGGGACAGATTTCAGTCTCGCCATTAGCAA TGTGCAGTCTGAAGACCTGGCAGATTATTTCTGTCAGCAATATAGC ACCTATCCGTTCACGTTCGGAGGGGGGACCAATCTAGAAATAAAA |
| hSIRPα.50A mouse VL (amino acid sequence) | 32 | DIVMTQSHKFMSTSVGDRVNITCKASQGVGTAVGWYQQKPGQSPRL LIYWASTRHTGVPDRFTGSGSGTDFSLAISNVQSEDLADYFCQQYS TYPFTFGGGTNLEIK |
| human SIRPαV1 (nucleotide sequence) | 33 | ATGGAGCCCGCCGGCCCGGCCCCCGGCCGCCTCGGGCCGCTGCTCT GCCTGCTGCTCGCCGCGTCCTGCCTGGTCAGGAGTGGCGGGTGA GGAGGAGCTGCAGGTGATTCAGCCTGACAAGTCCGTGTTGGTTGCA GCTGGAGAGACAGCCACTCTGCGCTGCACTGCGACCTCTCTGATCC CTGTGGGGCCCATCCAGTGGTTCAGAGGAGCTGGACCAGGCCGGGA ATTAATCTACAATCAAAAGAAGGCCACTTCCCCCGGGTAACAACT GTTTCAGACCTCACAAAGAGAAACAACATGGACTTTTCCATCCGCA TCGGTAACATCACCCCAGCAGATGCCGGCACCTACTACTGTGTGAA GTTCCGGAAAGGGAGCCCCGATGACGTGGAGTTTAAGTCTGGAGCA GGCACTGAGCTGTCTGTGCGCGCCAAACCCTCTGCCCCCGTGGTAT CGGGCCCTGCGGCGAGGGCCACACCTCAGCACACAGTGAGCTTCAC CTGCGAGTCCCACGGCTTCTCACCCAGAGACATCACCCTGAAATGG TTCAAAAATGGGAATGAGCTCTCAGACTTCCAGACCAACGTGGACC CCGTAGGAGAGAGCGTGTCCTACAGCATCCACAGCACAGCCAAGGT GGTGCTGACCCGCGAGGACGTTCACTCTCAAGTCATCTGCGAGGTG GCCCACGTCACCTTGCAGGGGACCCTCTTCGTGGGACTGCCAACT TGTCTGAGACCATCCGAGTTCCACCCACCTTGGAGGTTACTCAACA GCCCGTGAGGGCAGAGAACCAGGTGAATGTCACCTGCCAGGTGAGG AAGTTCTACCCCCAGAGACTACAGCTGACCTGGTTGGAGAATGGAA ACGTGTCCCGGACAGAAACGGCCTCAACCGTTACAGAGAACAAGGA TGGTACCTACAACTGGATGAGCTGGCTCCTGGTGAATGTATCTGCC CACAGGGATGATGTGAAGCTCACCTGCCAGGTGGAGCATGACGGGC AGCCAGCGGTCAGCAAAAGCCATGACCTGAAGGTCTCAGCCCACCC GAAGGAGCAGGGCTCAAATACCGCCGCTGAGAACACTGGATCTAAT GAACGGAACATCTATATTGTGGTGGGTGTGGTGTGCACCTTGCTGG TGGCCCTACTGATGGCGGCCCTCTACCTCGTCCGAATCAGACAGAA GAAAGCCCAGGGCTCCACTTCTTCTACAAGGTTGCATGAGCCCGAG AAGAATGCCAGAGAAATAACACAGGACACAAATGATATCACATATG CAGACCTGAACCTGCCCAAGGGGAAGAAGCCTGCTCCCCAGGCTGC GGAGCCCAACAACCACACGGAGTATGCCAGCATTCAGACCAGCCCG CAGCCCGCGTCGGAGGACACCCTCACCTATGCTGACCTGGACATGG TCCACCTCAACCGGACCCCCAAGCAGCCGGCCCCCAAGCCTGAGCC GTCCTTCTCAGAGTACGCCAGCGTCCAGGTCCCGAGGAAG |

-continued

| Description | SEQ ID NO: | SEQUENCE |
|---|---|---|
| human SIRPαV1 (amino acid sequence) | 34 | MEPAGPAPGRLGPLLCLLLAASCAWSGVAGEEELQVIQPDKSVLVA<br>AGETATLRCTATSLIPVGPIQWFRGAGPGRELIYNQKEGHFPRVTT<br>VSDLTKRNNMDFSIRIGNITPADAGTYYCVKFRKGSPDDVEFKSGA<br>GTELSVRAKPSAPVVSGPAARATPQHTVSFTCESHGFSPRDITLKW<br>FKNGNELSDFQTNVDPVGESVSYSIHSTAKVVLTREDVHSQVICEV<br>AHVTLQGDPLRGTANLSETIRVPPTLEVTQQPVRAENQVNVTCQVR<br>KFYPQRLQLTWLENGNVSRTETASTVTENKDGTYNWMSWLLVNVSA<br>HRDDVKLTCQVEHDGQPAVSKSHDLKVSAHPKEQGSNTAAENTGSN<br>ERNIYIVVGVVCTLLVALLMAALYLVRIRQKKAQGSTSSTRLHEPE<br>KNAREITQDTNDITYADLNLPKGKKPAPQAAEPNNHTEYASIQTSP<br>QPASEDTLTYADLDMVHLNRTPKQPAPKPEPSFSEYASVQVPRK |
| human SIRPαV2 (nucleotide sequence) | 35 | ATGGAACCTGCCGGACCTGCCCCTGGCAGACTGGGACCTCTGCTGT<br>GTCTGCTGCTGGCCGCCTCTTGTGCTTGGAGCGGAGTGGCTGGCGA<br>AGAGGAACTGCAAGTGATCCAGCCCGACAAGAGCGTGTCCGTGGCT<br>GCTGGCGAGTCTGCCATCCTGCACTGTACCGTGACCAGCCTGATCC<br>CCGTGGGCCCCATCCAGTGGTTTAGAGGCGCTGGCCCTGCCAGAGA<br>GCTGATCTACAACCAGAAAGAGGGCCACTTCCCCAGAGTGACCACC<br>GTGTCCGAGAGCACCAAGCGCGAGAACATGGACTTCAGCATCAGCA<br>TCTCCAACATCACCCCTGCCGACGCCGGCACCTACTACTGCGTGAA<br>GTTCAGAAAGGGCAGCCCCGACACCGAGTTCAAGAGCGGCGCTGGA<br>ACCGAGCTGTCTGTGCGGGCTAAGCCTTCTGCCCCTGTGGTGTCTG<br>GACCTGCCGCCAGAGCTACACCTCAGCACACCGTGTCTTTCACATG<br>CGAGAGCCACGGCTTCAGCCCCAGAGACATCACCCTGAAGTGGTTC<br>AAGAACGGCAACGAGCTGAGCGACTTCCAGACCAACGTGGACCCTG<br>TGGGCGAGTCCGTGTCCTACAGCATCCACAGCACCGCCAAGGTGGT<br>GCTGACCCGCGAGGATGTGCACAGCCAAGTGATCTGCGAGGTGGCC<br>CACGTGACACTGCAGGGCGATCCTCTGAGAGGCACCGCTAACCTGA<br>GCGAGACAATCAGAGTGCCCCCCACCCTGGAAGTGACCCAGCAGCC<br>CGTGCGGGCTGAGAACCAAGTGAACGTGACCTGCCAAGTGCGGAAG<br>TTCTACCCTCAGAGACTGCAGCTGACCTGGCTGGAAAACGGAAACG<br>TGTCCAGAACCGAGACAGCCAGCACCGTGACAGAGAACAAGGACGG<br>CACATACAACTGGATGAGCTGGCTGCTCGTGAACGTGTCCGCCCAC<br>AGAGATGACGTGAAGCTGACATGCCAGGTGGAACACGACGGCCAGC<br>CTGCCGTGTCTAAGAGCCACGACCTGAAGGTGTCCGCTCACCCCAA<br>AGAGCAGGGCAGCAACACCGCCGCTGAGAACACAGGCAGCAACGAG<br>AGAAACATCTACATCGTCGTGGGCGTCGTGTGCACCCTGCTGGTGG<br>CTCTGCTGATGGCTGCCCTGTACCTCGTGCGGATCAGACAGAAGAA<br>GGCCCAGGGCTCCACCTCCAGCACCAGACTGCACGAGCCTGAGAAG<br>AACGCCCGCGAGATCACCCAGGACACCAACGACATCACCTACGCCG<br>ACCTGAACCTGCCCAAGGGCAAGAAGCCTGCCCCTCAGGCTGCCGA<br>GCCTAACAACCACACAGAGTACGCCAGCATCCAGACCAGCCCTCAG<br>CCTGCCAGCGAGGACACACTGACATACGCCGATCTGGACATGGTGC<br>ACCTGAACAGAACCCCCAAGCAGCCCGCTCCCAAGCCCGAGCCTAG<br>CTTCTCTGAGTACGCCTCCGTGCAGGTGCCCAGAAAA |
| human SIRPαV2 (amino acid sequence) | 36 | MEPAGPAPGRLGPLLCLLLAASCAWSGVAGEEELQVIQPDKSVSVA<br>AGESAILHCTVTSLIPVGPIQWFRGAGPARELIYNQKEGHFPRVTT<br>VSESTKRENMDFSISISNITPADAGTYYCVKFRKGSPDTEFKSGAG<br>TELSVRAKPSAPVVSGPAARATPQHTVSFTCESHGFSPRDITLKWF<br>KNGNELSDFQTNVDPVGESVSYSIHSTAKVVLTREDVHSQVICEVA<br>HVTLQGDPLRGTANLSETIRVPPTLEVTQQPVRAENQVNVTCQVRK<br>FYPQRLQLTWLENGNVSRTETASTVTENKDGTYNWMSWLLVNVSAH<br>RDDVKLTCQVEHDGQPAVSKSHDLKVSAHPKEQGSNTAAENTGSNE<br>RNIYIVVGVVCTLLVALLMAALYLVRIRQKKAQGSTSSTRLHEPEK<br>NAREITQDTNDITYADLNLPKGKKPAPQAAEPNNHTEYASIQTSPQ<br>PASEDTLTYADLDMVHLNRTPKQPAPKPEPSFSEYASVQVPRK |
| human SIRPβ1 (nucleotide sequence) | 37 | ATGCCCGTGCCAGCCTCCTGGCCCCACCTTCCTAGTCCTTTCCTGC<br>TGATGACGCTACTGCTGGGGAGACTCACAGGAGTGGCAGGTGGGA<br>CGAGCTACAGGTGATTCAGCCTGAAAAGTCCGTATCAGTTGCAGCT<br>GGAGAGTCGGCCACTCTGCGCTGTGCTATGACGTCCCTGATCCCTG<br>TGGGGCCCATCATGTGGTTTAGAGGAGCTGGAGCAGGCCGGGAATT<br>AATCTACAATCAGAAAGAAGGCCACTTCCCACGGGTAACAACTGTT<br>TCAGAACTCACAAAGAGAAACAACCTGGACTTTTCCATCAGCATCA<br>GTAACATCACCCCAGCAGACGCCGGCACCTACTACTGTGTGAAGTT<br>CCGGAAAGGGAGCCCTGACGACGTGGAGTTTAAGTCTGGAGCAGGC<br>ACTGAGCTGTCTGTGCGCGCCAAACCCTCTGCCCCCGTGGTATCGG<br>GCCCTGCGGTGAGGGCCACACCTGAGCACACAGTGAGCTTCACCTG<br>CGAGTCCCATGGCTTCTCTCCCAGAGACATCACCCTGAAATGGTTC<br>AAAAATGGGAATGAGCTCTCAGACTTCCAGACCAACGTGGACCCCG<br>CAGGAGACAGTGTGTCCTACAGCATCCACAGCACAGCCAGGGTGGT<br>GCTGACCCGTGGGGACGTTCACTCTCAAGTCATCTGCGAGATAGCC<br>CACATCACCTTGCAGGGGGACCCTCTTCGTGGGACTGCCAACTTGT<br>CTGAGGCCATCCGAGTTCCACCCACCTTGGAGGTTACTCAACAGCC<br>CATGAGGGCAGAGAACCAGGCAAACGTCACCTGCCAGGTGAGCAAT |

| Description | SEQ ID NO: | SEQUENCE |
|---|---|---|
| | | TTCTACCCCCGGGGACTACAGCTGACCTGGTTGGAGAATGGAAATG<br>TGTCCCGGACAGAAACAGCTTCGACCCTCATAGAGAACAAGGATGG<br>CACCTACAACTGGATGAGCTGGCTCCTGGTGAACACCTGTGCCCAC<br>AGGGACGATGTGGTGCTCACCTGTCAGGTGGAGCATGATGGGCAGC<br>AAGCAGTCAGCAAAAGCTATGCCCTGGAGATCTCAGCGCACCAGAA<br>GGAGCACGGCTCAGATATCACCCATGAAGCAGCGCTGGCTCCTACT<br>GCTCCACTCCTCGTAGCTCTCCTCCTGGGCCCCAAGCTGCTACTGG<br>TGGTTGGTGTCTCTGCCATCTACATCTGCTGGAAACAGAAGGCC |
| human SIRPβ1 (amino acid sequence) | 38 | MPVPASWPHLPSPFLLMTLLLGRLTGVAGEDELQVIQPEKSVSVAA<br>GESATLRCAMTSLIPVGPIMWFRGAGAGRELIYNQKEGHFPRVTTV<br>SELTKRNNLDFSISISNITPADAGTYYCVKFRKGSPDDVEFKSGAG<br>TELSVRAKPSAPVVSGPAVRATPEHTVSFTCESHGFSPRDITLKWF<br>KNGNELSDFQTNVDPAGDSVSYSIHSTARVVLTRGDVHSQVICEIA<br>HITLQGDPLRGTANLSEAIRVPPTLEVTQQPMRAENQANVTCQVSN<br>FYPRGLQLTWLENGNVSRTETASTLIENKDGTYNWMSWLLVNTCAH<br>RDDVVLTCQVEHDGQQAVSKSYALEISAHQKEHGSDITHEAALAPT<br>APLLVALLLGPKLLLVVGVSAIYICWKQKA |
| human SIRPγ (nucleotide sequence) | 39 | ATGCCTGTCCCAGCCTCCTGGCCCCATCCTCCTGGTCCTTTCCTGC<br>TTCTGACTCTACTGCTGGGACTTACAGAAGTGGCAGGTGAGGAGGA<br>GCTACAGATGATTCAGCCTGAGAAGCTCCTGTTGGTCACAGTTGGA<br>AAGACAGCCACTCTGCACTGCACTGTGACCTCCCTGCTTCCCGTGG<br>GACCCGTCCTGTGGTTCAGAGGAGTTGGACCAGGCCGGGAATTAAT<br>CTACAATCAAAAGAAGGCCACTTCCCCAGGGTAACAACAGTTTCA<br>GACCTCACAAAGAGAAACAACATGGACTTTTCCATCCGCATCAGTA<br>GCATCACCCCAGCAGATGTCGGCACATACTACTGTGTGAAGTTTCG<br>AAAAGGGAGCCCTGAGAACGTGGAGTTTAAGTCTGGACCAGGCACT<br>GAGATGGCTTTGGGTGCCAAACCCTCTGCCCCCGTGGTATTGGGCC<br>CTGCGGCGAGGACCACACCTGAGCATACAGTGAGTTTCACCTGTGA<br>GTCCCATGGCTTCTCTCCCAGAGACATCACCCTGAAATGGTTCAAA<br>AATGGGAATGAGCTCTCAGACTTCCAGACCAACGTGGACCCCACAG<br>GACAGAGTGTGGCCTACAGCATCCGCAGCACAGCCAGGGTGGTACT<br>GGACCCCTGGGACGTTCGCTCTCAGGTCATCTGCGAGGTGGCCCAT<br>GTCACCTTGCAGGGGGACCCTCTTCGTGGGACTGCCAACTTGTCTG<br>AGGCCATCCGAGTTCCACCCACCTTGGAGGTTACTCAACAGCCCAT<br>GAGGGTGGGGAACCAGGTAAACGTCACCTGCCAGGTGAGGAAGTTC<br>TACCCCCAGAGCCTACAGCTGACCTGGTCGGAGAATGGAAACGTGT<br>GCCAGAGAGAAACAGCCTCGACCCTTACAGAGAACAAGGATGGTAC<br>CTACAACTGGACAAGCTGGTTCCTGGTGAACATATCTGACCAAAGG<br>GATGATGTGGTCCTCACCTGCCAGGTGAAGCATGATGGGCAGCTGG<br>CGGTCAGCAAACGCCTTGCCCTAGAGGTCACAGTCCACCAGAAGGA<br>CCAGAGCTCAGATGCTACCCCTGGCCCGGCATCATCCCTTACTGCG<br>CTGCTCCTCATAGCTGTCCTCCTGGGCCCCATCTACGTCCCCTGGA<br>AGCAGAAGACC |
| human SIRPγ (amino acid sequence) | 40 | MPVPASWPHPPGPFLLLTLLLGLTEVAGEEELQMIQPEKLLLVTVG<br>KTATLHCTVTSLLPVGPVLWFRGVGPGRELIYNQKEGHFPRVTTVS<br>DLTKRNNMDFSIRISSITPADVGTYYCVKFRKGSPENVEFKSGPGT<br>EMALGAKPSAPVVLGPAARTTPEHTVSFTCESHGFSPRDITLKWFK<br>NGNELSDFQTNVDPTGQSVAYSIRSTARVVLDPWDVRSQVICEVAH<br>VTLQGDPLRGTANLSEAIRVPPTLEVTQQPMRVGNQVNVTCQVRKF<br>YPQSLQLTWSENGNVCQRETASTLTENKDGTYNWTSWFLVNISDQR<br>DDVVLTCQVKHDGQLAVSKRLALEVTVHQKDQSSDATPGPASSLTA<br>LLLIAVLLGPIYVPWKQKT |
| human CD47 (nucleotide sequence) | 41 | ATGTGGCCTCTGGTGGCCGTCTGCTGCTGGGCTCTGCTTGTTGTG<br>GATCCGCCCAGCTGCTGTTCAACAAGACCAAGTCCGTGGAGTTCAC<br>CTTCTGCAACGATACCGTCGTGATCCCCTGCTTCGTGACCAACATG<br>GAAGCCCAGAACACCACCGAGGTGTACGTGAAGTGGAAGTTCAAGG<br>GCCGGGACATCTACACCTTCGACGGCGCCCTGAACAAGTCCACCGT<br>GCCCACCGATTTCTCCAGCGCCAAGATCGAGGTGTCACAGCTGCTG<br>AAGGGCGACGCCTCCCTGAAGATGGACAAGTCCGACGCCGTGTCCC<br>ACACCGGCAACTACACCTGTGAAGTGACCGAGCTGACCAGAGAGGG<br>CGAGACAATCATCGAGCTGAAGTACCGGGTGGTGTCCTGGTTCAGC<br>CCCAACGAGAACATCCTGATCGTGATCTTCCCCATCTTCGCCATCC<br>TGCTGTTCTGGGGCCAGTTCGGCATCAAGACCCTGAAGTACAGATC<br>CGGCGGCATGGACGAAAAGACAATCGCCCTGCTGGTGGCTGGCCTC<br>GTGATCACCGTGATTGTGATCGTGGGCGCTATCCTGTTCGTGCCCG<br>GCGAGTACAGCCTGAAGAATGCTACCGGCCTGGGCCTGATTGTGAC<br>CTCCACCGGAATCCTGATCCTGCTGCACTACTACGTGTTCTCCACC<br>GCTATCGGCCTGACCTCCTTCGTGATCGCCATTCTCGTGATCCAAG<br>TGATCGCCTACATCCTGGCCGTCGTGGGCCTGTCCCTGTGTATCGC<br>CGCCTGCATCCCTATGCACGGCCCCCTGCTGATCTCCGGCCTGTCT<br>ATTCTGGCCCTGGCTCAGCTGCTGGGACTGGTGTACATGAAGTTCG<br>TGGCCTCCAACCAGAAAACCATCCAGCCCCCTCGGAAGGCCGTGGA |

-continued

| Description | SEQ ID NO: | SEQUENCE |
|---|---|---|
| | | AGAACCCCTGAACGCCTTCAAAGAATCCAAGGGCATGATGAACGAC GAA |
| human CD47 (amino acid sequence) | 42 | MWPLVAALLLGSACCGSAQLLFNKTKSVEFTFCNDTVVIPCFVTNM EAQNTTEVYVKWKFKGRDIYTFDGALNKSTVPTDFSSAKIEVSQLL KGDASLKMDKSDAVSHTGNYTCEVTELTREGETIIELKYRVVSWFS PNENILIVIFPIFAILLFWGQFGIKTLKYRSGGMDEKTIALLVAGL VITVIVIVGAILFVPGEYSLKNATGLGLIVTSTGILILLHYVFST AIGLTSFVIAILVIQVIAYILAVVGLSLCIAACIPMHGPLLISGLS ILALAQLLGLVYMKFVASNQKTIQPPRKAVEEPLNAFKESKGMMND E |
| human SIRPαV3 (nucleotide sequence) | 43 | ATGGAACCTGCCGGCCCTGCTCCTGGTAGACTGGGACCTCTGCTGT GTCTGCTGCTGGCCGCCTCTTGTGCTTGGAGCGGAGTGGCTGGCGA AGAGGAACTGCAAGTGATCCAGCCCGACAAGTCCGTGTCTGTGGCC GCTGGCGAGTCTGCCATCCTGCTGTGTACCGTGACCTCCCTGATCC CCGTGGGCCCCATCCAGTGGTTTAGAGGCGCTGGCCCTGCCAGAGA GCTGATCTACAACCAGAAAGAGGGCCACTTCCCCAGAGTGACCACC GTGTCCGAGTCCACCAAGCGCGAGAACATGGACTTCTCCATCTCCA TCAGCAACATCACCCCTGCCGACGCCGGCACCTACTACTGCGTGAA GTTCCGGAAGGGCTCCCCCGACACCGAGTTCAAGTCTGGCGCTGGC ACCGAGCTGTCTGTGCGGGCTAAACCTTCTGCCCCTGTGGTGTCTG GACCTGCCGCTAGAGCTACCCCTCAGCACACCGTGTCTTTTACCTG CGAGTCCCACGGCTTCAGCCCTCGGGACATCACCCTGAAGTGGTTC AAGAACGGCAACGAGCTGAGCGACTTCCAGACCAACGTGGACCCTG TGGGCGAGAGCGTGTCCTACTCCATCCACTCCACCGCCAAGGTGGT GCTGACACGCGAGGACGTGCACTCCCAAGTGATCTGCGAGGTGGCC CACGTGACACTGCAGGGCGATCCTCTGAGAGGCACCGCCAACCTGT CCGAGACAATCAGAGTGCCCCCCACCCTGGAAGTGACCCAGCAGCC AGTGCGGGCCGAGAACCAAGTGAACGTGACCTGCCAAGTGCGGAAG TTCTACCCCCAGCGGCTGCAGCTGACCTGGCTGGAAAACGGCAATG TGTCCCGGACCGAGACAGCCAGCACCGTGACCGAGAACAAGGATGG CACCTACAATTGGATGTCTTGGCTGCTCGTGAACGTGTCCGCCCAC CGGGACGATGTGAAGCTGACATGCCAGGTGGAACACGACGGCCAGC CTGCCGTGTCCAAGAGCCACGATCTGAAGGTGTCCGCTCATCCCAA AGAGCAGGGCTCCAACACCGCCGCTGAGAACACCGGCTCTAACGAG CGGAACATCTACATCGTCGTGGGCGTCGTGTGCACCCTGCTGGTGG CTCTGCTGATGGCTGCCCTGTACCTCGTGCGGATCCGGCAGAAGAA GGCCCAGGGCTCTACCTCCTCCACCAGACTGCACGAGCCCGAGAAG AACGCCAGAGAGATCACCCAGGACACCAACGACATCACCTACGCCG ACCTGAACCTGCCCAAGGGCAAGAAGCCTGCCCCTCAGGCTGCCGA GCCTAACAACCACACCGAGTACGCCTCCATCCAGACCAGCCCTCAG CCTGCCTCTGAGGACACCCTGACCTACGCTGATCTGGACATGGTGC ACCTGAACCGGACCCCCAAGCAGCCAGCTCCTAAGCCCGAGCCTAG CTTCTCTGAGTACGCCAGCGTGCAGGTGCCCCGGAAA |
| human SIRPαV3 (amino acid sequence) | 44 | MEPAGPAPGRLGPLLCLLLAASCAWSGVAGEEELQVIQPDKSVSVA AGESAILLCTVTSLIPVGPIQWFRGAGPARELIYNQKEGHFPRVTT VSESTKRENMDFSISISNITPADAGTYYCVKFRKGSPDTEFKSGAG TELSVRAKPSAPVVSGPAARATPQHTVSFTCESHGFSPRDITLKWF KNGNELSDFQTNVDPVGESVSYSIHSTAKVVLTREDVHSQVICEVA HVTLQGDPLRGTANLSETIRVPPTLEVTQQPVRAENQVNVTCQVRK FYPQRLQLTWLENGNVSRTETASTVTENKDGTYNWMSWLLVNVSAH RDDVKLTCQVEHDGQPAVSKSHDLKVSAHPKEQGSNTAAENTGSNE RNIYIVVGVVCTLLVALLMAALYLVRIRQKKAQGSTSSTRLHEPEK NAREITQDTNDITYADLNLPKGKKPAPQAAEPNNHTEYASIQTSPQ PASEDTLTYADLDMVHLNRTPKQPAPKPEPSFSEYASVQVPRK |
| human SIRPαV4 (nucleotide sequence) | 45 | ATGGAACCTGCCGGCCCTGCTCCTGGTAGACTGGGACCTCTGCTGT GTCTGCTGCTGGCCGCCTCTTGTGCTTGGAGCGGAGTGGCTGGCGA AGAGGGCCTGCAAGTGATCCAGCCCGACAAGTCCGTGTCTGTGGCC GCTGGCGAGTCTGCCATCCTGCACTGTACCGCCACCTCCCTGATCC CCGTGGGACCCATCCAGTGGTTTAGAGGCGCTGGCCCTGGCAGAGA GCTGATCTACAACCAGAAAGAGGGCCACTTCCCCAGAGTGACCACC GTGTCCGACCTGACCAAGCGGAACAACATGGACTTCTCCATCCGGA TCGGCAACATCACCCCTGCCGATGCCGGCACCTACTACTGCGTGAA GTTCCGGAAGGGCTCCCCCGACGACGTGGAGTTCAAATCCGGCGCT GGCACCGAGCTGTCTGTGCGGGCTAAACCTTCTGCCCCTGTGGTGT CTGGCCCTGCCGCTAGAGCTACCCCTCAGCACACCGTGTCTTTTAC CTGCGAGTCCCACGGCTTCAGCCCTCGGGACATCACCCTGAAGTGG TTCAAGAACGGCAACGAGCTGAGCGACTTCCAGACCAACGTGGACC CTGTGGGCGAGAGCGTGTCCTACTCCATCCACTCCACCGCCAAGGT GGTGCTGACACGCGAGGACGTGCACTCCCAAGTGATCTGCGAGGTG GCCCACGTGACACTGCAGGGCGATCCTCTGAGAGGCACCGCCAACC TGTCCGAGACAATCAGAGTGCCCCCCACCCTGGAAGTGACCCAGCA GCCAGTGCGGGCCGAGAACCAAGTGAACGTGACCTGCCAAGTGCGG |

| Description | SEQ ID NO: | SEQUENCE |
|---|---|---|
| | | AAGTTCTACCCCCAGCGGCTGCAGCTGACCTGGCTGGAAAACGGCA |
| | | ATGTGTCCCGGACCGAGACAGCCTCCACCGTGACCGAGAACAAGGA |
| | | TGGCACCTACAATTGGATGTCTTGGCTGCTCGTGAACGTGTCCGCC |
| | | CACCGGGACGATGTGAAGCTGACATGCCAGGTGGAACACGACGGCC |
| | | AGCCTGCCGTGTCCAAGTCCCACGATCTGAAGGTGTCCGCTCATCC |
| | | CAAAGAGCAGGGCTCCAACACCGCCGCTGAGAACACCGGCTCTAAC |
| | | GAGCGGAACATCTACATCGTCGTGGGCGTCGTGTGCACCCTGCTGG |
| | | TGGCTCTGCTGATGGCTGCCCTGTACCTCGTCGGATCCGGCAGAA |
| | | GAAGGCCCAGGGCTCTACCTCCTCCACCAGACTGCACGAGCCCGAG |
| | | AAGAACGCCAGAGAGATCACCCAGGACACCAACGACATCACCTACG |
| | | CCGACCTGAACCTGCCCAAGGGCAAGAAGCCTGCCCCTCAGGCTGC |
| | | CGAGCCTAACAACCACACCGAGTACGCCTCCATCCAGACCAGCCCT |
| | | CAGCCTGCCTCTGAGGACACCCTGACCTACGCTGATCTGGACATGG |
| | | TGCACCTGAACCGGACCCCCAAGCAGCCAGCTCCTAAGCCCGAGCC |
| | | TAGCTTCTCTGAGTACGCCAGCGTGCAGGTGCCCCGGAAA |
| human SIRPαV4 (amino acid sequence) | 46 | MEPAGPAPGRLGPLLCLLLAASCAWSGVAGEEGLQVIQPDKSVSVA AGESAILHCTATSLIPVGPIQWFRGAGPGRELIYNQKEGHFPRVTT VSDLTKRNNMDFSIRIGNITPADAGTYYCVKFRKGSPDDVEFKSGA GTELSVRAKPSAPVVSGPAARATPQHTVSFTCESHGFSPRDITLKW FKNGNELSDFQTNVDPVGESVSYSIHSTAKVVLTREDVHSQVICEV AHVTLQGDPLRGTANLSETIRVPPTLEVTQQPVRAENQVNVTCQVR KFYPQRLQLTWLENGNVSRTETASTVTENKDGTYNWMSWLLVNVSA HRDDVKLTCQVEHDGQPAVSKSHDLKVSAHPKEQGSNTAAENTGSN ERNIYIVVGVVCTLLVALLMAALYLVRIRQKKAQGSTSSTRLHEPE KNAREITQDTNDITYADLNLPKGKKPAPQAAEPNNHTEYASIQTSP QPASEDTLTYADLDMVHLNRTPKQPAPKPEPSFSEYASVQVPRK |
| human SIRPαV5 (nucleotide sequence) | 47 | ATGGAACCTGCCGGCCCTGCTCCTGGTAGACTGGGACCTCTGCTGT GTCTGCTGCTGGCCGCCTCTTGTGCTTGGAGCGGAGTGGCTGGCGA AGAGGAACTGCAAGTGATCCAGCCCGACAAGTTCGTGCTGGTGGCC GCTGGCGAGACAGCCACCCTGAGATGTACCGCCACCTCCCTGATCC CCGTGGGCCCTATCCAGTGGTTTAGAGGCGCTGGCCCTGGCAGAGA GCTGATCTACAACCAGAAAGAGGGCCACTTCCCCAGAGTGACCACC GTGTCCGACCTGACCAAGCGGAACAACATGGACTTCTCCATCCGGA TCGGCAACATCACCCCTGCCGATGCCGGCACCTACTACTGCGTGAA GTTCCGGAAGGGCTCCCCCGACGACGTGGAGTTCAAATCCGGCGCT GGCACCGAGCTGTCTGTGCGGGCTAAACCTTCTGCCCCTGTGGTGT CTGGCCCTGCCGCTAGAGCTACCCCTCAGCACACCGTGTCTTTTAC CTGCGAGTCCCACGGCTTCAGCCCTCGGGACATCACCCTGAAGTGG TTCAAGAACGGCAACGAGCTGAGCGACTTCCAGACCAACGTGGACC CTGTGGGCGAGTCCGTGTCCTACTCCATCCACTCCACCGCCAAGGT GGTGCTGACACGCGAGGACGTGCACTCCCAAGTGATCTGCGAGGTG GCCCACGTGACACTGCAGGGCGATCCTCTGAGAGGCACCGCCAACC TGTCCGAGACAATCAGAGTGCCCCCCACCCTGGAAGTGACCCAGCA GCCAGTGCGGGCCGAGAACCAAGTGAACGTGACCTGCCAAGTGCGG AAGTTCTACCCCCAGCGGCTGCAGCTGACCTGGCTGGAAAACGGCA ATGTGTCCCGGACCGAGACTGCCTCCACCGTGACCGAGAACAAGGA TGGCACCTACAATTGGATGTCTTGGCTGCTCGTGAACGTGTCCGCC CACCGGGACGATGTGAAGCTGACATGCCAGGTGGAACACGACGGCC AGCCTGCCGTGTCCAAGTCCCACGATCTGAAGGTGTCCGCTCATCC CAAAGAGCAGGGCTCCAACACCGCCGCTGAGAACACCGGCTCTAAC GAGCGGAACATCTACATCGTCGTGGGCGTCGTGTGCACCCTGCTGG TGGCTCTGCTGATGGCTGCCCTGTACCTCGTCGGATCCGGCAGAA GAAGGCCCAGGGCTCTACCTCCTCCACCAGACTGCACGAGCCCGAG AAGAACGCCAGAGAGATCACCCAGGACACCAACGACATCACCTACG CCGACCTGAACCTGCCCAAGGGCAAGAAGCCTGCCCCTCAGGCTGC CGAGCCTAACAACCACACCGAGTACGCCTCCATCCAGACCAGCCCT CAGCCTGCCTCTGAGGACACCCTGACCTACGCTGATCTGGACATGG TGCACCTGAACCGGACCCCCAAGCAGCCAGCTCCTAAGCCCGAGCC TAGCTTCTCTGAGTACGCCAGCGTGCAGGTGCCCCGGAAA |
| human SIRPαV5 (amino acid sequence) | 48 | MEPAGPAPGRLGPLLCLLLAASCAWSGVAGEEELQVIQPDKFVLVA AGETATLRCTATSLIPVGPIQWFRGAGPGRELIYNQKEGHFPRVTT VSDLTKRNNMDFSIRIGNITPADAGTYYCVKFRKGSPDDVEFKSGA GTELSVRAKPSAPVVSGPAARATPQHTVSFTCESHGFSPRDITLKW FKNGNELSDFQTNVDPVGESVSYSIHSTAKVVLTREDVHSQVICEV AHVTLQGDPLRGTANLSETIRVPPTLEVTQQPVRAENQVNVTCQVR KFYPQRLQLTWLENGNVSRTETASTVTENKDGTYNWMSWLLVNVSA HRDDVKLTCQVEHDGQPAVSKSHDLKVSAHPKEQGSNTAAENTGSN ERNIYIVVGVVCTLLVALLMAALYLVRIRQKKAQGSTSSTRLHEPE KNAREITQDTNDITYADLNLPKGKKPAPQAAEPNNHTEYASIQTSP QPASEDTLTYADLDMVHLNRTPKQPAPKPEPSFSEYASVQVPRK |

| Description | SEQ ID NO: | SEQUENCE |
|---|---|---|
| human SIRPαV6 (nucleotide sequence) | 49 | ATGGAACCTGCCGGCCCTGCTCCTGGTAGACTGGGACCTCTGCTGT<br>GTCTGCTGCTGGCCGCCTCTTGTGCTTGGAGCGGAGTGGCTGGCGA<br>AGAGGAACTGCAAGTGATCCAGCCCGACAAGTCCGTGCTGGTGGCT<br>GCTGGCGAGACTGCCACCCTGAGATGTACCGCCACCTCCCTGATCC<br>CCGTGGGCCCTATCCAGTGGTTTAGAGGCGCTGGCCCTGGCAGAGA<br>GCTGATCTACAACCAGAAAGAGGGCCACTTCCCCAGAGTGACCACC<br>GTGTCCGACCTGACCAAGCGGAACAACATGGACTTCCCCATCCGGA<br>TCGGCAACATCACCCCTGCCGATGCCGGCACCTACTACTGCGTGAA<br>GTTCCGGAAGGGCTCCCCCGACGACGTGGAGTTCAAATCCGGCGCT<br>GGCACCGAGCTGTCTGTGCGGGCTAAACCTTCTGCCCCTGTGGTGT<br>CTGGCCCTGCCGCTAGAGCTACCCCTCAGCACACCGTGTCTTTTAC<br>CTGCGAGTCCCACGGCTTCAGCCCTCGGGACATCACCCTGAAGTGG<br>TTCAAGAACGGCAACGAGCTGAGCGACTTCCAGACCAACGTGGACC<br>CTGTGGGCGAGTCCGTGTCCTACTCCATCCACTCCACCGCCAAGGT<br>GGTGCTGACACGCGAGGACGTGCACTCCCAAGTGATCTGCGAGGTG<br>GCCCACGTGACACTGCAGGGCGATCCTCTGAGAGGCACCGCCAACC<br>TGTCCGAGACAATCAGAGTGCCCCCCACCCTGGAAGTGACCCAGCA<br>GCCCGTGCGGGCTGAGAACCAAGTGAACGTGACCTGCCAAGTGCGG<br>AAGTTCTACCCCCAGCGGCTGCAGCTGACCTGGCTGGAAAACGGCA<br>ATGTGTCCCGGACCGAGACAGCCTCCACCGTGACCGAGAACAAGGA<br>TGGCACCTACAATTGGATGTCCTGGCTGCTCGTGAACGTGTCCGCC<br>CACCGGGACGATGTGAAGCTGACATGCCAGGTGGAACACGACGGCC<br>AGCCTGCCGTGTCCAAGTCCCACGATCTGAAGGTGTCCGCTCATCC<br>CAAAGAGCAGGGCTCCAACACCGCCGCTGAGAACACCGGCTCTAAC<br>GAGCGGAACATCTACATCGTCGTGGGCGTCGTGTGCACCCTGCTGG<br>TGGCACTGCTGATGGCCGCTCTGTACCTCGTGCGGATCCGGCAGAA<br>GAAGGCCCAGGGCTCTACCTCCTCCACCAGACTGCACGAGCCCGAG<br>AAGAACGCCAGAGAGATCACCCAGGACACCAACGACATCACCTACG<br>CCGACCTGAACCTGCCCAAGGGCAAGAAGCCTGCCCCTCAGGCTGC<br>CGAGCCTAACAACCACACCGAGTACGCCTCCATCCAGACCAGCCCT<br>CAGCCTGCCTCTGAGGACACCCTGACCTACGCTGATCTGGACATGG<br>TGCACCTGAACCGGACCCCCAAGCAGCCAGCTCCTAAGCCCGAGCC<br>TAGCTTCTCTGAGTACGCCAGCGTGCAGGTGCCCCGGAAA |
| human SIRPαV6 (amino acid sequence) | 50 | MEPAGPAPGRLGPLLCLLLAASCAWSGVAGEEELQVIQPDKSVLVA<br>AGETATLRCTATSLIPVGPIQWFRGAGPGRELIYNQKEGHFPRVTT<br>VSDLTKRNNMDFPIRIGNITPADAGTYYCVKFRKGSPDDVEFKSGA<br>GTELSVRAKPSAPVVSGPAARATPQHTVSFTCESHGFSPRDITLKW<br>FKNGNELSDFQTNVDPVGESVSYSIHSTAKVVLTREDVHSQVICEV<br>AHVTLQGDPLRGTANLSETIRVPPTLEVTQQPVRAENQVNVTCQVR<br>KFYPQRLQLTWLENGNVSRTETASTVTENKDGTYNWMSWLLVNVSA<br>HRDDVKLTCQVEHDGQPAVSKSHDLKVSAHPKEQGSNTAAENTGSN<br>ERNIYIVVGVVCTLLVALLMAALYLVRIRQKKAQGSTSSTRLHEPE<br>KNAREITQDTNDITYADLNLPKGKKPAPQAAEPNNHTEYASIQTSP<br>QPASEDTLTYADLDMVHLNRTPKQPAPKPEPSFSEYASVQVPRK |
| human SIRPαV8 (nucleotide sequence) | 51 | ATGGAACCTGCCGGCCCTGCTCCTGGTAGACTGGGACCTCTGCTGT<br>GTCTGCTGCTGGCCGCCTCTTGTGCTTGGAGCGGAGTGGCTGGCGA<br>AGAGGAACTGCAAGTGATCCAGCCCGACAAGTCCGTGCTGGTGGCT<br>GCTGGCGAGACTGCCACCCTGAGATGTACCGCCACCTCCCTGATCC<br>CCGTGGGCCCTATCCAGTGGTTTAGAGGCGCTGGCCCTGCCAGAGA<br>GCTGATCTACAACCAGAAAGAGGGCCACTTCCCCAGAGTGACCACC<br>GTGTCCGAGTCCACCAAGCGCGAGAACATGGACTTCTCCATCTCCA<br>TCAGCAACATCACCCCTGCCGACGCCGGCACCTACTACTGCGTGAA<br>GTTCCGGAAGGGCTCCCCCGACACCGAGTTCAAGTCTGGCGCTGGC<br>ACCGAGCTGTCTGTGCGGGCTAAACCTTCTGCCCCTGTGGTGTCTG<br>GACCTGCCGCTAGAGCTACCCCTCAGCACACCGTGTCTTTTACCTG<br>CGAGTCCCACGGCTTCAGCCCTCGGGACATCACCCTGAAGTGGTTC<br>AAGAACGGCAACGAGCTGAGCGACTTCCAGACCAACGTGGACCCTG<br>TGGGCGAGTCCGTGTCCTACTCCATCCACTCCACCGCCAAGGTGGT<br>GCTGACACGCGAGGACGTGCACTCCCAAGTGATCTGCGAGGTGGCC<br>CACGTGACACTGCAGGGCGATCCTCTGAGAGGCACCGCCAACCTGT<br>CCGAGACAATCAGAGTGCCCCCCACCCTGGAAGTGACCCAGCAGCC<br>CGTGCGGGCTGAGAACCAAGTGAACGTGACCTGCCAAGTGCGGAAG<br>TTCTACCCCCAGCGGCTGCAGCTGACCTGGCTGGAAAACGGCAATG<br>TGTCCCGGACCGAGACAGCCAGCACCGTGACCGAGAACAAGGATGG<br>CACCTACAATTGGATGTCCTGGCTGCTCGTGAACGTGTCCGCCCAC<br>CGGGACGATGTGAAGCTGACATGCCAGGTGGAACACGACGGCCAGC<br>CTGCCGTGTCCAAGTCCCACGATCTGAAGGTGTCCGCTCATCCCAA<br>AGAGCAGGGCTCCAACACCGCCGCTGAGAACACCGGCTCTAACGAG<br>CGGAACATCTACATCGTCGTGGGCGTCGTGTGCACCCTGCTGGTGG<br>CACTGCTGATGGCCGCTCTGTACCTCGTGCGGATCCGGCAGAAGAA<br>GGCCCAGGGCTCTACCTCCTCCACCAGACTGCACGAGCCCGAGAAG<br>AACGCCAGAGAGATCACCCAGGACACCAACGACATCACCTACGCCG<br>ACCTGAACCTGCCCAAGGGCAAGAAGCCTGCCCCTCAGGCTGCCGA |

| Description | SEQ ID NO: | SEQUENCE |
|---|---|---|
| | | GCCTAACAACCACACCGAGTACGCCTCCATCCAGACCAGCCCTCAG<br>CCTGCCTCTGAGGACACCCTGACCTACGCTGATCTGGACATGGTGC<br>ACCTGAACCGGACCCCCAAGCAGCCAGCTCCTAAGCCCGAGCCTAG<br>CTTCTCTGAGTACGCCAGCGTGCAGGTGCCCCGGAAA |
| human SIRPαV8<br>(amino acid sequence) | 52 | MEPAGPAPGRLGPLLCLLLAASCAWSGVAGEEELQVIQPDKSVLVA<br>AGETATLRCTATSLIPVGPIQWFRGAGPARELIYNQKEGHFPRVTT<br>VSESTKRENMDFSISISNITPADAGTYYCVKFRKGSPDTEFKSGAG<br>TELSVRAKPSAPVVSGPAARATPQHTVSFTCESHGFSPRDITLKWF<br>KNGNELSDFQTNVDPVGESVSYSIHSTAKVVLTREDVHSQVICEVA<br>HVTLQGDPLRGTANLSETIRVPPTLEVTQQPVRAENQVNVTCQVRK<br>FYPQRLQLTWLENGNVSRTETASTVTENKDGTYNWMSWLLVNVSAH<br>RDDVKLTCQVEHDGQPAVSKSHDLKVSAHPKEQGSNTAAENTGSNE<br>RNIYIVVGVVCTLLVALLMAALYLVRIRQKKAQGSTSSTRLHEPEK<br>NAREITQDTNDITYADLNLPKGKKPAPQAAEPNNHTEYASIQTSPQ<br>PASEDTLTYADLDMVHLNRTPKQPAPKPEPSFSEYASVQVPRK |
| human SIRPαV9<br>(nucleotide sequence) | 53 | ATGGAACCTGCCGGCCCTGCTCCTGGTAGACTGGGACCTCTGCTGT<br>GTCTGCTGCTGGCCGCCTCTTGTGCTTGGAGCGGAGTGGCTGGCGA<br>AGAGGAACTGCAAGTGATCCAGCCCGACAAGTCCGTGCTGGTGGCT<br>GCTGGCGAGACTGCCACCCTGAGATGTACCGCCACCTCCCTGATCC<br>CCGTGGGCCCTATCCAGTGGTTTAGAGGCGCTGGCCCTGGCAGAGA<br>GCTGATCTACAACCAGAAAGAGGGCCACTTCCCCAGAGTGACCACC<br>GTGTCCGACCTGACCAAGCGGAACAACATGGACTTCTCCATCCGGA<br>TCTCCAACATCACCCCTGCCGACGCCGGCACCTACTACTGCGTGAA<br>GTTCCGGAAGGGCTCCCCCGACGACGTGGAGTTCAAATCCGGCGCT<br>GGCACCGAGCTGTCTGTGCGGGCTAAACCTTCTGCCCCTGTGGTGT<br>CTGGCCCTGCCGCTAGAGCTACCCCTCAGCACACCGTGTCTTTTAC<br>CTGCGAGTCCCACGGCTTCAGCCCTCGGGACATCACCCTGAAGTGG<br>TTCAAGAACGGCAACGAGCTGAGCGACTTCCAGACCAACGTGGACC<br>CTGTGGGCGAGTCCGTGTCCTACTCCATCCACTCCACCGCCAAGGT<br>GGTGCTGACACGCGAGGACGTGCACTCCCAAGTGATCTGCGAGGTG<br>GCCCACGTGACACTGCAGGGCGATCCTCTGAGAGGCACCGCCAACC<br>TGTCCGAGACAATCAGAGTGCCCCCCACCCTGGAAGTGACCCAGCA<br>GCCCGTGCGGGCTGAGAACCAAGTGAACGTGACCTGCCAAGTGCGG<br>AAGTTCTACCCCCAGCGGCTGCAGCTGACCTGGCTGGAAAACGGCA<br>ATGTGTCCCGGACCGAGACAGCCTCCACCGTGACCGAGAACAAGGA<br>TGGCACCTACAATTGGATGTCCTGGCTGCTCGTGAACGTGTCCGCC<br>CACCGGGACGATGTGAAGCTGACATGCCAGGTGGAACACGACGGCC<br>AGCCTGCCGTGTCCAAGTCCCACGATCTGAAGGTGTCCGCTCATCC<br>CAAAGAGCAGGGCTCCAACACCGCCGCTGAGAACACCGGCTCTAAC<br>GAGCGGAACATCTACATCGTCGTGGGCGTCGTGTGCACCCTGCTGG<br>TGGCACTGCTGATGGCCGCTCTGTACCTCGTCGGATCCGGCAGAA<br>GAAGGCCCAGGGCTCTACCTCCTCCACCAGACTGCACGAGCCCGAG<br>AAGAACGCCAGAGAGATCACCCAGGACACCAACGACATCACCTACG<br>CCGACCTGAACCTGCCCAAGGGCAAGAAGCCTGCCCCTCAGGCTGC<br>CGAGCCTAACAACCACACCGAGTACGCCTCCATCCAGACCAGCCCT<br>CAGCCTGCCTCTGAGGACACCCTGACCTACGCTGATCTGGACATGG<br>TGCACCTGAACCGGACCCCCAAGCAGCCAGCTCCTAAGCCCGAGCC<br>TAGCTTCTCTGAGTACGCCAGCGTGCAGGTGCCCCGGAAA |
| human SIRPαV9<br>(amino acid sequence) | 54 | MEPAGPAPGRLGPLLCLLLAASCAWSGVAGEEELQVIQPDKSVLVA<br>AGETATLRCTATSLIPVGPIQWFRGAGPGRELIYNQKEGHFPRVTT<br>VSDLTKRNNMDFSIRISNITPADAGTYYCVKFRKGSPDDVEFKSGA<br>GTELSVRAKPSAPVVSGPAARATPQHTVSFTCESHGFSPRDITLKW<br>FKNGNELSDFQTNVDPVGESVSYSIHSTAKVVLTREDVHSQVICEV<br>AHVTLQGDPLRGTANLSETIRVPPTLEVTQQPVRAENQVNVTCQVR<br>KFYPQRLQLTWLENGNVSRTETASTVTENKDGTYNWMSWLLVNVSA<br>HRDDVKLTCQVEHDGQPAVSKSHDLKVSAHPKEQGSNTAAENTGSN<br>ERNIYIVVGVVCTLLVALLMAALYLVRIRQKKAQGSTSSTRLHEPE<br>KNAREITQDTNDITYADLNLPKGKKPAPQAAEPNNHTEYASIQTSP<br>QPASEDTLTYADLDMVHLNRTPKQPAPKPEPSFSEYASVQVPRK |
| hSIRPαa-VβC1αC2α<br>(nucleotide sequence) | 55 | ATGGAACCTGCCGGCCCTGCTCCTGGTAGACTGGGACCTCTGCTGT<br>GTCTGCTGCTGGCCGCCTCTTGTGCTTGGAGCGGAGTGGCTGGCGA<br>GGACGAGCTGCAAGTGATCCAGCCCGAGAAGTCCGTGTCTGTGGCC<br>GCTGGCGAGTCTGCCACCCTGAGATGCGCTATGACCTCCCTGATCC<br>CCGTGGGCCCCATCATGTGGTTTAGAGGCGCTGGCGCTGGCAGAGA<br>GCTGATCTACAACCAGAAAGAGGGCCACTTCCCCAGAGTGACCACC<br>GTGTCCGAGCTGACCAAGCGGAACAACCTGGACTTCTCCATCTCCA<br>TCAGCAACATCACCCCTGCCGACGCCGGCACCTACTACTGCGTGAA<br>GTTCCGGAAGGGCTCCCCCGACGACGTGGAGTTCAAATCCGGCGCT<br>GGAACCGAGCTGTCCGTGCGGGCTAAACCTTCTGCCCCTGTGGTGT<br>CTGGCCCTGCCGCTAGAGCTACCCCTCAGCACACCGTGTCTTTTAC<br>CTGCGAGTCCCACGGCTTCAGCCCTCGGGACATCACCCTGAAGTGG<br>TTCAAGAACGGCAACGAGCTGAGCGACTTCCAGACCAACGTGGACC |

| Description | SEQ ID NO: | SEQUENCE |
|---|---|---|
| | | CTGTGGGCGAGAGCGTGTCCTACTCCATCCACTCCACCGCCAAGGT GGTGCTGACACGCGAGGACGTGCACTCCCAAGTGATCTGCGAGGTG GCCCACGTGACACTGCAGGGCGATCCTCTGAGAGGCACCGCCAACC TGTCCGAGACAATCAGAGTGCCCCCCACCCTGGAAGTGACCCAGCA GCCTGTGCGGGCCGAGAACCAAGTGAACGTGACCTGCCAAGTGCGG AAGTTCTACCCCCAGCGGCTGCAGCTGACCTGGCTGGAAAACGGCA ATGTGTCCCGGACCGAGACAGCCAGCACCGTGACCGAGAACAAGGA TGGCACCTACAATTGGATGTCCTGGCTGCTCGTGAACGTGTCCGCC CACCGGGACGATGTGAAGCTGACATGCCAGGTGGAACACGACGGCC AGCCTGCCGTGTCCAAGTCCCACGATCTGAAGGTGTCCGCTCATCC CAAAGAGCAGGGCTCCAACACCGCCGCTGAGAACACCGGCTCTAAC GAGCGGAACATCTACATCGTCGTGGGCGTCGTGTGCACCCTGCTGG TGGCTCTGCTGATGGCTGCCCTGTACCTCGTGCGGATCCGGCAGAA GAAGGCCCAGGGCTCTACCTCCTCCACCAGACTGCACGAGCCTGAG AAGAACGCCAGAGAGATCACCCAGGACACCAACGACATCACCTACG CCGACCTGAACCTGCCCAAGGGCAAGAAGCCTGCCCCTCAGGCCGC CGAGCCTAACAACCACACCGAGTACGCCTCCATCCAGACCAGCCCT CAGCCTGCCTCTGAGGACACCCTGACCTACGCTGATCTGGACATGG TGCACCTGAACCGGACCCCCAAGCAGCCAGCTCCTAAGCCCGAGCC TAGCTTCTCTGAGTACGCCAGCGTGCAGGTGCCCCGGAAA |
| hSIRPα-VβC1αC2α (amino acid sequence) | 56 | MEPAGPAPGRLGPLLCLLLAASCAWSGVAGEDELQVIQPEKSVSVA AGESATLRCAMTSLIPVGPIMWFRGAGAGRELIYNQKEGHFPRVTT VSELTKRNNLDFSISISNITPADAGTYYCVKFRKGSPDDVEFKSGA GTELSVRAKPSAPVVSGPAARATPQHTVSFTCESHGFSPRDITLKW FKNGNELSDFQTNVDPVGESVSYSIHSTAKVVLTREDVHSQVICEV AHVTLQGDPLRGTANLSETIRVPPTLEVTQQPVRAENQVNVTCQVR KEYPQRLQLTWLENGNVSRTETASTVTENKDGTYNWMSWLLVNVSA HRDDVKLTCQVEHDGQPAVSKSHDLKVSAHPKEQGSNTAAENTGSN ERNIYIVVGVVCTLLVALLMAALYLVRIRQKKAQGSTSSTRLHEPE KNAREITQDTNDITYADLNLPKGKKPAPQAAEPNNHTEYASIQTSP QPASEDTLTYADLDMVHLNRTPKQPAPKPEPSFSEYASVQVPRK |
| hSIRPα-VαC1βC2α (nucleotide sequence) | 57 | ATGGAACCTGCCGGCCCTGCTCCTGGTAGACTGGGACCTCTGCTGT GTCTGCTGCTGGCCGCCTCTTGTGCTTGGAGCGGAGTGGCTGGCGA AGAGGAACTGCAAGTGATCCAGCCCGACAAGTCCGTGCTGGTGGCT GCTGGCGAGACTGCCACCCTGAGATGTACCGCCACCTCCCTGATCC CCGTGGGCCCTATCCAGTGGTTTAGAGGCGCTGGCCCTGGCAGAGA GCTGATCTACAACCAGAAAGAGGGCCACTTCCCCAGAGTGACCACC GTGTCCGACCTGACCAAGCGGAACAACATGGACTTCTCCATCCGGA TCGGCAACATCACCCCTGCCGATGCCGGCACCTACTACTGCGTGAA GTTCCGGAAGGGCTCCCCCGACGACGTGGAGTTCAAATCCGGCGCT GGCACCGAGCTGTCTGTGCGGGCTAAACCTTCTGCCCCCGTGGTGT CTGGACCTGCCGGTGCGAGCTACCCCTGAGCACACCGTGTCTTTTAC CTGCGAGTCCCACGGCTTCAGCCCTCGGGACATCACCCTGAAGTGG TTCAAGAACGGCAACGAGCTGAGCGACTTCCAGACCAACGTGGACC CAGCCGGCGACTCCGTGTCCTACTCCATCCACTCTACCGCCAGAGT GGTGCTGACCAGAGGCGACGTGCACTCCCAAGTGATCTGCGAGATC GCCCATATCACACTGCAGGGCGACCCCCTGAGAGGCACCGCTAACC TGTCTGAGACAATCCGGGTGCCCCCCACCCTGGAAGTGACTCAGCA GCCAGTGCGGGCCGAGAACCAAGTGAACGTGACCTGCCAAGTGCGG AAGTTCTACCCCCAGCGGCTGCAGCTGACCTGGCTGGAAAACGGCA ATGTGTCCCGGACCGAGACAGCCTCCACCGTGACCGAGAACAAGGA TGGCACCTACAATTGGATGTCTTGGCTGCTCGTGAACGTGTCCGCC CACCGGGACGATGTGAAGCTGACATGCCAGGTGGAACACGACGGCC AGCCTGCCGTGTCCAAGTCCCACGATCTGAAGGTGTCCGCTCATCC CAAAGAGCAGGGCTCCAACACCGCCGCTGAGAACACCGGCTCTAAC GAGCGGAACATCTACATCGTCGTGGGCGTCGTGTGCACCCTGCTGG TGGCACTGCTGATGGCCGCTCTGTACCTCGTGCGGATCCGGCAGAA GAAGGCCCAGGGCTCTACCTCCTCCACCAGACTGCACGAGCCCGAG AAGAACGCCAGAGAGATCACCCAGGACACCAACGACATCACCTACG CCGACCTGAACCTGCCCAAGGGCAAGAAGCCTGCCCCTCAGGCCGC CGAGCCTAACAACCACACCGAGTACGCCTCCATCCAGACCAGCCCT CAGCCTGCCTCTGAGGACACCCTGACCTACGCTGATCTGGACATGG TGCACCTGAACCGGACCCCCAAGCAGCCAGCTCCTAAGCCCGAGCC TAGCTTCTCTGAGTACGCCAGCGTGCAGGTGCCCCGGAAA |
| hSIRPα-VαC1βC2α (amino acid sequence) | 58 | MEPAGPAPGRLGPLLCLLLAASCAWSGVAGEEELQVIQPDKSVLVA AGETATLRCTATSLIPVGPIQWFRGAGPGRELIYNQKEGHFPRVTT VSDLTKRNNMDFSIRIGNITPADAGTYYCVKFRKGSPDDVEFKSGA GTELSVRAKPSAPVVSGPAVRATPEHTVSFTCESHGFSPRDITLKW FKNGNELSDFQTNVDPAGDSVSYSIHSTARVVLTRGDVHSQVICEI AHITLQGDPLRGTANLSETIRVPPTLEVTQQPVRAENQVNVTCQVR KFYPQRLQLTWLENGNVSRTETASTVTENKDGTYNWMSWLLVNVSA HRDDVKLTCQVEHDGQPAVSKSHDLKVSAHPKEQGSNTAAENTGSN ERNIYIVVGVVCTLLVALLMAALYLVRIRQKKAQGSTSSTRLHEPE |

| Description | SEQ ID NO: | SEQUENCE |
|---|---|---|
| | | KNAREITQDTNDITYADLNLPKGKKPAPQAAEPNNHTEYASIQTSP QPASEDTLTYADLDMVHLNRTPKQPAPKPEPSFSEYASVQVPRK |
| hSIRPα-VαC1αC2β (nucleotide sequence) | 59 | ATGGAACCTGCCGGCCCTGCTCCTGGTAGACTGGGACCTCTGCTGT GTCTGCTGCTGGCCGCCTCTTGTGCTTGGAGCGGAGTGGCTGGCGA AGAGGAACTGCAAGTGATCCAGCCCGACAAGTCCGTGCTGGTGGCT GCTGGCGAGACTGCCACCCTGAGATGTACCGCCACCTCCCTGATCC CCGTGGGCCCTATCCAGTGGTTTAGAGGCGCTGGCCCTGGCAGAGA GCTGATCTACAACCAGAAAGAGGGCCACTTCCCCAGAGTGACCACC GTGTCCGACCTGACCAAGCGGAACAACATGGACTTCTCCATCCGGA TCGGCAACATCACCCCTGCCGATGCCGGCACCTACTACTGCGTGAA GTTCCGGAAGGGCTCCCCCGACGACGTGGAGTTCAAATCCGGCGCT GGCACCGAGCTGTCTGTGCGGGCTAAACCTTCTGCCCCTGTGGTGT CTGGCCCTGCCGCTAGAGCTACCCCTCAGCACACCGTGTCTTTTAC CTGCGAGTCCCACGGCTTCAGCCCTCGGGACATCACCCTGAAGTGG TTCAAGAACGGCAACGAGCTGAGCGACTTCCAGACCAACGTGGACC CTGTGGGCGAGTCCGTGTCCTACTCCATCCACTCCACCGCCAAGGT GGTGCTGACACGCGAGGACGTGCACTCCCAGTGATCTGCGAGGTG GCCCACGTGACACTGCAGGGCGATCCTCTGAGAGGCACCGCCAACC TGTCCGAGACAATCAGAGTGCCCCCCACCCTGGAAGTGACCCAGCA GCCTATGAGAGCCGAGAACCAGGCCAACGTGACCTGCCAGGTGTCC AACTTCTACCCTCGGGGCCTGCAGCTGACCTGGCTGGAAAACGGCA ATGTGTCCCGGACCGAGACAGCCTCCACCCTGATCGAGAACAAGGA TGGCACCTACAATTGGATGTCCTGGCTGCTCGTGAACACCTGTGCC CACCGGGACGATGTGGTGCTGACCTGTCAGGTGGAACACGATGGCC AGCAGGCCGTGTCCAAGTCCTACGCTCTGGAAGTGTCCGCCCACCC CAAAGAGCAGGGCTCTAATACCGCCGCTGAGAACACCGGCTCCAAC GAGCGGAACATCTACATCGTCGTGGGCGTCGTGTGCACCCTGCTGG TGGCACTGCTGATGGCCGCTCTGTACCTCGTGCGGATCCGGCAGAA GAAGGCTCAGGGCTCCACCTCCTCCACCAGACTGCACGAGCCTGAG AAGAACGCCAGAGAGATCACCCAGGACACCAACGACATCACCTACG CCGACCTGAACCTGCCCAAGGGCAAGAAGCCTGCCCCTCAGGCTGC CGAGCCTAACAACCACACCGAGTACGCCTCCATCCAGACCAGCCCT CAGCCTGCCTCTGAGGACACCCTGACCTACGCTGATCTGGACATGG TGCACCTGAACCGGACCCCCAAGCAGCCAGCTCCTAAGCCCGAGCC TAGCTTCTCTGAGTACGCCAGCGTGCAGGTGCCCCGGAAA |
| hSIRPα-VαC1αC2β (amino acid sequence) | 60 | MEPAGPAPGRLGPLLCLLLAASCAWSGVAGEEELQVIQPDKSVLVA AGETATLRCTATSLIPVGPIQWFRGAGPGRELIYNQKEGHFPRVTT VSDLTKRNNMDFSIRIGNITPADAGTYYCVKFRKGSPDDVEFKSGA GTELSVRAKPSAPVVSGPAARATPQHTVSFTCESHGFSPRDITLKW FKNGNELSDFQTNVDPVGESVSYSIHSTAKVVLTREDVHSQVICEV AHVTLQGDPLRGTANLSETIRVPPTLEVTQQPMRAENQANVTCQVS NFYPRGLQLTWLENGNVSRTETASTLIENKDGTYNWMSWLLVNTCA HRDDVVLTCQVEHDGQQAVSKSYALEVSAHPKEQGSNTAAENTGSN ERNIYIVVGVVCTLLVALLMAALYLVRIRQKKAQGSTSSTRLHEPE KNAREITQDTNDITYADLNLPKGKKPAPQAAEPNNHTEYASIQTSP QPASEDTLTYADLDMVHLNRTPKQPAPKPEPSFSEYASVQVPRK |
| human SIRPαV1(P74A) (nucleotide sequence) | 61 | ATGGAGCCCGCCGGCCCGGCCCCGGCCGCCTCGGGCCGCTGCTCT GCCTGCTGCTCGCCGCGTCCTGCGCCTGGTCAGGAGTGGCGGGTGA GGAGGAGCTGCAGGTGATTCAGCCTGACAAGTCCGTGTTGGTTGCA GCTGGAGAGACAGCCACTCTGCGCTGCACTGCGACCTCTCTGATCC CTGTGGGGCCCATCCAGTGGTTCAGAGGAGCTGGA:CAGGCCGGGA ATTAATCTACAATCAAAAGAAGGCCACTTCCCCGGGTAACAACT GTTTCAGACCTCACAAAGAGAAACATGGACTTTTCCATCCGCA TCGGTAACATCACCCCAGCAGATGCCGGCACCTACTACTGTGTGAA GTTCCGGAAAGGGAGCCCCGATGACGTGGAGTTTAAGTCTGGAGCA GGCACTGAGCTGTCTGTGCGCGCCAAACCCTCTGCCCCCGTGGTAT CGGGCCCTGCGGCGAGGGCCACACCTCAGCACACAGTGAGCTTCAC CTGCGAGTCCCACGGCTTCTCACCCAGAGACATCACCCTGAAATGG TTCAAAAATGGGAATGAGCTCTCAGACTTCCAGACCAACGTGGACC CCGTAGGAGAGAGCGTGTCCTACAGCATCCACAGCACAGCCAAGGT GGTGCTGACCCGCGAGGACGTTCACTCTCAAGTCATCTGCGAGGTG GCCCACGTCACCTTGCAGGGGGACCCTCTTCGTGGGACTGCCAACT TGTCTGAGACCATCCGAGTTCCACCCACCTTGGAGGTTACTCAACA GCCCGTGAGGGCAGAGAACCAGGTGAATGTCACCTGCCAGGTGAGG AAGTTCTACCCCAGAGACTACAGCTGACCTGGTTGGAGAATGGAA ACGTGTCCCGGACAGAAACGGCCTCAACCGTTACAGAGAACAAGGA TGGTACCTACAACTGGATGAGCTGGCTCCTGGTGAATGTATCTGCC CACAGGGATGATGTGAAGCTCACCTGCCAGGTGGAGCATGACGGGC AGCCAGCGGTCAGCAAAAGCCATGACCTGAAGGTCTCAGCCCACCC GAAGGAGCAGGGCTCAAATACCGCCGCTGAGAACACTGGATCTAAT GAACGGAACATCTATATTGTGGTGGGTGTGGTGTGCACCTTGCTGG TGGCCCTACTGATGGCGGCCCTCTACCTCGTCCGAATCAGACAGAA GAAAGCCCAGGGCTCCACTTCTTCTACAAGGTTGCATGAGCCCGAG |

| Description | SEQ ID NO: | SEQUENCE |
|---|---|---|
| | | AAGAATGCCAGAGAAATAACACAGGACACAAATGATATCACATATG<br>CAGACCTGAACCTGCCCAAGGGGAAGAAGCCTGCTCCCCAGGCTGC<br>GGAGCCCAACAACCACACGGAGTATGCCAGCATTCAGACCAGCCCG<br>CAGCCCGCGTCGGAGGACACCCTCACCTATGCTGACCTGGACATGG<br>TCCACCTCAACCGGACCCCCAAGCAGCCGGCCCCCAAGCCTGAGCC<br>GTCCTTCTCAGAGTACGCCAGCGTCCAGGTCCCGAGGAAG |
| human<br>SIRPαV1(P74A)<br>(amino acid sequence) | 62 | MEPAGPAPGRLGPLLCLLLAASCAWSGVAGEEELQVIQPDKSVLVA<br>AGETATLRCTATSLIPVGPIQWFRGAGAGRELIYNQKEGHFPRVTT<br>VSDLTKRNNMDFSIRIGNITPADAGTYYCVKFRKGSPDDVEFKSGA<br>GTELSVRAKPSAPVVSGPAARATPQHTVSFTCESHGFSPRDITLKW<br>FKNGNELSDFQTNVDPVGESVSYSIHSTAKVVLTREDVHSQVICEV<br>AHVTLQGDPLRGTANLSETIRVPPTLEVTQQPVRAENQVNVTCQVR<br>KFYPQRLQLTWLENGNVSRTETASTVTENKDGTYNWMSWLLVNVSA<br>HRDDVKLTCQVEHDGQPAVSKSHDLKVSAHPKEQGSNTAAENTGSN<br>ERNIYIVVGVVCTLLVALLMAALYLVRIRQKKAQGSTSSTRLHEPE<br>KNAREITQDTNDITYADLNLPKGKKPAPQAAEPNNHTEYASIQTSP<br>QPASEDTLTYADLDMVHLNRTPKQPAPKPEPSFSEYASVQVPRK |
| human kappa constant<br>domain (nucleotide<br>sequence) | 63 | CGGACCGTGGCCGCTCCCTCCGTGTTCATCTTCCCACCTTCCGACG<br>AGCAGCTGAAGTCCGGCACCGCTTCTGTCGTGTGCCTGCTGAACAA<br>CTTCTACCCCCGCGAGGCCAAGGTGCAGTGGAAGGTGGACAACGCC<br>CTGCAGTCCGGCAACTCCCAGGAATCCGTGACCGAGCAGGACTCCA<br>AGGACAGCACCTACTCCCTGTCCTCCACCCTGACCCTGTCCAAGGC<br>CGACTACGAGAAGCACAAGGTGTACGCCTGCGAAGTGACCCACCAG<br>GGCCTGTCTAGCCCTGTGACCAAGTCCTTCAACCGGGGCGAGTGC |
| human kappa constant<br>domain (protein<br>sequence) | 64 | RTVAAPSVFIFPPSDEQLKSGTASVVCLLNNFYPREAKVQWKVDNA<br>LQSGNSQESVTEQDSKDSTYSLSSTLTLSKADYEKHKVYACEVTHQ<br>GLSSPVTKSFNRGEC |
| human IgG4 constant<br>domains (including<br>S228P)<br>(nucleotide sequence) | 65 | GCTTCCACCAAGGGCCCCTCCGTGTTTCCTCTGGCCCCTTGCTCCA<br>GATCCACCTCCGAGTCTACCGCCGCTCTGGGCTGCCTCGTGAAGGA<br>CTACTTCCCCGAGCCTGTGACAGTGTCCTGGAACTCTGGCGCCCTG<br>ACCTCTGGCGTGCACACCTTTCCAGCTGTGCTGCAGTCCTCCGGCC<br>TGTACTCCCTGTCCAGCGTCGTGACAGTGCCCTCCAGCTCTCTGGG<br>CACCAAGACCTACACCTGTAACGTGGACCACAAGCCCTCCAACACC<br>AAGGTGGACAAGCGGGTGGAATCTAAGTACGGCCCTCCCTGCCCTC<br>CTTGCCCAGCCCCTGAATTTCTGGGCGGACCTTCTGTGTTTCTGTT<br>CCCCCCAAAGCCCAAGGACACCCTGATGATCTCCCGGACCCCCGAA<br>GTGACCTGCGTGGTGGTGGATGTGTCCCAGGAAGATCCCGAGGTGC<br>AGTTCAATTGGTACGTGGACGGCGTGGAAGTGCACAACGCCAAGAC<br>CAAGCCTAGAGAGGAACAGTTCAACTCCACCTACCGGGTGGTGTCC<br>GTGCTGACCGTGCTGCACCAGGATTGGCTGAACGGCAAGAGTACA<br>AGTGCAAGGTGTCCAACAAGGGCCTGCCCAGCTCCATCGAAAAGAC<br>CATCTCCAAGGCCAAGGGCCAGCCCCGGGAACCCCAGGTGTACACA<br>CTGCCTCCAAGCCAGGAAGAGATGACCAAGAACCAGGTGTCCCTGA<br>CCTGTCTCGTGAAAGGCTTCTACCCCTCCGATATCGCCGTGGAATG<br>GGAGTCCAACGGCCAGCCTGAGAACAACTACAAGACCACCCCCCCT<br>GTGCTGGACTCCGACGGCTCCTTCTTTCTGTACTCTCGCCTGACCG<br>TGGACAAGTCCCGGTGGCAGGAAGGCAACGTGTTCTCCTGCAGCGT<br>GATGCACGAGGCCCTGCACAACCACTACACCCAGAAGTCCCTGTCC<br>CTGTCTCTGGGAAAA |
| human IgG4 constant<br>domains (including<br>S228P)<br>(protein sequence) | 66 | ASTKGPSVFPLAPCSRSTSESTAALGCLVKDYFPEPVTVSWNSGAL<br>TSGVHTFPAVLQSSGLYSLSSVVTVPSSSLGTKTYTCNVDHKPSNT<br>KVDKRVESKYGPPCPPCPAPEFLGGPSVFLFPPKPKDTLMISRTPE<br>VTCVVVDVSQEDPEVQFNWYVDGVEVHNAKTKPREEQFNSTYRVVS<br>VLTVLHQDWLNGKEYKCKVSNKGLPSSIEKTISKAKGQPREPQVYT<br>LPPSQEEMTKNQVSLTCLVKGFYPSDIAVEWESNGQPENNYKTTPP<br>VLDSDGSFFLYSRLTVDKSRWQEGNVFSCSVMHEALHNHYTQKSLS<br>LSLGK |
| human IgG2 constant<br>domains (nucleotide<br>sequence) | 67 | GCTTCTACAAAGGGCCCCAGCGTGTTCCCTCTGGCTCCTTGTAGCA<br>GAAGCACCAGCGAGTCTACAGCCGCTCTGGGCTGTCTGGTCAAGGA<br>CTACTTTCCCGAGCCTGTGACCGTGTCCTGGAATAGCGGAGCACTG<br>ACAAGCGGCGTGCACACCTTTCCAGCTGTGCTGCAAAGCTCCGGCC<br>TGTACTCTCTGTCCAGCGTGGTCACAGTGCCCAGCAGCAATTTTGG<br>CACCCAGACCTACACCTGTAATGTGGACCACAAGCCTAGCAACACC<br>AAGGTGGACAAGACCGTGGAACGGAAGTGCTGCGTGGAATGCCCTC<br>CTTGTCCTGCTCCTCCAGTGGCTGGCCCTTCCGTGTTTCTGTTCCC<br>TCCAAAGCCTAAGGACACCCTGATGATCAGCAGAACCCCTGAAGTG<br>ACCTGCGTGGTGGTGGATGTGTCCCACGAGGATCCTGAGGTGCAGT<br>TCAATTGGTACGTGGACGGCGTGGAAGTGCACAACGCCAAGACCAA<br>GCCTAGAGAGGAACAGTTCAACAGCACCTTCAGAGTGGTGTCCGTG<br>CTGACCGTGGTGCATCAGGATTGGCTGAACGGCAAAGAGTACAAGT |

| Description | SEQ ID NO: | SEQUENCE |
|---|---|---|
| | | GCAAGGTGTCCAACAAGGGCCTGCCTGCTCCTATCGAGAAAACCAT<br>CAGCAAGACCAAAGGCCAGCCTCGCGAGCCCCAGGTTTACACACTT<br>CCTCCAAGCCGGGAAGAGATGACCAAGAACCAGGTGTCCCTGACCT<br>GCCTCGTGAAGGGCTTCTACCCCAGCGACATCX$_1$CCGTGGAATGGG<br>AGAGCAATGGCCAGCCTGAGAACAACTACAAGACCACACCTCCTAT<br>GCTGGACTCCGACGGCTCATTCTTCCTGTACAGCAAGCTGACAGTG<br>GACAAGTCCAGATGGCAGCAGGGCAACGTGTTCTCCTGCAGCGTGA<br>TGCACGAGGCCCTGCACAACCACTACACCCAGAAGTCCCTGTCTCT<br>GAGCCCCGGCAAA<br>wherein:<br>X$_1$ = G, T |
| human IgG2 constant domains (protein sequence) | 68 | ASTKGPSVFPLAPCSRSTSESTAALGCLVKDYFPEPVTVSWNSGAL<br>TSGVHTFPAVLQSSGLYSLSSVVTVPSSNFGTQTYTCNVDHKPSNT<br>KVDKTVERKCCVECPPCPAPPVAGPSVFLFPPKPKDTLMISRTPEV<br>TCVVVDVSHEDPEVQFNWYVDGVEVHNAKTKPREEQFNSTFRVVSV<br>LTVVHQDWLNGKEYKCKVSNKGLPAPIEKTISKTKGQPREPQVYTL<br>PPSREEMTKNQVSLTCLVKGFYPSDIX$_1$VEWESNGQPENNYKTTPP<br>MLDSDGSFFLYSKLTVDKSRWQQGNVFSCSVMHEALHNHYTQKSLS<br>LSPGK<br>wherein:<br>X$_1$ = A, S |
| 40A heavy chain CDR1 (amino acid sequence) | 69 | SYWMH |
| 40A heavy chain CDR2 (amino acid sequence) | 70 | AIYPVNNDTTYNQKFKG |
| 40A heavy chain CDR3 (amino acid sequence) | 71 | SFYYSLDAAWFVY |
| 40A light chain CDR1 (amino acid sequence) | 72 | RASQDIGSRLN |
| 40A light chain CDR2 (amino acid sequence) | 73 | ATSSLDS |
| 40A light chain CDR3 (amino acid sequence) | 74 | LQYASSPFT |
| humanized 40 heavy chain variable region (consensus sequence) | 75 | EVQX$_1$X$_2$QSGAX$_3$X$_4$X$_5$KPGASVKX$_6$CKASGSTFTSYWMHWVX$_7$QX$_8$<br>PGQGLEWX$_9$GAIYPVNSDTTYNQKFKGX$_{10}$X$_{11}$TX$_{12}$TVX$_{13}$X$_{14}$SX$_{15}$S<br>TX$_{16}$YMX$_{17}$LSSLX$_{18}$X$_{19}$EDX$_{20}$AVYYCX$_{21}$RSFYYSLDAAWFVYWGQG<br>TX$_{22}$X$_{23}$TVSS<br>wherein:<br>X$_1$ = F, L<br>X$_2$ = Q, R, V<br>X$_3$ = E, V<br>X$_4$ = L, V<br>X$_5$ = A, K, V<br>X$_6$ = L, M, V<br>X$_7$ = K, R<br>X$_8$ = A, R, T<br>X$_9$ = I, M<br>X$_{10}$ = K, R<br>X$_{11}$ = A, V<br>X$_{12}$ = L, M<br>X$_{13}$ = D, V<br>X$_{14}$ = K, T<br>X$_{15}$ = A, S, T<br>X$_{16}$ = A, V<br>X$_{17}$ = E, Q<br>X$_{18}$ = R, T<br>X$_{19}$ = F, S<br>X$_{20}$ = S, T<br>X$_{21}$ = A, T<br>X$_{22}$ = L, T<br>X$_{23}$ = L, V |
| humanized 40 light chain variable region (consensus sequence) | 76 | DIQMTQSPSSLSASX$_1$GX$_2$RVX$_3$ITCRASQDIGSRLNWLQQX$_4$PGKA<br>X$_5$KRLIYATSSLDSGVPX$_6$RFSGSX$_7$SGX$_8$X$_9$X$_{10}$X$_{11}$LTISX$_{12}$LQPE<br>DFATYYCLQYASSPFTFGX$_{13}$GTKX$_{14}$EIX$_{15}$ |

| Description | SEQ ID NO: | SEQUENCE |
|---|---|---|
| | | wherein:<br>$X_1$ = L, V<br>$X_2$ = D, E<br>$X_3$ = S, T<br>$X_4$ = K, T<br>$X_5$ = I, P<br>$X_6$ = K, S<br>$X_7$ = G, R<br>$X_8$ = S, T<br>$X_9$ = D, E<br>$X_{10}$ = F, Y<br>$X_{11}$ = S, T<br>$X_{12}$ = G, S<br>$X_{13}$ = G, Q<br>$X_{14}$ = L, V<br>$X_{15}$ = H, K |
| hSIRPα.40AVH1 (nucleotide sequence) | 77 | GAGGTGCAGTTCTTGCAGTCTGGTGCCGTGCTGGCTAGACCTGGAA<br>CCTCCGTGAAGATCTCCTGCAAGGCCTCCGGCTCCACCTTCACCTC<br>TTACTGGATGCACTGGGTCAAGCAGAGGCCTGGACAGGGACTCGAA<br>TGGATCGGCGCTCTGTACCCTGTGAACTCCGACACCACCTACAACC<br>AGAAGTTCAAGGGCAGAGCCAAGCTGACCGTGGCCACCTCTGCTTC<br>TATCGCCTACCTGGAATTTTCCAGCCTGACCAACGAGGACTCCGCC<br>GTGTACTACTGCGCCCGGTCCTTCTACTACTCTCTGGACGCCGCTT<br>GGTTTGTGTACTGGGGCCAGGGAACTCTGGTGACCGTGTCCTCT |
| hSIRPα.40AVH1 (amino acid sequence) | 78 | EVQFLQSGAVLARPGTSVKISCKASGSTFTSYWMHWVKQRPGQGLE<br>WIGALYPVNSDTTYNQKFKGRAKLTVATSASIAYLEFSSLTNEDSA<br>VYYCARSFYYSLDAAWFVYWGQGTLVTVSS |
| hSIRPα.40AVH2 (nucleotide sequence) | 79 | GAGGTGCAGCTGGTTCAGTCTGGCGCTGAGGTTGTGAAGCCTGGCG<br>CTTCCGTGAAGCTGTCCTGCAAGGCTTCTGGCTCCACCTTCACCAG<br>CTACTGGATGCACTGGGTCAAGCAGGCCCCTGGACAAGGCCTGGAA<br>TGGATCGGCGCTATCTACCCCGTGAACTCCGACACCACCTACAACC<br>AGAAGTTCAAGGGCAAAGCTACCCTGACCGTGGACAAGTCTGCCTC<br>CACCGCCTACATGGAACTGTCCAGCCTGAGATCTGAGGACACCGCC<br>GTGTACTACTGCACCCGGTCCTTCTACTACTCCCTGGACGCCGCTT<br>GGTTTGTGTATTGGGGCCAGGGAACACTGGTGACCGTGTCCTCT |
| hSIRPα.40AVH2 (amino acid sequence) | 80 | EVQLVQSGAEVVKPGASVKLSCKASGSTFTSYWMHWVKQAPGQGLE<br>WIGAIYPVNSDTTYNQKFKGKATLTVDKSASTAYMELSSLRSEDTA<br>VYYCTRSFYYSLDAAWFVYWGQGTLVTVSS |
| hSIRPα.40AVH3 (nucleotide sequence) | 81 | GAGGTGCAGCTGAGACAGTCTGGCGCTGTGCTTGTGAAGCCTGGCG<br>CCTCCGTGAAGATGTCCTGCAAGGCTTCTGGCTCCACCTTCACCAG<br>CTACTGGATGCACTGGGTCAAGCAGACCCCTGGACAGGGACTCGAG<br>TGGATCGGCGCTATCTACCCTGTGAACTCCGACACCACCTACAACC<br>AGAAGTTCAAGGGCAAAGCTACCCTGACCGTGGACAAGTCCTCCTC<br>CACCGCTTACATGCAGCTGTCCAGCCTGACCTCTGAGGACTCCGCC<br>GTGTACTACTGCGCCCGGTCCTTCTACTACTCTCTGGACGCCGCTT<br>GGTTTGTGTACTGGGGCCAGGGCACAACCCTGACAGTGTCCTCT |
| hSIRPα.40AVH3 (amino acid sequence) | 82 | EVQLRQSGAVLVKPGASVKMSCKASGSTFTSYWMHWVKQTPGQGLE<br>WIGAIYPVNSDTTYNQKFKGKATLTVDKSSSTAYMQLSSLTSEDSA<br>VYYCARSFYYSLDAAWFVYWGQGTTLTVSS |
| hSIRPα.40AVH4 (nucleotide sequence) | 83 | GAGGTGCAGTTCGTTCAGTCTGGCGCCGAAGTGAAGAAACCTGGCG<br>CCTCTGTGAAGGTGTCCTGCAAGGCTTCTGGCTCCACCTTCACCAG<br>CTACTGGATGCACTGGGTCCGACAGGCTCCAGGACAAGGCTTGGAA<br>TGGATGGGCGCTATCTACCCCGTGAACTCCGACACCACCTACAACC<br>AGAAATTCAAGGGCAGAGTGACCATGACCGTCGTGACCTCCACCTC<br>CACCGTGTACATGGAACTGTCCAGCCTGAGATCCGAGGACACCGCC<br>GTGTACTACTGCGCCCGGTCCTTCTACTACTCTCTGGACGCCGCTT<br>GGTTTGTGTACTGGGGCCAGGGAACTCTGGTGACCGTGTCCTCT |
| hSIRPα.40AVH4 (amino acid sequence) | 84 | EVQFVQSGAEVKKPGASVKVSCKASGSTFTSYWMHWVRQAPGQGLE<br>WMGAIYPVNSDTTYNQKFKGRVTMTVVTSTSTVYMELSSLRSEDTA<br>VYYCARSFYYSLDAAWFVYWGQGTLVTVSS |
| hSIRPα.40AVH5 (nucleotide sequence) | 85 | GAGGTCCAGCTGCAACAGTCTGGTGCCGTGTTGGCTAAGCCTGGCG<br>CCTCCGTGAAGATGTCCTGCAAGGCTTCTGGCTCCACCTTCACCAG<br>CTACTGGATGCACTGGGTCAAGCAGAGGCCTGGACAGGGACTCGAG<br>TGGATCGGCGCTATCTACCCTGTGAACTCCGACACCACCTACAACC<br>AGAAGTTCAAGGGCAAAGCTACCCTGACCGTGGACAAGTCCTCCTC |

| Description | SEQ ID NO: | SEQUENCE |
|---|---|---|
| | | CACCGCTTACATGCAGCTGTCCAGCCTGACCTTCGAGGACTCCGCC<br>GTGTACTACTGCGCCCGGTCCTTCTACTACTCTCTGGACGCCGCTT<br>GGTTTGTGTACTGGGGCCAGGGCACAACCCTGACAGTGTCCTCT |
| hSIRPα.40AVH5<br>(amino acid sequence) | 86 | EVQLQQSGAVLAKPGASVKMSCKASGSTFTSYWMHWVKQRPGQGLE<br>WIGAIYPVNSDTTYNQKFKGKATLTVDKSSSTAYMQLSSLTFEDSA<br>VYYCARSFYYSLDAAWFVYWGQGTTLTVSS |
| hSIRPα.40AVH6<br>(nucleotide sequence) | 87 | GAGGTGCAGCTGGTTCAGTCTGGCGCCGAAGTGAAGAAACCTGGCG<br>CCTCTGTGAAGGTGTCCTGCAAGGCTTCTGGCTCCACCTTCACCAG<br>CTACTGGATGCACTGGGTCCGACAGGCTCCAGGACAAGGCTTGGAA<br>TGGATGGGCGCTATCTACCCCGTGAACTCCGACACCACCTACAACC<br>AGAAATTCAAGGGCAGAGTGACCATGACCGTGGACACCTCCACCAG<br>CACCGTGTACATGGAACTGTCCAGCCTGAGATCCGAGGACACCGCC<br>GTGTACTACTGCGCCCGGTCCTTCTACTACTCTCTGGACGCCGCTT<br>GGTTTGTGTACTGGGGCCAGGGAACTCTGGTGACCGTGTCCTCT |
| hSIRPα.40AVH6<br>(amino acid sequence) | 88 | EVQLVQSGAEVKKPGASVKVSCKASGSTFTSYWMHWVRQAPGQGLE<br>WMGAIYPVNSDTTYNQKFKGRVTMTVDTSTSTVYMELSSLRSEDTA<br>VYYCARSFYYSLDAAWFVYWGQGTLVTVSS |
| hSIRPα.40AVL1<br>(nucleotide sequence) | 89 | GACATCCAGATGACCCAGTCTCCATCCTCTCTGTCCGCCTCTGTGG<br>GCGACAGAGTGACCATCACCTGTAGAGCCTCTCAGGACATCGGCTC<br>CAGACTGAACTGGCTGCAGCAGACCCCTGGCAAGGCCATCAAGAGA<br>CTGATCTACGCCACCTCCAGCCTGGATTCTGGCGTGCCCTCTAGAT<br>TCTCCGGCTCTAGATCTGGCACCGACTTCTCCCTGACCATCTCTGG<br>ACTGCAGCCTGAGGACTTCGCCACCTACTACTGTCTGCAGTACGCC<br>AGCTCTCCATTCACCTTTGGCGGAGGCACCAAGGTGGAAATCCAC |
| hSIRPα.40AVL1<br>(amino acid sequence) | 90 | DIQMTQSPSSLSASVGDRVTITCRASQDIGSRLNWLQQTPGKAIKR<br>LIYATSSLDSGVPSRFSGSRSGTDFSLTISGLQPEDFATYYCLQYA<br>SSPFTFGGGTKVEIH |
| hSIRPα.40AVL2<br>(nucleotide sequence) | 91 | GACATCCAGATGACCCAGTCTCCATCCTCTCTGTCCGCCTCTGTGG<br>GCGACAGAGTGACCATCACCTGTAGAGCCTCTCAGGACATCGGCTC<br>CAGACTGAACTGGCTGCAGCAGAAGCCTGGCAAGGCCATCAAGAGA<br>CTGATCTACGCCACCTCCAGCCTGGATTCTGGCGTGCCCTCTAGAT<br>TCTCCGGCTCTAGATCTGGCACCGACTTTACCCTGACAATCAGCTC<br>CCTGCAGCCTGAGGACTTCGCCACCTACTACTGTCTGCAGTACGCC<br>TCCTCTCCATTCACCTTTGGCCAGGGCACCAAGGTGGAAATCAAG |
| hSIRPα.40AVL2<br>(amino acid sequence) | 92 | DIQMTQSPSSLSASVGDRVTITCRASQDIGSRLNWLQQKPGKAIKR<br>LIYATSSLDSGVPSRFSGSRSGTDFTLTISSLQPEDFATYYCLQYA<br>SSPFTFGQGTKVEIK |
| hSIRPα.40AVL3<br>(nucleotide sequence) | 93 | GACATCCAGATGACCCAGTCTCCATCCTCTCTGTCCGCCTCTGTGG<br>GCGACAGAGTGACCATCACCTGTAGAGCCTCTCAGGACATCGGCTC<br>CAGACTGAACTGGCTGCAGCAGAAGCCTGGCAAGGCCATCAAGAGA<br>CTGATCTACGCCACCTCCAGCCTGGATTCTGGCGTGCCCTCTAGAT<br>TCTCCGGCTCTAGATCTGGCACCGACTTTACCCTGACAATCAGCTC<br>CCTGCAGCCTGAGGACTTCGCCACCTACTACTGTCTGCAGTACGCC<br>AGCTCTCCATTCACCTTTGGCGGAGGCACCAAGCTGGAAATCAAG |
| hSIRPα.40AVL3<br>(amino acid sequence) | 94 | DIQMTQSPSSLSASVGDRVTITCRASQDIGSRLNWLQQKPGKAIKR<br>LIYATSSLDSGVPSRFSGSRSGTDFTLTISSLQPEDFATYYCLQYA<br>SSPFTFGGGTKLEIK |
| hSIRPα.40AVL4<br>(nucleotide sequence) | 95 | GACATCCAGATGACCCAGTCTCCATCCTCTCTGTCCGCCTCTGTGG<br>GCGACAGAGTGACCATCACCTGTAGAGCCTCTCAGGACATCGGCTC<br>CAGACTGAACTGGCTGCAGCAGAAGCCTGGCAAGGCCCCTAAGAGA<br>CTGATCTACGCCACCTCCAGCCTGGATTCTGGCGTGCCCTCTAGAT<br>TCTCCGGCTCTGGCTCTGGCACCGAGTTTACCCTGACAATCAGCTC<br>CCTGCAGCCTGAGGACTTCGCCACCTACTACTGTCTGCAGTACGCC<br>AGCTCTCCATTCACCTTTGGCGGAGGCACCAAGGTGGAAATCAAG |
| hSIRPα.40AVL4<br>(amino acid sequence) | 96 | DIQMTQSPSSLSASVGDRVTITCRASQDIGSRLNWLQQKPGKAPKR<br>LIYATSSLDSGVPSRFSGSGSGTEFTLTISSLQPEDFATYYCLQYA<br>SSPFTFGGGTKVEIK |
| hSIRPα.40AVL5<br>(nucleotide sequence) | 97 | GACATCCAGATGACCCAGTCTCCATCCTCTCTGTCCGCCTCTGTGG<br>GCGACAGAGTGACCATCACCTGTAGAGCCTCTCAGGACATCGGCTC<br>CAGACTGAACTGGCTGCAGCAGAAGCCTGGCAAGGCCATCAAGAGA<br>CTGATCTACGCCACCTCCAGCCTGGATTCTGGCGTGCCCAAGAGAT<br>TCTCCGGCTCTAGATCCGGCTCCGACTATACCCTGACAATCAGCTC<br>CCTGCAGCCTGAGGACTTCGCCACCTACTACTGTCTGCAGTACGCC<br>TCCTCTCCATTCACCTTTGGCCAGGGCACCAAGGTGGAAATCAAG |

-continued

| Description | SEQ ID NO: | SEQUENCE |
|---|---|---|
| hSIRPα.40AVL5 (amino acid sequence) | 98 | DIQMTQSPSSLSASVGDRVTITCRASQDIGSRLNWLQQKPGKAIKR LIYATSSLDSGVPKRFSGSRSGSDYTLTISSLQPEDFATYYCLQYA SSPFTFGQGTKVEIK |
| hSIRPα.40AVL6 (nucleotide sequence) | 99 | GACATCCAGATGACCCAGTCTCCATCCTCTCTGTCTGCTTCCCTGG GCGAGAGAGTGTCCATCACCTGTAGAGCCTCTCAGGACATCGGCTC CAGACTGAACTGGCTGCAGCAGAAGCCTGGCAAGGCCATCAAGAGA CTGATCTACGCCACCTCCAGCCTGGATTCTGGCGTGCCCTCTAGAT TCTCCGGCTCTAGATCTGGCACCGACTTTACCCTGACAATCAGCTC CCTGCAGCCTGAGGACTTCGCCACCTACTACTGTCTGCAGTACGCC AGCTCTCCATTCACCTTTGGCGGAGGCACCAAGGTGGAAATCAAG |
| hSIRPα.40AVL6 (amino acid sequence) | 100 | DIQMTQSPSSLSASLGERVSITCRASQDIGSRLNWLQQKPGKAIKR LIYATSSLDSGVPSRFSGSRSGTDFTLTISSLQPEDFATYYCLQYA SSPFTFGGGTKVEIK |
| hSIRPα.40A mouse VH (nucleotide sequence) | 101 | GAGGTTCAGTTCCAGCAGTCTGGGACTGTGCTGGCAAGGCCAGGGA CTTCAGTGAAGATGTCCTGCAAGGCTTCTGGCTCCACCTTTACCAG CTACTGGATGCACTGGGTAAAACAGGGGCCTGGACAGGGTCTGCAA TGGATTGGCGCTATTTATCCTGTAAATAATGATACTACCTATAATC AGAAGTTCAAGGGCAAGGCCGAACTCACTGTAGTCACTTCCACCAG CACTGCCTACATGGAGGTCAGTAGTCTGACAAATGAGGACTCTGCG GTCTATTACTGTACAAGATCGTTCTACTATAGTCTCGACGCGGCCT GGTTTGTTTACTGGGGCCAAGGGACTCTGGTCACTGTCTCTGCA |
| hSIRPα.40A mouse VH (amino acid sequence) | 102 | EVQFQQSGTVLARPGTSVKMSCKASGSTFTSYWMHWVKQGPGQGLQ WIGAIYPVNNDTTYNQKFKGKAELTVVTSTSTAYMEVSSLTNEDSA VYYCTRSFYYSLDAAWFVYWGQGTLVTVSA |
| hSIRPα.40A mouse VL (nucleotide sequence) | 103 | GACATCCAGATGACCCAGTCTCCATCTCCTTATCTGCCTCTCTGG GAGAAAGAGTCAGTCTCACTTGTCGGGCAAGTCAGGACATTGGTAG TAGGTTAAACTGGCTTCAGCAGGAACCAGATGGAACTATTAAACGC CTGATCTACGCCACATCCAGTTTAGATTCTGGTGTCCCCAAAGGT TCAGTGGCAGTAGGTCTGGGTCAGATTATTCTCACCATCAGCGG CCTTGAGTCTGAAGACTTTGTAGACATTACTGTCTACAATATGCT AGTTCTCCGTTCACGTTCGGAGGGGGGACCAAGCTGGAAATAAAC |
| hSIRPα.40A mouse VL (amino acid sequence) | 104 | DIQMTQSPSSLSASLGERVSLTCRASQDIGSRLNWLQQEPDGTIKR LIYATSSLDSGVPKRFSGSRSGSDYSLTISGLESEDFVDYYCLQYA SSPFTFGGGTKLEIN |
| hSIRPα.40A mouse heavy chain (amino acid sequence; constant domain underlined, signal peptide not shown) | 105 | EVQFQQSGTVLARPGTSVKMSCKASGSTFTSYWMHWVKQGPGQGLQ WIGAIYPVNNDTTYNQKFKGKAELTVVTSTSTAYMEVSSLTNEDSA VYYCTRSFYYSLDAAWFVYWGQGTLVTVSA<u>AKTTPPSVYPLAPGSA AQTNSMVTLGCLVKGYFPEPVTVTWNSGSLSSGVHTFPAVLQSDLY TLSSSVTVPSSTWPSETVTCNVAHPASSTKVDKKIVPRDCGCKPCI CTVPEVSSVFIFPPKPKDVLTITLTPKVTCVVVDISKDDPEVQFSW FVDDVEVHTAQTQPREEQFNSTFRSVSELPIMHQDWLNGKEFKCRV NSAAFPAPIEKTISKTKGRPKAPQVYTIPPPKEQMAKDKVSLTCMI TDFFPEDITVEWQWNGQPAENYKNTQPIMDTDGSYFVYSKLNVQKS NWEAGNTFTCSVLHEGLHNHHTEKSLSHSPGK</u> |
| hSIRPα.40A mouse light chain (amino acid sequence; constant domain underlined, signal peptide not shown) | 106 | DIQMTQSPSSLSASLGERVSLTCRASQDIGSRLNWLQQEPDGTIKR LIYATSSLDSGVPKRFSGSRSGSDYSLTISGLESEDFVDYYCLQYA SSPFTFGGGTKLEIN<u>RADAAPTVSIFPPSSEQLTSGGASVVCFLNN FYPKDINVKWKIDGSERQNGVLNSWTDQDSKDSTYSMSSTLTLTKD EYERHNSYTCEATHKTSTSPIVKSFNRNEC</u> |
| rhSIRPα/Fc (amino acid sequence) | 107 | (GVAG)EEELQVIQPDKSVLVAAGETATLRCTATSLIPVGPIQWFR GAGPGRELIYNQKEGHFPRVTTVSDLTKRNNMDFSIRIGNITPADA GTYYCVKFRKGSPDDVEFKSGAGTELSVRAKPSAPVVSGPAARATP QHTVSFTCESHGFSPRDITLKWFKNGNELSDFQTNVDPVGESVSYS IHSTAKVVLTREDVHSQVICEVAHVTLQGDPLRGTANLSETIRVPP TLEVTQQPVRAENQVNVTCQVRKFYPQRLQLTWLENGNVSRTETAS TVTENKDGTYNWMSWLLVNVSAHRDDVKLTCQVEHDGQPAVSKSHD LKVSAHPKEQGSNTAAENTGSNERIEGRMDPKSCDKTHTCPPCPAP ELLGGPSVFLFPPKPKDTLMISRTPEVTCVVVDVSHEDPEVKFNWY VDGVEVHNAKTKPREEQYNSTYRVVSVLTVLHQDWLNGKEYKCKVS NKALPAPIEKTISKAKGQPREPQVYTLPPSRDELTKNQVSLTCLVK GFYPSDIAVEWESNGQPENNYKTTPPVLDSDGSFFLYSKLTVDKSR WQQGNVFSCSVMHEALHNHYTQKSLSLSPGK |
| rhSIRPγ/Fc (amino acid sequence) | 108 | VLWFRGVGPGRELIYNQKEGHFPRVTTVSDLTKRNNMDFSIRISSI TPADVGTYYCVKFRKGSPENVEFKSGPGTEMALGAKPSAPVVLGPA |

| Description | SEQ ID NO: | SEQUENCE |
|---|---|---|
| | | ARTTPEHTVSFTCESHGFSPRDITLKWFKNGNELSDFQTNVDPTGQ SVAYSIRSTARVVLDPWDVRSQVICEVAHVTLQGDPLRGTANLSEA IRVPPTLEVTQQPMRAGNQVNVTCQVRKFYPQSLQLTWLENGNVCQ RETASTLTENKDGTYNWTSWFLVNISDQRDDVVLTCQVKHDGQLAV SKRLALEVTVHQKDQSSDATPGPASIEGRMDPKSCDKTHTCPPCPA PELLGGPSVFLFPPKPKDTLMISRTPEVTCVVVDVSHEDPEVKFNW YVDGVEVHNAKTKPREEQYNSTYRVVSVLTVLHQDWLNGKEYKCKV SNKALPAPIEKTISKAKGQPREPQVYTLPPSRDELTKNQVSLTCLV KGFYPSDIAVEWESNGQPENNYKTTPPVLDSDGSFFLYSKLTVDKS RWQQGNVFSCSVMHEALHNHYTQKSLSLSPGK |
| rhCD47/Fc (amino acid sequence) | 109 | QLLFNKTKSVEFTFCNDTVVIPCFVTNMEAQNTTEVYVKWKFKGRD IYTFDGALNKSTVPTDFSSAKIEVSQLLKGDASLKMDKSDAVSHTG NYTCEVTELTREGETIIELKYRVVSWFSPIEGRMDPKSCDKTHTCP PCPAPELLGGPSVFLFPPKPKDTLMISRTPEVTCVVVDVSHEDPEV KFNWYVDGVEVHNAKTKPREEQYNSTYRVVSVLTVLHQDWLNGKEY KCKVSNKALPAPIEKTISKAKGQPREPQVYTLPPSRDELTKNQVSL TCLVKGFYPSDIAVEWESNGQPENNYKTTPPVLDSDGSFFLYSKLT VDKSRWQQGNVFSCSVMHEALHNHYTQKSLSLSPGK |
| hSIRP-VγC1βC2β (nucleotide sequence) | 110 | ATGCCCGTGCCTGCCTCTTGGCCTCATCTGCCCAGCCCCTTTCTGC TGATGACCCTGCTGCTGGGCAGGCTGACAGGCGTGGCAGGCGAAGA GGAACTGCAGATGATCCAGCCCGAGAAGCTGCTGCTCGTGACCGTG GGCAAGACCGCCACCCTGCACTGCACCGTGACATCCCTGCTGCCTG TGGGACCCGTGCTGTGGTTTAGAGGCGTGGGCCCTGGCAGAGAGCT GATCTACAACCAGAAAGAGGGCCACTTCCCCAGAGTGACCACCGTG TCCGACCTGACCAAGCGGAACAACATGGACTTCTCCATCCGGATCT CCAGCATCACCCCTGCCGACGTGGGCACCTACTACTGCGTGAAGTT CCGGAAGGGCTCCCCCGAGAACGTGGAGTTCAAGTCTGGCCCAGGC ACCGAGATGGCCCTGGGCGCTAAACCTTCTGCCCCTGTGGTGTCTG GACCTGCCGTGCGGGCTACCCCTGAGCACACCGTGTCTTTTACCTG CGAGTCCCACGGCTTCAGCCCTCGGGACATCACCCTGAAGTGGTTC AAGAACGGCAACGAGCTGTCCGACTTCCAGACCAACGTGGACCCTG CCGGCGACTCCGTGTCCTACTCCATCCACTCTACCGCCAGAGTGGT GCTGACCAGAGGCGACGTGCACTCCCAAGTGATCTGCGAGATCGCC CATATCACACTGCAGGGCGACCCCCTGAGAGGCACCGCCAATCTGT CTGAGGCCATCAGAGTGCCCCCCACCCTGGAAGTGACCCAGCAGCC TATGAGAGCCGAGAACCAGGCCAACGTGACCTGTCAGGTGTCCAAC TTCTACCCTCGGGGCCTGCAGCTGACCTGGCTGGAAAACGGCAATG TGTCCCGGACCGAGACAGCCTCCACCCTGATCGAGAACAAGGACGG CACCTACAATTGGATGTCCTGGCTGCTCGTGAACACCTGTGCCCAC AGGGACGACGTGGTGCTGACATGCCAGGTGGAAACACGATGGCCAGC AGGCCGTGTCCAAGTCCTACGCCCTGGAAATCTCCGCCCATCAGAA AGAGCACGGCTCCGATATCACCCACGAGGCCGCTCTGGCTCCTACC GCTCCTCTGCTGGTGGCTCTGCTGCTGGGACCTAAGCTGCTGCTGG TCGTGGGCGTGTCCGCCATCTACATCTGCTGGAAGCAGAAGGCCTG A |
| hSIRP-VγC1βC2β (amino acid sequence) | 111 | MPVPASWPHLPSPFLLMTLLLGRLTGVAGEEELQMIQPEKLLLVTV GKTATLHCTVTSLLPVGPVLWFRGVGPGRELIYNQKEGHFPRVTTV SDLTKRNNMDFSIRISSITPADVGTYYCVKFRKGSPENVEFKSGPG TEMALGAKPSAPVVSGPAVRATPEHTVSFTCESHGFSPRDITLKWF KNGNELSDFQTNVDPAGDSVSYSIHSTARVVLTRGDVHSQVICEIA HITLQGDPLRGTANLSEAIRVPPTLEVTQQPMRAENQANVTCQVSN FYPRGLQLTWLENGNVSRTETASTLIENKDGTYNWMSWLLVNTCAH RDDVVLTCQVEHDGQQAVSKSYALEISAHQKEHGSDITHEAALAPT APLLVALLLGPKLLLVVGVSAIYICWKQKA |
| hSIRP-VβC1γC2β (nucleotide sequence) | 112 | ATGCCCGTGCCTGCCTCTTGGCCTCATCTGCCCAGCCCCTTTCTGC TGATGACCCTGCTGCTGGGCAGGCTGACAGGCGTGGCAGGCGAAGA TGAGCTGCAAGTGATCCAGCCCGAGAAGTCCGTGTCTGTGGCCGCT GGCGAGTCTGCCACCCTGAGATGCGCTATGACCTCCCTGATCCCCG TGGGCCCCATCATGTGGTTTAGAGGCGCTGGCGCTGGCAGAGAGCT GATCTACAACCAGAAAGAGGGCCACTTCCCCAGAGTGACCACCGTG TCCGAGCTGACCAAGCGGAACAACCTGGACTTCTCCATCTCCATCA GCAACATCACCCCTGCCGACGCCGGCACCTACTACTGCGTGAAGTT CCGGAAGGGCTCCCCCGACGACGTGGAGTTCAAATCCGGCGCTGGA ACCGAGCTGTCCGTGCGGGCTAAACCTTCTGCCCCTGTGGTGCTGG GACCTGCCGCTAGAACCACCCCTGAGCACACCGTGTCTTTTACCTG CGAGTCCCACGGCTTCAGCCCTCGGGACATCACCCTGAAGTGGTTC AAGAACGGCAACGAGCTGAGCGACTTCCAGACCAACGTGGACCCTA CCGGCCAGTCCGTGGCCTACTCCATCAGATCCACCGCCAGAGTGGT GCTGGACCCTGGGATGTGCGGTCCAAGTGATCTGCGAGGTGGCC CATGTGACACTGCAGGGCGATCCTCTGAGAGGCACCGCCAATCTGT CTGAGGCCATCAGAGTGCCCCCCACCCTGGAAGTGACCCAGCAGCC TATGAGAGCCGAGAACCAGGCCAACGTGACCTGCCAGGTGTCCAAC |

| Description | SEQ ID NO: | SEQUENCE |
|---|---|---|
| | | TTCTACCCTCGGGGCCTGCAGCTGACCTGGCTGGAAAACGGCAATG<br>TGTCCCGGACCGAGACAGCCTCCACCCTGATCGAGAACAAGGATGG<br>CACCTACAATTGGATGTCCTGGCTGCTCGTGAACACCTGTGCCCAC<br>CGGGATGACGTGGTGCTGACTTGTCAGGTGGAACACGACGGCCAGC<br>AGGCCGTGTCCAAGTCCTACGCCCTGGAAATCTCCGCCCATCAGAA<br>AGAGCACGGCTCCGATATCACCCACGAGGCCGCTCTGGCTCCTACC<br>GCTCCTCTGCTGGTGGCTCTGCTGCTGGGACCTAAGCTGCTGCTGG<br>TCGTGGGCGTGTCCGCCATCTACATCTGCTGGAAGCAGAAGGCCTG<br>A |
| hSIRP-VβC1γC2β<br>(amino acid sequence) | 113 | MPVPASWPHLPSPFLLMTLLLGRLTGVAGEDELQVIQPEKSVSVAA<br>GESATLRCAMTSLIPVGPIMWFRGAGAGRELIYNQKEGHFPRVTTV<br>SELTKRNNLDFSISISNITPADAGTYYCVKFRKGSPDDVEFKSGAG<br>TELSVRAKPSAPVVLGPAARTTPEHTVSFTCESHGFSPRDITLKWF<br>KNGNELSDFQTNVDPTGQSVAYSIRSTARVVLDPWDVRSQVICEVA<br>HVTLQGDPLRGTANLSEAIRVPPTLEVTQQPMRAENQANVTCQVSN<br>FYPRGLQLTWLENGNVSRTETASTLIENKDGTYNWMSWLLVNTCAH<br>RDDVVLTCQVEHDGQQAVSKSYALEISAHQKEHGSDITHEAALAPT<br>APLLVALLLGPKLLLVVGVSAIYICWKQKA |
| hSIRP-VβC1βC2γ<br>(nucleotide sequence) | 114 | ATGCCCGTGCCTGCCTCTTGGCCTCATCTGCCCAGCCCCTTTCTGC<br>TGATGACCCTGCTGCTGGGCAGGCTGACAGGCGTGGCAGGCGAAGA<br>TGAGCTGCAAGTGATCCAGCCCGAGAAGTCCGTGTCTGTGGCCGCT<br>GGCGAGTCTGCCACCCTGAGATGCGCTATGACCTCCCTGATCCCCG<br>TGGGCCCCATCATGTGGTTTAGAGGCGCTGGCGCTGGCAGAGAGCT<br>GATCTACAACCAGAAAGAGGGCCACTTCCCCAGAGTGACCACCGTG<br>TCCGAGCTGACCAAGCGGAACAACCTGGACTTCTCCATCTCCATCA<br>GCAACATCACCCCTGCCGACGCCGGCACCTACTACTGCGTGAAGTT<br>CCGGAAGGGCTCCCCCGACGACGTGGAGTTCAAATCCGGCGCTGGA<br>ACCGAGCTGTCCGTGCGGGCTAAACCTTCTGCCCCTGTGGTGTCTG<br>GACCTGCTGTGCGCGCTACCCCTGAGCACACCGTGTCTTTTACCTG<br>CGAGTCCCACGGCTTCAGCCCTCGGGACATCACCCTGAAGTGGTTC<br>AAGAACGGCAACGAGCTGAGCGACTTCCAGACCAACGTGGACCCTG<br>CCGGCGACTCCGTGTCCTACTCCATCCACTCTACCGCCAGAGTGGT<br>GCTGACCAGAGGCGACGTGCACTCCCAAGTGATCTGCGAGATCGCC<br>CATATCACACTGCAGGGCGACCCCCTGAGAGGCACCGCCAATCTGT<br>CTGAGGCCATCAGAGTGCCCCCCACCCTGGAAGTGACCCAGCAGCC<br>TATGAGAGTGGGCAACCAAGTGAACGTGACCTGCCAAGTGCGGAAG<br>TTCTACCCCCAGTCCCTGCAGCTGACTTGGAGCGAGAATGGCAACG<br>TGTGCCAGAGAGAGACAGCCTCCACCCTGACCGAGAACAAGGACGG<br>AACCTACAACTGGACCTCCTGGTTCCTCGTGAACATCTCCGACCAG<br>CGGGACGACGTGGTGCTGACATGCCAAGTGAAGCACGATGGACAGC<br>TGGCCGTGTCCAAGCGGCTGGCTCTGGAAGTGACAGTGCACCAGAA<br>AGAGCACGGCTCCGACATCACCCACGAGGCCGCTCTGGCTCCTACA<br>GCTCCTCTGCTGGTGGCTCTGCTGCTGGGACCTAAGCTGCTGCTGG<br>TCCTGTGGGCGTGTCCGCCATCTACATCTGCTGGAAGCAGAAGGCCTG<br>A |
| hSIRP-VβC1βC2γ<br>(amino acid sequence) | 115 | MPVPASWPHLPSPFLLMTLLLGRLTGVAGEDELQVIQPEKSVSVAA<br>GESATLRCAMTSLIPVGPIMWFRGAGAGRELIYNQKEGHFPRVTTV<br>SELTKRNNLDFSISISNITPADAGTYYCVKFRKGSPDDVEFKSGAG<br>TELSVRAKPSAPVVSGPAVRATPEHTVSFTCESHGFSPRDITLKWF<br>KNGNELSDFQTNVDPAGDSVSYSIHSTARVVLTRGDVHSQVICEIA<br>HITLQGDPLRGTANLSEAIRVPPTLEVTQQPMRVGNQVNVTCQVRK<br>FYPQSLQLTWSENGNVCQRETASTLTENKDGTYNWTSWFLVNISDQ<br>RDDVVLTCQVKHDGQLAVSKRLALEVTVHQKEHGSDITHEAALAPT<br>APLLVALLLGPKLLLVVGVSAIYICWKQKA |
| human SIRPβL<br>(nucleotide sequence) | 116 | ATGCCTGTGCCTGCCTCTTGGCCTCATCTGCCCTCTCCATTTCTGC<br>TGATGACCCTGCTGCTGGGCAGACTGACAGGTGTTGCTGGCGAGA<br>GGAACTGCAAGTGATCCAGCCTGACAAGAGCATCTCTGTGGCCGCT<br>GGCGAATCTGCCACACTGCACTGTACCGTGACATCTCTGATCCCTG<br>TGGGCCCCATCCAGTGGTTTAGAGGTGCTGGACCTGGCAGAGAGCT<br>GATCTACAACCAGAAAGAGGGACACTTCCCCAGAGTGACCACCGTG<br>TCCGACCTGACCAAGCGGAACAACATGGACTTCAGCATCCGGATCA<br>GCAACATCACCCCTGCCGATGCCGGCACCTACTACTGCGTGAAGTT<br>CAGAAAGGGCAGCCCCGACCACGTCGAGTTTAAAAGCGGAGCCGGC<br>ACAGAGCTGAGCGTGCGGGCTAAACCTTCTGCCTCCTGTGGTGTCTG<br>GACCAGCCGCTAGAGCTACACCTCAGCACACCGTGTCTTTTACCTG<br>CGAGAGCCACGGCTTCAGCCCCAGAGATATCACCCTGAAGTGGTTC<br>AAGAACGGCAACGAGCTGTCCGACTTCCAGACCAATGTGGACCCAG<br>CCGGCGATAGCGTGTCCTACAGCATTCACAGCACCGCCAAGGTGGT<br>GCTGACCCGGGAAGATGTGCACAGCCAAGTGATTTGCGAGGTGGCC<br>CACGTTACCCTGCAAGGCGATCCTCTGAGAGGAACCGCCAACCTGA<br>GCGAGACAATCCGGGTGCCACTCTACACTGGAAGTGACCCAGCAGCC<br>TGTGCGGGCCGAGAATCAAGTGAACGTGACCTGCCAAGTGCGGAAG |

-continued

| Description | SEQ ID NO: | SEQUENCE |
|---|---|---|
| | | TTCTACCCTCAGAGACTGCAGCTGACCTGGCTGGAAAACGGCAATG<br>TGTCCCGGACCGAGACAGCCAGCACACTGACCGAGAACAAGGATGG<br>CACCTACAATTGGATGAGCTGGCTGCTGGTCAATGTGTCTGCCCAC<br>CGGGACGATGTGAAGCTGACATGCCAGGTGGAACACGATGGCCAGC<br>CTGCCGTGTCTAAGAGCCACGACCTGAAGGTGTCCGCTCATCCCAA<br>AGAGCAGGGCAGCAATACTGCCCCTGGACCTGCTCTTGCTTCTGCC<br>GCTCCTCTGCTGATCGCCTTTCTGCTGGGACCTAAGGTGCTGCTGG<br>TTGTGGGAGTGTCCGTGATCTACGTGTACTGGAAGCAGAAGGCC |
| human SIRPβL(amino acid sequence) | 117 | MPVPASWPHLPSPFLLMTLLLGRLTGVAGEEELQVIQPDKSISVAA<br>GESATLHCTVTSLIPVGPIQWFRGAGPGRELIYNQKEGHFPRVTTV<br>SDLTKRNNMDFSIRISNITPADAGTYYCVKFRKGSPDHVEFKSGAG<br>TELSVRAKPSAPVVSGPAARATPQHTVSFTCESHGFSPRDITLKWF<br>KNGNELSDFQTNVDPAGDSVSYSIHSTAKVVLTREDVHSQVICEVA<br>HVTLQGDPLRGTANLSETIRVPPTLEVTQQPVRAENQVNVTCQVRK<br>FYPQRLQLTWLENGNVSRTETASTLTENKDGTYNWMSWLLVNVSAH<br>RDDVKLTCQVEHDGQPAVSKSHDLKVSAHPKEQGSNTAPGPALASA<br>APLLIAFLLGPKVLLVVGVSVIYVYWKQKA |
| human IgG1 constant domains (nucleotide sequence) | 118 | GCCAGCACCAAGGGCCCATCGGTCTTCCCCCTGGCACCCTCCTCCA<br>AGAGCACCTCTGGGGGCACAGCGGCCCTGGGCTGCCTGGTCAAGGA<br>CTACTTCCCCGAACCGGTGACGGTGTCGTGGAACTCAGGCGCCCTG<br>ACCAGCGGCGTGCACACCTTCCCGGCTGTCCTACAGTCCTCAGGAC<br>TCTACTCCCTCAGCAGCGTGGTGACCGTGCCCTCCAGCAGCTTGGG<br>CACCCAGACCTACATCTGCAACGTGAATCACAAGCCCAGCAACACC<br>AAGGTGGACAAGAAAGTTGAGCCCAAATCTTGTGACAAAACTCACA<br>CATGCCCACCGTGCCCAGCACCTGAACTCCTGGGGGGACCGTCAGT<br>CTTCCTCTTCCCCCCAAAACCCAAGGACACCCTCATGATCTCCCGG<br>ACCCCTGAGGTCACATGCGTGGTGGTGGACGTGAGCCACGAAGACC<br>CTGAGGTCAAGTTCAACTGGTACGTGGACGGCGTGGAGGTGCATAA<br>TGCCAAGACAAAGCCGCGGGAGGAGCAGTACAACAGCACGTACCGG<br>GTGGTCAGCGTCCTCACCGTCCTGCACCAGGACTGGCTGAATGGCA<br>AGGAGTACAAGTGCAAGGTCTCCAACAAAGCCCTCCCAGCCCCCAT<br>CGAGAAAACCATCTCCAAAGCCAAAGGGCAGCCCCGAGAACCACAG<br>GTGTACACCCTGCCCCCATCCCGGGATGAGCTGACCAAGAACCAGG<br>TCAGCCTGACCTGCCTGGTCAAAGGCTTCTATCCCAGCGACATCGC<br>CGTGGAGTGGGAGAGCAATGGGCAGCCGGAGAACAACTACAAGACC<br>ACGCCTCCCGTGCTGGACTCCGACGGCTCCTTCTTCCTCTACAGCA<br>AGCTCACCGTGGACAAGAGCAGGTGGCAGCAGGGGAACGTCTTCTC<br>ATGCTCCGTGATGCATGAGGCTCTGCACAACCACTACACGCAGAAG<br>AGCCTCTCCCTGTCTCCGGGTAAA |
| human IgG1 constant domains (amino acid sequence) | 119 | ASTKGPSVFPLAPSSKSTSGGTAALGCLVKDYFPEPVTVSWNSGAL<br>TSGVHTFPAVLQSSGLYSLSSVVTVPSSSLGTQTYICNVNHKPSNT<br>KVDKKVEPKSCDKTHTCPPCPAPELLGGPSVFLFPPKPKDTLMISR<br>TPEVTCVVVDVSHEDPEVKFNWYVDGVEVHNAKTKPREEQYNSTYR<br>VVSVLTVLHQDWLNGKEYKCKVSNKALPAPIEKTISKAKGQPREPQ<br>VYTLPPSRDELTKNQVSLTCLVKGFYPSDIAVEWESNGQPENNYKT<br>TPPVLDSDGSFFLYSKLTVDKSRWQQGNVFSCSVMHEALHNHYTQK<br>SLSLSPGK |
| mouse IgG1 constant domains (amino acid sequence) | 120 | AKTTPPSVYPLAPGCGDTTGSSVTLGCLVKGYFPESVTVTWNSGSL<br>SSSVHTFPALLQSGLYTMSSSVTVPSSTWPSQTVTCSVAHPASSTT<br>VDKKLEPSGPISTINPCPPCKECHKCPAPNLEGGPSVFIFPPNIKD<br>VLMISLTPKVTCVVVDVSEDDPDVQISWFVNNVEVHTAQTQTHRED<br>YNSTIRVVSTLPIQHQDWMSGKEFKCKVNNKDLPSPIERTISKIKG<br>LVRAPQVYILPPPAEQLSRKDVSLTCLVVGFNPGDISVEWTSNGHT<br>EENYKDTAPVLDSDGSYFIYSKLNMKTSKWEKTDSFSCNVRHEGLK<br>NYYLKKTISRSPGK |
| mouse kappa constant domain (amino acid sequence) | 121 | RADAAPTVSIFPPSSEQLTSGGASVVCFLNNFYPKDINVKWKIDGS<br>ERQNGVLNSWTDQDSKDSTYSMSSTLTLTKDEYERHNSYTCEATHK<br>TSTSPIVKSFNRNEC |
| human IgG2 constant domains, V234A-G237A-P238S-H268A-V309L-A330S-P331S (Sigma) mutant (amino acid sequence) | 122 | ASTKGPSVFPLAPCSRSTSESTAALGCLVKDYFPEPVTVSWNSGAL<br>TSGVHTFPAVLQSSGLYSLSSVVTVPSSNFGTQTYTCNVDHKPSNT<br>KVDKTVERKCCVECPPCPAPPAAASSVFLFPPKPKDTLMISRTPEV<br>TCVVVDVSAEDPEVQFNWYVDGVEVHNAKTKPREEQFNSTFRVVSV<br>LTVLHQDWLNGKEYKCKVSNKGLPSSIEKTISKTKGQPREPQVYTL<br>PPSREEMTKNQVSLTCLVKGFYPSDIX$_1$VEWESNGQPENNYKTTPP<br>MLDSDGSFFLYSKLTVDKSRWQQGNVFSCSVMHEALHNHYTQKSLS<br>LSPGK<br>wherein:<br>X$_1$ = A, S |

| Description | SEQ ID NO: | SEQUENCE |
|---|---|---|
| human IgG1 constant domains, L234A-L235A mutant (amino acid sequence) | 123 | ASTKGPSVFPLAPSSKSTSGGTAALGCLVKDYFPEPVTVSWNSGAL TSGVHTFPAVLQSSGLYSLSSVVTVPSSSLGTQTYICNVNHKPSNT KVDKKVEPKSCDKTHTCPPCPAPEAAGGPSVFLFPPKPKDTLMISR TPEVTCVVVDVSHEDPEVKFNWYVDGVEVHNAKTKPREEQYNSTYR VVSVLTVLHQDWLNGKEYKCKVSNKALPAPIEKTISKAKGQPREPQ VYTLPPSRDELTKNQVSLTCLVKGFYPSDIAVEWESNGQPENNYKT TPPVLDSDGSFFLYSKLTVDKSRWQQGNVFSCSVMHEALHNHYTQK SLSLSPGK |
| human IgG1 constant domains, L234A-L235A-P329G mutant (nucleotide sequence) | 124 | GCTAGCACAAAGGGCCCTAGTGTGTTTCCTCTGGCTCCCTCTTCCA AATCCACTTCTGGTGGCACTGCTGCTCTGGGATGCCTGGTGAAGGA TTACTTTCCTGAACCTGTGACTGTCTCATGGAACTCTGGTGCTCTG ACTTCTGGTGTCCACACTTTCCCTGCTGTGCTGCAGTCTAGTGGAC TGTACTCTCTGTCATCTGTGGTCACTGTGCCCTCTTCATCTCTGG AACCCAGACCTACATTTGTAATGTGAACCACAAACCATCCAACACT AAAGTGGACAAAAAGTGGAACCCAAATCCTGTGACAAAACCCACA CCTGCCCACCTTGTCCGGCGCCTGAAGCGGCGGGAGGACCTTCTGT GTTTCTGTTCCCCCCCAAACCAAAGGATACCCTGATGATCTCGCGA ACCCCTGAGGTGACATGTGTGGTGGTGGATGTGTCTCATGAGGACC CCGAAGTCAAATTTAATTGGTATGTCGACGGCGTCGAGGTGCATAA TGCCAAAACCAAGCCTAGAGAGGAACAGTACAATTCAACCTACAGA GTCGTCAGTGTGCTGACTGTGCTGCATCAGGATTGGCTGAATGGCA AGGAATACAAGTGTAAAGTCTCAAACAAGGCCCTGGGAGCTCCAAT TGAGAAAACAATCTCAAAGGCCAAGGACAGCCTAGGGAACCCCAG GTCTACACCCTGCCACCTTCGAGAGACGAACTGACCAAAAACCAGG TGTCCCTGACATGCCTGGTCAAAGGCTTCTACCCTTCTGACATTGC TGTGGAGTGGGAGTCAAATGGACAGCCTGAGAACAACTACAAAACA ACCCCCCCTGTGCTGGATTCTGATGGCTCTTTCTTTCTGTACTCCA AACTGACTGTGGACAAGTCTAGATGGCAGCAGGGGAATGTCTTTTC TTGCTCTGTCATGCATGAGGCTCTGCATAACCACTACACTCAGAAA TCCCTGTCTCTGTCTCCCGGGAAA |
| human IgG1 constant domains, L234A-L235A-P329G mutant (amino acid sequence) | 125 | ASTKGPSVFPLAPSSKSTSGGTAALGCLVKDYFPEPVTVSWNSGAL TSGVHTFPAVLQSSGLYSLSSVVTVPSSSLGTQTYICNVNHKPSNT KVDKKVEPKSCDKTHTCPPCPAPEAAGGPSVFLFPPKPKDTLMISR TPEVTCVVVDVSHEDPEVKFNWYVDGVEVHNAKTKPREEQYNSTYR VVSVLTVLHQDWLNGKEYKCKVSNKALGAPIEKTISKAKGQPREPQ VYTLPPSRDELTKNQVSLTCLVKGFYPSDIAVEWESNGQPENNYKT TPPVLDSDGSFFLYSKLTVDKSRWQQGNVFSCSVMHEALHNHYTQK SLSLSPGK |
| human IgG1 constant domains, N297Q mutant (amino acid sequence) | 126 | ASTKGPSVFPLAPSSKSTSGGTAALGCLVKDYFPEPVTVSWNSGAL TSGVHTFPAVLQSSGLYSLSSVVTVPSSSLGTQTYICNVNHKPSNT KVDKKVEPKSCDKTHTCPPCPAPELLGGPSVFLFPPKPKDTLMISR TPEVTCVVVDVSHEDPEVKFNWYVDGVEVHNAKTKPREEQYQSTYR VVSVLTVLHQDWLNGKEYKCKVSNKALPAPIEKTISKAKGQPREPQ VYTLPPSRDELTKNQVSLTCLVKGFYPSDIAVEWESNGQPENNYKT TPPVLDSDGSFFLYSKLTVDKSRWQQGNVFSCSVMHEALHNHYTQK SLSLSPGK |
| human IgG4 constant domains, S228P-N297Q mutant (amino acid sequence) | 127 | ASTKGPSVFPLAPCSRSTSESTAALGCLVKDYFPEPVTVSWNSGAL TSGVHTFPAVLQSSGLYSLSSVVTVPSSSLGTKTYTCNVDHKPSNT KVDKRVESKYGPPCPPCPAPEFLGGPSVFLFPPKPKDTLMISRTPE VTCVVVDVSQEDPEVQFNWYVDGVEVHNAKTKPREEQFQSTYRVVS VLTVLHQDWLNGKEYKCKVSNKGLPSSIEKTISKAKGQPREPQVYT LPPSQEEMTKNQVSLTCLVKGFYPSDIAVEWESNGQPENNYKTTPP VLDSDGSFFLYSRLTVDKSRWQEGNVFSCSVMHEALHNHYTQKSLS LSLGK |
| 18D5 VH (amino acid sequence) | 128 | QVQLQQPGAELVRPGSSVKLSCKASGYTFTSYWVHWVKQRPIQGLE WIGNIDPSDSDTHYNQKFKDKASLTVDKSSSTAYMQLSSLTFEDSA VYYCVRGGTGTMAWFAYWGQGTLVTVSA |
| 18D5 VL (amino acid sequence) | 129 | DVVMTQTPLSLPVSLGDQASISCRSSQSLVHSYGNTYLYWYLQKPG QSPKLLIYRVSNRFSGVPDRFSGSGSGTDFTLKISRVEAEDLGVYF CFQGTHVPYTFGSGTKLEIK |
| KWAR23 VH (amino acid sequence) | 130 | EVQLQQSGAELVKPGASVKLSCTASGFNIKDYYIHWVQQRTEQGLE WIGRIDPEDGETKYAPKFQDKATITADTSSNTAYLHLSSLTSEDTA VYYCARWGAYWGQGTLVTVSS |
| KWAR23 VL (amino acid sequence) | 131 | QIVLTQSPAIMSASPGEKVTLTCSASSSVSSSYLYWYQQKPGSSPK LWIYSTSNLASGVPARFSGSGSGTSYSLTISSMEAEDAASYFCHQW SSYPRTFGAGTKLELK |

| Description | SEQ ID NO: | SEQUENCE |
|---|---|---|
| rhSIRPα-HIS (amino acid sequence) | 132 | MEPAGPAPGRLGPLLCLLLAASCAWSGVAGEEELQVIQPDKSVLVA AGETATLRCTATSLIPVGPIQWFRGAGPGRELIYNQKEGHFPRVTT VSDLTKRNNMDFSIRIGNITPADAGTYYCVKFRKGSPDDVEFKSGA GTELSVRAKPSAPVVSGPAARATPQHTVSFTCESHGFSPRDITLKW FKNGNELSDFQTNVDPVGESVSYSIHSTAKVVLTREDVHSQVICEV AHVTLQGDPLRGTANLSETIRVPPTLEVTQQPVRAENQVNVTCQVR KFYPQRLQLTWLENGNVSRTETASTVTENKDGTYNWMSWLLVNVSA HRDDVKLTCQVEHDGQPAVSKSHDLKVSAHPKEQGSNTAAENTGSN ERHHHHHH |

All references cited herein are incorporated by reference to the same extent as if each individual publication, database entry (e.g. Genbank sequences or GeneID entries), patent application, or patent, was specifically and individually indicated to be incorporated by reference. This statement of incorporation by reference is intended by Applicants, pursuant to 37 C.F.R. § 1.57(b)(1), to relate to each and every individual publication, database entry (e.g. Genbank sequences or GeneID entries), patent application, or patent, each of which is clearly identified in compliance with 37 C.F.R. § 1.57(b)(2), even if such citation is not immediately adjacent to a dedicated statement of incorporation by reference. The inclusion of dedicated statements of incorporation by reference, if any, within the specification does not in any way weaken this general statement of incorporation by reference. Citation of the references herein is not intended as an admission that the reference is pertinent prior art, nor does it constitute any admission as to the contents or date of these publications or documents. To the extent that the references provide a definition for a claimed term that conflicts with the definitions provided in the instant specification, the definitions provided in the instant specification shall be used to interpret the claimed invention.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

The foregoing written specification is considered to be sufficient to enable one skilled in the art to practice the invention. Various modifications of the invention in addition to those shown and described herein will become apparent to those skilled in the art from the foregoing description and fall within the scope of the appended claims.

The invention claimed is:

1. An antibody or antigen binding fragment thereof that binds to human SIRPαV1 having the sequence of SEQ ID NO: 34 with an $EC_{50}$ between 4.83 nM and 0.022 nM, wherein the antibody or antigen binding fragment comprises each of:
   a. a heavy chain variable region CDR1 comprising the amino acid sequence SYWMH (SEQ ID NO:69),
   b. a heavy chain variable region CDR2 comprising the amino acid sequence AIYPVNNDTTYNQKFKG (SEQ ID NO:70), AIYPVNSDTTYNQKFKG (SEQ ID NO: 136) or ALYPVNSDTTYNQKFKG (SEQ ID NO: 137),
   c. a heavy chain variable region CDR3 comprising the amino acid sequence SFYYSLDAAWFVY (SEQ ID NO:71),
   d. a light chain variable region CDR1 comprising the amino acid sequence RASQDIGSRLN (SEQ ID NO:72),
   e. a light chain variable region CDR2 comprising the amino acid sequence ATSSLDS (SEQ ID NO:73), and
   f. a light chain variable region CDR3 comprising the amino acid sequence LQYASSPFT (SEQ ID NO:74),
or wherein the antibody or antigen binding fragment comprises each of:
   g. a heavy chain variable region CDR1 comprising the amino acid sequence NYYIH (SEQ ID NO:1),
   h. a heavy chain variable region CDR2 comprising the amino acid sequence WIYPGNVNTKYNEKFKA (SEQ ID NO:2),
   i. a heavy chain variable region CDR3 comprising the amino acid sequence PTIIATDFDV (SEQ ID NO:3),
   j. a light chain variable region CDR1 comprising the amino acid sequence KASQGVGTAVG (SEQ ID NO:4),
   k. a light chain variable region CDR2 comprising the amino acid sequence WASTRHT (SEQ ID NO:5), and
   l. a light chain variable region CDR3 comprising the amino acid sequence QQYSTYPFT (SEQ ID NO:6).

2. The antibody or antigen binding fragment of claim 1, wherein the antibody or antigen binding fragment comprises
   a heavy chain variable region comprising an amino acid sequence selected from the group consisting of:
      SEQ ID NO: 75 or an amino acid sequence at least 95% identical thereto,
      SEQ ID NO: 78 or an amino acid sequence at least 95% identical thereto,
      SEQ ID NO: 80 or an amino acid sequence at least 95% identical thereto,
      SEQ ID NO: 82 or an amino acid sequence at least 95% identical thereto,
      SEQ ID NO: 84 or an amino acid sequence at least 95% identical thereto,
      SEQ ID NO: 86 or an amino acid sequence at least 95% identical thereto,
      SEQ ID NO: 88 or an amino acid sequence at least 95% identical thereto, and
      SEQ ID NO: 102 or an amino acid sequence at least 95% identical thereto;
   and
   a light chain variable region comprising an amino acid sequence selected from the group consisting of:
      SEQ ID NO: 76 or an amino acid sequence at least 95% identical thereto,
      SEQ ID NO: 90 or an amino acid sequence at least 95% identical thereto,
      SEQ ID NO: 92 or an amino acid sequence at least 95% identical thereto,
      SEQ ID NO: 94 or an amino acid sequence at least 95% identical thereto,
      SEQ ID NO: 96 or an amino acid sequence at least 95% identical thereto,
      SEQ ID NO: 98 or an amino acid sequence at least 95% identical thereto,
      SEQ ID NO: 100 or an amino acid sequence at least 95% identical thereto, and
      SEQ ID NO: 104 or an amino acid sequence at least 95% identical thereto;
or wherein the antibody or antigen binding fragment comprises
   a heavy chain variable region comprising an amino acid sequence selected from the group consisting of:
      SEQ ID NO: 7 or an amino acid sequence at least 95% identical thereto,
      SEQ ID NO: 10 or an amino acid sequence at least 95% identical thereto,
      SEQ ID NO: 12 or an amino acid sequence at least 95% identical thereto,
      SEQ ID NO: 14 or an amino acid sequence at least 95% identical thereto,
      SEQ ID NO: 16 or an amino acid sequence at least 95% identical thereto,
      SEQ ID NO: 18 or an amino acid sequence at least 95% identical thereto, and
      SEQ ID NO: 30 or an amino acid sequence at least 95% identical thereto;
   and
   a light chain variable region comprising an amino acid sequence selected from the group consisting of:
      SEQ ID NO: 8 or an amino acid sequence at 95% identical thereto,
      SEQ ID NO: 20 or an amino acid sequence at least 95% identical thereto,
      SEQ ID NO: 22 or an amino acid sequence at least 95% identical thereto,
      SEQ ID NO: 24 or an amino acid sequence at least 95% identical thereto,
      SEQ ID NO: 26 or an amino acid sequence at least 95% identical thereto, and
      SEQ ID NO: 28 or an amino acid sequence at least 95% identical thereto, and SEQ ID NO: 32 or an amino acid sequence at least 95% identical thereto.

3. The antibody or antigen binding fragment of claim 1, wherein the antibody or antigen binding fragment thereof comprises one of the following combinations of heavy chain variable region sequence and light chain variable region sequence:

a heavy chain variable region comprising an amino acid sequence of SEQ ID NO: 78 and a light chain variable region comprising an amino acid sequence of SEQ ID NO: 90,
a heavy chain variable region comprising an amino acid sequence of SEQ ID NO: 78 and a light chain variable region comprising an amino acid sequence of SEQ ID NO: 92,
a heavy chain variable region comprising an amino acid sequence of SEQ ID NO: 78 and a light chain variable region comprising an amino acid sequence of SEQ ID NO: 94,
a heavy chain variable region comprising an amino acid sequence of SEQ ID NO: 78 and a light chain variable region comprising an amino acid sequence of SEQ ID NO: 96,
a heavy chain variable region comprising an amino acid sequence of SEQ ID NO: 78 and a light chain variable region comprising an amino acid sequence of SEQ ID NO: 98,
a heavy chain variable region comprising an amino acid sequence of SEQ ID NO: 78 and a light chain variable region comprising an amino acid sequence of SEQ ID NO: 100,
a heavy chain variable region comprising an amino acid sequence of SEQ ID NO: 80 and a light chain variable region comprising an amino acid sequence of SEQ ID NO: 90,
a heavy chain variable region comprising an amino acid sequence of SEQ ID NO: 80 and a light chain variable region comprising an amino acid sequence of SEQ ID NO: 92,
a heavy chain variable region comprising an amino acid sequence of SEQ ID NO: 80 and a light chain variable region comprising an amino acid sequence of SEQ ID NO: 94,
a heavy chain variable region comprising an amino acid sequence of SEQ ID NO: 80 and a light chain variable region comprising an amino acid sequence of SEQ ID NO: 96,
a heavy chain variable region comprising an amino acid sequence of SEQ ID NO: 80 and a light chain variable region comprising an amino acid sequence of SEQ ID NO: 98,
a heavy chain variable region comprising an amino acid sequence of SEQ ID NO: 80 and a light chain variable region comprising an amino acid sequence of SEQ ID NO: 100,
a heavy chain variable region comprising an amino acid sequence of SEQ ID NO: 82 and a light chain variable region comprising an amino acid sequence of SEQ ID NO: 90,
a heavy chain variable region comprising an amino acid sequence of SEQ ID NO: 82 and a light chain variable region comprising an amino acid sequence of SEQ ID NO: 92,
a heavy chain variable region comprising an amino acid sequence of SEQ ID NO: 82 and a light chain variable region comprising an amino acid sequence of SEQ ID NO: 94,
a heavy chain variable region comprising an amino acid sequence of SEQ ID NO: 82 and a light chain variable region comprising an amino acid sequence of SEQ ID NO: 96,
a heavy chain variable region comprising an amino acid sequence of SEQ ID NO: 82 and a light chain variable region comprising an amino acid sequence of SEQ ID NO: 98,
a heavy chain variable region comprising an amino acid sequence of SEQ ID NO: 82 and a light chain variable region comprising an amino acid sequence of SEQ ID NO: 100,
a heavy chain variable region comprising an amino acid sequence of SEQ ID NO: 84 and a light chain variable region comprising an amino acid sequence of SEQ ID NO: 90,
a heavy chain variable region comprising an amino acid sequence of SEQ ID NO: 84 and a light chain variable region comprising an amino acid sequence of SEQ ID NO: 92,
a heavy chain variable region comprising an amino acid sequence of SEQ ID NO: 84 and a light chain variable region comprising an amino acid sequence of SEQ ID NO: 94,
a heavy chain variable region comprising an amino acid sequence of SEQ ID NO: 84 and a light chain variable region comprising an amino acid sequence of SEQ ID NO: 96,
a heavy chain variable region comprising an amino acid sequence of SEQ ID NO: 84 and a light chain variable region comprising an amino acid sequence of SEQ ID NO: 98,
a heavy chain variable region comprising an amino acid sequence of SEQ ID NO: 84 and a light chain variable region comprising an amino acid sequence of SEQ ID NO: 100,
a heavy chain variable region comprising an amino acid sequence of SEQ ID NO: 86 and a light chain variable region comprising an amino acid sequence of SEQ ID NO: 90,
a heavy chain variable region comprising an amino acid sequence of SEQ ID NO: 86 and a light chain variable region comprising an amino acid sequence of SEQ ID NO: 92,
a heavy chain variable region comprising an amino acid sequence of SEQ ID NO: 86 and a light chain variable region comprising an amino acid sequence of SEQ ID NO: 94,
a heavy chain variable region comprising an amino acid sequence of SEQ ID NO: 86 and a light chain variable region comprising an amino acid sequence of SEQ ID NO: 96,
a heavy chain variable region comprising an amino acid sequence of SEQ ID NO: 86 and a light chain variable region comprising an amino acid sequence of SEQ ID NO: 98,
a heavy chain variable region comprising an amino acid sequence of SEQ ID NO: 86 and a light chain variable region comprising an amino acid sequence of SEQ ID NO: 100,
a heavy chain variable region comprising an amino acid sequence of SEQ ID NO: 88 and a light chain variable region comprising an amino acid sequence of SEQ ID NO: 90, a heavy chain variable region comprising an amino acid sequence of SEQ ID NO: 88 and a light chain variable region comprising an amino acid sequence of SEQ ID NO: 92, a heavy chain variable region comprising an amino acid sequence of SEQ ID NO: 88 and a light chain variable region comprising an amino acid sequence of SEQ ID NO: 94, a heavy chain variable region comprising an amino acid sequence of SEQ ID NO: 88 and a light chain variable region comprising an amino acid sequence of SEQ ID NO: 96, a heavy chain variable region comprising an amino acid sequence of SEQ ID NO: 88 and a light chain variable region comprising an amino acid sequence of SEQ ID NO: 98, a heavy chain variable region comprising an amino acid sequence of SEQ ID NO: 88 and a light chain variable region comprising an amino acid sequence of SEQ ID NO: 100, a heavy chain variable region comprising an amino acid sequence of SEQ ID NO: 10 and a light chain variable region comprising an amino acid sequence of SEQ ID NO: 20, a heavy chain variable region comprising an amino acid sequence of SEQ ID NO: 10 and a light chain variable region comprising an amino acid sequence of SEQ ID NO: 22, a heavy chain variable region comprising an amino acid sequence of SEQ ID NO: 10 and a light chain variable region comprising an amino acid sequence of SEQ ID NO: 24, a heavy chain variable region comprising an amino acid sequence of SEQ ID NO: 10 and a light chain variable region comprising an amino acid sequence of SEQ ID NO: 26, a heavy chain variable region comprising an amino acid sequence of SEQ ID NO: 10 and a light chain variable region comprising an amino acid sequence of SEQ ID NO: 28, a heavy chain variable region comprising an amino acid sequence of SEQ ID NO: 12 and a light chain variable region comprising an amino acid sequence of SEQ ID NO: 20, a heavy chain variable region comprising an amino acid sequence of SEQ ID NO: 12 and a light chain variable region comprising an amino acid sequence of SEQ ID NO: 22, a heavy chain variable region comprising an amino acid sequence of SEQ ID NO: 12 and a light chain variable region comprising an amino acid sequence of SEQ ID NO: 24, a heavy chain variable region comprising an amino acid sequence of SEQ ID NO: 12 and a light chain variable region comprising an amino acid sequence of SEQ ID NO: 26, a heavy chain variable region comprising an amino acid sequence of SEQ ID NO: 12 and a light chain variable region comprising an amino acid sequence of SEQ ID NO: 28, a heavy chain variable region comprising an amino acid sequence of SEQ ID NO: 14 and a light chain variable region comprising an amino acid sequence of SEQ ID NO: 20, a heavy chain variable region comprising an amino acid sequence of SEQ ID NO: 14 and a light chain variable region comprising an amino acid sequence of SEQ ID NO: 22, a heavy chain variable region comprising an amino acid sequence of SEQ ID NO: 14 and a light chain variable region comprising an amino acid sequence of SEQ ID NO: 24, a heavy chain variable region comprising an amino acid sequence of SEQ ID NO: 14 and a light chain variable region comprising an amino acid sequence of SEQ ID NO: 26, a heavy chain variable region comprising an amino acid sequence of SEQ ID NO: 14 and a light chain variable region comprising an amino acid sequence of SEQ ID NO: 28, a heavy chain variable region comprising an amino acid sequence of SEQ ID NO: 16 and a light chain variable region comprising an amino acid sequence of SEQ ID NO: 20, a heavy chain variable region comprising an amino acid sequence of SEQ ID NO: 16 and a light chain variable region comprising an amino acid sequence of SEQ ID NO: 22, a heavy chain variable region comprising an amino acid sequence of SEQ ID NO: 16 and a light chain variable region comprising an amino acid sequence of SEQ ID NO: 24, a heavy chain variable region comprising an amino acid sequence of SEQ ID NO: 16 and a light chain variable region comprising an amino acid sequence of SEQ ID NO: 26, a heavy chain variable region comprising an amino acid sequence of SEQ ID NO: 16 and a light chain variable region comprising an amino acid sequence of SEQ ID NO: 28, a heavy chain variable region comprising an amino acid sequence of SEQ ID NO: 18 and a light chain variable region comprising an amino acid sequence of SEQ ID NO: 20, a heavy chain variable region comprising an amino acid sequence of SEQ ID NO: 18 and a light chain variable region comprising an amino acid sequence of SEQ ID NO: 22, a heavy chain variable region comprising an amino acid sequence of SEQ ID NO: 18 and a light chain variable region comprising an amino acid sequence of SEQ ID NO: 24, a heavy chain variable region comprising an amino acid sequence of SEQ ID NO: 18 and a light chain variable region comprising an amino acid sequence of SEQ ID NO: 26, a heavy chain variable region comprising an amino acid sequence of SEQ ID NO: 18 and a light chain variable region comprising an amino acid sequence of SEQ ID NO: 28, or, in each case, at least 95% identical to a respective SEQ ID.

4. The antibody or antigen binding fragment of claim 3, wherein the antibody is an intact IgG.

5. The antibody or antigen binding fragment of claim 4, wherein the antibody comprises a wild-type or mutated IgG2 Fc region.

6. The antibody or antigen binding fragment of claim 4, wherein the antibody comprises a mutated IgG1 Fc region.

7. The antibody or antigen binding fragment of claim 4, wherein the antibody comprises a mutated IgG4 Fc region.

8. The antibody or antigen binding fragment of claim 3, wherein the antibody or antigen binding fragment thereof comprises a heavy chain variable region comprising an amino acid sequence of SEQ ID NO: 80 and a light chain variable region comprising an amino acid sequence of SEQ ID NO: 90.

9. The antibody or antigen binding fragment of claim 3, wherein the antibody or antigen binding fragment thereof comprises a heavy chain variable region comprising an amino acid sequence of SEQ ID NO: 80 and a light chain variable region comprising an amino acid sequence of SEQ ID NO: 92.

10. The antibody or antigen binding fragment of claim 3, wherein the antibody or antigen binding fragment thereof comprises a heavy chain variable region comprising an amino acid sequence of SEQ ID NO: 80 and a light chain variable region comprising an amino acid sequence of SEQ ID NO: 94.

11. The antibody or antigen binding fragment of claim 3, wherein the antibody or antigen binding fragment thereof comprises a heavy chain variable region comprising an amino acid sequence of SEQ ID NO: 80 and a light chain variable region comprising an amino acid sequence of SEQ ID NO: 96.

12. The antibody or antigen binding fragment of claim 3, wherein the antibody or antigen binding fragment thereof comprises a heavy chain variable region comprising an amino acid sequence of SEQ ID NO: 80 and a light chain variable region comprising an amino acid sequence of SEQ ID NO: 98.

13. The antibody or antigen binding fragment of claim 3, wherein the antibody or antigen binding fragment thereof comprises a heavy chain variable region comprising an amino acid sequence of SEQ ID NO: 80 and a light chain variable region comprising an amino acid sequence of SEQ ID NO: 100.

14. The antibody or antigen binding fragment of claim 1, wherein the heavy chain variable region CDR1 comprises the amino acid sequence of SEQ ID NO:69, the heavy chain variable region CDR2 comprises the amino acid sequence of SEQ ID NO: 136, the heavy chain variable region CDR3 comprises the amino acid sequence of SEQ ID NO:71, the light chain variable region CDR1 comprises the amino acid sequence of SEQ ID NO:72, the light chain variable region CDR2 comprises the amino acid sequence of SEQ ID NO:73, and the light chain variable region CDR3 comprises the amino acid sequence of SEQ ID NO:74.

15. A composition comprising:
an antibody or antigen binding fragment of claim 1; and
a pharmaceutically acceptable carrier or diluent.

16. The composition of claim 15, further comprising a second antibody or antigen binding fragment thereof that induces ADCC and/or ADCP.

17. An isolated nucleic acid encoding any one of the antibodies or antigen binding fragments of claim 1.

18. An expression vector comprising the isolated nucleic acid of claim 17.

19. A host cell comprising expression vector of claim 18.

* * * * *

SEQUENCE LISTING

```
<160> NUMBER OF SEQ ID NOS: 137

<210> SEQ ID NO 1
<211> LENGTH: 5
<212> TYPE: PRT
<213> ORGANISM: Artificial Sequence
<220> FEATURE:
<223> OTHER INFORMATION: Synthetic: 50A heavy chain CDR1

<400> SEQUENCE: 1

Asn Tyr Tyr Ile His
1               5

<210> SEQ ID NO 2
<211> LENGTH: 17
<212> TYPE: PRT
<213> ORGANISM: Artificial Sequence
<220> FEATURE:
<223> OTHER INFORMATION: Synthetic: 50A heavy chain CDR2

<400> SEQUENCE: 2

Trp Ile Tyr Pro Gly Asn Val Asn Thr Lys Tyr Asn Glu Lys Phe Lys
1               5                   10                  15

Ala

<210> SEQ ID NO 3
<211> LENGTH: 10
<212> TYPE: PRT
<213> ORGANISM: Artificial Sequence
<220> FEATURE:
<223> OTHER INFORMATION: Synthetic: 50A heavy chain CDR3
```

```
<400> SEQUENCE: 3

Pro Thr Ile Ile Ala Thr Asp Phe Asp Val
1               5                   10

<210> SEQ ID NO 4
<211> LENGTH: 11
<212> TYPE: PRT
<213> ORGANISM: Artificial Sequence
<220> FEATURE:
<223> OTHER INFORMATION: Synthetic: 50A light chain CDR1

<400> SEQUENCE: 4

Lys Ala Ser Gln Gly Val Gly Thr Ala Val Gly
1               5                   10

<210> SEQ ID NO 5
<211> LENGTH: 7
<212> TYPE: PRT
<213> ORGANISM: Artificial Sequence
<220> FEATURE:
<223> OTHER INFORMATION: Synthetic: 50A light chain CDR2

<400> SEQUENCE: 5

Trp Ala Ser Thr Arg His Thr
1               5

<210> SEQ ID NO 6
<211> LENGTH: 9
<212> TYPE: PRT
<213> ORGANISM: Artificial Sequence
<220> FEATURE:
<223> OTHER INFORMATION: Synthetic: 50A light chain CDR3

<400> SEQUENCE: 6

Gln Gln Tyr Ser Thr Tyr Pro Phe Thr
1               5

<210> SEQ ID NO 7
<211> LENGTH: 119
<212> TYPE: PRT
<213> ORGANISM: Artificial Sequence
<220> FEATURE:
<223> OTHER INFORMATION: Synthetic: humanized 50 heavy chain variable
      region (consensus sequence)
<220> FEATURE:
<221> NAME/KEY: misc_feature
<222> LOCATION: (5)..(5)
<223> OTHER INFORMATION: X = Q or V
<220> FEATURE:
<221> NAME/KEY: misc_feature
<222> LOCATION: (6)..(6)
<223> OTHER INFORMATION: X = Q or E
<220> FEATURE:
<221> NAME/KEY: misc_feature
<222> LOCATION: (9)..(9)
<223> OTHER INFORMATION: X = A or S
<220> FEATURE:
<221> NAME/KEY: misc_feature
<222> LOCATION: (11)..(11)
<223> OTHER INFORMATION: X = V or L
<220> FEATURE:
<221> NAME/KEY: misc_feature
<222> LOCATION: (19)..(19)
<223> OTHER INFORMATION: X = K or M
<220> FEATURE:
<221> NAME/KEY: misc_feature
<222> LOCATION: (20)..(20)
<223> OTHER INFORMATION: X = V or I
<220> FEATURE:
<221> NAME/KEY: misc_feature
<222> LOCATION: (40)..(40)
```

```
<223> OTHER INFORMATION: X = A or R
<220> FEATURE:
<221> NAME/KEY: misc_feature
<222> LOCATION: (42)..(42)
<223> OTHER INFORMATION: X = G or E
<220> FEATURE:
<221> NAME/KEY: misc_feature
<222> LOCATION: (48)..(48)
<223> OTHER INFORMATION: X = I or M
<220> FEATURE:
<221> NAME/KEY: misc_feature
<222> LOCATION: (67)..(67)
<223> OTHER INFORMATION: X = R or K
<220> FEATURE:
<221> NAME/KEY: misc_feature
<222> LOCATION: (68)..(68)
<223> OTHER INFORMATION: X = V or A
<220> FEATURE:
<221> NAME/KEY: misc_feature
<222> LOCATION: (69)..(69)
<223> OTHER INFORMATION: X = T or I
<220> FEATURE:
<221> NAME/KEY: misc_feature
<222> LOCATION: (70)..(70)
<223> OTHER INFORMATION: X = I or M
<220> FEATURE:
<221> NAME/KEY: misc_feature
<222> LOCATION: (79)..(79)
<223> OTHER INFORMATION: X = A or V
<220> FEATURE:
<221> NAME/KEY: misc_feature
<222> LOCATION: (82)..(82)
<223> OTHER INFORMATION: X = D or E or Q
<220> FEATURE:
<221> NAME/KEY: misc_feature
<222> LOCATION: (87)..(87)
<223> OTHER INFORMATION: X = R or T
<220> FEATURE:
<221> NAME/KEY: misc_feature
<222> LOCATION: (89)..(89)
<223> OTHER INFORMATION: X = E or D
<220> FEATURE:
<221> NAME/KEY: misc_feature
<222> LOCATION: (91)..(91)
<223> OTHER INFORMATION: X = T or M
<220> FEATURE:
<221> NAME/KEY: misc_feature
<222> LOCATION: (114)..(114)
<223> OTHER INFORMATION: X = T or L

<400> SEQUENCE: 7

Glu Val Gln Leu Xaa Xaa Ser Gly Xaa Glu Xaa Val Lys Pro Gly Ala
1               5                   10                  15

Ser Val Xaa Xaa Ser Cys Lys Ala Ser Gly Phe Thr Phe Thr Asn Tyr
            20                  25                  30

Tyr Ile His Trp Val Arg Gln Xaa Pro Xaa Gln Gly Leu Glu Trp Xaa
        35                  40                  45

Gly Trp Ile Tyr Pro Gly Asn Val Asn Thr Lys Tyr Asn Glu Lys Phe
    50                  55                  60

Lys Ala Xaa Xaa Xaa Xaa Thr Ala Asp Lys Ser Thr Ser Thr Xaa Tyr
65                  70                  75                  80

Met Xaa Leu Ser Ser Leu Xaa Ser Xaa Asp Xaa Ala Val Tyr Tyr Cys
            85                  90                  95

Ala Arg Pro Thr Ile Ile Ala Thr Asp Phe Asp Val Trp Gly Gln Gly
            100                 105                 110

Thr Xaa Val Thr Val Ser Ser
        115

<210> SEQ ID NO 8
<211> LENGTH: 107
```

```
<212> TYPE: PRT
<213> ORGANISM: Artificial Sequence
<220> FEATURE:
<223> OTHER INFORMATION: Synthetic: humanized 50 light chain variable
      region (consensus sequence)
<220> FEATURE:
<221> NAME/KEY: misc_feature
<222> LOCATION: (1)..(4)
<223> OTHER INFORMATION: X = D or E
<220> FEATURE:
<221> NAME/KEY: misc_feature
<222> LOCATION: (2)..(2)
<223> OTHER INFORMATION: X = I or L
<220> FEATURE:
<221> NAME/KEY: misc_feature
<222> LOCATION: (3)..(3)
<223> OTHER INFORMATION: X = V or Q
<220> FEATURE:
<221> NAME/KEY: misc_feature
<222> LOCATION: (4)..(4)
<223> OTHER INFORMATION: X = L or M
<220> FEATURE:
<221> NAME/KEY: misc_feature
<222> LOCATION: (10)..(10)
<223> OTHER INFORMATION: X = F or S
<220> FEATURE:
<221> NAME/KEY: misc_feature
<222> LOCATION: (38)..(38)
<223> OTHER INFORMATION: X = Q or K
<220> FEATURE:
<221> NAME/KEY: misc_feature
<222> LOCATION: (43)..(43)
<223> OTHER INFORMATION: X = A or S or V
<220> FEATURE:
<221> NAME/KEY: misc_feature
<222> LOCATION: (70)..(70)
<223> OTHER INFORMATION: X = E or D
<220> FEATURE:
<221> NAME/KEY: misc_feature
<222> LOCATION: (74)..(74)
<223> OTHER INFORMATION: X = T or A
<220> FEATURE:
<221> NAME/KEY: misc_feature
<222> LOCATION: (76)..(76)
<223> OTHER INFORMATION: X = S or N
<220> FEATURE:
<221> NAME/KEY: misc_feature
<222> LOCATION: (77)..(77)
<223> OTHER INFORMATION: X = S or N or G
<220> FEATURE:
<221> NAME/KEY: misc_feature
<222> LOCATION: (83)..(83)
<223> OTHER INFORMATION: X = F or I or V
<220> FEATURE:
<221> NAME/KEY: misc_feature
<222> LOCATION: (85)..(85)
<223> OTHER INFORMATION: X = A or D or T
<220> FEATURE:
<221> NAME/KEY: misc_feature
<222> LOCATION: (104)..(104)
<223> OTHER INFORMATION: X = L or V

<400> SEQUENCE: 8

Xaa Xaa Xaa Xaa Thr Gln Ser Pro Ser Xaa Leu Ser Ala Ser Val Gly
1               5                   10                  15

Asp Arg Val Thr Ile Thr Cys Lys Ala Ser Gln Gly Val Gly Thr Ala
            20                  25                  30

Val Gly Trp Tyr Gln Xaa Lys Pro Gly Lys Xaa Pro Lys Leu Leu Ile
        35                  40                  45

Tyr Trp Ala Ser Thr Arg His Thr Gly Val Pro Asp Arg Phe Ser Gly
    50                  55                  60

Ser Gly Ser Gly Thr Xaa Phe Thr Leu Xaa Ile Xaa Xaa Leu Gln Pro
65                  70                  75                  80
```

Glu Asp Xaa Ala Xaa Tyr Tyr Cys Gln Gln Tyr Ser Thr Tyr Pro Phe
            85                  90                  95

Thr Phe Gly Gly Gly Thr Lys Xaa Glu Ile Lys
            100                 105

<210> SEQ ID NO 9
<211> LENGTH: 357
<212> TYPE: DNA
<213> ORGANISM: Artificial Sequence
<220> FEATURE:
<223> OTHER INFORMATION: Synthetic: hSIRP alpha.50AVH1

<400> SEQUENCE: 9
gaagtgcagc tgcagcagtc tggcgccgag gtcgtgaaac ctggcgcctc tgtgaaggtg      60
tcctgcaagg cctccggctt caccttcacc aactactaca tccactgggt gcgacaggcc     120
ccaggccagg gactggaatg gatcggctgg atctaccccg gcaacgtgaa caccaagtac     180
aacgagaagt tcaaggcccg cgtgaccatc accgccgaca gtctacctc caccgcctac      240 atggacctgt cctccctgag atccgaggac accgccgtgt actactgcgc cagacccacc     300
atcattgcca ccgacttcga cgtgtggggc cagggcacaa ccgtgaccgt gtcctct        357

<210> SEQ ID NO 10
<211> LENGTH: 119
<212> TYPE: PRT
<213> ORGANISM: Artificial Sequence
<220> FEATURE:
<223> OTHER INFORMATION: Synthetic: hSIRP alpha.50AVH1

<400> SEQUENCE: 10

Glu Val Gln Leu Gln Gln Ser Gly Ala Glu Val Val Lys Pro Gly Ala
1               5                   10                  15

Ser Val Lys Val Ser Cys Lys Ala Ser Gly Phe Thr Phe Thr Asn Tyr
            20                  25                  30

Tyr Ile His Trp Val Arg Gln Ala Pro Gly Gln Gly Leu Glu Trp Ile
        35                  40                  45

Gly Trp Ile Tyr Pro Gly Asn Val Asn Thr Lys Tyr Asn Glu Lys Phe
    50                  55                  60

Lys Ala Arg Val Thr Ile Thr Ala Asp Lys Ser Thr Ser Thr Ala Tyr
65                  70                  75                  80

Met Asp Leu Ser Ser Leu Arg Ser Glu Asp Thr Ala Val Tyr Tyr Cys
                85                  90                  95

Ala Arg Pro Thr Ile Ile Ala Thr Asp Phe Asp Val Trp Gly Gln Gly
            100                 105                 110

Thr Thr Val Thr Val Ser Ser
        115

<210> SEQ ID NO 11
<211> LENGTH: 357
<212> TYPE: DNA
<213> ORGANISM: Artificial Sequence
<220> FEATURE:
<223> OTHER INFORMATION: Synthetic: hSIRP alpha.50AVH2

<400> SEQUENCE: 11
gaagtgcagc tggtggaatc cggctccgag ctcgtgaagc ctggcgcctc cgtgaaggtg      60
tcctgcaagg cctctggctt caccttcacc aactactaca tccactgggt gcgacaggcc     120
ccaggccagg gactggaatg gatgggctgg atctaccccg gcaacgtgaa caccaagtac     180
aacgagaagt tcaaggccaa ggccaccatc accgccgaca gtccacctc caccgcctac      240

```
atggaactgt cctccctgcg gagcgaggac accgccgtgt actactgtgc cggcctacc      300 atcattgcca ccgacttcga tgtgtggggc cagggcacac tcgtgaccgt gtcctct        357
```

<210> SEQ ID NO 12
<211> LENGTH: 119
<212> TYPE: PRT
<213> ORGANISM: Artificial Sequence
<220> FEATURE:
<223> OTHER INFORMATION: Synthetic: hSIRP alpha.50AVH2

<400> SEQUENCE: 12

```
Glu Val Gln Leu Val Glu Ser Gly Ser Glu Leu Val Lys Pro Gly Ala
1               5                   10                  15

Ser Val Lys Val Ser Cys Lys Ala Ser Gly Phe Thr Phe Thr Asn Tyr
            20                  25                  30

Tyr Ile His Trp Val Arg Gln Ala Pro Gly Gln Gly Leu Glu Trp Met
        35                  40                  45

Gly Trp Ile Tyr Pro Gly Asn Val Asn Thr Lys Tyr Asn Glu Lys Phe
    50                  55                  60

Lys Ala Lys Ala Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Pro Thr Ile Ile Ala Thr Asp Phe Asp Val Trp Gly Gln Gly
            100                 105                 110

Thr Leu Val Thr Val Ser Ser
        115
```

<210> SEQ ID NO 13
<211> LENGTH: 357
<212> TYPE: DNA
<213> ORGANISM: Artificial Sequence
<220> FEATURE:
<223> OTHER INFORMATION: Synthetic: hSIRP alpha.50AVH3

<400> SEQUENCE: 13

```
gaagtgcagc tggtgcagtc tggcgccgag gtcgtgaaac tggcgcctc cgtgatgatc      60 tcctgcaagg cctccggctt caccttcacc aactactaca tccactgggt gcgacagcgg   120
ccaggccagg gactggaatg gatcggctgg atctaccccg gcaacgtgaa caccaagtac   180
aacgagaagt tcaaggcccg cgtgatcatg accgccgaca gtccacctc caccgtgtac   240 atgcagctgt cctccctgac ctccgaggac accgccgtgt actactgcgc cagacccacc   300
atcattgcca ccgacttcga cgtgtggggc cagggcacac tcgtgaccgt gtcctct      357
```

<210> SEQ ID NO 14
<211> LENGTH: 119
<212> TYPE: PRT
<213> ORGANISM: Artificial Sequence
<220> FEATURE:
<223> OTHER INFORMATION: Synthetic: hSIRP alpha.50AVH3

<400> SEQUENCE: 14

```
Glu Val Gln Leu Val Gln Ser Gly Ala Glu Val Val Lys Pro Gly Ala
1               5                   10                  15

Ser Val Met Ile Ser Cys Lys Ala Ser Gly Phe Thr Phe Thr Asn Tyr
            20                  25                  30

Tyr Ile His Trp Val Arg Gln Arg Pro Gly Gln Gly Leu Glu Trp Ile
        35                  40                  45
```

```
Gly Trp Ile Tyr Pro Gly Asn Val Asn Thr Lys Tyr Asn Glu Lys Phe
        50                  55                  60

Lys Ala Arg Val Ile Met Thr Ala Asp Lys Ser Thr Ser Thr Val Tyr
65                  70                  75                  80

Met Gln Leu Ser Ser Leu Thr Ser Glu Asp Thr Ala Val Tyr Tyr Cys
                85                  90                  95

Ala Arg Pro Thr Ile Ile Ala Thr Asp Phe Asp Val Trp Gly Gln Gly
            100                 105                 110

Thr Leu Val Thr Val Ser Ser
        115
```

```
<210> SEQ ID NO 15
<211> LENGTH: 357
<212> TYPE: DNA
<213> ORGANISM: Artificial Sequence
<220> FEATURE:
<223> OTHER INFORMATION: Synthetic: hSIRP alpha.50AVH4

<400> SEQUENCE: 15
gaagtgcagc tgcagcagtc tggcgccgag ctcgtgaaac ctggcgcctc tgtgaaggtg    60
tcctgcaagg cctccggctt caccttcacc aactactaca tccactgggt gcgacagcgg   120
ccaggccagg gactggaatg gatgggctgg atctaccccg gcaacgtgaa caccaagtac   180
aacgagaagt tcaaggccaa ggccaccatc accgccgaca gtccactctc accgcctac    240 atggaactgt cctccctgac ctccgaggac accgccgtgt actactgcgc cagacccacc   300
atcattgcca ccgacttcga cgtgtggggc cagggcacaa ccgtgaccgt gtcctct      357
```

```
<210> SEQ ID NO 16
<211> LENGTH: 119
<212> TYPE: PRT
<213> ORGANISM: Artificial Sequence
<220> FEATURE:
<223> OTHER INFORMATION: Synthetic: hSIRP alpha.50AVH4

<400> SEQUENCE: 16

Glu Val Gln Leu Gln Gln Ser Gly Ala Glu Leu Val Lys Pro Gly Ala
1               5                   10                  15

Ser Val Lys Val Ser Cys Lys Ala Ser Gly Phe Thr Phe Thr Asn Tyr
            20                  25                  30

Tyr Ile His Trp Val Arg Gln Arg Pro Gly Gln Gly Leu Glu Trp Met
        35                  40                  45

Gly Trp Ile Tyr Pro Gly Asn Val Asn Thr Lys Tyr Asn Glu Lys Phe
    50                  55                  60

Lys Ala Lys Ala Thr Ile Thr Ala Asp Lys Ser Thr Ser Thr Ala Tyr
65                  70                  75                  80

Met Glu Leu Ser Ser Leu Thr Ser Glu Asp Thr Ala Val Tyr Tyr Cys
                85                  90                  95

Ala Arg Pro Thr Ile Ile Ala Thr Asp Phe Asp Val Trp Gly Gln Gly
            100                 105                 110

Thr Thr Val Thr Val Ser Ser
        115
```

```
<210> SEQ ID NO 17
<211> LENGTH: 357
<212> TYPE: DNA
<213> ORGANISM: Artificial Sequence
<220> FEATURE:
<223> OTHER INFORMATION: Synthetic: hSIRP alpha.50AVH5
```

<400> SEQUENCE: 17

```
gaagtgcagc tggtgcagtc tggcgccgag gtcgtgaaac ctggcgcctc tgtgaaggtg      60
tcctgcaagg cctccggctt caccttcacc aactactaca tccactgggt gcgacaggcc     120
cccgagcagg gactggaatg gatcggctgg atctaccccg gcaacgtgaa caccaagtac     180
aacgagaagt tcaaggcccg cgtgaccatg accgccgaca gtctacctc caccgcctac      240
atggaactgt cctccctgcg gagcgacgac atggccgtgt actactgcgc cagacccacc     300
atcattgcca ccgacttcga cgtgtgggc cagggcacaa ccgtgaccgt gtcctct         357
```

<210> SEQ ID NO 18
<211> LENGTH: 119
<212> TYPE: PRT
<213> ORGANISM: Artificial Sequence
<220> FEATURE:
<223> OTHER INFORMATION: Synthetic: hSIRP alpha.50AVH5

<400> SEQUENCE: 18

```
Glu Val Gln Leu Val Gln Ser Gly Ala Glu Val Val Lys Pro Gly Ala
1               5                   10                  15
Ser Val Lys Val Ser Cys Lys Ala Ser Gly Phe Thr Phe Thr Asn Tyr
            20                  25                  30
Tyr Ile His Trp Val Arg Gln Ala Pro Glu Gln Gly Leu Glu Trp Ile
        35                  40                  45
Gly Trp Ile Tyr Pro Gly Asn Val Asn Thr Lys Tyr Asn Glu Lys Phe
    50                  55                  60
Lys Ala Arg Val Thr Met Thr Ala Asp Lys Ser Thr Ser Thr Ala Tyr
65                  70                  75                  80
Met Glu Leu Ser Ser Leu Arg Ser Asp Asp Met Ala Val Tyr Tyr Cys
                85                  90                  95
Ala Arg Pro Thr Ile Ile Ala Thr Asp Phe Asp Val Trp Gly Gln Gly
            100                 105                 110
Thr Thr Val Thr Val Ser Ser
        115
```

<210> SEQ ID NO 19
<211> LENGTH: 321
<212> TYPE: DNA
<213> ORGANISM: Artificial Sequence
<220> FEATURE:
<223> OTHER INFORMATION: Synthetic: hSIRP alpha.50AVL1

<400> SEQUENCE: 19

```
gacatcgtgc tgacccagtc ccccagcttc ctgtctgcct ctgtgggcga cagagtgacc      60
atcacatgca aggcctctca gggcgtgggc accgctgtgg atggtatca gcagaagcct     120
ggcaaggccc ccaagctgct gatctactgg gcctctacca gacacaccgg cgtgcccgac     180
agattctccg gctctggctc tggcaccgag tttaccctga ccatctccag cctgcagccc     240
gaggatttcg ccgcctacta ctgccagcag tactccacct accccttcac cttcggcgga     300
ggcaccaagc tggaaatcaa g                                                 321
```

<210> SEQ ID NO 20
<211> LENGTH: 107
<212> TYPE: PRT
<213> ORGANISM: Artificial Sequence
<220> FEATURE:
<223> OTHER INFORMATION: Synthetic: hSIRP alpha.50AVL1

```
<400> SEQUENCE: 20

Asp Ile Val Leu Thr Gln Ser Pro Ser Phe Leu Ser Ala Ser Val Gly
1               5                   10                  15

Asp Arg Val Thr Ile Thr Cys Lys Ala Ser Gln Gly Val Gly Thr Ala
                20                  25                  30

Val Gly Trp Tyr Gln Gln Lys Pro Gly Lys Ala Pro Lys Leu Leu Ile
            35                  40                  45

Tyr Trp Ala Ser Thr Arg His Thr Gly Val Pro Asp Arg Phe Ser Gly
50                  55                  60

Ser Gly Ser Gly Thr Glu Phe Thr Leu Thr Ile Ser Ser Leu Gln Pro
65                  70                  75                  80

Glu Asp Phe Ala Ala Tyr Tyr Cys Gln Gln Tyr Ser Thr Tyr Pro Phe
                85                  90                  95

Thr Phe Gly Gly Gly Thr Lys Leu Glu Ile Lys
            100                 105

<210> SEQ ID NO 21
<211> LENGTH: 321
<212> TYPE: DNA
<213> ORGANISM: Artificial Sequence
<220> FEATURE:
<223> OTHER INFORMATION: Synthetic: hSIRP alpha.50AVL2

<400> SEQUENCE: 21
gacatcgtga tgacccagtc cccctccagc ctgtctgcct ctgtgggcga cagagtgacc      60
atcacatgca aggcctctca gggcgtgggc accgctgtgg gatggtatca gcagaagcct     120
ggcaaggccc ccaagctgct gatctactgg gcctctacca gacacaccgg cgtgcccgac     180
agattctccg gctctggctc tggcaccgac ttcaccctga ccatctccaa cctgcagccc     240
gaggacttcg ccgactacta ctgccagcag tactccacct acccccttca cttcggcgga    300
ggcaccaagg tggaaatcaa g                                               321

<210> SEQ ID NO 22
<211> LENGTH: 107
<212> TYPE: PRT
<213> ORGANISM: Artificial Sequence
<220> FEATURE:
<223> OTHER INFORMATION: Synthetic: hSIRP alpha.50AVL2

<400> SEQUENCE: 22

Asp Ile Val Met Thr Gln Ser Pro Ser Ser Leu Ser Ala Ser Val Gly
1               5                   10                  15

Asp Arg Val Thr Ile Thr Cys Lys Ala Ser Gln Gly Val Gly Thr Ala
                20                  25                  30

Val Gly Trp Tyr Gln Gln Lys Pro Gly Lys Ala Pro Lys Leu Leu Ile
            35                  40                  45

Tyr Trp Ala Ser Thr Arg His Thr Gly Val Pro Asp Arg Phe Ser Gly
50                  55                  60

Ser Gly Ser Gly Thr Asp Phe Thr Leu Thr Ile Ser Asn Leu Gln Pro
65                  70                  75                  80

Glu Asp Phe Ala Asp Tyr Tyr Cys Gln Gln Tyr Ser Thr Tyr Pro Phe
                85                  90                  95

Thr Phe Gly Gly Gly Thr Lys Val Glu Ile Lys
            100                 105

<210> SEQ ID NO 23
<211> LENGTH: 321
```

<212> TYPE: DNA
<213> ORGANISM: Artificial Sequence
<220> FEATURE:
<223> OTHER INFORMATION: Synthetic: hSIRP alpha.50AVL3

<400> SEQUENCE: 23

```
gagctcgtga tgacccagtc cccttccagc ctgtctgcct ccgtgggcga cagagtgacc    60
atcacatgca aggcctctca gggcgtgggc accgctgtgg gatggtatca gcagaagcct   120
ggcaaggccc ccaagctgct gatctactgg gcctctacca gacacaccgg cgtgcccgac   180
agattctccg gctctggctc tggcaccgac tttaccctgg ccatctccag cctgcagccc   240
gaggatatcg ccgactacta ctgccagcag tactccacct accccttcac cttcggcgga   300
ggcaccaagg tggaaatcaa g                                             321
```

<210> SEQ ID NO 24
<211> LENGTH: 107
<212> TYPE: PRT
<213> ORGANISM: Artificial Sequence
<220> FEATURE:
<223> OTHER INFORMATION: Synthetic: hSIRP alpha.50AVL3

<400> SEQUENCE: 24

```
Glu Leu Val Met Thr Gln Ser Pro Ser Ser Leu Ser Ala Ser Val Gly
1               5                   10                  15
Asp Arg Val Thr Ile Thr Cys Lys Ala Ser Gln Gly Val Gly Thr Ala
            20                  25                  30
Val Gly Trp Tyr Gln Gln Lys Pro Gly Lys Ala Pro Lys Leu Leu Ile
        35                  40                  45
Tyr Trp Ala Ser Thr Arg His Thr Gly Val Pro Asp Arg Phe Ser Gly
    50                  55                  60
Ser Gly Ser Gly Thr Asp Phe Thr Leu Ala Ile Ser Ser Leu Gln Pro
65                  70                  75                  80
Glu Asp Ile Ala Asp Tyr Tyr Cys Gln Gln Tyr Ser Thr Tyr Pro Phe
                85                  90                  95
Thr Phe Gly Gly Gly Thr Lys Val Glu Ile Lys
            100                 105
```

<210> SEQ ID NO 25
<211> LENGTH: 321
<212> TYPE: DNA
<213> ORGANISM: Artificial Sequence
<220> FEATURE:
<223> OTHER INFORMATION: Synthetic: hSIRP alpha.50AVL4

<400> SEQUENCE: 25

```
gacatccaga tgacccagtc cccctccagc ctgtctgcct ctgtgggcga cagagtgacc    60
atcacatgca aggcctctca gggcgtgggc accgctgtgg gctggtatca gaaaaagccc   120
ggcaaggtgc ccaagctgct gatctactgg gcctccacca gacacaccgg cgtgcccgat   180
agattctccg gctctggctc tggcaccgac ttcaccctga ccatcaacgg cctgcagcct   240
gaggacgtgg ccacctacta ctgccagcag tactccacct accccttcac cttcggcgga   300
ggcaccaagc tggaaatcaa g                                             321
```

<210> SEQ ID NO 26
<211> LENGTH: 107
<212> TYPE: PRT
<213> ORGANISM: Artificial Sequence
<220> FEATURE:
<223> OTHER INFORMATION: Synthetic: hSIRP alpha.50AVL4

<400> SEQUENCE: 26

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Gly Val Gly Thr Ala
            20                  25                  30

Val Gly Trp Tyr Gln Lys Lys Pro Gly Lys Val Pro Lys Leu Leu Ile
        35                  40                  45

Tyr Trp Ala Ser Thr Arg His Thr Gly Val Pro Asp Arg Phe Ser Gly
50                  55                  60

Ser Gly Ser Gly Thr Asp Phe Thr Leu Thr Ile Asn Gly Leu Gln Pro
65                  70                  75                  80

Glu Asp Val Ala Thr Tyr Tyr Cys Gln Gln Tyr Ser Thr Tyr Pro Phe
                85                  90                  95

Thr Phe Gly Gly Gly Thr Lys Leu Glu Ile Lys
            100                 105
```

<210> SEQ ID NO 27
<211> LENGTH: 321
<212> TYPE: DNA
<213> ORGANISM: Artificial Sequence
<220> FEATURE:
<223> OTHER INFORMATION: Synthetic: hSIRP alpha.50AVL5

<400> SEQUENCE: 27

```
gacatcgtgc tgacccagtc ccccagcttc ctgtctgcct ctgtgggcga cagagtgacc      60
atcacatgca aggcctctca gggcgtgggc accgctgtgg gatggtatca gcagaagccc     120
ggcaagtccc ccaagctgct gatctactgg gcctccacca gacacaccgg cgtgcccgat     180
agattctccg gctctggctc tggcaccgag ttcaccctga ccatctccaa cctgcagccc     240
gaggacttcg ccgcctacta ctgccagcag tactccacct accccttcac cttcggcgga     300
ggcaccaagc tggaaatcaa g                                                321
```

<210> SEQ ID NO 28
<211> LENGTH: 107
<212> TYPE: PRT
<213> ORGANISM: Artificial Sequence
<220> FEATURE:
<223> OTHER INFORMATION: Synthetic: hSIRP alpha.50AVL5

<400> SEQUENCE: 28

```
Asp Ile Val Leu Thr Gln Ser Pro Ser Phe Leu Ser Ala Ser Val Gly
1               5                   10                  15

Asp Arg Val Thr Ile Thr Cys Lys Ala Ser Gln Gly Val Gly Thr Ala
            20                  25                  30

Val Gly Trp Tyr Gln Gln Lys Pro Gly Lys Ser Pro Lys Leu Leu Ile
        35                  40                  45

Tyr Trp Ala Ser Thr Arg His Thr Gly Val Pro Asp Arg Phe Ser Gly
50                  55                  60

Ser Gly Ser Gly Thr Glu Phe Thr Leu Thr Ile Ser Asn Leu Gln Pro
65                  70                  75                  80

Glu Asp Phe Ala Ala Tyr Tyr Cys Gln Gln Tyr Ser Thr Tyr Pro Phe
                85                  90                  95

Thr Phe Gly Gly Gly Thr Lys Leu Glu Ile Lys
            100                 105
```

<210> SEQ ID NO 29

```
<211> LENGTH: 357
<212> TYPE: DNA
<213> ORGANISM: Artificial Sequence
<220> FEATURE:
<223> OTHER INFORMATION: Synthetic: hSIRP alpha.50A mouse VH

<400> SEQUENCE: 29
caggtccagc tgcagcagtc tggacctgaa ctggtgaagc ctggggcttc agttaggata      60
tcctgcaagg cttctggctt caccttcaca aactactata tacactgggt gaagcagagg     120
cctggacagg gacttgagtg gattggatgg atttatcctg gaaatgttaa tactaagtac     180
aatgagaagt tcaaggccaa ggccacactg actgcagaca atcctccac  cacagcctac     240 atgcagctca gcagcctggc ctctgaggac tctgcggtct atttctgtgc aagacctacg     300
ataatagcta cggacttcga tgtctggggc gcagggacca cggtcaccgt ctcctca       357

<210> SEQ ID NO 30
<211> LENGTH: 119
<212> TYPE: PRT
<213> ORGANISM: Artificial Sequence
<220> FEATURE:
<223> OTHER INFORMATION: Synthetic: hSIRP alpha.50A mouse VH

<400> SEQUENCE: 30

Gln Val Gln Leu Gln Gln Ser Gly Pro Glu Leu Val Lys Pro Gly Ala
1               5                   10                  15

Ser Val Arg Ile Ser Cys Lys Ala Ser Gly Phe Thr Phe Thr Asn Tyr
            20                  25                  30

Tyr Ile His Trp Val Lys Gln Arg Pro Gly Gln Gly Leu Glu Trp Ile
        35                  40                  45

Gly Trp Ile Tyr Pro Gly Asn Val Asn Thr Lys Tyr Asn Glu Lys Phe
    50                  55                  60

Lys Ala Lys Ala Thr Leu Thr Ala Asp Lys Ser Ser Thr Thr Ala Tyr
65                  70                  75                  80

Met Gln Leu Ser Ser Leu Ala Ser Glu Asp Ser Ala Val Tyr Phe Cys
                85                  90                  95

Ala Arg Pro Thr Ile Ile Ala Thr Asp Phe Asp Val Trp Gly Ala Gly
            100                 105                 110

Thr Thr Val Thr Val Ser Ser
        115

<210> SEQ ID NO 31
<211> LENGTH: 321
<212> TYPE: DNA
<213> ORGANISM: Artificial Sequence
<220> FEATURE:
<223> OTHER INFORMATION: Synthetic: hSIRP alpha.50A mouse VL

<400> SEQUENCE: 31
gacattgtca tgacccagtc tcacaaattc atgtccacat cagtaggaga cagggtcaac      60
atcacctgca aggccagtca gggtgtgggt actgctgtag ctggtatca  acagaaacca     120 gggcaatctc ctagactact gatttactgg gcatccaccc ggcacactgg agtccctgat     180
cgcttcacag gcagtggatc tgggacagat ttcagtctcg ccattagcaa tgtgcagtct     240
gaagacctgg cagattattt ctgtcagcaa tatagcacct atccgttcac gttcggaggg     300
gggaccaatc tagaaataaa a                                               321

<210> SEQ ID NO 32
<211> LENGTH: 107
```

<212> TYPE: PRT
<213> ORGANISM: Artificial Sequence
<220> FEATURE:
<223> OTHER INFORMATION: Synthetic: hSIRP alpha.50A mouse VL

<400> SEQUENCE: 32

Asp Ile Val Met Thr Gln Ser His Lys Phe Met Ser Thr Ser Val Gly
1               5                   10                  15

Asp Arg Val Asn Ile Thr Cys Lys Ala Ser Gln Gly Val Gly Thr Ala
            20                  25                  30

Val Gly Trp Tyr Gln Gln Lys Pro Gly Gln Ser Pro Arg Leu Leu Ile
        35                  40                  45

Tyr Trp Ala Ser Thr Arg His Thr Gly Val Pro Asp Arg Phe Thr Gly
    50                  55                  60

Ser Gly Ser Gly Thr Asp Phe Ser Leu Ala Ile Ser Asn Val Gln Ser
65                  70                  75                  80

Glu Asp Leu Ala Asp Tyr Phe Cys Gln Gln Tyr Ser Thr Tyr Pro Phe
                85                  90                  95

Thr Phe Gly Gly Gly Thr Asn Leu Glu Ile Lys
            100                 105

<210> SEQ ID NO 33
<211> LENGTH: 1512
<212> TYPE: DNA
<213> ORGANISM: Homo sapiens
<220> FEATURE:
<221> NAME/KEY: misc_feature
<222> LOCATION: (1)..(1512)
<223> OTHER INFORMATION: human SIRP alpha V1

<400> SEQUENCE: 33
atggagcccg ccggcccggc ccccggccgc ctcgggccgc tgctctgcct gctgctcgcc      60
gcgtcctgcg cctggtcagg agtggcgggt gaggaggagc tgcaggtgat tcagcctgac     120
aagtccgtgt tggttgcagc tggagagaca gccactctgc gctgcactgc gacctctctg     180
atccctgtgg ggcccatcca gtggttcaga ggagctggac caggccggga attaatctac     240
aatcaaaaag aaggccactt ccccggggta caaactgttt cagacctcac aaagagaaac     300
aacatggact tttccatccg catcggtaac atcacccccag cagatgccgg cacctactac     360
tgtgtgaagt tccggaaagg gagccccgat gacgtggagt ttaagtctgg agcaggcact     420
gagctgtctg tgcgcgccaa accctctgcc cccgtggtat cgggccctgc ggcgagggcc     480
acacctcagc acacagtgag cttcacctgc gagtcccacg gcttctcacc cagagacatc     540
accctgaaat ggttcaaaaa tgggaatgag ctctcagact ccagaccaa cgtggacccc     600 gtaggagaga gcgtgtccta cagcatccac agcacagcca aggtggtgct gacccgcgag     660
gacgttcact ctcaagtcat ctgcgaggtg gcccacgtca ccttgcaggg ggaccctctt     720
cgtgggactg ccaacttgtc tgagaccatc cgagttccac ccaccttgga ggttactcaa     780
cagcccgtga gggcagagaa ccaggtgaat gtcacctgcc aggtgaggaa gttctacccc     840
cagagactac agctgacctg gttggagaat ggaaacgtgt cccggacaga aacggcctca     900
accgttacag agaacaagga tggtacctac aactggatga ctggctcct ggtgaatgta     960 tctgcccaca gggatgatgt gaagctcacc tgccaggtgg agcatgacgg gcagccagcg    1020
gtcagcaaaa gccatgacct gaaggtctca gcccacccga aggagcaggg ctcaaatacc    1080
gccgctgaga cactggatc taatgaacgg aacatctata ttgtggtggg tgtggtgtgc    1140
accttgctgg tggccctact gatggcggcc ctctacctcg tccgaatcag acagaagaaa    1200

-continued

```
gcccagggct ccacttcttc tacaaggttg catgagcccg agaagaatgc cagagaaata    1260
acacaggaca caaatgatat cacatatgca gacctgaacc tgcccaaggg gaagaagcct    1320
gctccccagg ctgcggagcc caacaaccac acggagtatg ccagcattca gaccagcccg    1380
cagcccgcgt cggaggacac cctcacctat gctgacctgg acatggtcca cctcaaccgg    1440 accccccaagc agccggcccc caagcctgag ccgtccttct cagagtacgc cagcgtccag    1500
gtcccgagga ag                                                        1512
```

<210> SEQ ID NO 34
<211> LENGTH: 504
<212> TYPE: PRT
<213> ORGANISM: Homo sapiens
<220> FEATURE:
<221> NAME/KEY: misc_feature
<222> LOCATION: (1)..(504)
<223> OTHER INFORMATION: human SIRP alpha V1

<400> SEQUENCE: 34

```
Met Glu Pro Ala Gly Pro Ala Pro Gly Arg Leu Gly Pro Leu Leu Cys
 1               5                  10                  15

Leu Leu Leu Ala Ala Ser Cys Ala Trp Ser Gly Val Ala Gly Glu Glu
             20                  25                  30

Glu Leu Gln Val Ile Gln Pro Asp Lys Ser Val Leu Val Ala Ala Gly
         35                  40                  45

Glu Thr Ala Thr Leu Arg Cys Thr Ala Thr Ser Leu Ile Pro Val Gly
     50                  55                  60

Pro Ile Gln Trp Phe Arg Gly Ala Gly Pro Gly Arg Glu Leu Ile Tyr
 65                  70                  75                  80

Asn Gln Lys Glu Gly His Phe Pro Arg Val Thr Thr Val Ser Asp Leu
                 85                  90                  95

Thr Lys Arg Asn Asn Met Asp Phe Ser Ile Arg Ile Gly Asn Ile Thr
            100                 105                 110

Pro Ala Asp Ala Gly Thr Tyr Tyr Cys Val Lys Phe Arg Lys Gly Ser
        115                 120                 125

Pro Asp Asp Val Glu Phe Lys Ser Gly Ala Gly Thr Glu Leu Ser Val
    130                 135                 140

Arg Ala Lys Pro Ser Ala Pro Val Val Ser Gly Pro Ala Ala Arg Ala
145                 150                 155                 160

Thr Pro Gln His Thr Val Ser Phe Thr Cys Glu Ser His Gly Phe Ser
                165                 170                 175

Pro Arg Asp Ile Thr Leu Lys Trp Phe Lys Asn Gly Asn Glu Leu Ser
            180                 185                 190

Asp Phe Gln Thr Asn Val Asp Pro Val Gly Glu Ser Val Ser Tyr Ser
        195                 200                 205

Ile His Ser Thr Ala Lys Val Val Leu Thr Arg Glu Asp Val His Ser
    210                 215                 220

Gln Val Ile Cys Glu Val Ala His Val Thr Leu Gln Gly Asp Pro Leu
225                 230                 235                 240

Arg Gly Thr Ala Asn Leu Ser Glu Thr Ile Arg Val Pro Pro Thr Leu
                245                 250                 255

Glu Val Thr Gln Gln Pro Val Arg Ala Glu Asn Gln Val Asn Val Thr
            260                 265                 270

Cys Gln Val Arg Lys Phe Tyr Pro Gln Arg Leu Gln Leu Thr Trp Leu
        275                 280                 285
```

```
Glu Asn Gly Asn Val Ser Arg Thr Glu Thr Ala Ser Thr Val Thr Glu
    290                 295                 300
Asn Lys Asp Gly Thr Tyr Asn Trp Met Ser Trp Leu Leu Val Asn Val
305                 310                 315                 320
Ser Ala His Arg Asp Asp Val Lys Leu Thr Cys Gln Val Glu His Asp
                325                 330                 335
Gly Gln Pro Ala Val Ser Lys Ser His Asp Leu Lys Val Ser Ala His
            340                 345                 350
Pro Lys Glu Gln Gly Ser Asn Thr Ala Ala Glu Asn Thr Gly Ser Asn
        355                 360                 365
Glu Arg Asn Ile Tyr Ile Val Val Gly Val Val Cys Thr Leu Leu Val
    370                 375                 380
Ala Leu Leu Met Ala Ala Leu Tyr Leu Val Arg Ile Arg Gln Lys Lys
385                 390                 395                 400
Ala Gln Gly Ser Thr Ser Ser Thr Arg Leu His Glu Pro Glu Lys Asn
                405                 410                 415
Ala Arg Glu Ile Thr Gln Asp Thr Asn Asp Ile Thr Tyr Ala Asp Leu
            420                 425                 430
Asn Leu Pro Lys Gly Lys Lys Pro Ala Pro Gln Ala Ala Glu Pro Asn
        435                 440                 445
Asn His Thr Glu Tyr Ala Ser Ile Gln Thr Ser Pro Gln Pro Ala Ser
    450                 455                 460
Glu Asp Thr Leu Thr Tyr Ala Asp Leu Asp Met Val His Leu Asn Arg
465                 470                 475                 480
Thr Pro Lys Gln Pro Ala Pro Lys Pro Glu Pro Ser Phe Ser Glu Tyr
                485                 490                 495
Ala Ser Val Gln Val Pro Arg Lys
            500

<210> SEQ ID NO 35
<211> LENGTH: 1509
<212> TYPE: DNA
<213> ORGANISM: Homo sapiens
<220> FEATURE:
<221> NAME/KEY: misc_feature
<222> LOCATION: (1)..(1509)
<223> OTHER INFORMATION: human SIRP alpha V2

<400> SEQUENCE: 35
atggaacctg ccggacctgc ccctggcaga ctgggacctc tgctgtgtct gctgctggcc      60
gcctcttgtg cttggagcgg agtggctggc gaagaggaac tgcaagtgat ccagcccgac     120
aagagcgtgt ccgtggctgc tggcgagtct gccatcctgc actgtaccgt gaccagcctg     180
atccccgtgg cccccatcca gtggtttaga ggcgctggcc ctgccagaga gctgatctac     240
aaccagaaag agggccactt ccccagagtg accaccgtgt ccgagagcac caagcgcgag     300
aacatggact tcagcatcag catctccaac atcacccctg ccgacgccgg cacctactac     360
tgcgtgaagt tcagaaaggg cagccccgac accgagttca gagcggcgc tggaaccgag     420 ctgtctgtgc gggctaagcc ttctgcccct gtggtgtctg acctgccgc cagagctaca     480 cctcagcaca ccgtgtcttt cacatgcgag agccacggct tcagcccag agacatcacc     540 ctgaagtggt tcaagaacgg caacgagctg agcgacttcc agaccaacgt ggaccctgtg     600
ggcgagtccg tgtcctacag catccacagc accgccaagg tggtgctgac ccgcgaggat     660
gtgcacagcc aagtgatctg cgaggtggcc cacgtgacac tgcagggcga tcctctgaga     720
ggcaccgcta acctgagcga gacaatcaga gtgcccccca ccctggaagt gacccagcag     780
```

```
cccgtgcggg ctgagaacca agtgaacgtg acctgccaag tgcggaagtt ctaccctcag    840
agactgcagc tgacctggct ggaaaacgga acgtgtcca gaaccgagac agccagcacc    900
gtgacagaga caaggacgg cacatacaac tggatgagct ggctgctcgt gaacgtgtcc    960
gcccacagag atgacgtgaa gctgacatgc caggtggaac acgacggcca gcctgccgtg   1020
tctaagagcc acgacctgaa ggtgtccgct caccccaaag agcagggcag caacaccgcc   1080
gctgagaaca caggcagcaa cgagagaaac atctacatcg tcgtgggcgt cgtgtgcacc   1140
ctgctggtgg ctctgctgat ggctgccctg tacctcgtgc ggatcagaca agaagaggcc   1200
cagggctcca cctccagcac cagactgcac gagcctgaga gaacgcccg cgagatcacc   1260
caggacacca acgacatcac ctacgccgac ctgaacctgc caagggcaa gaagcctgcc   1320
cctcaggctg ccgagcctaa caaccacaca gagtacgcca gcatccagac agccctcag   1380
cctgccagcg aggacacact gacatacgcc gatctggaca tggtgcacct gaacagaacc   1440
cccaagcagc ccgctcccaa gcccgagcct agcttctctg agtacgcctc cgtgcaggtg   1500
cccagaaaa                                                           1509
```

<210> SEQ ID NO 36
<211> LENGTH: 503
<212> TYPE: PRT
<213> ORGANISM: Homo sapiens
<220> FEATURE:
<221> NAME/KEY: misc_feature
<222> LOCATION: (1)..(503)
<223> OTHER INFORMATION: human SIRP alpha V2

<400> SEQUENCE: 36

```
Met Glu Pro Ala Gly Pro Ala Pro Gly Arg Leu Gly Pro Leu Leu Cys
1               5                   10                  15

Leu Leu Leu Ala Ala Ser Cys Ala Trp Ser Gly Val Ala Gly Glu Glu
            20                  25                  30

Glu Leu Gln Val Ile Gln Pro Asp Lys Ser Val Ser Val Ala Ala Gly
        35                  40                  45

Glu Ser Ala Ile Leu His Cys Thr Val Thr Ser Leu Ile Pro Val Gly
    50                  55                  60

Pro Ile Gln Trp Phe Arg Gly Ala Gly Pro Ala Arg Glu Leu Ile Tyr
65                  70                  75                  80

Asn Gln Lys Glu Gly His Phe Pro Arg Val Thr Thr Val Ser Glu Ser
                85                  90                  95

Thr Lys Arg Glu Asn Met Asp Phe Ser Ile Ser Ile Ser Asn Ile Thr
            100                 105                 110

Pro Ala Asp Ala Gly Thr Tyr Tyr Cys Val Lys Phe Arg Lys Gly Ser
        115                 120                 125

Pro Asp Thr Glu Phe Lys Ser Gly Ala Gly Thr Glu Leu Ser Val Arg
    130                 135                 140

Ala Lys Pro Ser Ala Pro Val Val Ser Gly Pro Ala Ala Arg Ala Thr
145                 150                 155                 160

Pro Gln His Thr Val Ser Phe Thr Cys Glu Ser His Gly Phe Ser Pro
                165                 170                 175

Arg Asp Ile Thr Leu Lys Trp Phe Lys Asn Gly Asn Glu Leu Ser Asp
            180                 185                 190

Phe Gln Thr Asn Val Asp Pro Val Gly Glu Ser Val Ser Tyr Ser Ile
        195                 200                 205

His Ser Thr Ala Lys Val Val Leu Thr Arg Glu Asp Val His Ser Gln
```

|   |   |   |   |   |   |   |   |   |   |   |   |   |   |   |   |
|---|---|---|---|---|---|---|---|---|---|---|---|---|---|---|---|
|   |   |   | 210 |   |   |   | 215 |   |   |   | 220 |   |   |   |   |
| Val | Ile | Cys | Glu | Val | Ala | His | Val | Thr | Leu | Gln | Gly | Asp | Pro | Leu | Arg |
| 225 |   |   |   | 230 |   |   |   | 235 |   |   |   | 240 |   |   |   |
| Gly | Thr | Ala | Asn | Leu | Ser | Glu | Thr | Ile | Arg | Val | Pro | Pro | Thr | Leu | Glu |
|   |   |   |   | 245 |   |   |   | 250 |   |   |   | 255 |   |   |   |
| Val | Thr | Gln | Gln | Pro | Val | Arg | Ala | Glu | Asn | Gln | Val | Asn | Val | Thr | Cys |
|   |   |   | 260 |   |   |   | 265 |   |   |   | 270 |   |   |   |   |
| Gln | Val | Arg | Lys | Phe | Tyr | Pro | Gln | Arg | Leu | Gln | Leu | Thr | Trp | Leu | Glu |
|   |   | 275 |   |   |   | 280 |   |   |   | 285 |   |   |   |   |   |
| Asn | Gly | Asn | Val | Ser | Arg | Thr | Glu | Thr | Ala | Ser | Thr | Val | Thr | Glu | Asn |
|   | 290 |   |   |   | 295 |   |   |   | 300 |   |   |   |   |   |   |
| Lys | Asp | Gly | Thr | Tyr | Asn | Trp | Met | Ser | Trp | Leu | Leu | Val | Asn | Val | Ser |
| 305 |   |   |   | 310 |   |   |   | 315 |   |   |   | 320 |   |   |   |
| Ala | His | Arg | Asp | Asp | Val | Lys | Leu | Thr | Cys | Gln | Val | Glu | His | Asp | Gly |
|   |   |   | 325 |   |   |   | 330 |   |   |   | 335 |   |   |   |   |
| Gln | Pro | Ala | Val | Ser | Lys | Ser | His | Asp | Leu | Lys | Val | Ser | Ala | His | Pro |
|   |   |   | 340 |   |   |   | 345 |   |   |   | 350 |   |   |   |   |
| Lys | Glu | Gln | Gly | Ser | Asn | Thr | Ala | Ala | Glu | Asn | Thr | Gly | Ser | Asn | Glu |
|   |   | 355 |   |   |   | 360 |   |   |   | 365 |   |   |   |   |   |
| Arg | Asn | Ile | Tyr | Ile | Val | Val | Gly | Val | Val | Cys | Thr | Leu | Leu | Val | Ala |
|   | 370 |   |   |   | 375 |   |   |   | 380 |   |   |   |   |   |   |
| Leu | Leu | Met | Ala | Ala | Leu | Tyr | Leu | Val | Arg | Ile | Arg | Gln | Lys | Lys | Ala |
| 385 |   |   |   | 390 |   |   |   | 395 |   |   |   | 400 |   |   |   |
| Gln | Gly | Ser | Thr | Ser | Ser | Thr | Arg | Leu | His | Glu | Pro | Glu | Lys | Asn | Ala |
|   |   |   |   | 405 |   |   |   | 410 |   |   |   | 415 |   |   |   |
| Arg | Glu | Ile | Thr | Gln | Asp | Thr | Asn | Asp | Ile | Thr | Tyr | Ala | Asp | Leu | Asn |
|   |   |   | 420 |   |   |   | 425 |   |   |   | 430 |   |   |   |   |
| Leu | Pro | Lys | Gly | Lys | Lys | Pro | Ala | Pro | Gln | Ala | Ala | Glu | Pro | Asn | Asn |
|   |   | 435 |   |   |   | 440 |   |   |   | 445 |   |   |   |   |   |
| His | Thr | Glu | Tyr | Ala | Ser | Ile | Gln | Thr | Ser | Pro | Gln | Pro | Ala | Ser | Glu |
|   |   | 450 |   |   |   | 455 |   |   |   | 460 |   |   |   |   |   |
| Asp | Thr | Leu | Thr | Tyr | Ala | Asp | Leu | Asp | Met | Val | His | Leu | Asn | Arg | Thr |
| 465 |   |   |   | 470 |   |   |   | 475 |   |   |   | 480 |   |   |   |
| Pro | Lys | Gln | Pro | Ala | Pro | Lys | Pro | Glu | Pro | Ser | Phe | Ser | Glu | Tyr | Ala |
|   |   |   | 485 |   |   |   | 490 |   |   |   | 495 |   |   |   |   |
| Ser | Val | Gln | Val | Pro | Arg | Lys |   |   |   |   |   |   |   |   |   |
|   |   |   | 500 |   |   |   |   |   |   |   |   |   |   |   |   |

<210> SEQ ID NO 37
<211> LENGTH: 1194
<212> TYPE: DNA
<213> ORGANISM: Homo sapiens
<220> FEATURE:
<221> NAME/KEY: misc_feature
<222> LOCATION: (1)..(1194)
<223> OTHER INFORMATION: human SIRP beta 1

<400> SEQUENCE: 37

```
atgcccgtgc cagcctcctg gccccacctt cctagtcctt tcctgctgat gacgctactg    60
ctggggagac tcacaggagt ggcaggtgag gacgagctac aggtgattca gcctgaaaag   120
tccgtatcag ttgcagctgg agagtcggcc actctgcgct gtgctatgac gtccctgatc   180
cctgtggggc ccatcatgtg gtttagagga gctggagcag gccgggaatt aatctacaat   240
cagaaagaag ccacttccc acgggtaaca actgtttcag aactcacaaa gagaaacaac   300
ctggactttt ccatcagcat cagtaacatc accccagcag acgccggcac ctactactgt   360
```

```
gtgaagttcc ggaaagggag ccctgacgac gtggagttta agtctggagc aggcactgag    420
ctgtctgtgc gcgccaaacc ctctgccccc gtggtatcgg gccctgcggt gagggccaca    480
cctgagcaca cagtgagctt cacctgcgag tcccatggct ctctcccag  agacatcacc    540 ctgaaatggt tcaaaatgg  gaatgagctc tcagacttcc agaccaacgt ggaccccgca    600
ggagacagtg tgtcctacag catccacagc acagccaggg tggtgctgac ccgtggggac    660
gttcactctc aagtcatctg cgagatagcc cacatcacct gcaggggga  ccctcttcgt    720 gggactgcca acttgtctga ggccatccga gttccaccca ccttggaggt tactcaacag    780
cccatgaggg cagagaacca ggcaaacgtc acctgccagg tgagcaattt ctacccccgg    840
ggactacagc tgacctggtt ggagaatgga aatgtgtccc ggacagaaac agcttcgacc    900
ctcatagaga caaggatgg  cacctacaac tggatgagct ggctcctggt gaacacctgt    960
gcccacaggg acgatgtggt gctcacctgt caggtggagc atgatgggca gcaagcagtc    1020
agcaaaagct atgccctgga gatctcagcg caccagaagg agcacggctc agatatcacc    1080
catgaagcag cgctggctcc tactgctcca ctcctcgtag ctctcctcct gggccccaag    1140
ctgctactgg tggttggtgt ctctgccatc tacatctgct ggaaacagaa ggcc          1194
```

<210> SEQ ID NO 38
<211> LENGTH: 398
<212> TYPE: PRT
<213> ORGANISM: Homo sapiens
<220> FEATURE:
<221> NAME/KEY: misc_feature
<222> LOCATION: (1)..(398)
<223> OTHER INFORMATION: human SIRP beta 1

<400> SEQUENCE: 38

```
Met Pro Val Pro Ala Ser Trp Pro His Leu Pro Ser Pro Phe Leu Leu
1               5                   10                  15

Met Thr Leu Leu Leu Gly Arg Leu Thr Gly Val Ala Gly Glu Asp Glu
            20                  25                  30

Leu Gln Val Ile Gln Pro Glu Lys Ser Val Ser Val Ala Ala Gly Glu
        35                  40                  45

Ser Ala Thr Leu Arg Cys Ala Met Thr Ser Leu Ile Pro Val Gly Pro
    50                  55                  60

Ile Met Trp Phe Arg Gly Ala Gly Ala Gly Arg Glu Leu Ile Tyr Asn
65                  70                  75                  80

Gln Lys Glu Gly His Phe Pro Arg Val Thr Thr Val Ser Glu Leu Thr
                85                  90                  95

Lys Arg Asn Asn Leu Asp Phe Ser Ile Ser Ile Ser Asn Ile Thr Pro
            100                 105                 110

Ala Asp Ala Gly Thr Tyr Tyr Cys Val Lys Phe Arg Lys Gly Ser Pro
        115                 120                 125

Asp Asp Val Glu Phe Lys Ser Gly Ala Gly Thr Glu Leu Ser Val Arg
    130                 135                 140

Ala Lys Pro Ser Ala Pro Val Val Ser Gly Pro Ala Val Arg Ala Thr
145                 150                 155                 160

Pro Glu His Thr Val Ser Phe Thr Cys Glu Ser His Gly Phe Ser Pro
                165                 170                 175

Arg Asp Ile Thr Leu Lys Trp Phe Lys Asn Gly Asn Glu Leu Ser Asp
            180                 185                 190

Phe Gln Thr Asn Val Asp Pro Ala Gly Asp Ser Val Ser Tyr Ser Ile
        195                 200                 205
```

-continued

His Ser Thr Ala Arg Val Val Leu Thr Arg Gly Asp Val His Ser Gln
    210                 215                 220

Val Ile Cys Glu Ile Ala His Ile Thr Leu Gln Gly Asp Pro Leu Arg
225                 230                 235                 240

Gly Thr Ala Asn Leu Ser Glu Ala Ile Arg Val Pro Pro Thr Leu Glu
                245                 250                 255

Val Thr Gln Gln Pro Met Arg Ala Glu Asn Gln Ala Asn Val Thr Cys
            260                 265                 270

Gln Val Ser Asn Phe Tyr Pro Arg Gly Leu Gln Leu Thr Trp Leu Glu
        275                 280                 285

Asn Gly Asn Val Ser Arg Thr Glu Thr Ala Ser Thr Leu Ile Glu Asn
    290                 295                 300

Lys Asp Gly Thr Tyr Asn Trp Met Ser Trp Leu Leu Val Asn Thr Cys
305                 310                 315                 320

Ala His Arg Asp Asp Val Val Leu Thr Cys Gln Val Glu His Asp Gly
                325                 330                 335

Gln Gln Ala Val Ser Lys Ser Tyr Ala Leu Glu Ile Ser Ala His Gln
            340                 345                 350

Lys Glu His Gly Ser Asp Ile Thr His Glu Ala Ala Leu Ala Pro Thr
        355                 360                 365

Ala Pro Leu Leu Val Ala Leu Leu Leu Gly Pro Lys Leu Leu Leu Val
    370                 375                 380

Val Gly Val Ser Ala Ile Tyr Ile Cys Trp Lys Gln Lys Ala
385                 390                 395

<210> SEQ ID NO 39
<211> LENGTH: 1161
<212> TYPE: DNA
<213> ORGANISM: Homo sapiens
<220> FEATURE:
<221> NAME/KEY: misc_feature
<222> LOCATION: (1)..(1161)
<223> OTHER INFORMATION: human SIRP?

<400> SEQUENCE: 39

```
atgcctgtcc cagcctcctg gccccatcct cctggtcctt tcctgcttct gactctactg     60
ctgggactta cagaagtggc aggtgaggag gagctacaga tgattcagcc tgagaagctc    120
ctgttggtca cagttggaaa gacagccact ctgcactgca ctgtgacctc cctgcttccc    180
gtgggacccg tcctgtggtt cagaggagtt ggaccaggcc gggaattaat ctacaatcaa    240
aaagaaggcc acttccccag ggtaacaaca gtttcagacc tcacaaagag aaacaacatg    300
gacttttcca tccgcatcag tagcatcacc ccagcagatg tcggcacata ctactgtgtg    360
aagtttcgaa aagggagccc tgagaacgtg gagtttaagt ctggaccagg cactgagatg    420
gctttgggtg ccaaaccctc tgccccgtg gtattgggcc ctgcggcgag gaccacacct    480
gagcatacag tgagtttcac ctgtgagtcc atggcttct ctcccagaga catcaccctg    540
aaatggttca aaaatgggaa tgagctctca gacttccaga ccaacgtgga ccccacagga    600
cagagtgtgg cctacagcat ccgcagcaca gccagggtgg tactggaccc ctgggacgtt    660
cgctctcagg tcatctgcga ggtggcccat gtcaccttgc aggggaccc tcttcgtggg    720 actgccaact tgtctgaggc catccgagtt ccacccacct tggaggttac tcaacagccc    780
atgagggtgg ggaaccaggt aaacgtcacc tgccaggtga ggaagttcta cccccagagc    840
ctacagctga cctggtcgga gaatggaaac gtgtgccaga gagaaacagc ctcgaccctt    900
```

-continued

```
acagagaaca aggatggtac ctacaactgg acaagctggt tcctggtgaa catatctgac      960
caaagggatg atgtggtcct cacctgccag gtgaagcatg atgggcagct ggcggtcagc     1020
aaacgccttg ccctagaggt cacagtccac cagaaggacc agagctcaga tgctacccct     1080
ggcccggcat catccttac  tgcgctgctc ctcatagctg tcctcctggg ccccatctac     1140
gtcccctgga agcagaagac c                                               1161
```

<210> SEQ ID NO 40
<211> LENGTH: 387
<212> TYPE: PRT
<213> ORGANISM: Homo sapiens
<220> FEATURE:
<221> NAME/KEY: misc_feature
<222> LOCATION: (1)..(387)
<223> OTHER INFORMATION: human SIRP?

<400> SEQUENCE: 40

```
Met Pro Val Pro Ala Ser Trp Pro His Pro Gly Pro Phe Leu Leu
 1               5                  10                  15

Leu Thr Leu Leu Leu Gly Leu Thr Glu Val Ala Gly Glu Glu Leu
                20                  25                  30

Gln Met Ile Gln Pro Glu Lys Leu Leu Leu Val Thr Val Gly Lys Thr
                35                  40                  45

Ala Thr Leu His Cys Thr Val Thr Ser Leu Leu Pro Val Gly Pro Val
            50                  55                  60

Leu Trp Phe Arg Gly Val Gly Pro Gly Arg Glu Leu Ile Tyr Asn Gln
65                  70                  75                  80

Lys Glu Gly His Phe Pro Arg Val Thr Thr Val Ser Asp Leu Thr Lys
                85                  90                  95

Arg Asn Asn Met Asp Phe Ser Ile Arg Ile Ser Ser Ile Thr Pro Ala
            100                 105                 110

Asp Val Gly Thr Tyr Tyr Cys Val Lys Phe Arg Lys Gly Ser Pro Glu
        115                 120                 125

Asn Val Glu Phe Lys Ser Gly Pro Gly Thr Glu Met Ala Leu Gly Ala
    130                 135                 140

Lys Pro Ser Ala Pro Val Val Leu Gly Pro Ala Ala Arg Thr Thr Pro
145                 150                 155                 160

Glu His Thr Val Ser Phe Thr Cys Glu Ser His Gly Phe Ser Pro Arg
                165                 170                 175

Asp Ile Thr Leu Lys Trp Phe Lys Asn Gly Asn Glu Leu Ser Asp Phe
            180                 185                 190

Gln Thr Asn Val Asp Pro Thr Gly Gln Ser Val Ala Tyr Ser Ile Arg
        195                 200                 205

Ser Thr Ala Arg Val Val Leu Asp Pro Trp Asp Val Arg Ser Gln Val
    210                 215                 220

Ile Cys Glu Val Ala His Val Thr Leu Gln Gly Asp Pro Leu Arg Gly
225                 230                 235                 240

Thr Ala Asn Leu Ser Glu Ala Ile Arg Val Pro Pro Thr Leu Glu Val
                245                 250                 255

Thr Gln Gln Pro Met Arg Val Gly Asn Gln Val Asn Val Thr Cys Gln
            260                 265                 270

Val Arg Lys Phe Tyr Pro Gln Ser Leu Gln Leu Thr Trp Ser Glu Asn
        275                 280                 285

Gly Asn Val Cys Gln Arg Glu Thr Ala Ser Thr Leu Thr Glu Asn Lys
    290                 295                 300
```

-continued

```
Asp Gly Thr Tyr Asn Trp Thr Ser Trp Phe Leu Val Asn Ile Ser Asp
305                 310                 315                 320

Gln Arg Asp Asp Val Val Leu Thr Cys Gln Val Lys His Asp Gly Gln
                325                 330                 335

Leu Ala Val Ser Lys Arg Leu Ala Leu Glu Val Thr Val His Gln Lys
            340                 345                 350

Asp Gln Ser Ser Asp Ala Thr Pro Gly Pro Ala Ser Ser Leu Thr Ala
        355                 360                 365

Leu Leu Leu Ile Ala Val Leu Leu Gly Pro Ile Tyr Val Pro Trp Lys
    370                 375                 380

Gln Lys Thr
385
```

<210> SEQ ID NO 41
<211> LENGTH: 969
<212> TYPE: DNA
<213> ORGANISM: Homo sapiens
<220> FEATURE:
<221> NAME/KEY: misc_feature
<222> LOCATION: (1)..(969)
<223> OTHER INFORMATION: human CD47

<400> SEQUENCE: 41

```
atgtggcctc tggtggccgc tctgctgctg ggctctgctt gttgtggatc cgcccagctg    60
ctgttcaaca agaccaagtc cgtggagttc accttctgca cgataccgt cgtgatcccc    120
tgcttcgtga ccaacatgga agcccagaac accaccgagg tgtacgtgaa gtggaagttc    180
aagggccggg acatctacac cttcgacggc gccctgaaca gtccaccgt gcccaccgat    240
ttctccagcg ccaagatcga ggtgtcacag ctgctgaagg gcgacgcctc cctgaagatg    300
gacaagtccg acgccgtgtc ccacaccggc aactacacct gtgaagtgac cgagctgacc    360
agagagggcg agacaatcat cgagctgaag taccgggtgg tgtcctggtt cagccccaac    420
gagaacatcc tgatcgtgat cttccccatc ttcgccatcc tgctgttctg gggccagttc    480
ggcatcaaga ccctgaagta cagatccggc ggcatggacg aaaagacaat cgccctgctg    540
gtggctggcc tcgtgatcac cgtgattgtg atcgtgggcg ctatcctgtt cgtgcccggc    600
gagtacagcc tgaagaatgc taccggcctg ggcctgattg tgacctccac cggaatcctg    660
atcctgctgc actactacgt gttctccacc gctatcggcc tgacctcctt cgtgatcgcc    720
attctcgtga tccaagtgat cgcctacatc ctggccgtcg tgggcctgtc cctgtgtatc    780
gccgcctgca tccctatgca cggccccctg ctgatctccg gctgtctat tctggccctg    840
gctcagctgc tgggactggt gtacatgaag ttcgtggcct ccaaccagaa aaccatccag    900
cccctcgga aggccgtgga agaacccctg aacgccttca agaatccaa gggcatgatg    960
aacgacgaa                                                            969
```

<210> SEQ ID NO 42
<211> LENGTH: 323
<212> TYPE: PRT
<213> ORGANISM: Homo sapiens
<220> FEATURE:
<221> NAME/KEY: misc_feature
<222> LOCATION: (1)..(323)
<223> OTHER INFORMATION: human CD47

<400> SEQUENCE: 42

```
Met Trp Pro Leu Val Ala Ala Leu Leu Leu Gly Ser Ala Cys Cys Gly
1               5                   10                  15
```

| | | | | | | | | | | |
|---|---|---|---|---|---|---|---|---|---|---|
|Ser|Ala|Gln|Leu|Leu|Phe|Asn|Lys|Thr|Lys|Ser|Val|Glu|Phe|Thr|Phe|
| | | |20| | | |25| | | |30| | | |

Cys Asn Asp Thr Val Val Ile Pro Cys Phe Val Thr Asn Met Glu Ala
            35                  40                  45

Gln Asn Thr Thr Glu Val Tyr Val Lys Trp Lys Phe Lys Gly Arg Asp
    50                  55                  60

Ile Tyr Thr Phe Asp Gly Ala Leu Asn Lys Ser Thr Val Pro Thr Asp
65                  70                  75                  80

Phe Ser Ser Ala Lys Ile Glu Val Ser Gln Leu Leu Lys Gly Asp Ala
                85                  90                  95

Ser Leu Lys Met Asp Lys Ser Asp Ala Val Ser His Thr Gly Asn Tyr
                100                 105                 110

Thr Cys Glu Val Thr Glu Leu Thr Arg Glu Gly Glu Thr Ile Ile Glu
            115                 120                 125

Leu Lys Tyr Arg Val Val Ser Trp Phe Ser Pro Asn Glu Asn Ile Leu
    130                 135                 140

Ile Val Ile Phe Pro Ile Phe Ala Ile Leu Leu Phe Trp Gly Gln Phe
145                 150                 155                 160

Gly Ile Lys Thr Leu Lys Tyr Arg Ser Gly Gly Met Asp Glu Lys Thr
                165                 170                 175

Ile Ala Leu Leu Val Ala Gly Leu Val Ile Thr Val Ile Val Ile Val
                180                 185                 190

Gly Ala Ile Leu Phe Val Pro Gly Glu Tyr Ser Leu Lys Asn Ala Thr
                195                 200                 205

Gly Leu Gly Leu Ile Val Thr Ser Thr Gly Ile Leu Ile Leu Leu His
                210                 215                 220

Tyr Tyr Val Phe Ser Thr Ala Ile Gly Leu Thr Ser Phe Val Ile Ala
225                 230                 235                 240

Ile Leu Val Ile Gln Val Ile Ala Tyr Ile Leu Ala Val Val Gly Leu
                245                 250                 255

Ser Leu Cys Ile Ala Ala Cys Ile Pro Met His Gly Pro Leu Leu Ile
                260                 265                 270

Ser Gly Leu Ser Ile Leu Ala Leu Ala Gln Leu Leu Gly Leu Val Tyr
                275                 280                 285

Met Lys Phe Val Ala Ser Asn Gln Lys Thr Ile Gln Pro Pro Arg Lys
                290                 295                 300

Ala Val Glu Glu Pro Leu Asn Ala Phe Lys Glu Ser Lys Gly Met Met
305                 310                 315                 320

Asn Asp Glu

<210> SEQ ID NO 43
<211> LENGTH: 1509
<212> TYPE: DNA
<213> ORGANISM: Homo sapiens
<220> FEATURE:
<221> NAME/KEY: misc_feature
<222> LOCATION: (1)..(1509)
<223> OTHER INFORMATION: human SIRP alpha V3

<400> SEQUENCE: 43

```
atggaacctg ccggccctgc tcctggtaga ctgggaccte tgctgtgtct gctgctggcc      60
gcctcttgtg cttggagcgg agtggctggc gaagaggaac tgcaagtgat ccagcccgac     120
aagtccgtgt ctgtggccgc tggcgagtct gccatcctgc tgtgtaccgt gacctccctg     180
atccccgtgg gccccatcca gtggtttaga ggcgctggcc ctgccagaga gctgatctac     240
```

```
aaccagaaag agggccactt ccccagagtg accaccgtgt ccgagtccac caagcgcgag      300
aacatggact ctccatctc catcagcaac atcacccctg ccgacgccgg cacctactac       360
tgcgtgaagt tccggaaggg ctcccccgac accgagttca agtctggcgc tggcaccgag      420
ctgtctgtgc gggctaaacc ttctgcccct gtggtgtctg acctgccgc tagagctacc       480 cctcagcaca ccgtgtcttt tacctgcgag tcccacggct tcagccctcg ggacatcacc      540
ctgaagtggt tcaagaacgg caacgagctg agcgacttcc agaccaacgt ggaccctgtg      600
ggcgagagcg tgtcctactc catccactcc accgccaagg tggtgctgac acgcgaggac      660
gtgcactccc aagtgatctg cgaggtggcc cacgtgacac tgcagggcga tcctctgaga      720
ggcaccgcca acctgtccga caatcaga gtgcccccca ccctggaagt gacccagcag        780
ccagtgcggg ccgagaacca agtgaacgtg acctgccaag tgcggaagtt ctaccccag      840 cggctgcagc tgacctggct ggaaaacggc aatgtgtccc ggaccgagac agccagcacc      900
gtgaccgaga acaaggatgg cacctacaat tggatgtctt ggctgctcgt gaacgtgtcc      960
gcccaccggg acgatgtgaa gctgacatgc caggtggaac acgacggcca gcctgccgtg     1020
tccaagagcc acgatctgaa ggtgtccgct catcccaaag agcagggctc caacaccgcc     1080
gctgagaaca ccggctctaa cgagcggaac atctacatcg tcgtgggcgt cgtgtgcacc     1140
ctgctggtgg ctctgctgat ggctgccctg tacctcgtgc ggatccggca agaagaaggcc    1200 cagggctcta cctcctccac cagactgcac gagcccgaga gaacgccag agagatcacc      1260 caggacacca acgacatcac ctacgccgac ctgaacctgc ccaagggcaa gaagcctgcc     1320
cctcaggctg ccgagcctaa caaccacacc gagtacgcct ccatccagac cagccctcag     1380
cctgcctctg aggacacccct gacctacgct gatctggaca tggtgcacct gaaccggacc     1440
cccaagcagc cagctcctaa gcccgagcct agcttctctg agtacgccag cgtgcaggtg     1500
ccccggaaa                                                             1509
```

<210> SEQ ID NO 44
<211> LENGTH: 503
<212> TYPE: PRT
<213> ORGANISM: Homo sapiens
<220> FEATURE:
<221> NAME/KEY: misc_feature
<222> LOCATION: (1)..(503)
<223> OTHER INFORMATION: human SIRP alpha V3

<400> SEQUENCE: 44

```
Met Glu Pro Ala Gly Pro Ala Pro Gly Arg Leu Gly Pro Leu Leu Cys
1               5                   10                  15

Leu Leu Leu Ala Ala Ser Cys Ala Trp Ser Gly Val Ala Gly Glu Glu
            20                  25                  30

Glu Leu Gln Val Ile Gln Pro Asp Lys Ser Val Ser Val Ala Ala Gly
        35                  40                  45

Glu Ser Ala Ile Leu Leu Cys Thr Val Thr Ser Leu Ile Pro Val Gly
    50                  55                  60

Pro Ile Gln Trp Phe Arg Gly Ala Gly Pro Ala Arg Glu Leu Ile Tyr
65                  70                  75                  80

Asn Gln Lys Glu Gly His Phe Pro Arg Val Thr Thr Val Ser Glu Ser
                85                  90                  95

Thr Lys Arg Glu Asn Met Asp Phe Ser Ile Ser Ile Ser Asn Ile Thr
            100                 105                 110

Pro Ala Asp Ala Gly Thr Tyr Tyr Cys Val Lys Phe Arg Lys Gly Ser
        115                 120                 125
```

Pro Asp Thr Glu Phe Lys Ser Gly Ala Gly Thr Glu Leu Ser Val Arg
130                 135                 140

Ala Lys Pro Ser Ala Pro Val Val Ser Gly Pro Ala Ala Arg Ala Thr
145                 150                 155                 160

Pro Gln His Thr Val Ser Phe Thr Cys Glu Ser His Gly Phe Ser Pro
                165                 170                 175

Arg Asp Ile Thr Leu Lys Trp Phe Lys Asn Gly Asn Glu Leu Ser Asp
            180                 185                 190

Phe Gln Thr Asn Val Asp Pro Val Gly Glu Ser Val Ser Tyr Ser Ile
        195                 200                 205

His Ser Thr Ala Lys Val Val Leu Thr Arg Glu Asp Val His Ser Gln
    210                 215                 220

Val Ile Cys Glu Val Ala His Val Thr Leu Gln Gly Asp Pro Leu Arg
225                 230                 235                 240

Gly Thr Ala Asn Leu Ser Glu Thr Ile Arg Val Pro Pro Thr Leu Glu
                245                 250                 255

Val Thr Gln Gln Pro Val Arg Ala Glu Asn Gln Val Asn Val Thr Cys
                260                 265                 270

Gln Val Arg Lys Phe Tyr Pro Gln Arg Leu Gln Leu Thr Trp Leu Glu
            275                 280                 285

Asn Gly Asn Val Ser Arg Thr Glu Thr Ala Ser Thr Val Thr Glu Asn
290                 295                 300

Lys Asp Gly Thr Tyr Asn Trp Met Ser Trp Leu Leu Val Asn Val Ser
305                 310                 315                 320

Ala His Arg Asp Asp Val Lys Leu Thr Cys Gln Val Glu His Asp Gly
                325                 330                 335

Gln Pro Ala Val Ser Lys Ser His Asp Leu Lys Val Ser Ala His Pro
                340                 345                 350

Lys Glu Gln Gly Ser Asn Thr Ala Ala Glu Asn Thr Gly Ser Asn Glu
            355                 360                 365

Arg Asn Ile Tyr Ile Val Val Gly Val Val Cys Thr Leu Leu Val Ala
            370                 375                 380

Leu Leu Met Ala Ala Leu Tyr Leu Val Arg Ile Arg Gln Lys Lys Ala
385                 390                 395                 400

Gln Gly Ser Thr Ser Ser Thr Arg Leu His Glu Pro Glu Lys Asn Ala
                405                 410                 415

Arg Glu Ile Thr Gln Asp Thr Asn Asp Ile Thr Tyr Ala Asp Leu Asn
            420                 425                 430

Leu Pro Lys Gly Lys Lys Pro Ala Pro Gln Ala Ala Glu Pro Asn Asn
        435                 440                 445

His Thr Glu Tyr Ala Ser Ile Gln Thr Ser Pro Gln Pro Ala Ser Glu
    450                 455                 460

Asp Thr Leu Thr Tyr Ala Asp Leu Asp Met Val His Leu Asn Arg Thr
465                 470                 475                 480

Pro Lys Gln Pro Ala Pro Lys Pro Glu Pro Ser Phe Ser Glu Tyr Ala
                485                 490                 495

Ser Val Gln Val Pro Arg Lys
            500

<210> SEQ ID NO 45
<211> LENGTH: 1512
<212> TYPE: DNA
<213> ORGANISM: Homo sapiens
<220> FEATURE:

```
<221> NAME/KEY: misc_feature
<222> LOCATION: (1)..(1512)
<223> OTHER INFORMATION: human SIRP alpha V4

<400> SEQUENCE: 45
atggaacctg ccggccctgc tcctggtaga ctgggacctc tgctgtgtct gctgctggcc      60
gcctcttgtg cttggagcgg agtggctggc gaagagggcc tgcaagtgat ccagcccgac     120
aagtccgtgt ctgtggccgc tggcgagtct gccatcctgc actgtaccgc cacctccctg    180
atccccgtgg acccatcca gtggtttaga ggcgctggcc ctggcagaga gctgatctac     240
aaccagaaag agggccactt ccccagagtg accaccgtgt ccgacctgac caagcggaac    300
aacatggact ctccatccg gatcggcaac atcacccctg ccgatgccgg cacctactac     360
tgcgtgaagt tccggaaggg ctcccccgac gacgtggagt tcaaatccgg cgctggcacc    420
gagctgtctg tgcgggctaa accttctgcc cctgtggtgt ctggccctgc cgctagagct    480
accccctcagc acaccgtgtc ttttacctgc gagtcccacg gcttcagccc tcgggacatc   540
accctgaagt ggttcaagaa cggcaacgag ctgagcgact ccagaccaa cgtggacccc    600
gtgggcgaga gcgtgtccta ctccatccac tccaccgcca aggtggtgct gacacgcgag   660
gacgtgcact cccaagtgat ctgcgaggtg gcccacgtga cactgcaggg cgatcctctg    720
agaggcaccg ccaacctgtc cgagacaatc agagtgcccc ccacctggaa gtgacccag    780
cagccagtgc gggccgagaa ccaagtgaac gtgacctgcc aagtgcggaa gttctaccccc    840
cagcggctgc agctgacctg gctggaaaac ggcaatgtgt ccggaccga cagcctcc       900
accgtgacc agaacaagga tggcacctac aattggatgt cttggctgct cgtgaacgtg     960
tccgcccacc gggacgatgt gaagctgaca tgccaggtgg aacacgacgg ccagcctgcc   1020
gtgtccaagt cccacgatct gaaggtgtcc gctcatccca agagcagggc ctccaacacc    1080
gccgctgaga caccggctc taacgagcgg aacatctaca tcgtcgtggg cgtcgtgtgc   1140
accctgctgg tggctctgct gatggctgcc ctgtacctcg tgcggatccg gcagaagaag   1200
gcccagggct ctacctcctc caccagactg cacgagcccg agaagaacgc cagagagatc   1260
acccaggaca ccaacgacat cacctacgcc gacctgaacc tgcccaaggg caagaagcct   1320
gcccctcagg ctgccgagcc taacaaccac accgagtacg cctccatcca gaccagccct    1380
cagcctgcct ctgaggacac cctgacctac gctgatctgg acatggtgca cctgaaccgg   1440
acccccaagc agccagctcc taagcccgag cctagcttct ctgagtacgc cagcgtgcag   1500
gtgcccccgga aa                                                       1512

<210> SEQ ID NO 46
<211> LENGTH: 504
<212> TYPE: PRT
<213> ORGANISM: Homo sapiens
<220> FEATURE:
<221> NAME/KEY: misc_feature
<222> LOCATION: (1)..(504)
<223> OTHER INFORMATION: human SIRP alpha V4

<400> SEQUENCE: 46

Met Glu Pro Ala Gly Pro Ala Pro Gly Arg Leu Gly Pro Leu Leu Cys
1               5                   10                  15

Leu Leu Leu Ala Ala Ser Cys Ala Trp Ser Gly Val Ala Gly Glu Glu
                20                  25                  30

Gly Leu Gln Val Ile Gln Pro Asp Lys Ser Val Ser Val Ala Ala Gly
            35                  40                  45
```

-continued

```
Glu Ser Ala Ile Leu His Cys Thr Ala Thr Ser Leu Ile Pro Val Gly
 50                  55                  60

Pro Ile Gln Trp Phe Arg Gly Ala Gly Pro Gly Arg Glu Leu Ile Tyr
 65                  70                  75                  80

Asn Gln Lys Glu Gly His Phe Pro Arg Val Thr Thr Val Ser Asp Leu
                 85                  90                  95

Thr Lys Arg Asn Asn Met Asp Phe Ser Ile Arg Ile Gly Asn Ile Thr
             100                 105                 110

Pro Ala Asp Ala Gly Thr Tyr Tyr Cys Val Lys Phe Arg Lys Gly Ser
         115                 120                 125

Pro Asp Asp Val Glu Phe Lys Ser Gly Ala Gly Thr Glu Leu Ser Val
 130                 135                 140

Arg Ala Lys Pro Ser Ala Pro Val Val Ser Gly Pro Ala Ala Arg Ala
145                 150                 155                 160

Thr Pro Gln His Thr Val Ser Phe Thr Cys Glu Ser His Gly Phe Ser
                165                 170                 175

Pro Arg Asp Ile Thr Leu Lys Trp Phe Lys Asn Gly Asn Glu Leu Ser
            180                 185                 190

Asp Phe Gln Thr Asn Val Asp Pro Val Gly Glu Ser Val Ser Tyr Ser
        195                 200                 205

Ile His Ser Thr Ala Lys Val Val Leu Thr Arg Glu Asp Val His Ser
210                 215                 220

Gln Val Ile Cys Glu Val Ala His Val Thr Leu Gln Gly Asp Pro Leu
225                 230                 235                 240

Arg Gly Thr Ala Asn Leu Ser Glu Thr Ile Arg Val Pro Pro Thr Leu
                245                 250                 255

Glu Val Thr Gln Gln Pro Val Arg Ala Glu Asn Gln Val Asn Val Thr
            260                 265                 270

Cys Gln Val Arg Lys Phe Tyr Pro Gln Arg Leu Gln Leu Thr Trp Leu
        275                 280                 285

Glu Asn Gly Asn Val Ser Arg Thr Glu Thr Ala Ser Thr Val Thr Glu
290                 295                 300

Asn Lys Asp Gly Thr Tyr Asn Trp Met Ser Trp Leu Leu Val Asn Val
305                 310                 315                 320

Ser Ala His Arg Asp Asp Val Lys Leu Thr Cys Gln Val Glu His Asp
                325                 330                 335

Gly Gln Pro Ala Val Ser Lys Ser His Asp Leu Lys Val Ser Ala His
            340                 345                 350

Pro Lys Glu Gln Gly Ser Asn Thr Ala Ala Glu Asn Thr Gly Ser Asn
        355                 360                 365

Glu Arg Asn Ile Tyr Ile Val Val Gly Val Val Cys Thr Leu Leu Val
370                 375                 380

Ala Leu Leu Met Ala Ala Leu Tyr Leu Val Arg Ile Arg Gln Lys Lys
385                 390                 395                 400

Ala Gln Gly Ser Thr Ser Ser Thr Arg Leu His Glu Pro Glu Lys Asn
                405                 410                 415

Ala Arg Glu Ile Thr Gln Asp Thr Asn Asp Ile Thr Tyr Ala Asp Leu
            420                 425                 430

Asn Leu Pro Lys Gly Lys Lys Pro Ala Pro Gln Ala Ala Glu Pro Asn
        435                 440                 445

Asn His Thr Glu Tyr Ala Ser Ile Gln Thr Ser Pro Gln Pro Ala Ser
450                 455                 460

Glu Asp Thr Leu Thr Tyr Ala Asp Leu Asp Met Val His Leu Asn Arg
```

465                 470                 475                 480
Thr Pro Lys Gln Pro Ala Pro Lys Pro Glu Pro Ser Phe Ser Glu Tyr
                     485                 490                 495

Ala Ser Val Gln Val Pro Arg Lys
            500

<210> SEQ ID NO 47
<211> LENGTH: 1512
<212> TYPE: DNA
<213> ORGANISM: Homo sapiens
<220> FEATURE:
<221> NAME/KEY: misc_feature
<222> LOCATION: (1)..(1512)
<223> OTHER INFORMATION: human SIRP alpha V5

<400> SEQUENCE: 47

| | | | | | |
|---|---|---|---|---|---|
| atggaacctg | ccggccctgc | tcctggtaga | ctgggacctc | tgctgtgtct | gctgctggcc | 60 |
| gcctcttgtg | cttggagcgg | agtggctggc | gaagaggaac | tgcaagtgat | ccagcccgac | 120 |
| aagttcgtgc | tggtggccgc | tggcgagaca | gccaccctga | gatgtaccgc | cacctccctg | 180 |
| atccccgtgg | gccctatcca | gtggtttaga | ggcgctggcc | ctggcagaga | gctgatctac | 240 |
| aaccagaaag | agggccactt | ccccagagtg | accaccgtgt | ccgacctgac | caagcggaac | 300 |
| aacatggact | tctccatccg | gatcggcaac | atcaccctg | ccgatgccgg | cacctactac | 360 |
| tgcgtgaagt | tccggaaggg | ctcccccgac | gacgtggagt | caaatccgg | cgctggcacc | 420 |
| gagctgtctg | tgcgggctaa | accttctgcc | ctgtggtgt | ctggccctgc | cgctagagct | 480 |
| acccctcagc | acaccgtgtc | ttttacctgc | gagtcccacg | gcttcagccc | tcgggacatc | 540 |
| accctgaagt | ggttcaagaa | cggcaacgag | ctgagcgact | tccagaccaa | cgtggaccct | 600 |
| gtgggcgagt | ccgtgtccta | ctccatccac | tccaccgcca | aggtggtgct | gacacgcgag | 660 |
| gacgtgcact | cccaagtgat | ctgcgaggtg | gcccacgtga | cactgcaggg | cgatcctctg | 720 |
| agaggcaccg | ccaacctgtc | cgagacaatc | agagtgcccc | ccaccctgga | agtgacccag | 780 |
| cagccagtgc | gggccgagaa | ccaagtgaac | gtgacctgcc | aagtgcggaa | gttctacccc | 840 |
| cagcggctgc | agctgacctg | gctggaaaac | ggcaatgtgt | cccggaccga | gactgcctcc | 900 |
| accgtgaccg | agaacaagga | tggcacctac | aattggatgt | cttggctgct | cgtgaacgtg | 960 |
| tccgcccacc | gggacgatgt | gaagctgaca | tgccaggtgg | aacacgacgg | ccagcctgcc | 1020 |
| gtgtccaagt | cccacgatct | gaaggtgtcc | gctcatccca | agagcagggg | ctccaacacc | 1080 |
| gccgctgaga | caccggctc | taacgagcgg | aacatctaca | tcgtcgtggg | cgtcgtgtgc | 1140 |
| accctgctgg | tggctctgct | gatggctgcc | ctgtacctcg | tgcggatccg | gcagaagaag | 1200 |
| gcccagggct | ctacctcctc | caccagactg | cacgagcccg | agaagaacgc | cagagagatc | 1260 |
| acccaggaca | ccaacgacat | cacctacgcc | gacctgaacc | tgcccaaggg | caagaagcct | 1320 |
| gcccctcagg | ctgccgagcc | taacaaccac | accgagtacg | cctccatcca | gaccagccct | 1380 |
| cagcctgcct | ctgaggacac | cctgacctac | gctgatctgg | acatggtgca | cctgaaccgg | 1440 |
| acccccaagc | agccagctcc | taagcccgag | cctagcttct | ctgagtacgc | cagcgtgcag | 1500 |
| gtgccccgga | aa | | | | | 1512 |

<210> SEQ ID NO 48
<211> LENGTH: 504
<212> TYPE: PRT
<213> ORGANISM: Homo sapiens
<220> FEATURE:
<221> NAME/KEY: misc_feature
<222> LOCATION: (1)..(504)
<223> OTHER INFORMATION: human SIRP alpha V5

<400> SEQUENCE: 48

```
Met Glu Pro Ala Gly Pro Ala Pro Gly Arg Leu Gly Pro Leu Leu Cys
1               5                   10                  15

Leu Leu Leu Ala Ala Ser Cys Ala Trp Ser Gly Val Ala Gly Glu Glu
                20                  25                  30

Glu Leu Gln Val Ile Gln Pro Asp Lys Phe Val Leu Val Ala Ala Gly
            35                  40                  45

Glu Thr Ala Thr Leu Arg Cys Thr Ala Thr Ser Leu Ile Pro Val Gly
        50                  55                  60

Pro Ile Gln Trp Phe Arg Gly Ala Gly Pro Gly Arg Glu Leu Ile Tyr
65                  70                  75                  80

Asn Gln Lys Glu Gly His Phe Pro Arg Val Thr Thr Val Ser Asp Leu
                85                  90                  95

Thr Lys Arg Asn Asn Met Asp Phe Ser Ile Arg Ile Gly Asn Ile Thr
            100                 105                 110

Pro Ala Asp Ala Gly Thr Tyr Tyr Cys Val Lys Phe Arg Lys Gly Ser
        115                 120                 125

Pro Asp Asp Val Glu Phe Lys Ser Gly Ala Gly Thr Glu Leu Ser Val
    130                 135                 140

Arg Ala Lys Pro Ser Ala Pro Val Val Ser Gly Pro Ala Ala Arg Ala
145                 150                 155                 160

Thr Pro Gln His Thr Val Ser Phe Thr Cys Glu Ser His Gly Phe Ser
                165                 170                 175

Pro Arg Asp Ile Thr Leu Lys Trp Phe Lys Asn Gly Asn Glu Leu Ser
            180                 185                 190

Asp Phe Gln Thr Asn Val Asp Pro Val Gly Glu Ser Val Ser Tyr Ser
        195                 200                 205

Ile His Ser Thr Ala Lys Val Val Leu Thr Arg Glu Asp Val His Ser
    210                 215                 220

Gln Val Ile Cys Glu Val Ala His Val Thr Leu Gln Gly Asp Pro Leu
225                 230                 235                 240

Arg Gly Thr Ala Asn Leu Ser Glu Thr Ile Arg Val Pro Pro Thr Leu
                245                 250                 255

Glu Val Thr Gln Gln Pro Val Arg Ala Glu Asn Gln Val Asn Val Thr
            260                 265                 270

Cys Gln Val Arg Lys Phe Tyr Pro Gln Arg Leu Gln Leu Thr Trp Leu
        275                 280                 285

Glu Asn Gly Asn Val Ser Arg Thr Glu Thr Ala Ser Thr Val Thr Glu
    290                 295                 300

Asn Lys Asp Gly Thr Tyr Asn Trp Met Ser Trp Leu Leu Val Asn Val
305                 310                 315                 320

Ser Ala His Arg Asp Asp Val Lys Leu Thr Cys Gln Val Glu His Asp
                325                 330                 335

Gly Gln Pro Ala Val Ser Lys Ser His Asp Leu Lys Val Ser Ala His
            340                 345                 350

Pro Lys Glu Gln Gly Ser Asn Thr Ala Ala Glu Asn Thr Gly Ser Asn
        355                 360                 365

Glu Arg Asn Ile Tyr Ile Val Val Gly Val Val Cys Thr Leu Leu Val
    370                 375                 380

Ala Leu Leu Met Ala Ala Leu Tyr Leu Val Arg Ile Arg Gln Lys Lys
385                 390                 395                 400
```

```
Ala Gln Gly Ser Thr Ser Ser Thr Arg Leu His Glu Pro Glu Lys Asn
            405                 410                 415

Ala Arg Glu Ile Thr Gln Asp Thr Asn Asp Ile Thr Tyr Ala Asp Leu
            420                 425                 430

Asn Leu Pro Lys Gly Lys Lys Pro Ala Pro Gln Ala Ala Glu Pro Asn
            435                 440                 445

Asn His Thr Glu Tyr Ala Ser Ile Gln Thr Ser Pro Gln Pro Ala Ser
    450                 455                 460

Glu Asp Thr Leu Thr Tyr Ala Asp Leu Asp Met Val His Leu Asn Arg
465                 470                 475                 480

Thr Pro Lys Gln Pro Ala Pro Lys Pro Glu Pro Ser Phe Ser Glu Tyr
            485                 490                 495

Ala Ser Val Gln Val Pro Arg Lys
            500

<210> SEQ ID NO 49
<211> LENGTH: 1512
<212> TYPE: DNA
<213> ORGANISM: Homo sapiens
<220> FEATURE:
<221> NAME/KEY: misc_feature
<222> LOCATION: (1)..(1512)
<223> OTHER INFORMATION: human SIRP alpha V6

<400> SEQUENCE: 49
atggaacctg ccggccctgc tcctggtaga ctgggacctc tgctgtgtct gctgctggcc      60
gcctcttgtg cttggagcgg agtggctggc gaagaggaac tgcaagtgat ccagcccgac     120
aagtccgtgc tggtggctgc tggcgagact gccaccctga gatgtaccgc cacctccctg     180
atccccgtgg gcctatccca gtggtttaga ggcgctggcc ctggcagaga gctgatctac     240
aaccagaaag agggccactt ccccagagtg accaccgtgt ccgacctgac caagcggaac     300
aacatggact tccccatccg gatcggcaac atcacccctg ccgatgccgg cacctactac     360
tgcgtgaagt tccggaaggg ctccccccga cgacgtggagt tcaaatccgg cgctggcacc     420
gagctgtctg tgcgggctaa accttctgcc cctgtggtgt ctggccctgc cgctagagct     480
accccctcag caccgtgtc ttttacctgc gagtcccacg gcttcagccc tcgggacatc     540
accctgaagt ggttcaagaa cggcaacgag ctgagcgact ccagaccaa cgtgaccct     600
gtgggcgagt ccgtgtccta ctccatccac tccaccgcca aggtggtgct gacacgcgag     660
gacgtgcact cccaagtgat ctgcgaggtg gcccacgtga cactgcaggg cgatcctctg     720
agaggcaccg ccaacctgtc cgagacaatc agagtgcccc ccaccctgga agtgacccag     780
cagcccgtgc gggctgagaa ccaagtgaac gtgacctgcc aagtgcggaa gttctacccc     840
cagcggctgc agctgacctg gctggaaaac ggcaatgtgt cccggaccga cagcctcc     900
accgtgaccg agaacaagga tggcaccta aattggatgt cctggctgct cgtgaacgtg     960
tccgcccacc gggacgatgt gaagctgaca tgccaggtgg aacacgacgg ccagcctgcc    1020
gtgtccaagt cccacgatct gaaggtgtcc gctcatccca agagcaggg ctccaacacc    1080
gccgctgaga caccggctc taacgagcgg aacatctaca tcgtcgtggg cgtcgtgtgc    1140
accctgctgg tggcactgct gatggccgct ctgtacctcg tgcggatccg gcagaagaag    1200
gcccagggct ctaccctcc caccagactg cacgagcccg agaagaacgc cagagagatc    1260
acccaggaca ccaacgacat cacctacgcc gactgaacc tgcccaaggg caagaagcct    1320
gccccctcagg ctgccgagcc taacaaccac accgagtacg cctccatcca gaccagccct    1380
```

```
cagcctgcct ctgaggacac cctgacctac gctgatctgg acatggtgca cctgaaccgg    1440
acccccaagc agccagctcc taagcccgag cctagcttct ctgagtacgc cagcgtgcag    1500
gtgccccgga aa                                                        1512
```

<210> SEQ ID NO 50
<211> LENGTH: 504
<212> TYPE: PRT
<213> ORGANISM: Homo sapiens
<220> FEATURE:
<221> NAME/KEY: misc_feature
<222> LOCATION: (1)..(504)
<223> OTHER INFORMATION: human SIRP alpha V6

<400> SEQUENCE: 50

```
Met Glu Pro Ala Gly Pro Ala Pro Gly Arg Leu Gly Pro Leu Leu Cys
1               5                   10                  15

Leu Leu Leu Ala Ala Ser Cys Ala Trp Ser Gly Val Ala Gly Glu Glu
            20                  25                  30

Glu Leu Gln Val Ile Gln Pro Asp Lys Ser Val Leu Val Ala Ala Gly
        35                  40                  45

Glu Thr Ala Thr Leu Arg Cys Thr Ala Thr Ser Leu Ile Pro Val Gly
    50                  55                  60

Pro Ile Gln Trp Phe Arg Gly Ala Gly Pro Gly Arg Glu Leu Ile Tyr
65                  70                  75                  80

Asn Gln Lys Glu Gly His Phe Pro Arg Val Thr Thr Val Ser Asp Leu
                85                  90                  95

Thr Lys Arg Asn Asn Met Asp Phe Pro Ile Arg Ile Gly Asn Ile Thr
            100                 105                 110

Pro Ala Asp Ala Gly Thr Tyr Tyr Cys Val Lys Phe Arg Lys Gly Ser
        115                 120                 125

Pro Asp Asp Val Glu Phe Lys Ser Gly Ala Gly Thr Glu Leu Ser Val
    130                 135                 140

Arg Ala Lys Pro Ser Ala Pro Val Val Ser Gly Pro Ala Ala Arg Ala
145                 150                 155                 160

Thr Pro Gln His Thr Val Ser Phe Thr Cys Glu Ser His Gly Phe Ser
                165                 170                 175

Pro Arg Asp Ile Thr Leu Lys Trp Phe Lys Asn Gly Asn Glu Leu Ser
            180                 185                 190

Asp Phe Gln Thr Asn Val Asp Pro Val Gly Glu Ser Val Ser Tyr Ser
        195                 200                 205

Ile His Ser Thr Ala Lys Val Val Leu Thr Arg Glu Asp Val His Ser
    210                 215                 220

Gln Val Ile Cys Glu Val Ala His Val Thr Leu Gln Gly Asp Pro Leu
225                 230                 235                 240

Arg Gly Thr Ala Asn Leu Ser Glu Thr Ile Arg Val Pro Pro Thr Leu
                245                 250                 255

Glu Val Thr Gln Gln Pro Val Arg Ala Glu Asn Gln Val Asn Val Thr
            260                 265                 270

Cys Gln Val Arg Lys Phe Tyr Pro Gln Arg Leu Gln Leu Thr Trp Leu
        275                 280                 285

Glu Asn Gly Asn Val Ser Arg Thr Glu Thr Ala Ser Thr Val Thr Glu
    290                 295                 300

Asn Lys Asp Gly Thr Tyr Asn Trp Met Ser Trp Leu Leu Val Asn Val
305                 310                 315                 320
```

| | | | | | | | | | | | |
|---|---|---|---|---|---|---|---|---|---|---|---|
Ser | Ala | His | Arg | Asp | Asp | Val | Lys | Leu | Thr | Cys | Gln | Val | Glu | His | Asp
 | | | 325 | | | | 330 | | | | 335

Gly Gln Pro Ala Val Ser Lys Ser His Asp Leu Lys Val Ser Ala His
            340                 345                 350

Pro Lys Glu Gln Gly Ser Asn Thr Ala Ala Glu Asn Thr Gly Ser Asn
        355                 360                 365

Glu Arg Asn Ile Tyr Ile Val Gly Val Val Cys Thr Leu Leu Val
370                 375                 380

Ala Leu Leu Met Ala Ala Leu Tyr Leu Val Arg Ile Arg Gln Lys Lys
385                 390                 395                 400

Ala Gln Gly Ser Thr Ser Ser Thr Arg Leu His Glu Pro Glu Lys Asn
            405                 410                 415

Ala Arg Glu Ile Thr Gln Asp Thr Asn Asp Ile Thr Tyr Ala Asp Leu
        420                 425                 430

Asn Leu Pro Lys Gly Lys Lys Pro Ala Pro Gln Ala Ala Glu Pro Asn
        435                 440                 445

Asn His Thr Glu Tyr Ala Ser Ile Gln Thr Ser Pro Gln Pro Ala Ser
    450                 455                 460

Glu Asp Thr Leu Thr Tyr Ala Asp Leu Asp Met Val His Leu Asn Arg
465                 470                 475                 480

Thr Pro Lys Gln Pro Ala Pro Lys Pro Glu Pro Ser Phe Ser Glu Tyr
                485                 490                 495

Ala Ser Val Gln Val Pro Arg Lys
            500

```
<210> SEQ ID NO 51
<211> LENGTH: 1509
<212> TYPE: DNA
<213> ORGANISM: Homo sapiens
<220> FEATURE:
<221> NAME/KEY: misc_feature
<222> LOCATION: (1)..(1509)
<223> OTHER INFORMATION: human SIRP alpha V8

<400> SEQUENCE: 51
atggaacctg ccggccctgc tcctggtaga ctgggacctc tgctgtgtct gctgctggcc      60
gcctcttgtg cttggagcgg agtggctggc gaagaggaac tgcaagtgat ccagcccgac     120
aagtccgtgc tggtggctgc tggcgagact gccaccctga gatgtaccgc acctcccctg    180
atccccgtgg gccctatcca gtggtttaga ggcgctggcc ctgccagaga gctgatctac    240
aaccagaaag agggccactt ccccagagtg accaccgtgt ccgagtccac caagcgcgag    300
aacatggact tctccatctc catcagcaac atcacccctg ccgacgccgg cacctactac    360
tgcgtgaagt tccggaaggg ctccccccga accgagttca gtctggcgc tggcaccgag    420 ctgtctgtgc gggctaaacc ttctgcccct gtggtgtctg acctgccgc tagagctacc    480 cctcagcaca ccgtgtcttt tacctgcgag tcccacggct tcagccctcg ggacatcacc    540
ctgaagtggt tcaagaacgg caacgagctg agcgacttcc agaccaacgt ggaccctgtg    600
ggcgagtccg tgtcctactc catccactcc accgccaagg tggtgctgac acgcgaggac    660
gtgcactccc aagtgatctg cgaggtggcc cacgtgacac tgcagggcga tcctctgaga    720
ggcaccgcca acctgtccga acaatcaga gtgccccca ccctggaagt gacccagcag    780
cccgtgcggg ctgagaacca agtgaacgtg acctgccaag tgcggaagtt ctaccccag    840 cggctgcagc tgacctggct ggaaaacggc aatgtgtccc ggaccgagac agccagcacc    900
gtgaccgaga acaaggatgg cacctacaat tggatgtcct ggctgctcgt gaacgtgtcc    960
```

```
gcccaccggg acgatgtgaa gctgacatgc caggtggaac acgacggcca gcctgccgtg    1020
tccaagagcc acgatctgaa ggtgtccgct catcccaaag agcagggctc caacaccgcc    1080
gctgagaaca ccggctctaa cgagcggaac atctacatcg tcgtgggcgt cgtgtgcacc    1140
ctgctggtgg cactgctgat ggccgctctg tacctcgtgc ggatccggca agaaggcc     1200 cagggctcta cctcctccac cagactgcac gagcccgaga agaacgccag agagatcacc    1260
caggacacca acgacatcac ctacgccgac ctgaacctgc ccaagggcaa gaagcctgcc    1320
cctcaggctg ccgagcctaa caaccacacc gagtacgcct ccatccagac cagccctcag    1380
cctgcctctg aggacaccct gacctacgct gatctggaca tggtgcacct gaaccggacc    1440
cccaagcagc cagctcctaa gcccgagcct agcttctctg agtacgccag cgtgcaggtg    1500
ccccggaaa                                                            1509
```

<210> SEQ ID NO 52
<211> LENGTH: 503
<212> TYPE: PRT
<213> ORGANISM: Homo sapiens
<220> FEATURE:
<221> NAME/KEY: misc_feature
<222> LOCATION: (1)..(503)
<223> OTHER INFORMATION: human SIRP alpha V8

<400> SEQUENCE: 52

```
Met Glu Pro Ala Gly Pro Ala Pro Gly Arg Leu Gly Pro Leu Leu Cys
1               5                   10                  15

Leu Leu Leu Ala Ala Ser Cys Ala Trp Ser Gly Val Ala Gly Glu Glu
            20                  25                  30

Glu Leu Gln Val Ile Gln Pro Asp Lys Ser Val Leu Val Ala Ala Gly
        35                  40                  45

Glu Thr Ala Thr Leu Arg Cys Thr Ala Thr Ser Leu Ile Pro Val Gly
    50                  55                  60

Pro Ile Gln Trp Phe Arg Gly Ala Gly Pro Ala Arg Glu Leu Ile Tyr
65                  70                  75                  80

Asn Gln Lys Glu Gly His Phe Pro Arg Val Thr Thr Val Ser Glu Ser
                85                  90                  95

Thr Lys Arg Glu Asn Met Asp Phe Ser Ile Ser Ile Ser Asn Ile Thr
            100                 105                 110

Pro Ala Asp Ala Gly Thr Tyr Tyr Cys Val Lys Phe Arg Lys Gly Ser
        115                 120                 125

Pro Asp Thr Glu Phe Lys Ser Gly Ala Gly Thr Glu Leu Ser Val Arg
    130                 135                 140

Ala Lys Pro Ser Ala Pro Val Val Ser Gly Pro Ala Ala Arg Ala Thr
145                 150                 155                 160

Pro Gln His Thr Val Ser Phe Thr Cys Glu Ser His Gly Phe Ser Pro
                165                 170                 175

Arg Asp Ile Thr Leu Lys Trp Phe Lys Asn Gly Asn Glu Leu Ser Asp
            180                 185                 190

Phe Gln Thr Asn Val Asp Pro Val Gly Glu Ser Val Ser Tyr Ser Ile
        195                 200                 205

His Ser Thr Ala Lys Val Val Leu Thr Arg Glu Asp Val His Ser Gln
    210                 215                 220

Val Ile Cys Glu Val Ala His Val Thr Leu Gln Gly Asp Pro Leu Arg
225                 230                 235                 240

Gly Thr Ala Asn Leu Ser Glu Thr Ile Arg Val Pro Pro Thr Leu Glu
```

245                 250                 255
Val Thr Gln Gln Pro Val Arg Ala Glu Asn Gln Val Asn Val Thr Cys
                260                 265                 270

Gln Val Arg Lys Phe Tyr Pro Gln Arg Leu Gln Leu Thr Trp Leu Glu
            275                 280                 285

Asn Gly Asn Val Ser Arg Thr Glu Thr Ala Ser Thr Val Thr Glu Asn
        290                 295                 300

Lys Asp Gly Thr Tyr Asn Trp Met Ser Trp Leu Leu Val Asn Val Ser
305                 310                 315                 320

Ala His Arg Asp Asp Val Lys Leu Thr Cys Gln Val Glu His Asp Gly
                325                 330                 335

Gln Pro Ala Val Ser Lys Ser His Asp Leu Lys Val Ser Ala His Pro
            340                 345                 350

Lys Glu Gln Gly Ser Asn Thr Ala Ala Glu Asn Thr Gly Ser Asn Glu
        355                 360                 365

Arg Asn Ile Tyr Ile Val Val Gly Val Val Cys Thr Leu Leu Val Ala
    370                 375                 380

Leu Leu Met Ala Ala Leu Tyr Leu Val Arg Ile Arg Gln Lys Lys Ala
385                 390                 395                 400

Gln Gly Ser Thr Ser Ser Thr Arg Leu His Glu Pro Glu Lys Asn Ala
                405                 410                 415

Arg Glu Ile Thr Gln Asp Thr Asn Asp Ile Thr Tyr Ala Asp Leu Asn
            420                 425                 430

Leu Pro Lys Gly Lys Lys Pro Ala Pro Gln Ala Ala Glu Pro Asn Asn
        435                 440                 445

His Thr Glu Tyr Ala Ser Ile Gln Thr Ser Pro Gln Pro Ala Ser Glu
    450                 455                 460

Asp Thr Leu Thr Tyr Ala Asp Leu Asp Met Val His Leu Asn Arg Thr
465                 470                 475                 480

Pro Lys Gln Pro Ala Pro Lys Pro Glu Pro Ser Phe Ser Glu Tyr Ala
                485                 490                 495

Ser Val Gln Val Pro Arg Lys
            500

<210> SEQ ID NO 53
<211> LENGTH: 1512
<212> TYPE: DNA
<213> ORGANISM: Homo sapiens
<220> FEATURE:
<221> NAME/KEY: misc_feature
<222> LOCATION: (1)..(1512)
<223> OTHER INFORMATION: human SIRP alpha V9

<400> SEQUENCE: 53
atggaacctg ccggccctgc tcctggtaga ctgggacctc tgctgtgtct gctgctggcc    60
gcctcttgtg cttggagcgg agtggctggc gaagaggaac tgcaagtgat ccagcccgac   120
aagtccgtgc tggtggctgc tggcgagact gccaccctga gatgtaccgc cacctccctg   180
atccccgtgg gcctatccca gtggtttaga ggcgctggcc ctggcagaga gctgatctac   240
aaccagaaag agggccactt ccccagagtg accaccgtgt ccgacctgac caagcggaac   300
aacatggact tctccatccg gatctccaac atcacccctg ccgacgccgg cacctactac   360
tgcgtgaagt tccggaaggg ctcccccgac gacgtggagt tcaaatccgg cgctggcacc   420
gagctgtctg tgcgggctaa accttctgcc cctgtggtgt ctggccctgc cgctagagct   480
accccctcag caccgtgtc ttttacctgc gagtcccacg gcttcagccc tcgggacatc   540

```
accctgaagt ggttcaagaa cggcaacgag ctgagcgact tccagaccaa cgtggaccct      600
gtgggcgagt ccgtgtccta ctccatccac tccaccgcca aggtggtgct gacacgcgag      660
gacgtgcact cccaagtgat ctgcgaggtg gcccacgtga cactgcaggg cgatcctctg      720
agaggcaccg ccaacctgtc cgagacaatc agagtgcccc ccaccctgga agtgacccag      780
cagcccgtgc gggctgagaa ccaagtgaac gtgacctgcc aagtgcggaa gttctacccc      840
cagcggctgc agctgacctg gctggaaaac ggcaatgtgt cccggaccga dacagcctcc      900
accgtgaccg agaacaagga tggcacctac aattggatgt cctggctgct cgtgaacgtg      960
tccgcccacc gggacgatgt gaagctgaca tgccaggtgg aacacgacgg ccagcctgcc     1020
gtgtccaagt cccacgatct gaaggtgtcc gctcatccca agagcagggg ctccaacacc     1080
gccgctgaga caccggctc taacgagcgg aacatctaca cgtcgtgggg cgtcgtgtgc     1140
accctgctgg tggcactgct gatggccgct ctgtacctcg tgcggatccg gcagaagaag     1200
gcccagggct ctacctcctc caccagactg cacgagcccg agaagaacgc cagagagatc     1260
acccaggaca ccaacgacat cacctacgcc gacctgaacc tgcccaaggg caagaagcct     1320
gcccctcagg ctgccgagcc taacaaccac accgagtacg cctccatcca gaccagccct     1380
cagcctgcct ctgaggacac cctgacctac gctgatctgg acatggtgca cctgaaccgg     1440 accccaagc agccagctcc taagcccgag cctagcttct ctgagtacgc cagcgtgcag     1500
gtgccccgga aa                                                         1512

<210> SEQ ID NO 54
<211> LENGTH: 504
<212> TYPE: PRT
<213> ORGANISM: Homo sapiens
<220> FEATURE:
<221> NAME/KEY: misc_feature
<222> LOCATION: (1)..(504)
<223> OTHER INFORMATION: human SIRP alpha V9

<400> SEQUENCE: 54
```

Met Glu Pro Ala Gly Pro Ala Pro Gly Arg Leu Gly Pro Leu Leu Cys
1               5                   10                  15

Leu Leu Leu Ala Ala Ser Cys Ala Trp Ser Gly Val Ala Gly Glu Glu
                20                  25                  30

Glu Leu Gln Val Ile Gln Pro Asp Lys Ser Val Leu Val Ala Ala Gly
            35                  40                  45

Glu Thr Ala Thr Leu Arg Cys Thr Ala Thr Ser Leu Ile Pro Val Gly
        50                  55                  60

Pro Ile Gln Trp Phe Arg Gly Ala Gly Pro Gly Arg Glu Leu Ile Tyr
65                  70                  75                  80

Asn Gln Lys Glu Gly His Phe Pro Arg Val Thr Thr Val Ser Asp Leu
                85                  90                  95

Thr Lys Arg Asn Asn Met Asp Phe Ser Ile Arg Ile Ser Asn Ile Thr
            100                 105                 110

Pro Ala Asp Ala Gly Thr Tyr Tyr Cys Val Lys Phe Arg Lys Gly Ser
        115                 120                 125

Pro Asp Asp Val Glu Phe Lys Ser Gly Ala Gly Thr Glu Leu Ser Val
    130                 135                 140

Arg Ala Lys Pro Ser Ala Pro Val Val Ser Gly Pro Ala Ala Arg Ala
145                 150                 155                 160

Thr Pro Gln His Thr Val Ser Phe Thr Cys Glu Ser His Gly Phe Ser
                165                 170                 175

```
Pro Arg Asp Ile Thr Leu Lys Trp Phe Lys Asn Gly Asn Glu Leu Ser
            180                 185                 190

Asp Phe Gln Thr Asn Val Asp Pro Val Gly Glu Ser Val Ser Tyr Ser
        195                 200                 205

Ile His Ser Thr Ala Lys Val Val Leu Thr Arg Glu Asp Val His Ser
    210                 215                 220

Gln Val Ile Cys Glu Val Ala His Val Thr Leu Gln Gly Asp Pro Leu
225                 230                 235                 240

Arg Gly Thr Ala Asn Leu Ser Glu Thr Ile Arg Val Pro Pro Thr Leu
                245                 250                 255

Glu Val Thr Gln Gln Pro Val Arg Ala Glu Asn Gln Val Asn Val Thr
            260                 265                 270

Cys Gln Val Arg Lys Phe Tyr Pro Gln Arg Leu Gln Leu Thr Trp Leu
        275                 280                 285

Glu Asn Gly Asn Val Ser Arg Thr Glu Thr Ala Ser Thr Val Thr Glu
    290                 295                 300

Asn Lys Asp Gly Thr Tyr Asn Trp Met Ser Trp Leu Leu Val Asn Val
305                 310                 315                 320

Ser Ala His Arg Asp Asp Val Lys Leu Thr Cys Gln Val Glu His Asp
                325                 330                 335

Gly Gln Pro Ala Val Ser Lys Ser His Asp Leu Lys Val Ser Ala His
            340                 345                 350

Pro Lys Glu Gln Gly Ser Asn Thr Ala Ala Glu Asn Thr Gly Ser Asn
        355                 360                 365

Glu Arg Asn Ile Tyr Ile Val Val Gly Val Val Cys Thr Leu Leu Val
    370                 375                 380

Ala Leu Leu Met Ala Ala Leu Tyr Leu Val Arg Ile Arg Gln Lys Lys
385                 390                 395                 400

Ala Gln Gly Ser Thr Ser Ser Thr Arg Leu His Glu Pro Glu Lys Asn
                405                 410                 415

Ala Arg Glu Ile Thr Gln Asp Thr Asn Asp Ile Thr Tyr Ala Asp Leu
            420                 425                 430

Asn Leu Pro Lys Gly Lys Lys Pro Ala Pro Gln Ala Ala Glu Pro Asn
        435                 440                 445

Asn His Thr Glu Tyr Ala Ser Ile Gln Thr Ser Pro Gln Pro Ala Ser
    450                 455                 460

Glu Asp Thr Leu Thr Tyr Ala Asp Leu Asp Met Val His Leu Asn Arg
465                 470                 475                 480

Thr Pro Lys Gln Pro Ala Pro Lys Pro Glu Pro Ser Phe Ser Glu Tyr
                485                 490                 495

Ala Ser Val Gln Val Pro Arg Lys
            500

<210> SEQ ID NO 55
<211> LENGTH: 1512
<212> TYPE: DNA
<213> ORGANISM: Artificial Sequence
<220> FEATURE:
<223> OTHER INFORMATION: Synthetic: hSIRP alpha-V beta C1 alphaC2 alpha

<400> SEQUENCE: 55
atggaacctg ccggccctgc tcctggtaga ctgggacctc tgctgtgtct gctgctggcc      60
gcctcttgtg cttggagcgg agtggctggc gaggacgagc tgcaagtgat ccagccgag     120 aagtccgtgt ctgtggccgc tggcgagtct gccaccctga gatgcgctat gacctccctg    180
```

-continued

```
atccccgtgg gccccatcat gtggtttaga ggcgctggcg ctggcagaga gctgatctac        240
aaccagaaag agggccactt ccccagagtg accaccgtgt ccgagctgac caagcggaac        300
aacctggact tctccatctc catcagcaac atcacccctg ccgacgccgg cacctactac        360
tgcgtgaagt tccggaaggg ctcccccgac gacgtggagt caaatccgg cgctggaacc         420 gagctgtccg tgcgggctaa accttctgcc cctgtggtgt ctggccctgc cgctagagct        480
acccctcagc acaccgtgtc ttttacctgc gagtcccacg gcttcagccc tcgggacatc        540
accctgaagt ggttcaagaa cggcaacgag ctgagcgact ccagaccaa cgtggaccct         600 gtgggcgaga gcgtgtccta ctccatccac tccaccgcca aggtggtgct gacacgcgag        660
gacgtgcact cccaagtgat ctgcgaggtg gcccacgtga cactgcaggg cgatcctctg        720
agaggcaccg ccaacctgtc cgagacaatc agagtgcccc ccaccctgga agtgacccag        780
cagcctgtgc gggccgagaa ccaagtgaac gtgacctgcc aagtgcggaa gttctacccc        840
cagcggctgc agctgacctg gctggaaaac ggcaatgtgt cccggaccga cagccagc         900 accgtgaccg agaacaagga tggcacctac aattggatgt cctggctgct cgtgaacgtg        960
tccgcccacc gggacgatgt gaagctgaca tgccaggtgg aacacgacgg ccagcctgcc       1020
gtgtccaagt cccacgatct gaaggtgtcc gctcatccca agagcagggg ctccaacacc       1080
gccgctgaga caccggctc taacgagcgg aacatctaca tcgtcgtggg cgtcgtgtgc        1140
accctgctgg tggctctgct gatggctgcc ctgtacctcg tgcggatccg gcagaagaag       1200
gcccagggct ctacctcctc caccagactg cacgagcctg agaagaacgc cagagagatc       1260
acccaggaca ccaacgacat cacctacgcc gacctgaacc tgcccaaggg caagaagcct       1320
gcccctcagg ccgccgagcc taacaaccac accgagtacg cctccatcca gaccagccct       1380
cagcctgcct ctgaggacac cctgacctac gctgatctgg acatggtgca cctgaaccgg       1440 accccccaagc agccagctcc taagcccgag cctagcttct ctgagtacgc cagcgtgcag       1500
gtgccccgga aa                                                            1512
```

<210> SEQ ID NO 56
<211> LENGTH: 504
<212> TYPE: PRT
<213> ORGANISM: Artificial Sequence
<220> FEATURE:
<223> OTHER INFORMATION: Synthetic: hSIRP alpha-V beta C1 alphaC2 alpha

<400> SEQUENCE: 56

Met Glu Pro Ala Gly Pro Ala Pro Gly Arg Leu Gly Pro Leu Leu Cys
1               5                   10                  15

Leu Leu Leu Ala Ala Ser Cys Ala Trp Ser Gly Val Ala Gly Glu Asp
            20                  25                  30

Glu Leu Gln Val Ile Gln Pro Glu Lys Ser Val Ser Val Ala Ala Gly
        35                  40                  45

Glu Ser Ala Thr Leu Arg Cys Ala Met Thr Ser Leu Ile Pro Val Gly
    50                  55                  60

Pro Ile Met Trp Phe Arg Gly Ala Gly Ala Gly Arg Glu Leu Ile Tyr
65                  70                  75                  80

Asn Gln Lys Glu Gly His Phe Pro Arg Val Thr Thr Val Ser Glu Leu
                85                  90                  95

Thr Lys Arg Asn Asn Leu Asp Phe Ser Ile Ser Ile Ser Asn Ile Thr
            100                 105                 110

Pro Ala Asp Ala Gly Thr Tyr Tyr Cys Val Lys Phe Arg Lys Gly Ser

```
               115                 120                 125
Pro Asp Asp Val Glu Phe Lys Ser Gly Ala Gly Thr Glu Leu Ser Val
130                 135                 140

Arg Ala Lys Pro Ser Ala Pro Val Val Ser Gly Pro Ala Ala Arg Ala
145                 150                 155                 160

Thr Pro Gln His Thr Val Ser Phe Thr Cys Glu Ser His Gly Phe Ser
                165                 170                 175

Pro Arg Asp Ile Thr Leu Lys Trp Phe Lys Asn Gly Asn Glu Leu Ser
                180                 185                 190

Asp Phe Gln Thr Asn Val Asp Pro Val Gly Glu Ser Val Ser Tyr Ser
                195                 200                 205

Ile His Ser Thr Ala Lys Val Val Leu Thr Arg Glu Asp Val His Ser
210                 215                 220

Gln Val Ile Cys Glu Val Ala His Val Thr Leu Gln Gly Asp Pro Leu
225                 230                 235                 240

Arg Gly Thr Ala Asn Leu Ser Glu Thr Ile Arg Val Pro Pro Thr Leu
                245                 250                 255

Glu Val Thr Gln Gln Pro Val Arg Ala Glu Asn Gln Val Asn Val Thr
                260                 265                 270

Cys Gln Val Arg Lys Phe Tyr Pro Gln Arg Leu Gln Leu Thr Trp Leu
                275                 280                 285

Glu Asn Gly Asn Val Ser Arg Thr Glu Thr Ala Ser Thr Val Thr Glu
290                 295                 300

Asn Lys Asp Gly Thr Tyr Asn Trp Met Ser Trp Leu Leu Val Asn Val
305                 310                 315                 320

Ser Ala His Arg Asp Asp Val Lys Leu Thr Cys Gln Val Glu His Asp
                325                 330                 335

Gly Gln Pro Ala Val Ser Lys Ser His Asp Leu Lys Val Ser Ala His
                340                 345                 350

Pro Lys Glu Gln Gly Ser Asn Thr Ala Ala Glu Asn Thr Gly Ser Asn
                355                 360                 365

Glu Arg Asn Ile Tyr Ile Val Val Gly Val Val Cys Thr Leu Leu Val
370                 375                 380

Ala Leu Leu Met Ala Ala Leu Tyr Leu Val Arg Ile Arg Gln Lys Lys
385                 390                 395                 400

Ala Gln Gly Ser Thr Ser Ser Thr Arg Leu His Glu Pro Glu Lys Asn
                405                 410                 415

Ala Arg Glu Ile Thr Gln Asp Thr Asn Asp Ile Thr Tyr Ala Asp Leu
                420                 425                 430

Asn Leu Pro Lys Gly Lys Lys Pro Ala Pro Gln Ala Ala Glu Pro Asn
                435                 440                 445

Asn His Thr Glu Tyr Ala Ser Ile Gln Thr Ser Pro Gln Pro Ala Ser
                450                 455                 460

Glu Asp Thr Leu Thr Tyr Ala Asp Leu Asp Met Val His Leu Asn Arg
465                 470                 475                 480

Thr Pro Lys Gln Pro Ala Pro Lys Pro Glu Pro Ser Phe Ser Glu Tyr
                485                 490                 495

Ala Ser Val Gln Val Pro Arg Lys
                500

<210> SEQ ID NO 57
<211> LENGTH: 1512
<212> TYPE: DNA
<213> ORGANISM: Artificial Sequence
```

<220> FEATURE:
<223> OTHER INFORMATION: Synthetic: hSIRP alpha-V alphaC1 beta C2 alpha

<400> SEQUENCE: 57

```
atggaacctg ccggccctgc tcctggtaga ctgggacctc tgctgtgtct gctgctggcc      60
gcctcttgtg cttggagcgg agtggctggc gaagaggaac tgcaagtgat ccagcccgac     120
aagtccgtgc tggtggctgc tggcgagact gccaccctga tgtaccgc acctccctg        180
atccccgtgg ccctatcca gtggtttaga ggcgctggcc ctggcagaga gctgatctac      240
aaccagaaag agggccactt ccccagagtg accaccgtgt ccgacctgac caagcggaac     300
aacatggact tctccatccg gatcggcaac atcaccctg ccgatgccgg cacctactac      360
tgcgtgaagt tccggaaggg ctcccccgac gacgtggagt caaatccgg cgctggcacc     420
gagctgtctg tgcgggctaa accttctgcc ccgtggtgt ctggacctgc cgtgcgagct     480
acccctgagc acaccgtgtc ttttacctgc gagtcccacg gcttcagccc tcgggacatc    540
accctgaagt ggttcaagaa cggcaacgag ctgagcgact tccagaccaa cgtggaccca    600
gccggcgact ccgtgtccta ctccatccac tctaccgcca gagtggtgct gaccagaggc    660
gacgtgcact cccaagtgat ctgcgagatc gcccatatca cactgcaggg cgaccccctg    720
agaggcaccg ctaacctgtc tgagacaatc cgggtgcccc ccaccctgga agtgactcag    780
cagccagtgc gggccgagaa ccaagtgaac gtgacctgcc aagtgcggaa gttctacccc    840
cagcggctgc agctgacctg gctggaaaac ggcaatgtgt cccggaccga cagcctcc     900
accgtgaccg agaacaagga tgcaacctac aattggatgt cttggctgct cgtgaacgtg    960
tccgcccacc gggacgatgt gaagctgaca tgccaggtgg aacacgacgg ccagcctgcc   1020
gtgtccaagt cccacgatct gaaggtgtcc gctcatccca agagcaggg ctccaacacc    1080
gccgctgaga caccggctc taacgagcgg aacatctaca tcgtcgtggg cgtcgtgtgc    1140
accctgctgg tggcactgct gatggccgct ctgtacctcg tgcggatccg gcagaagaag   1200
gcccagggct ctacctcctc caccagactg cacgagcccg agaagaacgc cagagagatc   1260
acccaggaca ccaacgacat cacctacgcc gacctgaacc tgcccaaggg caagaagcct   1320
gcccctcagg ccgccgagcc taacaaccac accgagtacg cctccatcca gaccagccct   1380
cagcctgcct ctgaggacac cctgacctac gctgatctgg acatggtgca cctgaaccgg   1440
accccaagc agccagctcc taagcccgag cctagcttct ctgagtacgc cagcgtgcag   1500
gtgccccgga aa                                                        1512
```

<210> SEQ ID NO 58
<211> LENGTH: 504
<212> TYPE: PRT
<213> ORGANISM: Artificial Sequence
<220> FEATURE:
<223> OTHER INFORMATION: Synthetic: hSIRP alpha-V alphaC1 beta C2 alpha

<400> SEQUENCE: 58

```
Met Glu Pro Ala Gly Pro Ala Pro Gly Arg Leu Gly Pro Leu Leu Cys
1               5                   10                  15

Leu Leu Leu Ala Ala Ser Cys Ala Trp Ser Gly Val Ala Gly Glu Glu
            20                  25                  30

Glu Leu Gln Val Ile Gln Pro Asp Lys Ser Val Leu Val Ala Ala Gly
        35                  40                  45

Glu Thr Ala Thr Leu Arg Cys Thr Ala Thr Ser Leu Ile Pro Val Gly
    50                  55                  60
```

```
Pro Ile Gln Trp Phe Arg Gly Ala Gly Pro Gly Arg Glu Leu Ile Tyr
 65                  70                  75                  80

Asn Gln Lys Glu Gly His Phe Pro Arg Val Thr Thr Val Ser Asp Leu
                 85                  90                  95

Thr Lys Arg Asn Asn Met Asp Phe Ser Ile Arg Ile Gly Asn Ile Thr
            100                 105                 110

Pro Ala Asp Ala Gly Thr Tyr Tyr Cys Val Lys Phe Arg Lys Gly Ser
            115                 120                 125

Pro Asp Asp Val Glu Phe Lys Ser Gly Ala Gly Thr Glu Leu Ser Val
        130                 135                 140

Arg Ala Lys Pro Ser Ala Pro Val Val Ser Gly Pro Ala Val Arg Ala
145                 150                 155                 160

Thr Pro Glu His Thr Val Ser Phe Thr Cys Glu Ser His Gly Phe Ser
                165                 170                 175

Pro Arg Asp Ile Thr Leu Lys Trp Phe Lys Asn Gly Asn Glu Leu Ser
                180                 185                 190

Asp Phe Gln Thr Asn Val Asp Pro Ala Gly Asp Ser Val Ser Tyr Ser
                195                 200                 205

Ile His Ser Thr Ala Arg Val Val Leu Thr Arg Gly Asp Val His Ser
            210                 215                 220

Gln Val Ile Cys Glu Ile Ala His Ile Thr Leu Gln Gly Asp Pro Leu
225                 230                 235                 240

Arg Gly Thr Ala Asn Leu Ser Glu Thr Ile Arg Val Pro Pro Thr Leu
                245                 250                 255

Glu Val Thr Gln Gln Pro Val Arg Ala Glu Asn Gln Val Asn Val Thr
                260                 265                 270

Cys Gln Val Arg Lys Phe Tyr Pro Gln Arg Leu Gln Leu Thr Trp Leu
            275                 280                 285

Glu Asn Gly Asn Val Ser Arg Thr Glu Thr Ala Ser Thr Val Thr Glu
            290                 295                 300

Asn Lys Asp Gly Thr Tyr Asn Trp Met Ser Trp Leu Leu Val Asn Val
305                 310                 315                 320

Ser Ala His Arg Asp Asp Val Lys Leu Thr Cys Gln Val Glu His Asp
                325                 330                 335

Gly Gln Pro Ala Val Ser Lys Ser His Asp Leu Lys Val Ser Ala His
                340                 345                 350

Pro Lys Glu Gln Gly Ser Asn Thr Ala Ala Glu Asn Thr Gly Ser Asn
                355                 360                 365

Glu Arg Asn Ile Tyr Ile Val Val Gly Val Val Cys Thr Leu Leu Val
            370                 375                 380

Ala Leu Leu Met Ala Ala Leu Tyr Leu Val Arg Ile Arg Gln Lys Lys
385                 390                 395                 400

Ala Gln Gly Ser Thr Ser Ser Thr Arg Leu His Glu Pro Glu Lys Asn
                405                 410                 415

Ala Arg Glu Ile Thr Gln Asp Thr Asn Asp Ile Thr Tyr Ala Asp Leu
            420                 425                 430

Asn Leu Pro Lys Gly Lys Lys Pro Ala Pro Gln Ala Ala Glu Pro Asn
            435                 440                 445

Asn His Thr Glu Tyr Ala Ser Ile Gln Thr Ser Pro Gln Pro Ala Ser
            450                 455                 460

Glu Asp Thr Leu Thr Tyr Ala Asp Leu Asp Met Val His Leu Asn Arg
465                 470                 475                 480

Thr Pro Lys Gln Pro Ala Pro Lys Pro Glu Pro Ser Phe Ser Glu Tyr
```

485                 490                 495
Ala Ser Val Gln Val Pro Arg Lys
        500

<210> SEQ ID NO 59
<211> LENGTH: 1512
<212> TYPE: DNA
<213> ORGANISM: Artificial Sequence
<220> FEATURE:
<223> OTHER INFORMATION: Synthetic: hSIRP alpha-V alphaC1 alphaC2 beta

<400> SEQUENCE: 59

| | | | | | |
|---|---|---|---|---|---|
| atggaacctg | ccggccctgc | tcctggtaga | ctgggacctc | tgctgtgtct | gctgctggcc | 60 |
| gcctcttgtg | cttggagcgg | agtggctggc | gaagaggaac | tgcaagtgat | ccagcccgac | 120 |
| aagtccgtgc | tggtggctgc | tggcgagact | gccaccctga | gatgtaccgc | cacctccctg | 180 |
| atccccgtgg | gccctatcca | gtggtttaga | ggcgctggcc | ctggcagaga | gctgatctac | 240 |
| aaccagaaag | agggccactt | ccccagagtg | accaccgtgt | ccgacctgac | caagcggaac | 300 |
| aacatggact | tctccatccg | gatcggcaac | atcacccctg | ccgatgccgg | cacctactac | 360 |
| tgcgtgaagt | tccggaaggg | ctcccccgac | gacgtggagt | caaatccgg | cgctggcacc | 420 |
| gagctgtctg | tgcgggctaa | accttctgcc | cctgtggtgt | ctggccctgc | cgctagagct | 480 |
| accccctcagc | acaccgtgtc | ttttacctgc | gagtcccacg | gcttcagccc | tcgggacatc | 540 |
| accctgaagt | ggttcaagaa | cggcaacgag | ctgagcgact | tccagaccaa | cgtggaccct | 600 |
| gtgggcgagt | ccgtgtccta | ctccatccac | tccaccgcca | aggtggtgct | gacacgcgag | 660 |
| gacgtgcact | cccaagtgat | ctgcgaggtg | gcccacgtga | cactgcaggg | cgatcctctg | 720 |
| agaggcaccg | ccaacctgtc | cgagacaatc | agagtgcccc | ccaccctgga | agtgacccag | 780 |
| cagcctatga | gagccgagaa | ccaggccaac | gtgacctgcc | aggtgtccaa | cttctacccc | 840 |
| cggggcctgc | agctgacctg | gctggaaaac | ggcaatgtgt | cccggaccga | gacagcctcc | 900 |
| accctgatcg | agaacaagga | tggcacctac | aattggatgt | cctggctgct | cgtgaacacc | 960 |
| tgtgcccacc | gggacgatgt | ggtgctgacc | tgtcaggtgg | aacacgatgg | ccagcaggcc | 1020 |
| gtgtccaagt | cctacgctct | ggaagtgtcc | gcccacccca | agagcagggg | ctctaatacc | 1080 |
| gccgctgaga | caccggctc | caacgagcgg | aacatctaca | tcgtcgtggg | cgtcgtgtgc | 1140 |
| accctgctgg | tggcactgct | gatggccgct | ctgtacctcg | tgcggatccg | gcagaagaag | 1200 |
| gctcagggct | ccacctcctc | caccagactg | cacgagcctg | agaagaacgc | cagagagatc | 1260 |
| acccaggaca | ccaacgacat | cacctacgcc | gacctgaacc | tgcccaaggg | caagaagcct | 1320 |
| gccccctcagg | ctgccgagcc | taacaaccac | accgagtacg | cctccatcca | gaccagccct | 1380 |
| cagcctgcct | ctgaggacac | cctgacctac | gctgatctgg | acatggtgca | cctgaaccgg | 1440 |
| acccccaagc | agccagctcc | taagcccgag | cctagcttct | ctgagtacgc | cagcgtgcag | 1500 |
| gtgccccgga | aa | | | | | 1512 |

<210> SEQ ID NO 60
<211> LENGTH: 504
<212> TYPE: PRT
<213> ORGANISM: Artificial Sequence
<220> FEATURE:
<223> OTHER INFORMATION: Synthetic: hSIRP alpha-V alphaC1 alphaC2 beta

<400> SEQUENCE: 60

Met Glu Pro Ala Gly Pro Ala Pro Gly Arg Leu Gly Pro Leu Leu Cys
1               5                   10                  15

```
Leu Leu Leu Ala Ala Ser Cys Ala Trp Ser Gly Val Ala Gly Glu Glu
            20                  25                  30

Glu Leu Gln Val Ile Gln Pro Asp Lys Ser Val Leu Val Ala Ala Gly
        35                  40                  45

Glu Thr Ala Thr Leu Arg Cys Thr Ala Thr Ser Leu Ile Pro Val Gly
    50                  55                  60

Pro Ile Gln Trp Phe Arg Gly Ala Gly Pro Gly Arg Glu Leu Ile Tyr
65                  70                  75                  80

Asn Gln Lys Glu Gly His Phe Pro Arg Val Thr Thr Val Ser Asp Leu
                85                  90                  95

Thr Lys Arg Asn Asn Met Asp Phe Ser Ile Arg Ile Gly Asn Ile Thr
            100                 105                 110

Pro Ala Asp Ala Gly Thr Tyr Tyr Cys Val Lys Phe Arg Lys Gly Ser
        115                 120                 125

Pro Asp Asp Val Glu Phe Lys Ser Gly Ala Gly Thr Glu Leu Ser Val
    130                 135                 140

Arg Ala Lys Pro Ser Ala Pro Val Val Ser Gly Pro Ala Ala Arg Ala
145                 150                 155                 160

Thr Pro Gln His Thr Val Ser Phe Thr Cys Glu Ser His Gly Phe Ser
                165                 170                 175

Pro Arg Asp Ile Thr Leu Lys Trp Phe Lys Asn Gly Asn Glu Leu Ser
            180                 185                 190

Asp Phe Gln Thr Asn Val Asp Pro Val Gly Glu Ser Val Ser Tyr Ser
        195                 200                 205

Ile His Ser Thr Ala Lys Val Val Leu Thr Arg Glu Asp Val His Ser
    210                 215                 220

Gln Val Ile Cys Glu Val Ala His Val Thr Leu Gln Gly Asp Pro Leu
225                 230                 235                 240

Arg Gly Thr Ala Asn Leu Ser Glu Thr Ile Arg Val Pro Pro Thr Leu
                245                 250                 255

Glu Val Thr Gln Gln Pro Met Arg Ala Glu Asn Gln Ala Asn Val Thr
            260                 265                 270

Cys Gln Val Ser Asn Phe Tyr Pro Arg Gly Leu Gln Leu Thr Trp Leu
        275                 280                 285

Glu Asn Gly Asn Val Ser Arg Thr Glu Thr Ala Ser Thr Leu Ile Glu
    290                 295                 300

Asn Lys Asp Gly Thr Tyr Asn Trp Met Ser Trp Leu Leu Val Asn Thr
305                 310                 315                 320

Cys Ala His Arg Asp Asp Val Val Leu Thr Cys Gln Val Glu His Asp
                325                 330                 335

Gly Gln Gln Ala Val Ser Lys Ser Tyr Ala Leu Glu Val Ser Ala His
            340                 345                 350

Pro Lys Glu Gln Gly Ser Asn Thr Ala Ala Glu Asn Thr Gly Ser Asn
        355                 360                 365

Glu Arg Asn Ile Tyr Ile Val Val Gly Val Val Cys Thr Leu Leu Val
    370                 375                 380

Ala Leu Leu Met Ala Ala Leu Tyr Leu Val Arg Ile Arg Gln Lys Lys
385                 390                 395                 400

Ala Gln Gly Ser Thr Ser Ser Thr Arg Leu His Glu Pro Glu Lys Asn
                405                 410                 415

Ala Arg Glu Ile Thr Gln Asp Thr Asn Asp Ile Thr Tyr Ala Asp Leu
            420                 425                 430
```

```
Asn Leu Pro Lys Gly Lys Lys Pro Ala Pro Gln Ala Ala Glu Pro Asn
            435                 440                 445

Asn His Thr Glu Tyr Ala Ser Ile Gln Thr Ser Pro Gln Pro Ala Ser
    450                 455                 460

Glu Asp Thr Leu Thr Tyr Ala Asp Leu Asp Met Val His Leu Asn Arg
465                 470                 475                 480

Thr Pro Lys Gln Pro Ala Pro Lys Pro Glu Pro Ser Phe Ser Glu Tyr
                485                 490                 495

Ala Ser Val Gln Val Pro Arg Lys
            500
```

<210> SEQ ID NO 61
<211> LENGTH: 1512
<212> TYPE: DNA
<213> ORGANISM: Homo sapiens
<220> FEATURE:
<221> NAME/KEY: misc_feature
<222> LOCATION: (1)..(1512)
<223> OTHER INFORMATION: human SIRP alpha V1(P74A)

<400> SEQUENCE: 61

```
atggagcccg ccggcccggc ccccggccgc ctcgggccgc tgctctgcct gctgctcgcc      60
gcgtcctgcg cctggtcagg agtggcgggt gaggaggagc tgcaggtgat tcagcctgac     120
aagtccgtgt tggttgcagc tggagagaca gccactctgc gctgcactgc gacctctctg     180
atccctgtgg ggcccatcca gtggttcaga ggagctggag caggccggga attaatctac     240
aatcaaaaag aaggccactt ccccggggta caactgtttt cagacctcac aaagagaaac     300
aacatggact tttccatccg catcggtaac atcaccccag cagatgccgg cacctactac     360
tgtgtgaagt tccggaaagg agccccgat gacgtggagt taagtctgg agcaggcact      420 gagctgtctg tgcgcgccaa accctctgcc ccgtggtat cgggccctgc ggcgagggcc      480
acacctcagc acacagtgag cttcacctgc gagtcccacg gcttctcacc agagacatc      540 accctgaaat ggttcaaaaa tgggaatgag ctctcagact ccagaccaa cgtggacccc      600 gtaggagaga gcgtgtccta cagcatccac agcacagcca aggtggtgct gacccgcgag     660
gacgttcact ctcaagtcat ctgcgaggtg gcccacgtca ccttgcaggg ggacccctctt    720 cgtgggactg ccaacttgtc tgagaccatc cgagttccac ccaccttgga ggttactcaa     780
cagcccgtga gggcagagaa ccaggtgaat gtcacctgcc aggtgaggaa gttctacccc    840
cagagactac agctgacctg gttggagaat ggaaacgtgt ccggacagaa acggcctca     900 accgttacag agaacaagga tggtacctac aactggatga gctggctcct ggtgaatgta     960
tctgcccaca gggatgatgt gaagctcacc tgccaggtgg agcatgacgg gcagccagcg    1020
gtcagcaaaa gccatgacct gaaggtctca gcccaccccga aggagcaggg ctcaaatacc    1080
gccgctgaga cactggatc taatgaacgg aacatctata ttgtggtggg tgtggtgtgc    1140
accttgctgg tggccctact gatggcggcc ctctacctcg tccgaatcag acagaagaaa     1200
gcccagggct ccacttcttc tacaaggttg catgagcccg agaagaatgc cagagaaata    1260
acacaggaca caaatgatat cacatatgca gacctgaacc tgcccaaggg gaagaagcct    1320
gctccccagg ctgcggagcc caacaaccac acggagtatg ccagcattca gaccagcccg    1380
cagcccgcgt cggaggacac cctcacctat gctgacctgg acatggtcca cctcaaccgg    1440 accccccaagc agccggcccc caagcctgag ccgtccttct cagagtacgc cagcgtccag    1500
gtcccgagga ag                                                          1512
```

<210> SEQ ID NO 62
<211> LENGTH: 504
<212> TYPE: PRT
<213> ORGANISM: Homo sapiens
<220> FEATURE:
<221> NAME/KEY: misc_feature
<222> LOCATION: (1)..(504)
<223> OTHER INFORMATION: human SIRP alpha V1(P74A)

<400> SEQUENCE: 62

```
Met Glu Pro Ala Gly Pro Ala Pro Gly Arg Leu Gly Pro Leu Leu Cys
1               5                   10                  15

Leu Leu Leu Ala Ala Ser Cys Ala Trp Ser Gly Val Ala Gly Glu Glu
                20                  25                  30

Glu Leu Gln Val Ile Gln Pro Asp Lys Ser Val Leu Val Ala Ala Gly
            35                  40                  45

Glu Thr Ala Thr Leu Arg Cys Thr Ala Thr Ser Leu Ile Pro Val Gly
        50                  55                  60

Pro Ile Gln Trp Phe Arg Gly Ala Gly Ala Gly Arg Glu Leu Ile Tyr
65                  70                  75                  80

Asn Gln Lys Glu Gly His Phe Pro Arg Val Thr Thr Val Ser Asp Leu
                85                  90                  95

Thr Lys Arg Asn Asn Met Asp Phe Ser Ile Arg Ile Gly Asn Ile Thr
            100                 105                 110

Pro Ala Asp Ala Gly Thr Tyr Tyr Cys Val Lys Phe Arg Lys Gly Ser
        115                 120                 125

Pro Asp Asp Val Glu Phe Lys Ser Gly Ala Gly Thr Glu Leu Ser Val
130                 135                 140

Arg Ala Lys Pro Ser Ala Pro Val Val Ser Gly Pro Ala Ala Arg Ala
145                 150                 155                 160

Thr Pro Gln His Thr Val Ser Phe Thr Cys Glu Ser His Gly Phe Ser
                165                 170                 175

Pro Arg Asp Ile Thr Leu Lys Trp Phe Lys Asn Gly Asn Glu Leu Ser
            180                 185                 190

Asp Phe Gln Thr Asn Val Asp Pro Val Gly Glu Ser Val Ser Tyr Ser
        195                 200                 205

Ile His Ser Thr Ala Lys Val Val Leu Thr Arg Glu Asp Val His Ser
    210                 215                 220

Gln Val Ile Cys Glu Val Ala His Val Thr Leu Gln Gly Asp Pro Leu
225                 230                 235                 240

Arg Gly Thr Ala Asn Leu Ser Glu Thr Ile Arg Val Pro Pro Thr Leu
                245                 250                 255

Glu Val Thr Gln Gln Pro Val Arg Ala Glu Asn Gln Val Asn Val Thr
            260                 265                 270

Cys Gln Val Arg Lys Phe Tyr Pro Gln Arg Leu Gln Leu Thr Trp Leu
        275                 280                 285

Glu Asn Gly Asn Val Ser Arg Thr Glu Thr Ala Ser Thr Val Thr Glu
    290                 295                 300

Asn Lys Asp Gly Thr Tyr Asn Trp Met Ser Trp Leu Leu Val Asn Val
305                 310                 315                 320

Ser Ala His Arg Asp Asp Val Lys Leu Thr Cys Gln Val Glu His Asp
                325                 330                 335

Gly Gln Pro Ala Val Ser Lys Ser His Asp Leu Lys Val Ser Ala His
            340                 345                 350

Pro Lys Glu Gln Gly Ser Asn Thr Ala Ala Glu Asn Thr Gly Ser Asn
```

```
                355                 360                 365
Glu Arg Asn Ile Tyr Ile Val Val Gly Val Val Cys Thr Leu Leu Val
            370                 375                 380

Ala Leu Leu Met Ala Ala Leu Tyr Leu Val Arg Ile Arg Gln Lys Lys
385                 390                 395                 400

Ala Gln Gly Ser Thr Ser Ser Thr Arg Leu His Glu Pro Glu Lys Asn
                405                 410                 415

Ala Arg Glu Ile Thr Gln Asp Thr Asn Asp Ile Thr Tyr Ala Asp Leu
            420                 425                 430

Asn Leu Pro Lys Gly Lys Lys Pro Ala Pro Gln Ala Ala Glu Pro Asn
        435                 440                 445

Asn His Thr Glu Tyr Ala Ser Ile Gln Thr Ser Pro Gln Pro Ala Ser
        450                 455                 460

Glu Asp Thr Leu Thr Tyr Ala Asp Leu Asp Met Val His Leu Asn Arg
465                 470                 475                 480

Thr Pro Lys Gln Pro Ala Pro Lys Pro Glu Pro Ser Phe Ser Glu Tyr
                485                 490                 495

Ala Ser Val Gln Val Pro Arg Lys
            500

<210> SEQ ID NO 63
<211> LENGTH: 321
<212> TYPE: DNA
<213> ORGANISM: Homo sapiens
<220> FEATURE:
<221> NAME/KEY: misc_feature
<222> LOCATION: (1)..(321)
<223> OTHER INFORMATION: human kappa constant domain

<400> SEQUENCE: 63
cggaccgtgg ccgctccctc cgtgttcatc ttcccacctt ccgacgagca gctgaagtcc      60
ggcaccgctt ctgtcgtgtg cctgctgaac aacttctacc ccgcgaggc caaggtgcag     120 tggaaggtgg acaacgccct gcagtccggc aactcccagg aatccgtgac cgagcaggac     180
tccaaggaca gcacctactc cctgtcctcc accctgaccc tgtccaaggc cgactacgag     240
aagcacaagg tgtacgcctg cgaagtgacc caccagggcc tgtctagccc tgtgaccaag     300
tccttcaacc ggggcgagtg c                                               321

<210> SEQ ID NO 64
<211> LENGTH: 107
<212> TYPE: PRT
<213> ORGANISM: Homo sapiens
<220> FEATURE:
<221> NAME/KEY: misc_feature
<222> LOCATION: (1)..(107)
<223> OTHER INFORMATION: human kappa constant domain

<400> SEQUENCE: 64

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80
```

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 65
<211> LENGTH: 981
<212> TYPE: DNA
<213> ORGANISM: Homo sapiens
<220> FEATURE:
<221> NAME/KEY: misc_feature
<222> LOCATION: (1)..(981)
<223> OTHER INFORMATION: human IgG4 constant domains (including S228P)

<400> SEQUENCE: 65
gcttccacca agggcccctc cgtgtttcct ctggcccctt gctccagatc cacctccgag      60
tctaccgccg ctctgggctg cctcgtgaag gactacttcc ccgagcctgt gacagtgtcc     120
tggaactctg gcgccctgac ctctggcgtg cacacctttc cagctgtgct gcagtcctcc     180
ggcctgtact ccctgtccag cgtcgtgaca gtgccctcca gctctctggg caccaagacc     240
tacacctgta acgtggacca caagccctcc aacaccaagg tggacaagcg ggtggaatct     300
aagtacggcc ctccctgccc tccttgccca gcccctgaat tctgggcgg accttctgtg      360
tttctgttcc ccccaaagcc caaggacacc ctgatgatct cccggacccc cgaagtgacc     420
tgcgtggtgg tggatgtgtc ccaggaagat cccgaggtgc agttcaattg gtacgtggac     480
ggcgtggaag tgcacaacgc caagaccaag cctagagagg aacagttcaa ctccacctac     540
cgggtggtgt ccgtgctgac cgtgctgcac caggattggc tgaacggcaa agagtacaag     600
tgcaaggtgt ccaacaaggg cctgcccagc tccatcgaaa agaccatctc caaggccaag     660
ggccagcccc gggaacccca ggtgtacaca ctgcctccaa gccaggaaga gatgaccaag     720
aaccaggtgt ccctgacctg tctcgtgaaa ggcttctacc cctccgatat cgccgtggaa     780
tgggagtcca acggccagcc tgagaacaac tacaagacca cccccctgt gctggactcc      840
gacggctcct tctttctgta ctctcgcctg accgtggaca gtccggtg caggaaggc       900
aacgtgttct cctgcagcgt gatgcacgag gccctgcaca ccactacac ccagaagtcc     960
ctgtccctgt ctctgggaaa a                                              981

<210> SEQ ID NO 66
<211> LENGTH: 327
<212> TYPE: PRT
<213> ORGANISM: Homo sapiens
<220> FEATURE:
<221> NAME/KEY: misc_feature
<222> LOCATION: (1)..(327)
<223> OTHER INFORMATION: human IgG4 constant domains (including S228P)

<400> SEQUENCE: 66

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
            85                  90                  95

Arg Val Glu Ser Lys Tyr Gly Pro Pro Cys Pro Pro Cys Pro Ala Pro
        100                 105                 110

Glu Phe Leu Gly Gly Pro Ser Val Phe Leu Phe Pro Pro Lys Pro Lys
    115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Gln Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 67
<211> LENGTH: 978
<212> TYPE: DNA
<213> ORGANISM: Homo sapiens
<220> FEATURE:
<221> NAME/KEY: misc_feature
<222> LOCATION: (1)..(978)
<223> OTHER INFORMATION: human IgG2 constant domains
<220> FEATURE:
<221> NAME/KEY: misc_feature
<222> LOCATION: (769)..(769)
<223> OTHER INFORMATION: n is g or t

<400> SEQUENCE: 67
gcttctacaa agggcccag cgtgttccct ctggctcctt gtagcagaag caccagcgag      60
tctacagccg ctctgggctg tctggtcaag gactactttc ccgagcctgt gaccgtgtcc    120
tggaatagcg gagcactgac aagcggcgtg cacacctttc cagctgtgct gcaaagctcc    180
ggcctgtact ctctgtccag cgtggtcaca gtgcccagca gcaattttgg cacccagacc    240
tacacctgta atgtggacca caagcctagc aacaccaagg tggacaagac cgtggaacgg    300
aagtgctgcg tggaatgccc tccttgtcct gctcctccag tggctggccc ttccgtgttt    360
ctgttccctc caaagcctaa ggacaccctg atgatcagca gaaccctga agtgacctgc    420

```
gtggtggtgg atgtgtccca cgaggatcct gaggtgcagt tcaattggta cgtggacggc    480
gtggaagtgc acaacgccaa gaccaagcct agagaggaac agttcaacag caccttcaga    540
gtggtgtccg tgctgaccgt ggtgcatcag gattggctga acggcaaaga gtacaagtgc    600
aaggtgtcca acaagggcct gcctgctcct atcgagaaaa ccatcagcaa gaccaaaggc    660
cagcctcgcg agccccaggt ttacacactt cctccaagcc gggaagagat gaccaagaac    720
caggtgtccc tgacctgcct cgtgaagggc ttctacccca gcgacatcnc cgtggaatgg    780
gagagcaatg gccagcctga gaacaactac aagaccacac tcctatgct ggactccgac    840
ggctcattct cctgtacag caagctgaca gtggacaagt ccagatggca gcagggcaac    900
gtgttctcct gcagcgtgat gcacgaggcc ctgcacaacc actacaccca gaagtccctg    960
tctctgagcc ccggcaaa                                                  978
```

<210> SEQ ID NO 68
<211> LENGTH: 326
<212> TYPE: PRT
<213> ORGANISM: Homo sapiens
<220> FEATURE:
<221> NAME/KEY: misc_feature
<222> LOCATION: (1)..(326)
<223> OTHER INFORMATION: human IgG2 constant domains
<220> FEATURE:
<221> NAME/KEY: misc_feature
<222> LOCATION: (257)..(257)
<223> OTHER INFORMATION: X is A or S

<400> SEQUENCE: 68

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
```

```
                225                 230                 235                 240
Gln Val Ser Leu Thr Cys Leu Val Lys Gly Phe Tyr Pro Ser Asp Ile
                245                 250                 255

Xaa Val Glu Trp Glu Ser Asn Gly Gln Pro Glu Asn Asn Tyr Lys Thr
                260                 265                 270

Thr Pro Pro Met Leu Asp Ser Asp Gly Ser Phe Phe Leu Tyr Ser Lys
                275                 280                 285

Leu Thr Val Asp Lys Ser Arg Trp Gln Gln Gly Asn Val Phe Ser Cys
            290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 69
<211> LENGTH: 5
<212> TYPE: PRT
<213> ORGANISM: Artificial Sequence
<220> FEATURE:
<223> OTHER INFORMATION: Synthetic: 40A heavy chain CDR1

<400> SEQUENCE: 69

Ser Tyr Trp Met His
1               5

<210> SEQ ID NO 70
<211> LENGTH: 17
<212> TYPE: PRT
<213> ORGANISM: Artificial Sequence
<220> FEATURE:
<223> OTHER INFORMATION: Synthetic: 40A heavy chain CDR2

<400> SEQUENCE: 70

Ala Ile Tyr Pro Val Asn Asn Asp Thr Thr Tyr Asn Gln Lys Phe Lys
1               5                   10                  15

Gly

<210> SEQ ID NO 71
<211> LENGTH: 13
<212> TYPE: PRT
<213> ORGANISM: Artificial Sequence
<220> FEATURE:
<223> OTHER INFORMATION: Synthetic: 40A heavy chain CDR3

<400> SEQUENCE: 71

Ser Phe Tyr Tyr Ser Leu Asp Ala Ala Trp Phe Val Tyr
1               5                   10

<210> SEQ ID NO 72
<211> LENGTH: 11
<212> TYPE: PRT
<213> ORGANISM: Artificial Sequence
<220> FEATURE:
<223> OTHER INFORMATION: Synthetic: 40A light chain CDR1

<400> SEQUENCE: 72

Arg Ala Ser Gln Asp Ile Gly Ser Arg Leu Asn
1               5                   10

<210> SEQ ID NO 73
<211> LENGTH: 7
<212> TYPE: PRT
<213> ORGANISM: Artificial Sequence
```

```
<220> FEATURE:
<223> OTHER INFORMATION: Synthetic: 40A light chain CDR2

<400> SEQUENCE: 73

Ala Thr Ser Ser Leu Asp Ser
1               5

<210> SEQ ID NO 74
<211> LENGTH: 9
<212> TYPE: PRT
<213> ORGANISM: Artificial Sequence
<220> FEATURE:
<223> OTHER INFORMATION: Synthetic: 40A light chain CDR3

<400> SEQUENCE: 74

Leu Gln Tyr Ala Ser Ser Pro Phe Thr
1               5

<210> SEQ ID NO 75
<211> LENGTH: 122
<212> TYPE: PRT
<213> ORGANISM: Artificial Sequence
<220> FEATURE:
<223> OTHER INFORMATION: Synthetic: humanized 40 heavy chain variable
      region (consensus sequence)
<220> FEATURE:
<221> NAME/KEY: misc_feature
<222> LOCATION: (4)..(4)
<223> OTHER INFORMATION: X = F or L
<220> FEATURE:
<221> NAME/KEY: misc_feature
<222> LOCATION: (5)..(5)
<223> OTHER INFORMATION: X = Q or R or V
<220> FEATURE:
<221> NAME/KEY: misc_feature
<222> LOCATION: (10)..(10)
<223> OTHER INFORMATION: X = E or V
<220> FEATURE:
<221> NAME/KEY: misc_feature
<222> LOCATION: (11)..(11)
<223> OTHER INFORMATION: X = L or V
<220> FEATURE:
<221> NAME/KEY: misc_feature
<222> LOCATION: (12)..(12)
<223> OTHER INFORMATION: X = A or K or V
<220> FEATURE:
<221> NAME/KEY: misc_feature
<222> LOCATION: (20)..(20)
<223> OTHER INFORMATION: X = L or M or V
<220> FEATURE:
<221> NAME/KEY: misc_feature
<222> LOCATION: (38)..(38)
<223> OTHER INFORMATION: X = K or R
<220> FEATURE:
<221> NAME/KEY: misc_feature
<222> LOCATION: (40)..(40)
<223> OTHER INFORMATION: X = A or R or T
<220> FEATURE:
<221> NAME/KEY: misc_feature
<222> LOCATION: (48)..(48)
<223> OTHER INFORMATION: X = I or M
<220> FEATURE:
<221> NAME/KEY: misc_feature
<222> LOCATION: (67)..(67)
<223> OTHER INFORMATION: X = K or R
<220> FEATURE:
<221> NAME/KEY: misc_feature
<222> LOCATION: (68)..(68)
<223> OTHER INFORMATION: X = A or V
<220> FEATURE:
<221> NAME/KEY: misc_feature
<222> LOCATION: (70)..(70)
<223> OTHER INFORMATION: X = L or M
<220> FEATURE:
<221> NAME/KEY: misc_feature
```

```
<222> LOCATION: (73)..(73)
<223> OTHER INFORMATION: X = D or V
<220> FEATURE:
<221> NAME/KEY: misc_feature
<222> LOCATION: (74)..(74)
<223> OTHER INFORMATION: X = K or T
<220> FEATURE:
<221> NAME/KEY: misc_feature
<222> LOCATION: (76)..(76)
<223> OTHER INFORMATION: X = A or S or T
<220> FEATURE:
<221> NAME/KEY: misc_feature
<222> LOCATION: (79)..(79)
<223> OTHER INFORMATION: X = A or V
<220> FEATURE:
<221> NAME/KEY: misc_feature
<222> LOCATION: (82)..(82)
<223> OTHER INFORMATION: X = E or Q
<220> FEATURE:
<221> NAME/KEY: misc_feature
<222> LOCATION: (87)..(87)
<223> OTHER INFORMATION: X = R or T
<220> FEATURE:
<221> NAME/KEY: misc_feature
<222> LOCATION: (88)..(88)
<223> OTHER INFORMATION: X = F or S
<220> FEATURE:
<221> NAME/KEY: misc_feature
<222> LOCATION: (91)..(91)
<223> OTHER INFORMATION: X = S or T
<220> FEATURE:
<221> NAME/KEY: misc_feature
<222> LOCATION: (97)..(97)
<223> OTHER INFORMATION: X = A or T
<220> FEATURE:
<221> NAME/KEY: misc_feature
<222> LOCATION: (117)..(117)
<223> OTHER INFORMATION: X = L or T
<220> FEATURE:
<221> NAME/KEY: misc_feature
<222> LOCATION: (118)..(118)
<223> OTHER INFORMATION: X = L or V

<400> SEQUENCE: 75

Glu Val Gln Xaa Xaa Gln Ser Gly Ala Xaa Xaa Xaa Lys Pro Gly Ala
1               5                   10                  15

Ser Val Lys Xaa Ser Cys Lys Ala Ser Gly Ser Thr Phe Thr Ser Tyr
            20                  25                  30

Trp Met His Trp Val Xaa Gln Xaa Pro Gly Gln Gly Leu Glu Trp Xaa
        35                  40                  45

Gly Ala Ile Tyr Pro Val Asn Ser Asp Thr Thr Tyr Asn Gln Lys Phe
    50                  55                  60

Lys Gly Xaa Xaa Thr Xaa Thr Val Xaa Xaa Ser Xaa Ser Thr Xaa Tyr
65                  70                  75                  80

Met Xaa Leu Ser Ser Leu Xaa Xaa Glu Asp Xaa Ala Val Tyr Tyr Cys
            85                  90                  95

Xaa Arg Ser Phe Tyr Tyr Ser Leu Asp Ala Ala Trp Phe Val Tyr Trp
        100                 105                 110

Gly Gln Gly Thr Xaa Xaa Thr Val Ser Ser
    115                 120

<210> SEQ ID NO 76
<211> LENGTH: 107
<212> TYPE: PRT
<213> ORGANISM: Artificial Sequence
<220> FEATURE:
<223> OTHER INFORMATION: Synthetic: humanized 40 light chain variable
      region (consensus sequence)
<220> FEATURE:
<221> NAME/KEY: misc_feature
```

```
<222> LOCATION: (15)..(15)
<223> OTHER INFORMATION: X = L or V
<220> FEATURE:
<221> NAME/KEY: misc_feature
<222> LOCATION: (17)..(17)
<223> OTHER INFORMATION: X = D or E
<220> FEATURE:
<221> NAME/KEY: misc_feature
<222> LOCATION: (20)..(20)
<223> OTHER INFORMATION: X = S or T
<220> FEATURE:
<221> NAME/KEY: misc_feature
<222> LOCATION: (39)..(39)
<223> OTHER INFORMATION: X = K or T
<220> FEATURE:
<221> NAME/KEY: misc_feature
<222> LOCATION: (44)..(44)
<223> OTHER INFORMATION: X = I or P
<220> FEATURE:
<221> NAME/KEY: misc_feature
<222> LOCATION: (60)..(60)
<223> OTHER INFORMATION: X = K or S
<220> FEATURE:
<221> NAME/KEY: misc_feature
<222> LOCATION: (66)..(66)
<223> OTHER INFORMATION: X = G or R
<220> FEATURE:
<221> NAME/KEY: misc_feature
<222> LOCATION: (69)..(69)
<223> OTHER INFORMATION: X = S or T
<220> FEATURE:
<221> NAME/KEY: misc_feature
<222> LOCATION: (70)..(70)
<223> OTHER INFORMATION: X = D or E
<220> FEATURE:
<221> NAME/KEY: misc_feature
<222> LOCATION: (71)..(71)
<223> OTHER INFORMATION: X = F or Y
<220> FEATURE:
<221> NAME/KEY: misc_feature
<222> LOCATION: (72)..(72)
<223> OTHER INFORMATION: X = S or T
<220> FEATURE:
<221> NAME/KEY: misc_feature
<222> LOCATION: (77)..(77)
<223> OTHER INFORMATION: X = G or S
<220> FEATURE:
<221> NAME/KEY: misc_feature
<222> LOCATION: (100)..(100)
<223> OTHER INFORMATION: X = G or Q
<220> FEATURE:
<221> NAME/KEY: misc_feature
<222> LOCATION: (104)..(104)
<223> OTHER INFORMATION: X = L or V
<220> FEATURE:
<221> NAME/KEY: misc_feature
<222> LOCATION: (107)..(107)
<223> OTHER INFORMATION: X = H or K

<400> SEQUENCE: 76

Asp Ile Gln Met Thr Gln Ser Pro Ser Ser Leu Ser Ala Ser Xaa Gly
1               5                   10                  15

Xaa Arg Val Xaa Ile Thr Cys Arg Ala Ser Gln Asp Ile Gly Ser Arg
            20                  25                  30

Leu Asn Trp Leu Gln Gln Xaa Pro Gly Lys Ala Xaa Lys Arg Leu Ile
        35                  40                  45

Tyr Ala Thr Ser Ser Leu Asp Ser Gly Val Pro Xaa Arg Phe Ser Gly
    50                  55                  60

Ser Xaa Ser Gly Xaa Xaa Xaa Leu Thr Ile Ser Xaa Leu Gln Pro
65                  70                  75                  80

Glu Asp Phe Ala Thr Tyr Tyr Cys Leu Gln Tyr Ala Ser Ser Pro Phe
                85                  90                  95
```

Thr Phe Gly Xaa Gly Thr Lys Xaa Glu Ile Xaa
             100                 105

<210> SEQ ID NO 77
<211> LENGTH: 366
<212> TYPE: DNA
<213> ORGANISM: Artificial Sequence
<220> FEATURE:
<223> OTHER INFORMATION: Synthetic: hSIRP alpha.40AVH1

<400> SEQUENCE: 77

```
gaggtgcagt tcttgcagtc tggtgccgtg ctggctagac ctggaacctc cgtgaagatc      60
tcctgcaagg cctccggctc caccttcacc tcttactgga tgcactgggt caagcagagg     120
cctggacagg gactcgaatg gatcggcgct ctgtaccctg taactccga caccacctac     180 aaccagaagt tcaagggcag agccaagctg accgtggcca cctctgcttc tatcgcctac     240
ctggaatttt ccagcctgac caacgaggac tccgccgtgt actactgcgc ccggtccttc     300
tactactctc tggacgccgc ttggtttgtg tactggggcc agggaactct ggtgaccgtg     360
tcctct                                                               366
```

<210> SEQ ID NO 78
<211> LENGTH: 122
<212> TYPE: PRT
<213> ORGANISM: Artificial Sequence
<220> FEATURE:
<223> OTHER INFORMATION: Synthetic: hSIRP alpha.40AVH1

<400> SEQUENCE: 78

Glu Val Gln Phe Leu Gln Ser Gly Ala Val Leu Ala Arg Pro Gly Thr
1               5                   10                  15

Ser Val Lys Ile Ser Cys Lys Ala Ser Gly Ser Thr Phe Thr Ser Tyr
            20                  25                  30

Trp Met His Trp Val Lys Gln Arg Pro Gly Gln Gly Leu Glu Trp Ile
        35                  40                  45

Gly Ala Leu Tyr Pro Val Asn Ser Asp Thr Thr Tyr Asn Gln Lys Phe
    50                  55                  60

Lys Gly Arg Ala Lys Leu Thr Val Ala Thr Ser Ala Ser Ile Ala Tyr
65                  70                  75                  80

Leu Glu Phe Ser Ser Leu Thr Asn Glu Asp Ser Ala Val Tyr Tyr Cys
                85                  90                  95

Ala Arg Ser Phe Tyr Tyr Ser Leu Asp Ala Ala Trp Phe Val Tyr Trp
            100                 105                 110

Gly Gln Gly Thr Leu Val Thr Val Ser Ser
        115                 120

<210> SEQ ID NO 79
<211> LENGTH: 366
<212> TYPE: DNA
<213> ORGANISM: Artificial Sequence
<220> FEATURE:
<223> OTHER INFORMATION: Synthetic: hSIRP alpha.40AVH2

<400> SEQUENCE: 79

```
gaggtgcagc tggttcagtc tggcgctgag gttgtgaagc tggcgcttc cgtgaagctg      60 tcctgcaagg cttctggctc caccttcacc agctactgga tgcactgggt caagcaggcc    120
cctggacaag gcctggaatg gatcggcgct atctacccg taactccga caccacctac     180 aaccagaagt tcaagggcaa agctaccctg accgtggaca gtctgcctc caccgcctac     240
```

```
atggaactgt ccagcctgag atctgaggac accgccgtgt actactgcac ccggtccttc    300
tactactccc tggacgccgc ttggtttgtg tattggggcc agggaacact ggtgaccgtg    360
tcctct                                                               366
```

<210> SEQ ID NO 80
<211> LENGTH: 122
<212> TYPE: PRT
<213> ORGANISM: Artificial Sequence
<220> FEATURE:
<223> OTHER INFORMATION: Synthetic: hSIRP alpha.40AVH2

<400> SEQUENCE: 80

```
Glu Val Gln Leu Val Gln Ser Gly Ala Glu Val Val Lys Pro Gly Ala
1               5                   10                  15

Ser Val Lys Leu Ser Cys Lys Ala Ser Gly Ser Thr Phe Thr Ser Tyr
            20                  25                  30

Trp Met His Trp Val Lys Gln Ala Pro Gly Gln Gly Leu Glu Trp Ile
        35                  40                  45

Gly Ala Ile Tyr Pro Val Asn Ser Asp Thr Thr Tyr Asn Gln Lys Phe
    50                  55                  60

Lys Gly Lys Ala Thr Leu Thr Val Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Ser Phe Tyr Tyr Ser Leu Asp Ala Ala Trp Phe Val Tyr Trp
            100                 105                 110

Gly Gln Gly Thr Leu Val Thr Val Ser Ser
        115                 120
```

<210> SEQ ID NO 81
<211> LENGTH: 366
<212> TYPE: DNA
<213> ORGANISM: Artificial Sequence
<220> FEATURE:
<223> OTHER INFORMATION: Synthetic: hSIRP alpha.40AVH3

<400> SEQUENCE: 81

```
gaggtgcagc tgagacagtc tggcgctgtg cttgtgaagc ctggcgcctc cgtgaagatg    60
tcctgcaagg cttctggctc caccttcacc agctactgga tgcactgggt caagcagacc    120
cctggacagg gactcgagtg gatcggcgct atctaccctg tgaactccga caccacctac    180
aaccagaagt tcaagggcaa agctaccctg accgtggaca gtcctcctc caccgcttac    240 atgcagctgt ccagcctgac ctctgaggac tccgccgtgt actactgcgc ccggtccttc    300
tactactctc tggacgccgc ttggtttgtg tactggggcc agggcacaac cctgacagtg    360
tcctct                                                               366
```

<210> SEQ ID NO 82
<211> LENGTH: 122
<212> TYPE: PRT
<213> ORGANISM: Artificial Sequence
<220> FEATURE:
<223> OTHER INFORMATION: Synthetic: hSIRP alpha.40AVH3

<400> SEQUENCE: 82

```
Glu Val Gln Leu Arg Gln Ser Gly Ala Val Leu Val Lys Pro Gly Ala
1               5                   10                  15

Ser Val Lys Met Ser Cys Lys Ala Ser Gly Ser Thr Phe Thr Ser Tyr
            20                  25                  30
```

Trp Met His Trp Val Lys Gln Thr Pro Gly Gln Gly Leu Glu Trp Ile
            35                  40                  45

Gly Ala Ile Tyr Pro Val Asn Ser Asp Thr Thr Tyr Asn Gln Lys Phe
        50                  55                  60

Lys Gly Lys Ala Thr Leu Thr Val Asp Lys Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Ser Phe Tyr Tyr Ser Leu Asp Ala Ala Trp Phe Val Tyr Trp
                100                 105                 110

Gly Gln Gly Thr Thr Leu Thr Val Ser Ser
            115                 120

<210> SEQ ID NO 83
<211> LENGTH: 366
<212> TYPE: DNA
<213> ORGANISM: Artificial Sequence
<220> FEATURE:
<223> OTHER INFORMATION: Synthetic: hSIRP alpha.40AVH4

<400> SEQUENCE: 83
gaggtgcagt tcgttcagtc tggcgccgaa gtgaagaaac ctggcgcctc tgtgaaggtg      60
tcctgcaagg cttctggctc caccttcacc agctactgga tgcactgggt ccgacaggct     120
ccaggacaag gcttggaatg gatgggcgct atctaccccg tgaactccga caccacctac     180
aaccagaaat tcaagggcag agtgaccatg accgtcgtga cctccacctc caccgtgtac     240
atggaactgt ccagcctgag atccgaggac accgccgtgt actactgcgc ccggtccttc     300
tactactctc tggacgccgc ttggtttgtg tactggggcc agggaactct ggtgaccgtg     360
tcctct                                                                366

<210> SEQ ID NO 84
<211> LENGTH: 122
<212> TYPE: PRT
<213> ORGANISM: Artificial Sequence
<220> FEATURE:
<223> OTHER INFORMATION: Synthetic: hSIRP alpha.40AVH4

<400> SEQUENCE: 84

Glu Val Gln Phe Val Gln Ser Gly Ala Glu Val Lys Lys Pro Gly Ala
1               5                   10                  15

Ser Val Lys Val Ser Cys Lys Ala Ser Gly Ser Thr Phe Thr Ser Tyr
            20                  25                  30

Trp Met His Trp Val Arg Gln Ala Pro Gly Gln Gly Leu Glu Trp Met
            35                  40                  45

Gly Ala Ile Tyr Pro Val Asn Ser Asp Thr Thr Tyr Asn Gln Lys Phe
        50                  55                  60

Lys Gly Arg Val Thr Met Thr Val Val Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ser Phe Tyr Tyr Ser Leu Asp Ala Ala Trp Phe Val Tyr Trp
                100                 105                 110

Gly Gln Gly Thr Leu Val Thr Val Ser Ser
            115                 120

<210> SEQ ID NO 85

<211> LENGTH: 366
<212> TYPE: DNA
<213> ORGANISM: Artificial Sequence
<220> FEATURE:
<223> OTHER INFORMATION: Synthetic: hSIRP alpha.40AVH5

<400> SEQUENCE: 85

```
gaggtccagc tgcaacagtc tggtgccgtg ttggctaagc ctggcgcctc cgtgaagatg    60
tcctgcaagg cttctggctc caccttcacc agctactgga tgcactgggt caagcagagg   120
cctggacagg gactcgagtg gatcggcgct atctaccctg tgaactccga caccacctac   180
aaccagaagt tcaagggcaa agctaccctg accgtggaca gtcctcctc caccgcttac   240
atgcagctgt ccagcctgac cttcgaggac tccgccgtgt actactgcgc ccggtccttc   300
tactactctc tggacgccgc ttggtttgtg tactggggcc agggcacaac cctgacagtg   360
tcctct                                                              366
```

<210> SEQ ID NO 86
<211> LENGTH: 122
<212> TYPE: PRT
<213> ORGANISM: Artificial Sequence
<220> FEATURE:
<223> OTHER INFORMATION: Synthetic: hSIRP alpha.40AVH5

<400> SEQUENCE: 86

Glu Val Gln Leu Gln Gln Ser Gly Ala Val Leu Ala Lys Pro Gly Ala
1               5                   10                  15

Ser Val Lys Met Ser Cys Lys Ala Ser Gly Ser Thr Phe Thr Ser Tyr
            20                  25                  30

Trp Met His Trp Val Lys Gln Arg Pro Gly Gln Gly Leu Glu Trp Ile
        35                  40                  45

Gly Ala Ile Tyr Pro Val Asn Ser Asp Thr Thr Tyr Asn Gln Lys Phe
    50                  55                  60

Lys Gly Lys Ala Thr Leu Thr Val Asp Lys Ser Ser Ser Thr Ala Tyr
65                  70                  75                  80

Met Gln Leu Ser Ser Leu Thr Phe Glu Asp Ser Ala Val Tyr Tyr Cys
                85                  90                  95

Ala Arg Ser Phe Tyr Tyr Ser Leu Asp Ala Ala Trp Phe Val Tyr Trp
            100                 105                 110

Gly Gln Gly Thr Thr Leu Thr Val Ser Ser
        115                 120

<210> SEQ ID NO 87
<211> LENGTH: 366
<212> TYPE: DNA
<213> ORGANISM: Artificial Sequence
<220> FEATURE:
<223> OTHER INFORMATION: Synthetic: hSIRP alpha.40AVH6

<400> SEQUENCE: 87

```
gaggtgcagc tggttcagtc tggcgccgaa gtgaagaaac tggcgcctc tgtgaaggtg    60
tcctgcaagg cttctggctc caccttcacc agctactgga tgcactgggt ccgacaggct   120
ccaggacaag gcttggaatg gatgggcgct atctaccccg tgaactccga caccacctac   180
aaccagaaat tcaagggcag agtgaccatg accgtggaca cctccaccag caccgtgtac   240
atggaactgt ccagcctgag atccgaggac accgccgtgt actactgcgc ccggtccttc   300
tactactctc tggacgccgc ttggtttgtg tactggggcc agggaactct ggtgaccgtg   360
tcctct                                                              366
```

<210> SEQ ID NO 88
<211> LENGTH: 122
<212> TYPE: PRT
<213> ORGANISM: Artificial Sequence
<220> FEATURE:
<223> OTHER INFORMATION: Synthetic: hSIRP alpha.40AVH6

<400> SEQUENCE: 88

```
Glu Val Gln Leu Val Gln Ser Gly Ala Glu Val Lys Lys Pro Gly Ala
1               5                   10                  15

Ser Val Lys Val Ser Cys Lys Ala Ser Gly Ser Thr Phe Thr Ser Tyr
            20                  25                  30

Trp Met His Trp Val Arg Gln Ala Pro Gly Gln Gly Leu Glu Trp Met
        35                  40                  45

Gly Ala Ile Tyr Pro Val Asn Ser Asp Thr Thr Tyr Asn Gln Lys Phe
    50                  55                  60

Lys Gly Arg Val Thr Met Thr Val Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ser Phe Tyr Tyr Ser Leu Asp Ala Ala Trp Phe Val Tyr Trp
            100                 105                 110

Gly Gln Gly Thr Leu Val Thr Val Ser Ser
        115                 120
```

<210> SEQ ID NO 89
<211> LENGTH: 321
<212> TYPE: DNA
<213> ORGANISM: Artificial Sequence
<220> FEATURE:
<223> OTHER INFORMATION: Synthetic: hSIRP alpha.40AVL1

<400> SEQUENCE: 89

```
gacatccaga tgacccagtc tccatcctct ctgtccgcct ctgtgggcga cagagtgacc      60
atcacctgta gagcctctca ggacatcggc tccagactga actggctgca gcagacccct     120
ggcaaggcca tcaagagact gatctacgcc acctccagcc tggattctgg cgtgccctct     180
agattctccg gctctagatc tggcaccgac ttctccctga ccatctctgg actgcagcct     240
gaggacttcg ccacctacta ctgtctgcag tacgccagct ctccattcac ctttggcgga     300
ggcaccaagg tggaaatcca c                                               321
```

<210> SEQ ID NO 90
<211> LENGTH: 107
<212> TYPE: PRT
<213> ORGANISM: Artificial Sequence
<220> FEATURE:
<223> OTHER INFORMATION: Synthetic: hSIRP alpha.40AVL1

<400> SEQUENCE: 90

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Gly Ser Arg
            20                  25                  30

Leu Asn Trp Leu Gln Gln Thr Pro Gly Lys Ala Ile Lys Arg Leu Ile
        35                  40                  45

Tyr Ala Thr Ser Ser Leu Asp Ser Gly Val Pro Ser Arg Phe Ser Gly
    50                  55                  60
```

Ser Arg Ser Gly Thr Asp Phe Ser Leu Thr Ile Ser Gly Leu Gln Pro
 65                  70                  75                  80

Glu Asp Phe Ala Thr Tyr Tyr Cys Leu Gln Tyr Ala Ser Ser Pro Phe
                 85                  90                  95

Thr Phe Gly Gly Gly Thr Lys Val Glu Ile His
            100                 105

<210> SEQ ID NO 91
<211> LENGTH: 321
<212> TYPE: DNA
<213> ORGANISM: Artificial Sequence
<220> FEATURE:
<223> OTHER INFORMATION: Synthetic: hSIRP alpha.40AVL2

<400> SEQUENCE: 91
gacatccaga tgacccagtc tccatcctct ctgtccgcct ctgtgggcga cagagtgacc    60
atcacctgta gagcctctca ggacatcggc tccagactga actggctgca gcagaagcct   120
ggcaaggcca tcaagagact gatctacgcc acctccagcc tggattctgg cgtgccctct   180
agattctccg gctctagatc tggcaccgac tttaccctga caatcagctc cctgcagcct   240
gaggacttcg ccacctacta ctgtctgcag tacgcctcct ctccattcac ctttggccag   300
ggcaccaagg tggaaatcaa g                                             321

<210> SEQ ID NO 92
<211> LENGTH: 107
<212> TYPE: PRT
<213> ORGANISM: Artificial Sequence
<220> FEATURE:
<223> OTHER INFORMATION: Synthetic: hSIRP alpha.40AVL2

<400> SEQUENCE: 92

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Asp Ile Gly Ser Arg
                 20                  25                  30

Leu Asn Trp Leu Gln Gln Lys Pro Gly Lys Ala Ile Lys Arg Leu Ile
             35                  40                  45

Tyr Ala Thr Ser Ser Leu Asp Ser Gly Val Pro Ser Arg Phe Ser Gly
 50                  55                  60

Ser Arg Ser Gly Thr Asp Phe Thr Leu Thr Ile Ser Ser Leu Gln Pro
 65                  70                  75                  80

Glu Asp Phe Ala Thr Tyr Tyr Cys Leu Gln Tyr Ala Ser Ser Pro Phe
                 85                  90                  95

Thr Phe Gly Gln Gly Thr Lys Val Glu Ile Lys
            100                 105

<210> SEQ ID NO 93
<211> LENGTH: 321
<212> TYPE: DNA
<213> ORGANISM: Artificial Sequence
<220> FEATURE:
<223> OTHER INFORMATION: Synthetic: hSIRP alpha.40AVL3

<400> SEQUENCE: 93
gacatccaga tgacccagtc tccatcctct ctgtccgcct ctgtgggcga cagagtgacc    60
atcacctgta gagcctctca ggacatcggc tccagactga actggctgca gcagaagcct   120
ggcaaggcca tcaagagact gatctacgcc acctccagcc tggattctgg cgtgccctct   180
agattctccg gctctagatc tggcaccgac tttaccctga caatcagctc cctgcagcct   240

```
gaggacttcg ccacctacta ctgtctgcag tacgccagct ctccattcac ctttggcgga    300
ggcaccaagc tggaaatcaa g                                              321
```

<210> SEQ ID NO 94
<211> LENGTH: 107
<212> TYPE: PRT
<213> ORGANISM: Artificial Sequence
<220> FEATURE:
<223> OTHER INFORMATION: Synthetic: hSIRP alpha.40AVL3

<400> SEQUENCE: 94

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Gly Ser Arg
            20                  25                  30

Leu Asn Trp Leu Gln Gln Lys Pro Gly Lys Ala Ile Lys Arg Leu Ile
        35                  40                  45

Tyr Ala Thr Ser Ser Leu Asp Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Leu Gln Tyr Ala Ser Ser Pro Phe
                85                  90                  95

Thr Phe Gly Gly Gly Thr Lys Leu Glu Ile Lys
            100                 105
```

<210> SEQ ID NO 95
<211> LENGTH: 321
<212> TYPE: DNA
<213> ORGANISM: Artificial Sequence
<220> FEATURE:
<223> OTHER INFORMATION: Synthetic: hSIRP alpha.40AVL4

<400> SEQUENCE: 95

```
gacatccaga tgacccagtc tccatcctct ctgtccgcct ctgtgggcga cagagtgacc    60
atcacctgta gagcctctca ggacatcggc tccagactga actggctgca gcagaagcct    120
ggcaaggccc ctaagagact gatctacgcc acctccagcc tggattctgg cgtgccctct    180
agattctccg gctctggctc tggcaccgag tttaccctga caatcagctc cctgcagcct    240
gaggacttcg ccacctacta ctgtctgcag tacgccagct ctccattcac ctttggcgga    300
ggcaccaagg tggaaatcaa g                                              321
```

<210> SEQ ID NO 96
<211> LENGTH: 107
<212> TYPE: PRT
<213> ORGANISM: Artificial Sequence
<220> FEATURE:
<223> OTHER INFORMATION: Synthetic: hSIRP alpha.40AVL4

<400> SEQUENCE: 96

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Gly Ser Arg
            20                  25                  30

Leu Asn Trp Leu Gln Gln Lys Pro Gly Lys Ala Pro Lys Arg Leu Ile
        35                  40                  45

Tyr Ala Thr Ser Ser Leu Asp Ser Gly Val Pro Ser Arg Phe Ser Gly
    50                  55                  60
```

```
Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln Tyr Ala Ser Ser Pro Phe
                85                  90                  95

Thr Phe Gly Gly Gly Thr Lys Val Glu Ile Lys
            100                 105

<210> SEQ ID NO 97
<211> LENGTH: 321
<212> TYPE: DNA
<213> ORGANISM: Artificial Sequence
<220> FEATURE:
<223> OTHER INFORMATION: Synthetic: hSIRP alpha.40AVL5

<400> SEQUENCE: 97
gacatccaga tgacccagtc tccatcctct ctgtccgcct ctgtgggcga cagagtgacc       60
atcacctgta gagcctctca ggacatcggc tccagactga actggctgca gcagaagcct      120
ggcaaggcca tcaagagact gatctacgcc acctccagcc tggattctgg cgtgcccaag      180
agattctccg gctctagatc cggctccgac tataccctga caatcagctc cctgcagcct      240
gaggacttcg ccacctacta ctgtctgcag tacgcctcct ctccattcac ctttggccag      300
ggcaccaagg tggaaatcaa g                                                321

<210> SEQ ID NO 98
<211> LENGTH: 107
<212> TYPE: PRT
<213> ORGANISM: Artificial Sequence
<220> FEATURE:
<223> OTHER INFORMATION: Synthetic: hSIRP alpha.40AVL5

<400> SEQUENCE: 98

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Gly Ser Arg
            20                  25                  30

Leu Asn Trp Leu Gln Gln Lys Pro Gly Lys Ala Ile Lys Arg Leu Ile
        35                  40                  45

Tyr Ala Thr Ser Ser Leu Asp Ser Gly Val Pro Lys Arg Phe Ser Gly
    50                  55                  60

Ser Arg Ser Gly Ser Asp Tyr Thr Leu Thr Ile Ser Ser Leu Gln Pro
65                  70                  75                  80

Glu Asp Phe Ala Thr Tyr Tyr Cys Leu Gln Tyr Ala Ser Ser Pro Phe
                85                  90                  95

Thr Phe Gly Gln Gly Thr Lys Val Glu Ile Lys
            100                 105

<210> SEQ ID NO 99
<211> LENGTH: 321
<212> TYPE: DNA
<213> ORGANISM: Artificial Sequence
<220> FEATURE:
<223> OTHER INFORMATION: Synthetic: hSIRP alpha.40AVL6

<400> SEQUENCE: 99
gacatccaga tgacccagtc tccatcctct ctgtctgctt ccctgggcga gagagtgtcc       60
atcacctgta gagcctctca ggacatcggc tccagactga actggctgca gcagaagcct      120
ggcaaggcca tcaagagact gatctacgcc acctccagcc tggattctgg cgtgccctct      180
```

```
agattctccg gctctagatc tggcaccgac tttaccctga caatcagctc cctgcagcct    240
gaggacttcg ccacctacta ctgtctgcag tacgccagct ctccattcac ctttggcgga    300
ggcaccaagg tggaaatcaa g                                              321
```

<210> SEQ ID NO 100
<211> LENGTH: 107
<212> TYPE: PRT
<213> ORGANISM: Artificial Sequence
<220> FEATURE:
<223> OTHER INFORMATION: Synthetic: hSIRP alpha.40AVL6

<400> SEQUENCE: 100

```
Asp Ile Gln Met Thr Gln Ser Pro Ser Ser Leu Ser Ala Ser Leu Gly
1               5                   10                  15

Glu Arg Val Ser Ile Thr Cys Arg Ala Ser Gln Asp Ile Gly Ser Arg
            20                  25                  30

Leu Asn Trp Leu Gln Gln Lys Pro Gly Lys Ala Ile Lys Arg Leu Ile
        35                  40                  45

Tyr Ala Thr Ser Ser Leu Asp Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Leu Gln Tyr Ala Ser Ser Pro Phe
                85                  90                  95

Thr Phe Gly Gly Gly Thr Lys Val Glu Ile Lys
            100                 105
```

<210> SEQ ID NO 101
<211> LENGTH: 366
<212> TYPE: DNA
<213> ORGANISM: Artificial Sequence
<220> FEATURE:
<223> OTHER INFORMATION: Synthetic: hSIRP alpha.40A mouse VH

<400> SEQUENCE: 101

```
gaggttcagt tccagcagtc tgggactgtg ctggcaaggc cagggacttc agtgaagatg    60
tcctgcaagg cttctggctc cacctttacc agctactgga tgcactgggt aaaacagggg    120
cctggacagg gtctgcaatg gattggcgct atttatcctg taaataatga tactacctat    180
aatcagaagt tcaagggcaa ggccgaactc actgtagtca cttccaccag cactgcctac    240
atggaggtca gtagtctgac aaatgaggac tctgcggtct attactgtac aagatcgttc    300
tactatagtc tcgacgcggc ctggtttgtt tactggggcc aagggactct ggtcactgtc    360
tctgca                                                               366
```

<210> SEQ ID NO 102
<211> LENGTH: 122
<212> TYPE: PRT
<213> ORGANISM: Artificial Sequence
<220> FEATURE:
<223> OTHER INFORMATION: Synthetic: hSIRP alpha.40A mouse VH

<400> SEQUENCE: 102

```
Glu Val Gln Phe Gln Gln Ser Gly Thr Val Leu Ala Arg Pro Gly Thr
1               5                   10                  15

Ser Val Lys Met Ser Cys Lys Ala Ser Gly Ser Thr Phe Thr Ser Tyr
            20                  25                  30

Trp Met His Trp Val Lys Gln Gly Pro Gly Gln Gly Leu Gln Trp Ile
        35                  40                  45
```

```
Gly Ala Ile Tyr Pro Val Asn Asn Asp Thr Thr Tyr Asn Gln Lys Phe
        50                  55                  60

Lys Gly Lys Ala Glu Leu Thr Val Val Thr Ser Thr Ser Thr Ala Tyr
 65                  70                  75                  80

Met Glu Val Ser Ser Leu Thr Asn Glu Asp Ser Ala Val Tyr Tyr Cys
                     85                  90                  95

Thr Arg Ser Phe Tyr Tyr Ser Leu Asp Ala Ala Trp Phe Val Tyr Trp
                100                 105                 110

Gly Gln Gly Thr Leu Val Thr Val Ser Ala
            115                 120
```

<210> SEQ ID NO 103
<211> LENGTH: 321
<212> TYPE: DNA
<213> ORGANISM: Artificial Sequence
<220> FEATURE:
<223> OTHER INFORMATION: Synthetic: hSIRP alpha.40A mouse VL

<400> SEQUENCE: 103

```
gacatccaga tgacccagtc tccatcctcc ttatctgcct ctctgggaga aagagtcagt    60
ctcacttgtc gggcaagtca ggacattggt agtaggttaa actggcttca gcaggaacca   120
gatggaacta ttaaacgcct gatctacgcc acatccagtt tagattctgg tgtccccaaa   180
aggttcagtg gcagtaggtc tgggtcagat tattctctca ccatcagcgg ccttgagtct   240
gaagactttg tagactatta ctgtctacaa tatgctagtt ctccgttcac gttcggaggg   300
gggaccaagc tggaaataaa c                                             321
```

<210> SEQ ID NO 104
<211> LENGTH: 107
<212> TYPE: PRT
<213> ORGANISM: Artificial Sequence
<220> FEATURE:
<223> OTHER INFORMATION: Synthetic: hSIRP alpha.40A mouse VL

<400> SEQUENCE: 104

```
Asp Ile Gln Met Thr Gln Ser Pro Ser Ser Leu Ser Ala Ser Leu Gly
 1               5                  10                  15

Glu Arg Val Ser Leu Thr Cys Arg Ala Ser Gln Asp Ile Gly Ser Arg
             20                  25                  30

Leu Asn Trp Leu Gln Gln Glu Pro Asp Gly Thr Ile Lys Arg Leu Ile
         35                  40                  45

Tyr Ala Thr Ser Ser Leu Asp Ser Gly Val Pro Lys Arg Phe Ser Gly
     50                  55                  60

Ser Arg Ser Gly Ser Asp Tyr Ser Leu Thr Ile Ser Gly Leu Glu Ser
 65                  70                  75                  80

Glu Asp Phe Val Asp Tyr Tyr Cys Leu Gln Tyr Ala Ser Ser Pro Phe
                 85                  90                  95

Thr Phe Gly Gly Gly Thr Lys Leu Glu Ile Asn
            100                 105
```

<210> SEQ ID NO 105
<211> LENGTH: 446
<212> TYPE: PRT
<213> ORGANISM: Artificial Sequence
<220> FEATURE:
<223> OTHER INFORMATION: Synthetic: hSIRP alpha.40A mouse heavy chain

<400> SEQUENCE: 105

```
Glu Val Gln Phe Gln Gln Ser Gly Thr Val Leu Ala Arg Pro Gly Thr
1               5                   10                  15

Ser Val Lys Met Ser Cys Lys Ala Ser Gly Thr Phe Thr Ser Tyr
        20                  25                  30

Trp Met His Trp Val Lys Gln Gly Pro Gly Gln Gly Leu Gln Trp Ile
            35                  40                  45

Gly Ala Ile Tyr Pro Val Asn Asn Asp Thr Thr Tyr Asn Gln Lys Phe
50                      55                  60

Lys Gly Lys Ala Glu Leu Thr Val Val Thr Thr Ser Thr Ala Tyr
65                      70                  75                  80

Met Glu Val Ser Ser Leu Thr Asn Glu Asp Ser Ala Val Tyr Tyr Cys
                    85                  90                  95

Thr Arg Ser Phe Tyr Tyr Ser Leu Asp Ala Ala Trp Phe Val Tyr Trp
                100                 105                 110

Gly Gln Gly Thr Leu Val Thr Val Ser Ala Ala Lys Thr Thr Pro Pro
                115                 120                 125

Ser Val Tyr Pro Leu Ala Pro Gly Ser Ala Ala Gln Thr Asn Ser Met
        130                 135                 140

Val Thr Leu Gly Cys Leu Val Lys Gly Tyr Phe Pro Glu Pro Val Thr
145                 150                 155                 160

Val Thr Trp Asn Ser Gly Ser Leu Ser Ser Gly Val His Thr Phe Pro
                165                 170                 175

Ala Val Leu Gln Ser Asp Leu Tyr Thr Leu Ser Ser Ser Val Thr Val
                180                 185                 190

Pro Ser Ser Thr Trp Pro Ser Glu Thr Val Thr Cys Asn Val Ala His
        195                 200                 205

Pro Ala Ser Ser Thr Lys Val Asp Lys Lys Ile Val Pro Arg Asp Cys
210                 215                 220

Gly Cys Lys Pro Cys Ile Cys Thr Val Pro Glu Val Ser Ser Val Phe
225                 230                 235                 240

Ile Phe Pro Pro Lys Pro Lys Asp Val Leu Thr Ile Thr Leu Thr Pro
                245                 250                 255

Lys Val Thr Cys Val Val Val Asp Ile Ser Lys Asp Asp Pro Glu Val
                260                 265                 270

Gln Phe Ser Trp Phe Val Asp Asp Val Glu Val His Thr Ala Gln Thr
        275                 280                 285

Gln Pro Arg Glu Glu Gln Phe Asn Ser Thr Phe Arg Ser Val Ser Glu
        290                 295                 300

Leu Pro Ile Met His Gln Asp Trp Leu Asn Gly Lys Glu Phe Lys Cys
305                 310                 315                 320

Arg Val Asn Ser Ala Ala Phe Pro Ala Pro Ile Glu Lys Thr Ile Ser
                325                 330                 335

Lys Thr Lys Gly Arg Pro Lys Ala Pro Gln Val Tyr Thr Ile Pro Pro
                340                 345                 350

Pro Lys Glu Gln Met Ala Lys Asp Lys Val Ser Leu Thr Cys Met Ile
        355                 360                 365

Thr Asp Phe Phe Pro Glu Asp Ile Thr Val Glu Trp Gln Trp Asn Gly
        370                 375                 380

Gln Pro Ala Glu Asn Tyr Lys Asn Thr Gln Pro Ile Met Asp Thr Asp
385                 390                 395                 400

Gly Ser Tyr Phe Val Tyr Ser Lys Leu Asn Val Gln Lys Ser Asn Trp
                405                 410                 415

Glu Ala Gly Asn Thr Phe Thr Cys Ser Val Leu His Glu Gly Leu His
```

```
                    420                 425                 430
Asn His His Thr Glu Lys Ser Leu Ser His Ser Pro Gly Lys
        435                 440                 445

<210> SEQ ID NO 106
<211> LENGTH: 214
<212> TYPE: PRT
<213> ORGANISM: Artificial Sequence
<220> FEATURE:
<223> OTHER INFORMATION: Synthetic: hSIRP alpha.40A mouse light chain

<400> SEQUENCE: 106

Asp Ile Gln Met Thr Gln Ser Pro Ser Ser Leu Ser Ala Ser Leu Gly
1               5                   10                  15

Glu Arg Val Ser Leu Thr Cys Arg Ala Ser Gln Asp Ile Gly Ser Arg
            20                  25                  30

Leu Asn Trp Leu Gln Gln Glu Pro Asp Gly Thr Ile Lys Arg Leu Ile
        35                  40                  45

Tyr Ala Thr Ser Ser Leu Asp Ser Gly Val Pro Lys Arg Phe Ser Gly
    50                  55                  60

Ser Arg Ser Gly Ser Asp Tyr Ser Leu Thr Ile Ser Gly Leu Glu Ser
65                  70                  75                  80

Glu Asp Phe Val Asp Tyr Tyr Cys Leu Gln Tyr Ala Ser Ser Pro Phe
                85                  90                  95

Thr Phe Gly Gly Gly Thr Lys Leu Glu Ile Asn Arg Ala Asp Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
    130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Asn Glu Cys
    210

<210> SEQ ID NO 107
<211> LENGTH: 581
<212> TYPE: PRT
<213> ORGANISM: Artificial Sequence
<220> FEATURE:
<223> OTHER INFORMATION: Synthetic: rhSIRP alpha/Fc

<400> SEQUENCE: 107

Gly Val Ala Gly Glu Glu Glu Leu Gln Val Ile Gln Pro Asp Lys Ser
1               5                   10                  15

Val Leu Val Ala Ala Gly Glu Thr Ala Thr Leu Arg Cys Thr Ala Thr
            20                  25                  30

Ser Leu Ile Pro Val Gly Pro Ile Gln Trp Phe Arg Gly Ala Gly Pro
        35                  40                  45

Gly Arg Glu Leu Ile Tyr Asn Gln Lys Glu Gly His Phe Pro Arg Val
    50                  55                  60
```

```
Thr Thr Val Ser Asp Leu Thr Lys Arg Asn Asn Met Asp Phe Ser Ile
 65                  70                  75                  80

Arg Ile Gly Asn Ile Thr Pro Ala Asp Ala Gly Thr Tyr Tyr Cys Val
                 85                  90                  95

Lys Phe Arg Lys Gly Ser Pro Asp Asp Val Glu Phe Lys Ser Gly Ala
            100                 105                 110

Gly Thr Glu Leu Ser Val Arg Ala Lys Pro Ser Ala Pro Val Val Ser
        115                 120                 125

Gly Pro Ala Ala Arg Ala Thr Pro Gln His Thr Val Ser Phe Thr Cys
    130                 135                 140

Glu Ser His Gly Phe Ser Pro Arg Asp Ile Thr Leu Lys Trp Phe Lys
145                 150                 155                 160

Asn Gly Asn Glu Leu Ser Asp Phe Gln Thr Asn Val Asp Pro Val Gly
                165                 170                 175

Glu Ser Val Ser Tyr Ser Ile His Ser Thr Ala Lys Val Val Leu Thr
            180                 185                 190

Arg Glu Asp Val His Ser Gln Val Ile Cys Glu Val Ala His Val Thr
        195                 200                 205

Leu Gln Gly Asp Pro Leu Arg Gly Thr Ala Asn Leu Ser Glu Thr Ile
    210                 215                 220

Arg Val Pro Pro Thr Leu Glu Val Thr Gln Gln Pro Val Arg Ala Glu
225                 230                 235                 240

Asn Gln Val Asn Val Thr Cys Gln Val Arg Lys Phe Tyr Pro Gln Arg
                245                 250                 255

Leu Gln Leu Thr Trp Leu Glu Asn Gly Asn Val Ser Arg Thr Glu Thr
            260                 265                 270

Ala Ser Thr Val Thr Glu Asn Lys Asp Gly Thr Tyr Asn Trp Met Ser
        275                 280                 285

Trp Leu Leu Val Asn Val Ser Ala His Arg Asp Asp Val Lys Leu Thr
    290                 295                 300

Cys Gln Val Glu His Asp Gly Gln Pro Ala Val Ser Lys Ser His Asp
305                 310                 315                 320

Leu Lys Val Ser Ala His Pro Lys Glu Gln Gly Ser Asn Thr Ala Ala
                325                 330                 335

Glu Asn Thr Gly Ser Asn Glu Arg Ile Glu Gly Arg Met Asp Pro Lys
            340                 345                 350

Ser Cys Asp Lys Thr His Thr Cys Pro Pro Cys Pro Ala Pro Glu Leu
        355                 360                 365

Leu Gly Gly Pro Ser Val Phe Leu Phe Pro Pro Lys Pro Lys Asp Thr
    370                 375                 380

Leu Met Ile Ser Arg Thr Pro Glu Val Thr Cys Val Val Val Asp Val
385                 390                 395                 400

Ser His Glu Asp Pro Glu Val Lys Phe Asn Trp Tyr Val Asp Gly Val
                405                 410                 415

Glu Val His Asn Ala Lys Thr Lys Pro Arg Glu Glu Gln Tyr Asn Ser
            420                 425                 430

Thr Tyr Arg Val Val Ser Val Leu Thr Val Leu His Gln Asp Trp Leu
        435                 440                 445

Asn Gly Lys Glu Tyr Lys Cys Lys Val Ser Asn Lys Ala Leu Pro Ala
    450                 455                 460

Pro Ile Glu Lys Thr Ile Ser Lys Ala Lys Gly Gln Pro Arg Glu Pro
465                 470                 475                 480

Gln Val Tyr Thr Leu Pro Pro Ser Arg Asp Glu Leu Thr Lys Asn Gln
```

|     |     |     |     |     | 485 |     |     |     | 490 |     |     |     |     | 495 |
| --- | --- | --- | --- | --- | --- | --- | --- | --- | --- | --- | --- | --- | --- | --- |

Val Ser Leu Thr Cys Leu Val Lys Gly Phe Tyr Pro Ser Asp Ile Ala
            500                 505                 510

Val Glu Trp Glu Ser Asn Gly Gln Pro Glu Asn Asn Tyr Lys Thr Thr
        515                 520                 525

Pro Pro Val Leu Asp Ser Asp Gly Ser Phe Phe Leu Tyr Ser Lys Leu
    530                 535                 540

Thr Val Asp Lys Ser Arg Trp Gln Gln Gly Asn Val Phe Ser Cys Ser
545                 550                 555                 560

Val Met His Glu Ala Leu His Asn His Tyr Thr Gln Lys Ser Leu Ser
                565                 570                 575

Leu Ser Pro Gly Lys
            580

<210> SEQ ID NO 108
<211> LENGTH: 538
<212> TYPE: PRT
<213> ORGANISM: Artificial Sequence
<220> FEATURE:
<223> OTHER INFORMATION: Synthetic: rhSIRPg/Fc

<400> SEQUENCE: 108

Val Leu Trp Phe Arg Val Gly Pro Gly Arg Glu Leu Ile Tyr Asn
1               5                   10                  15

Gln Lys Glu Gly His Phe Pro Arg Val Thr Thr Val Ser Asp Leu Thr
            20                  25                  30

Lys Arg Asn Asn Met Asp Phe Ser Ile Arg Ile Ser Ser Ile Thr Pro
        35                  40                  45

Ala Asp Val Gly Thr Tyr Tyr Cys Val Lys Phe Arg Lys Gly Ser Pro
    50                  55                  60

Glu Asn Val Glu Phe Lys Ser Gly Pro Gly Thr Glu Met Ala Leu Gly
65                  70                  75                  80

Ala Lys Pro Ser Ala Pro Val Val Leu Gly Pro Ala Ala Arg Thr Thr
                85                  90                  95

Pro Glu His Thr Val Ser Phe Thr Cys Glu Ser His Gly Phe Ser Pro
            100                 105                 110

Arg Asp Ile Thr Leu Lys Trp Phe Lys Asn Gly Asn Glu Leu Ser Asp
        115                 120                 125

Phe Gln Thr Asn Val Asp Pro Thr Gly Gln Ser Val Ala Tyr Ser Ile
    130                 135                 140

Arg Ser Thr Ala Arg Val Val Leu Asp Pro Trp Asp Val Arg Ser Gln
145                 150                 155                 160

Val Ile Cys Glu Val Ala His Val Thr Leu Gln Gly Asp Pro Leu Arg
                165                 170                 175

Gly Thr Ala Asn Leu Ser Glu Ala Ile Arg Val Pro Pro Thr Leu Glu
            180                 185                 190

Val Thr Gln Gln Pro Met Arg Ala Gly Asn Gln Val Asn Val Thr Cys
        195                 200                 205

Gln Val Arg Lys Phe Tyr Pro Gln Ser Leu Gln Leu Thr Trp Leu Glu
    210                 215                 220

Asn Gly Asn Val Cys Gln Arg Glu Thr Ala Ser Thr Leu Thr Glu Asn
225                 230                 235                 240

Lys Asp Gly Thr Tyr Asn Trp Thr Ser Trp Phe Leu Val Asn Ile Ser
                245                 250                 255

Asp Gln Arg Asp Asp Val Val Leu Thr Cys Gln Val Lys His Asp Gly

```
                260                 265                 270
Gln Leu Ala Val Ser Lys Arg Leu Ala Leu Glu Val Thr Val His Gln
            275                 280                 285

Lys Asp Gln Ser Ser Asp Ala Thr Pro Gly Pro Ala Ser Ile Glu Gly
        290                 295                 300

Arg Met Asp Pro Lys Ser Cys Asp Lys Thr His Thr Cys Pro Pro Cys
305                 310                 315                 320

Pro Ala Pro Glu Leu Leu Gly Gly Pro Ser Val Phe Leu Phe Pro Pro
                325                 330                 335

Lys Pro Lys Asp Thr Leu Met Ile Ser Arg Thr Pro Glu Val Thr Cys
            340                 345                 350

Val Val Val Asp Val Ser His Glu Asp Pro Glu Val Lys Phe Asn Trp
        355                 360                 365

Tyr Val Asp Gly Val Glu Val His Asn Ala Lys Thr Lys Pro Arg Glu
    370                 375                 380

Glu Gln Tyr Asn Ser Thr Tyr Arg Val Val Ser Val Leu Thr Val Leu
385                 390                 395                 400

His Gln Asp Trp Leu Asn Gly Lys Glu Tyr Lys Cys Lys Val Ser Asn
                405                 410                 415

Lys Ala Leu Pro Ala Pro Ile Glu Lys Thr Ile Ser Lys Ala Lys Gly
            420                 425                 430

Gln Pro Arg Glu Pro Gln Val Tyr Thr Leu Pro Pro Ser Arg Asp Glu
        435                 440                 445

Leu Thr Lys Asn Gln Val Ser Leu Thr Cys Leu Val Lys Gly Phe Tyr
    450                 455                 460

Pro Ser Asp Ile Ala Val Glu Trp Glu Ser Asn Gly Gln Pro Glu Asn
465                 470                 475                 480

Asn Tyr Lys Thr Thr Pro Pro Val Leu Asp Ser Asp Gly Ser Phe Phe
                485                 490                 495

Leu Tyr Ser Lys Leu Thr Val Asp Lys Ser Arg Trp Gln Gln Gly Asn
            500                 505                 510

Val Phe Ser Cys Ser Val Met His Glu Ala Leu His Asn His Tyr Thr
        515                 520                 525

Gln Lys Ser Leu Ser Leu Ser Pro Gly Lys
    530                 535

<210> SEQ ID NO 109
<211> LENGTH: 358
<212> TYPE: PRT
<213> ORGANISM: Artificial Sequence
<220> FEATURE:
<223> OTHER INFORMATION: Synthetic: rhCD47/Fc

<400> SEQUENCE: 109

Gln Leu Leu Phe Asn Lys Thr Lys Ser Val Glu Phe Thr Phe Cys Asn
1               5                   10                  15

Asp Thr Val Val Ile Pro Cys Phe Val Thr Asn Met Glu Ala Gln Asn
            20                  25                  30

Thr Thr Glu Val Tyr Val Lys Trp Lys Phe Lys Gly Arg Asp Ile Tyr
        35                  40                  45

Thr Phe Asp Gly Ala Leu Asn Lys Ser Thr Val Pro Thr Asp Phe Ser
    50                  55                  60

Ser Ala Lys Ile Glu Val Ser Gln Leu Leu Lys Gly Asp Ala Ser Leu
65                  70                  75                  80

Lys Met Asp Lys Ser Asp Ala Val Ser His Thr Gly Asn Tyr Thr Cys
```

```
                85                  90                  95
Glu Val Thr Glu Leu Thr Arg Glu Gly Glu Thr Ile Ile Glu Leu Lys
                100                 105                 110

Tyr Arg Val Val Ser Trp Phe Ser Pro Ile Glu Gly Arg Met Asp Pro
            115                 120                 125

Lys Ser Cys Asp Lys Thr His Thr Cys Pro Pro Cys Pro Ala Pro Glu
        130                 135                 140

Leu Leu Gly Gly Pro Ser Val Phe Leu Phe Pro Pro Lys Pro Lys Asp
145                 150                 155                 160

Thr Leu Met Ile Ser Arg Thr Pro Glu Val Thr Cys Val Val Val Asp
                165                 170                 175

Val Ser His Glu Asp Pro Glu Val Lys Phe Asn Trp Tyr Val Asp Gly
            180                 185                 190

Val Glu Val His Asn Ala Lys Thr Lys Pro Arg Glu Glu Gln Tyr Asn
        195                 200                 205

Ser Thr Tyr Arg Val Val Ser Val Leu Thr Val Leu His Gln Asp Trp
    210                 215                 220

Leu Asn Gly Lys Glu Tyr Lys Cys Lys Val Ser Asn Lys Ala Leu Pro
225                 230                 235                 240

Ala Pro Ile Glu Lys Thr Ile Ser Lys Ala Lys Gly Gln Pro Arg Glu
                245                 250                 255

Pro Gln Val Tyr Thr Leu Pro Pro Ser Arg Asp Glu Leu Thr Lys Asn
            260                 265                 270

Gln Val Ser Leu Thr Cys Leu Val Lys Gly Phe Tyr Pro Ser Asp Ile
        275                 280                 285

Ala Val Glu Trp Glu Ser Asn Gly Gln Pro Glu Asn Asn Tyr Lys Thr
    290                 295                 300

Thr Pro Pro Val Leu Asp Ser Asp Gly Ser Phe Phe Leu Tyr Ser Lys
305                 310                 315                 320

Leu Thr Val Asp Lys Ser Arg Trp Gln Gln Gly Asn Val Phe Ser Cys
                325                 330                 335

Ser Val Met His Glu Ala Leu His Asn His Tyr Thr Gln Lys Ser Leu
            340                 345                 350

Ser Leu Ser Pro Gly Lys
        355

<210> SEQ ID NO 110
<211> LENGTH: 1197
<212> TYPE: DNA
<213> ORGANISM: Artificial Sequence
<220> FEATURE:
<223> OTHER INFORMATION: Synthetic: hSIRP-V?C1 beta C2 beta

<400> SEQUENCE: 110
atgcccgtgc ctgcctcttg gcctcatctg cccagcccct ttctgctgat gaccctgctg      60
ctgggcaggc tgacaggcgt ggcaggcgaa gaggaactgc agatgatcca gcccgagaag     120
ctgctgctcg tgaccgtggg caagaccgcc accctgcact gcaccgtgac atccctgctg     180
cctgtgggac ccgtgctgtg gtttagaggc gtgggccctg cagagagct gatctacaac      240 cagaaagagg gccacttccc cagagtgacc accgtgtccg acctgaccaa gcggaacaac     300
atggacttct ccatccggat ctccagcatc acccctgccg acgtgggcac ctactactgc     360
gtgaagttcc ggaagggctc ccccgagaac gtggagttca gtctggccc aggcaccgag      420 atggccctgg gcgctaaacc ttctgcccct gtggtgtctg acctgccgt gcgggctacc     480
```

-continued

```
cctgagcaca ccgtgtcttt tacctgcgag tcccacggct tcagccctcg ggacatcacc    540
ctgaagtggt tcaagaacgg caacgagctg tccgacttcc agaccaacgt ggaccctgcc    600
ggcgactccg tgtcctactc catccactct accgccagag tggtgctgac cagaggcgac    660
gtgcactccc aagtgatctg cgagatcgcc catatcacac tgcagggcga ccccctgaga    720
ggcaccgcca atctgtctga ggccatcaga gtgccccca ccctggaagt gacccagcag    780
cctatgagag ccgagaacca ggccaacgtg acctgtcagg tgtccaactt ctaccctcgg    840
ggcctgcagc tgacctggct ggaaaacggc aatgtgtccc ggaccgagac agcctccacc    900
ctgatcgaga caaggacgg cacctacaat tggatgtcct ggctgctcgt gaacacctgt    960
gcccacaggg acgacgtggt gctgacatgc caggtggaac acgatggcca gcaggccgtg    1020
tccaagtcct acgccctgga aatctccgcc catcagaaag agcacggctc cgatatcacc    1080
cacgaggccg ctctggctcc taccgctcct ctgctggtgg ctctgctgct gggacctaag    1140
ctgctgctgg tcgtgggcgt gtccgccatc tacatctgct ggaagcagaa ggcctga      1197
```

<210> SEQ ID NO 111
<211> LENGTH: 398
<212> TYPE: PRT
<213> ORGANISM: Artificial Sequence
<220> FEATURE:
<223> OTHER INFORMATION: Synthetic: hSIRP-V?C1 beta C2 beta

<400> SEQUENCE: 111

```
Met Pro Val Pro Ala Ser Trp Pro His Leu Pro Ser Pro Phe Leu Leu
1               5                   10                  15
Met Thr Leu Leu Leu Gly Arg Leu Thr Gly Val Ala Gly Glu Glu Glu
            20                  25                  30
Leu Gln Met Ile Gln Pro Glu Lys Leu Leu Leu Val Thr Val Gly Lys
        35                  40                  45
Thr Ala Thr Leu His Cys Thr Val Thr Ser Leu Leu Pro Val Gly Pro
    50                  55                  60
Val Leu Trp Phe Arg Gly Val Gly Pro Gly Arg Glu Leu Ile Tyr Asn
65                  70                  75                  80
Gln Lys Glu Gly His Phe Pro Arg Val Thr Thr Val Ser Asp Leu Thr
                85                  90                  95
Lys Arg Asn Asn Met Asp Phe Ser Ile Arg Ile Ser Ser Ile Thr Pro
            100                 105                 110
Ala Asp Val Gly Thr Tyr Tyr Cys Val Lys Phe Arg Lys Gly Ser Pro
        115                 120                 125
Glu Asn Val Glu Phe Lys Ser Gly Pro Gly Thr Glu Met Ala Leu Gly
    130                 135                 140
Ala Lys Pro Ser Ala Pro Val Val Ser Gly Pro Ala Val Arg Ala Thr
145                 150                 155                 160
Pro Glu His Thr Val Ser Phe Thr Cys Glu Ser His Gly Phe Ser Pro
                165                 170                 175
Arg Asp Ile Thr Leu Lys Trp Phe Lys Asn Gly Asn Glu Leu Ser Asp
            180                 185                 190
Phe Gln Thr Asn Val Asp Pro Ala Gly Asp Ser Val Ser Tyr Ser Ile
        195                 200                 205
His Ser Thr Ala Arg Val Val Leu Thr Arg Gly Asp Val His Ser Gln
    210                 215                 220
Val Ile Cys Glu Ile Ala His Ile Thr Leu Gln Gly Asp Pro Leu Arg
225                 230                 235                 240
```

```
Gly Thr Ala Asn Leu Ser Glu Ala Ile Arg Val Pro Pro Thr Leu Glu
                245                 250                 255

Val Thr Gln Gln Pro Met Arg Ala Glu Asn Gln Ala Asn Val Thr Cys
            260                 265                 270

Gln Val Ser Asn Phe Tyr Pro Arg Gly Leu Gln Leu Thr Trp Leu Glu
        275                 280                 285

Asn Gly Asn Val Ser Arg Thr Glu Thr Ala Ser Thr Leu Ile Glu Asn
    290                 295                 300

Lys Asp Gly Thr Tyr Asn Trp Met Ser Trp Leu Leu Val Asn Thr Cys
305                 310                 315                 320

Ala His Arg Asp Val Val Leu Thr Cys Gln Val Glu His Asp Gly
                325                 330                 335

Gln Gln Ala Val Ser Lys Ser Tyr Ala Leu Glu Ile Ser Ala His Gln
            340                 345                 350

Lys Glu His Gly Ser Asp Ile Thr His Glu Ala Ala Leu Ala Pro Thr
        355                 360                 365

Ala Pro Leu Leu Val Ala Leu Leu Leu Gly Pro Lys Leu Leu Leu Val
    370                 375                 380

Val Gly Val Ser Ala Ile Tyr Ile Cys Trp Lys Gln Lys Ala
385                 390                 395
```

<210> SEQ ID NO 112
<211> LENGTH: 1197
<212> TYPE: DNA
<213> ORGANISM: Artificial Sequence
<220> FEATURE:
<223> OTHER INFORMATION: Synthetic: hSIRP-V beta C1?C2 beta

<400> SEQUENCE: 112

```
atgcccgtgc ctgcctcttg gcctcatctg cccagcccct ttctgctgat gaccctgctg      60
ctgggcaggc tgacaggcgt ggcaggcgaa gatgagctgc aagtgatcca gcccgagaag     120
tccgtgtctg tggccgctgg cgagtctgcc accctgagat gcgctatgac ctccctgatc     180
cccgtgggcc ccatcatgtg gtttagaggc gctggcgctg gcagagagct gatctacaac     240
cagaaagagg gccacttccc cagagtgacc accgtgtccg agctgaccaa gcggaacaac     300
ctggacttct ccatctccat cagcaacatc accccctgcc gcgccggcac ctactactgc     360
gtgaagttcc ggaagggctc ccccgacgac gtggagttca atccggcgc tggaaccgag     420
ctgtccgtgc gggctaaacc ttctgcccct gtggtgctgg acctgccgc tagaaccacc     480
cctgagcaca ccgtgtcttt tacctgcgag tcccacggct tcagccctcg ggacatcacc     540
ctgaagtggt tcaagaacgg caacgagctg agcgacttcc agaccaacgt ggaccctacc     600
ggccagtccg tggcctactc catcagatcc accgccagag tggtgctgga cccttgggat     660
gtgcggtccc aagtgatctg cgaggtggcc catgtgacac tgcagggcga tcctctgaga     720
ggcaccgcca atctgtctga ggccatcaga gtgccccca ccctggaagt gacccagcag     780
cctatgagag ccgagaacca ggccaacgtg acctgccagg tgtccaactt ctaccctcgg     840
ggcctgcagc tgacctggct ggaaaacggc aatgtgtccc ggaccgagac agcctccacc     900
ctgatcgaga caaggatgg cacctacaat tggatgtcct ggctgctcgt gaacacctgt     960
gcccaccggg atgacgtggt gctgacttgt caggtggaac acgacggcca gcaggccgtg    1020
tccaagtcct acgccctgga aatctccgcc catcagaaag agcacggctc cgatatcacc    1080
cacgaggccg ctctggctcc taccgctcct ctgctggtgg ctctgctgct gggacctaag    1140
ctgctgctgg tcgtgggcgt gtccgccatc tacatctgct ggaagcagaa ggcctga      1197
```

<210> SEQ ID NO 113
<211> LENGTH: 398
<212> TYPE: PRT
<213> ORGANISM: Artificial Sequence
<220> FEATURE:
<223> OTHER INFORMATION: Synthetic: hSIRP-V beta C1?C2 beta

<400> SEQUENCE: 113

Met Pro Val Pro Ala Ser Trp Pro His Leu Pro Ser Pro Phe Leu Leu
1               5                   10                  15

Met Thr Leu Leu Leu Gly Arg Leu Thr Gly Val Ala Gly Glu Asp Glu
            20                  25                  30

Leu Gln Val Ile Gln Pro Glu Lys Ser Val Ser Val Ala Ala Gly Glu
        35                  40                  45

Ser Ala Thr Leu Arg Cys Ala Met Thr Ser Leu Ile Pro Val Gly Pro
    50                  55                  60

Ile Met Trp Phe Arg Gly Ala Gly Ala Gly Arg Glu Leu Ile Tyr Asn
65                  70                  75                  80

Gln Lys Glu Gly His Phe Pro Arg Val Thr Val Ser Glu Leu Thr
                85                  90                  95

Lys Arg Asn Asn Leu Asp Phe Ser Ile Ser Ile Ser Asn Ile Thr Pro
            100                 105                 110

Ala Asp Ala Gly Thr Tyr Tyr Cys Val Lys Phe Arg Lys Gly Ser Pro
        115                 120                 125

Asp Asp Val Glu Phe Lys Ser Gly Ala Gly Thr Glu Leu Ser Val Arg
    130                 135                 140

Ala Lys Pro Ser Ala Pro Val Val Leu Gly Pro Ala Ala Arg Thr Thr
145                 150                 155                 160

Pro Glu His Thr Val Ser Phe Thr Cys Glu Ser His Gly Phe Ser Pro
                165                 170                 175

Arg Asp Ile Thr Leu Lys Trp Phe Lys Asn Gly Asn Glu Leu Ser Asp
            180                 185                 190

Phe Gln Thr Asn Val Asp Pro Thr Gly Gln Ser Val Ala Tyr Ser Ile
        195                 200                 205

Arg Ser Thr Ala Arg Val Val Leu Asp Pro Trp Asp Val Arg Ser Gln
    210                 215                 220

Val Ile Cys Glu Val Ala His Val Thr Leu Gln Gly Asp Pro Leu Arg
225                 230                 235                 240

Gly Thr Ala Asn Leu Ser Glu Ala Ile Arg Val Pro Pro Thr Leu Glu
                245                 250                 255

Val Thr Gln Gln Pro Met Arg Ala Glu Asn Gln Ala Asn Val Thr Cys
            260                 265                 270

Gln Val Ser Asn Phe Tyr Pro Arg Gly Leu Gln Leu Thr Trp Leu Glu
        275                 280                 285

Asn Gly Asn Val Ser Arg Thr Glu Thr Ala Ser Thr Leu Ile Glu Asn
    290                 295                 300

Lys Asp Gly Thr Tyr Asn Trp Met Ser Trp Leu Leu Val Asn Thr Cys
305                 310                 315                 320

Ala His Arg Asp Asp Val Val Leu Thr Cys Gln Val Glu His Asp Gly
                325                 330                 335

Gln Gln Ala Val Ser Lys Ser Tyr Ala Leu Glu Ile Ser Ala His Gln
            340                 345                 350

Lys Glu His Gly Ser Asp Ile Thr His Glu Ala Ala Leu Ala Pro Thr
        355                 360                 365

Ala Pro Leu Leu Val Ala Leu Leu Leu Gly Pro Lys Leu Leu Leu Val
    370                 375                 380

Val Gly Val Ser Ala Ile Tyr Ile Cys Trp Lys Gln Lys Ala
385                 390                 395

<210> SEQ ID NO 114
<211> LENGTH: 1197
<212> TYPE: DNA
<213> ORGANISM: Artificial Sequence
<220> FEATURE:
<223> OTHER INFORMATION: Synthetic: hSIRP-V beta C1 beta C2?

<400> SEQUENCE: 114

| | |
|---|---|
| atgcccgtgc ctgcctcttg gcctcatctg cccagcccct ttctgctgat gaccctgctg | 60 |
| ctgggcaggc tgacaggcgt ggcaggcgaa gatgagctgc aagtgatcca gcccgagaag | 120 |
| tccgtgtctg tggccgctgg cgagtctgcc accctgagat gcgctatgac ctccctgatc | 180 |
| cccgtgggcc ccatcatgtg gtttagaggc gctggcgctg cagagagct gatctacaac | 240 |
| cagaaagagg gccacttccc cagagtgacc accgtgtccg agctgaccaa gcggaacaac | 300 |
| ctggacttct ccatctccat cagcaacatc acccctgccg acgccggcac ctactactgc | 360 |
| gtgaagttcc ggaagggctc ccccgacgac gtggagttca atccggcgc tggaaccgag | 420 |
| ctgtccgtgc gggctaaacc ttctgcccct gtggtgtctg acctgctgt gcgcgctacc | 480 |
| cctgagcaca ccgtgtcttt tacctgcgag tcccacggct tcagccctcg ggacatcacc | 540 |
| ctgaagtggt tcaagaacgg caacgagctg agcgacttcc agaccaacgt ggaccctgcc | 600 |
| ggcgactccg tgtcctactc catccactct accgccagag tggtgctgac cagaggcgac | 660 |
| gtgcactccc aagtgatctg cgagatcgcc catatcacac tgcagggcga ccccctgaga | 720 |
| ggcaccgcca atctgtctga ggccatcaga gtgccccca cctggaagt gacccagcag | 780 |
| cctatgagag tgggcaacca agtgaacgtg acctgccaag tgcggaagtt ctaccccag | 840 |
| tccctgcagc tgacttggag cgagaatggc aacgtgtgcc agagagagac agcctccacc | 900 |
| ctgaccgaga caaggacgg aacctacaac tggaccctcc tggttcctcgt gaacatctcc | 960 |
| gaccagcggg acgacgtggt gctgacatgc caagtgaagc acgatggaca gctggccgtg | 1020 |
| tccaagcggc tggctctgga gtgacagtg caccagaaag agcacggctc cgacatcacc | 1080 |
| cacgaggccg ctctggctcc tacagctcct ctgctggtgg ctctgctgct gggacctaag | 1140 |
| ctgctgctgg tcgtgggcgt gtccgccatc tacatctgct ggaagcagaa ggcctga | 1197 |

<210> SEQ ID NO 115
<211> LENGTH: 398
<212> TYPE: PRT
<213> ORGANISM: Artificial Sequence
<220> FEATURE:
<223> OTHER INFORMATION: Synthetic: hSIRP-V beta C1 beta C2?

<400> SEQUENCE: 115

Met Pro Val Pro Ala Ser Trp Pro His Leu Pro Ser Pro Phe Leu Leu
1               5                   10                  15

Met Thr Leu Leu Leu Gly Arg Leu Thr Gly Val Ala Gly Glu Asp Glu
                20                  25                  30

Leu Gln Val Ile Gln Pro Glu Lys Ser Val Ser Val Ala Ala Gly Glu
            35                  40                  45

Ser Ala Thr Leu Arg Cys Ala Met Thr Ser Leu Ile Pro Val Gly Pro
        50                  55                  60

```
Ile Met Trp Phe Arg Gly Ala Gly Ala Gly Arg Glu Leu Ile Tyr Asn
 65                  70                  75                  80

Gln Lys Glu Gly His Phe Pro Arg Val Thr Thr Val Ser Glu Leu Thr
                 85                  90                  95

Lys Arg Asn Asn Leu Asp Phe Ser Ile Ser Ile Ser Asn Ile Thr Pro
            100                 105                 110

Ala Asp Ala Gly Thr Tyr Tyr Cys Val Lys Phe Arg Lys Gly Ser Pro
        115                 120                 125

Asp Asp Val Glu Phe Lys Ser Gly Ala Gly Thr Glu Leu Ser Val Arg
    130                 135                 140

Ala Lys Pro Ser Ala Pro Val Val Ser Gly Pro Ala Val Arg Ala Thr
145                 150                 155                 160

Pro Glu His Thr Val Ser Phe Thr Cys Glu Ser His Gly Phe Ser Pro
                165                 170                 175

Arg Asp Ile Thr Leu Lys Trp Phe Lys Asn Gly Asn Glu Leu Ser Asp
            180                 185                 190

Phe Gln Thr Asn Val Asp Pro Ala Gly Asp Ser Val Ser Tyr Ser Ile
        195                 200                 205

His Ser Thr Ala Arg Val Val Leu Thr Arg Gly Asp Val His Ser Gln
    210                 215                 220

Val Ile Cys Glu Ile Ala His Ile Thr Leu Gln Gly Asp Pro Leu Arg
225                 230                 235                 240

Gly Thr Ala Asn Leu Ser Glu Ala Ile Arg Val Pro Pro Thr Leu Glu
                245                 250                 255

Val Thr Gln Gln Pro Met Arg Val Gly Asn Gln Val Asn Val Thr Cys
            260                 265                 270

Gln Val Arg Lys Phe Tyr Pro Gln Ser Leu Gln Leu Thr Trp Ser Glu
        275                 280                 285

Asn Gly Asn Val Cys Gln Arg Glu Thr Ala Ser Thr Leu Thr Glu Asn
    290                 295                 300

Lys Asp Gly Thr Tyr Asn Trp Thr Ser Trp Phe Leu Val Asn Ile Ser
305                 310                 315                 320

Asp Gln Arg Asp Val Val Leu Thr Cys Gln Val Lys His Asp Gly
                325                 330                 335

Gln Leu Ala Val Ser Lys Arg Leu Ala Leu Glu Val Thr Val His Gln
        340                 345                 350

Lys Glu His Gly Ser Asp Ile Thr His Glu Ala Ala Leu Ala Pro Thr
    355                 360                 365

Ala Pro Leu Leu Val Ala Leu Leu Leu Gly Pro Lys Leu Leu Leu Val
370                 375                 380

Val Gly Val Ser Ala Ile Tyr Ile Cys Trp Lys Gln Lys Ala
385                 390                 395

<210> SEQ ID NO 116
<211> LENGTH: 1194
<212> TYPE: DNA
<213> ORGANISM: Homo sapiens
<220> FEATURE:
<221> NAME/KEY: misc_feature
<222> LOCATION: (1)..(1194)
<223> OTHER INFORMATION: human SIRP beta L

<400> SEQUENCE: 116
atgcctgtgc ctgcctcttg gcctcatctg ccctctccat ttctgctgat gaccctgctg      60
ctgggcagac tgacaggtgt tgctggcgaa gaggaactgc aagtgatcca gcctgacaag     120
```

```
agcatctctg tggccgctgg cgaatctgcc acactgcact gtaccgtgac atctctgatc    180
cctgtgggcc ccatccagtg gtttagaggt gctggacctg cagagagct gatctacaac    240 cagaaagagg gacacttccc cagagtgacc accgtgtccg acctgaccaa gcggaacaac    300
atggacttca gcatccggat cagcaacatc accctgccg atgccggcac ctactactgc    360
gtgaagttca gaaagggcag ccccgaccac gtcgagttta aaagcggagc cggcacagag    420
ctgagcgtgc gggctaaacc ttctgctcct gtggtgtctg gaccagccgc tagagctaca    480
cctcagcaca ccgtgtcttt tacctgcgag agccacggct tcagccccag agatatcacc    540
ctgaagtggt tcaagaacgg caacgagctg tccgacttcc agaccaatgt ggacccagcc    600
ggcgatagcg tgtcctacag cattcacagc accgccaagg tggtgctgac ccgggaagat    660
gtgcacagcc aagtgatttg cgaggtggcc acgttaccc tgcaaggcga tcctctgaga    720
ggaaccgcca acctgagcga acaatccgg gtgccaccta cactggaagt gacccagcag    780
cctgtgcggg ccgagaatca agtgaacgtg acctgccaag tgcggaagtt ctaccctcag    840
agactgcagc tgacctggct ggaaaacggc aatgtgtccc ggaccgagac agccagcaca    900
ctgaccgaga acaaggatgg cacctacaat tggatgagct ggctgctggt caatgtgtct    960
gcccaccggg acgatgtgaa gctgacatgc caggtggaac acgatggcca gcctgccgtg   1020
tctaagagcc acgacctgaa ggtgtccgct catcccaaag agcagggcag caatactgcc   1080
cctggacctg ctcttgcttc tgccgctcct ctgctgatcg cctttctgct gggacctaag   1140
gtgctgctgg ttgtgggagt gtccgtgatc tacgtgtact ggaagcagaa ggcc         1194

<210> SEQ ID NO 117
<211> LENGTH: 398
<212> TYPE: PRT
<213> ORGANISM: Homo sapiens
<220> FEATURE:
<221> NAME/KEY: misc_feature
<222> LOCATION: (1)..(398)
<223> OTHER INFORMATION: human SIRP beta L

<400> SEQUENCE: 117

Met Pro Val Pro Ala Ser Trp Pro His Leu Pro Ser Pro Phe Leu Leu
1               5                   10                  15

Met Thr Leu Leu Leu Gly Arg Leu Thr Gly Val Ala Gly Glu Glu Glu
            20                  25                  30

Leu Gln Val Ile Gln Pro Asp Lys Ser Ile Ser Val Ala Ala Gly Glu
        35                  40                  45

Ser Ala Thr Leu His Cys Thr Val Thr Ser Leu Ile Pro Val Gly Pro
    50                  55                  60

Ile Gln Trp Phe Arg Gly Ala Gly Pro Gly Arg Glu Leu Ile Tyr Asn
65                  70                  75                  80

Gln Lys Glu Gly His Phe Pro Arg Val Thr Thr Val Ser Asp Leu Thr
                85                  90                  95

Lys Arg Asn Asn Met Asp Phe Ser Ile Arg Ile Ser Asn Ile Thr Pro
            100                 105                 110

Ala Asp Ala Gly Thr Tyr Tyr Cys Val Lys Phe Arg Lys Gly Ser Pro
        115                 120                 125

Asp His Val Glu Phe Lys Ser Gly Ala Gly Thr Glu Leu Ser Val Arg
    130                 135                 140

Ala Lys Pro Ser Ala Pro Val Val Ser Gly Pro Ala Ala Arg Ala Thr
145                 150                 155                 160

Pro Gln His Thr Val Ser Phe Thr Cys Glu Ser His Gly Phe Ser Pro
```

```
                165                 170                 175
Arg Asp Ile Thr Leu Lys Trp Phe Lys Asn Gly Asn Glu Leu Ser Asp
                180                 185                 190

Phe Gln Thr Asn Val Asp Pro Ala Gly Asp Ser Val Ser Tyr Ser Ile
            195                 200                 205

His Ser Thr Ala Lys Val Val Leu Thr Arg Glu Asp Val His Ser Gln
        210                 215                 220

Val Ile Cys Glu Val Ala His Val Thr Leu Gln Gly Asp Pro Leu Arg
225                 230                 235                 240

Gly Thr Ala Asn Leu Ser Glu Thr Ile Arg Val Pro Pro Thr Leu Glu
                245                 250                 255

Val Thr Gln Gln Pro Val Arg Ala Glu Asn Gln Val Asn Val Thr Cys
            260                 265                 270

Gln Val Arg Lys Phe Tyr Pro Gln Arg Leu Gln Leu Thr Trp Leu Glu
        275                 280                 285

Asn Gly Asn Val Ser Arg Thr Glu Thr Ala Ser Thr Leu Thr Glu Asn
290                 295                 300

Lys Asp Gly Thr Tyr Asn Trp Met Ser Trp Leu Leu Val Asn Val Ser
305                 310                 315                 320

Ala His Arg Asp Asp Val Lys Leu Thr Cys Gln Val Glu His Asp Gly
                325                 330                 335

Gln Pro Ala Val Ser Lys Ser His Asp Leu Lys Val Ser Ala His Pro
            340                 345                 350

Lys Glu Gln Gly Ser Asn Thr Ala Pro Gly Pro Ala Leu Ala Ser Ala
        355                 360                 365

Ala Pro Leu Leu Ile Ala Phe Leu Leu Gly Pro Lys Val Leu Leu Val
370                 375                 380

Val Gly Val Ser Val Ile Tyr Val Tyr Trp Lys Gln Lys Ala
385                 390                 395

<210> SEQ ID NO 118
<211> LENGTH: 990
<212> TYPE: DNA
<213> ORGANISM: Homo sapiens
<220> FEATURE:
<221> NAME/KEY: misc_feature
<222> LOCATION: (1)..(990)
<223> OTHER INFORMATION: human IgG1 constant domains

<400> SEQUENCE: 118
gccagcacca agggcccatc ggtcttcccc ctggcaccct cctccaagag cacctctggg      60
ggcacagcgg ccctgggctg cctggtcaag gactacttcc ccgaaccggt gacggtgtcg     120
tggaactcag gcgccctgac cagcggcgtg cacaccttcc cggctgtcct acagtcctca     180
ggactctact ccctcagcag cgtggtgacc gtgccctcca gcagcttggg cacccagacc     240
tacatctgca acgtgaatca caagcccagc aacaccaagg tggacaagaa agttgagccc     300
aaatcttgtg acaaaactca cacatgccca ccgtgcccag cacctgaact cctggggggga    360 ccgtcagtct tcctcttccc cccaaaaccc aaggacaccc tcatgatctc ccggacccct     420
gaggtcacat gcgtggtggt ggacgtgagc cacgaagacc ctgaggtcaa gttcaactgg     480
tacgtggacg gcgtggaggt gcataatgcc aagacaaagc cgcgggagga gcagtacaac     540
agcacgtacc gggtggtcag cgtcctcacc gtcctgcacc aggactggct gaatggcaag     600
gagtacaagt gcaaggtctc caacaaagcc ctcccagccc ccatcgagaa aaccatctcc     660
aaagccaaag ggcagccccg agaaccacag gtgtacaccc tgcccccatc ccgggatgag     720
```

```
ctgaccaaga accaggtcag cctgacctgc ctggtcaaag gcttctatcc cagcgacatc    780
gccgtggagt gggagagcaa tgggcagccg gagaacaact acaagaccac gcctcccgtg    840
ctggactccg acggctcctt cttcctctac agcaagctca ccgtggacaa gagcaggtgg    900
cagcagggga acgtcttctc atgctccgtg atgcatgagg ctctgcacaa ccactacacg    960
cagaagagcc tctccctgtc tccgggtaaa                                     990
```

<210> SEQ ID NO 119
<211> LENGTH: 330
<212> TYPE: PRT
<213> ORGANISM: Homo sapiens
<220> FEATURE:
<221> NAME/KEY: misc_feature
<222> LOCATION: (1)..(330)
<223> OTHER INFORMATION: human IgG1 constant domains

<400> SEQUENCE: 119

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300
```

```
Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 120
<211> LENGTH: 336
<212> TYPE: PRT
<213> ORGANISM: Mus musculus
<220> FEATURE:
<221> NAME/KEY: misc_feature
<222> LOCATION: (1)..(336)
<223> OTHER INFORMATION: mouse IgG1 constant domains

<400> SEQUENCE: 120

Ala Lys Thr Thr Pro Pro Ser Val Tyr Pro Leu Ala Pro Gly Cys Gly
1               5                   10                  15

Asp Thr Thr Gly Ser Ser Val Thr Leu Gly Cys Leu Val Lys Gly Tyr
                20                  25                  30

Phe Pro Glu Ser Val Thr Val Thr Trp Asn Ser Gly Ser Leu Ser Ser
            35                  40                  45

Ser Val His Thr Phe Pro Ala Leu Leu Gln Ser Gly Leu Tyr Thr Met
        50                  55                  60

Ser Ser Ser Val Thr Val Pro Ser Ser Thr Trp Pro Ser Gln Thr Val
65                  70                  75                  80

Thr Cys Ser Val Ala His Pro Ala Ser Ser Thr Thr Val Asp Lys Lys
                85                  90                  95

Leu Glu Pro Ser Gly Pro Ile Ser Thr Ile Asn Pro Cys Pro Pro Cys
            100                 105                 110

Lys Glu Cys His Lys Cys Pro Ala Pro Asn Leu Glu Gly Gly Pro Ser
        115                 120                 125

Val Phe Ile Phe Pro Pro Asn Ile Lys Asp Val Leu Met Ile Ser Leu
130                 135                 140

Thr Pro Lys Val Thr Cys Val Val Val Asp Val Ser Glu Asp Asp Pro
145                 150                 155                 160

Asp Val Gln Ile Ser Trp Phe Val Asn Asn Val Glu Val His Thr Ala
                165                 170                 175

Gln Thr Gln Thr His Arg Glu Asp Tyr Asn Ser Thr Ile Arg Val Val
            180                 185                 190

Ser Thr Leu Pro Ile Gln His Gln Asp Trp Met Ser Gly Lys Glu Phe
        195                 200                 205

Lys Cys Lys Val Asn Asn Lys Asp Leu Pro Ser Pro Ile Glu Arg Thr
210                 215                 220

Ile Ser Lys Ile Lys Gly Leu Val Arg Ala Pro Gln Val Tyr Ile Leu
225                 230                 235                 240

Pro Pro Pro Ala Glu Gln Leu Ser Arg Lys Asp Val Ser Leu Thr Cys
                245                 250                 255

Leu Val Val Gly Phe Asn Pro Gly Asp Ile Ser Val Glu Trp Thr Ser
            260                 265                 270

Asn Gly His Thr Glu Glu Asn Tyr Lys Asp Thr Ala Pro Val Leu Asp
        275                 280                 285

Ser Asp Gly Ser Tyr Phe Ile Tyr Ser Lys Leu Asn Met Lys Thr Ser
            290                 295                 300

Lys Trp Glu Lys Thr Asp Ser Phe Ser Cys Asn Val Arg His Glu Gly
305                 310                 315                 320
```

```
Leu Lys Asn Tyr Tyr Leu Lys Lys Thr Ile Ser Arg Ser Pro Gly Lys
                325                 330                 335

<210> SEQ ID NO 121
<211> LENGTH: 107
<212> TYPE: PRT
<213> ORGANISM: Mus musculus
<220> FEATURE:
<221> NAME/KEY: misc_feature
<222> LOCATION: (1)..(107)
<223> OTHER INFORMATION: mouse kappa constant domain

<400> SEQUENCE: 121

Arg Ala Asp Ala Ala Pro Thr Val Ser Ile Phe Pro Pro Ser Ser Glu
1               5                   10                  15

Gln Leu Thr Ser Gly Gly Ala Ser Val Val Cys Phe Leu Asn Asn Phe
            20                  25                  30

Tyr Pro Lys Asp Ile Asn Val Lys Trp Lys Ile Asp Gly Ser Glu Arg
        35                  40                  45

Gln Asn Gly Val Leu Asn Ser Trp Thr Asp Gln Asp Ser Lys Asp Ser
    50                  55                  60

Thr Tyr Ser Met Ser Ser Thr Leu Thr Leu Thr Lys Asp Glu Tyr Glu
65                  70                  75                  80

Arg His Asn Ser Tyr Thr Cys Glu Ala Thr His Lys Thr Ser Thr Ser
                85                  90                  95

Pro Ile Val Lys Ser Phe Asn Arg Asn Glu Cys
            100                 105

<210> SEQ ID NO 122
<211> LENGTH: 326
<212> TYPE: PRT
<213> ORGANISM: Homo sapiens
<220> FEATURE:
<221> NAME/KEY: misc_feature
<222> LOCATION: (1)..(326)
<223> OTHER INFORMATION: human IgG2 constant domains,
      V234A-G237A-P238S-H268A-V309L-A330S-P331S (Sigma) mutant
<220> FEATURE:
<221> NAME/KEY: misc_feature
<222> LOCATION: (257)..(257)
<223> OTHER INFORMATION: X is A or S

<400> SEQUENCE: 122

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Ala Ala Ala Ser Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140
```

```
Val Ser Ala Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Leu His Gln Asp Trp
            180                 185                 190

Leu Asn Gly Lys Glu Tyr Lys Cys Lys Val Ser Asn Lys Gly Leu Pro
        195                 200                 205

Ser Ser Ile Glu Lys Thr Ile Ser Lys Thr Lys Gly Gln Pro Arg Glu
    210                 215                 220

Pro Gln Val Tyr Thr Leu Pro Pro Ser Arg Glu Met Thr Lys Asn
225                 230                 235                 240

Gln Val Ser Leu Thr Cys Leu Val Lys Gly Phe Tyr Pro Ser Asp Ile
                245                 250                 255

Xaa Val Glu Trp Glu Ser Asn Gly Gln Pro Glu Asn Asn Tyr Lys Thr
                260                 265                 270

Thr Pro Pro Met Leu Asp Ser Asp Gly Ser Phe Phe Leu Tyr Ser Lys
            275                 280                 285

Leu Thr Val Asp Lys Ser Arg Trp Gln Gln Gly Asn Val Phe Ser Cys
        290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 123
<211> LENGTH: 330
<212> TYPE: PRT
<213> ORGANISM: Homo sapiens
<220> FEATURE:
<221> NAME/KEY: misc_feature
<222> LOCATION: (1)..(330)
<223> OTHER INFORMATION: human IgG1 constant domains, L234A-L235A mutant

<400> SEQUENCE: 123

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160
```

```
Tyr Val Asp Gly Val Glu Val His Asn Ala Lys Thr Lys Pro Arg Glu
            165                 170                 175
Glu Gln Tyr Asn Ser Thr Tyr Arg Val Val Ser Val Leu Thr Val Leu
        180                 185                 190
His Gln Asp Trp Leu Asn Gly Lys Glu Tyr Lys Cys Lys Val Ser Asn
    195                 200                 205
Lys Ala Leu Pro Ala Pro Ile Glu Lys Thr Ile Ser Lys Ala Lys Gly
210                 215                 220
Gln Pro Arg Glu Pro Gln Val Tyr Thr Leu Pro Pro Ser Arg Asp Glu
225                 230                 235                 240
Leu Thr Lys Asn Gln Val Ser Leu Thr Cys Leu Val Lys Gly Phe Tyr
            245                 250                 255
Pro Ser Asp Ile Ala Val Glu Trp Glu Ser Asn Gly Gln Pro Glu Asn
        260                 265                 270
Asn Tyr Lys Thr Thr Pro Pro Val Leu Asp Ser Asp Gly Ser Phe Phe
    275                 280                 285
Leu Tyr Ser Lys Leu Thr Val Asp Lys Ser Arg Trp Gln Gln Gly Asn
290                 295                 300
Val Phe Ser Cys Ser Val Met His Glu Ala Leu His Asn His Tyr Thr
305                 310                 315                 320
Gln Lys Ser Leu Ser Leu Ser Pro Gly Lys
            325                 330

<210> SEQ ID NO 124
<211> LENGTH: 990
<212> TYPE: DNA
<213> ORGANISM: Homo sapiens
<220> FEATURE:
<221> NAME/KEY: misc_feature
<222> LOCATION: (1)..(990)
<223> OTHER INFORMATION: human IgG1 constant domains, L234A-L235A-P329G
      mutant

<400> SEQUENCE: 124
gctagcacaa agggccctag tgtgtttcct ctggctccct cttccaaatc cacttctggt      60
ggcactgctg ctctgggatg cctggtgaag gattactttc ctgaacctgt gactgtctca     120
tggaactctg gtgctctgac ttctggtgtc cacactttcc ctgctgtgct gcagtctagt     180
ggactgtact ctctgtcatc tgtggtcact gtgccctctt catctctggg aacccagacc     240
tacatttgta atgtgaacca caaaccatcc aacactaaag tggacaaaaa agtggaaccc     300
aaatcctgtg acaaaaccca cacctgccca ccttgtccgg cgcctgaagc ggcgggagga     360
ccttctgtgt ttctgttccc ccccaaacca aggatacccc tgatgatctc gcgaacccct     420
gaggtgacat gtgtggtggt ggatgtgtct catgaggacc ccgaagtcaa atttaattgg     480
tatgtcgacg gcgtcgaggt gcataatgcc aaaaccaagc tagagagga acagtacaat     540 tcaacctaca gtcgtcagt gtgctgact gtgctgcatc aggattggct gaatggcaag     600
gaatacaagt gtaaagtctc aaacaaggcc ctggagctc aattgagaa acaatctca     660 aaggccaaag gacagcctag ggaaccccag gtctacaccc tgccaccttc gagagacgaa     720
ctgaccaaaa accaggtgtc cctgacatgc ctggtcaaag gcttctaccc ttctgacatt     780
gctgtggagt gggagtcaaa tggacagcct gagaacaact acaaaacaac cccccctgtg     840
ctggattctg atggctcttt ctttctgtac tccaaactga ctgtggacaa gtctagatgg     900
cagcagggga atgtctttc ttgctctgtc atgcatgagg ctctgcataa ccactacact     960
cagaaatccc tgtctctgtc tcccgggaaa                                     990
```

<210> SEQ ID NO 125
<211> LENGTH: 330
<212> TYPE: PRT
<213> ORGANISM: Homo sapiens
<220> FEATURE:
<221> NAME/KEY: misc_feature
<222> LOCATION: (1)..(330)
<223> OTHER INFORMATION: human IgG1 constant domains, L234A-L235A-P329G
    mutant

<400> SEQUENCE: 125

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Gly Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 126

<211> LENGTH: 330
<212> TYPE: PRT
<213> ORGANISM: Homo sapiens
<220> FEATURE:
<221> NAME/KEY: misc_feature
<222> LOCATION: (1)..(330)
<223> OTHER INFORMATION: human IgG1 constant domains, N297Q mutant

<400> SEQUENCE: 126

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Gln Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 127
<211> LENGTH: 327
<212> TYPE: PRT
<213> ORGANISM: Homo sapiens
<220> FEATURE:

```
<221> NAME/KEY: misc_feature
<222> LOCATION: (1)..(327)
<223> OTHER INFORMATION: human IgG4 constant domains, S228P-N297Q mutant

<400> SEQUENCE: 127

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Gln Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 128
<211> LENGTH: 120
<212> TYPE: PRT
<213> ORGANISM: Artificial Sequence
<220> FEATURE:
<223> OTHER INFORMATION: Synthetic: 18D5 VH

<400> SEQUENCE: 128
```

Gln Val Gln Leu Gln Gln Pro Gly Ala Glu Leu Val Arg Pro Gly Ser
1               5                   10                  15

Ser Val Lys Leu Ser Cys Lys Ala Ser Gly Tyr Thr Phe Thr Ser Tyr
            20                  25                  30

Trp Val His Trp Val Lys Gln Arg Pro Ile Gln Gly Leu Glu Trp Ile
        35                  40                  45

Gly Asn Ile Asp Pro Ser Asp Ser Asp Thr His Tyr Asn Gln Lys Phe
    50                  55                  60

Lys Asp Lys Ala Ser Leu Thr Val Asp Lys Ser Ser Thr Ala Tyr
65                  70                  75                  80

Met Gln Leu Ser Ser Leu Thr Phe Glu Asp Ser Ala Val Tyr Tyr Cys
                85                  90                  95

Val Arg Gly Gly Thr Gly Thr Met Ala Trp Phe Ala Tyr Trp Gly Gln
            100                 105                 110

Gly Thr Leu Val Thr Val Ser Ala
            115                 120

<210> SEQ ID NO 129
<211> LENGTH: 112
<212> TYPE: PRT
<213> ORGANISM: Artificial Sequence
<220> FEATURE:
<223> OTHER INFORMATION: Synthetic: 18D5 VL

<400> SEQUENCE: 129

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Tyr Gly Asn Thr Tyr Leu Tyr Trp Tyr Leu Gln Lys Pro Gly Gln Ser
        35                  40                  45

Pro Lys Leu Leu Ile Tyr Arg Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Phe Gln Gly
                85                  90                  95

Thr His Val Pro Tyr Thr Phe Gly Ser Gly Thr Lys Leu Glu Ile Lys
            100                 105                 110

<210> SEQ ID NO 130
<211> LENGTH: 113
<212> TYPE: PRT
<213> ORGANISM: Artificial Sequence
<220> FEATURE:
<223> OTHER INFORMATION: Synthetic: KWAR23 VH

<400> SEQUENCE: 130

Glu Val Gln Leu Gln Gln Ser Gly Ala Glu Leu Val Lys Pro Gly Ala
1               5                   10                  15

Ser Val Lys Leu Ser Cys Thr Ala Ser Gly Phe Asn Ile Lys Asp Tyr
            20                  25                  30

Tyr Ile His Trp Val Gln Gln Arg Thr Glu Gln Gly Leu Glu Trp Ile
        35                  40                  45

Gly Arg Ile Asp Pro Glu Asp Gly Glu Thr Lys Tyr Ala Pro Lys Phe
    50                  55                  60

Gln Asp Lys Ala Thr Ile Thr Ala Asp Thr Ser Ser Asn Thr Ala Tyr
65                  70                  75                  80

```
Leu His Leu Ser Ser Leu Thr Ser Glu Asp Thr Ala Val Tyr Tyr Cys
                85                  90                  95

Ala Arg Trp Gly Ala Tyr Trp Gly Gln Gly Thr Leu Val Thr Val Ser
            100                 105                 110

Ser

<210> SEQ ID NO 131
<211> LENGTH: 108
<212> TYPE: PRT
<213> ORGANISM: Artificial Sequence
<220> FEATURE:
<223> OTHER INFORMATION: Synthetic: KWAR23 VL

<400> SEQUENCE: 131

Gln Ile Val Leu Thr Gln Ser Pro Ala Ile Met Ser Ala Ser Pro Gly
1               5                   10                  15

Glu Lys Val Thr Leu Thr Cys Ser Ala Ser Ser Val Ser Ser Ser
            20                  25                  30

Tyr Leu Tyr Trp Tyr Gln Gln Lys Pro Gly Ser Ser Pro Lys Leu Trp
            35                  40                  45

Ile Tyr Ser Thr Ser Asn Leu Ala Ser Gly Val Pro Ala Arg Phe Ser
50                  55                  60

Gly Ser Gly Ser Gly Thr Ser Tyr Ser Leu Thr Ile Ser Ser Met Glu
65                  70                  75                  80

Ala Glu Asp Ala Ala Ser Tyr Phe Cys His Gln Trp Ser Ser Tyr Pro
                85                  90                  95

Arg Thr Phe Gly Ala Gly Thr Lys Leu Glu Leu Lys
            100                 105

<210> SEQ ID NO 132
<211> LENGTH: 376
<212> TYPE: PRT
<213> ORGANISM: Artificial Sequence
<220> FEATURE:
<223> OTHER INFORMATION: Synthetic: rhSIRP alpha-HIS

<400> SEQUENCE: 132

Met Glu Pro Ala Gly Pro Ala Pro Gly Arg Leu Gly Pro Leu Leu Cys
1               5                   10                  15

Leu Leu Leu Ala Ala Ser Cys Ala Trp Ser Gly Val Ala Gly Glu Glu
            20                  25                  30

Glu Leu Gln Val Ile Gln Pro Asp Lys Ser Val Leu Val Ala Ala Gly
            35                  40                  45

Glu Thr Ala Thr Leu Arg Cys Thr Ala Thr Ser Leu Ile Pro Val Gly
50                  55                  60

Pro Ile Gln Trp Phe Arg Gly Ala Gly Pro Gly Arg Glu Leu Ile Tyr
65                  70                  75                  80

Asn Gln Lys Glu Gly His Phe Pro Arg Val Thr Thr Val Ser Asp Leu
                85                  90                  95

Thr Lys Arg Asn Asn Met Asp Phe Ser Ile Arg Ile Gly Asn Ile Thr
            100                 105                 110

Pro Ala Asp Ala Gly Thr Tyr Tyr Cys Val Lys Phe Arg Lys Gly Ser
            115                 120                 125

Pro Asp Asp Val Glu Phe Lys Ser Gly Ala Gly Thr Glu Leu Ser Val
            130                 135                 140

Arg Ala Lys Pro Ser Ala Pro Val Val Ser Gly Pro Ala Ala Arg Ala
145                 150                 155                 160
```

```
Thr Pro Gln His Thr Val Ser Phe Thr Cys Glu Ser His Gly Phe Ser
            165                 170                 175

Pro Arg Asp Ile Thr Leu Lys Trp Phe Lys Asn Gly Asn Glu Leu Ser
        180                 185                 190

Asp Phe Gln Thr Asn Val Asp Pro Val Gly Glu Ser Val Ser Tyr Ser
        195                 200                 205

Ile His Ser Thr Ala Lys Val Val Leu Thr Arg Glu Asp Val His Ser
        210                 215                 220

Gln Val Ile Cys Glu Val Ala His Val Thr Leu Gln Gly Asp Pro Leu
225                 230                 235                 240

Arg Gly Thr Ala Asn Leu Ser Glu Thr Ile Arg Val Pro Pro Thr Leu
                245                 250                 255

Glu Val Thr Gln Gln Pro Val Arg Ala Glu Asn Gln Val Asn Val Thr
            260                 265                 270

Cys Gln Val Arg Lys Phe Tyr Pro Gln Arg Leu Gln Leu Thr Trp Leu
        275                 280                 285

Glu Asn Gly Asn Val Ser Arg Thr Glu Thr Ala Ser Thr Val Thr Glu
        290                 295                 300

Asn Lys Asp Gly Thr Tyr Asn Trp Met Ser Trp Leu Leu Val Asn Val
305                 310                 315                 320

Ser Ala His Arg Asp Asp Val Lys Leu Thr Cys Gln Val Glu His Asp
                325                 330                 335

Gly Gln Pro Ala Val Ser Lys Ser His Asp Leu Lys Val Ser Ala His
            340                 345                 350

Pro Lys Glu Gln Gly Ser Asn Thr Ala Ala Glu Asn Thr Gly Ser Asn
        355                 360                 365

Glu Arg His His His His His His
        370                 375

<210> SEQ ID NO 133
<211> LENGTH: 107
<212> TYPE: PRT
<213> ORGANISM: Artificial Sequence
<220> FEATURE:
<223> OTHER INFORMATION: Synthetic: hSIRP alphaV1

<400> SEQUENCE: 133

Glu Glu Glu Leu Gln Val Ile Gln Pro Asp Lys Ser Val Leu Val Ala
1               5                   10                  15

Ala Gly Glu Thr Ala Thr Leu Arg Cys Thr Ala Thr Ser Leu Ile Pro
            20                  25                  30

Val Gly Pro Ile Gln Trp Phe Arg Gly Ala Gly Pro Gly Arg Glu Leu
        35                  40                  45

Ile Tyr Asn Gln Lys Glu Gly His Phe Pro Arg Val Thr Thr Val Ser
    50                  55                  60

Asp Leu Thr Lys Arg Asn Asn Met Asp Phe Ser Ile Arg Ile Gly Asn
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly
            100                 105

<210> SEQ ID NO 134
<211> LENGTH: 106
<212> TYPE: PRT
<213> ORGANISM: Artificial Sequence
```

<220> FEATURE:
<223> OTHER INFORMATION: Synthetic: hSIRP alphaV2

<400> SEQUENCE: 134

```
Glu Glu Glu Leu Gln Val Ile Gln Pro Asp Lys Ser Val Ser Val Ala
1               5                   10                  15

Ala Gly Glu Ser Ala Ile Leu His Cys Thr Val Thr Ser Leu Ile Pro
            20                  25                  30

Val Gly Pro Ile Gln Trp Phe Arg Gly Ala Gly Pro Ala Arg Glu Leu
        35                  40                  45

Ile Tyr Asn Gln Lys Glu Gly His Phe Pro Arg Val Thr Thr Val Ser
    50                  55                  60

Glu Ser Thr Lys Arg Glu Asn Met Asp Phe Ser Ile Ser Ile Ser Asn
65                  70                  75                  80

Ile Thr Pro Ala Asp Ala Gly Thr Tyr Tyr Cys Val Lys Phe Arg Lys
                85                  90                  95

Gly Ser Pro Asp Thr Glu Phe Lys Ser Gly
            100                 105
```

<210> SEQ ID NO 135
<211> LENGTH: 107
<212> TYPE: PRT
<213> ORGANISM: Artificial Sequence
<220> FEATURE:
<223> OTHER INFORMATION: Synthetic: hSIRP beta 1

<400> SEQUENCE: 135

```
Glu Asp Glu Leu Gln Val Ile Gln Pro Glu Lys Ser Val Ser Val Ala
1               5                   10                  15

Ala Gly Glu Ser Ala Thr Leu Arg Cys Ala Met Thr Ser Leu Ile Pro
            20                  25                  30

Val Gly Pro Ile Met Trp Phe Arg Gly Ala Gly Ala Gly Arg Glu Leu
        35                  40                  45

Ile Tyr Asn Gln Lys Glu Gly His Phe Pro Arg Val Thr Thr Val Ser
    50                  55                  60

Glu Leu Thr Lys Arg Asn Asn Leu Asp Phe Ser Ile Ser Ile Ser Asn
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly
            100                 105
```

<210> SEQ ID NO 136
<211> LENGTH: 17
<212> TYPE: PRT
<213> ORGANISM: Artificial Sequence
<220> FEATURE:
<223> OTHER INFORMATION: Synthetic: subsequence from SEQ ID NO: 78

<400> SEQUENCE: 136

```
Ala Ile Tyr Pro Val Asn Ser Asp Thr Thr Tyr Asn Gln Lys Phe Lys
1               5                   10                  15

Gly
```

<210> SEQ ID NO 137
<211> LENGTH: 17
<212> TYPE: PRT
<213> ORGANISM: Artificial Sequence
<220> FEATURE:
<223> OTHER INFORMATION: Synthetic: subsequence from SEQ ID NO: 80

<400> SEQUENCE: 137

Ala Leu Tyr Pro Val Asn Ser Asp Thr Thr Tyr Asn Gln Lys Phe Lys
1               5                   10                  15

Gly